US012799182B2

(12) United States Patent
Wesselhoeft et al.

(10) Patent No.: US 12,799,182 B2

(45) Date of Patent: Nov. 17, 2026

(54) CIRCULAR RNA COMPOSITIONS AND METHODS

(71) Applicants: Massachusetts Institute of Technology, Cambridge, MA (US); Orna Therapeutics, Inc., Cambridge, MA (US)

(72) Inventors: Robert Alexander Wesselhoeft, Watertown, MA (US); Daniel G. Anderson, Watertown, MA (US); Shinichiro Fuse, Watertown, MA (US); Brian Goodman, Watertown, MA (US); Allen T. Horhota, Watertown, MA (US); Raffaella Squilloni, Watertown, MA (US)

(73) Assignees: Massachusetts Institute of Technology, Cambridge, MA (US); Orna Therapeutics, Inc., Watertown, MA (US)

( * ) Notice: Subject to any disclaimer, the term of this patent is extended or adjusted under 35 U.S.C. 154(b) by 615 days.

(21) Appl. No.: 18/069,621

(22) Filed: Dec. 21, 2022

(65) Prior Publication Data

US 2023/0331806 A1 Oct. 19, 2023

Related U.S. Application Data

(63) Continuation of application No. 17/548,247, filed on Dec. 10, 2021, now Pat. No. 11,603,396, which is a continuation of application No. 17/384,460, filed on Jul. 23, 2021, now Pat. No. 11,802,144, which is a continuation of application No. PCT/US2020/034418, filed on May 22, 2020.

(60) Provisional application No. 62/972,194, filed on Feb. 10, 2020, provisional application No. 62/943,796, filed on Dec. 4, 2019, provisional application No. 62/943,779, filed on Dec. 4, 2019, provisional application No. 62/857,121, filed on Jun. 4, 2019, provisional application No. 62/851,548, filed on May 22, 2019.

(30) Foreign Application Priority Data

Jun. 5, 2019 (WO) ................ PCT/US2019/035531

(51) Int. Cl.

| | |
|---|---|
| ***C07K 14/725*** | (2006.01) |
| ***A61K 9/51*** | (2006.01) |
| ***A61K 40/11*** | (2025.01) |
| ***A61K 40/17*** | (2025.01) |
| ***A61K 40/24*** | (2025.01) |
| ***A61K 40/31*** | (2025.01) |
| ***A61K 40/32*** | (2025.01) |
| ***A61K 40/42*** | (2025.01) |
| ***C07K 14/705*** | (2006.01) |
| ***C07K 16/28*** | (2006.01) |
| *A61K 38/00* | (2006.01) |
| *A61K 39/00* | (2006.01) |

(52) U.S. Cl.

CPC ............ *C07K 14/7051* (2013.01); *A61K 9/51* (2013.01); *A61K 40/11* (2025.01); *A61K 40/17* (2025.01); *A61K 40/24* (2025.01); *A61K 40/31* (2025.01); *A61K 40/32* (2025.01); *A61K 40/4211* (2025.01); *A61K 40/4215* (2025.01); *C07K 16/28* (2013.01); *A61K 38/00* (2013.01); *A61K 2039/505* (2013.01); *C07K 2319/30* (2013.01); *C12N 2310/532* (2013.01); *C12N 2840/203* (2013.01); *C12N 2840/60* (2013.01)

(58) Field of Classification Search

None

See application file for complete search history.

(56) References Cited

U.S. PATENT DOCUMENTS

| | | | |
|---|---|---|---|
| 3,832,253 | A | 8/1974 | Di et al. |
| 3,854,480 | A | 12/1974 | Zaffaroni |
| 4,235,871 | A | 11/1980 | Papahadjopoulos et al. |
| 4,323,689 | A | 4/1982 | Vogel et al. |
| 4,450,150 | A | 5/1984 | Sidman |
| 4,452,775 | A | 6/1984 | Kent |

(Continued)

FOREIGN PATENT DOCUMENTS

| | | | |
|---|---|---|---|
| CA | 3137519 | A1 | 10/2020 |
| CN | 101016264 | A | 8/2007 |

(Continued)

OTHER PUBLICATIONS

Krause et al. "Antigen-dependent CD28 signaling selectively enhances survival and proliferation in genetically modified activated human primary T lymphocytes," J Exp Med., 1998, 188(4):619-26.

(Continued)

*Primary Examiner* — Michael D Burkhart

(74) *Attorney, Agent, or Firm* — Goodwin Procter LLP

(57) ABSTRACT

Circular RNA and transfer vehicles, along with related compositions and methods are described herein. In some embodiments, the inventive circular RNA comprises group I intron fragments, spacers, an IRES, duplex forming regions, and an expression sequence. In some embodiments, the expression sequence encodes a chimeric antigen receptor (CAR). In some embodiments, circular RNA of the invention has improved expression, functional stability, immunogenicity, ease of manufacturing, and/or half-life when compared to linear RNA. In some embodiments, inventive methods and constructs result in improved circularization efficiency, splicing efficiency, and/or purity when compared to existing RNA circularization approaches.

12 Claims, 69 Drawing Sheets

Specification includes a Sequence Listing.

(56) References Cited

U.S. PATENT DOCUMENTS

| | | | |
|---|---|---|---|
| 4,501,728 | A | 2/1985 | Geho et al. |
| 4,661,450 | A | 4/1987 | Kempe et al. |
| 4,667,014 | A | 5/1987 | Nestor, Jr. et al. |
| 4,737,323 | A | 4/1988 | Martin et al. |
| 4,748,034 | A | 5/1988 | de Rham |
| 4,837,028 | A | 6/1989 | Allen |
| 4,897,355 | A | 1/1990 | Eppstein et al. |
| 5,019,369 | A | 5/1991 | Presant et al. |
| 5,075,109 | A | 12/1991 | Tice et al. |
| 5,087,616 | A | 2/1992 | Myers et al. |
| 5,171,678 | A | 12/1992 | Behr et al. |
| 5,239,660 | A | 8/1993 | Ooi |
| 5,334,761 | A | 8/1994 | Gebeyehu et al. |
| 5,434,261 | A | 7/1995 | Schoen et al. |
| 5,580,859 | A | 12/1996 | Felgner et al. |
| 5,591,737 | A | 1/1997 | Doherty et al. |
| 5,625,047 | A | 4/1997 | Been et al. |
| 5,629,304 | A | 5/1997 | Murakata et al. |
| 5,656,606 | A | 8/1997 | Nargund et al. |
| 5,672,596 | A | 9/1997 | Wyvratt et al. |
| 5,712,128 | A | 1/1998 | Been et al. |
| 5,744,335 | A | 4/1998 | Wolff et al. |
| 5,747,485 | A | 5/1998 | Doherty et al. |
| 5,755,903 | A | 5/1998 | Garant et al. |
| 5,766,903 | A | 6/1998 | Sarnow |
| 5,773,244 | A | 6/1998 | Ares, Jr. et al. |
| 5,885,613 | A | 3/1999 | Holland et al. |
| 5,948,902 | A | 9/1999 | Honkanen et al. |
| 5,972,964 | A | 10/1999 | Perregaard |
| 6,043,026 | A | 3/2000 | Patchett et al. |
| 6,066,626 | A | 5/2000 | Yew et al. |
| 6,210,931 | B1 | 4/2001 | Feldstein et al. |
| 6,211,174 | B1 | 4/2001 | Devita et al. |
| 6,319,494 | B1 | 11/2001 | Capon et al. |
| 6,368,802 | B1 | 4/2002 | Kool |
| 6,417,326 | B1 | 7/2002 | Cullis et al. |
| 6,576,628 | B1 | 6/2003 | Grams et al. |
| 6,620,597 | B1 | 9/2003 | Chen et al. |
| 6,986,902 | B1 | 1/2006 | Chen et al. |
| 7,709,226 | B2 | 5/2010 | Foote |
| 7,741,465 | B1 | 6/2010 | Eshhar et al. |
| 8,071,082 | B2 | 12/2011 | Zugates et al. |
| 8,158,601 | B2 | 4/2012 | Chen et al. |
| 8,492,359 | B2 | 7/2013 | Yaworski et al. |
| 8,609,089 | B2 | 12/2013 | Langermann et al. |
| 8,805,972 | B1 | 8/2014 | Merkulov et al. |
| 8,829,170 | B2 | 9/2014 | Dale et al. |
| 9,708,628 | B2 | 7/2017 | Tange et al. |
| 9,765,022 | B2 | 9/2017 | Xu et al. |
| 10,799,463 | B2 | 10/2020 | Benenato et al. |
| 11,203,767 | B2 | 12/2021 | Anderson et al. |
| 11,352,640 | B2 | 6/2022 | Anderson et al. |
| 11,352,641 | B2 | 6/2022 | Anderson et al. |
| 11,447,796 | B2 | 9/2022 | Anderson et al. |
| 11,603,396 | B2 | 3/2023 | Wesselhoeft et al. |
| 11,679,120 | B2 | 6/2023 | Horhota et al. |
| 2003/0022649 | A1 | 1/2003 | Voyer |
| 2004/0014194 | A1 | 1/2004 | Beyer et al. |
| 2004/0110709 | A1 | 6/2004 | Li et al. |
| 2004/0262223 | A1 | 12/2004 | Strook et al. |
| 2005/0222064 | A1 | 10/2005 | Vargeese et al. |
| 2006/0008910 | A1 | 1/2006 | MacLachlan et al. |
| 2006/0051405 | A1 | 3/2006 | MacLachlan et al. |
| 2006/0083780 | A1 | 4/2006 | Heyes et al. |
| 2006/0199851 | A1 | 9/2006 | Kempf et al. |
| 2009/0023673 | A1 | 1/2009 | Manoharan et al. |
| 2010/0028330 | A1 | 2/2010 | Collins et al. |
| 2010/0062967 | A1 | 3/2010 | Keil et al. |
| 2010/0130588 | A1 | 5/2010 | Yaworski et al. |
| 2010/0137407 | A1 | 6/2010 | Abe et al. |
| 2010/0305197 | A1 | 12/2010 | Che |
| 2010/0324120 | A1 | 12/2010 | Chen et al. |
| 2011/0019782 | A1 | 1/2011 | Kobayashi et al. |
| 2011/0076335 | A1 | 3/2011 | Yaworski et al. |
| 2011/0117125 | A1 | 5/2011 | Hope et al. |
| 2011/0256175 | A1 | 10/2011 | Hope et al. |
| 2011/0293703 | A1 | 12/2011 | Mahon et al. |
| 2012/0027796 | A1 | 2/2012 | Manoharan et al. |
| 2012/0058144 | A1 | 3/2012 | Manoharan et al. |
| 2012/0101148 | A1 | 4/2012 | Aking et al. |
| 2012/0114649 | A1 | 5/2012 | Langermann et al. |
| 2012/0128760 | A1 | 5/2012 | Manoharan et al. |
| 2012/0149894 | A1 | 6/2012 | Cameron et al. |
| 2012/0178702 | A1 | 7/2012 | Huang et al. |
| 2012/0202871 | A1 | 8/2012 | Heyes et al. |
| 2012/0276209 | A1 | 11/2012 | Cullis et al. |
| 2013/0065939 | A1 | 3/2013 | Judge et al. |
| 2013/0090372 | A1 | 4/2013 | Budzik et al. |
| 2013/0116307 | A1 | 5/2013 | Heyes et al. |
| 2013/0123338 | A1 | 5/2013 | Heyes et al. |
| 2013/0156845 | A1 | 6/2013 | Manoharan et al. |
| 2013/0164400 | A1 | 6/2013 | Knopov et al. |
| 2013/0178541 | A1 | 7/2013 | Stanton et al. |
| 2013/0195920 | A1 | 8/2013 | Maier et al. |
| 2013/0202684 | A1 | 8/2013 | Geall et al. |
| 2013/0274504 | A1 | 10/2013 | Colletti et al. |
| 2013/0274523 | A1 | 10/2013 | Bawiec, III et al. |
| 2013/0303587 | A1 | 11/2013 | Yaworski et al. |
| 2013/0323269 | A1 | 12/2013 | Manoharan et al. |
| 2013/0338210 | A1 | 12/2013 | Manoharan et al. |
| 2014/0039032 | A1 | 2/2014 | Kuboyama et al. |
| 2014/0141070 | A1 | 5/2014 | Geall et al. |
| 2014/0200257 | A1 | 7/2014 | Rajeev et al. |
| 2014/0255472 | A1 | 9/2014 | Geall et al. |
| 2014/0308304 | A1 | 10/2014 | Manoharan et al. |
| 2015/0057373 | A1 | 2/2015 | Stanton et al. |
| 2015/0064242 | A1 | 3/2015 | Heyes et al. |
| 2015/0079630 | A1 | 3/2015 | Abe et al. |
| 2015/0140070 | A1 | 5/2015 | Heartlein et al. |
| 2015/0141678 | A1 | 5/2015 | Payne et al. |
| 2015/0203446 | A1 | 7/2015 | Manoharan et al. |
| 2015/0239926 | A1 | 8/2015 | Payne et al. |
| 2015/0366997 | A1 | 12/2015 | Guild et al. |
| 2015/0376115 | A1 | 12/2015 | Ansell et al. |
| 2016/0083747 | A1 | 3/2016 | Kruse |
| 2016/0151284 | A1 | 6/2016 | Heyes et al. |
| 2016/0194368 | A1 | 7/2016 | Hoge et al. |
| 2016/0311759 | A1 | 10/2016 | Brito et al. |
| 2016/0317458 | A1 | 11/2016 | Brito et al. |
| 2016/0331828 | A1 | 11/2016 | Ciaramella et al. |
| 2016/0376224 | A1 | 12/2016 | Du et al. |
| 2017/0114010 | A1 | 4/2017 | Payne et al. |
| 2017/0119904 | A1 | 5/2017 | Ansell et al. |
| 2017/0190661 | A1 | 7/2017 | Payne et al. |
| 2017/0204422 | A1 | 7/2017 | Nelson et al. |
| 2017/0210697 | A1 | 7/2017 | Benenato et al. |
| 2018/0005363 | A1 | 1/2018 | Nagatomo et al. |
| 2018/0010175 | A1 | 1/2018 | Cheng |
| 2018/0028664 | A1 | 2/2018 | Besin et al. |
| 2018/0080041 | A1 | 3/2018 | Kruse |
| 2018/0153822 | A1 | 6/2018 | Karve et al. |
| 2018/0230225 | A1 | 8/2018 | Fan et al. |
| 2018/0311343 | A1 | 11/2018 | Huang et al. |
| 2018/0326045 | A1 | 11/2018 | Ciaramella et al. |
| 2019/0091164 | A1 | 3/2019 | Horhota et al. |
| 2019/0275170 | A1 | 9/2019 | Benenato et al. |
| 2019/0290694 | A1 | 9/2019 | Gautron et al. |
| 2019/0314284 | A1 | 10/2019 | Guild et al. |
| 2019/0314291 | A1 | 10/2019 | ModernaTX |
| 2019/0314524 | A1 | 10/2019 | Ansell et al. |
| 2019/0321489 | A1 | 10/2019 | Guild et al. |
| 2019/0328769 | A1 | 10/2019 | Uchida et al. |
| 2019/0345503 | A1 | 11/2019 | Chang et al. |
| 2019/0390181 | A1 | 12/2019 | Benenato et al. |
| 2020/0040370 | A1 | 2/2020 | Eber et al. |
| 2020/0080106 | A1 | 3/2020 | Anderson et al. |
| 2021/0085719 | A1 | 3/2021 | Jensen |
| 2021/0130799 | A1 | 5/2021 | Siksnys et al. |
| 2021/0371494 | A1 | 12/2021 | Wesselhoeft et al. |
| 2022/0106259 | A1 | 4/2022 | Benenato et al. |
| 2022/0323480 | A1 | 10/2022 | Goodman et al. |
| 2022/0362295 | A1 | 11/2022 | Kieffer-Kwon et al. |
| 2023/0050306 | A1 | 2/2023 | Anderson et al. |
| 2023/0058784 | A1 | 2/2023 | Goodman et al. |

(56) References Cited

U.S. PATENT DOCUMENTS

| | | | |
|---|---|---|---|
| 2023/0062665 A1 | 3/2023 | Goodman et al. |
| 2023/0226096 A1 | 7/2023 | Goodman et al. |
| 2024/0042015 A1 | 2/2024 | Wesselhoeft et al. |
| 2024/0052049 A1 | 2/2024 | Barnes et al. |
| 2024/0131049 A1 | 4/2024 | Goodman et al. |
| 2024/0245805 A1 | 7/2024 | Wesselhoeft et al. |

FOREIGN PATENT DOCUMENTS

| | | | |
|---|---|---|---|
| CN | 105176981 | A | 12/2015 |
| CN | 106801050 | A | 6/2017 |
| EP | 3630966 | A1 | 4/2020 |
| EP | 3819377 | A1 | 5/2021 |
| GB | 2308064 | A | 6/1997 |
| JP | 2016521133 | A | 7/2016 |
| JP | 2017043556 | A | 3/2017 |
| JP | 6284181 | B2 | 2/2018 |
| KR | 20110095439 | A | 8/2011 |
| WO | 1995011029 | A1 | 4/1995 |
| WO | 1995024207 | A1 | 9/1995 |
| WO | 1999055743 | A1 | 11/1999 |
| WO | 2005044201 | A2 | 5/2005 |
| WO | 2005079803 | A1 | 9/2005 |
| WO | 2005120152 | A2 | 12/2005 |
| WO | 2005121348 | A1 | 12/2005 |
| WO | 2006000830 | A2 | 1/2006 |
| WO | 2006007712 | A1 | 1/2006 |
| WO | 2006069782 | A2 | 7/2006 |
| WO | 2006121168 | A1 | 11/2006 |
| WO | 2006138380 | A2 | 12/2006 |
| WO | 2007044627 | A2 | 4/2007 |
| WO | 2008042973 | A2 | 4/2008 |
| WO | 2008103276 | A2 | 8/2008 |
| WO | 2009035541 | A1 | 3/2009 |
| WO | 2009086558 | A1 | 7/2009 |
| WO | 2009101611 | A1 | 8/2009 |
| WO | 2009114335 | A2 | 9/2009 |
| WO | 2009127060 | A1 | 10/2009 |
| WO | 2009132131 | A1 | 10/2009 |
| WO | 2010027827 | A2 | 3/2010 |
| WO | 2010042877 | A1 | 4/2010 |
| WO | 2010048536 | A2 | 4/2010 |
| WO | 2010053572 | A2 | 5/2010 |
| WO | 2010054384 | A1 | 5/2010 |
| WO | 2010054401 | A1 | 5/2010 |
| WO | 2010054405 | A1 | 5/2010 |
| WO | 2010054406 | A1 | 5/2010 |
| WO | 2010084371 | A1 | 7/2010 |
| WO | 2010088537 | A2 | 8/2010 |
| WO | 2010129709 | A1 | 11/2010 |
| WO | 2010138652 | A1 | 12/2010 |
| WO | 2010138659 | A1 | 12/2010 |
| WO | 2010138685 | A1 | 12/2010 |
| WO | 2010138695 | A1 | 12/2010 |
| WO | 2010138706 | A1 | 12/2010 |
| WO | 2010138758 | A1 | 12/2010 |
| WO | 2010144740 | A1 | 12/2010 |
| WO | 2011000106 | A1 | 1/2011 |
| WO | 2011000107 | A1 | 1/2011 |
| WO | 2011022460 | A1 | 2/2011 |
| WO | 2011038160 | A2 | 3/2011 |
| WO | 2011066342 | A2 | 6/2011 |
| WO | 2011066651 | A1 | 6/2011 |
| WO | 2011068810 | A1 | 6/2011 |
| WO | 2011071860 | A2 | 6/2011 |
| WO | 2011075656 | A1 | 6/2011 |
| WO | 2011090965 | A1 | 7/2011 |
| WO | 2011127255 | A1 | 10/2011 |
| WO | 2011141704 | A1 | 11/2011 |
| WO | 2011141705 | A1 | 11/2011 |
| WO | 2011153120 | A1 | 12/2011 |
| WO | 2012000104 | A1 | 1/2012 |
| WO | 2012016184 | A2 | 2/2012 |
| WO | 2012024526 | A2 | 2/2012 |
| WO | 2012031043 | A1 | 3/2012 |
| WO | 2012040184 | A2 | 3/2012 |
| WO | 2012044638 | A1 | 4/2012 |
| WO | 2012054365 | A2 | 4/2012 |
| WO | 2012099755 | A1 | 7/2012 |
| WO | 2012162210 | A1 | 11/2012 |
| WO | 2012170889 | A1 | 12/2012 |
| WO | 2012170930 | A1 | 12/2012 |
| WO | 2013006825 | A1 | 1/2013 |
| WO | 2013012476 | A2 | 1/2013 |
| WO | 2013016058 | A1 | 1/2013 |
| WO | 2013033563 | A1 | 3/2013 |
| WO | 2013049328 | A1 | 4/2013 |
| WO | 2013076509 | A1 | 5/2013 |
| WO | 2013086322 | A1 | 6/2013 |
| WO | 2013086354 | A1 | 6/2013 |
| WO | 2013086373 | A1 | 6/2013 |
| WO | 2013089151 | A1 | 6/2013 |
| WO | 2013093648 | A2 | 6/2013 |
| WO | 2013116126 | A1 | 8/2013 |
| WO | 2013118878 | A1 | 8/2013 |
| WO | 2013126803 | A1 | 8/2013 |
| WO | 2013148541 | A1 | 10/2013 |
| WO | 2013149140 | A1 | 10/2013 |
| WO | 2014136086 | A1 | 9/2014 |
| WO | 2014144871 | A1 | 9/2014 |
| WO | 2014186334 | A1 | 11/2014 |
| WO | 2014193857 | A1 | 12/2014 |
| WO | 2015034925 | A1 | 3/2015 |
| WO | 2015061467 | A1 | 4/2015 |
| WO | 2015074085 | A1 | 5/2015 |
| WO | 2015095340 | A1 | 6/2015 |
| WO | 2015095346 | A1 | 6/2015 |
| WO | 2015130584 | A2 | 9/2015 |
| WO | 2015199952 | A1 | 12/2015 |
| WO | 2016020373 | A1 | 2/2016 |
| WO | 2016081029 | | 5/2016 |
| WO | 2016197121 | A1 | 12/2016 |
| WO | 2017004143 | A1 | 1/2017 |
| WO | 2017046203 | A1 | 3/2017 |
| WO | 2017049245 | A2 | 3/2017 |
| WO | 2017055487 | A2 | 4/2017 |
| WO | 2017059357 | A1 | 4/2017 |
| WO | 2017075531 | A1 | 5/2017 |
| WO | 2017099823 | A1 | 6/2017 |
| WO | 2017112865 | A1 | 6/2017 |
| WO | 2017117528 | A1 | 7/2017 |
| WO | 2017118734 | A1 | 7/2017 |
| WO | 2017172698 | A1 | 10/2017 |
| WO | 2017173054 | A1 | 10/2017 |
| WO | 2017185054 | A1 | 10/2017 |
| WO | 2017201332 | A1 | 11/2017 |
| WO | 2017201333 | A1 | 11/2017 |
| WO | 2017201340 | A2 | 11/2017 |
| WO | 2017201342 | A1 | 11/2017 |
| WO | 2017201346 | A1 | 11/2017 |
| WO | 2017201348 | A1 | 11/2017 |
| WO | 2017201349 | A1 | 11/2017 |
| WO | 2017201350 | A1 | 11/2017 |
| WO | 2017222911 | A1 | 12/2017 |
| WO | 2018011633 | A1 | 1/2018 |
| WO | 2018078053 | A1 | 5/2018 |
| WO | 2018144775 | A1 | 8/2018 |
| WO | 2018157009 | A1 | 8/2018 |
| WO | 2018170260 | A1 | 9/2018 |
| WO | 2018170306 | A1 | 9/2018 |
| WO | 2018191722 | A1 | 10/2018 |
| WO | 2018222890 | A1 | 12/2018 |
| WO | 2018237372 | A1 | 12/2018 |
| WO | 2019067999 | A1 | 4/2019 |
| WO | 2019089818 | A1 | 5/2019 |
| WO | 2019089828 | A1 | 5/2019 |
| WO | 2019118919 | A1 | 6/2019 |
| WO | 2019131770 | A1 | 7/2019 |
| WO | 2019152557 | A1 | 8/2019 |
| WO | 2019152848 | A1 | 8/2019 |
| WO | 2019191780 | A1 | 10/2019 |
| WO | 2019213308 | A1 | 11/2019 |
| WO | 2019222275 | A2 | 11/2019 |
| WO | 2019236673 | A1 | 12/2019 |

(56) References Cited

FOREIGN PATENT DOCUMENTS

| | | | |
|---|---|---|---|
| WO | 2020010242 | A1 | 1/2020 |
| WO | 2020023595 | A1 | 1/2020 |
| WO | 2020035070 | A1 | 2/2020 |
| WO | 2020061367 | A1 | 3/2020 |
| WO | 2020061457 | A1 | 3/2020 |
| WO | 2020198403 | A2 | 10/2020 |
| WO | 2020219563 | A1 | 10/2020 |
| WO | 2020237227 | A1 | 11/2020 |
| WO | 2020252436 | A1 | 12/2020 |
| WO | 2021041541 | A1 | 3/2021 |
| WO | 2021055849 | A1 | 3/2021 |
| WO | 2021113777 | A2 | 6/2021 |
| WO | 2021189059 | A2 | 9/2021 |
| WO | 2021236855 | A1 | 11/2021 |
| WO | 2022261490 | A2 | 12/2022 |
| WO | 2023141586 | A1 | 7/2023 |

OTHER PUBLICATIONS

Kuball J et al. "Increasing functional avidity of TCR-redirected T cells by removing defined N-glycosylation sites in the TCR constant domain," J Exp Med, 2009, 206(2):463-475.
Lasic et al. "Gelation of liposome interior. A novel method for drug encapsulation," FEBS Lett, 1992, 312(2-3):255-8.
Lasic. "Novel applications of liposomes," Trends Biotechnol, 1998, 16(7):307-21.
Legnini et al., "Circ-ZNF609 Is a Circular RNA that Can Be Translated and Functions in Myogenesis," Mol Cell. 2017, 66(1):22-37.
Lehtimaki et al. "Regulatory T cells control immune responses through their non-redundant tissue specific features," Frontiers in Immunol., 2013, 4(294): 1-10.
Lenzi et al., "Gene Transfer Research: The Evolution of the Clinical Science," National Academies Press (US), 2014. Available from: https://www.ncbi.nlm.nih.gov/books/NBK195893/.
Li et al. "In vivo gene transfer via intravenous administration of cationic lipid-protamine-DNA (LPD) complexes," Gene Ther, 1997, 4(9):891-900.
Li et al. "The Biogenesis, Functions, and Challenges of Circular RNAs," Mol Cell., 2018, 71(3):428-442.
Li, J., et al., "Protein Trans-Splicing as a Means for Viral Vector-Mediated In Vivo Gene Therapy", Human Gene Therapy, 19(9):958-964 (2008).
Liang et al. "Short intronic repeat sequences facilitate circular RNA production," Genes & Development, 2014, 28:2233-2247.
Liang et al. "The Output of Protein-Coding Genes Shifts to Circular RNAs When the Pre-mRNA Processing Machinery Is Limiting," Molecular Cell, 2017, 68:940-954.
Litke et al. "Trans ligation of RNAs to generate hybrid circular RNAs using highly efficient autocatalytic transcripts," Methods, 2021, S1046-2023(21)00135-3.
Litke, J. L., et al. "Highly efficient expression of circular RNA aptamers in cells using autocatalytic transcripts", Nat. Biotech., 37(6):667-75, (2019).
Liu, Z., et al. "Systematic comparison of 2A peptides for cloning multi-genes in a polycistronic vector," Sci Rep, 2017, 7 (1):2193.
Maier et al. "Biodegradable Lipids Enabling Rapidly Eliminated Lipid Nanoparticles for Systemic Delivery of RNAi Therapeutics," Mol. Ther., 2013, 21(8):1570-78.
Mangraviti et al. "Polymeric nanoparticles for nonviral gene therapy extend brain tumor survival in vivo," ACS Nano, 2015, 9(2):1236-49.
Mao et al. "Biological roles and therapeutic potential of circular RNAs in osteoarthritis," Mol Ther Nucleic Acids, 2021, 24:856-867.
McPherson. "Crystallization of proteins from polyethylene glycol," J Biol Chem., 1976, 251(20):6300-3.
McPherson. "Current approaches to macromolecular crystallization," Eur J Biochem., 1990, 189(1):1-23.
Meganck et al. "Engineering highly efficient backsplicing and translation of synthetic circRNAs," Mol Ther Nucleic Acids, 2021, 23:821-834.
Memczak et al., "Circular RNAs and a large class of animal RNAs with regulatory potency," 2013, 495:333-338.
Merten et al. "Production of lentiviral vectors," Mol Ther, 2016, 3:16017.
Metzgar et al. "Abrupt emergence of diverse species B adenoviruses at US military recruit training centers," J Infect Dis. 2007, 196(10):1465-73.
Moldenhauer et al. "Identity of HML-1 antigen on intestinal intraepithelial T cells and of B-ly7 antigen on hairy cell leukaemia," Scand. J. Immunol., 1990, 32(2):77-82.
Morel et al. "Monoclonal antibodies to bovine serum albumin: Affinity and specificity determinations," Mol Immunol, 1988, 25(1):7-15.
Morrissey et al. "Potent and persistent in vivo anti-HBV activity of chemically modified siRNAs," Nat Biotechnol, 2005, 23(8):1002-7.
Mosser et al. "Use of a dicistronic expression cassette encoding the green fluorescent protein for the screening and selection of cells expressing inducible gene products," Biotechniques, 1997, 22(1):150-4, 156, 158-61.
Mu et al., "An origin of the immunogenicity of in vitro transcribed RNA," Nucleic Acids Res. 2018, 46(10): 5239-5249.
Müller, S., et al., "In vitro circularization of RNA", RNA Biology, 14(8):1018-27, (2017).
Nakamoto et al. "Chemical Synthesis of Circular RNAs with Phosphoramidate Linkages for Rolling-Circle Translation," Curr Protoc., 2021, 1(3):e43.
Nambiar et al. "Total synthesis and cloning of a gene coding for the ribonuclease S protein," Science, 1984, 223 (4642):1299-301.
Oberli et al. "Lipid Nanoparticle Assisted mRNA Delivery for Potent Cancer Immunotherapy," Nano Letters, 2017, 17:1326-1335.
Obi et al. "The design and synthesis of circular RNAs," Methods, 2021, S1046-2023(21)00065-7.
Ochi et al., "Non-enzymatic in vitro production of circular hammerhead ribozyme targeting the template region of human telomerase RNA," Nucleic Acids Symp Ser (Oxf). 2009, 53:275-276.
Onishi, M. et al. "Identification and characterization of a constitutively active STAT5 mutant that promotes cell proliferation," Mol. Cell. Biol., 1998, 18(7):3871-3879.
Pamudurti et al., "Translation of CircRNAs," Mol Cell. 2017, 66(1):9-21.
Pena, M., et al., "A Singular and Widespread Group of Mobile Genetic Elements: RNA Circles with Autocatalytic Ribozymes", Cells, 9(12):2555, (2020).
Petkovic et al. "RNA circularization strategies in vivo and in vitro," Nucleic Acids Res. 2015, 43(4):2454-65.
Porter et al. "Chimeric antigen receptor-modified T cells in chronic lymphoid leukemia," N Engl J Med, 2011, 365 (8):725-33.
Presolski et al. "Copper-Catalyzed Azide-Alkyne Click Chemistry for Bioconjugation," Curr Protoc Chem Biol, 2011, 3 (4):153-162.
Puttaraju and Been, "Circular Ribozymes Generated in Escherichia coli Using Group I Self-splicing Permuted Intron-Exon Sequences," J. Biol. Chem., 1996, 271(42):26081-87.
Puttaraju et al. "Group I Permuted Intron-exon (PIE) Sequences Self-splice to Produce Circular Exons," Nucleic Acids Research, 1992, 20(20):5357-5364.
Queen et al. "A humanized antibody that binds to the interleukin 2 receptor," PNAS, 1989, 86:10029-10033.
Rafiq et al. "Targeted delivery of a PD-1-blocking scFv by CAR-T cells enhances anti-tumor efficacy in vivo," Nat Biotechnol., 2018, 36(9):847-856.
Ramesh et al. "High-titer bicistronic retroviral vectors employing foot-and-mouth disease virus internal ribosome entry site," Nucleic Acids Res, 1996, 24(14):2697-700.
Rausch et al. "Characterizing and circumventing sequence restrictions for synthesis of circular RNA in vitro," Nucleic Acids Res., 2021, 49(6):e35.
Rees et al. "Bicistronic vector for the creation of stable mammalian cell lines that predisposes all antibiotic-resistant cells to express recombinant protein," Biotechniques, 1996, 20(1):102-4, 106, 108-10.

(56) References Cited

OTHER PUBLICATIONS

Riechmann et al. "Reshaping human antibodies for therapy," Nature, 1988, 332(6162):323-7.
Romberg, B., et al., "Sheddable Coatings for Long-Circulating Nanoparticles", Pharm. Res., 25(1):55-71, (2008).
Akinc et al. "A combinatorial library of lipid-like materials for delivery of RNAi therapeutics," Nature Biotechnology, 2008, 26:561-569.
Al-Lazikani et al. "Standard conformations for the canonical structures of immunoglobulins," J Mol Biol, 1997, 273 (4):927-48.
Badelt et al. "Computational Design of a Circular RNA with Prionlike Behavior," Artif Life., 2016, 22(2):172-84.
Bail et al. "Tri- to be mono- for bacterial mRNA decay," Structure, 2009, 17(3):317-9.
Barretina et al. "The Cancer Cell Line Encyclopedia enables predictive modelling of anticancer drug sensitivity," Nature, 2012, 483(7391):603-7.
Barrett et al. "Circular RNAs: analysis, expression and potential functions," Development, 2016, 1143(11):1838-47.
Barrett, D.M., et al., "Chimeric Antigen Receptor Therapy for Cancer", Annual Review of Medicine, 65 (1):333-347, Jan. 14, 2014.
Behr et al. "Efficient gene transfer into mammalian primary endocrine cells with lipopolyamine-coated DNA," PNAS 1989, 86(18):6982-6986.
Belliveau, N.M. et al. "Microfluidic Synthesis of Highly Potent Limit-size Lipid Nanoparticles for In Vivo Delivery of siRNA," Mol. Ther. Nucleic. Acids. 2012, 1(8):e37.
Berge et al. "Pharmaceutical salts," J. Pharmaceutical Sciences, 1977, 66(1):1-19.
Bloomfield. "Quasi-Elastic Light Scattering Applications in Biochemistry and Biology," Ann. Rev. Biophys. Bioeng., 1981, 10:421-50.
Bohjanen, et al., "A small circular TAR RNA decoy specifically inhibits Tat-activated HIV-1 transcription," , Nucleic Acids Res., 1996, 24(19):3733-8.
Bohjanen, et al., "TAR RNA decoys inhibit Tat-activated HIV-1 transcription after preinitiation complex formation", Nucleic Acids Res., 1997, 25(22): 4481-6.
Borchardt et al. "Inducing circular RNA formation using the CRISPR endoribonuclease Csy4," RNA, 2017, 23 (5):619-627.
Branch et al. "Unusual properties of two branched RNA's with circular and linear components," Nucleic Acids Res., 1985, 13(13):4889-903.
Bricogne. "[23] Bayesian statistical viewpoint on structure determination: Basic concepts and examples," Methods Enzymol, 1997, 276:361-423.
Bricogne. "Direct phase determination by entropy maximization and likelihood ranking: status report and perspectives," Acta Crystallogr D Biol Crystallogr, 1993, 49(Pt 1):37-60.
Brown et al. "Biophotonic cytotoxicity assay for high-throughput screening of cytolytic killing," J Immunol Methods, 2005, 297(1-2):39-52.
Budker et al. "Protein/Amphipathic Polyamine Complexes Enable Highly Efficient Transfection with Minimal Toxicity," BioTechniques, 1997, 23:139-147.
Cao et al. "Development and application of a multiplexable flow cytometry-based assay to quantify cell-mediated cytolysis," Cytometry A, 2010, 77(6):534-45.
Caplen et al. "In vitro liposome-mediated DNA transfection of epithelial cell lines using the cationic liposome DC-Chol/DOPE," Gene Ther, 1995, 2(9):603-13.
Carmona, Ellese Marie. 2019. Circular RNA: Design Criteria for Optimal Therapeutical Utility. Doctoral dissertation, Harvard University, Graduate School of Arts & Sciences.
Cech, "Self-Splicing of Group 1 Introns," Annu Rev Biochem., 1990, 59:543-68.
Chayen. "The role of oil in macromolecular crystallization," Structure, 1997, 5(10):1269-74.
Chen and Sarnow, "Initiation of protein synthesis by the eukaryotic translational apparatus on circular RNAs," Science. 1995, 268(5209):415-417.
Chen et al. "Promising diagnostic and therapeutic circRNAs for skeletal and chondral disorders," Int J Biol Sci., 2021, 17(5):1428-1439.
Chen et al. "Sensing Self and Foreign Circular RNAs by Intron Identify," Molecular Cell, 2017, 67:228-238.
Chen, D. et al. "Rapid discovery of potent siRNA-containing lipid nanoparticles enabled by controlled microfluidic formulation," J. Am. Chem. Soc., 2012, 134(16):6948-51.
Cheung et al. "Epitope-specific antibody response to the surface antigen of duck hepatitis B virus in infected ducks," Virology, 1990, 176(2):546-52.
Chothia et al. "Canonical structures for the hypervariable regions of immunoglobulins," J Mol Biol, 1987, 196(4):901-17.
Chothia et al. "Structural repertoire of the human VH segments," J Mol Biol, 1992, 227(3):799-817.
Costello et al. "Reinventing the Wheel: Synthetic Circular RNAs for Mammalian Cell Engineering." Trends Biotechnol., 2020, 38(2):217-230.
Dahlman et al., "Barcoded nanoparticles for high throughput in vivo discovery of targeted therapeutics," Proc Natl Acad Sci U S A. 2017, 114(8):2060-2065.
Devaux et al., "Circular RNAs in heart failure", Eur J Heart Fail. 2017, 19(6):701-709.
Dhamne et al., "Peripheral and thymic Foxp3+ regulatory T cells in search of origin, distinction, and function," Frontiers in Immunol., 2013, 4 (253): 1-11.
Dobrikova et al. "Activity of a type 1 picornavirus internal ribosomal entry site is determined by sequences within the 3? nontranslated region," PNAS, 2003, 100(25):15125-15130.
Dong et al. "Lipopeptide nanoparticles for potent and selective siRNA delivery in rodents and nonhuman primates," PNAS, 2014, 111(11):3955-3960.
Donnelly et al. "The 'cleavage' activities of foot-and-mouth disease virus 2A site-directed mutants and naturally occurring '2A-like' sequences." J Gen Virol., 2001, 82(5):1027-1041.
Duan, D., "Systemic AAV Micro-dystrophin Gene Therapy for Duchenne Muscular Dystrophy", Molecular Therapy, 26(10):2337-2356, Oct. 1, 2018.
Durymanov and Reineke, "Non-viral Delivery of Nucleic Acids: Insight Into Mechanisms of Overcoming Intracellular Barriers," Front Pharmacol. 2018, 9:971.
Eastwood et al. "Monoclonal antibody TGN1412 trial failure explained by species differences in CD28 expression on CD4+ effector memory T-cells," Br J Clin Pharmacol, 2010, 161(3):512-526.
Eastwood et al. "Severity of the TGN1412 trial disaster cytokine storm correlated with IL-2 release," Br J Clin Pharmacol, 2013, 76(2): 299-315.
Edge et al. "Total synthesis of a human leukocyte interferon gene," Nature, 1981, 292(5825):756-62.
Eshhar et al., Cancer Immunol Immunotherapy (1997) 45: 131-136.
Eshhar, Z., "Tumor-specific T-bodies: towards clinical application", Cancer Immunol Immunotherapy, 45:131-136, (1997).
Examination Report issued in EP19739422.4 dated Mar. 17, 2022. 6 pages.
Felgner et al. "Lipofection: A highly efficient, lipid-mediated DNA-transfection procedure," PNAS, 1987, 84:7413-7417.
Fenton et al., "Customizable Lipid Nanoparticle Materials for the Delivery of siRNAs and mRNAs," Angew Chem Int Ed Engl. 2018, 57(41):13582-86.
Finney et al. "Chimeric receptors providing both primary and costimulatory signaling in T cells from a single gene product," J Immunol, 1998, 161(6):2791-7.
Ford et al. "Synthesis of circular RNA in bacteria and yeast using RNA cyclase ribozymes derived from a group I intron of phage T4," PNAS, 1994, 91:3117-3121.
Fortunato, F., et al., "The DMD gene and therapeutic approaches to restore dystrophin", Neuromuscular Disorders, 31 (10):1013-1020, Oct. 1, 2021.

(56) References Cited

OTHER PUBLICATIONS

Foster et al. "Purification of mRNA Encoding Chimeric Antigen Receptor Is Critical for Generation of a Robust T-Cell Response," Hum Gene Ther, 2019, 30(2):168-178.
Gao et al. "A novel cationic liposome reagent for efficient transfection of mammalian cells," Biochem Biophys Res Commun, 1991, 179(1):280-5.
Gao, Q., et al., "The Dystrophin Complex: structure, function and implications for therapy", Compr Physiol., 5 (3): 1223-1239, Jul. 1, 2015.
Garlapati et al. "Identification of a novel internal ribosome entry site in giardiavirus that extends to both sides of the initiation codon," J Biol Chem, 2004, 279(5):3389-97.
Giegé et al. "Crystallogenesis of biological macromolecules: facts and perspectives," Acta Crystallogr D Biol Crystallogr, 1994, 50(Pt 4):339-50.
Greene et al., "Circular RNAs: Biogenesis, Function and Role in Human Diseases," Front Mol Biosci. 2017, 4:38.
Gross et al. "Therapeutic Potential of T Cell Chimeric Antigen Receptors (CARs) in Cancer Treatment: Counteracting Off-Tumor Toxicities for Safe Car T Cell Therapy," Annu Rev Pharmacol Toxicol, 2016, 56:59-83.
Gurtu et al. "IRES bicistronic expression vectors for efficient creation of stable mammalian cell lines," Biochem Biophys Res Commun, 1996, 229(1):295-8.
Han et al. "Multi-antigen-targeted chimeric antigen receptor T cells for cancer therapy," J Hematol Oncol., 2019, 12 (1):128.
Harrer et al. "RNA-transfection of gamma/delta T cells with a chimeric antigen receptor or an alpha/beta T-cell receptor: a safer alternative to genetically engineered alpha/beta T cells for the immunotherapy of melanoma," BMC Cancer, 2017, 17:551, 17 pages.
He et al. "Circular RNAs and cancer", Cancer Lett . 2017, 396:138-144.
Heyes et al. "Cationic lipid saturation influences intracellular delivery of; encapsulated nucleic acids," Journal of Controlled Release, 2005, 107:276-287.
Hoekstra, D., et al., "Characterization and transfection properties of lipoplexes stabilized with novel exchangeable polyethylene glycol-lipid conjugates", Biochimica et Biophysica, 1660:41-52, (2004).
Holdt et al. "Circular RNAs as Therapeutic Agents and Targets," Front Physiol., 2018, 9:1262.
International Preliminary Report on Patentability and Written Opinion for International Application No. PCT/US2019/035531, mailed Dec. 8, 2020, 8 pages.
International Preliminary Report on Patentability for International Application No. PCT/US2020/034418, mailed Nov. 16, 2021, 8 pages.
International Search Report and Written Opinion for International Application No. PCT/US2019/035531, mailed Sep. 27, 2019, 13 pages.
International Search Report and Written Opinion for International Application No. PCT/US2020/034418, mailed Sep. 28, 2020, 15 pages.
International Search Report and Written Opinion for International Application No. PCT/US2020/063494, mailed Aug. 6, 2021, 24 pages.
International Search Report and Written Opinion for International Application No. PCT/US2021/023540, mailed Oct. 11, 2021, 30 pages.
International Search Report and Written Opinion for International Application No. PCT/US2021/031629, mailed Feb. 4, 2022, 24 pages.
International Search Report and Written Opinion for International Appliction No. PCT/US2021/033276, mailed Oct. 18, 2021, 34 pages.
International Search Report and Written Opinion for International Patent Application No. PCT/US2023/061018, mailed Jun. 5, 2023.
International Search Report and Written Opinion for International Patent Application No. PCT/US2023/068812, mailed Oct. 20, 2023.
Jang et al. "Initiation of Protein Synthesis by Internal Entry of Ribosomes into the 5' Nontranslated Region of Encephalomyocarditis Virus RNA in Vivo," J. Virol., 1989, 63(4):1651-1660.
Jay. "A general procedure for the end labeling of proteins and positioning of amino acids in the sequence," J Biol Chem, 1984, 259(24):15572-8.
Jayaraman et al. "Maximizing the potency of siRNA lipid nanoparticles for hepatic gene silencing in vivo," Angew. Chem. Int. Ed., 2012, 51(34):8529-8533.
Jayaraman et al. "Polymerase chain reaction-mediated gene synthesis: synthesis of a gene coding for isozyme c of horseradish peroxidase," PNAS, 1991, 88(10):4084-8.
Jeck et al. "Detecting and characterizing circular RNAs," Nat Biotechnol., 2014, 32(5):453-61.
Jemielity et al. "Synthetic mRNA cap analogs with a modified triphosphate bridge - synthesis, applications and prospects," New Journal of Chemistry, 2010, 34:829-844.
Josefowicz, S. Z et al. "Extrathymically generated regulatory T cells control mucosal TH2 inflammation," Nature, 2012, 482(7385):395-9.
Kabat et al. "Attempts to locate complementarity-determining residues in the variable positions of light and heavy chains," Annals of the New York Academy of Sciences, 1971, 190(1):382-393.
Kaczmarek et al. "Advances in the Delivery of RNA Therapeutics: from Concept to Clinical Reality," Genome Medicine, 2017, 9(1):60.
Kalos et al. "T Cells with Chimeric Antigen Receptors Have Potent Antitumor Effects and Can Establish Memory in Patients with Advanced Leukemia," Sci Transl Med, 2011, 3:95.
Kao and Puck, "Genetics of somatic mammalian cells, VII. Induction and isolation of nutritional mutants in Chinese hamster cells," Proc. Natl. Acad Sci USA, 1968; 60(4):1275-81.
Kariko et al., "Generating the optimal mRNA for therapy: HPLC purification eliminates immune activation and improves translation of nucleoside-modified, protein-encoding mRNA," Nucleic Acids Res. 2011, 39(21):e142.
Kariko et al., "Incorporation of Pseudouridine Into mRNA Yields Superior Nonimmunogenic Vector With Increased Translational Capacity and Biological Stability," Mol Ther. 2008, 16(11):1833-40.
Kauffman et al. "Optimization of Lipid Nanoparticle Formulations for mRNA Delivery in Vivo with Fractional Factorial and Definitive Screening Designs," Nano Lett, 2015, 15(11):7300-6.
Kauffman et al., "Efficacy and Immunogenicity of Unmodified and Pseudouridine-Modified mRNA Delivered Systemically with Lipid Nanoparticles in Vivo," Biomaterials, 2016, 109:78-87.
Kauffman et al., "Rapid, Single-cell Analysis and Discovery of Vectored mRNA Transfection in Vivo wth a loxP-Flanked tdTomato Reporter Mouse," Molecular Therapy: Nucleic Acids, 2018, 10:55-63.
Kauffman, "Optimization and analysis of lipid nanoparticles for in vivo mRNA delivery," Ph.D. Thesis, Massachusetts Institute of Technology, Department of Chemical Engineering, 2017, 167 pages.
Kaufman et al. "Improved vectors for stable expression of foreign genes in mammalian cells by use of the untranslated leader sequence from EMC virus," Nucleic Acids Res, 1991, 19(16): 4485-90.
Kirkland et al. "Analysis of the fine specificity and cross-reactivity of monoclonal anti-lipid A antibodies," J Immunol, 1986, 137(11):3614-9.
Klibanov et al. "Amphipathic polyethyleneglycols effectively prolong the circulation time of liposomes," FEBS Lett., 1990, 268(1):235-7.
Kobayashi et al. "Improved dicistronic mRNA expression vectors for efficient selection of transfectants highly expressing foreign genes," Biotechniques, 1996, 21(3):398-402.
Koltover, et al. Science (1998) 281: 78-81.
Koltover, I., et al., "An Inverted Hexagonal Phase of Catonic Liposome-DNA Complexes Related to DNA Release and Delivery", Science, 281:78-81, (1998).
Koos et al. "Influence of structure on antimicrobial activity of some heterocycles. IV. 1-(3-alkylamino-2-hydroxypropyl)-2-methyl-5-nitroimidazoles," Chem Papers. 1994, 48(1):54-57.
Kotterman and Schaffer. "Engineering adeno-associated viruses for clinical gene therapy," Nat Rev Genet. 2014, 15 (7):445-51.

(56) References Cited

OTHER PUBLICATIONS

Yang et al. "Circular RNAs: Expression, localization, and therapeutic potentials," Mol Ther, 2021, 29(5):1683-1702.
Yang et al., "Decay Rates of Human mRNAs: Correlation with Functional Characteristics and Sequence Attributes," Genome Res. 2003, 13(8):1863-72.
Yeku et al. "Armored CAR T-cells: utilizing cytokines and proinflammatory ligands to enhance CAR T-cell anti-tumour efficacy," Biochem Soc Trans, 2016, 44(2):412-8.
Zeng et al., "A Circular RNA Binds to and Activates AKT Phosphorylation and Nuclear Localization Reducing Apoptosis and Enhancing Cardia Repair," Theranostics, 2017, 7(16):3842-3855.
Zhang et al. "A novel protein encoded by the circular form of the SHPRH gene suppresses glioma tumorigenesis," Oncogene, 2018, 37(13):1805-1814.
Zhigaltsev, I.V et al. "Bottom-up design and synthesis of limit size lipid nanoparticle systems with aqueous and triglyceride cores using millisecond microfluidic mixing," Langmuir, 2012, 28(7):3633-40.
Rosenberg et al., "Adoptive cell transfer: a clinical path to effective cancer immunotherapy," Nat Rev Cancer, 2008, 8 (4): 299-308.
Roversi et al. "Modelling prior distributions of atoms for macromolecular refinement and completion," Acta Crystallogr D Biol Crystallogr, 2000, 56(Pt 10):1316-23.
Sahin et al., "mRNA-based therapeutics—developing a new class of drugs," Nat Rev Drug Discov. 2014, 13(10):759-80.
Sasso, J.M., et al., "The Progress and Promise of RNA Medicine-An Arsenal of Targeted Treatments", Journal of Medicinal Chemistry, 65(10):6975-7015, May 26, 2022.
Semple et al. "Rational design of cationic lipids for siRNA delivery," Nat Biotechnol, 2010, 28(2):172-6.
Shim et al., "Nonviral Delivery Systems for Cancer Gene Therapy: Strategies and Challenges," Curr Gene Ther. 2018, 18(1):3-20.
Shobaki et al. "Mixing lipids to manipulate the ionization status of lipid nanoparticles for specific tissue targeting," Int J Nanomedicine, 2018, 13:8395-8410.
Song et al. "CD27 costimulation augments the survival and antitumor activity of redirected human T cells in vivo," Blood, 2012, 119(3):696-706.
Stahli et al. "Distinction of epitopes by monoclonal antibodies," Methods Enzymol, 1983, 92:242-53.
Starke et al. "Exon Circularization Requires Canonical Splice Signals," Cell Reports, 2015, 10:103-111.
STN Registry Database Entry for 1333432-38-4 entered STN Sep. 27, 2011.
STN Registry Database Entry for 1333626-46-2 entered STN Sep. 28, 2011.
STN Registry Database Entry for 156811-31-3 entered STN Aug. 5, 1994.
STN Registry Database Entry for 157493-54-4 entered STN Sep. 7, 1994.
STN Registry Database Entry for 1609534-48-6 entered STN Jun. 4, 2014.
STN Registry Database Entry for 2086785-24-0 entered STN Mar. 17, 2017.
STN Registry Database Entry for 2086785-25-1 entered STN Mar. 17, 2017.
STN Registry Database Entry for 2086785-26-2 entered STN Mar. 17, 2017.
STN Registry Database Entry for 2086785-27-3 entered STN Mar. 17, 2017.
STN Registry Database Entry for 2086785-32-0 entered STN Mar. 17, 2017.
STN Registry Database Entry for 2086785-33-1 entered STN Mar. 17, 2017.
STN Registry Database Entry for 2089251-16-9 entered STN Apr. 10, 2017.
STN Registry Database Entry for 79111-60-7 entered STN Nov. 16, 1984.
Stroock et al. "Chaotic Mixer for Microchannels," Science 2002, 295(5555):647-51.
Structures of lipids from Benenato et al., Ciaramella et al., Huang et al., and Benenato et al. (28 pages).
Sullenger et al. "From the RNA world to the clinic," Science, 2016, 352(6292):1417-1420.
Szoka et al. "Comparative properties and methods of preparation of lipid vesicles (liposomes)," Annu Rev Biophys Bioeng, 1980, 9:467-508.
Taewoong, C., et al., "Chimeric antigen receptor (CAR) T-cell therapy for multiple myeloma", Pharmacology & Therapeutics, 232:1-9, Apr. 1, 2022.
Tramontano et al. "Framework residue 71 is a major determinant of the position and conformation of the second hypervariable region in the VH domains of immunoglobulins," J Mol Biol, 1990, 215(1):175-82.
Umekage et al. "In vivo circular RNA production using a constitutive promoter for high-level expression," J Biosci Bioeng, 2009, 108(4):354-6.
Umekage et al., "In Vivo Circular RNA Expression by the Permuted Intron-Exon Method," InTech, 2012, 17 pages.
Valdmanis and Kay, "The Expanding Repertoire of Circular RNAs," Mol Ther. 2013, 21(6):1112-4.
Van Esch et al. "Aggregation behavior and copper-binding properties of surfactants containing imidazole and pyrazole ligands," Recl Trav Chim Pays-Bas. 1994, 113(4):186-193.
Verhoeyen et al. "Reshaping human antibodies: grafting an antilysozyme activity," Science, 1988, 239(4847):1534-6.
Vessillier et al. "Cytokine release assays for the prediction of therapeutic mAb safety in first-in man trials—Whole blood cytokine release assays are poorly predictive for TGN1412 cytokine storm," J Immunol Methods, 2015, 424:43-52.
Wadhwa et al. "Receptor mediated glycotargeting," J Drug Target, 1995, 3(2):111-27.
Wang and Ruffner. "Oligoribonucleotide circularization by 'template-mediated' ligation with T4 RNA ligase: synthesis of circular hammerhead ribozymes," Nucleic Acids Research, 1998, 26(10):2502-2504.
Wang and Wang, "Efficient backsplicing produces translatable circular mRNAs," RNA, 2015, 21(2):172-179.
Wang et al. "Combinatorially designed lipid-like nanoparticles for intracellular delivery of cytotoxic protein for cancer therapy," Angew Chem Int Ed Engl. 2014, 53(11):2893-2898.
Wang et al., "A combinatorial library of unsaturated lipidoids for efficient intracellular gene delivery," ACS Synthetic Biology, 1, 403-07 (2012).
Wender, et al., "The design of guanidinium-rich transporters and their internalization mechanisms," Adv. Drug Del. Rev., 2008, 60(4-5): 452-472.
Wesselhoeft et al. "Engineering Circular RNA for Potent and Stable Translation in Eukaryotic Cells," Nature Communications, 2018, 9(1):2629, 10 pages.
Wesselhoeft et al. "RNA Circulation Diminishes Immunogenicity and can Extend Translation Duration In Vivo," Molecular Cell, 2019, 74(3):508-520.
Wesselhoeft, A. R., et al., "Engineering circular RNA for potent and stable translation in eukaryotic cells", Nature Communications, 9(1):1-10, Dec. 1, 2018.
Wesselhoeft, A. R., et al., "RNA Circularization Diminishes Immunogenicity and Can Extend Translation Duration In Vivo", Molecular Cell, 74(3):508-520, May 2, 2019.
Whitesides. "The origins and the future of microfluidics," Nature, 2006, 442(7101): 368-373.
Wiesinger et al. "Clinical-Scale Production of CAR-T Cells for the Treatment of Melanoma Patients by mRNA Transfection of a CSPG4-Specific CAR under Full GMP Compliance," Cancers (Basel), 2019, 11(8):1198.
Wilen et al., "Strategies in optical resolutions," Tetrahedron, 1977, 33(21):2725-36.
Xin, Y., et al., "Developing a Novel Anti-BCMA CAR-T for Relapsed or Refractory Multiple Myeloma", Blood, American Society of Hematology, 134:50, Nov. 13, 2019.
Xue et al. "Lipid-based nanocarriers for RNA delivery," Curr Pharm Des, 2015, 21(22):3140-7.

SEQUENCE LISTING

```
Sequence total quantity: 336
SEQ ID NO: 1           moltype = DNA  length = 585
FEATURE                Location/Qualifiers
source                 1..585
                       mol_type = genomic DNA
                       organism = Encephalomyocarditis virus
SEQUENCE: 1
ccccctctc cctccccccc taacgttact ggccgaagcc gcttggaata aggccggtgt  60
gcgtttgtct atatgttatt ttccaccata ttgccgtctt ttggcaatgt gagggcccgg  120
aaacctggcc ctgtcttctt gacgagcatt cctaggggtc tttcccctct cgccaaagga  180
atgcaaggtc tgttgaatgt cgtgaaggaa gcagttcctc tggaagcttc ttgaagacaa  240
acaacgtctg tagcgaccct ttgcaggcag cggaaccccc cacctggcga caggtgcctc  300
tgcggccaaa agccacgtgt ataagataca cctgcaaagg cggcacaacc ccagtgccac  360
```

-continued

```
gttgtgagtt ggatagttgt ggaaagagtc aaatggctct cctcaagcgt attcaacaag  420
gggctgaagg atgcccagaa ggtaccccat tgtatgggat ctgatctggg gcctcggtgc  480
acatgcttta catgtgttta gtcgaggtta aaaaacgtct aggccccccg aaccacgggg  540
acgtggtttt cctttgaaaa acacgatgat aatatggcca caacc                  585

SEQ ID NO: 2            moltype = DNA  length = 568
FEATURE                 Location/Qualifiers
source                  1..568
                        mol_type = genomic DNA
                        organism = Encephalomyocarditis virus
SEQUENCE: 2
ctccccctcc ccccccttac tatactggcc gaagccactt ggaataaggc cggtgtgcgt  60
ttgtctacat gctattttct accgcattac cgtcttatgg taatgtgagg gtccagaacc  120
tgaccctgtc ttcttgacga acactcctag ggtctttcc cctctcgaca aaggagtgta  180
aggtctgttg aatgtcgtga aggaagcagt tcctctggaa gcttcttaaa gacaaacaac  240
gtctgtagcg accctttgca ggcagcggaa ccccccacct ggtgacaggt gcctctgcgg  300
ccaaaagcca cgtgtataag atacacctgc aaaggcggca caaccccagt gccacgttgt  360
gagttggata gttgtggaaa gagtcaaatg gctctcctca agcgtattca acaaggggct  420
gaaggatgcc cagaaggtac cccattgtat gggatctgat ctggggcctc ggtgcacgtg  480
ctttacacgt gttgagtcga ggtgaaaaaa cgtctaggcc ccccgaacca cggggacgtg  540
gttttccttt gaaaaccacg attacaat                                    568

SEQ ID NO: 3            moltype = DNA  length = 696
FEATURE                 Location/Qualifiers
source                  1..696
                        mol_type = genomic DNA
                        organism = Encephalomyocarditis virus
SEQUENCE: 3
ttgccagtct gctcgatatc gcaggctggg tccgtgacta cccactcccc ctttcaacgt  60
gaaggctacg atagtgccag ggcgggtact gccgtaagtg ccaccccaaa caacaacaac  120
aaaacaaact ccccctcccc ccccttacta tactggccga agccacttgg aataaggccg  180
gtgtgcgttt gtctacatgc tattttctac cgcattaccg tcttatggta atgtgagggt  240
ccagaacctg accctgtctt cttgacgaac actcctaggg gtctttcccc tctcgacaaa  300
ggagtgtaag gtctgttgaa tgtcgtgaag gaagcagttc ctctggaagc ttcttaaaga  360
caaacaacgt ctgtagcgac cctttgcagg cagcggaacc ccccacctgg tgacaggtgc  420
ctctgcggcc aaaagccacg tgtataagat acacctgcaa aggcggcaca accccagtgc  480
cacgttgtga gttggatagt tgtggaaaga gtcaaatggc tctcctcaag cgtattcaac  540
aaggggctga aggatgccca gaaggtaccc cattgtatgg gatctgatct ggggcctcgg  600
tgcacgtgct ttacacgtgt tgagtcgagg tgaaaaaacg tctaggcccc ccgaaccacg  660
gggacgtggt tttcctttga aaaccacgat tacaat                           696

SEQ ID NO: 4            moltype = DNA  length = 697
FEATURE                 Location/Qualifiers
source                  1..697
                        mol_type = genomic DNA
                        organism = Encephalomyocarditis virus
SEQUENCE: 4
ttgccagtct gctcgatatc gcaggctggg tccgtgacta cccactcccc ctttcaacgt  60
gaaggctacg atagtgccag ggcgggtact gccgtaagtg ccaccccaaa acaacaacaa  120
cccccccctct ccctcctccc cccctaacgt tactggccga agccgcttgg aataaggccg  180
gtgtgcgttt gtctatatgt tattttccac catattgccg tcttttggca atgtgagggc  240
ccggaaacct ggccctgtct tcttgacgag cattcctagg ggtctttccc ctctcgccaa  300
aggaatgcaa ggtctgttga atgtcgtgaa ggaagcagtt cctctggaag cttcttgaag  360
acaaacaacg tctgtagcga ccctttgcag gcagcggaac cccccacctg gcgacaggtg  420
cctctgcggc caaaagccac gtgtataaga tacacctgca aaggcggcac aaccccagtg  480
ccacgttgtg agttggatag ttgtggaaag agtcaaatgg ctctcctcaa gcgtattcaa  540
caaggggctg aaggatgccc agaaggtacc ccattgtatg ggatctgatc tggggcctcg  600
gtgcacatgc tttacatgtg tttagtcgag gttaaaaaac gtctaggccc cccgaaccac  660
ggggacgtgg ttttcctttg aaaaacacga tgataat                          697

SEQ ID NO: 5            moltype = DNA  length = 562
FEATURE                 Location/Qualifiers
source                  1..562
                        mol_type = genomic DNA
                        organism = Encephalomyocarditis virus
SEQUENCE: 5
ccccccccct aacgttactg gccgaagccg cttggaataa ggccggtgtg cgtttgtcta  60
tatgttattt tccaccatat tgccgtcttt tggcaatgtg agggcccgga aacctggccc  120
tgtcttcttg acgagcattc ctaggggtct ttcccctctc gccaaaggaa tgcaaggtct  180
gttgaatgtc gtgaaggaag cagttcctct ggaagcttct tgaagacaaa caacgtctgt  240
agcgaccctt tgcaggcagc ggaacccccc acctggcgac aggtgcctct gcggccaaaa  300
gccacgtgta taagatacac ctgcaaaggc ggcacaaccc cagtgccacg ttgtgagttg  360
gatagttgtg gaaagagtca aatggctctc ctcaagcgta ttcaacaagg ggctgaagga  420
tgcccagaag gtaccccatt gtatgggatc tgatctgggg cctcggtgca catgctttac  480
atgtgtttag tcgaggttaa aaaacgtcta ggccccccga accacgggga cgtggttttc  540
ctttgaaaaa cacgatgata at                                          562

SEQ ID NO: 6            moltype = DNA  length = 156
FEATURE                 Location/Qualifiers
```

```
source                  1..156
                        mol_type = genomic DNA
                        organism = Picobirnavirus sp.
SEQUENCE: 6
gtaaattaaa tgctatttac aaaatttaaa cagaaaggag agatgttatg aaccggtttt  60
acaaggtttc atacatcgaa aatagcacta cctggggcag ccgacacact aacatcgtct  120
gtttaaccag aagtgttact gaaaggaggt tattta                            156

SEQ ID NO: 7            moltype = DNA  length = 340
FEATURE                 Location/Qualifiers
source                  1..340
                        mol_type = genomic DNA
                        organism = Hepatitis C virus
SEQUENCE: 7
acctgcccct aataggggcg acactccgcc atgaatcact cccctgtgag gaactactgt  60
cttcacgcag aaagcgtcta gccatggcgt tagtatgagt gtcgtacagc ctccaggccc  120
ccccctcccg ggagagccat agtggtctgc ggaaccggtg agtacaccgg aattgccggg  180
aagactgggt cctttcttgg ataaacccac tctatgcccg gacatttggg cgtgcccccg  240
caagactgct agccgagtag cgttgggttg cgaaaggcct tgtggtactg cctgataggg  300
tgcttgcgag tgccccggga ggtctcgtag accgtgcatc                        340

SEQ ID NO: 8            moltype = DNA  length = 315
FEATURE                 Location/Qualifiers
source                  1..315
                        mol_type = genomic DNA
                        organism = Human cosavirus
SEQUENCE: 8
ctacaagctt tgtgtaaaca aactttttgtt tggctttttct caagcttctc tcacatcagg  60
ccccaaagat gtcctgaagg taccccgtgt atctgaggat gagcaccatc gactacccgg  120
acctgcaaaa ttttgcaaac gcatgtggta tcccagcccc ctcctctcgg ggagggggct  180
ttgctcactc agcacaggat ctgatcagga gatccacctc cggtgcttta caccggggcg  240
tggatttaaa aattgcccaa ggcctggcgc acaacctagg ggactaggtt ttccttatat  300
tttaaagctg tcaat                                                   315

SEQ ID NO: 9            moltype = DNA  length = 182
FEATURE                 Location/Qualifiers
source                  1..182
                        mol_type = genomic DNA
                        organism = Human cosavirus
SEQUENCE: 9
gtcttaggac gacgcatgtg gtatcccagc ccccgcctac attggcgggg gcttttgaag  60
caccagacac tggatctgat caggaggagg gtagctgctt tacagcccct cttaaaaatt  120
gcccaaggtc cggccaccca acctagggga ctaggtttc ctttttatttt taaattgtca  180
tt                                                                 182

SEQ ID NO: 10           moltype = DNA  length = 759
FEATURE                 Location/Qualifiers
source                  1..759
                        mol_type = genomic DNA
                        organism = Human cosavirus
SEQUENCE: 10
acatggggga gactgcatgt ggcagtcttg aaacgtgtgg tttgacgtct accttatatg  60
gcagtgggtg gagtactgca aagatgtcac cgtgctttac acggtttttg aaccccacac  120
cggctgtttg acgctcgtag ggcagcaggt ttattttcat taaaattctt actttctagc  180
tgcatgagtt ctattcatgc agacggagtg atactcccgt tccttcttgg acaggttgcc  240
tccacgccct ttgtggatct taaggtgacc aagtcactgg tgttggaggt gaagatagag  300
agtcctcttg ggaatgtcat gtggctgtgc caggggttgt agcgatgcca ttcgtgtgtg  360
cggatttcct ctcgtggtga cacgagcctc acaggccaaa agccccgtcc gaaaggaccc  420
gaatggtgga gtgaccctga ctcccccctg catagttttg tgattaggaa cttgaggaat  480
ttctgtcata aatctctatc acatcaggcc ccaaagatgt cctgaaggta ccctgtgtat  540
ctgaggatga gcaccaccga ctacccggac ttgcattagc agacacatgt ggttgcccag  600
ccccacctct tcagaggtgg ggctttgctc actcagcaca ggatctgatc aggagccccg  660
ctcgtgtgct ttacactcga cgcggggtta aaaattgccc aaggcctggc acaacaacct  720
aggggactag gttttcctat ttttgtaaat tatgtcaat                         759

SEQ ID NO: 11           moltype = DNA  length = 478
FEATURE                 Location/Qualifiers
source                  1..478
                        mol_type = genomic DNA
                        organism = Human rhinovirus
SEQUENCE: 11
gtgacaatca gccagattgt taacggtcaa gcacttctgt ttccccggta cccttgtata  60
cgcttcaccc gaggcgaaaa gtgaggttat cgttatccgc aaagtgccta cgagaagcct  120
agtagcactt ttgaagccta tggctggtcg ctcaactgtt tacccagcag tagacctggc  180
agatgaggct agatgttccc caccagcgat ggtgatctag cctgcgtggc tgcctgcaca  240
ctctattgag tgtgaagcca gaaagtggac aaggtgtgaa gagcctattg tgctcacttt  300
gagtcctccg gcccctgaat gtggctaatc ctaaccccgt agctgttgca tgtaatccaa  360
catgtctgca gtcgtaatgg gcaactatgg gatggaacca actactttgg gtgtccgtgt  420
ttcttgtttt tctttatgct tgcttatggt gacaactgta gttattacat ttgttacc    478
```

-continued

```
SEQ ID NO: 12          moltype = DNA  length = 628
FEATURE                Location/Qualifiers
source                 1..628
                       mol_type = genomic DNA
                       organism = Human rhinovirus
SEQUENCE: 12
ttaaaacagc ggatgggtat cccaccattc gacccattgg gtgtagtact ctggtactat  60
gtacctttgt acgcctgttt ctccccaacc acccttcctt aaaattccca cccatgaaac  120
gttagaagct tgacattaaa gtacaatagg tggcgccata tccaatggtg tctatgtaca  180
agcacttctg tttcccagga gcgaggtata ggctgtaccc actgccaaaa gcctttaacc  240
gttatccgcc aaccaactac gtaacagtta gtaccatctt gttcttgact ggacgttcga  300
tcaggtggat tttccctcca ctagtttggt cgatgaggct aggaattccc cacgggtgac  360
cgtgtcctag cctgcgtggc ggccaaccca gcttatgctg ggacgccctt ttaaggacat  420
ggtgtgaaga ctcgcatgtg cttggttgtg agtcctccgg cccctgaatg cggctaacct  480
taaccctaga gccttatgcc acgatccagt ggttgtaagg tcgtaatgag caattccggg  540
acgggaccga ctactttggg tgtccgtgtt tctcattttt cttcatattg tcttatggtc  600
acagcatata tatacatata ctgtgatc                                    628

SEQ ID NO: 13          moltype = DNA  length = 618
FEATURE                Location/Qualifiers
source                 1..618
                       mol_type = genomic DNA
                       organism = Human rhinovirus
SEQUENCE: 13
ttaaaactgg gagtgggttg ttcccactca ctccacccat gcggtgttgt actctgttat  60
tacggtaact ttgtacgcca gtttttccca cccttcccca taatgtaact tagaagtttg  120
tacaatatga ccaataggtg acaatcatcc agactgtcaa aggtcaagca cttctgtttc  180
cccggtcaat gaggatatgc tttacccaag gcaaaaacct tagagatcgt tatccccaca  240
ctgcctacac agagcccagt accatttttg atataattgg gttggtcgct ccctgcaaac  300
ccagcagtag acctggcaga tgaggctgga cattccccac tggcgacagt ggtccagcct  360
gcgtggctgc ctgctcaccc ttcttgggtg agaagcctaa ttattgacaa ggtgtgaaga  420
gccgcgtgtg ctcagtgtgc ttcctccggc ccctgaatgt ggctaacctt aaccctgcag  480
ccgttgccca taatccaatg ggtttgcggt cgtaatgcgt aagtgcggga tgggaccaac  540
tactttgggt gtccgtgttt cctgtttttc ttttgattgc attttatggt gacaatttat  600
agtgtataga ttgtcatc                                              618

SEQ ID NO: 14          moltype = DNA  length = 610
FEATURE                Location/Qualifiers
source                 1..610
                       mol_type = genomic DNA
                       organism = Human rhinovirus
SEQUENCE: 14
ttaaaactgg gtacaggttg ttcccacctg tatcacccac gtggtgtggt gctcttgtat  60
tccggtacac ttgcacgcca gtttgccacc cctcacccgt cgtaacttag aagctaacaa  120
ctcgaccaac aggcggtggt aaaccatacc acttacggtc aagcactcct gtttccccgg  180
tatgcgagga atagactcct acagggttga agcctcaagt atcgttatcc gcattggtac  240
tacgcaaagc ttagtagtgc cttgaaagtc ccttggttgg tcgctccgct agtttcccct  300
agtagacctg gcagatgagg caggacactc cccactggcg acagtggtcc tgcctgcgtg  360
gctgcctgcg cacccttagg ggtgcgaagc caagtgacag acaaggtgtg aagagccccg  420
tgtgctacca atgagtcctc cggcccctga atgcggctaa tccaacccca cagctattgc  480
acacaagcca gtgtgtatgt agtcgtaatg agcaattgtg ggacggaacc gactactttg  540
ggtgtccgtg tttcctttta ttcttatcat tctgcttatg gtgacaatac tgtgaaatag  600
tgttgttacc                                                        610

SEQ ID NO: 15          moltype = DNA  length = 614
FEATURE                Location/Qualifiers
source                 1..614
                       mol_type = genomic DNA
                       organism = Human rhinovirus
SEQUENCE: 15
taaaactgga tccaggttgt tcccacctgg atctcctatt gggagttgta ctctattatt  60
ccggtaattt tgtacgccag ttttatcttc cccctcccca attgtaactt agaaggttat  120
caatacgacc aataggtggt agttagccaa actaccaaag gtcaagcact tctgtttccc  180
cggtcaaagt tgatatgctc caacaggca aaaacaactg agatcgttat ccgcaaagtg  240
cctacgcaaa gcctagtaac acctttgaag atttatggtt ggtcgttccg ctatttccca  300
tagtagacct ggcagatgag gctagaaatc ccccactggc gacagtgctc tagcctgcgt  360
ggctgcctgc gcaccccttg ggtgcgaagc catacattgg acaaggtgtg aagagccccg  420
tgtgctcact ttgagtcctc cggcccctga atgtggctaa ccttaaccct gcagctagtg  480
catgtaatcc aacatgttgc tagtcgtaat gagtaattgc gggacgggac caactacttt  540
gggtgtccgt gtttcacttt ttcctttttaa tattgcttat ggtgacaata tatatagcta  600
tatatattga cacc                                                  614

SEQ ID NO: 16          moltype = DNA  length = 624
FEATURE                Location/Qualifiers
source                 1..624
                       mol_type = genomic DNA
                       organism = Salivirus A
```

```
SEQUENCE: 16
ttcccctgca accattacgc ttactcgcat gtgcattgag tggtgcatgt gttgaacaaa  60
cagctacact cacatggggg cgggttttcc cgccctacgg cttctcgcga ggcccacccc  120
tcccctttct cccataacta cagtgctttg gtaggtaagc atcctgatcc cccgcggaag  180
ctgctcacgt ggcaactgtg gggacccaga caggttatca aaggcacccg gtctttccgc  240
cttcaggagt atccctgcta gcgaattcta gtagggctct gcttggtgcc aacctccccc  300
aaatgcgcgc tgcgggagtg ctcttcccca actcacccta gtatcctctc atgtgtgtgc  360
ttggtcagca tatctgagac gatgttccgc tgtcccagac cagtccagta atggacgggc  420
cagtgtgcgt agtcgtcttc cggcttgtcc ggcgcatgtt tggtgaaccg gtggggtaag  480
gttggtgtgc ccaacgcccg tactcagggg atacctcaag gcacccagga atgccaggga  540
ggtaccccgc ttcacagcgg gatctgaccc tggggtaaat gtctgcgggg ggtcttcttg  600
gcccacttct cagtactttt cagg                                          624

SEQ ID NO: 17          moltype = DNA  length = 730
FEATURE                Location/Qualifiers
source                 1..730
                       mol_type = genomic DNA
                       organism = Salivirus FHB
SEQUENCE: 17
acatgggggg tctgcggacg gcttcggccc acccgcgaca agaatgccgt catctgtcct  60
cattacccgt attccttccc ttcccccgca accaccacgc ttactcgcgc acgtgttgag  120
tggcacgtgc gttgtccaaa cagctacacc cacacccttc ggggcgggtt tgtcccgccc  180
tcgggttcct cgcggaaccc ccccctccct ctctctcttt ctatccgccc tcacttccca  240
taactacagt gctttggtag gtgagcaccc tgaccccccg cggaagctgc taacgtggca  300
actgtgggga tccaggcagg ttatcaaagg cacccggtct ttccgccttc aggagtatct  360
ctgccggtga attccggtag ggctctgctt ggtgccaacc tcccccaaat gcgcgctgcg  420
ggagtgctct tccccaactc atcttagtaa cctctcatgt gtgtgcttgg tcagcatatc  480
tgaggcgacg ttccgctgtc ccagaccagt ccagcaatgg acgggccagt gtgcgtagtc  540
gctttccggt tttccggcgc atgtttggcg aaacgctgag gtaaggttgg tgtgcccaac  600
gcccgtaatt tggtgatacc tcaagaccac ccaggaatgc cagggaggta ccccacttcg  660
gtgggatctg accctgggct aattgtctac ggtggttctt cttgcttcca cttctctttt  720
ttctggcatg                                                          730

SEQ ID NO: 18          moltype = DNA  length = 709
FEATURE                Location/Qualifiers
source                 1..709
                       mol_type = genomic DNA
                       organism = Salivirus NG-J1
SEQUENCE: 18
tatggcaggc gggcttgtgg acggcttcgg cccacccaca gcaagaatgc catcatctgt  60
cctcaccccc aattttccct tttcttcccc tgcaaccatt acgcttactc gcatgtgcat  120
tgagtggtgc atgtgttgaa caaacagcta cactcacatg ggggcgggtt ttcccgccct  180
acggcctctc gcgaggccca ccccttccct ccccttataa ctacagtgct ttggtaggta  240
agcatcctga tcccccgcgg aagctgctca cgtggcaact gtggggaccc agacaggtta  300
tcaaaggcac ccggtctttc cgccttcagg agtatcccta ctagtgaatt ctagcggggc  360
tctgcttggt gccaacctcc cccaaatgcg cgctgcggga gtgctcttcc ccaactcacc  420
ctagtatcct ctcatgtgtg tgcttggtca gcatatctga gacgatgttc cgctgtccca  480
gaccagtcca gtaatggacg ggccagtgcg tgtagtcgtc ttccggcttg tccggggcat  540
gtttggtgaa ccggtggggt aaggttggtg tgcccaacgc ccgtactttg gtgacacctc  600
aagaccaccc aggaatgcca gggaggtacc ccacctcacg gtgggatctg accctgggct  660
aattgtctac ggtggttctt cttgcttcca cttctttctt ctgttcacg               709

SEQ ID NO: 19          moltype = DNA  length = 708
FEATURE                Location/Qualifiers
source                 1..708
                       mol_type = genomic DNA
                       organism = Human parechovirus
SEQUENCE: 19
tttgaaaggg gtctcctaga gagcttggcc gtcgggcctt ataccccgac ttgctgagtt  60
tctctaggag agcccttttc ccagccctga ggcggctggt caataaaagc ctcaaacgta  120
actaacacct aagaagatca tgtaaaccct atgcctggtc tccactattc gaaggcaact  180
tgcaataaga agagtgggat caagacgctt aaagcataga gacagttttc ttttctaacc  240
cacatttgtg tggggtggca gatggcgtgc cataactcta atagtgagat accacgcttg  300
tggaccttat gctcacacag ccatcctcta gtaagtttgt gagacgtctg gtgacgtgtg  360
ggaacttatt ggaaacaaca ttttgctgca aagcatccta ctgccagcgg aaaaacacct  420
ggtaacaggt gcctctgggg ccaaaagcca aggtttaaca gaccctttag gattggttct  480
aaacctgaga tgttgtggaa gatatttagt acctgctgat ctggtagtta tgcaaacact  540
agttgtaagg cccatgaagg atgcccagaa ggtacccgta ggtaacaagt gacactatgg  600
atctgatttg gggccagata cctctatctt ggtgatctgg ttaaaaaaca tctaatgggc  660
caaacccggg ggggatcccc ggtttcctct tattctatca atgccact                708

SEQ ID NO: 20          moltype = DNA  length = 508
FEATURE                Location/Qualifiers
source                 1..508
                       mol_type = genomic DNA
                       organism = Crohivirus B
SEQUENCE: 20
gtataagaga caggtgtttg ccttgtcttc ggactggcat cttgggacca accccccttt  60
tccccagcca tgggttaaat ggcaataaag gacgtaacaa ctttgtaacc attaagcttt  120
```

```
gtaattttgt aaccactaag ctttgtgcac ataatgtaac catcaagctt gttagtccca  180
gcaggaggtt tgcatgcttg tagccgaaat ggggctcgac cccccatagt aggatacttg  240
attttgcatt ccattgtgga cctgcaaact ctacacatag aggctttgtc ttgcatctaa  300
acacctgagt acagtgtgta cctagaccct atagtacggg aggaccgttt gtttcctcaa  360
taaccctaca taataggcta ggtgggcatg cccaatttgc aagatcccag actgggggtc  420
ggtctgggca gggttagatc cctgttagct actgcctgat agggtggtgc tcaaccatgt  480
gtagtttaaa ttgagctgtt catatacc                                     508

SEQ ID NO: 21          moltype = DNA  length = 248
FEATURE                Location/Qualifiers
source                 1..248
                       mol_type = genomic DNA
                       organism = Picornaviridae sp.
SEQUENCE: 21
actgaagatc ctacagtaac tactgcccca atgaacgcca cagatgggtc tgctgatgac  60
tacctatctt agtgctagtt gaggtttgaa gtgagccggt ttttagaaga accagtttct  120
gaacattatc atccccagca tctattctat acgcacaaga tagatagtca tcagcagaca  180
catctgtgct actgcttgat agagttgcgg ctggtcaact tagattggta taaccagttg  240
agtggcaa                                                           248

SEQ ID NO: 22          moltype = DNA  length = 516
FEATURE                Location/Qualifiers
source                 1..516
                       mol_type = genomic DNA
                       organism = Rosavirus M-7
SEQUENCE: 22
tatgcatcac tggacggcct aacctcggtc gtggcttctt gccgatttca gcgctaccag  60
gctttctggt ctcgccaggc gttgattagt aggtgcactg tctaagtgaa gacagcagtg  120
ctctctgtga aaagttgatg acactcttca ggtttgtagc gatcactcaa ggctagcgga  180
tttccccgtg tggtaacaca cgcctctagg cccagaaggc acggtgttga cagcacccct  240
tgagtggctg gtcttcccca ccagcacctg atttgtggat tcttcctagt aacggacaag  300
catggctgct cttaagcatt cagtgcgtcc ggggctgaag gatgcccaga aggtacccgc  360
aggtaacgat aagctcactg tggatctgat ctggggctgc gggctgggtg tctttccacc  420
cagccaaaac ccgtaaaacg gtagtcgcag ttaaaaaacg tctaggcccc acccccccag  480
ggatgggggg ttcccttaaa ccctcacaag ttcaac                             516

SEQ ID NO: 23          moltype = DNA  length = 478
FEATURE                Location/Qualifiers
source                 1..478
                       mol_type = genomic DNA
                       organism = Shanbavirus A
SEQUENCE: 23
tgaaaagggg gcgcagggtg gtggtggtta ctaaataccc accatcgccc tgcacttccc  60
ttttcccctg tggctcaggg tcacttagcc ccctctttgg gttaccagta gttttctacc  120
cctgggcaca gggttaacta tgcaagacgg aacaacaatc tcttagtccc cctcgccgat  180
agtgggctcg acccccatgt gtaggagtgg ataagggacg gagtgagccg atacggggaa  240
gagtgtgcgg tcacacctta attccatgag cgctgcgaag aaggaagctg tgaacaatgg  300
cgacctgaac cgtacacatg gagctccaca ggcatggtac tcgttagact acgcagcctg  360
gttgggagtg ggtataccct gggtgagccg ccagtgaatg ggagttcact ggttaacaca  420
cactgcctga tagggtcagg gcctcctgtc cccgccgtaa tgaggtagac catatgcc    478

SEQ ID NO: 24          moltype = DNA  length = 403
FEATURE                Location/Qualifiers
source                 1..403
                       mol_type = genomic DNA
                       organism = Pasivirus A
SEQUENCE: 24
gcggctggat attctggccg tgcaactgct tttgaccagt ggctctgggt aacttagcca  60
aagtgtcctt ctcccttcc  ctattatatg ttttatggct ttgtctggtc ttgtttagtt  120
tatatataag atcctttccg ccgatataga cctcgacagt ctagtgtagg aggattggtg  180
atattaattt gccccagaag agtgaccgtg acacatagaa accatgagta catgtgtatc  240
cgtggaggat cgcccgggac tggattccat atcccattgc catcccaaca agcggagggt  300
atacccacta tgtgcacgtc tgcagtggga gtctgcagat ttagtcatac tgcctgatag  360
ggtgtgggcc tgcactctgg ggtactcagg ctgtttatat aat                    403

SEQ ID NO: 25          moltype = DNA  length = 404
FEATURE                Location/Qualifiers
source                 1..404
                       mol_type = genomic DNA
                       organism = Pasivirus A
SEQUENCE: 25
gctggacttt ctggctgcgc aactgctttt aaccagtggc tctgggttac ttagccaaaa  60
ccccctttcc ccgtacccta gtttgtgtgt gtattattat tttgttgttg ttttgtaaat  120
ttttatataa gatcctttcc gccgatatag acctcgacag tctagtgtag gaggattggt  180
gatattaata tgccccagaa gagtgaccgt gacacataga aaccatgagt acatgtgtat  240
ccgtggagga tcgcccggga ctggattcca tatcccattg ccatcccaac aaacggaggg  300
tatacccgct atgtgcgcgt ctacagtggg aatctgtaga tttagtcata ctgcctgata  360
gggtgtgggc ctgcactctg ggtactcag gctgtttata taat                    404
```

```
SEQ ID NO: 26          moltype = DNA  length = 744
FEATURE                Location/Qualifiers
source                 1..744
                       mol_type = genomic DNA
                       organism = Echovirus E14
SEQUENCE: 26
ttaaaacagc ctgtgggttg ttcccatcca cagggcccac tgggcgccag cactctggta  60
ttgcggtacc ttagtgcgcc tgttttatat acccgtcccc caaacgtaac ttagacgcat  120
gtcaacgaag accaatagta agcgcagcac accagctgtg ttccggtcaa gcacttctgt  180
taccccggac cgagtatcaa taagctactc acgtggctga aggagaaaac gttcgttacc  240
cgaccaatta cttcaagaaa cctagtaaca ccatgaaggt tgcgcagtgt ttcgctccgc  300
acaaccccag tgtagatcag gtcgatgagt caccgcattc cccacgggtg accgtggcgg  360
tggctgcgct ggcggcctgc ccatggggaa acccatggga cgcttcaata ctgacatggt  420
gcgaagagtc tattgagcta attggtagtc ctccggcccc tgaatgcggc taatcctaac  480
tgcggagcag atacccacac accagtgggc agtctgtcgt aacgggcaac tctgcagcgg  540
aaccgactac tttgggtgtc cgtgtttctc tttatcctta tactggctgc ttatggtgac  600
aattgagaga ttgttaccat atagctattg gattggccat ccggtgacaa atagagcaat  660
tgtgtatttg tttgttggtt tcgtgccatt aaattacaag gttctaaaca cccttaatct  720
tattatagca ttcaacacaa caaa                                           744

SEQ ID NO: 27          moltype = DNA  length = 663
FEATURE                Location/Qualifiers
source                 1..663
                       mol_type = genomic DNA
                       organism = Human Parechovirus
SEQUENCE: 27
gtacattaga tgcgtcatct gcaactttag tcaataaatt acctccaatg tcattaccaa  60
cattccctac cttttcacta acacctaaga caacaagtac ctatgcctgg tctccactat  120
tcgaaggcaa cttgcaataa gaagagtgga attaagacgc ttaaagcata gagctagtta  180
tcttttctaa cccacaaagt tttgtggggt ggcagatggc gtgccataac tctattagtg  240
agataccatg cttgtggatc ttatgctcac acagccatcc tctagtaagt tgataaggtg  300
tctggtgata tgtgggaact cacatgaacc attaatttac cgtaaggtat cctatagcca  360
gcggaatcac atctggtgac agatgcctct ggggccgaaa gccaaggttt aacagaccct  420
ataggattgg tttcaaaacc tgaattgatg tggattgtgt atagtacctg ttgatctggt  480
aacagtgtca acactagttg taaggcccac gaaggatgcc cagaaggtac ccgtaggtaa  540
caagtgacac tatggatctg atctggggcc agctacctct atcatggtga gttggttaaa  600
aaacgtctag tgggccaaac ccagggggga tccctggttt ccttttacct aatcaaagcc  660
act                                                                  663

SEQ ID NO: 28          moltype = DNA  length = 744
FEATURE                Location/Qualifiers
source                 1..744
                       mol_type = genomic DNA
                       organism = Aichi virus
SEQUENCE: 28
tttgaaaagg gggtgggggg gcctcggccc cctcaccctc ttttccggtg gtctggtccc  60
ggaccaccgt tactccattc agcttcttcg gaacctgttc ggaggaatta aacgggcacc  120
catactcccc ccacccccct tttgtaacta agtatgtgtg ctcgtgatct tgactcccac  180
ggaacggacc gatccgttgg tgaacaaaca gctaggtcca catcctccct tcccctggga  240
gggcccccgc cctcccacat cctcccccca gcctgacgta tcacaggctg tgtgaagccc  300
ccgcgaaagc tgctcacgtg gcaattgtgg gtccccccct catcaagaca ccaggtcttt  360
cctccttaag gctagccccg gcgtgtgaat tcacgttggg caactagtgg tgtcactgtg  420
cgctcccaat ctcggccgcg gagtgctgtt ccccaagcca aacccctggc ccttcactat  480
gtgcctggca agcatatctg agaaggtgtt ccgctgtggc tgccaacctg gtgacaggtg  540
ccccagtgtg cgtaaccttc ttccgtctcc ggacggtagt gattggttaa gatttggtgt  600
aaggttcatg tgccaacgcc ctgtgcggga tgaaacctct actgccctag gaatgccagg  660
caggtacccc acctccgggt gggatctgag cctgggctaa ttgtctacgg gtagtttcat  720
ttccaatcct tttatgtcgg agtc                                           744

SEQ ID NO: 29          moltype = DNA  length = 734
FEATURE                Location/Qualifiers
source                 1..734
                       mol_type = genomic DNA
                       organism = Hepatitis A virus
SEQUENCE: 29
ttcaagaggg gtctccggag ttttccggaa cccctcttgg aagtccatgg tgaggggact  60
tgatacctca ccgccgtttg cctaggctat aggctaaatt tccctttccc tgtccttccc  120
ctatttcctt ttgttttgtt tgtaaatatt aattcctgca ggttcagggt tctttaatct  180
gtttctctat aagaacactc aatttttcac gctttctgtc tcctttcttc cagggctctc  240
cccttgccct aggctctggc cgttgcgccc ggcggggtca actccatgat tagcatggag  300
ctgtaggagt ctaaattggg gacgcagatg tttgggacgt cgccttgcag tgttaacttg  360
gctttcatga acctctttga tcttccacaa ggggtaggct acgggtgaaa cctcttaggc  420
taatacttca atgaagagat gccttggata gggtaacagc ggcggatatt ggtgagttgt  480
taagacaaaa accattcaac gccggaggac tggctctcat ccagtggatg cattgaggga  540
attgattgtc agggctgtct ctaggtttaa tctcagacct ctctgtgctt agggcaaaca  600
ctatttggcc ttaaatggga tcctgtgaga gggggtccct ccattgacag ctggactgtt  660
ctttggggcc ttatgtggtg tttgcctctg aggtactcag ggcatttag gtttttcctc  720
attcttaaat aata                                                      734
```

-continued

```
SEQ ID NO: 30          moltype = DNA  length = 638
FEATURE                Location/Qualifiers
source                 1..638
                       mol_type = genomic DNA
                       organism = Phopivirus
SEQUENCE: 30
gggagtaaac ctcaccaccg tttgccgtgg tttacggcta cctatttttg gatgtaaata  60
ttaattcctg caggttcagg tctcttgaat tatgtccacg ctagtggcac tctcttaccc  120
ataagtgacg ccttagcgga acctttctac acttgatgtg gttaggggtt acattatttc  180
cctgggcctt ctttggccct ttttcccctg cactatcatt ctttcttccg ggctctcagc  240
atgccaatgt tccgaccggt gcgcccgccg gggttaactc catggttagc atggagctgt  300
aggccctaaa agtgctgaca ctggaactgg actattgaag catacactgt taactgaaac  360
atgtaactcc aatcgatctt ctacaagggg taggctacgg gtgaaacccc ttaggttaat  420
actcatattg agagatactt ctgataggtt aaggttgctg gataatggtg agtttaacga  480
caaaaaccat tcaacagctg tgggccaacc tcatcaggta gatgcttttg gagccaagtg  540
cgtaggggtg tgtgtggaaa tgcttcagtg gaaggtgccc tcccgaaagg tcgtaggggt  600
aatcaggggc agttaggttt ccacaattac aatttgaa                          638

SEQ ID NO: 31          moltype = DNA  length = 743
FEATURE                Location/Qualifiers
source                 1..743
                       mol_type = genomic DNA
                       organism = Coxsackievirus A10
SEQUENCE: 31
gctcttccga tctgggttgt tcccacccac agggcccact gggcgccagc actctgattc  60
cacggaatct ttgtgcgcct gttttacaac ccttcccaat ttgtaacgta gaagcaatac  120
acactactga tcaatagtag gcatggcgcg ccagtcatgt catgatcaag cacttctgtt  180
cccccggact gagtatcaat agactgctca cgcggttgaa ggagaaaacg ttcgttaccc  240
ggctaactac ttcgagaaac ctagtagcac catggaagct gcggagtgtt tcgctcagca  300
ctttccccgt gtagatcagg tcgatgagtc actgcaatcc ccacgggcga ccgtggcagt  360
ggctgcgttg gcggcctgcc tatggggcaa cccataggac gctctaatgt ggacatggtg  420
cgaagagtct attgagctag ttagtagtcc tccggcccct gaatgcggct aatcctaact  480
gcggagcaca tgccttcaac ccaggaggtg gtgtgtcgta acgggtaact ctgcagcgga  540
accgactact ttgggtgtcc gtgtttcctt ttatccttat attggctgct tatggtgaca  600
atcacggaat tgttgccata tagctattgg attggccatc cggtgtctaa cagagctatt  660
gtatacctat ttgttggatt tactccccta tcatacaaat ctctgaacac tttgtgcttt  720
atactgaact taaacacacg aaa                                          743

SEQ ID NO: 32          moltype = DNA  length = 746
FEATURE                Location/Qualifiers
source                 1..746
                       mol_type = genomic DNA
                       organism = Enterovirus C
SEQUENCE: 32
ttaaaacagc tctggggttg ttcccacccc agaggcccac gtggcggcca gtacaccggt  60
accacggtac ccttgtacgc ctgttttata ctcccctccc cgtaaactag aagcacgaaa  120
cacaagttca atagaagggg gtacagacca gtaccaccac gaacaagcac ttctgttccc  180
ccggtgaggt cacatagact gtccccacgg tcaaaagtga ctgatccgtt atccgctcac  240
gtacttcgga aagcctagta ccaccttgga atctacgatg cgttgcgctc agcactcgac  300
cccggagtgt agcttaggct gatgagtctg gacgttcccc actggtgaca gtggtccagg  360
ctgcgttggc ggcctacctg tggtccaaaa ccacaggacg ctagtagtga acaaggtgtg  420
aagagcccac tgagctacct gagaatcctc cggcccctga atgcggctaa tcccaaccac  480
ggagcaggta atcgcaaacc agcggtcagc ctgtcgtaac gcgtaagtct gtggcggaac  540
cgactacttt gggtgtccgt gtttcctttt atttttatgg tggctgctta tggtgacaat  600
catagattgt tatcataaag caaattggat tggccatccg gagtgagcta aactatctat  660
ttctctgagt gttggattcg tttcacccac attctgaaca atcagcctca ttagtgttac  720
cctgttaata agacgatatc atcacg                                       746

SEQ ID NO: 33          moltype = DNA  length = 726
FEATURE                Location/Qualifiers
source                 1..726
                       mol_type = genomic DNA
                       organism = Enterovirus D
SEQUENCE: 33
ttaaaacagc tctggggttg ttcccacccc agaggcccac gtggcggcta gtactccggt  60
accccggtac ccttgtacgc ctgttttata ctccctttcc caagtaactt tagaagaaat  120
aaactaatgt tcaacaggag ggggtacaaa ccagtaccac cacgaacaca cacttctgtt  180
tccccggtga agttgcatag actgtaccca cggttgaaag cgatgaatcc gttacccgct  240
taggtacttc gagaagccta gtatcatctt ggaatcttcg atgcgttgcg atcagcactc  300
taccccgagt gtagcttggg tcgatgagtc tggacacccc acaccggcga cgtggtccag  360
gctgcgttgg cggcctaccc atggctagca ccatgggacg ctagttgtga acaaggtgcg  420
aagagcctat tgagctacct gagagtcctc cggcccctga atgcggctaa tcccaaccac  480
ggagcaaatg ctcacaatcc agtgagtggt ttgtcgtaat gcgcaagtct gtggcggaac  540
cgactacttt gggtgtccgt gtttcctttt atttttatta tggctgctta tggtgacaat  600
ctgagattgt tatcatatag ctattggatt agccatccgg tgatatcttg aaattttgcc  660
ataacttttt cacaaatcct acaacattac actacacttt ctcttgaata attgagacaa  720
ctcata                                                             726

SEQ ID NO: 34          moltype = DNA  length = 737
```

-continued

```
FEATURE                Location/Qualifiers
source                 1..737
                       mol_type = genomic DNA
                       organism = Enterovirus J
SEQUENCE: 34
ttaaaatagc ctcagggttg ttcccaccct gagggcccac gtggtgtagt actctggtat  60
tacggtacct ttgtacgcct attttatacc cccttcccca agtaatttag aagcaagcac  120
aaaccagttc agtagtaagc agtacaatcc agtactgtaa tgaacaagta cttctgttac  180
cccggaaggg tctatcggta agctgtaccc acggctgaag aatgacctac cgttaaccgg  240
ctacctactt cgagaagcct agtaatgccg ttgaagtttt attgacgtta cgctcagcac  300
actaccccgt gtgtagtttt ggctgatgag tcacggcact ccccacgggc gaccgtggcc  360
gtggctgcgt tggcggccaa ccaaggagtg caagctcctt ggacgtcata ttacagacat  420
ggtgtgaaga gcctattgag ctaggtggta gtcctccggc ccctgaatgc ggctaatcct  480
aactccggag catatcggtg cgaaccagca cttggtgtgt tgtaatacgt aagtctggag  540
cggaaccgac tactttgggt gtccgtgttt cctgttttaa cttttatggc tgcttatggt  600
gacaatttaa cattgttacc atatagctgt tgggttggcc atccggattt tgttataaaa  660
ccatttcctc gtgccttgac ctttaacaca tttgtgaact tctttaaatc ccttttatta  720
gtccttaaat actaaga                                                 737

SEQ ID NO: 35          moltype = DNA  length = 327
FEATURE                Location/Qualifiers
source                 1..327
                       mol_type = genomic DNA
                       organism = Human Pegivirus 2
SEQUENCE: 35
aactgttgtt gtagcaatgc gcatattgct acttcggtac gcctaattgg taggcgcccg  60
gccgaccggc cccgcaaggg cctagtagga cgtgtgacaa tgccatgagg gatcatgaca  120
ctggggtgag cggaggcagc accgaagtcg ggtgaactcg actcccagtg cgaccacctg  180
gcttggtcgt tcatggaggg catgcccacg ggaacgctga tcgtgcaaag ggatgggtcc  240
ctgcactggt gccatgcgcg gcaccactcc gtacagcctg atagggtggc ggcgggcccc  300
cccagtgtga cgtccgtgga gcgcaac                                      327

SEQ ID NO: 36          moltype = DNA  length = 281
FEATURE                Location/Qualifiers
source                 1..281
                       mol_type = genomic DNA
                       organism = GB virus C
SEQUENCE: 36
tgacgtgggg gggttgattt tcccccccg gcactgggtg caagccccag aaaccgacgc  60
ctatctaagt agacgcaatg actcggcgcc gactcggcga ccggccaaaa ggtggtggat  120
gggtgatgac agggttggta ggtcgtaaat cccggtcatc ctggtagcca ctataggtgg  180
gtcttaagag aaggtcaaga ttcctcttac gcctgcggcg agaccgcgca cggtccacag  240
gtgttggccc taccggtgtg aataagggcc cgacatcagg c                      281

SEQ ID NO: 37          moltype = DNA  length = 459
FEATURE                Location/Qualifiers
source                 1..459
                       mol_type = genomic DNA
                       organism = GB virus C
SEQUENCE: 37
gacgtggggg ggttgatccc cccctttgg cactgggtgc aagccccaga aaccgacgcc  60
tatttaaaca gacgttaaga accggcgccg acccggcgac cggccaaaag gtggtggatg  120
ggtgatgcca gggttggtag gtcgtaaatc ccggtcatct tggtagccac tataggtggg  180
tcttaagggt tggttaaggt ccctctggcg cttgtggcga gaaagcgcac ggtccacagg  240
tgttggccct accggtgtga ataagggccc gacgtcaggc tcgtcgttaa accgagccca  300
ctacccacct gggcaaacaa cgcccacgta cggtccacgt cgcccttcaa tgtctctctt  360
gaccaatagg cttagccggc gagttgacaa ggaccagtgg gggctgggcg gtaggggaag  420
gacccctgcc gctgcccttc ccggtggagt gggaaatgc                         459

SEQ ID NO: 38          moltype = DNA  length = 350
FEATURE                Location/Qualifiers
source                 1..350
                       mol_type = genomic DNA
                       organism = GB virus C
SEQUENCE: 38
tgacgtgggg gggttgatcc gcccccccg gcactcggtg caagccccat aaaccgacgc  60
ctatctaagt agacgcaatg actcggcgcc gactcggcga ccggccaaaa ggtggtggat  120
gggtggtgac agggttggta ggtcgtaaat cccggtcatc ctggtagcca ctataggtgg  180
gtcttaagag aaggtcaaga ctcctcttgt gcctgcggcg agaccgcgca cggtccacag  240
gtgctggccc taccggtgtg aataagggcc cgacgtcagg ctcgtcgtta aaccgagccc  300
gtcacccacc tgggcaaacg acgcccacgt acggtccacg tcgcccttca              350

SEQ ID NO: 39          moltype = DNA  length = 318
FEATURE                Location/Qualifiers
source                 1..318
                       mol_type = genomic DNA
                       organism = Pegivirus A
```

```
SEQUENCE: 39
tgtagcaatg cgcatattgc tacttcggta cgcctaattg gtaggcgccc ggccgaccgg  60
ccccgcaagg gcctagtagg acgtgtgaca atgccatgcg ggatcatgac actggggtga  120
gcggaggcag caccgaagtc gggtgaactc gactcccagt gcgaccacct ggcttggtcg  180
ttcatggagg gcatgcccac gggaacgctg atcgtgcaaa gggatgggtc cctgcactgg  240
tgccatgcgc ggcaccactc cgtacagcct gatagggtgg cggcgggccc ccccagtgtg  300
acgtccgtgg agcgcaac                                                318

SEQ ID NO: 40          moltype = DNA  length = 399
FEATURE                Location/Qualifiers
source                 1..399
                       mol_type = genomic DNA
                       organism = Pasivirus A
SEQUENCE: 40
attttctggc cgtgtagctg cttttgacca gtggctctgg gttacttagc caaatccccc  60
ttccttcacc cttttaaatt tgatggtctg tgttgtttgt tttgtcttgt ctaaataata  120
tataagatcc ttcccgccga tacagacctc gacagtctgg tgtaggaggg ttggtgttat  180
taatttgccc cagaagagtg accgtgacac atagaaacca tgagtacatg tgtatccgtg  240
gaggatcgcc cgggactgga ttccatatcc cattgccatc ccaacaagcg gagggtatac  300
ccactatgtg cgcgtttgca gtgggaatct gcaaatttag tcatactgcc tgatagggtg  360
tgggcctgca ctctggggta ctcaggctgt tcatataat                         399

SEQ ID NO: 41          moltype = DNA  length = 430
FEATURE                Location/Qualifiers
source                 1..430
                       mol_type = genomic DNA
                       organism = Sapelovirus sp.
SEQUENCE: 41
cccctccacc cttaaggtgg ttgtatccca cataccccac cctcccttcc aaagtggacg  60
gacaactgga ttttgactaa cggcaagtct gaatggtatg atttggatac gtttaaacgg  120
cagtagcgtg gcgagctatg gaaaaatcgc aattgtcgat agccatgtta gtgacgcgct  180
tcggcgtgct cctttggtga ttcggcgact ggttacagga gagtaggcag tgagctatgg  240
gcaaacctct acagtattac ttagagggaa tgtgcaattg agacttgacg agcgtctctt  300
tgagatgtgg cgcatgctct tggcattacc atagtgagct tccaggttgg gaaacctgga  360
ctgggcctat actacctgat agggtcgcgg ctggccgcct gtaactagta tagtcagttg  420
aaacccccc                                                          430

SEQ ID NO: 42          moltype = DNA  length = 504
FEATURE                Location/Qualifiers
source                 1..504
                       mol_type = genomic DNA
                       organism = Rosavirus B
SEQUENCE: 42
gtctctttag tgtctatgct tcagagagcg gtgaactgac accgttgctt cttgcacagc  60
ccttcgtgcc ggtctttccg gttctcgaca gcgttgggca tcatggctag ttaggctaag  120
atagtggatg atctagtgaa cagttttgga ttgtttggag ttttgtagcg atgctagtag  180
tgtgtgtgga cctccccacg tggtaacacg tgccccacag gccaaaagcc aaggtgttga  240
aagcacccct actagtccca gactcaccca tctgggaact cctctcatga aaaatcttag  300
taacttttga ttcggctatt catcaacctc tctagtcaag ggctgaagga tgcccggaag  360
gtacccgcag gtaacgataa gctcactgtg gatctgatcc ggggctttgg tgcgaccgtc  420
tgtccggcgt agccagagtt aaaaaacgtc taggcccttc caccccaagg gattggggtt  480
tccccaatca tttgaaagtt cact                                         504

SEQ ID NO: 43          moltype = DNA  length = 532
FEATURE                Location/Qualifiers
source                 1..532
                       mol_type = genomic DNA
                       organism = Bakunsa virus
SEQUENCE: 43
ttttgaacgc cacctcggag cgatatccgg ggaccccctc cccttttttcc ttcctacctt  60
cttcccaaat ttccctcttc ccttgttatt ttggtttgga tttcctggac atgactcgga  120
cggatctatc tcatttgctt tgtgtctgct ccaccagtgg catggtcgaa agatcatcaa  180
cactggacgt gtactgtaat ggccaaacgt gcccacaggg gaaaccatgc cggtcgctgt  240
agcggcgggt ggacgtggtg gacccctctc cctgctcata aactttgggt aggtgaaggg  300
ttcaagcgac gcttgccgtg agggcgcatc cggatggtgg gaaccaacaa actaggctgt  360
aatggccgac ctcaggtgga tgagctaggg ctgctgcacc aaaagggact cgattcgata  420
tcccggcctg gtagcctagt gcagtggact cgtagttggg aatctacgac tggcctagta  480
cagggtgata gccccgtttc ccacgcccac ctgttgtagg gacacccccc cc          532

SEQ ID NO: 44          moltype = DNA  length = 494
FEATURE                Location/Qualifiers
source                 1..494
                       mol_type = genomic DNA
                       organism = Tremovirus A
SEQUENCE: 44
tttgaaagag gcctccggag tgtccggagg ctctctttcg acccaaccca tactgggggg  60
tgtgtgggac cgtacctgga gtgcacggta tatatgcatt cccgcatggc aagggcgtgc  120
taccttgccc cttgacgcat ggtatgcgtc atcatttgcc ttggttaagc cccatagaaa  180
cgaggcgtca cgtgccgaaa atccctttgc gtttcacaga accatcctaa ccatgggtgt  240
```

```
agtatgggaa tcgtgtatgg ggatgattag gatctctcgt agagggatag gtgtgccatt  300
caaatccagg gagtactctg gctctgacat tgggacattt gatgtaaccg gacctggttc  360
agtatccggg ttgtcctgta ttgttacggt gtatccgtct tggcacactg aaagggtatt  420
tttgggtaat cctttcctac tgcctgatag ggtggcgtgc ccggccacga gagattaagg  480
gtagcaattt aaac                                                    494

SEQ ID NO: 45          moltype = DNA  length = 378
FEATURE                Location/Qualifiers
source                 1..378
                       mol_type = genomic DNA
                       organism = Swine Pasivirus 1
SEQUENCE: 45
gcttttgacc agtggctctg ggttacttag ccaagtccct ttctcttatt ttcactagtt  60
tatgttgtgt gttgtctgtt ttgttttgtt taaattgtat acaagatcct tcccgccgac  120
acagacctcg acagtctggt gtaggagggt tggtgatatt aatttgcccc aaaagagtga  180
ccgtgatacg tggaaaccat gagtacatgt gtatccgtgg aggatcgccc gggactggat  240
tccatatccc attgccatcc caacaaacgg agggtatacc caccacgtgc gcgtttgcag  300
tgggaatctg caaatttagt catactgcct gatagggtgt gggcctgcac tttggggtac  360
tcaggctgtt catataat                                                378

SEQ ID NO: 46          moltype = DNA  length = 319
FEATURE                Location/Qualifiers
source                 1..319
                       mol_type = genomic DNA
                       organism = Parechovirus-like virus PLV-CHN
SEQUENCE: 46
acatggggta tgttgtctgt cctgttttgt tgaaacaata tataagatcc tttccgccga  60
tatagacctc gacagtctag tgtaggagga ttggtgatag taacttgccc cagaagagtg  120
accgtgacac atagaaacca tgagtacatg tgtatccgtg gaggatcgcc cgggactgga  180
ttccatatcc cattgccatc ccaacaaacg gagggtatac ccactatgtg cgcgtttgca  240
gtgggagcct gcaaatttag tcatactgcc tgatagggtg tgggcctgca ctctggggta  300
ctcaggctgt ttatataat                                               319

SEQ ID NO: 47          moltype = DNA  length = 420
FEATURE                Location/Qualifiers
source                 1..420
                       mol_type = genomic DNA
                       organism = Pasivirus A
SEQUENCE: 47
tgaaaaagtg gttgtgcagc tggattttcc ggctgtgcaa ctgcttttga ccagtggctc  60
tgggttactt agccaaattc ctttccctta tccctattgg tttgtgttgt gtgttgtttg  120
ttttgttttg tcttaactat atacaagatc cttcccgccg atacagacct cgacagtctg  180
gtgtaggagg gttggtgtta ttaatttgcc ccaaaagagt gaccgtgaca cgtggaaacc  240
atgagtacat gtgtatccgt ggaggatcgc ccgggactgg attccatatc ccattgccat  300
cccaacaaac ggagggtata cccaccacgt gcgcgtttgc agtgggaatc tgcaaattta  360
gtcatactgc ctgatagggt gtgggcctgc actttggggt actcaggctg tttatataat  420

SEQ ID NO: 48          moltype = DNA  length = 373
FEATURE                Location/Qualifiers
source                 1..373
                       mol_type = genomic DNA
                       organism = Sicinivirus sp.
SEQUENCE: 48
gtgtcattaa ggtgtgtttg gaagttcgaa ttagctggtt tgtggtgatt agtagacccc  60
ctggaggtac ccaattcgga tctgaccagg gacccgtgac tataccgctc cggtaattcg  120
ggtttaaaac aatgaacgtc accacacaat tacttttctc attttatttt catcattgtc  180
ttcctattta ccgattacac tcgatttcct tggatgttcc tggagatttc cctggttacc  240
tggaccctca ttattgttgt tgtttcaccc agcgagctgt cccaattgct tattatttgc  300
gcttacaact tcgtcctaat atttttctgg ttgatcgggt tgattgagct cccgggctat  360
cctgccattc aac                                                     373

SEQ ID NO: 49          moltype = DNA  length = 280
FEATURE                Location/Qualifiers
source                 1..280
                       mol_type = genomic DNA
                       organism = Hepacivirus K
SEQUENCE: 49
gggaacaatg gtccgtccgc ggaacgactc tagccatgag tctagtacga gtgcgtgcca  60
cccattagca caaaaaccac tgactgagcc acacccctcc cggaatcctg agtacaggac  120
attcgctcgg acgacgcatg agcctccatg ccgagaaaat tgggtatacc cacgggtaag  180
gggtggccac ccagcgggaa tctgggggct ggtcactgac tatggtacag cctgataggg  240
tgctgccgca gcgtcagtgg tatgcggctg ttcatggaac                        280

SEQ ID NO: 50          moltype = DNA  length = 384
FEATURE                Location/Qualifiers
source                 1..384
                       mol_type = genomic DNA
                       organism = Hepacivirus A
```

```
SEQUENCE: 50
acctccgtgc taggcacggt gcgttgtcag cgttttgcgc ttgcatgcgc tacacgcgtc  60
gtccaacgcg gagggaactt cacatcacca tgtgtcactc cccctatgga gggttccacc  120
ccgcttacac ggaaatgggt taaccatacc caaagtacgg gtatgcgggt cctcctaggg  180
ccccccccggc aggtcgaggg agctggaatt cgtgaattcg tgagtacacg aaaatcgcgg  240
cttgaacgtc tttgaccttc ggagccgaaa tttgggcgtg ccccacgaag gaaggcgggg  300
gcggtgttgg gccgccgccc cctttatccc acggtctgat aggatgcttg cgagggcacc  360
tgccggtctc gtagaccata ggac                                          384

SEQ ID NO: 51          moltype = DNA  length = 384
FEATURE                Location/Qualifiers
source                 1..384
                       mol_type = genomic DNA
                       organism = Bovine viral diarrhea virus 1
SEQUENCE: 51
gtatacgaga atttgcctag gacctcgttt acaatatggg caatctaaaa ttataattag  60
gcctaaggga caaatcctcc tcagcgaagg ccgaaaagag gctagccatg cccttagtag  120
gactagcaaa ataagggggg tagcaacagt ggtgagttcg ttggatggct gaagccctga  180
gtacagggta gtcgtcagtg gttcgacgct tcggaggaca agcctcgaga taccacgtgg  240
acgagggcat gcccacagca catcttaacc tggacggggg tcgttcaggt gaaaacggtt  300
taaccaaccg ctacgaatac agcctgatag ggtgctgcag aggcccactg tattgctact  360
gaaaatctct gctgtacatg gcac                                          384

SEQ ID NO: 52          moltype = DNA  length = 372
FEATURE                Location/Qualifiers
source                 1..372
                       mol_type = genomic DNA
                       organism = Border Disease virus
SEQUENCE: 52
gtatacggga gtagctcatg cccgtataca aaattggata ttccaaaact cgattgggtt  60
agggagccct cctagcgacg gccgaaccgt gttaaccata cacgtagtag gactagcaga  120
cgggaggact agccatcgtg gtgagatccc tgagcagtct aaatcctgag tacaggatag  180
tcgtcagtag ttcaacgcag gcacggttct gccttgagat gctacgtgga cgagggcatg  240
cccaagactt gctttaatct cggcgggggt cgcccgaggtg aaaacaccta acggtgttgg  300
ggttacagcc tgatagggtg ctgcagaggc ccacgaatag gctagtataa aaatctctgc  360
tgtacatggc ac                                                       372

SEQ ID NO: 53          moltype = DNA  length = 388
FEATURE                Location/Qualifiers
source                 1..388
                       mol_type = genomic DNA
                       organism = Bovine viral diarrhea virus 2
SEQUENCE: 53
gtatacgaga ttagctaaag tactcgtata tggattggac gtcaacaaat ttttaattgg  60
caacgtaggg aaccttcccc tcagcgaagg ccgaaaagag gctagccatg ccctttagta  120
ggactagcaa aagtaggggg actagcggta gcagtgagtt cgttggatgg ccgaacccct  180
gagtacaggg gagtcgtcaa tggttcgaca ctccattagt cgaggagtct cgagatgcca  240
tgtggacgag ggcatgccca cggcacatct taacccatgc gggggttgca tgggtgaaag  300
cgctaatcgt ggcgttatgg acacagcctg atagggtgta gcagagacct gctattccgc  360
tagtaaaaaa ctctgctgta catggcac                                      388

SEQ ID NO: 54          moltype = DNA  length = 373
FEATURE                Location/Qualifiers
source                 1..373
                       mol_type = genomic DNA
                       organism = Classical swine fever virus
SEQUENCE: 54
gtatacgagg ttagttcatt ctcgtatgca ttattggaca aatcaaaatt tcaatttggt  60
tcagggcctc cctccagcga cggccgaact gggctagcca tgcccatagt aggactagca  120
aacggaggga ctagccgtag tggcgagctc cctgggtgtt ctaagtcctg agtacaggac  180
agtcgtcagt agttcgacgt gagcagaagc ccacctcgag atgctatgtg gacgagggca  240
tgcccaagac gcaccttaac cctagcgggg gtcgctaggg tgaaatcaca ccacgtgatg  300
ggagtccgac ctgatagggt gctgcagagg ctcactatta ggctagtata aaaatctctg  360
ctgtacatgg cac                                                      373

SEQ ID NO: 55          moltype = DNA  length = 191
FEATURE                Location/Qualifiers
source                 1..191
                       mol_type = genomic DNA
                       organism = Human blood-associated dicistrovirus
SEQUENCE: 55
aaaaccgacc ccagagatca gaaagtcgtt gacgcgatct tttattagag gacgttgcgc  60
tggcgcgagc tttaattagc agacgccaaa aataaacaac aaaatgctga tcgcgagact  120
taattgtcag acgattggcc aaatccgatg tgatctttgc tgctcccaga ttgccgaaat  180
aggagtagta g                                                        191

SEQ ID NO: 56          moltype = DNA  length = 438
FEATURE                Location/Qualifiers
```

```
source                  1..438
                        mol_type = genomic DNA
                        organism = Hubei Picorna-like virus
SEQUENCE: 56
ccccaaaacc ccccccttaa actcaacact gtagtggatt cattttccgt tgcaaaacaa  60
aacattacta cccgcattta tgtaggctct gtgttttcta tgcgaccgtt acattaatct  120
ctactctgac ccactagttt ataaaaccga agacctgaat gaaacgattt tccttctttt  180
caacctctaa cgaacctctg acggcttgag aaacctgaag ttagtaatta tgtttaaaag  240
aaaggaaagt caaacgcgat gactcttaca tccctattcc ataccgttgc tccacaatgt  300
gagcgatgcg aggtcgggac tgcagtatta ggggaacgag ctacatggag agttaattat  360
ctctcccctc ctacgggagt ctcatgtgag ctgtagaaag cggttggcac ctctcgttac  420
ctcgcctgta catgatcc                                                438

SEQ ID NO: 57           moltype = DNA  length = 193
FEATURE                 Location/Qualifiers
source                  1..193
                        mol_type = genomic DNA
                        organism = Cricket paralysis virus
SEQUENCE: 57
aaaagcaaaa atgtgatctt gcttgtaaat acaattttga gaggttaata aattacaagt  60
agtgctattt ttgtatttag gttagctatt tagctttacg ttccaggatg cctagtggca  120
gccccacaat atccaggaag ccctctctgc ggtttttcag attaggtagt cgaaaaacct  180
aagaaattta cct                                                     193

SEQ ID NO: 58           moltype = DNA  length = 752
FEATURE                 Location/Qualifiers
source                  1..752
                        mol_type = genomic DNA
                        organism = Salivirus A
SEQUENCE: 58
tttcctcctt tcgaccgcct tacggcaggc gggtccgcgg acggcttcgg cctacccgcg  60
acaagaatgc cgtcatctgt ccttatcacc catattcttt cccttccccc gcaaccatca  120
cgcttactcg cgcacgtgtt gagtggcacg tgcgttgtcc aaacagttac actcacaccc  180
ttggggcggg tttgtcccgc cctcgggttc ctcgcggaac cctccctctt ctctctccct  240
ttctatccgc cttcactttc cataactaca gtgctttggt aggtaagcat cctgaccccc  300
cgcggaagct gccaacgtgg caactgtggg gatccaggca ggttatcaaa ggcacccggt  360
ctttccgcct tcaggagtat ccctgccggt gaattccgac agggctctgc ttggtgccaa  420
cctcccccaa atgcgcgctg cgggagtgct cttccccaac tcatcttagt aacctctcat  480
gtgtgtgctt ggtcagcata tctgaggcga cgttccgctg tcccagacca gtccagcaat  540
ggacgggcca gtgtgcgtag tcgctttccg gtttcccggc gcatgtttgg cgaaacgctg  600
aggtaaggtt ggtgtgccca atgcccgtaa tttggtgaca cctcaagacc acccaggaat  660
gccagggagg taccccactt cggtgggatc tgaccctggg ctaattgtct acggtggttc  720
ttcttgcttc cacttctctt ttttctggca tg                                752

SEQ ID NO: 59           moltype = DNA  length = 708
FEATURE                 Location/Qualifiers
source                  1..708
                        mol_type = genomic DNA
                        organism = Salivirus A
SEQUENCE: 59
tatggcaggc gggcttgtgg acggcttcgg cccacccaca gcaagaatgc catcatctgt  60
cctcaccccc atgtttcccc tttctttccc tgcaaccgtt acgcttactc gcaggtgcat  120
ttgagtggtg cacgtgttga ataaacagct acactcacat gggggcgggt tttcccgccc  180
tgcggcctct cgcgaggccc acccctcccc ttcctcccat aactacagtg ctttggtagg  240
taagcatcct gatcccccgc ggaagctgct cacgtggcaa ctgtggggac ccagacaggt  300
tatcaaaggc acccggtctt tccgccttca ggagtatccc tgctagtgaa ttctagtagg  360
gctctgcttg gtgccaacct cccccaaatg cgcgctgcgg gagtgctctt ccccaactca  420
ccctagtatc ctctcatgtg tgtgcttggt cagcatatct gagacgatgt tccgctgtcc  480
cagaccagtc cagtaatgga cgggccagtg tgcgtagtcg tcttccggct tttccggcgc  540
atgtttggtg aaccggtggg gtaaggttgg tgtgcccaac gcccgtactt tggtgatacc  600
tcaagaccac ccaggaatgc cagggaggta ccccgcttca cagcgggatc tgaccctggg  660
ctaattgtct acggtggttc ttcttgcttc cacttctttc tactgttc               708

SEQ ID NO: 60           moltype = DNA  length = 718
FEATURE                 Location/Qualifiers
source                  1..718
                        mol_type = genomic DNA
                        organism = Salivirus A
SEQUENCE: 60
tttcgaccgc cttatggcag gcgggcttgt ggacggcttc ggcccaccca cagcaagaat  60
gccatcatct gtcctcaccc ccatttctcc cctccttccc ctgcaaccat tacgcttact  120
cgcatgtgca ttgagtggtg cacgtgttga acaaacagct acactcacgt gggggcgggt  180
tttcccgccc ttcggcctct cgcgaggccc acccttcccc ttcctcccat aactacagtg  240
ctttggtagg taagcatcct gatcccccgc ggaagctgct cgcgtggcaa ctgtggggac  300
ccagacaggt tatcaaaggc acccggtctt tccgcctcca ggagtatccc tgctagtgaa  360
ttctagtggg gctctgcttg gtgccaacct cccccaaatg cgcgctgcgg gagtgctctt  420
ccccaactca ccctagtatc ctctcatgtg tgtgcttggt cagcatatct gagacgatgt  480
tccgctgtcc cagaccagtc cagcaatgga cgggccagtg tgcgtagtcg tcttccggct  540
tgtccggcgc atgtttggtg aaccggtggg gtaaggttgg tgtgcccaac gcccgtactt  600
```

```
tggtgacaac tcaagaccac ccaggaatgc cagggaggta ccccgcctca cggcgggatc  660
tgaccctggg ctaattgtct acggtggttc ttcttgcttc catttctttc ttctgttc    718

SEQ ID NO: 61          moltype = DNA  length = 699
FEATURE                Location/Qualifiers
source                 1..699
                       mol_type = genomic DNA
                       organism = Salivirus A
SEQUENCE: 61
tatggcaggc gggcttgtgg acggtttcgg cccacccaca gcaagaatgc catcatctgt  60
cctcaccccc aattttccct ttcttcccct gcaatcatca cgcttactcg catgtgcatt  120
gagtggtgca tgtgttgaac aaacagctac actcacatgg gggcgggttt tcccgcccta  180
cggcctctcg cgaggcccac ccttcccctc cccttataac tacagtgctt tggcaggtaa  240
gcatcctgat cccccgcgga agctgctcac gtggcaactg tggggaccca gacaggttat  300
caaaggcacc cggtctttcc gccttcagga gcatccccac tagtgaattc tagtggggct  360
ctgcttggtg ccaacctccc ccaaatgcgc gctgcgggag tgctcttccc caacccatcc  420
tagtatcctc tcatgtgtgt gcttggtcag catatctgag acgacgttcc gctgtcccag  480
accagtccag taatggacgg gccagtgtgc gtagtcgtct tccggcttgt ccggcgcatg  540
tttggtgaac cggtggggta aggttggtgt gcccaacgcc cgtactttgg tgacacctca  600
agaccaccca ggaatgccag ggaggtaccc cgcctcacgg cgggatctga ccctgggcta  660
attgtctacg gtggttcttc ttgcttccac ttctttctt                          699

SEQ ID NO: 62          moltype = DNA  length = 624
FEATURE                Location/Qualifiers
source                 1..624
                       mol_type = genomic DNA
                       organism = Salivirus A
SEQUENCE: 62
ttctcctgca accattacgc ttaatcgcat gtgcattgag tggtgcatgt gttgaacaaa  60
cagctacaat cacatggggg cgggttttcc cgcccccacgg cttctcgcga ggcccatccc  120
tccctttttct cccataacta cagtgctttg gtaggtaagc atcccgatct cccgcggaag  180
ctgctcacgt ggcaactgtg gggacccaga caggttatca aaggcacccg gtctttccgc  240
cttcaggagt atccctgcta gcgaattcta gtagggctct gcttggtgcc aacctctccc  300
aaatgcgcgc tgcgggagtg ctcttcccca aatcacccca gtatcctctc atgtgtgtgc  360
ctggtcagca tatctgagac gatgttccgc tgtcccagac cagtccagta atggacgggc  420
cagtgtgcgt agtcgtcctc cggcttgtcc ggcgcatgtt tggtgaaccg gtggggtaag  480
gttggtgtgc ccaacgcccg taatcagggg atacctcaag gcacccagga atgccaggga  540
ggtatcccgc ctcacagcgg gatctgaccc tggggtaaat gtctgcgggg ggtcctcttg  600
gcccaattct cagtaatttt cagg                                          624

SEQ ID NO: 63          moltype = DNA  length = 650
FEATURE                Location/Qualifiers
source                 1..650
                       mol_type = genomic DNA
                       organism = Salivirus A
SEQUENCE: 63
tctgtcctca ccccatcttc ccttctttcc tgcaccgtta cgcttactcg catgtgcatt  60
gagtggtgca cgtgcttgaa caaacagcta cactcacatg gggcgggtt ttcccgccct  120
gcggcctctc gcgaggccca cccctcccct tcctcccata actacagtgc tttggtaggt  180
aagcatcctg atcccccgcg gaagctgctc acgtggcaac tgtggggacc cagacaggtt  240
atcaaaggca cccggtcttt ccgccttcag gagtatccct gctagtgaat tctagtaggg  300
ctctgcttgg tgccaacctc cccaaatgc gcgctgcggg agtgctcttc cccaactcac  360
cctagtatcc tctcatgtgt gtgcttggtc agcatatctg agacgatgtt ccgctgtccc  420
agaccagtcc agtaatggac gggccagtgt gcgtagtcgt cttccggctt gtccggcgca  480
tgtttggtga accggtgggg taaggttggt gtgcccaacg cccgtacttt ggtgatacct  540
caagaccacc caggaatgcc agggaggtac cccgcttcac agcgggatct gaccctgggc  600
taattgtcta cggtggttct tcttgcttcc acttctttct actgttcatg              650

SEQ ID NO: 64          moltype = DNA  length = 730
FEATURE                Location/Qualifiers
source                 1..730
                       mol_type = genomic DNA
                       organism = Salivirus FHB
SEQUENCE: 64
acatgggggg tctgcggacg gcttcggccc acccgcgaca agaatgccgt catctgtcct  60
cattacccgt attccttccc ttcccccgca accaccacgc ttactcgcgc acgtgttgag  120
tggcacgtgc gttgtccaaa cagctacacc cacacccttc ggggcgggtt tgtcccgccc  180
tcgggttcct cgcggaaccc ccccctccct ctctctcttt ctatccgccc tcacttccca  240
taactacagt gctttggtag gtgagcaccc tgaccccccg cggaagctgc taacgtggca  300
actgtgggga tccaggcagg ttatcaaagg cacccggtct ttccgccttc aggagtatct  360
ctgccggtga attccggtag ggctctgctt ggtgccaacc tcccccaaat gcgcgctgcg  420
ggagtgctct tccccaactc atcttagtaa cctctcatgt gtgtgcttgg tcagcatatc  480
tgaggcgacg ttccgctgtc ccagaccagt ccagcaatgg acgggccagt gtgcgtagtc  540
gctttccggt tttccggcgc atgtttggcg aaacgctgag gtaaggttgg tgtgcccaac  600
gcccgtaatt tggtgatacc tcaagaccac ccaggaatgc cagggaggta ccccacttcg  660
gtgggatctg accctgggct aattgtctac ggtggttctt cttgcttcca cttctctttt  720
ttctggcatg                                                          730

SEQ ID NO: 65          moltype = DNA  length = 741
```

```
FEATURE                Location/Qualifiers
source                 1..741
                       mol_type = genomic DNA
                       organism = Coxsackievirus B3
SEQUENCE: 65
ttaaaacagc ctgtgggttg atcccaccca caggcccatt gggcgctagc actctggtat  60
cacggtacct ttgtgcgcct gttttatacc ccctccccca actgtaactt agaagtaaca  120
cacaccgatc aacagtcagc gtggcacacc agccacgttt tgatcaagca cttctgttac  180
cccggactga gtatcaatag actgctcacg cggttgaagg agaaagcgtt cgttatccgg  240
ccaactactt cgaaaaacct agtaacaccg tggaagttgc agagtgtttc gctcagcact  300
accccagtgt agatcaggtc gatgagtcac cgcattcccc acgggcgacc gtggcggtgg  360
ctgcgttggc ggcctgccca tggggaaacc catgggacgc tctaatacag acatggtgcg  420
aagagtctat tgagctagtt ggtagtcctc cggcccctga atgcggctaa tcctaactgc  480
ggagcacaca ccctcaagcc agagggcagt gtgtcgtaac gggcaactct gcagcggaac  540
cgactacttt gggtgtccgt gtttcatttt attcctatac tggctgctta tggtgacaat  600
tgagagatcg ttaccatata gctattggat tggccatccg gtgactaata gagctattat  660
atatcccttt gttgggttta taccacttag cttgaaagag gttaaaacat tacaattcat  720
tgttaagttg aatacagcaa a                                           741

SEQ ID NO: 66          moltype = DNA  length = 741
FEATURE                Location/Qualifiers
source                 1..741
                       mol_type = genomic DNA
                       organism = Coxsackievirus B1
SEQUENCE: 66
ttaaaacagc ctgtgggttg ttcccaccca caggcccatt gggcgctagc actctggtat  60
cacggtacct ttgtgcgcct gttttacatc ccctccccaa attgtaattt agaagtttca  120
cacaccgatc attagcaagc gtggcacacc agccatgttt tgatcaagca cttctgttac  180
cccggactga gtatcaatag accgctaacg cggttgaagg agaaaacgtt cgttacccgg  240
ccaactactt cgaaaaacct agtaacacca tggaagttgc ggagtgtttc gctcagcact  300
accccagtgt agatcaggtc gatgagtcac cgcgttcccc acgggcgacc gtggcggtgg  360
ctgcgttggc ggcctgccta cggggaaacc cgtaggacgc tctaatacag acatggtgcg  420
aagagtctat tgagctagtt ggtaatcctc cggcccctga atgcggctaa tcctaactgc  480
ggagcacata ccctcaaacc aggggggcagt gtgtcgtaac gggcaactct gcagcggaac  540
cgactacttt gggtgtccgt gtttcatttt attcctatac tggctgctta tggtgacaat  600
tgacaggttg ttaccatata gttattggat tggccatccg gtgactaaca gagcaattat  660
atatctcttt gttgggttta taccacttag cttgaaagag gttaaaacac tacatctcat  720
cattaaacta aatacaacaa a                                           741

SEQ ID NO: 67          moltype = DNA  length = 742
FEATURE                Location/Qualifiers
source                 1..742
                       mol_type = genomic DNA
                       organism = Echovirus 7
SEQUENCE: 67
ttaaaacagc ctgtgggttg ttcccaccca cagggcccat tgggcgtcag caccctggta  60
tcacggtacc tttgtgcgcc tgttttatat cccttccccc aattgtaact tagaagaaac  120
acacaccgat caacagcaag cgtggcacac cagccatgtt ttggtcaagc acttctgtta  180
ccccggactg agtatcaata gactgctcac gcggttgaag gagaaagcgt ccgttatccg  240
gccagctact tcgagaaacc tagtaacacc atggaagttg cggagtgttt cgctcagcac  300
taccccagtg tagatcaggt cgatgagtca ccgctttccc cacgggcgac cgtggcggtg  360
gctgcgttgg cggcctgcct atggggaac ccataggacg ctctaataca gacatggtgc  420
gaagagtcta ttgagctagc tggtattcct ccggcccctg aatgcggcta atcctaactg  480
tggagcacat gcccctaatc caaggggtag tgtgtcgtaa tgagcaattc cgcagcggaa  540
ccgactactt tgggtgtccg tgtttcctct tattcttgta ctggctgctt atggtgacaa  600
ttgagagatt gttaccatat agctattgga ttggccatcc ggtgactaat agagctattg  660
tgtatctctt tgttggattt gtaccactta atttgaaaga aatcaggaca ctacgctaca  720
ttttactatt gaacaccgca aa                                          742

SEQ ID NO: 68          moltype = DNA  length = 743
FEATURE                Location/Qualifiers
source                 1..743
                       mol_type = genomic DNA
                       organism = Coxsackievirus B5
SEQUENCE: 68
ttaaaacagc ctgtgggttg tacccaccca cagggcccac tgggcgctag cactctggta  60
tcacggtacc tttgtgcgcc tgttttatgc ccccttcccc caattgaaac ttagaagtta  120
cacacaccga tcaacagcgg gcgtggcata ccagccgcgt cttgatcaag cactcctgtt  180
tccccggacc gagtatcaat agactgctca cgcggttgaa ggagaaaacg ttcgttaccc  240
ggctaactac ttcgagaaac ctagtagcat catgaaagtt gcgaagcgtt tcgctcagca  300
catccccagt gtagatcagg tcgatgagtc accgcattcc ccacgggcga ccgtggcggt  360
ggctgcgttg gcggcctgcc tacggggcaa cccgtaggac gcttcaatac agacatggtg  420
cgaagagtcg attgagctag ttagtagtcc tccggcccct gaatccggct aatcctaact  480
gcggagcaca taccctcaac ccagggggca ttgtgtcgta acgggtaact ctgcagcgga  540
accgactact ttgggtgtcc gtgtttcctt ttattcttat aatggctgct tatggtgaca  600
attgaaagat tgttaccata tagctattgg attggccatc cggtgtctaa cagagctatt  660
atatacctct ttgttggatt tgtaccactt gatctaaagg aagtcaagac actacaattc  720
atcatacaat tgaacacagc aaa                                         743
```

```
SEQ ID NO: 69          moltype = DNA  length = 743
FEATURE                Location/Qualifiers
source                 1..743
                       mol_type = genomic DNA
                       organism = Enterovirus A71
SEQUENCE: 69
ttaaaacagc ctgtgggttg cacccactca cagggcccac tgggcgcaag cactctggca  60
cttcggtacc tttgtgcgcc tgttttatat cccctcccc  aatgaaattt agaagcagca  120
aaccccgatc aatagcaggc ataacgctcc agttatgtct tgatcaagca cttctgtttc  180
cccggactga gtatcaatag actgctcacg cggttgaagg agaaaacgtt cgttatccgg  240
ctaactactt cggaaagcct agtaacacca tggaagttgc ggagagtttc gttcagcact  300
tccccagtgt agatcaggtc gatgagtcac cgcattcccc acgggcgacc gtggcggtgg  360
ctgcgttggc ggcctgccca tggggtaacc catgggacgc tctaatacgg acatggtgtg  420
aagagtctac tgagctagtt agtagtcctc cggcccctga atgcggctaa tcccaactgc  480
ggagcacacg cccacaagcc agtgggtagt gtgtcgtaac gggcaactct gcagcggaac  540
cgactacttt gggtgtccgt gtttcctttt attcttatgt tggctgctta tggtgacaat  600
taaagagttg ttaccatata gctattggat tggccatccg gtgtgcaaca gagcgatcgt  660
ttacctattt attggttttg taccattgac actgaagtct gtgatcaccc ttaattttat  720
cttaaccctc aacacagcca aac                                          743

SEQ ID NO: 70          moltype = DNA  length = 742
FEATURE                Location/Qualifiers
source                 1..742
                       mol_type = genomic DNA
                       organism = Coxsackievirus A3
SEQUENCE: 70
ttaaaacagc ctgtgggttg tacccaccca cagggcccac tgggcgctag cacactggta  60
ttacggtacc tttgtgcgcc tgttttatac cccccccaac ctcgaaactt agaagtaaag  120
caaacccgat caatagcagg tgcggcgcac cagtcgcatc ttgatcaagc acttctgtaa  180
ccccggaccg agtatcaata gactgctcac gcggttgaag gagaaaacgt tcgttacccg  240
gctaactact tcgagaaacc cagtagcatc atgaaagttg cagagtgttt cgctcagcac  300
tacccccgtg tagatcaggc cgatgagtca ccgcacttcc ccacgggcga ccgtggcggt  360
ggctgcgttg gcggcctgcc tatggggcaa cccataggac gctctaatac ggacatggtg  420
cgaagagtct attgagctag ttagtagtcc tccggcccct gaatgcggct aatcctaact  480
gcggagcaca tacccttaat ccaaagggca gtgtgtcgta acgggtaact ctgcagcgga  540
accgactact ttgggtgtcc gtgtttcctt ttaattttta ctggctgctt atggtgacaa  600
ttgaggaatt gttgccatat agctattgga ttggccatcc ggtgactaac agagctattg  660
tgttccaatt tgttggattt accccgctca cactcacagt cgtaagaacc cttcattacg  720
tgttatttct caactcaaga aa                                           742

SEQ ID NO: 71          moltype = DNA  length = 745
FEATURE                Location/Qualifiers
source                 1..745
                       mol_type = genomic DNA
                       organism = Coxsackievirus A12
SEQUENCE: 71
ttaaaacagc ctgtgggttg tacccaccca cagggcccac tgggcgctag cactctggta  60
ctacggtacc tttgtgtgcc tgttttaagc ccctacccc  cactcgtaac ttagaaggct  120
tctcacactc gatcaatagt aggtgtggca cgccagtcac accgtgatca agcacttctg  180
ttaccccggt ctgagtacca ataagctgct aacgcggctg aaggggaaaa cgatcgttat  240
ccggctaact acttcgagaa acccagtacc accatgaacg ttgcagggtg tttcgctcgg  300
cacaacccca gtgtagatca ggtcgatgag tcaccgtatt ccccacgggc gaccgtggcg  360
gtggctgcgt tggcggcctg cccatggggt gacccatggg acgctctaat actgacatgg  420
tgcgaagagt ctattgagct agttagtagt cctccggccc ctgaatgcgg ctaatcctaa  480
ctgcggagca cataccctta atccaaaggg cagtgtgtcg taacgggcaa ctctgcagcg  540
gaaccgacta ctttgggtgt ccgtgtttcc ttttattctt acattggctg cttatggtga  600
caattgaaaa gttgttacca tatagctatt ggattggcca tccggtgaca aatagagcta  660
ttgtatatct ttttgttggt tacgtacccc ttaattacaa agtggtttca actttgaaat  720
acatcctaac actaaattgt agaaa                                        745

SEQ ID NO: 72          moltype = DNA  length = 742
FEATURE                Location/Qualifiers
source                 1..742
                       mol_type = genomic DNA
                       organism = Echovirus E24
SEQUENCE: 72
ttaaaacagc ctgtgggttg cacccaccca cagggcccac agggcgctag cactctggta  60
tcacggtacc tttgtgcgcc tgttttatta cccttcccc  aattgaaaat tagaagcaat  120
gcacaccgat caacagcagg cgtggcgcac cagtcacgtc tcgatcaagc acttctgttt  180
ccccggaccg agtatcaata gactgctcac gcggttgaag gagaaagtgt tcgttatccg  240
gctaaccact tcgagaaacc cagtaacacc atgaaagttg cagggtgttt cgctcagcac  300
ttccccagtg tagatcaggt cgatgagtca ccgcgttccc cacgggcgac cgtggcggtg  360
gctgcgttgg cggcctgcct atgggttaac ccataggacg ctctaataca gacatggtgc  420
gaagagttta ttgagctggt tagtatccct ccggcccctg aatgcggcta atcctaactg  480
cggagcacgt gcctccaatc caggggggttg catgtcgtaa cgggtaactc tgcagcggaa  540
ccgactactt tgggtgtccg tgtttccttt tattcttata ctggctgctt atggtgacaa  600
tcgaggaatt gttaccatat agctattgga ttggccatcc ggtgtctaac agagcgatta  660
tatacctctt tgttggattt atgcagctca ataccaccaa ctttaacaca ttgaaatata  720
tcttaaagtt aaacacagca aa                                           742
```

```
SEQ ID NO: 73          moltype = DNA  length = 240
FEATURE                Location/Qualifiers
source                 1..240
                       mol_type = genomic DNA
                       organism = Anabaena sp.
SEQUENCE: 73
gaagaaattc tttaagtgga tgctctcaaa ctcagggaaa cctaaatcta gttatagaca  60
aggcaatcct gagccaagcc gaagtagtaa ttagtaagtt aacaatagat gacttacaac  120
taatcggaag gtgcagagac tcgacgggag ctaccctaac gtcaagacga gggtaaagag  180
agagtccaat tctcaaagcc aataggcagt agcgaaagct gcaagagaat gaaaatccgt  240

SEQ ID NO: 74          moltype = DNA  length = 239
FEATURE                Location/Qualifiers
source                 1..239
                       mol_type = genomic DNA
                       organism = Anabaena sp.
SEQUENCE: 74
aagaaattct ttaagtggat gctctcaaac tcagggaaac ctaaatctag ttatagacaa  60
ggcaatcctg agccaagccg aagtagtaat tagtaagtta acaatagatg acttacaact  120
aatcggaagg tgcagagact cgacgggagc taccctaacg tcaagacgag ggtaaagaga  180
gagtccaatt ctcaaagcca ataggcagta gcgaaagctg caagagaatg aaaatccgt   239

SEQ ID NO: 75          moltype = DNA  length = 238
FEATURE                Location/Qualifiers
source                 1..238
                       mol_type = genomic DNA
                       organism = Anabaena sp.
SEQUENCE: 75
agaaattctt taagtggatg ctctcaaact cagggaaacc taaatctagt tatagacaag  60
gcaatcctga gccaagccga agtagtaatt agtaagttaa caatagatga cttacaacta  120
atcggaaggt gcagagactc gacgggagct accctaacgt caagacgagg gtaaagagag  180
agtccaattc tcaaagccaa taggcagtag cgaaagctgc aagagaatga aaatccgt    238

SEQ ID NO: 76          moltype = DNA  length = 190
FEATURE                Location/Qualifiers
source                 1..190
                       mol_type = genomic DNA
                       organism = Anabaena sp.
SEQUENCE: 76
gttatagaca aggcaatcct gagccaagcc gaagtagtaa ttagtaagtt aacaatagat  60
gacttacaac taatcggaag gtgcagagac tcgacgggag ctaccctaac gtcaagacga  120
gggtaaagag agagtccaat tctcaaagcc aataggcagt agcgaaagct gcaagagaat  180
gaaaatccgt                                                         190

SEQ ID NO: 77          moltype = DNA  length = 189
FEATURE                Location/Qualifiers
source                 1..189
                       mol_type = genomic DNA
                       organism = Anabaena sp.
SEQUENCE: 77
ttatagacaa ggcaatcctg agccaagccg aagtagtaat tagtaagtta acaatagatg  60
acttacaact aatcggaagg tgcagagact cgacgggagc taccctaacg tcaagacgag  120
ggtaaagaga gagtccaatt ctcaaagcca ataggcagta gcgaaagctg caagagaatg  180
aaaatccgt                                                          189

SEQ ID NO: 78          moltype = DNA  length = 188
FEATURE                Location/Qualifiers
source                 1..188
                       mol_type = genomic DNA
                       organism = Anabaena sp.
SEQUENCE: 78
tatagacaag gcaatcctga gccaagccga agtagtaatt agtaagttaa caatagatga  60
cttacaacta atcggaaggt gcagagactc gacgggagct accctaacgt caagacgagg  120
gtaaagagag agtccaattc tcaaagccaa taggcagtag cgaaagctgc aagagaatga  180
aaatccgt                                                           188

SEQ ID NO: 79          moltype = DNA  length = 187
FEATURE                Location/Qualifiers
source                 1..187
                       mol_type = genomic DNA
                       organism = Anabaena sp.
SEQUENCE: 79
atagacaagg caatcctgag ccaagccgaa gtagtaatta gtaagttaac aatagatgac  60
ttacaactaa tcggaaggtg cagagactcg acgggagcta ccctaacgtc aagacgaggg  120
taaagagaga gtccaattct caaagccaat aggcagtagc gaaagctgca agagaatgaa  180
aatccgt                                                            187

SEQ ID NO: 80          moltype = DNA  length = 186
```

```
FEATURE                Location/Qualifiers
source                 1..186
                       mol_type = genomic DNA
                       organism = Anabaena sp.
SEQUENCE: 80
tagacaaggc aatcctgagc caagccgaag tagtaattag taagttaaca atagatgact  60
tacaactaat cggaaggtgc agagactcga cgggagctac cctaacgtca agacgagggt  120
aaagagagag tccaattctc aaagccaata ggcagtagcg aaagctgcaa gagaatgaaa  180
atccgt                                                             186

SEQ ID NO: 81          moltype = DNA  length = 139
FEATURE                Location/Qualifiers
source                 1..139
                       mol_type = genomic DNA
                       organism = Anabaena sp.
SEQUENCE: 81
acaatagatg acttacaact aatcggaagg tgcagagact cgacgggagc taccctaacg  60
tcaagacgag ggtaaagaga gagtccaatt ctcaaagcca ataggcagta gcgaaagctg  120
caagagaatg aaaatccgt                                               139

SEQ ID NO: 82          moltype = DNA  length = 138
FEATURE                Location/Qualifiers
source                 1..138
                       mol_type = genomic DNA
                       organism = Anabaena sp.
SEQUENCE: 82
caatagatga cttacaacta atcggaaggt gcagagactc gacgggagct accctaacgt  60
caagacgagg gtaaagagag agtccaattc tcaaagccaa taggcagtag cgaaagctgc  120
aagagaatga aaatccgt                                                138

SEQ ID NO: 83          moltype = DNA  length = 137
FEATURE                Location/Qualifiers
source                 1..137
                       mol_type = genomic DNA
                       organism = Anabaena sp.
SEQUENCE: 83
aatagatgac ttacaactaa tcggaaggtg cagagactcg acgggagcta ccctaacgtc  60
aagacgaggg taaagagaga gtccaattct caaagccaat aggcagtagc gaaagctgca  120
agagaatgaa aatccgt                                                 137

SEQ ID NO: 84          moltype = DNA  length = 136
FEATURE                Location/Qualifiers
source                 1..136
                       mol_type = genomic DNA
                       organism = Anabaena sp.
SEQUENCE: 84
atagatgact tacaactaat cggaaggtgc agagactcga cgggagctac cctaacgtca  60
agacgagggt aaagagagag tccaattctc aaagccaata ggcagtagcg aaagctgcaa  120
gagaatgaaa atccgt                                                  136

SEQ ID NO: 85          moltype = DNA  length = 135
FEATURE                Location/Qualifiers
source                 1..135
                       mol_type = genomic DNA
                       organism = Anabaena sp.
SEQUENCE: 85
tagatgactt acaactaatc ggaaggtgca gagactcgac gggagctacc ctaacgtcaa  60
gacgagggta aagagagagt ccaattctca aagccaatag gcagtagcga aagctgcaag  120
agaatgaaaa tccgt                                                   135

SEQ ID NO: 86          moltype = DNA  length = 134
FEATURE                Location/Qualifiers
source                 1..134
                       mol_type = genomic DNA
                       organism = Anabaena sp.
SEQUENCE: 86
agatgactta caactaatcg gaaggtgcag agactcgacg ggagctaccc taacgtcaag  60
acgagggtaa agagagagtc caattctcaa agccaatagg cagtagcgaa agctgcaaga  120
gaatgaaaat ccgt                                                    134

SEQ ID NO: 87          moltype = DNA  length = 133
FEATURE                Location/Qualifiers
source                 1..133
                       mol_type = genomic DNA
                       organism = Anabaena sp.
SEQUENCE: 87
gatgacttac aactaatcgg aaggtgcaga gactcgacgg gagctaccct aacgtcaaga  60
cgagggtaaa gagagagtcc aattctcaaa gccaataggc agtagcgaaa gctgcaagag  120
aatgaaaatc cgt                                                     133
```

```
SEQ ID NO: 88          moltype = DNA  length = 132
FEATURE                Location/Qualifiers
source                 1..132
                       mol_type = genomic DNA
                       organism = Anabaena sp.
SEQUENCE: 88
atgacttaca actaatcgga aggtgcagag actcgacggg agctacccta acgtcaagac  60
gagggtaaag agagagtcca attctcaaag ccaataggca gtagcgaaag ctgcaagaga  120
atgaaaatcc gt                                                      132

SEQ ID NO: 89          moltype = DNA  length = 131
FEATURE                Location/Qualifiers
source                 1..131
                       mol_type = genomic DNA
                       organism = Anabaena sp.
SEQUENCE: 89
tgacttacaa ctaatcggaa ggtgcagaga ctcgacggga gctaccctaa cgtcaagacg  60
agggtaaaga gagagtccaa ttctcaaagc caataggcag tagcgaaagc tgcaagagaa  120
tgaaaatccg t                                                       131

SEQ ID NO: 90          moltype = DNA  length = 78
FEATURE                Location/Qualifiers
source                 1..78
                       mol_type = genomic DNA
                       organism = Anabaena sp.
SEQUENCE: 90
caagacgagg gtaaagagag agtccaattc tcaaagccaa taggcagtag cgaaagctgc  60
aagagaatga aaatccgt                                                78

SEQ ID NO: 91          moltype = DNA  length = 77
FEATURE                Location/Qualifiers
source                 1..77
                       mol_type = genomic DNA
                       organism = Anabaena sp.
SEQUENCE: 91
aagacgaggg taaagagaga gtccaattct caaagccaat aggcagtagc gaaagctgca  60
agagaatgaa aatccgt                                                 77

SEQ ID NO: 92          moltype = DNA  length = 76
FEATURE                Location/Qualifiers
source                 1..76
                       mol_type = genomic DNA
                       organism = Anabaena sp.
SEQUENCE: 92
agacgagggt aaagagagag tccaattctc aaagccaata ggcagtagcg aaagctgcaa  60
gagaatgaaa atccgt                                                  76

SEQ ID NO: 93          moltype = DNA  length = 75
FEATURE                Location/Qualifiers
source                 1..75
                       mol_type = genomic DNA
                       organism = Anabaena sp.
SEQUENCE: 93
gacgagggta aagagagagt ccaattctca aagccaatag gcagtagcga aagctgcaag  60
agaatgaaaa tccgt                                                   75

SEQ ID NO: 94          moltype = DNA  length = 74
FEATURE                Location/Qualifiers
source                 1..74
                       mol_type = genomic DNA
                       organism = Anabaena sp.
SEQUENCE: 94
acgagggtaa agagagagtc caattctcaa agccaatagg cagtagcgaa agctgcaaga  60
gaatgaaaat ccgt                                                    74

SEQ ID NO: 95          moltype = DNA  length = 40
FEATURE                Location/Qualifiers
source                 1..40
                       mol_type = genomic DNA
                       organism = Anabaena sp.
SEQUENCE: 95
aataggcagt agcgaaagct gcaagagaat gaaaatccgt                        40

SEQ ID NO: 96          moltype = DNA  length = 39
FEATURE                Location/Qualifiers
source                 1..39
                       mol_type = genomic DNA
                       organism = Anabaena sp.
```

```
SEQUENCE: 96
ataggcagta gcgaaagctg caagagaatg aaaatccgt                        39

SEQ ID NO: 97           moltype = DNA  length = 38
FEATURE                 Location/Qualifiers
source                  1..38
                        mol_type = genomic DNA
                        organism = Anabaena sp.
SEQUENCE: 97
taggcagtag cgaaagctgc aagagaatga aaatccgt                         38

SEQ ID NO: 98           moltype = DNA  length = 37
FEATURE                 Location/Qualifiers
source                  1..37
                        mol_type = genomic DNA
                        organism = Anabaena sp.
SEQUENCE: 98
aggcagtagc gaaagctgca agagaatgaa aatccgt                          37

SEQ ID NO: 99           moltype = DNA  length = 36
FEATURE                 Location/Qualifiers
source                  1..36
                        mol_type = genomic DNA
                        organism = Anabaena sp.
SEQUENCE: 99
ggcagtagcg aaagctgcaa gagaatgaaa atccgt                           36

SEQ ID NO: 100          moltype = DNA  length = 27
FEATURE                 Location/Qualifiers
source                  1..27
                        mol_type = genomic DNA
                        organism = Anabaena sp.
SEQUENCE: 100
gaaagctgca agagaatgaa aatccgt                                     27

SEQ ID NO: 101          moltype = DNA  length = 26
FEATURE                 Location/Qualifiers
source                  1..26
                        mol_type = genomic DNA
                        organism = Anabaena sp.
SEQUENCE: 101
aaagctgcaa gagaatgaaa atccgt                                      26

SEQ ID NO: 102          moltype = DNA  length = 25
FEATURE                 Location/Qualifiers
source                  1..25
                        mol_type = genomic DNA
                        organism = Anabaena sp.
SEQUENCE: 102
aagctgcaag agaatgaaaa tccgt                                       25

SEQ ID NO: 103          moltype = DNA  length = 24
FEATURE                 Location/Qualifiers
source                  1..24
                        mol_type = genomic DNA
                        organism = Anabaena sp.
SEQUENCE: 103
agctgcaaga gaatgaaaat ccgt                                        24

SEQ ID NO: 104          moltype = DNA  length = 23
FEATURE                 Location/Qualifiers
source                  1..23
                        mol_type = genomic DNA
                        organism = Anabaena sp.
SEQUENCE: 104
gctgcaagag aatgaaaatc cgt                                         23

SEQ ID NO: 105          moltype = DNA  length = 22
FEATURE                 Location/Qualifiers
source                  1..22
                        mol_type = genomic DNA
                        organism = Anabaena sp.
SEQUENCE: 105
ctgcaagaga atgaaaatcc gt                                          22

SEQ ID NO: 106          moltype = DNA  length = 18
FEATURE                 Location/Qualifiers
```

```
source                  1..18
                        mol_type = genomic DNA
                        organism = Anabaena sp.
SEQUENCE: 106
aagagaatga aaatccgt                                             18

SEQ ID NO: 107          moltype = DNA  length = 17
FEATURE                 Location/Qualifiers
source                  1..17
                        mol_type = genomic DNA
                        organism = Anabaena sp.
SEQUENCE: 107
agagaatgaa aatccgt                                              17

SEQ ID NO: 108          moltype = DNA  length = 16
FEATURE                 Location/Qualifiers
source                  1..16
                        mol_type = genomic DNA
                        organism = Anabaena sp.
SEQUENCE: 108
gagaatgaaa atccgt                                               16

SEQ ID NO: 109          moltype = DNA  length = 35
FEATURE                 Location/Qualifiers
source                  1..35
                        mol_type = genomic DNA
                        organism = Anabaena sp.
SEQUENCE: 109
gcagtagcga aagctgcaag agaatgaaaa tccgt                          35

SEQ ID NO: 110          moltype = DNA  length = 33
FEATURE                 Location/Qualifiers
source                  1..33
                        mol_type = genomic DNA
                        organism = Anabaena sp.
SEQUENCE: 110
agtagcgaaa gctgcaagag aatgaaaatc cgt                            33

SEQ ID NO: 111          moltype = DNA  length = 32
FEATURE                 Location/Qualifiers
source                  1..32
                        mol_type = genomic DNA
                        organism = Anabaena sp.
SEQUENCE: 111
gtagcgaaag ctgcaagaga atgaaaatcc gt                             32

SEQ ID NO: 112          moltype = DNA  length = 26
FEATURE                 Location/Qualifiers
source                  1..26
                        mol_type = genomic DNA
                        organism = Anabaena sp.
SEQUENCE: 112
acggacttaa ataattgagc cttaaa                                    26

SEQ ID NO: 113          moltype = DNA  length = 27
FEATURE                 Location/Qualifiers
source                  1..27
                        mol_type = genomic DNA
                        organism = Anabaena sp.
SEQUENCE: 113
acggacttaa ataattgagc cttaaag                                   27

SEQ ID NO: 114          moltype = DNA  length = 28
FEATURE                 Location/Qualifiers
source                  1..28
                        mol_type = genomic DNA
                        organism = Anabaena sp.
SEQUENCE: 114
acggacttaa ataattgagc cttaaaga                                  28

SEQ ID NO: 115          moltype = DNA  length = 76
FEATURE                 Location/Qualifiers
source                  1..76
                        mol_type = genomic DNA
                        organism = Anabaena sp.
SEQUENCE: 115
acggacttaa ataattgagc cttaaagaag aaattcttta agtggatgct ctcaaactca  60
gggaaaccta aatcta                                               76
```

```
SEQ ID NO: 116          moltype = DNA  length = 77
FEATURE                 Location/Qualifiers
source                  1..77
                        mol_type = genomic DNA
                        organism = Anabaena sp.
SEQUENCE: 116
acggacttaa ataattgagc cttaaagaag aaattcttta agtggatgct ctcaaactca  60
gggaaaccta aatctag                                                 77

SEQ ID NO: 117          moltype = DNA  length = 78
FEATURE                 Location/Qualifiers
source                  1..78
                        mol_type = genomic DNA
                        organism = Anabaena sp.
SEQUENCE: 117
acggacttaa ataattgagc cttaaagaag aaattcttta agtggatgct ctcaaactca  60
gggaaaccta aatctagt                                                78

SEQ ID NO: 118          moltype = DNA  length = 79
FEATURE                 Location/Qualifiers
source                  1..79
                        mol_type = genomic DNA
                        organism = Anabaena sp.
SEQUENCE: 118
acggacttaa ataattgagc cttaaagaag aaattcttta agtggatgct ctcaaactca  60
gggaaaccta aatctagtt                                               79

SEQ ID NO: 119          moltype = DNA  length = 80
FEATURE                 Location/Qualifiers
source                  1..80
                        mol_type = genomic DNA
                        organism = Anabaena sp.
SEQUENCE: 119
acggacttaa ataattgagc cttaaagaag aaattcttta agtggatgct ctcaaactca  60
gggaaaccta aatctagtta                                              80

SEQ ID NO: 120          moltype = DNA  length = 127
FEATURE                 Location/Qualifiers
source                  1..127
                        mol_type = genomic DNA
                        organism = Anabaena sp.
SEQUENCE: 120
acggacttaa ataattgagc cttaaagaag aaattcttta agtggatgct ctcaaactca  60
gggaaaccta aatctagtta tagacaaggc aatcctgagc caagccgaag tagtaattag  120
taagtta                                                            127

SEQ ID NO: 121          moltype = DNA  length = 128
FEATURE                 Location/Qualifiers
source                  1..128
                        mol_type = genomic DNA
                        organism = Anabaena sp.
SEQUENCE: 121
acggacttaa ataattgagc cttaaagaag aaattcttta agtggatgct ctcaaactca  60
gggaaaccta aatctagtta tagacaaggc aatcctgagc caagccgaag tagtaattag  120
taagttaa                                                           128

SEQ ID NO: 122          moltype = DNA  length = 129
FEATURE                 Location/Qualifiers
source                  1..129
                        mol_type = genomic DNA
                        organism = Anabaena sp.
SEQUENCE: 122
acggacttaa ataattgagc cttaaagaag aaattcttta agtggatgct ctcaaactca  60
gggaaaccta aatctagtta tagacaaggc aatcctgagc caagccgaag tagtaattag  120
taagttaac                                                          129

SEQ ID NO: 123          moltype = DNA  length = 130
FEATURE                 Location/Qualifiers
source                  1..130
                        mol_type = genomic DNA
                        organism = Anabaena sp.
SEQUENCE: 123
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca                                                         130

SEQ ID NO: 124          moltype = DNA  length = 131
FEATURE                 Location/Qualifiers
```

-continued

```
source                1..131
                      mol_type = genomic DNA
                      organism = Anabaena sp.
SEQUENCE: 124
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca a                                                       131

SEQ ID NO: 125        moltype = DNA  length = 132
FEATURE               Location/Qualifiers
source                1..132
                      mol_type = genomic DNA
                      organism = Anabaena sp.
SEQUENCE: 125
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca at                                                      132

SEQ ID NO: 126        moltype = DNA  length = 133
FEATURE               Location/Qualifiers
source                1..133
                      mol_type = genomic DNA
                      organism = Anabaena sp.
SEQUENCE: 126
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca ata                                                     133

SEQ ID NO: 127        moltype = DNA  length = 134
FEATURE               Location/Qualifiers
source                1..134
                      mol_type = genomic DNA
                      organism = Anabaena sp.
SEQUENCE: 127
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atag                                                    134

SEQ ID NO: 128        moltype = DNA  length = 135
FEATURE               Location/Qualifiers
source                1..135
                      mol_type = genomic DNA
                      organism = Anabaena sp.
SEQUENCE: 128
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca ataga                                                   135

SEQ ID NO: 129        moltype = DNA  length = 188
FEATURE               Location/Qualifiers
source                1..188
                      mol_type = genomic DNA
                      organism = Anabaena sp.
SEQUENCE: 129
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgt                                                           188

SEQ ID NO: 130        moltype = DNA  length = 189
FEATURE               Location/Qualifiers
source                1..189
                      mol_type = genomic DNA
                      organism = Anabaena sp.
SEQUENCE: 130
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtc                                                          189

SEQ ID NO: 131        moltype = DNA  length = 190
FEATURE               Location/Qualifiers
source                1..190
                      mol_type = genomic DNA
                      organism = Anabaena sp.
SEQUENCE: 131
acggacttaa ataattgagc cttaaagaag aaattcttta agtggatgct ctcaaactca  60
gggaaaccta aatctagtta tagacaaggc aatcctgagc caagccgaag tagtaattag  120
```

```
taagttaaca atagatgact tacaactaat cggaaggtgc agagactcga cgggagctac  180
cctaacgtca                                                         190

SEQ ID NO: 132         moltype = DNA  length = 191
FEATURE                Location/Qualifiers
source                 1..191
                       mol_type = genomic DNA
                       organism = Anabaena sp.
SEQUENCE: 132
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca a                                                       191

SEQ ID NO: 133         moltype = DNA  length = 192
FEATURE                Location/Qualifiers
source                 1..192
                       mol_type = genomic DNA
                       organism = Anabaena sp.
SEQUENCE: 133
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca ag                                                      192

SEQ ID NO: 134         moltype = DNA  length = 226
FEATURE                Location/Qualifiers
source                 1..226
                       mol_type = genomic DNA
                       organism = Anabaena sp.
SEQUENCE: 134
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagcc                 226

SEQ ID NO: 135         moltype = DNA  length = 227
FEATURE                Location/Qualifiers
source                 1..227
                       mol_type = genomic DNA
                       organism = Anabaena sp.
SEQUENCE: 135
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagcca                227

SEQ ID NO: 136         moltype = DNA  length = 228
FEATURE                Location/Qualifiers
source                 1..228
                       mol_type = genomic DNA
                       organism = Anabaena sp.
SEQUENCE: 136
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaa               228

SEQ ID NO: 137         moltype = DNA  length = 229
FEATURE                Location/Qualifiers
source                 1..229
                       mol_type = genomic DNA
                       organism = Anabaena sp.
SEQUENCE: 137
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaat              229

SEQ ID NO: 138         moltype = DNA  length = 230
FEATURE                Location/Qualifiers
source                 1..230
                       mol_type = genomic DNA
                       organism = Anabaena sp.
SEQUENCE: 138
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata             230
```

```
SEQ ID NO: 139         moltype = DNA  length = 239
FEATURE                Location/Qualifiers
source                 1..239
                       mol_type = genomic DNA
                       organism = Anabaena sp.
SEQUENCE: 139
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagc   239

SEQ ID NO: 140         moltype = DNA  length = 240
FEATURE                Location/Qualifiers
source                 1..240
                       mol_type = genomic DNA
                       organism = Anabaena sp.
SEQUENCE: 140
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240

SEQ ID NO: 141         moltype = DNA  length = 241
FEATURE                Location/Qualifiers
source                 1..241
                       mol_type = genomic DNA
                       organism = Anabaena sp.
SEQUENCE: 141
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
a                                                                  241

SEQ ID NO: 142         moltype = DNA  length = 242
FEATURE                Location/Qualifiers
source                 1..242
                       mol_type = genomic DNA
                       organism = Anabaena sp.
SEQUENCE: 142
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
aa                                                                 242

SEQ ID NO: 143         moltype = DNA  length = 243
FEATURE                Location/Qualifiers
source                 1..243
                       mol_type = genomic DNA
                       organism = Anabaena sp.
SEQUENCE: 143
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
aaa                                                                243

SEQ ID NO: 144         moltype = DNA  length = 244
FEATURE                Location/Qualifiers
source                 1..244
                       mol_type = genomic DNA
                       organism = Anabaena sp.
SEQUENCE: 144
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
aaag                                                               244

SEQ ID NO: 145         moltype = DNA  length = 248
FEATURE                Location/Qualifiers
source                 1..248
                       mol_type = genomic DNA
                       organism = Anabaena sp.
SEQUENCE: 145
acggacttaa ataattgagc cttaaagaag aaattcttta agtggatgct ctcaaactca  60
gggaaaccta aatctagtta tagacaaggc aatcctgagc caagccgaag tagtaattag  120
```

```
taagttaaca atagatgact tacaactaat cggaaggtgc agagactcga cgggagctac  180
cctaacgtca agacgagggt aaagagagag tccaattctc aaagccaata ggcagtagcg  240
aaagctgc                                                           248

SEQ ID NO: 146         moltype = DNA  length = 249
FEATURE                Location/Qualifiers
source                 1..249
                       mol_type = genomic DNA
                       organism = Anabaena sp.
SEQUENCE: 146
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
aaagctgca                                                          249

SEQ ID NO: 147         moltype = DNA  length = 250
FEATURE                Location/Qualifiers
source                 1..250
                       mol_type = genomic DNA
                       organism = Anabaena sp.
SEQUENCE: 147
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggcagtagcg  240
aaagctgcaa                                                         250

SEQ ID NO: 148         moltype = DNA  length = 231
FEATURE                Location/Qualifiers
source                 1..231
                       mol_type = genomic DNA
                       organism = Anabaena sp.
SEQUENCE: 148
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata g           231

SEQ ID NO: 149         moltype = DNA  length = 233
FEATURE                Location/Qualifiers
source                 1..233
                       mol_type = genomic DNA
                       organism = Anabaena sp.
SEQUENCE: 149
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggc         233

SEQ ID NO: 150         moltype = DNA  length = 234
FEATURE                Location/Qualifiers
source                 1..234
                       mol_type = genomic DNA
                       organism = Anabaena sp.
SEQUENCE: 150
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata ggca        234

SEQ ID NO: 151         moltype = DNA  length = 104
FEATURE                Location/Qualifiers
source                 1..104
                       mol_type = genomic DNA
                       organism = Azoarcus sp.
SEQUENCE: 151
tgcgccgatg aaggtgtaga gactagacgg cacccaccta aggcaaacgc tatggtgaag  60
gcatagtcca gggagtggcg aaagtcacac aaaccggaat ccgt                   104

SEQ ID NO: 152         moltype = DNA  length = 141
FEATURE                Location/Qualifiers
source                 1..141
                       mol_type = genomic DNA
                       organism = Azoarcus sp.
SEQUENCE: 152
ccgggcgtat ggcaacgccg agccaagctt cggcgcctgc gccgatgaag gtgtagagac  60
tagacggcac ccacctaagg caaacgctat ggtgaaggca tagtccaggg agtggcgaaa  120
gtcacacaaa ccggaatccg t                                            141
```

```
SEQ ID NO: 153          moltype = DNA  length = 78
FEATURE                 Location/Qualifiers
source                  1..78
                        mol_type = genomic DNA
                        organism = Azoarcus sp.
SEQUENCE: 153
acggcaccca cctaaggcaa acgctatggt gaaggcatag tccagggagt ggcgaaagtc  60
acacaaaccg gaatccgt                                                78

SEQ ID NO: 154          moltype = DNA  length = 58
FEATURE                 Location/Qualifiers
source                  1..58
                        mol_type = genomic DNA
                        organism = Azoarcus sp.
SEQUENCE: 154
acgctatggt gaaggcatag tccagggagt ggcgaaagtc acacaaaccg gaatccgt    58

SEQ ID NO: 155          moltype = DNA  length = 75
FEATURE                 Location/Qualifiers
source                  1..75
                        mol_type = genomic DNA
                        organism = Thiomargarita sp.
SEQUENCE: 155
attaaagtta tagaattatc agagaatgat atagtccaag ccttatggta acatgagggc  60
acttgaccct ggtag                                                   75

SEQ ID NO: 156          moltype = DNA  length = 195
FEATURE                 Location/Qualifiers
source                  1..195
                        mol_type = genomic DNA
                        organism = Staphylococcus virus Twort
SEQUENCE: 156
aagatgtagg caatcctgag ctaagctctt agtaataaga gaaagtgcaa cgactattcc  60
gataggaagt agggtcaagt gactcgaaat ggggattacc cttctagggt agtgatatag  120
tctgaacata tatggaaaca tatagaagga taggagtaac gaacctattc gtaacataat  180
tgaactttta gttat                                                   195

SEQ ID NO: 157          moltype = DNA  length = 163
FEATURE                 Location/Qualifiers
source                  1..163
                        mol_type = genomic DNA
                        organism = Staphylococcus virus Twort
SEQUENCE: 157
taataagaga aagtgcaacg actattccga taggaagtag ggtcaagtga ctcgaaatgg  60
ggattaccct tctagggtag tgatatagtc tgaacatata tggaaacata tagaaggata  120
ggagtaacga acctattcgt aacataattg aacttttagt tat                    163

SEQ ID NO: 158          moltype = DNA  length = 133
FEATURE                 Location/Qualifiers
source                  1..133
                        mol_type = genomic DNA
                        organism = Staphylococcus virus Twort
SEQUENCE: 158
taggaagtag ggtcaagtga ctcgaaatgg ggattaccct tctagggtag tgatatagtc  60
tgaacatata tggaaacata tagaaggata ggagtaacga acctattcgt aacataattg  120
aacttttagt tat                                                     133

SEQ ID NO: 159          moltype = DNA  length = 92
FEATURE                 Location/Qualifiers
source                  1..92
                        mol_type = genomic DNA
                        organism = Staphylococcus virus Twort
SEQUENCE: 159
ctagggtagt gatatagtct gaacatatat ggaaacatat agaaggatag gagtaacgaa  60
cctattcgta acataattga acttttagtt at                                92

SEQ ID NO: 160          moltype = DNA  length = 92
FEATURE                 Location/Qualifiers
source                  1..92
                        mol_type = genomic DNA
                        organism = unidentified
                        note = LSUp1 sequence
SEQUENCE: 160
agttaataaa gatgatgaaa tagtctgaac cattttgaga aaagtggaaa taaaagaaaa  60
tcttttatga taacataaat tgaacaggct aa                                92

SEQ ID NO: 161          moltype = DNA  length = 62
FEATURE                 Location/Qualifiers
```

```
source                  1..62
                        mol_type = genomic DNA
                        organism = Bacteriophage Phi I
SEQUENCE: 161
caaagactga tgatatagtc cgacactcct agtaatagga gaatacagaa aggatgaaat  60
cc                                                                 62

SEQ ID NO: 162          moltype = DNA  length = 76
FEATURE                 Location/Qualifiers
source                  1..76
                        mol_type = genomic DNA
                        organism = Nostoc sp.
SEQUENCE: 162
agtcgagggt aaagggagag tccaattctc aaagcctatt ggcagtagcg aaagctgcgg  60
gagaatgaaa atccgt                                                  76

SEQ ID NO: 163          moltype = DNA  length = 76
FEATURE                 Location/Qualifiers
source                  1..76
                        mol_type = genomic DNA
                        organism = Nostoc sp.
SEQUENCE: 163
agccgagggt aaagggagag tccaattctc aaagccaata ggcagtagcg aaagctgcgg  60
gagaatgaaa atccgt                                                  76

SEQ ID NO: 164          moltype = DNA  length = 89
FEATURE                 Location/Qualifiers
source                  1..89
                        mol_type = genomic DNA
                        organism = Nodularia sp.
SEQUENCE: 164
agccgagggt aaagggagag tccaattctc aaagccgaag gttattaaaa cctggcagca  60
gtgaaagctg cgggagaatg aaaatccgt                                    89

SEQ ID NO: 165          moltype = DNA  length = 79
FEATURE                 Location/Qualifiers
source                  1..79
                        mol_type = genomic DNA
                        organism = Pleurocapsa sp.
SEQUENCE: 165
agctgagggt aaagagagag tccaattctc aaagccagca gatggcagta gcgaaagctg  60
cgggagaatg aaaatccgt                                               79

SEQ ID NO: 166          moltype = DNA  length = 76
FEATURE                 Location/Qualifiers
source                  1..76
                        mol_type = genomic DNA
                        organism = Planktothrix sp.
SEQUENCE: 166
agccgagggt aaagagagag tccaattctc aaagccaatt ggtagtagcg aaagctacgg  60
gagaatgaaa atccgt                                                  76

SEQ ID NO: 167          moltype = DNA  length = 118
FEATURE                 Location/Qualifiers
source                  1..118
                        mol_type = genomic DNA
                        organism = Azoarcus sp.
SEQUENCE: 167
gcggactcat atttcgatgt gccttgcgcc gggaaaccac gcaagggatg gtgtcaaatt  60
cggcgaaacc taagcgcccg cccgggcgta tggcaacgcc gagccaagct tcggcgcc    118

SEQ ID NO: 168          moltype = DNA  length = 81
FEATURE                 Location/Qualifiers
source                  1..81
                        mol_type = genomic DNA
                        organism = Azoarcus sp.
SEQUENCE: 168
gcggactcat atttcgatgt gccttgcgcc gggaaaccac gcaagggatg gtgtcaaatt  60
cggcgaaacc taagcgcccg c                                            81

SEQ ID NO: 169          moltype = DNA  length = 144
FEATURE                 Location/Qualifiers
source                  1..144
                        mol_type = genomic DNA
                        organism = Azoarcus sp.
SEQUENCE: 169
gcggactcat atttcgatgt gccttgcgcc gggaaaccac gcaagggatg gtgtcaaatt  60
cggcgaaacc taagcgcccg cccgggcgta tggcaacgcc gagccaagct tcggcgcctg  120
cgccgatgaa ggtgtagaga ctag                                         144
```

```
SEQ ID NO: 170          moltype = DNA  length = 164
FEATURE                 Location/Qualifiers
source                  1..164
                        mol_type = genomic DNA
                        organism = Azoarcus sp.
SEQUENCE: 170
gcggactcat atttcgatgt gccttgcgcc gggaaaccac gcaagggatg gtgtcaaatt  60
cggcgaaacc taagcgcccg cccgggcgta tggcaacgcc gagccaagct tcggcgcctg  120
cgccgatgaa ggtgtagaga ctagacggca cccacctaag gcaa                   164

SEQ ID NO: 171          moltype = DNA  length = 179
FEATURE                 Location/Qualifiers
source                  1..179
                        mol_type = genomic DNA
                        organism = Thiomargarita sp.
SEQUENCE: 171
aggattagat actacactaa gtgtccccca gactggtgac agtctggtgt gcatccagct  60
atatcggtga aaccccattg gggtaatacc gagggaagct atattatata tatattaata  120
aatagccccg tagagactat gtaggtaagg agatagaaga tgataaaatc aaaatcatc   179

SEQ ID NO: 172          moltype = DNA  length = 84
FEATURE                 Location/Qualifiers
source                  1..84
                        mol_type = genomic DNA
                        organism = Staphylococcus virus Twort
SEQUENCE: 172
actactgaaa gcataaataa ttgtgccttt atacagtaat gtatatcgaa aaatcctcta  60
attcagggaa cacctaaaca aact                                         84

SEQ ID NO: 173          moltype = DNA  length = 116
FEATURE                 Location/Qualifiers
source                  1..116
                        mol_type = genomic DNA
                        organism = Staphylococcus virus Twort
SEQUENCE: 173
actactgaaa gcataaataa ttgtgccttt atacagtaat gtatatcgaa aaatcctcta  60
attcagggaa cacctaaaca aactaagatg taggcaatcc tgagctaagc tcttag      116

SEQ ID NO: 174          moltype = DNA  length = 146
FEATURE                 Location/Qualifiers
source                  1..146
                        mol_type = genomic DNA
                        organism = Staphylococcus virus Twort
SEQUENCE: 174
actactgaaa gcataaataa ttgtgccttt atacagtaat gtatatcgaa aaatcctcta  60
attcagggaa cacctaaaca aactaagatg taggcaatcc tgagctaagc tcttagtaat  120
aagagaaagt gcaacgacta ttccga                                       146

SEQ ID NO: 175          moltype = DNA  length = 187
FEATURE                 Location/Qualifiers
source                  1..187
                        mol_type = genomic DNA
                        organism = Staphylococcus virus Twort
SEQUENCE: 175
actactgaaa gcataaataa ttgtgccttt atacagtaat gtatatcgaa aaatcctcta  60
attcagggaa cacctaaaca aactaagatg taggcaatcc tgagctaagc tcttagtaat  120
aagagaaagt gcaacgacta ttccgatagg aagtagggtc aagtgactcg aaatggggat  180
taccctt                                                            187

SEQ ID NO: 176          moltype = DNA  length = 216
FEATURE                 Location/Qualifiers
source                  1..216
                        mol_type = genomic DNA
                        organism = unidentified
                        note = LSUp1 sequence
SEQUENCE: 176
cgctagggat ttataactgt gagtcctcca atattataaa atgttggtaa tatattgggt  60
aaatttcaaa gacaactttt ctccacgtca ggatatagtg tatttgaagc gaaacttatt  120
ttagcagtga aaaagcaaat aaggacgttc aacgactaaa aggtgagtat tgctaacaat  180
aatccttttt tttaatgccc aacatcttta ttaact                            216

SEQ ID NO: 177          moltype = DNA  length = 559
FEATURE                 Location/Qualifiers
source                  1..559
                        mol_type = genomic DNA
                        organism = Bacteriophage Phi I
```

-continued

```
SEQUENCE: 177
gtgggtgcat aaactatttc attgtgcaca ttaaatctgg tgaactcggt gaaaccctaa  60
tggggcaata ccgagccaag ccatagggag gatatatgag aggcaagaag ttaattcttg  120
aggccactga gactggctgt atcatcccta cgtcacacaa acttaatgcc gatggttatt  180
tcagaaagaa aaccaatggc gtcttagaga tgtatcacag aacggtgtgg aaggagcata  240
acggagacat acctgatggc ttcgagatag accataagtg tcgcaatagg gcttgctgta  300
atatagagca tttacagatg cttgagggta cagcccacac tgttaagacc aatcgtgaac  360
gctacgcaga cagaaaggaa acagctaggg aatactggct ggagactgga tgtaccggcc  420
tagcactcgg tgagaagttt ggtgtgtcgt tctcttctgc ttgtaagtgg attagagaat  480
ggaaggcgta gagactatcc gaaaggagta gggccgaggg tgagactccc tcgtaacccg  540
aagcgccaga cagtcaact                                               559

SEQ ID NO: 178         moltype = DNA  length = 218
FEATURE                Location/Qualifiers
source                 1..218
                       mol_type = genomic DNA
                       organism = Nostoc sp.
SEQUENCE: 178
acggacttaa gtaattgagc cttaaagaag aaattcttta agtggcagct ctcaaactca  60
gggaaaccta aatctgttca cagacaaggc aatcctgagc caagccgaaa gagtcatgag  120
tgctgagtag tgagtaaaat aaaagctcac aactcagagg ttgtaactct aagctagtcg  180
gaaggtgcag agactcgacg ggagctaccc taacgtaa                          218

SEQ ID NO: 179         moltype = DNA  length = 165
FEATURE                Location/Qualifiers
source                 1..165
                       mol_type = genomic DNA
                       organism = Nostoc sp.
SEQUENCE: 179
acggacttaa actgaattga gccttagaga agaaattctt taagtgtcag ctctcaaact  60
cagggaaacc taaatctgtt gacagacaag gcaatcctga gccaagccga gaactctaag  120
ttattcggaa ggtgcagaga ctcgacggga gctaccctaa cgtca                  165

SEQ ID NO: 180         moltype = DNA  length = 181
FEATURE                Location/Qualifiers
source                 1..181
                       mol_type = genomic DNA
                       organism = Nodularia sp.
SEQUENCE: 180
acggacttag aaaactgagc cttgatcgag aaatctttca agtggaagct ctcaaattca  60
gggaaaccta aatctgttta cagatatggc aatcctgagc caagccgaaa caagtcctga  120
gtgttaaagc tcataactca tcggaaggtg cagagactcg acgggagcta ccctaacgtt  180
a                                                                  181

SEQ ID NO: 181         moltype = DNA  length = 188
FEATURE                Location/Qualifiers
source                 1..188
                       mol_type = genomic DNA
                       organism = Pleurocapsa sp.
SEQUENCE: 181
acggacttaa aaaaattgag ccttggcaga gaaatctgtc atgcgaacgc tctcaaattc  60
agggaaacct aagtctggca acagatatgg caatcctgag ccaagcctta atcaaggaaa  120
aaaacatttt taccttttac cttgaaagga aggtgcagag actcaacggg agctacccta  180
acaggtca                                                           188

SEQ ID NO: 182         moltype = DNA  length = 200
FEATURE                Location/Qualifiers
source                 1..200
                       mol_type = genomic DNA
                       organism = Planktothrix sp.
SEQUENCE: 182
acggacttaa agataaattg agccttgagg cgagaaatct ctcaagtgta agctgtcaaa  60
ttcagggaaa cctaaatctg taaattcaga caaggcaatc ctgagccaag cctaggggta  120
ttagaaatga gggagtttcc ccaatctaag atcaatacct aggaaggtgc agagactcga  180
cgggagctac cctaacgtta                                              200

SEQ ID NO: 183         moltype = DNA  length = 166
FEATURE                Location/Qualifiers
source                 1..166
                       mol_type = other DNA
                       organism = synthetic construct
SEQUENCE: 183
agtatataag aaacaaacca ctagatgact tacaactaat cggaaggtgc agagactcga  60
cgggagctac cctaacgtca agacgagggt aaagagagag tccaattctc aaagccaata  120
ggcagtagcg aaagctgcaa gagaatgaaa atccgtggct cgcagc                 166

SEQ ID NO: 184         moltype = DNA  length = 176
FEATURE                Location/Qualifiers
```

```
source                 1..176
                       mol_type = other DNA
                       organism = synthetic construct
SEQUENCE: 184
ctgaaattat acttatactc aaacaaacca ctagatgact tacaactaat cggaaggtgc  60
agagactcga cgggagctac cctaacgtca agacgagggt aaagagagag tccaattctc  120
aaagccaata ggcagtagcg aaagctgcaa gagaatgaaa atccgtggct cgcagc      176

SEQ ID NO: 185         moltype = DNA  length = 186
FEATURE                Location/Qualifiers
source                 1..186
                       mol_type = other DNA
                       organism = synthetic construct
SEQUENCE: 185
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 186         moltype = DNA  length = 196
FEATURE                Location/Qualifiers
source                 1..196
                       mol_type = other DNA
                       organism = synthetic construct
SEQUENCE: 186
catcaacaat atgaaattat acttatactc agtatatgac aaacaaacca ctagatgact  60
tacaactaat cggaaggtgc agagactcga cgggagctac cctaacgtca agacgagggt  120
aaagagagag tccaattctc aaagccaata ggcagtagcg aaagctgcaa gagaatgaaa  180
atccgtggct cgcagc                                                  196

SEQ ID NO: 187         moltype = DNA  length = 206
FEATURE                Location/Qualifiers
source                 1..206
                       mol_type = other DNA
                       organism = synthetic construct
SEQUENCE: 187
catcaacaat atgaaactat acttatactc agtatatgaa gcattatcgc aaacaaacca  60
ctagatgact tacaactaat cggaaggtgc agagactcga cgggagctac cctaacgtca  120
agacgagggt aaagagagag tccaattctc aaagccaata ggcagtagcg aaagctgcaa  180
gagaatgaaa atccgtggct cgcagc                                       206

SEQ ID NO: 188         moltype = DNA  length = 166
FEATURE                Location/Qualifiers
source                 1..166
                       mol_type = other DNA
                       organism = synthetic construct
SEQUENCE: 188
tagcgtcagc aaacaaacaa atagatgact tacaactaat cggaaggtgc agagactcga  60
cgggagctac cctaacgtca agacgagggt aaagagagag tccaattctc aaagccaata  120
ggcagtagcg aaagctgcaa gagaatgaaa atccgtggct cgcagc                 166

SEQ ID NO: 189         moltype = DNA  length = 176
FEATURE                Location/Qualifiers
source                 1..176
                       mol_type = other DNA
                       organism = synthetic construct
SEQUENCE: 189
atactcatac tagcgtcagc aaacaaacaa atagatgact tacaactaat cggaaggtgc  60
agagactcga cgggagctac cctaacgtca agacgagggt aaagagagag tccaattctc  120
aaagccaata ggcagtagcg aaagctgcaa gagaatgaaa atccgtggct cgcagc      176

SEQ ID NO: 190         moltype = DNA  length = 186
FEATURE                Location/Qualifiers
source                 1..186
                       mol_type = other DNA
                       organism = synthetic construct
SEQUENCE: 190
gtgtgaagct atactcatac tagcgtcagc aaacaaacaa atagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 191         moltype = DNA  length = 196
FEATURE                Location/Qualifiers
source                 1..196
                       mol_type = other DNA
                       organism = synthetic construct
```

-continued

```
SEQUENCE: 191
cctcacctga gtgtgaagct atactcatac tagcgtcagc aaacaaacaa atagatgact  60
tacaactaat cggaaggtgc agagactcga cgggagctac cctaacgtca agacgagggt  120
aaagagagag tccaattctc aaagccaata ggcagtagcg aaagctgcaa gagaatgaaa  180
atccgtggct cgcagc                                                  196

SEQ ID NO: 192          moltype = DNA  length = 206
FEATURE                 Location/Qualifiers
source                  1..206
                        mol_type = other DNA
                        organism = synthetic construct
SEQUENCE: 192
ccgaatgatg cctcacctga gtgtgaagct atactcatac tagcgtcagc aaacaaacaa  60
atagatgact tacaactaat cggaaggtgc agagactcga cgggagctac cctaacgtca  120
agacgagggt aaagagagag tccaattctc aaagccaata ggcagtagcg aaagctgcaa  180
gagaatgaaa atccgtggct cgcagc                                       206

SEQ ID NO: 193          moltype = DNA  length = 166
FEATURE                 Location/Qualifiers
source                  1..166
                        mol_type = other DNA
                        organism = synthetic construct
SEQUENCE: 193
cggtgcgagc aaacaaacaa atagatgact tacaactaat cggaaggtgc agagactcga  60
cgggagctac cctaacgtca agacgagggt aaagagagag tccaattctc aaagccaata  120
ggcagtagcg aaagctgcaa gagaatgaaa atccgtggct cgcagc                 166

SEQ ID NO: 194          moltype = DNA  length = 176
FEATURE                 Location/Qualifiers
source                  1..176
                        mol_type = other DNA
                        organism = synthetic construct
SEQUENCE: 194
cgctccgacc cagtgcgagc aaacaaacaa atagatgact tacaactaat cggaaggtgc  60
agagactcga cgggagctac cctaacgtca agacgagggt aaagagagag tccaattctc  120
aaagccaata ggcagtagcg aaagctgcaa gagaatgaaa atccgtggct cgcagc      176

SEQ ID NO: 195          moltype = DNA  length = 186
FEATURE                 Location/Qualifiers
source                  1..186
                        mol_type = other DNA
                        organism = synthetic construct
SEQUENCE: 195
ctgaaattat actaatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 196          moltype = DNA  length = 186
FEATURE                 Location/Qualifiers
source                  1..186
                        mol_type = other DNA
                        organism = synthetic construct
SEQUENCE: 196
ctgaaaatat actaatactc actatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 197          moltype = DNA  length = 186
FEATURE                 Location/Qualifiers
source                  1..186
                        mol_type = other DNA
                        organism = synthetic construct
SEQUENCE: 197
ctgataatat agtaatactc actatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 198          moltype = DNA  length = 186
FEATURE                 Location/Qualifiers
source                  1..186
                        mol_type = other DNA
                        organism = synthetic construct
```

SEQUENCE: 198
ctgataataa agtaatacac actataagac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

SEQ ID NO: 199 moltype = DNA length = 186
FEATURE Location/Qualifiers
source 1..186
mol_type = other DNA
organism = synthetic construct
SEQUENCE: 199
ctgaaattat acttatactc tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

SEQ ID NO: 200 moltype = DNA length = 186
FEATURE Location/Qualifiers
source 1..186
mol_type = other DNA
organism = synthetic construct
SEQUENCE: 200
ctgaaattat gtgtgttaca tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

SEQ ID NO: 201 moltype = DNA length = 186
FEATURE Location/Qualifiers
source 1..186
mol_type = other DNA
organism = synthetic construct
SEQUENCE: 201
gttgatcggt gtgtgttaca tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

SEQ ID NO: 202 moltype = DNA length = 186
FEATURE Location/Qualifiers
source 1..186
mol_type = other DNA
organism = synthetic construct
SEQUENCE: 202
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
aaacag 186

SEQ ID NO: 203 moltype = DNA length = 196
FEATURE Location/Qualifiers
source 1..196
mol_type = other DNA
organism = synthetic construct
SEQUENCE: 203
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
cacaatataa attacg 196

SEQ ID NO: 204 moltype = DNA length = 186
FEATURE Location/Qualifiers
source 1..186
mol_type = other DNA
organism = synthetic construct
SEQUENCE: 204
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
catagc 186

SEQ ID NO: 205 moltype = DNA length = 196
FEATURE Location/Qualifiers
source 1..196
mol_type = other DNA
organism = synthetic construct

```
SEQUENCE: 205
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggat  180
cgcagcataa tatccg                                                  196

SEQ ID NO: 206         moltype = DNA  length = 196
FEATURE                Location/Qualifiers
source                 1..196
                       mol_type = other DNA
                       organism = synthetic construct
SEQUENCE: 206
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagcgcgc ctaccg                                                  196

SEQ ID NO: 207         moltype = DNA  length = 219
FEATURE                Location/Qualifiers
source                 1..219
                       mol_type = other DNA
                       organism = synthetic construct
SEQUENCE: 207
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagcgcgc ctaccgaaag ccggcgtcga cgttagcgc                         219

SEQ ID NO: 208         moltype = DNA  length = 219
FEATURE                Location/Qualifiers
source                 1..219
                       mol_type = other DNA
                       organism = synthetic construct
SEQUENCE: 208
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggat  180
cgcagcataa tatccgaaac gaggatacaa gtgacatgc                         219

SEQ ID NO: 209         moltype = DNA  length = 219
FEATURE                Location/Qualifiers
source                 1..219
                       mol_type = other DNA
                       organism = synthetic construct
SEQUENCE: 209
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtgatt  180
cacaatctaa attacgaaac gataaatgat aactctaac                         219

SEQ ID NO: 210         moltype = DNA  length = 156
FEATURE                Location/Qualifiers
source                 1..156
                       mol_type = other DNA
                       organism = synthetic construct
SEQUENCE: 210
aaacaaacca ctagatgact tacaactaat cggaaggtgc agagactcga cgggagctac  60
cctaacgtca agacgagggt aaagagagag tccaattctc aaagccaata ggcagtagcg  120
aaagctgcaa gagaatgaaa atccgtggct cgcagc                            156

SEQ ID NO: 211         moltype = DNA  length = 161
FEATURE                Location/Qualifiers
source                 1..161
                       mol_type = other DNA
                       organism = synthetic construct
SEQUENCE: 211
cgggcaaaca aacaaataga tgacttacaa ctaatcggaa ggtgcagaga ctcgacggga  60
gctaccctaa cgtcaagacg agggtaaaga gagagtccaa ttctcaaagc caataggcag  120
tagcgaaagc tgcaagagaa tgaaaatccg tggctcgcag c                      161

SEQ ID NO: 212         moltype = DNA  length = 186
FEATURE                Location/Qualifiers
source                 1..186
                       mol_type = other DNA
                       organism = synthetic construct
```

```
SEQUENCE: 212
cgctccgacg agcttccggc cagtgcgagc aaacaaacaa atagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgtggct  180
cgcagc                                                             186

SEQ ID NO: 213         moltype = DNA  length = 57
FEATURE                Location/Qualifiers
source                 1..57
                       mol_type = other DNA
                       organism = synthetic construct
SEQUENCE: 213
aaacaaacca cggcagtagc gaaagctgca agagaatgaa aatccgtggc tcgcagc     57

SEQ ID NO: 214         moltype = DNA  length = 67
FEATURE                Location/Qualifiers
source                 1..67
                       mol_type = other DNA
                       organism = synthetic construct
SEQUENCE: 214
agtatataag aaacaaacca cggcagtagc gaaagctgca agagaatgaa aatccgtggc  60
tcgcagc                                                            67

SEQ ID NO: 215         moltype = DNA  length = 77
FEATURE                Location/Qualifiers
source                 1..77
                       mol_type = other DNA
                       organism = synthetic construct
SEQUENCE: 215
ctgaaattat acttatactc aaacaaacca cggcagtagc gaaagctgca agagaatgaa  60
aatccgtggc tcgcagc                                                 77

SEQ ID NO: 216         moltype = DNA  length = 87
FEATURE                Location/Qualifiers
source                 1..87
                       mol_type = other DNA
                       organism = synthetic construct
SEQUENCE: 216
ctgaaattat acttatactc agtatatgac aaacaaacca cggcagtagc gaaagctgca  60
agagaatgaa aatccgtggc tcgcagc                                      87

SEQ ID NO: 217         moltype = DNA  length = 67
FEATURE                Location/Qualifiers
source                 1..67
                       mol_type = other DNA
                       organism = synthetic construct
SEQUENCE: 217
tagcgtcagc aaacaaacaa aggcagtagc gaaagctgca agagaatgaa aatccgtggc  60
tcgcagc                                                            67

SEQ ID NO: 218         moltype = DNA  length = 77
FEATURE                Location/Qualifiers
source                 1..77
                       mol_type = other DNA
                       organism = synthetic construct
SEQUENCE: 218
atactcatac tagcgtcagc aaacaaacaa aggcagtagc gaaagctgca agagaatgaa  60
aatccgtggc tcgcagc                                                 77

SEQ ID NO: 219         moltype = DNA  length = 87
FEATURE                Location/Qualifiers
source                 1..87
                       mol_type = other DNA
                       organism = synthetic construct
SEQUENCE: 219
gtgtgaagct atactcatac tagcgtcagc aaacaaacaa aggcagtagc gaaagctgca  60
agagaatgaa aatccgtggc tcgcagc                                      87

SEQ ID NO: 220         moltype = DNA  length = 67
FEATURE                Location/Qualifiers
source                 1..67
                       mol_type = other DNA
                       organism = synthetic construct
SEQUENCE: 220
cggtgcgagc aaacaaacaa aggcagtagc gaaagctgca agagaatgaa aatccgtggc  60
tcgcagc                                                            67

SEQ ID NO: 221         moltype = DNA  length = 77
FEATURE                Location/Qualifiers
```

```
source                  1..77
                        mol_type = other DNA
                        organism = synthetic construct
SEQUENCE: 221
cgctccgacc cagtgcgagc aaacaaacaa aggcagtagc gaaagctgca agagaatgaa  60
aatccgtggc tcgcagc                                                 77

SEQ ID NO: 222          moltype = DNA  length = 87
FEATURE                 Location/Qualifiers
source                  1..87
                        mol_type = other DNA
                        organism = synthetic construct
SEQUENCE: 222
cgctccgacg agcttccggc cagtgcgagc aaacaaacaa aggcagtagc gaaagctgca  60
agagaatgaa aatccgtggc tcgcagc                                      87

SEQ ID NO: 223          moltype = DNA  length = 98
FEATURE                 Location/Qualifiers
source                  1..98
                        mol_type = other DNA
                        organism = synthetic construct
SEQUENCE: 223
aaacaaacca caagacgagg gtaaagagag agtccaattc tcaaagccaa taggcagtag  60
cgaaagctgc aagagaatga aaatccgtgg ctcgcagc                          98

SEQ ID NO: 224          moltype = DNA  length = 108
FEATURE                 Location/Qualifiers
source                  1..108
                        mol_type = other DNA
                        organism = synthetic construct
SEQUENCE: 224
agtatataag aaacaaacca caagacgagg gtaaagagag agtccaattc tcaaagccaa  60
taggcagtag cgaaagctgc aagagaatga aaatccgtgg ctcgcagc               108

SEQ ID NO: 225          moltype = DNA  length = 118
FEATURE                 Location/Qualifiers
source                  1..118
                        mol_type = other DNA
                        organism = synthetic construct
SEQUENCE: 225
ctgaaattat acttatactc aaacaaacca caagacgagg gtaaagagag agtccaattc  60
tcaaagccaa taggcagtag cgaaagctgc aagagaatga aaatccgtgg ctcgcagc    118

SEQ ID NO: 226          moltype = DNA  length = 128
FEATURE                 Location/Qualifiers
source                  1..128
                        mol_type = other DNA
                        organism = synthetic construct
SEQUENCE: 226
ctgaaattat acttatactc agtatatgac aaacaaacca caagacgagg gtaaagagag  60
agtccaattc tcaaagccaa taggcagtag cgaaagctgc aagagaatga aaatccgtgg  120
ctcgcagc                                                           128

SEQ ID NO: 227          moltype = DNA  length = 108
FEATURE                 Location/Qualifiers
source                  1..108
                        mol_type = other DNA
                        organism = synthetic construct
SEQUENCE: 227
tagcgtcagc aaacaaacaa aaagacgagg gtaaagagag agtccaattc tcaaagccaa  60
taggcagtag cgaaagctgc aagagaatga aaatccgtgg ctcgcagc               108

SEQ ID NO: 228          moltype = DNA  length = 118
FEATURE                 Location/Qualifiers
source                  1..118
                        mol_type = other DNA
                        organism = synthetic construct
SEQUENCE: 228
atactcatac tagcgtcagc aaacaaacaa aaagacgagg gtaaagagag agtccaattc  60
tcaaagccaa taggcagtag cgaaagctgc aagagaatga aaatccgtgg ctcgcagc    118

SEQ ID NO: 229          moltype = DNA  length = 128
FEATURE                 Location/Qualifiers
source                  1..128
                        mol_type = other DNA
                        organism = synthetic construct
```

```
SEQUENCE: 229
gtgtgaagct atactcatac tagcgtcagc aaacaaacaa aaagacgagg gtaaagagag  60
agtccaattc tcaaagccaa taggcagtag cgaaagctgc aagagaatga aaatccgtgg  120
ctcgcagc                                                           128

SEQ ID NO: 230         moltype = DNA  length = 108
FEATURE                Location/Qualifiers
source                 1..108
                       mol_type = other DNA
                       organism = synthetic construct
SEQUENCE: 230
cggtgcgagc aaacaaacaa aaagacgagg gtaaagagag agtccaattc tcaaagccaa  60
taggcagtag cgaaagctgc aagagaatga aaatccgtgg ctcgcagc               108

SEQ ID NO: 231         moltype = DNA  length = 118
FEATURE                Location/Qualifiers
source                 1..118
                       mol_type = other DNA
                       organism = synthetic construct
SEQUENCE: 231
cgctccgacc cagtgcgagc aaacaaacaa aaagacgagg gtaaagagag agtccaattc  60
tcaaagccaa taggcagtag cgaaagctgc aagagaatga aaatccgtgg ctcgcagc    118

SEQ ID NO: 232         moltype = DNA  length = 128
FEATURE                Location/Qualifiers
source                 1..128
                       mol_type = other DNA
                       organism = synthetic construct
SEQUENCE: 232
cgctccgacg agcttccggc cagtgcgagc aaacaaacaa aaagacgagg gtaaagagag  60
agtccaattc tcaaagccaa taggcagtag cgaaagctgc aagagaatga aaatccgtgg  120
ctcgcagc                                                           128

SEQ ID NO: 233         moltype = DNA  length = 176
FEATURE                Location/Qualifiers
source                 1..176
                       mol_type = other DNA
                       organism = synthetic construct
SEQUENCE: 233
ctgaaattat acttatactc agtatatgac aaacaaacca ctagatgact tacaactaat  60
cggaaggtgc agagactcga cgggagctac cctaacgtca agacgagggt aaagagagag  120
tccaattctc aaagccaata ggcagtagcg aaagctgcaa gagaatgaaa atccgt      176

SEQ ID NO: 234         moltype = DNA  length = 77
FEATURE                Location/Qualifiers
source                 1..77
                       mol_type = other DNA
                       organism = synthetic construct
SEQUENCE: 234
ctgaaattat acttatactc agtatatgac aaacaaacca cggcagtagc gaaagctgca  60
agagaatgaa aatccgt                                                 77

SEQ ID NO: 235         moltype = DNA  length = 87
FEATURE                Location/Qualifiers
source                 1..87
                       mol_type = other DNA
                       organism = synthetic construct
SEQUENCE: 235
ctgaaattat acttatactc agtatatgac aaacaaacca cggcagtagc gaaagctgca  60
agagaatgaa aatccgtgat taaacag                                      87

SEQ ID NO: 236         moltype = DNA  length = 97
FEATURE                Location/Qualifiers
source                 1..97
                       mol_type = other DNA
                       organism = synthetic construct
SEQUENCE: 236
ctgaaattat acttatactc agtatatgac aaacaaacca cggcagtagc gaaagctgca  60
agagaatgaa aatccgtgat tcacaatata aattacg                           97

SEQ ID NO: 237         moltype = DNA  length = 87
FEATURE                Location/Qualifiers
source                 1..87
                       mol_type = other DNA
                       organism = synthetic construct
SEQUENCE: 237
ctgaaattat acttatactc agtatatgac aaacaaacca cggcagtagc gaaagctgca  60
agagaatgaa aatccgtgga tcatagc                                      87
```

-continued

```
SEQ ID NO: 238          moltype = DNA  length = 97
FEATURE                 Location/Qualifiers
source                  1..97
                        mol_type = other DNA
                        organism = synthetic construct
SEQUENCE: 238
ctgaaattat acttatactc agtatatgac aaacaaacca cggcagtagc gaaagctgca  60
agagaatgaa aatccgtgga tcgcagcata atatccg                           97

SEQ ID NO: 239          moltype = DNA  length = 97
FEATURE                 Location/Qualifiers
source                  1..97
                        mol_type = other DNA
                        organism = synthetic construct
SEQUENCE: 239
ctgaaattat acttatactc agtatatgac aaacaaacca cggcagtagc gaaagctgca  60
agagaatgaa aatccgtggc tcgcagcgcg cctaccg                           97

SEQ ID NO: 240          moltype = DNA  length = 118
FEATURE                 Location/Qualifiers
source                  1..118
                        mol_type = other DNA
                        organism = synthetic construct
SEQUENCE: 240
ctgaaattat acttatactc agtatatgac aaacaaacca caagacgagg gtaaagagag  60
agtccaattc tcaaagccaa taggcagtag cgaaagctgc aagagaatga aaatccgt    118

SEQ ID NO: 241          moltype = DNA  length = 128
FEATURE                 Location/Qualifiers
source                  1..128
                        mol_type = other DNA
                        organism = synthetic construct
SEQUENCE: 241
ctgaaattat acttatactc agtatatgac aaacaaacca caagacgagg gtaaagagag  60
agtccaattc tcaaagccaa taggcagtag cgaaagctgc aagagaatga aaatccgtga  120
ttaaacag                                                           128

SEQ ID NO: 242          moltype = DNA  length = 138
FEATURE                 Location/Qualifiers
source                  1..138
                        mol_type = other DNA
                        organism = synthetic construct
SEQUENCE: 242
ctgaaattat acttatactc agtatatgac aaacaaacca caagacgagg gtaaagagag  60
agtccaattc tcaaagccaa taggcagtag cgaaagctgc aagagaatga aaatccgtga  120
ttcacaatat aaattacg                                                138

SEQ ID NO: 243          moltype = DNA  length = 128
FEATURE                 Location/Qualifiers
source                  1..128
                        mol_type = other DNA
                        organism = synthetic construct
SEQUENCE: 243
ctgaaattat acttatactc agtatatgac aaacaaacca caagacgagg gtaaagagag  60
agtccaattc tcaaagccaa taggcagtag cgaaagctgc aagagaatga aaatccgtgg  120
atcatagc                                                           128

SEQ ID NO: 244          moltype = DNA  length = 138
FEATURE                 Location/Qualifiers
source                  1..138
                        mol_type = other DNA
                        organism = synthetic construct
SEQUENCE: 244
ctgaaattat acttatactc agtatatgac aaacaaacca caagacgagg gtaaagagag  60
agtccaattc tcaaagccaa taggcagtag cgaaagctgc aagagaatga aaatccgtgg  120
atcgcagcat aatatccg                                                138

SEQ ID NO: 245          moltype = DNA  length = 138
FEATURE                 Location/Qualifiers
source                  1..138
                        mol_type = other DNA
                        organism = synthetic construct
SEQUENCE: 245
ctgaaattat acttatactc agtatatgac aaacaaacca caagacgagg gtaaagagag  60
agtccaattc tcaaagccaa taggcagtag cgaaagctgc aagagaatga aaatccgtgg  120
ctcgcagcgc gcctaccg                                                138

SEQ ID NO: 246          moltype = DNA  length = 162
FEATURE                 Location/Qualifiers
```

```
source                  1..162
                        mol_type = other DNA
                        organism = synthetic construct
SEQUENCE: 246
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aacttatata ct                     162

SEQ ID NO: 247          moltype = DNA  length = 172
FEATURE                 Location/Qualifiers
source                  1..172
                        mol_type = other DNA
                        organism = synthetic construct
SEQUENCE: 247
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagagtataa gtataatttc ag          172

SEQ ID NO: 248          moltype = DNA  length = 182
FEATURE                 Location/Qualifiers
source                  1..182
                        mol_type = other DNA
                        organism = synthetic construct
SEQUENCE: 248
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 249          moltype = DNA  length = 192
FEATURE                 Location/Qualifiers
source                  1..192
                        mol_type = other DNA
                        organism = synthetic construct
SEQUENCE: 249
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
atattgttga tg                                                      192

SEQ ID NO: 250          moltype = DNA  length = 202
FEATURE                 Location/Qualifiers
source                  1..202
                        mol_type = other DNA
                        organism = synthetic construct
SEQUENCE: 250
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagcgataat gcttcatata ctgagtataa  180
gtatagtttc atattgttga tg                                           202

SEQ ID NO: 251          moltype = DNA  length = 162
FEATURE                 Location/Qualifiers
source                  1..162
                        mol_type = other DNA
                        organism = synthetic construct
SEQUENCE: 251
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctgacgc ta                     162

SEQ ID NO: 252          moltype = DNA  length = 172
FEATURE                 Location/Qualifiers
source                  1..172
                        mol_type = other DNA
                        organism = synthetic construct
SEQUENCE: 252
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctgacgc tagtatgagt at          172

SEQ ID NO: 253          moltype = DNA  length = 182
FEATURE                 Location/Qualifiers
source                  1..182
                        mol_type = other DNA
                        organism = synthetic construct
```

```
SEQUENCE: 253
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctgacgc tagtatgagt atagcttcac  180
ac                                                                 182

SEQ ID NO: 254         moltype = DNA  length = 192
FEATURE                Location/Qualifiers
source                 1..192
                       mol_type = other DNA
                       organism = synthetic construct
SEQUENCE: 254
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctgacgc tagtatgagt atagcttcac  180
actcaggtga gg                                                      192

SEQ ID NO: 255         moltype = DNA  length = 202
FEATURE                Location/Qualifiers
source                 1..202
                       mol_type = other DNA
                       organism = synthetic construct
SEQUENCE: 255
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctgacgc tagtatgagt atagcttcac  180
actcaggtga ggcatcattc gg                                           202

SEQ ID NO: 256         moltype = DNA  length = 162
FEATURE                Location/Qualifiers
source                 1..162
                       mol_type = other DNA
                       organism = synthetic construct
SEQUENCE: 256
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctcgcac cg                     162

SEQ ID NO: 257         moltype = DNA  length = 172
FEATURE                Location/Qualifiers
source                 1..172
                       mol_type = other DNA
                       organism = synthetic construct
SEQUENCE: 257
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctcgcac tgggtcggag cg          172

SEQ ID NO: 258         moltype = DNA  length = 182
FEATURE                Location/Qualifiers
source                 1..182
                       mol_type = other DNA
                       organism = synthetic construct
SEQUENCE: 258
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 259         moltype = DNA  length = 182
FEATURE                Location/Qualifiers
source                 1..182
                       mol_type = other DNA
                       organism = synthetic construct
SEQUENCE: 259
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 260         moltype = DNA  length = 182
FEATURE                Location/Qualifiers
source                 1..182
                       mol_type = other DNA
                       organism = synthetic construct
```

```
SEQUENCE: 260
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 261         moltype = DNA  length = 182
FEATURE                Location/Qualifiers
source                 1..182
                       mol_type = other DNA
                       organism = synthetic construct
SEQUENCE: 261
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 262         moltype = DNA  length = 182
FEATURE                Location/Qualifiers
source                 1..182
                       mol_type = other DNA
                       organism = synthetic construct
SEQUENCE: 262
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtaactta gagagtataa gtataatttc  180
ag                                                                 182

SEQ ID NO: 263         moltype = DNA  length = 182
FEATURE                Location/Qualifiers
source                 1..182
                       mol_type = other DNA
                       organism = synthetic construct
SEQUENCE: 263
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtaactta gatgtaacac acataatttc  180
ag                                                                 182

SEQ ID NO: 264         moltype = DNA  length = 182
FEATURE                Location/Qualifiers
source                 1..182
                       mol_type = other DNA
                       organism = synthetic construct
SEQUENCE: 264
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtaactta gatgtaacac acaccgatca  180
ac                                                                 182

SEQ ID NO: 265         moltype = DNA  length = 182
FEATURE                Location/Qualifiers
source                 1..182
                       mol_type = other DNA
                       organism = synthetic construct
SEQUENCE: 265
ctgtttaatc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 266         moltype = DNA  length = 192
FEATURE                Location/Qualifiers
source                 1..192
                       mol_type = other DNA
                       organism = synthetic construct
SEQUENCE: 266
cgtaatttat attgtgaatc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca acacaaacac aagtcatata ctgagtataa  180
gtataatttc ag                                                      192

SEQ ID NO: 267         moltype = DNA  length = 182
FEATURE                Location/Qualifiers
source                 1..182
                       mol_type = other DNA
                       organism = synthetic construct
```

```
SEQUENCE: 267
gctatgatcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aagtcatata ctgagtataa gtataatttc  180
ag                                                                 182

SEQ ID NO: 268         moltype = DNA  length = 192
FEATURE                Location/Qualifiers
source                 1..192
                       mol_type = other DNA
                       organism = synthetic construct
SEQUENCE: 268
cggatattat gctgcgatcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca acacaaacac aagtcatata ctgagtataa  180
gtataatttc ag                                                      192

SEQ ID NO: 269         moltype = DNA  length = 192
FEATURE                Location/Qualifiers
source                 1..192
                       mol_type = other DNA
                       organism = synthetic construct
SEQUENCE: 269
cggtaggcgc gctgcgagcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca acacaaacac aagtcatata ctgagtataa  180
gtataatttc ag                                                      192

SEQ ID NO: 270         moltype = DNA  length = 215
FEATURE                Location/Qualifiers
source                 1..215
                       mol_type = other DNA
                       organism = synthetic construct
SEQUENCE: 270
gcgctaacgt cgacgccggc aaacggtagg cgcgctgcga gccacggact taaataattg  60
agccttaaag aagaaattct ttaagtggat gctctcaaac tcagggaaac ctaaatctag  120
ttatagacaa ggcaatcctg agccaagccg aagtagtaat tagtaagtta acaacacaaa  180
cacaagtcat atactgagta taagtataat ttcag                             215

SEQ ID NO: 271         moltype = DNA  length = 215
FEATURE                Location/Qualifiers
source                 1..215
                       mol_type = other DNA
                       organism = synthetic construct
SEQUENCE: 271
gcatgtcact tgtatcctcg aaacggatat tatgctgcga tccacggact taaataattg  60
agccttaaag aagaaattct ttaagtggat gctctcaaac tcagggaaac ctaaatctag  120
ttatagacaa ggcaatcctg agccaagccg aagtagtaat tagtaagtta acaacacaaa  180
cacaagtcat atactgagta taagtataat ttcag                             215

SEQ ID NO: 272         moltype = DNA  length = 215
FEATURE                Location/Qualifiers
source                 1..215
                       mol_type = other DNA
                       organism = synthetic construct
SEQUENCE: 272
gttagagtta tcatttatcg aaacgtaatt tagattgtga atcacggact taaataattg  60
agccttaaag aagaaattct ttaagtggat gctctcaaac tcagggaaac ctaaatctag  120
ttatagacaa ggcaatcctg agccaagccg aagtagtaat tagtaagtta acaacacaaa  180
cacaagtcat atactgagta taagtataat ttcag                             215

SEQ ID NO: 273         moltype = DNA  length = 152
FEATURE                Location/Qualifiers
source                 1..152
                       mol_type = other DNA
                       organism = synthetic construct
SEQUENCE: 273
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca acacaaacac aa                                152

SEQ ID NO: 274         moltype = DNA  length = 157
FEATURE                Location/Qualifiers
source                 1..157
                       mol_type = other DNA
                       organism = synthetic construct
```

```
SEQUENCE: 274
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagcccg                           157

SEQ ID NO: 275          moltype = DNA  length = 182
FEATURE                 Location/Qualifiers
source                  1..182
                        mol_type = other DNA
                        organism = synthetic construct
SEQUENCE: 275
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca aaacaaaaac aagctcgcac tggccggaag ctcgtcggag  180
cg                                                                 182

SEQ ID NO: 276          moltype = DNA  length = 251
FEATURE                 Location/Qualifiers
source                  1..251
                        mol_type = other DNA
                        organism = synthetic construct
SEQUENCE: 276
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca a                                                       251

SEQ ID NO: 277          moltype = DNA  length = 261
FEATURE                 Location/Qualifiers
source                  1..261
                        mol_type = other DNA
                        organism = synthetic construct
SEQUENCE: 277
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca acttatatac t                                            261

SEQ ID NO: 278          moltype = DNA  length = 271
FEATURE                 Location/Qualifiers
source                  1..271
                        mol_type = other DNA
                        organism = synthetic construct
SEQUENCE: 278
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca agagtataag tataatttca g                                 271

SEQ ID NO: 279          moltype = DNA  length = 281
FEATURE                 Location/Qualifiers
source                  1..281
                        mol_type = other DNA
                        organism = synthetic construct
SEQUENCE: 279
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca agtcatatac tgagtataag tataatttca g                      281

SEQ ID NO: 280          moltype = DNA  length = 261
FEATURE                 Location/Qualifiers
source                  1..261
                        mol_type = other DNA
                        organism = synthetic construct
SEQUENCE: 280
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctgacgct a                                            261

SEQ ID NO: 281          moltype = DNA  length = 271
FEATURE                 Location/Qualifiers
```

```
source                  1..271
                        mol_type = other DNA
                        organism = synthetic construct
SEQUENCE: 281
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctgacgct agtatgagta t                                 271

SEQ ID NO: 282          moltype = DNA  length = 281
FEATURE                 Location/Qualifiers
source                  1..281
                        mol_type = other DNA
                        organism = synthetic construct
SEQUENCE: 282
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctgacgct agtatgagta tagcttcaca c                      281

SEQ ID NO: 283          moltype = DNA  length = 261
FEATURE                 Location/Qualifiers
source                  1..261
                        mol_type = other DNA
                        organism = synthetic construct
SEQUENCE: 283
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctcgcacc g                                            261

SEQ ID NO: 284          moltype = DNA  length = 271
FEATURE                 Location/Qualifiers
source                  1..271
                        mol_type = other DNA
                        organism = synthetic construct
SEQUENCE: 284
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctcgcact gggtcggagc g                                 271

SEQ ID NO: 285          moltype = DNA  length = 281
FEATURE                 Location/Qualifiers
source                  1..281
                        mol_type = other DNA
                        organism = synthetic construct
SEQUENCE: 285
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
aacaaaaaca agctcgcact ggccggaagc tcgtcggagc g                      281

SEQ ID NO: 286          moltype = DNA  length = 210
FEATURE                 Location/Qualifiers
source                  1..210
                        mol_type = other DNA
                        organism = synthetic construct
SEQUENCE: 286
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa                                   210

SEQ ID NO: 287          moltype = DNA  length = 220
FEATURE                 Location/Qualifiers
source                  1..220
                        mol_type = other DNA
                        organism = synthetic construct
SEQUENCE: 287
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa cttatatact                        220
```

```
SEQ ID NO: 288         moltype = DNA  length = 230
FEATURE                Location/Qualifiers
source                 1..230
                       mol_type = other DNA
                       organism = synthetic construct
SEQUENCE: 288
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa gagtataagt ataatttcag             230

SEQ ID NO: 289         moltype = DNA  length = 240
FEATURE                Location/Qualifiers
source                 1..240
                       mol_type = other DNA
                       organism = synthetic construct
SEQUENCE: 289
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa gtcatatact gagtataagt ataatttcag  240

SEQ ID NO: 290         moltype = DNA  length = 220
FEATURE                Location/Qualifiers
source                 1..220
                       mol_type = other DNA
                       organism = synthetic construct
SEQUENCE: 290
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctgacgcta                        220

SEQ ID NO: 291         moltype = DNA  length = 230
FEATURE                Location/Qualifiers
source                 1..230
                       mol_type = other DNA
                       organism = synthetic construct
SEQUENCE: 291
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctgacgcta gtatgagtat             230

SEQ ID NO: 292         moltype = DNA  length = 240
FEATURE                Location/Qualifiers
source                 1..240
                       mol_type = other DNA
                       organism = synthetic construct
SEQUENCE: 292
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctgacgcta gtatgagtat agcttcacac  240

SEQ ID NO: 293         moltype = DNA  length = 220
FEATURE                Location/Qualifiers
source                 1..220
                       mol_type = other DNA
                       organism = synthetic construct
SEQUENCE: 293
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctcgcaccg                        220

SEQ ID NO: 294         moltype = DNA  length = 230
FEATURE                Location/Qualifiers
source                 1..230
                       mol_type = other DNA
                       organism = synthetic construct
SEQUENCE: 294
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctcgcactg ggtcggagcg             230

SEQ ID NO: 295         moltype = DNA  length = 240
```

-continued

```
FEATURE                 Location/Qualifiers
source                  1..240
                        mol_type = other DNA
                        organism = synthetic construct
SEQUENCE: 295
gctgcgagcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca acaaaaacaa gctcgcactg gccggaagct cgtcggagcg  240

SEQ ID NO: 296          moltype = DNA  length = 172
FEATURE                 Location/Qualifiers
source                  1..172
                        mol_type = other DNA
                        organism = synthetic construct
SEQUENCE: 296
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca acacaaacac aagtcatata ctgagtataa gtataatttc ag          172

SEQ ID NO: 297          moltype = DNA  length = 271
FEATURE                 Location/Qualifiers
source                  1..271
                        mol_type = other DNA
                        organism = synthetic construct
SEQUENCE: 297
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtca agacgagggt aaagagagag tccaattctc aaagccaata cacaaacaca  240
agtcatatac tgagtataag tataatttca g                                 271

SEQ ID NO: 298          moltype = DNA  length = 281
FEATURE                 Location/Qualifiers
source                  1..281
                        mol_type = other DNA
                        organism = synthetic construct
SEQUENCE: 298
ctgtttaatc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca agtcatatac tgagtataag tataatttca g                      281

SEQ ID NO: 299          moltype = DNA  length = 291
FEATURE                 Location/Qualifiers
source                  1..291
                        mol_type = other DNA
                        organism = synthetic construct
SEQUENCE: 299
cgtaatttat attgtgaatc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
agagactcga cgggagctac cctaacgtca agacgagggt aaagagagag tccaattctc  240
aaagccaata cacaaacaca agtcatatac tgagtataag tataatttca g           291

SEQ ID NO: 300          moltype = DNA  length = 281
FEATURE                 Location/Qualifiers
source                  1..281
                        mol_type = other DNA
                        organism = synthetic construct
SEQUENCE: 300
gctatgatcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtca agacgagggt aaagagagag tccaattctc aaagccaata  240
cacaaacaca agtcatatac tgagtataag tataatttca g                      281

SEQ ID NO: 301          moltype = DNA  length = 291
FEATURE                 Location/Qualifiers
source                  1..291
                        mol_type = other DNA
                        organism = synthetic construct
SEQUENCE: 301
cggatattat gctgcgatcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
agagactcga cgggagctac cctaacgtca agacgagggt aaagagagag tccaattctc  240
aaagccaata cacaaacaca agtcatatac tgagtataag tataatttca g           291
```

```
SEQ ID NO: 302          moltype = DNA  length = 291
FEATURE                 Location/Qualifiers
source                  1..291
                        mol_type = other DNA
                        organism = synthetic construct
SEQUENCE: 302
cggtaggcgc gctgcgagcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
agagactcga cgggagctac cctaacgtca agacgagggt aaagagagag tccaattctc  240
aaagccaata cacaaacaca agtcatatac tgagtataag tataatttca g           291

SEQ ID NO: 303          moltype = DNA  length = 230
FEATURE                 Location/Qualifiers
source                  1..230
                        mol_type = other DNA
                        organism = synthetic construct
SEQUENCE: 303
acggacttaa ataattgagc cttaaagaag aaattcttta agtggatgct ctcaaactca  60
gggaaaccta aatctagtta tagacaaggc aatcctgagc caagccgaag tagtaattag  120
taagttaaca atagatgact tacaactaat cggaaggtgc agagactcga cgggagctac  180
cctaacgtcc acaaacacaa gtcatatact gagtataagt ataatttcag             230

SEQ ID NO: 304          moltype = DNA  length = 240
FEATURE                 Location/Qualifiers
source                  1..240
                        mol_type = other DNA
                        organism = synthetic construct
SEQUENCE: 304
ctgtttaatc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa gtcatatact gagtataagt ataatttcag  240

SEQ ID NO: 305          moltype = DNA  length = 250
FEATURE                 Location/Qualifiers
source                  1..250
                        mol_type = other DNA
                        organism = synthetic construct
SEQUENCE: 305
cgtaatttat attgtgaatc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
agagactcga cgggagctac cctaacgtcc acaaacacaa gtcatatact gagtataagt  240
ataatttcag                                                         250

SEQ ID NO: 306          moltype = DNA  length = 240
FEATURE                 Location/Qualifiers
source                  1..240
                        mol_type = other DNA
                        organism = synthetic construct
SEQUENCE: 306
gctatgatcc acggacttaa ataattgagc cttaaagaag aaattcttta agtggatgct  60
ctcaaactca gggaaaccta aatctagtta tagacaaggc aatcctgagc caagccgaag  120
tagtaattag taagttaaca atagatgact tacaactaat cggaaggtgc agagactcga  180
cgggagctac cctaacgtcc acaaacacaa gtcatatact gagtataagt ataatttcag  240

SEQ ID NO: 307          moltype = DNA  length = 250
FEATURE                 Location/Qualifiers
source                  1..250
                        mol_type = other DNA
                        organism = synthetic construct
SEQUENCE: 307
cggatattat gctgcgatcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
agagactcga cgggagctac cctaacgtcc acaaacacaa gtcatatact gagtataagt  240
ataatttcag                                                         250

SEQ ID NO: 308          moltype = DNA  length = 250
FEATURE                 Location/Qualifiers
source                  1..250
                        mol_type = other DNA
                        organism = synthetic construct
SEQUENCE: 308
cggtaggcgc gctgcgagcc acggacttaa ataattgagc cttaaagaag aaattcttta  60
agtggatgct ctcaaactca gggaaaccta aatctagtta tagacaaggc aatcctgagc  120
caagccgaag tagtaattag taagttaaca atagatgact tacaactaat cggaaggtgc  180
```

-continued

```
agagactcga cgggagctac cctaacgtcc acaaacacaa gtcatatact gagtataagt  240
ataatttcag                                                         250

SEQ ID NO: 309          moltype = DNA  length = 1137
FEATURE                 Location/Qualifiers
source                  1..1137
                        mol_type = other DNA
                        organism = synthetic construct
SEQUENCE: 309
atgctgctgc tggtcacatc tctgctgctg tgcgagctgc cccatcctgc ctttctgctg  60
atccccgaca tccagatgac ccagaccaca agcagcctgt ctgccagcct gggcgataga  120
gtgaccatca gctgtagagc cagccaggac atcagcaagt acctgaactg gtatcagcaa  180
aagcccgacg gcaccgtgaa gctgctgatc taccacacca gcagactgca cagcggcgtg  240
ccaagcagat tttctggcag cggctctggc accgactaca gcctgacaat cagcaacctg  300
gaacaagagg atatcgctac ctacttctgc cagcaaggca acaccctgcc ttacaccttt  360
ggcggaggca ccaagctgga aatcaccggc tctacaagcg gcagcggcaa acctggatct  420
ggcgagggat ctaccaaggg cgaagtgaaa ctgcaagagt ctggccctgg actggtggcc  480
ccatctcagt ctctgagcgt gacctgtaca gtcagcggag tgtccctgcc tgattacggc  540
gtgtcctgga tcagacagcc tcctcggaaa ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tattgcgcca agcactacta ctacggcggc agctacgcca tggattattg gggccagggc  780
accagcgtga ccgtttcttc tgccgccgct atcgaagtga tgtaccctcc tccttacctg  840
gacaacgaga agtccaacgg caccatcatc cacgtgaagg gcaagcacct gtgtccttct  900
ccactgttcc ccggacctag caagcctttc tgggtgctcg ttgttgttgg cggcgtgctg  960
gcctgttaca gcctgctggt taccgtggcc ttcatcatct ttgggtcaa gagaggccgg  1020
aagaaacttc tttatatatt caagcagccc tttatgcgac ccgttcagac tacccaagag  1080
gaagatggat gcagttgccg ctttccagaa gaggaggagg gcgggtgcga actgtaa     1137

SEQ ID NO: 310          moltype = DNA  length = 1134
FEATURE                 Location/Qualifiers
source                  1..1134
                        mol_type = other DNA
                        organism = synthetic construct
SEQUENCE: 310
atgctgctgc tggtcacatc tctgctgctg tgcgagctgc cccatcctgc ctttctgctg  60
atccccgaca tccagatgac ccagaccaca agcagcctgt ctgccagcct gggcgataga  120
gtgaccatca gctgtagagc cagccaggac atcagcaagt acctgaactg gtatcagcaa  180
aagcccgacg gcaccgtgaa gctgctgatc taccacacca gcagactgca cagcggcgtg  240
ccaagcagat tttctggcag cggctctggc accgactaca gcctgacaat cagcaacctg  300
gaacaagagg atatcgctac ctacttctgc cagcaaggca acaccctgcc ttacaccttt  360
ggcggaggca ccaagctgga aatcaccggc tctacaagcg gcagcggcaa acctggatct  420
ggcgagggat ctaccaaggg cgaagtgaaa ctgcaagagt ctggccctgg actggtggcc  480
ccatctcagt ctctgagcgt gacctgtaca gtcagcggag tgtccctgcc tgattacggc  540
gtgtcctgga tcagacagcc tcctcggaaa ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tattgcgcca agcactacta ctacggcggc agctacgcca tggattattg gggccagggc  780
accagcgtga ccgtttcttc tgccgccgct atcgaagtga tgtaccctcc tccttacctg  840
gacaacgaga agtccaacgg caccatcatc cacgtgaagg gcaagcacct gtgtccttct  900
ccactgttcc ccggacctag caagcctttc tgggtgctcg ttgttgttgg cggcgtgctg  960
gcctgttaca gcctgctggt taccgtggcc ttcatcatct ttgggtccg aagcaagcgg  1020
agccggctgc tgcactccga ctacatgaac atgaccccta gacggcccgg accaaccaga  1080
aagcactacc agccttacgc tcctcctaga gacttcgccg cctaccggtc ctaa        1134

SEQ ID NO: 311          moltype = DNA  length = 1470
FEATURE                 Location/Qualifiers
source                  1..1470
                        mol_type = other DNA
                        organism = synthetic construct
SEQUENCE: 311
atgctgctgc tggtcacatc tctgctgctg tgcgagctgc cccatcctgc ctttctgctg  60
atccccgaca tccagatgac ccagaccaca agcagcctgt ctgccagcct gggcgataga  120
gtgaccatca gctgtagagc cagccaggac atcagcaagt acctgaactg gtatcagcaa  180
aagcccgacg gcaccgtgaa gctgctgatc taccacacca gcagactgca cagcggcgtg  240
ccaagcagat tttctggcag cggctctggc accgactaca gcctgacaat cagcaacctg  300
gaacaagagg atatcgctac ctacttctgc cagcaaggca acaccctgcc ttacaccttt  360
ggcggaggca ccaagctgga aatcaccggc tctacaagcg gcagcggcaa acctggatct  420
ggcgagggat ctaccaaggg cgaagtgaaa ctgcaagagt ctggccctgg actggtggcc  480
ccatctcagt ctctgagcgt gacctgtaca gtcagcggag tgtccctgcc tgattacggc  540
gtgtcctgga tcagacagcc tcctcggaaa ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tattgcgcca agcactacta ctacggcggc agctacgcca tggattattg gggccagggc  780
accagcgtga ccgtttcttc tgccgccgct atcgaagtga tgtaccctcc tccttacctg  840
gacaacgaga agtccaacgg caccatcatc cacgtgaagg gcaagcacct gtgtccttct  900
ccactgttcc ccggacctag caagcctttc tgggtgctcg ttgttgttgg cggcgtgctg  960
gcctgttaca gcctgctggt taccgtggcc ttcatcatct ttgggtccg aagcaagcgg  1020
agccggctgc tgcactccga ctacatgaac atgaccccta gacggcccgg accaaccaga  1080
```

-continued

```
aagcactacc agccttacgc tcctcctaga gacttcgccg cctaccggtc cagagtgaag  1140
ttcagcagat ccgccgatgc tcccgcctat cagcagggcc aaaaccagct gtacaacgag  1200
ctgaacctgg ggagaagaga agagtacgac gtgctggaca agcggagagg cagagatcct  1260
gaaatgggcg gcaagcccag acggaagaat cctcaagagg gcctgtataa tgagctgcag  1320
aaagacaaga tggccgaggc ctacagcgag atcggaatga agggcgagcg cagaagaggc  1380
aagggacacg atggactgta ccagggactg agcaccgcca ccaaggatac ctatgacgcc  1440
ctgcacatgc aggccctgcc tccaagataa                                     1470

SEQ ID NO: 312         moltype = DNA  length = 1347
FEATURE                Location/Qualifiers
source                 1..1347
                       mol_type = other DNA
                       organism = synthetic construct
SEQUENCE: 312
atgctgctgc tggtcacatc tctgctgctg tgcgagctgc cccatcctgc ctttctgctg  60
atccccgaca tccagatgac ccagaccaca agcagcctgt ctgccagcct gggcgataga  120
gtgaccatca gctgtagagc cagccaggac atcagcaagt acctgaactg gtatcagcaa  180
aagcccgacg gcaccgtgaa gctgctgatc taccacacca gcagactgca cagcggcgtg  240
ccaagcagat tttctggcag cggctctggc accgactaca gcctgacaat cagcaacctg  300
gaacaagagg atatcgctac ctacttctgc cagcaaggca acaccctgcc ttacaccttt  360
ggcggaggca ccaagctgga aatcaccggc tctacaagcg gcagcggcaa acctggatct  420
ggcgagggat ctaccaaggg cgaagtgaaa ctgcaagagt ctggccctgg actggtggcc  480
ccatctcagt ctctgagcgt gacctgtaca gtcagcggag tgtccctgcc tgattacggc  540
gtgtcctgga tcagacagcc tcctcggaaa ggcctggaat ggctgggagt gatctggggc  600
agcgagacaa cctactacaa cagcgccctg aagtcccggc tgaccatcat caaggacaac  660
tccaagagcc aggtgttcct gaagatgaac agcctgcaga ccgacgacac cgccatctac  720
tattgcgcca agcactacta ctacggcggc agctacgcca tggattattg gggccagggc  780
accagcgtga ccgtttcttc tgccgccgct atcgaagtga tgtaccctcc tccttacctg  840
gacaacgaga agtccaacgg caccatcatc cacgtgaagg gcaagcacct gtgtccttct  900
ccactgttcc ccggacctag caagcctttc tgggtgctcg ttgttgttgg cggcgtgctg  960
gcctgttaca gcctgctggt taccgtggcc ttcatcatct tttgggtcag agtgaagttc  1020
agcagatccg ccgatgctcc cgcctatcag cagggccaaa accagctgta caacgagctg  1080
aacctgggga gaagagaaga gtacgacgtg ctggacaagc ggagaggcag agatcctgaa  1140
atgggcggca agcccagacg gaagaatcct caagagggcc tgtataatga gctgcagaaa  1200
gacaagatgg ccgaggccta cagcgagatc ggaatgaagg gcgagcgcag aagaggcaag  1260
ggacacgatg gactgtacca gggactgagc accgccacca aggataccta tgacgccctg  1320
cacatgcagg ccctgcctcc aagataa                                        1347

SEQ ID NO: 313         moltype = DNA  length = 1461
FEATURE                Location/Qualifiers
source                 1..1461
                       mol_type = other DNA
                       organism = synthetic construct
SEQUENCE: 313
atggctctcc cggtcacagc ccttctcctg cccctggcac tcttgctgca tgcggcacga  60
cccgacatcc agatgaccca gaccacaagc agcctgtctg ccagcctggg cgatagagtg  120
accatcagct gtagagccag ccaggacatc agcaagtacc tgaactggta tcagcaaaag  180
cccgacggca ccgtgaagct gctgatctac cacaccagca gactgcacag cggcgtgcca  240
agcagatttt ctggcagcgg ctctggcacc gactacagcc tgacaatcag caacctggaa  300
caagaggata tcgctaccta cttctgccag caaggcaaca ccctgcctta cacctttggc  360
ggaggcacca agctggaaat caccggtgga ggtggttctg gcggaggggg atctggtgga  420
ggcggttcag aagtgaaact gcaagagtct ggccctggac tggtggcccc atctcagtct  480
ctgagcgtga cctgtacagt cagcggagtg tccctgcctg attacggcgt gtcctggatc  540
agacagcctc ctcggaaagg cctggaatgg ctgggagtga tctggggcag cgagacaacc  600
tactacaaca gcgccctgaa gtcccggctg accatcatca aggacaactc caagagccag  660
gtgttcctga agatgaacag cctgcagacc gacgacaccg ccatctacta ttgcgccaag  720
cactactact acggcggcag ctacgccatg gattattggg gccagggcac cagcgtgacc  780
gtttcttcta ccacaacgcc cgccccgcga ccgcctactc ccgctcccac aattgcatca  840
caacccctgt ctttgagacc cgaagcttgt cgaccagctg ccggtggcgc ggttcacacg  900
cgggggctcg atttcgcctg tgatatatat atatgggccc cattggctgg aacatgcgga  960
gtattgcttc tgagcctggt gattaccctc tactgtaaga gaggccggaa gaaacttctt  1020
tatatattca agcagccctt tatgcgaccc gttcagacta cccaagagga agatggatgc  1080
agttgccgct ttccagaaga ggaggagggc gggtgcgaac tgagagtgaa gttcagcaga  1140
tccgccgatg ctcccgccta tcagcagggc caaaaccagc tgtacaacga gctgaacctg  1200
gggagaagag aagagtacga cgtgctggac aagcggagag gcagagatcc tgaaatgggc  1260
ggcaagccca gacggaagaa tcctcaagag ggcctgtata atgagctgca gaaagacaag  1320
atggccgagg cctacagcga gatcggaatg aagggcgagc gcagaagagg caagggacac  1380
gatggactgt accagggact gagcaccgcc accaaggata cctatgacgc cctgcacatg  1440
caggccctgc ctccaagata a                                              1461

SEQ ID NO: 314         moltype = DNA  length = 1461
FEATURE                Location/Qualifiers
source                 1..1461
                       mol_type = other DNA
                       organism = synthetic construct
SEQUENCE: 314
atggctctcc cggtcacagc ccttctcctg cccctggcac tcttgctgca tgcggcacga  60
cccgacatcc agatgaccca gaccacaagc agcctgtctg ccagcctggg cgatagagtg  120
accatcagct gtagagccag ccaggacatc agcaagtacc tgaactggta tcagcaaaag  180
```

```
cccgacggca ccgtgaagct gctgatctac cacaccagca gactgcacag cggcgtgcca  240
agcagatttt ctggcagcgg ctctggcacc gactacagcc tgacaatcag caacctggaa  300
caagaggata tcgctaccta cttctgccag caaggcaaca ccctgcctta cacctttggc  360
ggaggcacca agctggaaat caccggtgga ggtggttctg gcggaggggg atctggtgga  420
ggcggttcag aagtgaaact gcaagagtct ggccctggac tggtggcccc atctcagtct  480
ctgagcgtga cctgtacagt cagcggagtg tccctgcctg attacggcgt gtcctggatc  540
agacagcctc ctcggaaagg cctggaatgg ctgggagtga tctggggcag cgagacaacc  600
tactacaaca gcgccctgaa gtcccggctg accatcatca aggacaactc caagagccag  660
gtgttcctga agatgaacag cctgcagacc gacgacaccg ccatctacta ttgcgccaag  720
cactactact acggcggcag ctacgccatg gattattggg gccagggcac cagcgtgacc  780
gtttcttcta ccacaacgcc cgccccgcga ccgcctactc ccgctcccac aattgcatca  840
caacccctgt ctttgagacc cgaagcttgt cgaccagctg ccggtggcgc ggttcacacg  900
cgggggctcg atttcgcctg tgatatatat atatgggccc cattggctgg aacatgcgga  960
gtattgcttc tgagcctggt gattaccctc tactgtaaga gaggccggaa gaaacttctt  1020
tatatattca agcagccctt tatgcgaccc gttcagacta cccaagagga agatggatgc  1080
agttgccgct ttccagaaga ggaggagggc gggtgcgaac tgagagtgaa gttcagcaga  1140
tccgccgatg ctcccgccta taagcagggc caaaaccagc tgtacaacga gctgaacctg  1200
gggagaagag aagagtacga cgtgctggac aagcggagag gcagagatcc tgaaatgggc  1260
ggcaagccca gacggaagaa tcctcaagag ggcctgtata atgagctgca gaaagacaag  1320
atggccgagg cctacagcga gatcggaatg aagggcgagc gcagaagagg caagggacac  1380
gatggactgt accagggact gagcaccgcc accaaggata cctatgacgc cctgcacatg  1440
caggccctgc ctccaagata a                                            1461
```

```
SEQ ID NO: 315          moltype = DNA  length = 1452
FEATURE                 Location/Qualifiers
source                  1..1452
                        mol_type = other DNA
                        organism = synthetic construct
SEQUENCE: 315
atgctgctgc tggtcacatc tctgctgctg tgcgagctgc cccatcctgc ctttctgctg  60
atcccccagg ttcaactcca gcagtctggt cccggcctcg ttaaaccaag ccagactttg  120
tctcttacct gtgctatcag tggcgatagc gtgtctagta attcagccgc atggaactgg  180
atccgacaat caccgagtag ggacttgaa tggctgggta gaacctatta ccggtccaaa  240
tggtacaatg actatgcagt gtctgtaaaa agcaggatca cgatcaaccc tgatacgtct  300
aaaaaccagt tttctctgca acttaatagt gtgacccctg aagacaccgc tgtgtattac  360
tgtgcacggg aggttaccgg tgatcttgaa gatgcttttg atatatgggg ccaaggtacg  420
atggtcacgg tgtctagtgg gggaggcggc agcgacatac agatgacgca gagcccatcc  480
agtctctccg cgtctgttgg tgacagagtg actattacat gtagggcgtc tcagaccatt  540
tggtcttacc tcaattggta tcaacagcga ccaggcaaag caccgaactt gctcatttac  600
gctgccagct cactccaaag tggtgtgccg tccagattta gtggtagggg cagtggcact  660
gatttcactc tgactatttc aagtcttcaa gctgaggatt ttgccacata ctactgccag  720
caaagttact caatacctca gacttttgga caggggacaa aattggagat taaatccgga  780
accacaacgc ccgccccgcg accgcctact cccgctccca caattgcatc acaacccctg  840
tctttgagac ccgaagcttg tcgaccagct gccggtggcg cggttcacac gcgggggctc  900
gatttcgcct gtgatatata tatatgggcc ccattggctg gaacatgcgg agtattgctt  960
ctgagcctgg tgattaccct ctactgtaag agaggccgga agaaacttct ttatatattc  1020
aagcagccct ttatgcgacc cgttcagact acccaagagg aagatggatg cagttgccgc  1080
tttccagaag aggaggaggg cgggtgcgaa ctgagagtga agttcagcag atccgccgat  1140
gctcccgcct ataagcaggg ccaaaaccag ctgtacaacg agctgaacct ggggagaaga  1200
gaagagtacg acgtgctgga caagcggaga ggcagagatc ctgaaatggg cggcaagccc  1260
agacggaaga atcctcaaga gggcctgtat aatgagctgc agaaagacaa gatggccgag  1320
gcctacagcg agatcggaat gaagggcgag cgcagaagag gcaagggaca cgatggactg  1380
taccagggac tgagcaccgc caccaaggat acctatgacg ccctgcacat gcaggccctg  1440
cctccaagat aa                                                    1452
```

```
SEQ ID NO: 316          moltype = DNA  length = 2202
FEATURE                 Location/Qualifiers
source                  1..2202
                        mol_type = other DNA
                        organism = synthetic construct
SEQUENCE: 316
atgctgctgc tggtcacatc tctgctgctg tgcgagctgc cccatcctgc ctttctgctg  60
atccccgaca tccagatgac ccagaccaca agcagcctgt ctgccagcct gggcgataga  120
gtgaccatca gctgtagagc cagccaggac atcagcaagt acctgaactg gtatcagcaa  180
aagcccgacg gcaccgtgaa gctgctgatc taccacacca gcagactgca cagcggcgtg  240
ccaagcagat tttctggcag cggctctggc accgactaca gcctgacaat cagcaacctg  300
gaacaagagg atatcgctac ctacttctgc cagcaaggca acaccctgcc ttacaccttt  360
ggcggaggca ccaagctgga aatcaccggc ggcggaggat cccaggttca actccagcag  420
tctggtcccg gcctcgttaa accaagccag actttgtctc ttacctgtgc tatcagtggc  480
gatagcgtgt ctagtaattc agccgcatgg aactggatcc gacaatcacc gagtagggga  540
cttgaatggc tgggtagaac ctattaccgg tccaaatggt acaatgacta tgcagtgtct  600
gtaaaaagca ggatcacgat caaccctgat acgtctaaaa accagttttc tctgcaactt  660
aatagtgtga cccctgaaga caccgctgtg tattactgtg cacgggaggt taccggtgat  720
cttgaagatg cttttgatat atggggccaa ggtacgatgg tcacggtgtc tagtggctct  780
acaagcggca gcggcaaacc tggatctggc gagggatcta ccaagggcga catacagatg  840
acgcagagcc catccagtct ctccgcgtct gttggtgaca gagtgactat tacatgtagg  900
gcgtctcaga ccatttggtc ttacctcaat tggtatcaac agcgaccagg caaagcaccg  960
aacttgctca tttacgctgc cagctcactc caaagtggtg tgccgtccag atttagtggt  1020
aggggcagtg gcactgattt cactctgact atttcaagtc ttcaagctga ggattttgcc  1080
```

-continued

```
acatactact gccagcaaag ttactcaata cctcagactt ttggacaggg gacaaaattg  1140
gagattaaag ggggaggcgg cagcgaagtg aaactgcaag agtctggccc tggactggtg  1200
gccccatctc agtctctgag cgtgacctgt acagtcagcg gagtgtccct gcctgattac  1260
ggcgtgtcct ggatcagaca gcctcctcgg aaaggcctgg aatggctggg agtgatctgg  1320
ggcagcgaga caacctacta caacagcgcc ctgaagtccc ggctgaccat catcaaggac  1380
aactccaaga gccaggtgtt cctgaagatg aacagcctgc agaccgacga caccgccatc  1440
tactattgcg ccaagcacta ctactacggc ggcagctacg ccatggatta ttggggccag  1500
ggcaccagcg tgaccgtttc ttcttccgga accacaacgc ccgccccgcg accgcctact  1560
cccgctccca caattgcatc acaacccctg tctttgagac ccgaagcttg tcgaccagct  1620
gccggtggcg cggttcacac gcgggggctc gatttcgcct gtgatatata tatatgggcc  1680
ccattggctg gaacatgcgg agtattgctt ctgagcctgg tgattaccct ctactgtaag  1740
agaggccgga agaaacttct ttatatattc aagcagccct ttatgcgacc cgttcagact  1800
acccaagagg aagatggatg cagttgccgc tttccagaag aggaggaggg cgggtgcgaa  1860
ctgagagtga agttcagcag atccgccgat gctcccgcct ataagcaggg ccaaaaccag  1920
ctgtacaacg agctgaacct ggggagaaga gaagagtacg acgtgctgga caagcggaga  1980
ggcagagatc ctgaaatggg cggcaagccc agacggaaga atcctcaaga gggcctgtat  2040
aatgagctgc agaaagacaa gatggccgag gcctacagcg agatcggaat gaagggcgag  2100
cgcagaagag gcaagggaca cgatggactg taccagggac tgagcaccgc caccaaggat  2160
acctatgacg ccctgcacat gcaggccctg cctccaagat aa                      2202

SEQ ID NO: 317          moltype = DNA  length = 2262
FEATURE                 Location/Qualifiers
source                  1..2262
                        mol_type = other DNA
                        organism = synthetic construct
SEQUENCE: 317
atgctgctgc tggtcacatc tctgctgctg tgcgagctgc cccatcctgc ctttctgctg  60
atcccccagg ttcaactcca gcagtctggt cccggcctcg ttaaaccaag ccagactttg  120
tctcttacct gtgctatcag tggcgatagc gtgtctagta attcagccgc atggaactgg  180
atccgacaat caccgagtag gggacttgaa tggctgggta gaacctatta ccggtccaaa  240
tggtacaatg actatgcagt gtctgtaaaa agcaggatca cgatcaaccc tgatacgtct  300
aaaaaccagt tttctctgca acttaatagt gtgacccctg aagacaccgc tgtgtattac  360
tgtgcacggg aggttaccgg tgatcttgaa gatgcttttg atatatgggg ccaaggtacg  420
atggtcacgg tgtctagtgg gggaggcggc agcgacatac agatgacgca gagcccatcc  480
agtctctccg cgtctgttgg tgacagagtg actattacat gtagggcgtc tcagaccatt  540
tggtcttacc tcaattggta tcaacagcga ccaggcaaag caccgaactt gctcatttac  600
gctgccagct cactccaaag tggtgtgccg tccagattta gtggtagggg cagtggcact  660
gatttcactc tgactatttc aagtcttcaa gctgaggatt ttgccacata ctactgccag  720
caaagttact caatacctca gacttttgga caggggacaa aattggagat taaaggggga  780
ggcggatccg gcggtggtgg ctccggcggt ggtggttctg gaggcggcgg aagcggtggg  840
ggtggtagcg acatccagat gacccagacc acaagcagcc tgtctgccag cctgggcgat  900
agagtgacca tcagctgtag agccagccag gacatcagca agtacctgaa ctggtatcag  960
caaaagcccg acggcaccgt gaagctgctg atctaccaca ccagcagact gcacagcggc  1020
gtgccaagca gattttctgg cagcggctct ggcaccgact acagcctgac aatcagcaac  1080
ctggaacaag aggatatcgc tacctacttc tgccagcaag gcaacaccct gccttacacc  1140
tttggcggag gcaccaagct ggaaatcacc ggctctacaa gcggcagcgg caaacctgga  1200
tctggcgagg gatctaccaa gggcgaagtg aaactgcaag agtctggccc tggactggtg  1260
gccccatctc agtctctgag cgtgacctgt acagtcagcg gagtgtccct gcctgattac  1320
ggcgtgtcct ggatcagaca gcctcctcgg aaaggcctgg aatggctggg agtgatctgg  1380
ggcagcgaga caacctacta caacagcgcc ctgaagtccc ggctgaccat catcaaggac  1440
aactccaaga gccaggtgtt cctgaagatg aacagcctgc agaccgacga caccgccatc  1500
tactattgcg ccaagcacta ctactacggc ggcagctacg ccatggatta ttggggccag  1560
ggcaccagcg tgaccgtttc ttcttccgga accacaacgc ccgccccgcg accgcctact  1620
cccgctccca caattgcatc acaacccctg tctttgagac ccgaagcttg tcgaccagct  1680
gccggtggcg cggttcacac gcgggggctc gatttcgcct gtgatatata tatatgggcc  1740
ccattggctg gaacatgcgg agtattgctt ctgagcctgg tgattaccct ctactgtaag  1800
agaggccgga agaaacttct ttatatattc aagcagccct ttatgcgacc cgttcagact  1860
acccaagagg aagatggatg cagttgccgc tttccagaag aggaggaggg cgggtgcgaa  1920
ctgagagtga agttcagcag atccgccgat gctcccgcct ataagcaggg ccaaaaccag  1980
ctgtacaacg agctgaacct ggggagaaga gaagagtacg acgtgctgga caagcggaga  2040
ggcagagatc ctgaaatggg cggcaagccc agacggaaga atcctcaaga gggcctgtat  2100
aatgagctgc agaaagacaa gatggccgag gcctacagcg agatcggaat gaagggcgag  2160
cgcagaagag gcaagggaca cgatggactg taccagggac tgagcaccgc caccaaggat  2220
acctatgacg ccctgcacat gcaggccctg cctccaagat aa                      2262

SEQ ID NO: 318          moltype = AA  length = 42
FEATURE                 Location/Qualifiers
source                  1..42
                        mol_type = protein
                        organism = synthetic construct
SEQUENCE: 318
KRGRKKLLYI FKQPFMRPVQ TTQEEDGCSC RFPEEEEGGC EL                      42

SEQ ID NO: 319          moltype = AA  length = 112
FEATURE                 Location/Qualifiers
source                  1..112
                        mol_type = protein
                        organism = synthetic construct
```

```
SEQUENCE: 319
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 320         moltype = AA  length = 241
FEATURE                Location/Qualifiers
source                 1..241
                       mol_type = protein
                       organism = synthetic construct
SEQUENCE: 320
QVQLVQSGAE VEKPGASVKV SCKASGYTFT DYYMHWVRQA PGQGLEWMGW INPNSGGTNY  60
AQKFQGRVTM TRDTSISTAY MELSRLRSDD TAVYYCASGW DFDYWGQGTL VTVSSGGGGS  120
GGGGSGGGGS GGGGSDIVMT QSPSSLSASV GDRVTITCRA SQSIRYYLSW YQQKPGKAPK  180
LLIYTASILQ NGVPSRFSGS GSGTDFTLTI SSLQPEDFAT YYCLQTYTTP DFGPGTKVEI  240
K                                                                   241

SEQ ID NO: 321         moltype = AA  length = 120
FEATURE                Location/Qualifiers
source                 1..120
                       mol_type = protein
                       organism = synthetic construct
SEQUENCE: 321
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 322         moltype = AA  length = 107
FEATURE                Location/Qualifiers
source                 1..107
                       mol_type = protein
                       organism = synthetic construct
SEQUENCE: 322
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT               107

SEQ ID NO: 323         moltype = AA  length = 493
FEATURE                Location/Qualifiers
source                 1..493
                       mol_type = protein
                       organism = synthetic construct
SEQUENCE: 323
MALPVTALLL PLALLLHAAR PDIVLTQSPA SLAVSLGERA TINCRASESV SVIGAHLIHW  60
YQQKPGQPPK LLIYLASNLE TGVPARFSGS GSGTDFTLTI SSLQAEDAAI YYCLQSRIFP  120
RTFGQGTKLE IKGSTSGSGK PGSGEGSTKG QVQLVQSGSE LKKPGASVKV SCKASGYTFT  180
DYSINWVRQA PGQGLEWMGW INTETREPAY AYDFRGRFVF SLDTSVSTAY LQISSLKAED  240
TAVYYCARDY SYAMDYWGQG TLVTVSSAAA TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                      493

SEQ ID NO: 324         moltype = AA  length = 207
FEATURE                Location/Qualifiers
source                 1..207
                       mol_type = protein
                       organism = synthetic construct
SEQUENCE: 324
KNQVEQSPQS LIILEGKNCT LQCNYTVSPF SNLRWYKQDT GRGPVSLTIM TFSENTKSNG  60
RYTATLDADT KQSSLHITAS QLSDSASYIC VVNHSGGSYI PTFGRGTSLI VHPYIQKPDP  120
AVYQLRDSKS SDKSVCLFTD FDSQTNVSQS KDSDVYITDK TVLDMRSMDF KSNSAVAWSN  180
KSDFACANAF NNSIIPEDTF FPSPESS                                       207

SEQ ID NO: 325         moltype = AA  length = 246
FEATURE                Location/Qualifiers
source                 1..246
                       mol_type = protein
                       organism = synthetic construct
SEQUENCE: 325
DVKVTQSSRY LVKRTGEKVF LECVQDMDHE NMFWYRQDPG LGLRLIYFSY DVKMKEKGDI  60
PEGYSVSREK KERFSLILES ASTNQTSMYL CASSFLMTSG DPYEQYFGPG TRLTVTEDLK  120
NVFPPEVAVF EPSEAEISHT QKATLVCLAT GFYPDHVELS WWVNGKEVHS GVSTDPQPLK  180
EQPALNDSRY CLSSRLRVSA TFWQNPRNHF RCQVQFYGLS ENDEWTQDRA KPVTQIVSAE  240
AWGRAD                                                              246

SEQ ID NO: 326         moltype = AA  length = 115
FEATURE                Location/Qualifiers
source                 1..115
                       mol_type = protein
                       organism = synthetic construct
```

```
SEQUENCE: 326
MQEVTQIPAA LSVPEGENLV LNCSFTDSAI YNLQWFRQDP GKGLTSLLLI QSSQREQTSG  60
RLNASLDKSS GRSTLYIAAS QPGDSATYLC AVRPTSGGSY IPTFGRGTSL IVHPY       115

SEQ ID NO: 327         moltype = AA  length = 112
FEATURE                Location/Qualifiers
source                 1..112
                       mol_type = protein
                       organism = synthetic construct
SEQUENCE: 327
MGVTQTPKFQ VLKTGQSMTL QCAQDMNHEY MSWYRQDPGM GLRLIHYSVG AGITDQGEVP  60
NGYNVSRSTT EDFPLRLLSA APSQTSVYFC ASSYVGNTGE LFFGEGSRLT VL          112

SEQ ID NO: 328         moltype = AA  length = 166
FEATURE                Location/Qualifiers
source                 1..166
                       mol_type = protein
                       organism = synthetic construct
SEQUENCE: 328
APPRLICDSR VLERYLLEAK EAENITTGCA EHCSLNENIT VPDTKVNFYA WKRMEVGQQA  60
VEVWQGLALL SEAVLRGQAL LVNSSQPWEP LQLHVDKAVS GLRSLTTLLR ALGAQKEAIS  120
PPDAASAAPL RTITADTFRK LFRVYSNFLR GKLKLYTGEA CRTGDR                166

SEQ ID NO: 329         moltype = AA  length = 452
FEATURE                Location/Qualifiers
source                 1..452
                       mol_type = protein
                       organism = synthetic construct
SEQUENCE: 329
MSTAVLENPG LGRKLSDFGQ ETSYIEDNCN QNGAISLIFS LKEEVGALAK VLRLFEENDV  60
NLTHIESRPS RLKKDEYEFF THLDKRSLPA LTNIIKILRH DIGATVHELS RDKKKDTVPW  120
FPRTIQELDR FANQILSYGA ELDADHPGFK DPVYRARRKQ FADIAYNYRH GQPIPRVEYM  180
EEEKKTWGTV FKTLKSLYKT HACYEYNHIF PLLEKYCGFH EDNIPQLEDV SQFLQTCTGF  240
RLRPVAGLLS SRDFLGGLAF RVFHCTQYIR HGSKPMYTPE PDICHELLGH VPLFSDRSFA  300
QFSQEIGLAS LGAPDEYIEK LATIYWFTVE FGLCKQGDSI KAYGAGLLSS FGELQYCLSE  360
KPKLLPLELE KTAIQNYTVT EFQPLYYVAE SFNDAKEKVR NFAATIPRPF SVRYDPYTQR  420
IEVLDNTQQL KILADSINSE IGILCSALQK IK                               452

SEQ ID NO: 330         moltype = AA  length = 1462
FEATURE                Location/Qualifiers
source                 1..1462
                       mol_type = protein
                       organism = synthetic construct
SEQUENCE: 330
LSVKAQTAHI VLEDGTKMKG YSFGHPSSVA GEVVFNTGLG GYPEAITDPA YKGQILTMAN  60
PIIGNGGAPD TTALDELGLS KYLESNGIKV SGLLVLDYSK DYNHWLATKS LGQWLQEEKV  120
PAIYGVDTRM LTKIIRDKGT MLGKIEFEGQ PVDFVDPNKQ NLIAEVSTKD VKVYGKGNPT  180
KVVAVDCGIK NNVIRLLVKR GAEVHLVPWN HDFTKMEYDG ILIAGGPGNP ALAEPLIQNV  240
RKILESDRKE PLFGISTGNL ITGLAAGAKT YKMSMANRGQ NQPVLNITNK QAFITAQNHG  300
YALDNTLPAG WKPLFVNVND QTNEGIMHES KPFFAVQFHP EVTPGPIDTE YLFDSFFSLI  360
KKGKATTITS VLPKPALVAS RVEVSKVLIL GSGGLSIGQA GEFDYSGSQA VKAMKEENVK  420
TVLMNPNIAS VQTNEVGLKQ ADTVYFLPIT PQFVTEVIKA EQPDGLILGM GGQTALNCGV  480
ELFKRGVLKE YGVKVLGTSV ESIMATEDRQ LFSDKLNEIN EKIAPSFAVE SIEDALKAAD  540
TIGYPVMIRS AYALGGLGSG ICPNRETLMD LSTKAFAMTN QILVEKSVTG WKEIEYEVVR  600
DADDNCVTVC NMENVDAMGV HTGDSVVVAP AQTLSNAEFQ MLRRTSINVV RHLGIVGECN  660
IQFALHPTSM EYCIIEVNAR LSRSSALASK ATGYPLAFIA AKIALGIPLP EIKNVVSGKT  720
SACFEPSLDY MVTKIPRWDL DRFHGTSSRI GSSMKSVGEV MAIGRTFEES FQKALRMCHP  780
SIEGFTPRLP MNKEWPSNLD LRKELSEPSS TRIYAIAKAI DDNMSLDEIE KLTYIDKWFL  840
YKMRDILNME KTLKGLNSES MTEETLKRAK EIGFSDKQIS KCLGLTEAQT RELRLKKNIH  900
PWVKQIDTLA AEYPSVTNYL YVTYNGQEHD VNFDDHGMMV LGCGPYHIGS SVEFDWCAVS  960
SIRTLRQLGK KTVVVNCNPE TVSTDFDECD KLYFEELSLE RILDIYHQEA CGGCIISVGG  1020
QIPNNLAVPL YKNGVKIMGT SPLQIDRAED RSIFSAVLDE LKVAQAPWKA VNTLNEALEF  1080
AKSVDYPCLL RPSYVLSGSA MNVVFSEDEM KKFLEEATRV SQEHPVVLTK FVEGAREVEM  1140
DAVGKDGRVI SHAISEHVED AGVHSGDATL MLPTQTISQG AIEKVKDATR KIAKAFAISG  1200
PFNVQFLVKG NDVLVIECNL RASRSFPFVS KTLGVDFIDV ATKVMIGENV DEKHLPTLDH  1260
PIIPADYVAI KAPMFSWPRL RDADPILRCE MASTGEVACF GEGIHTAFLK AMLSTGFKIP  1320
QKGILIGIQQ SFRPRFLGVA EQLHNEGFKL FATEATSDWL NANNVPATPV AWPSQEGQNP  1380
SLSSIRKLIR DGSIDLVINL PNNNTKFVHD NYVIRRTAVD SGIPLLTNFQ VTKLFAEAVQ  1440
KSRKVDSKSL FHYRQYSAGK AA                                          1462

SEQ ID NO: 331         moltype = AA  length = 1053
FEATURE                Location/Qualifiers
source                 1..1053
                       mol_type = protein
                       organism = synthetic construct
SEQUENCE: 331
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
```

```
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                              1053

SEQ ID NO: 332          moltype = AA  length = 1353
FEATURE                 Location/Qualifiers
source                  1..1353
                        mol_type = protein
                        organism = synthetic construct
SEQUENCE: 332
AAGGILHLEL LVAVGPDVFQ AHQEDTERYV LTNLNIGAEL LRDPSLGAQF RVHLVKMVIL  60
TEPEGAPNIT ANLTSSLLSV CGWSQTINPE DDTDPGHADL VLYITRFDLE LPDGNRQVRG  120
VTQLGGACSP TWSCLITEDT GFDLGVTIAH EIGHSFGLEH DGAPGSGCGP SGHVMASDGA  180
APRAGLAWSP CSRRQLLSLL SAGRARCVWD PPRPQPGSAG HPPDAQPGLY YSANEQCRVA  240
FGPKAVACTF AREHLDMCQA LSCHTDPLDQ SSCSRLLVPL LDGTECGVEK WCSKGRCRSL  300
VELTPIAAVH GRWSSWGPRS PCSRSCGGGV VTRRRQCNNP RPAFGGRACV GADLQAEMCN  360
TQACEKTQLE FMSQQCARTD GQPLRSSPGG ASFYHWGAAV PHSQGDALCR HMCRAIGESF  420
IMKRGDSFLD GTRCMPSGPR EDGTLSLCVS GSCRTFGCDG RMDSQQVWDR CQVCGGDNST  480
CSPRKGSFTA GRAREYVTFL TVTPNLTSVY IANHRPLFTH LAVRIGGRYV VAGKMSISPN  540
TTYPSLLEDG RVEYRVALTE DRLPRLEEIR IWGPLQEDAD IQVYRRYGEE YGNLTRPDIT  600
FTYFQPKPRQ AWVWAAVRGP CSVSCGAGLR WVNYSCLDQA RKELVETVQC QGSQQPPAWP  660
EACVLEPCPP YWAVGDFGPC SASCGGGLRE RPVRCVEAQG SLLKTLPPAR CRAGAQQPAV  720
ALETCNPQPC PARWEVSEPS SCTSAGGAGL ALENETCVPG ADGLEAPVTE GPGSVDEKLP  780
APEPCVGMSC PPGWGHLDAT SAGEKAPSPW GSIRTGAQAA HVWTPAAGSC SVSCGRGLME  840
LRFLCMDSAL RVPVQEELCG LASKPGSRRE VCQAVPCPAR WQYKLAACSV SCGRGVVRRI  900
LYCARAHGED DGEEILLDTQ CQGLPRPEPQ EACSLEPCPP RWKVMSLGPC SASCGLGTAR  960
RSVACVQLDQ GQDVEVDEAA CAALVRPEAS VPCLIADCTY RWHVGTWMEC SVSCGDGIQR  1020
RRDTCLGPQA QAPVPADFCQ HLPKPVTVRG CWAGPCVGQG TPSLVPHEEA AAPGRTTATP  1080
AGASLEWSQA RGLLFSPAPQ PRRLLPGPQE NSVQSSACGR QHLEPTGTID MRGPGQADCA  1140
VAIGRPLGEV VTLRVLESSL NCSAGDMLLL WGRLTWRKMC RKLLDMTFSS KTNTLVVRQR  1200
CGRPGGGVLL RYGSQLAPET FYRECDMQLF GPWGEIVSPS LSPATSNAGG CRLFINVAPH  1260
ARIAIHALAT NMGAGTEGAN ASYILIRDTH SLRTTAFHGQ QVLYWESESS QAEMEFSEGF  1320
LKAQASLRGQ YWTLQSWVPE MQDPQSWKGK EGT                              1353

SEQ ID NO: 333          moltype = AA  length = 431
FEATURE                 Location/Qualifiers
source                  1..431
                        mol_type = protein
                        organism = synthetic construct
SEQUENCE: 333
MPNPRPGKPS APSLALGPSP GASPSWRAAP KASDLLGARG PGGTFQGRDL RGGAHASSSS  60
LNPMPPSQLQ LPTLPLVMVA PSGARLGPLP HLQALLQDRP HFMHQLSTVD AHARTPVLQV  120
HPLESPAMIS LTPPTTATGV FSLKARPGLP PGINVASLEW VSREPALLCT FPNPSAPRKD  180
STLSAVPQSS YPLLANGVCK WPGCEKVFEE PEDFLKHCQA DHLLDEKGRA QCLLQREMVQ  240
SLEQQLVLEK EKLSAMQAHL AGKMALTKAS SVASSDKGSC CIVAAGSQGP VVPAWSGPRE  300
APDSLFAVRR HLWGSHGNST FPEFLHNMDY FKFHNMRPPF TYATLIRWAI LEAPEKQRTL  360
NEIYHWFTRM FAFFRNHPAT WKNAIRHNLS LHKCFVRVES EKGAVWTVDE LEFRKKRSQR  420
PSRCSNPTPG P                                                      431

SEQ ID NO: 334          moltype = AA  length = 160
FEATURE                 Location/Qualifiers
source                  1..160
                        mol_type = protein
                        organism = synthetic construct
SEQUENCE: 334
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                       160

SEQ ID NO: 335          moltype = AA  length = 133
FEATURE                 Location/Qualifiers
source                  1..133
                        mol_type = protein
                        organism = synthetic construct
```

-continued

```
SEQUENCE: 335
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 336          moltype = DNA  length = 37
FEATURE                 Location/Qualifiers
source                  1..37
                        mol_type = other DNA
                        organism = synthetic construct
SEQUENCE: 336
gagacgtttt cttgggtcta ccgtttaata ttgcgtc                           37
```

CIRCULAR RNA COMPOSITIONS AND METHODS

CROSS-REFERENCE TO RELATED APPLICATIONS

This application is a continuation of U.S. application Ser. No. 17/548,247, filed on Dec. 10, 2021, which is a continuation of U.S. application Ser. No. 17/384,460, filed on Jul. 23, 2021, which is a continuation of International Patent Application No. PCT/US2020/034418, filed on May 22, 2020, which claims the benefit of and priority to U.S. Provisional Patent Application No. 62/851,548, filed May 22, 2019; U.S. Provisional Patent Application No. 62/857,121, filed Jun. 4, 2019; International Patent Application No. PCT/US2019/035531, filed Jun. 5, 2019, U.S. Provisional Patent Application No. 62/943,796, filed Dec. 4, 2019; U.S. Provisional Patent Application No. 62/943,779, filed Dec. 4, 2019; and U.S. Provisional Patent Application No. 62/972,194, filed Feb. 10, 2020, the disclosures of each of which are hereby incorporated by reference in their entireties for all purposes.

SEQUENCE LISTING

The instant application contains a Sequence Listing which has been submitted electronically in XML format and is hereby incorporated by reference in its entirety. Said XML file, created on Jun. 27, 2023, is named OBS_101WOC3_Sequence_Listing.xml, and is 388,401 bytes in size.

BACKGROUND

Conventional gene therapy involves the use of DNA for insertion of desired genetic information into host cells. The DNA introduced into the cell is usually integrated to a certain extent into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as e.g., elimination or deleteriously reduced production of an essential enzyme or interruption of a gene critical for the regulation of cell growth, resulting in unregulated or cancerous cell proliferation. In addition, with conventional DNA-based gene therapy, it is necessary for effective expression of the desired gene product to include a strong promoter sequence, which again may lead to undesirable changes in the regulation of normal gene expression in the cell. It is also possible that the DNA-based genetic material will result in the induction of undesired anti-DNA antibodies, which in turn, may trigger a possibly fatal immune response. Gene therapy approaches using viral vectors can also result in an adverse immune response. In some circumstances, the viral vector may even integrate into the host genome. In addition, production of clinical grade viral vectors also is expensive and time consuming. Targeting delivery of the introduced genetic material using viral vectors can also be difficult to control. Thus, while DNA-based gene therapy has been evaluated for delivery of secreted proteins using viral vectors (U.S. Pat. No. 6,066,626; US2004/0110709), these approaches may be limited for these various reasons.

In contrast to DNA, the use of RNA as a gene therapy agent is substantially safer because RNA does not involve the risk of being stably integrated into the genome of the transfected cell, thus eliminating the concern that the introduced genetic material will disrupt the normal functioning of an essential gene, or cause a mutation that results in deleterious or oncogenic effects, and extraneous promoter sequences are not required for effective translation of the encoded protein, again avoiding possible deleterious side effects. In addition, it is not necessary for mRNA to enter the nucleus to perform its function, while DNA must overcome this major barrier.

Circular RNA is useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Use of T cells genetically modified to express Chimeric Antigen Receptors (CARs) and recombinant T Cell Receptors (TCRs) targeting antigens on cancer cells is an attractive therapeutic strategy for the treatment of cancer. However, current methods of modifying T cells to express CARs and TCRs and the resulting therapies are associated with toxicity in the form of Cytokine Release Syndrome (CRS) and other complications. There remains a need for safer methods of engineering cells to express CARs and recombinant TCRs.

Prior to this invention, there were three main techniques for making circularized RNA in vitro: the splint-mediated method, the permuted intron-exon method, and the RNA ligase-mediated method. However, the existing methodologies are limited by the size of RNA that can be circularized, thus limiting their therapeutic application.

SUMMARY

In one aspect, provided herein is a pharmaceutical composition comprising: a circular RNA polynucleotide comprising, in the following order, a 3' group I intron fragment, an Internal Ribosome Entry Site (IRES), an expression sequence encoding a chimeric antigen receptor (CAR) or T cell receptor (TCR) complex protein, and a 5' group I intron fragment, and a transfer vehicle comprising at least one of (i) an ionizable lipid, (ii) a structural lipid, and (iii) a PEG-modified lipid, wherein the transfer vehicle is capable of delivering the circular RNA polynucleotide to a human immune cell present in a human subject, such that the CAR is translated in the human immune cell and expressed on the surface of the human immune cell. 191 In some embodiments, the pharmaceutical composition is formulated for intravenous administration to the human subject in need thereof. In some embodiments, the 3' group I intron fragment and 5' group I intron fragment are Anabaena group I intron fragments.

In certain embodiments, the 3' intron fragment and 5' intron fragment are defined by the L9a-5 permutation site in the intact intron. In certain embodiments, the 3' intron fragment and 5' intron fragment are defined by the L8-2 permutation site in the intact intron.

In some embodiments, the IRES is from Taura syndrome virus, Triatoma virus, Theiler's encephalomyelitis virus, Simian Virus 40, Solenopsis invicta virus 1, Rhopalosiphum padi virus, Reticuloendotheliosis virus, Human poliovirus 1, Plautia stali intestine virus, Kashmir bee virus, Human rhinovirus 2, Homalodisca coagulata virus-1, Human Immunodeficiency Virus type 1, Homalodisca coagulata virus-1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, Drosophila C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, Drosophila antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BNS, Salivirus A BN2, Salivirus A 02394, Salivirus A GUT, Salivirus A CH, Salivirus A SZ1, Salivirus FHB, CVB3, CVB1, Echovirus 7, CVBS, EVA71, CVA3, CVA12, EV24 or an aptamer to eIF4G.

In some embodiments, the IRES comprises a CVB3 IRES or a fragment or variant thereof, or wherein the IRES comprises a sequence according to SEQ ID NO: 65. In some embodiments, the IRES comprises a salivirus SZ1 IRES or a fragment or variant thereof. In certain embodiments, the IRES comprises a sequence according to SEQ ID NO: 63. In some embodiments, the pharmaceutical composition comprises a first internal spacer between the 3' group I intron fragment and the IRES, and a second internal spacer between the expression sequence and the 5' group I intron fragment. In certain embodiments, the first and second internal spacers each have a length of about 10 to about 60 nucleotides.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disaloganglioside GD3, TNF receptor family member, B cell maturation antigen (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRCSD), chromosome X open reading frame 61 (CXORF61), CD97, and CD179a.

In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta. In some embodiments, the transfer vehicle comprises a lipid nanoparticle, a core-shell nanoparticle, a biodegradable nanoparticle, a biodegradable lipid nanoparticle, a polymer nanoparticle, or a biodegradable polymer nanoparticle.

In some embodiments, the pharmaceutical composition further comprises a targeting moiety. In certain embodiments, the targeting moiety mediates receptor-mediated endocytosis or direct fusion into selected cells of a selected cell population or tissue in the absence of cell isolation or purification. In certain embodiments, the targeting moiety is capable of binding to a protein selected from the group CD3, CD4, CD8, CD5, CD7, PD-1, 4-1BB, CD28, C1q, and CD2.

In certain embodiments, the targeting moiety comprises an antibody specific for a macrophage, dendritic cell, NK cell, NKT, or T cell antigen. In certain embodiments, the targeting moiety comprises a scFv, nanobody, peptide, minibody, polynucleotide aptamer, heavy chain variable region, light chain variable region or fragment thereof.

In some embodiments, the pharmaceutical composition is administered in an amount effective to treat cancer in the human subject. In some embodiments, the pharmaceutical composition has an enhanced safety profile when compared to a pharmaceutical composition comprising T cells or vectors comprising exogenous DNA encoding the same CAR.

In some embodiments, less than 1%, by weight, of the polynucleotides in the composition are double stranded RNA, DNA splints, or triphosphorylated RNA.

In some embodiments, less than 1%, by weight, of the polynucleotides and proteins in the pharmaceutical composition are double stranded RNA, DNA splints, triphosphorylated RNA, phosphatase proteins, protein ligases, and capping enzymes. In some embodiments, the transfer vehicle comprises more than one circular RNA polynucleotide.

In another aspect, the present disclosure provides a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment.

In some embodiments, the 3' group I intron fragment and 5' group I intron fragment are Anabaena group I intron fragments. In certain embodiments, the 3' intron fragment and 5' intron fragment are defined by the L9a-5 permutation site in the intact intron. In certain embodiments, the 3' intron fragment and 5' intron fragment are defined by the L8-2 permutation site in the intact intron. In certain embodiments, the IRES comprises a CVB3 IRES or a fragment or variant thereof. In certain embodiments, the IRES has a sequence according to SEQ ID NO: 65. In certain embodiments, the IRES comprises a salivirus SZ1 IRES or a fragment or variant thereof. In certain embodiments, the IRES has a sequence according to SEQ ID NO: 63.

In some embodiments, the circular RNA polynucleotide comprises a first internal spacer between the 3' group I intron fragment and the IRES, and a second internal spacer between the expression sequence and the 5' group I intron fragment.

In certain embodiments, the first and second internal spacers each have a length of about 10 to about 60 nucleotides.

In some embodiments, the circular RNA polynucleotide consists of natural nucleotides. In some embodiments, the circular RNA polynucleotide further comprises a second expression sequence encoding a therapeutic protein. In some embodiments, the therapeutic protein comprises a checkpoint inhibitor. In certain embodiments, the therapeutic protein comprises a cytokine.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disialoganglioside GD3, TNF receptor family member, B cell maturation antigen (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRCSD), chromosome X open reading frame 61 (CXORF61), CD97, and CD179a In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta.

In some embodiments, the circular RNA polynucleotide consists of natural nucleotides.

In some embodiments, the circular RNA polynucleotide expression sequence is codon optimized. In some embodiments, the circular RNA polynucleotide is optimized to lack at least one microRNA binding site present in an equivalent pre-optimized polynucleotide. In some embodiments, the circular RNA polynucleotide is optimized to lack at least one endonuclease susceptible site present in an equivalent pre-optimized polynucleotide. In some embodiments, the circular RNA polynucleotide is optimized to lack at least one RNA-editing susceptible site present in an equivalent pre-optimized polynucleotide.

In some embodiments, the circular RNA polynucleotide has an in vivo functional half-life in humans greater than that of an equivalent linear RNA polynucleotide having the same expression sequence. In some embodiments, the circular RNA polynucleotide has a length of about 100 nucleotides to about 10 kilobases. In some embodiments, the circular RNA polynucleotide has a functional half-life of at least about 20 hours. In some embodiments, the circular RNA polynucleotide has a duration of therapeutic effect in a human cell of at least about 20 hours. In some embodiments, the circular RNA polynucleotide has a duration of therapeutic effect in a human cell greater than or equal to that of an equivalent linear RNA polynucleotide comprising the same expression sequence. In some embodiments, the circular RNA polynucleotide has a functional half-life in a human cell greater than or equal to that of an equivalent linear RNA polynucleotide comprising the same expression sequence.

In another aspect, the present disclosure provides a DNA vector comprising, in the following order, a 5' duplex forming region, an Anabaena 3' group I intron fragment with a first permutation site, an Internal Ribosome Entry Site (IRES), an expression sequence encoding a chimeric antigen receptor (CAR) polypeptide, an Anabaena 5' group I intron fragment with a second permutation site, and a 3' duplex forming region.

In some embodiments, the 3' group I intron fragment and 5' group I intron fragment are Anabaena group I intron fragments. In some embodiments, the 3' intron fragment and 5' intron fragment are defined by the L9a-5 permutation site in the intact intron. In some embodiments, the 3' intron fragment and 5' intron fragment are defined by the L8-2 permutation site in the intact intron. In some embodiments, the IRES comprises a CVB3 IRES or a fragment or variant thereof.

In some embodiments, the IRES encodes a sequence according to SEQ ID NO: 65. In some embodiments, the IRES comprises a salivirus SZ1 IRES or a fragment or variant thereof. In some embodiments, the IRES encodes a sequence according to SEQ ID NO: 63. In some embodiments, the circular RNA polynucleotide comprises, in the following order, 5' duplex forming region, a 3' group I intron fragment, an Internal Ribosome Entry Site (IRES), an expression sequence encoding a chimeric antigen receptor (CAR) or TCR complex protein, a 5' group I intron fragment, and a 3' duplex forming region. In some embodiments, the 5' duplex forming region and 3' duplex forming region each have about 70% GC nucleotides. In some embodiments, the 5' duplex forming region and 3' duplex forming region each have a length of about 30 nucleotides.

In some embodiments, the DNA vector comprises a first external spacer between the 5' duplex forming region and the 3' group I intron fragment, and a second external spacer between the 5' group I intron fragment and the 3' duplex forming region. In some embodiments, the first and second external spacers each have a length of about 10 to about 60 nucleotides. In some embodiments, the 5' duplex forming region is directly adjacent to the 3' group I intron fragment, and wherein the 5' group I intron fragment is directly adjacent to the 3' duplex forming region. In some embodiments, the DNA vector comprises a first internal spacer between the 3' group I intron fragment and the IRES, and a second internal spacer between the expression sequence and the 5' group I intron fragment. In some embodiments, the first and second internal spacers each have a length of about 10 to about 60 nucleotides.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disialoganglioside GD3, TNF receptor family member, B cell maturation antigen (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRCSD), chromosome X open reading frame 61 (CXORF61), CD97, and CD179a In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta.

In another aspect, the present disclosure provides a eukaryotic cell comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment. In some embodiments, the eukaryotic cell comprises a human cell. In some embodiments, the eukaryotic cell comprises an immune cell. In some embodiments, the eukaryotic cell comprises a T cell.

In another aspect, the present disclosure provides a population of eukaryotic cells comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, wherein the population of eukaryotic cells express the CAR or TCR complex protein encoded by the circular RNA polynucleotide on its cell surface.

In some embodiments, the population of cells comprises NK cells, NKT cells, macrophages, dendritic cells, alphabeta T cells, gammadelta T cells, or combinations thereof. In some embodiments, the population of cells comprises T cells. In some embodiments, the population comprises CD3+ T cells. In some embodiments, the population comprises CD4+ T cells. In some embodiments, the population comprises CD8+ T cells. In some embodiments, the population of eukaryotic cells is administered in an amount effective to treat cancer in a human subject in need thereof. In some embodiments, the population of cells kills tumor cells more effectively or for longer than an equivalent population of eukaryotic cells comprising linear RNA encoding the same CAR.

In another aspect, provided herein is a method of making a population of eukaryotic cells comprising contacting cells in the population with a transfer vehicle comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, wherein the transfer vehicle comprises (i) an ionizable lipid, (ii) a structural lipid, and (iii) a PEG-modified lipid, wherein the transfer vehicle is capable of delivering the circular RNA polynucleotide to a human immune cell, such that the CAR is translated in the human immune cell and expressed on the surface of the human immune cell.

In another aspect, provided herein is a method of treating a subject in need thereof comprising administering a therapeutically effective amount of a pharmaceutical composition comprising: a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, and a transfer vehicle comprising (i) an ionizable lipid, (ii) a structural lipid, and (iii) a PEG-modified lipid, wherein the transfer vehicle is capable of delivering the circular RNA polynucleotide to a human immune cell, such that the CAR is translated in the human immune cell and expressed on the surface of the human immune cell.

In some embodiments, the subject has a cancer selected from the group acute lymphocytic cancer, acute myeloid leukemia (AML), alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

In another aspect, provided herein is an RNA polynucleotide comprising an Internal Ribosome Entry Site (IRES), an expression sequence encoding a chimeric antigen receptor (CAR) polypeptide, and at least one self-circularizing element.

In some embodiments, the RNA polynucleotide comprises a 5' duplex forming region, an Anabaena 3' group I intron fragment with a first permutation site, an Internal Ribosome Entry Site (IRES), an expression sequence encoding a chimeric antigen receptor (CAR) polypeptide, an Anabaena 5' group I intron fragment with a second permutation site, and a 3' duplex forming region. In some embodiments, the RNA polynucleotide comprises a 5' duplex forming region, a first permutation site, an Internal Ribosome Entry Site (IRES), an expression sequence encoding a chimeric antigen receptor (CAR) polypeptide, a second permutation site, and a 3' duplex forming region. In some embodiments, the self-circularizing element is a group I intron fragment. In some embodiments, a 3' group I intron fragment and a 5' intron fragment. In some embodiments, the 3' group I intron fragment and 5' group I intron fragment are Anabaena group I intron fragments. In some embodiments, the 3' intron fragment and 5' intron fragment are defined by the L9a-5 permutation site in the intact intron. In some embodiments, the 3' intron fragment and 5' intron fragment are defined by the L8-2 permutation site in the intact intron. In some embodiments, the RNA polynucleotide is capable of circularizing in the absence of an enzyme. In some embodiments, the RNA polynucleotide consists of natural nucleotides.

In another aspect, the present disclosures provides a DNA vector suitable for synthesizing the RNA polynucleotide of one of the above embodiments.

In some embodiments, a circular RNA polynucleotide of the present disclosure is delivered to a target cell in a non-lipid polymeric core-shell nanoparticle.

INCORPORATION BY REFERENCE

All publications, patents, and patent applications mentioned in this specification are herein incorporated by reference to the same extent as if each individual publication, patent, or patent application was specifically and individually indicated as being incorporated by reference herein.

BRIEF DESCRIPTION OF THE DRAWINGS

FIG. 40A shows the lysis of CD19+ Raji cells and CD19− K562 cells by primary human T cells electroporated with circRNA having an anti-CD19 CAR expression sequence and a CVB3 IRES or a Salivirus SZ1 IRES. FIG. 40B shows the lysis of CD19+ Raji cells and CD19− K562 cells by primary human T cells electroporated with different ratios of circRNA having an anti-CD19 CAR expression sequence or linear mRNA. FIG. 40C shows the lysis of CD19+ Raji cells and CD19− K562 cells by different ratios of primary human T cells electroporated with circRNA having an anti-CD19 CAR expression sequence.

FIG. 41A shows the specific lysis of anti-CD19 CAR-encoding circRNAs in lysing CD19+ Raji cells as compared to T-cell transduced with anti-CD19 CAR-encoding lentivirus at a ratio of 10 Raji cells to one T-cell. FIG. 41B shows the percentage of anti-CD19 CAR expressing T cells that were mock electroporated or electroporated with anti-CD19 CAR-encoding lentivirus or circRNA. FIG. 41C shows the induction of interferon gamma mRNA in T-cells electroporated with anti-CD19 CAR-encoding circRNAs co-cultured in the presence or absence of CD19+ Raji cells. (Oro-B1=circKymriah; CVB3 IRES, Oro-B6=linKymriah)

DETAILED DESCRIPTION

Figure 1A:
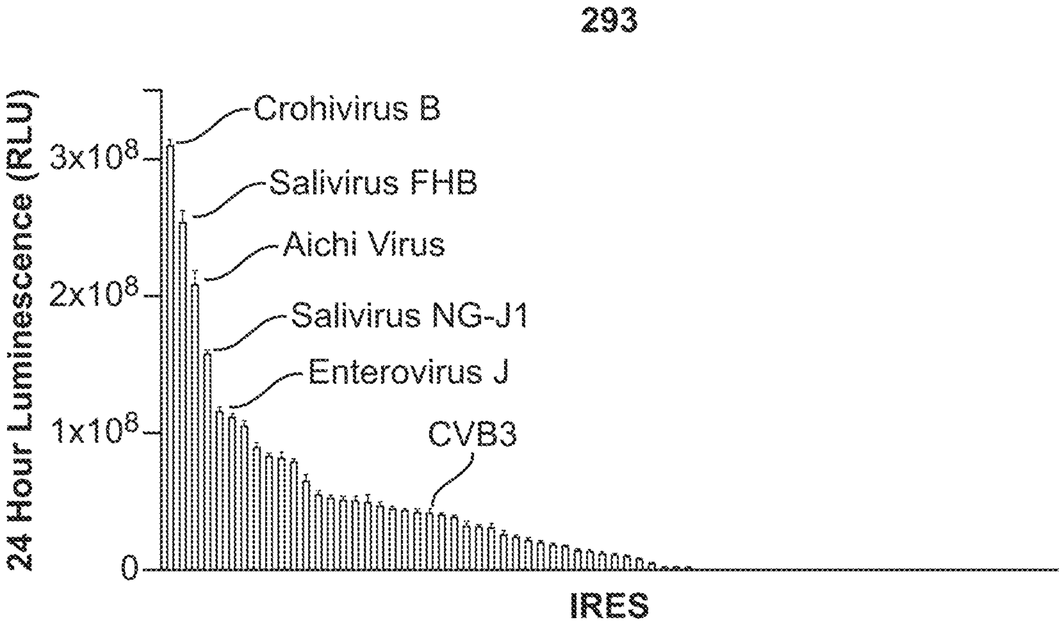
FIGS. 1A-1C depict luminescence in supernatants of HEK293 (FIG. 1A), HepG2 (FIG. 1B), or 1C1C7 (FIG. 1C) cells 24 hours after transfection with circular RNA comprising a *Gaussia* luciferase expression sequence and various IRES sequences.

Provided herein are pharmaceutical compositions and transfer vehicles, e.g., lipid nanoparticles, comprising circular RNA. The circular RNA provided herein may be delivered and/or targeted to a cell in a transfer vehicle, e.g., a nanoparticle, or a composition comprising a transfer vehicle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a non-lipid polymeric core-shell nanoparticle, or a biodegradable nanoparticle. In some embodiments, the transfer vehicle comprises one or more ionizable lipids, PEG modified lipids, helper lipids, and/or structural lipids.

In some embodiments, a transfer vehicle encapsulates circular RNA and comprises an ionizable lipid, a structural lipid, and a PEG-modified lipid. In some embodiments, a transfer vehicle encapsulates circular RNA and comprises an ionizable lipid, a structural lipid, a PEG-modified lipid, and a helper lipid.

Without wishing to be bound by theory, it is thought that transfer vehicles described herein shield encapsulated circular RNA from degradation and provide for effective delivery of circular RNA to target cells in vivo and in vitro.

Embodiments of the present disclosure provide lipid compositions described according to the respective molar ratios of the component lipids in the formulation. In one embodiment, the mol-% of the ionizable lipid may be from about 10 mol-% to about 80 mol-%. In one embodiment, the mol-% of the ionizable lipid may be from about 20 mol-% to about 70 mol-%. In one embodiment, the mol-% of the ionizable lipid may be from about 30 mol-% to about 60 mol-%. In one embodiment, the mol-% of the ionizable lipid may be from about 35 mol-% to about 55 mol-%. In one embodiment, the mol-% of the ionizable lipid may be from about 40 mol-% to about 50 mol-%. In some embodiments, the ionizable lipid mol-% of the transfer vehicle batch will be ±30%, ±25%, ±20%, ±15%, ±10%, ±5%, or ±2.5% of the target mol-%. In certain embodiments, transfer vehicle inter-lot variability will be less than 15%, less than 10% or less than 5%.

In one embodiment, the mol-% of the helper lipid may be from about 1 mol-% to about 50 mol-%. In one embodiment, the mol-% of the helper lipid may be from about 2 mol-% to about 45 mol-%. In one embodiment, the mol-% of the helper lipid may be from about 3 mol-% to about 40 mol-%. In one embodiment, the mol-% of the helper lipid may be from about 4 mol-% to about 35 mol-%. In one embodiment, the mol-% of the helper lipid may be from about 5 mol-% to about 30 mol-%. In one embodiment, the mol-% of the helper lipid may be from about 10 mol-% to about 20 mol-%. In some embodiments, the helper lipid mol-% of the transfer vehicle batch will be ±30%, ±25%, ±20%, ±15%, ±10%, ±5%, or ±2.5% of the target mol-%.

In one embodiment, the mol-% of the structural lipid may be from about 10 mol-% to about 80 mol-%. In one embodiment, the mol-% of the structural lipid may be from about 20 mol-% to about 70 mol-%. In one embodiment, the mol-% of the structural lipid may be from about 30 mol-% to about 60 mol-%. In one embodiment, the mol-% of the structural lipid may be from about 35 mol-% to about 55 mol-%. In one embodiment, the mol-% of the structural lipid may be from about 40 mol-% to about 50 mol-%. In some embodiments, the structural lipid mol-% of the transfer vehicle batch will be ±30%, ±25%, ±20%, ±15%, ±10%, ±5%, or ±2.5% of the target mol-%.

In one embodiment, the mol-% of the PEG modified lipid may be from about 0.1 mol-% to about 10 mol-%. In one embodiment, the mol-% of the PEG modified lipid may be from about 0.2 mol-% to about 5 mol-%. In one embodiment, the mol-% of the PEG modified lipid may be from about 0.5 mol-% to about 3 mol-%. In one embodiment, the mol-% of the PEG modified lipid may be from about 1 mol-% to about 2 mol-%. In one embodiment, the mol-% of the PEG modified lipid may be about 1.5 mol-%. In some embodiments, the PEG modified lipid mol-% of the transfer vehicle batch will be ±30%, ±25%, ±20%, ±15%, ±10%, ±5%, or ±2.5% of the target mol-%.

Also contemplated are pharmaceutical compositions, and in particular transfer vehicles, that comprise one or more of the compounds disclosed herein. In certain embodiments, such transfer vehicles comprise one or more of a PEG-modified lipid, an ionizable lipid, a helper lipid, and/or a structural lipid disclosed herein. Also contemplated are transfer vehicles that comprise one or more of the compounds disclosed herein and that further comprise one or more additional lipids. In certain embodiments, such transfer vehicles are loaded with or otherwise encapsulate circular RNA.

Transfer vehicles of the invention encapsulate circular RNA. In certain embodiments, the polynucleotides encapsulated by the compounds or pharmaceutical and liposomal compositions of the invention include RNA encoding a protein or enzyme (e.g., circRNA encoding, for example, phenylalanine hydroxylase (PAH)). The present invention contemplates the use of such polynucleotides as a therapeutic that is capable of being expressed by target cells for the production (and in certain instances, the excretion) of a functional enzyme or protein as disclosed, for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells, the production of a functional enzyme or protein in which a subject is deficient (e.g., a urea cycle enzyme or an enzyme associated with a lysosomal storage disorder) may be observed. As another example, circular RNA encapsulated by a transfer vehicle may encode a T cell receptor protein or a chimeric antigen receptor (CAR).

Also provided herein are methods of treating a disease in a subject by administering an effective amount of a composition comprising circular RNA encoding a functional protein and a transfer vehicle described herein to the subject. In some embodiments, the circular RNA is encapsulated within the transfer vehicle. In certain embodiments, such methods may enhance (e.g., increase) the expression of a polynucleotide and/or increase the production and secretion of a functional polypeptide product in one or more target cells and tissues (e.g., hepatocytes). Generally, such methods comprise contacting the target cells with one or more compounds and/or transfer vehicles that comprise or otherwise encapsulate the circRNA.

In certain embodiments, the transfer vehicles (e.g., lipid nanoparticles) are formulated based in part upon their ability to facilitate the transfection (e.g., of a circular RNA) of a target cell. In another embodiment, the transfer vehicles (e.g., lipid nanoparticles) may be selected and/or prepared to optimize delivery of circular RNA to a target cell, tissue or organ. For example, if the target cell is a hepatocyte the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in the target cell or organ. Alternatively, if the target tissue is the central nervous system, the selection and preparation of the transfer vehicle must consider penetration of, and retention within. the blood brain barrier and/or the use of alternate means of directly delivering such compositions (e.g., lipid nanoparticles) to such target tissue (e.g., via intracerebrovascular administration). In certain embodiments, the transfer vehicles may be combined with agents that facilitate the transfer of encapsulated materials across the blood brain barrier (e.g., agents which disrupt or improve the permeability of the blood brain barrier and thereby enhance the transfer of circular RNA to the target cells). While the transfer vehicles described herein (e.g., lipid nanoparticles) can facilitate introduction of circRNA into target cells, the addition of polycations (e.g., poly L-lysine and protamine) as a copolymer to one or more of the lipid nanoparticles that comprise the pharmaceutical compositions can in some instances markedly enhance the transfection efficiency of several types of transfer vehicles by 2-28 fold in a number of cell lines both in vitro and in vivo (See, N. J. Caplen, et al., Gene Ther. 1995; 2: 603; S. Li, et al., Gene Ther. 1997; 4, 891.). In some embodiments, a target cell is an immune cell. In some embodiments, a target cell is a T cell.

In certain embodiments, the transfer vehicles described herein (e.g., lipid nanoparticles) are prepared by combining multiple lipid components (e.g., one or more of the compounds disclosed herein) with one or more polymer components. For example, a lipid nanoparticle may be prepared using HGT4003, DOPE, cholesterol and DMG-PEG2000. A lipid nanoparticle may be comprised of additional lipid combinations in various ratios, including for example, HGT4001, DOPE and DMG-PEG2000. The selection of ionizable lipids, helper lipids, structural lipids, and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

Transfer vehicles described herein can allow the encapsulated polynucleotide to reach the target cell or may preferentially allow the encapsulated polynucleotide to reach the target cells or organs on a discriminatory basis (e.g., the transfer vehicles may concentrate in the liver or spleen of a subject to which such transfer vehicles are administered). Alternatively, the transfer vehicles may limit the delivery of encapsulated polynucleotides to other non-targeted cells or organs where the presence of the encapsulated polynucleotides may be undesirable or of limited utility.

Loading or encapsulating a polynucleotide, e.g., circRNA, into a transfer vehicle may serve to protect the polynucleotide from an environment (e.g., serum) which may contain enzymes or chemicals that degrade such polynucleotides and/or systems or receptors that cause the rapid excretion of such polynucleotides. Accordingly, in some embodiments, the compositions described herein are capable of enhancing the stability of the encapsulated polynucleotide (s), particularly with respect to the environments into which such polynucleotides will be exposed.

In certain embodiments, provided herein is a vector for making circular RNA, the vector comprising a 5' duplex forming region, a 3' group I intron fragment, optionally a first spacer, an Internal Ribosome Entry Site (IRES), an expression sequence, optionally a second spacer, a 5' group I intron fragment, and a 3' duplex forming region. In some embodiments, these elements are positioned in the vector in the above order. In some embodiments, the vector further comprises an internal 5' duplex forming region between the 3' group I intron fragment and the IRES and an internal 3' duplex forming region between the expression sequence and the 5' group I intron fragment. In some embodiments, the internal duplex forming regions are capable of forming a duplex between each other but not with the external duplex forming regions. In some embodiments, the internal duplex forming regions are part of the first and second spacers. Additional embodiments include circular RNA polynucleotides, including circular RNA polynucleotides made using the vectors provided herein, compositions comprising such circular RNA, cells comprising such circular RNA, methods of using and making such vectors, circular RNA, compositions and cells.

In some embodiments, provided herein are methods comprising administration of circular RNA polynucleotides provided herein into cells for therapy or production of useful proteins, such as chimeric antigen receptor (CAR) or T Cell Receptor (TCR) complex proteins. In some embodiments, the method is advantageous in providing the production of a desired polypeptide inside eukaryotic cells with a longer half-life than linear RNA, due to the resistance of the circular RNA to ribonucleases.

Circular RNA polynucleotides lack the free ends necessary for exonuclease-mediated degradation, causing them to be resistant to several mechanisms of RNA degradation and granting extended half-lives when compared to an equivalent linear RNA. Circularization allows for the stabilization of RNA polynucleotides that generally suffer from short half-lives and improves the overall efficacy of exogenous mRNA in a variety of applications. In an embodiment, the half-life of the circular RNA polynucleotides provided herein in eukaryotic cells (e.g., mammalian cells, such as human cells) is at least 20 hours (e.g., at least 80 hours).

1. Definitions

As used herein, the terms "circRNA" or "circular polyribonucleotide" or "circular RNA" are used interchangeably and refers to a polyribonucleotide that forms a circular structure through covalent bonds.

As used herein, the term "3' group I intron fragment" refers to a sequence with 75% or higher similarity to the 3'-proximal end of a natural group I intron including the splice site dinucleotide and optionally a stretch of natural exon sequence.

As used herein, the term "5' group I intron fragment" refers to a sequence with 75% or higher similarity to the 5'-proximal end of a natural group I intron including the splice site dinucleotide and optionally a stretch of natural exon sequence.

As used herein, the term "permutation site" refers to the site in a group I intron where a cut is made prior to permutation of the intron. This cut generates 3' and 5' group I intron fragments that are permuted to be on either side of a stretch of precursor RNA to be circularized.

As used herein, the term "splice site" refers to a dinucleotide that is partially or fully included in a group I intron and between which a phosphodiester bond is cleaved during RNA circularization.

As used herein, the term "therapeutic protein" refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term "immunogenic" refers to a potential to induce an immune response to a substance. An immune response may be induced when an immune system of an organism or a certain type of immune cell is exposed to an immunogenic substance. The term "non-immunogenic" refers to a lack of or absence of an immune response above a detectable threshold to a substance. No immune response is detected when an immune system of an organism or a certain type of immune cell is exposed to a non-immunogenic substance. In some embodiments, a non-immunogenic circular polyribonucleotide as provided herein, does not induce an immune response above a predetermined threshold when measured by an immunogenicity assay. In some embodiments, no innate immune response is detected when an immune system of an organism or a certain type of immune cell is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term "circularization efficiency" refers to a measurement of resultant circular polyribonucleotide as compared to its linear starting material.

As used herein, the term "translation efficiency" refers to a rate or amount of protein or peptide production from a ribonucleotide transcript. In some embodiments, translation efficiency can be expressed as amount of protein or peptide produced per given amount of transcript that codes for the protein or peptide.

The term "nucleotide" refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. Naturally occurring nucleic acids are comprised of nucleotides including guanine, cytosine, adenine, thymine, and uracil (G, C, A, T, and U respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90%-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

The terms "duplexed," "double-stranded" or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "unstructured" with regard to RNA refers to an RNA sequence that is not predicted by the RNAFold software or similar predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex forming regions," "homology arms," or "homology regions," complement, or are complementary, to one another when the two regions share a sufficient level of sequence identity to one another's reverse complement to act as substrates for a hybridization reaction. As used herein polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex forming region of an inventive polynucleotide is capable of forming a duplex with another internal duplex forming region and does not form a duplex with an external duplex forming region.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus.

"Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase can be used.

"Translation" means the formation of a polypeptide molecule by a ribosome based upon an RNA template.

It is to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about," is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

By "co-administering" is meant administering a therapeutic agent provided herein in conjunction with one or more additional therapeutic agents sufficiently close in time such that the therapeutic agent provided herein can enhance the effect of the one or more additional therapeutic agents, or vice versa.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. The treatment or prevention provided by the method disclosed herein can include treatment or prevention of one or more conditions or symptoms of the disease. Also, for purposes herein, "prevention" can encompass delaying the onset of the disease, or a symptom or condition thereof.

As used herein, the term "expression sequence" can refer to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon".

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex forming regions.

As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, an "miRNA site" refers to a stretch of nucleotides within a polynucleotide that is capable of forming a duplex with at least 8 nucleotides of a natural miRNA sequence.

As used herein, an "endonuclease site" refers to a stretch of nucleotides within a polynucleotide that is capable of being recognized and cleaved by an endonuclease protein.

As used herein, "bicistronic RNA" refers to a polynucleotide that includes two expression sequences coding for two distinct proteins. These expression sequences are often separated by a cleavable peptide such as a 2A site or an IRES sequence.

As used herein, the term "co-formulate" refers to a nanoparticle formulation comprising two or more nucleic acids or a nucleic acid and other active drug substance. Typically, the ratios are equimolar or defined in the ratiometric amount of the two or more nucleic acids or the nucleic acid and other active drug substance.

As used herein, "transfer vehicle" includes any of the standard pharmaceutical carriers, diluents, excipients, and the like, which are generally intended for use in connection with the administration of biologically active agents, including nucleic acids.

As used herein, the phrase "lipid nanoparticle" refers to a transfer vehicle comprising one or more lipids (e.g., in some embodiments, cationic lipids, non-cationic lipids, and PEG-modified lipids).

As used herein, the phrase "cationic lipid" refers to any of a number of lipid species that carry a net positive charge at a selected pH, such as physiological pH.

As used herein, the phrase "non-cationic lipid" refers to any neutral, zwitterionic or anionic lipid.

As used herein, the phrase "anionic lipid" refers to any of a number of lipid species that carry a net negative charge at a selected pH, such as physiological pH.

As used herein, the phrase "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally-occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated $C_6$-$C_{20}$ alkyl and/or an optionally substituted, variably saturated or unsaturated $C_6$-$C_{20}$ acyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur.

In certain embodiments the compounds and the transfer vehicles of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the ionizable lipid compounds disclosed herein). Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

As used herein, the phrases "non-cationic lipid", "non-cationic helper lipid", and "helper lipid" are used interchangeably and refer to any neutral, zwitterionic or anionic lipid.

As used herein, the phrase "anionic lipid" refers to any of a number of lipid species that carry a net negative charge at a selected pH, such as physiological pH.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

In certain embodiments of the present invention, the transfer vehicles (e.g., lipid nanoparticles) are prepared to encapsulate one or more materials or therapeutic agents (e.g., circRNA). The process of incorporating a desired therapeutic agent (e.g., circRNA) into a transfer vehicle is referred to herein as or "loading" or "encapsulating" (Lasic, et al., FEBS Lett., 312: 255-258, 1992). The transfer vehicle-loaded or -encapsulated materials (e.g., circRNA) may be completely or partially located in the interior space of the transfer vehicle, within a bilayer membrane of the transfer vehicle, or associated with the exterior surface of the transfer vehicle.

As used herein, the term "structural lipid" refers to sterols and also to lipids containing sterol moieties.

As defined herein, "sterols" are a subgroup of steroids consisting of steroid alcohols.

As used herein, the term "structural lipid" refers to sterols and also to lipids containing sterol moieties.

As used herein, the term "PEG" means any polyethylene glycol or other polyalkylene ether polymer.

As generally defined herein, a "PEG-OH lipid" (also referred to herein as "hydroxy-PEGylated lipid") is a PEGylated lipid having one or more hydroxyl (—OH) groups on the lipid.

As used herein, a "phospholipid" is a lipid that includes a phosphate moiety and one or more carbon chains, such as unsaturated fatty acid chains.

The term "antibody" (Ab) includes, without limitation, a glycoprotein immunoglobulin which binds specifically to an antigen. In general, and antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system. Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e. Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to BCMA. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some embodiments, the variable region is a human variable region. In some embodiments, the variable region comprises rodent or murine CDRs and human framework regions (FRs). In particular embodiments, the variable region is a primate (e.g., non-human primate) variable region. In some embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures. The term "Kabat numbering" and like terms are recognized in the art and refer to a system of numbering amino acid residues in the heavy and light chain variable regions of an antibody, or an antigen-binding molecule thereof. In certain aspects, the CDRs of an antibody may be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme. In certain aspects, the CDRs of an antibody may be determined according to the Chothia numbering scheme, which refers to the location of immunoglobulin structural loops (see, e.g., Chothia C & Lesk A M, (1987), J Mol Biol 196: 901-917; Al-Lazikani B et al, (1997) J Mol Biol 273: 927-948; Chothia C et al., (1992) J Mol Biol 227: 799-817; Tramontano A et al, (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant (KD or Kd). Affinity may be measured and/or expressed in a number of ways known in the art, including, but not limited to, equilibrium dissociation constant (KD), and equilibrium association constant (KA or Ka). The KD is calculated from the quotient of koff/kon, whereas KA is calculated from the quotient of kon/koff. kon refers to the association rate constant of, e.g., an antibody to an antigen, and koff refers to the dissociation of, e.g., an antibody to an antigen. The kon and koff may be determined by techniques known to one of ordinary skill in the art, such as BIACORE® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, one or more amino acid residues within a CDR(s) or within a framework region(s) of an antibody or antigen-binding molecule thereof may be replaced with an amino acid residue with a similar side chain.

As, used herein, the term "heterologous" means from any source other than naturally occurring sequences.

As used herein, an "epitope" is a term in the art and refers to a localized region of an antigen to which an antibody may specifically bind. An epitope may be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen NE (1997) Structure 5: 1269-1274; McPherson A (1976) J Biol Chem 251: 6300-6303). Antibody: antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323).

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In some embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays may be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a KA that is at least 2 logs, 2.5 logs, 3 logs, 4 logs or greater than the KA when the molecules bind to another antigen.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, neoplasm of the central nervous system (CNS), primary CNS lymphoma, tumor angiogenesis, spinal axis tumor, brain stem glioma, pituitary adenoma, epidermoid cancer, squamous cell cancer, T cell lymphoma, environmentally induced cancers including those induced by asbestos, other B cell malignancies, and combinations of said cancers. In some embodiments, the methods disclosed herein may be used to reduce the tumor size of a tumor derived from, for example, sarcomas and carcinomas, fibrosarcoma, myxosarcoma, liposarcoma, chondrosarcoma, osteogenic sarcoma, Kaposi's sarcoma, sarcoma of soft tissue, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, carcinoma of the fallopian tubes, carcinoma of the endometrium, carcinoma of the cervix, carcinoma of the vagina, carcinoma of the vulva, carcinoma of the renal pelvis, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, dendritic cells, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, IL-23, IL-27, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), TGF-beta, IL-35, and perforin. Examples of acute phase-proteins include, but are not limited to, C-reactive protein (CRP) and serum amyloid A (SAA).

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Ra+, but they also express large amounts of CD95, IL-2R[T CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ or CD4+ FoxP3+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells and plasma cells, both short-lived and long-lived, after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-IBB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), 0X40 ligand, PD-L2, or programmed death (PD) LI. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD 18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CD5, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, IT GAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), 0X40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

2. Vectors, Precursor RNA, and Circular RNA

In certain aspects, provided herein are circular RNA polynucleotides comprising a 3' post splicing group I intron fragment, optionally a first spacer, an Internal Ribosome Entry Site (IRES), an expression sequence, optionally a second spacer, and a 5' post splicing group I intron fragment. In some embodiments, these regions are in that order. In some embodiments, the circular RNA is made by a method provided herein or from a vector provided herein.

In certain embodiments, transcription of a vector provided herein (e.g., comprising a 5' homology region, a 3' group I intron fragment, optionally a first spacer, an Internal Ribosome Entry Site (IRES), an expression sequence, optionally a second spacer, a 5' group I intron fragment, and a 3' homology region) results in the formation of a precursor linear RNA polynucleotide capable of circularizing. In some embodiments, this precursor linear RNA polynucleotide circularizes when incubated in the presence of guanosine nucleotide or nucleoside (e.g., GTP) and divalent cation (e.g., Mg2+).

In some embodiments, the vectors and precursor RNA polynucleotides provided herein comprise a first (5') duplex forming region and a second (3') duplex forming region. In certain embodiments, the first and second homology regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex forming regions may be base paired with one another. In some embodiments, the duplex forming regions are predicted to have less than 50% (e.g., less than 45%, less than 40%, less than 35%, less than 30%, less than 25%) base pairing with unintended sequences in the RNA (e.g., non-duplex forming region sequences). In some embodiments, including such duplex forming regions on the ends of the precursor RNA strand, and adjacent or very close to the group I intron fragment, bring the group I intron fragments in close proximity to each other, increasing splicing efficiency. In some embodiments, the duplex forming regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex forming regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex forming regions have a length of about 9 to about 50 nucleotides. In one embodiment, the duplex forming regions have a length of about 9 to about 19 nucleotides. In some embodiments, the duplex forming regions have a length of about 20 to about 40 nucleotides. In certain embodiments, the duplex forming regions have a length of about 30 nucleotides.

Figure 25:
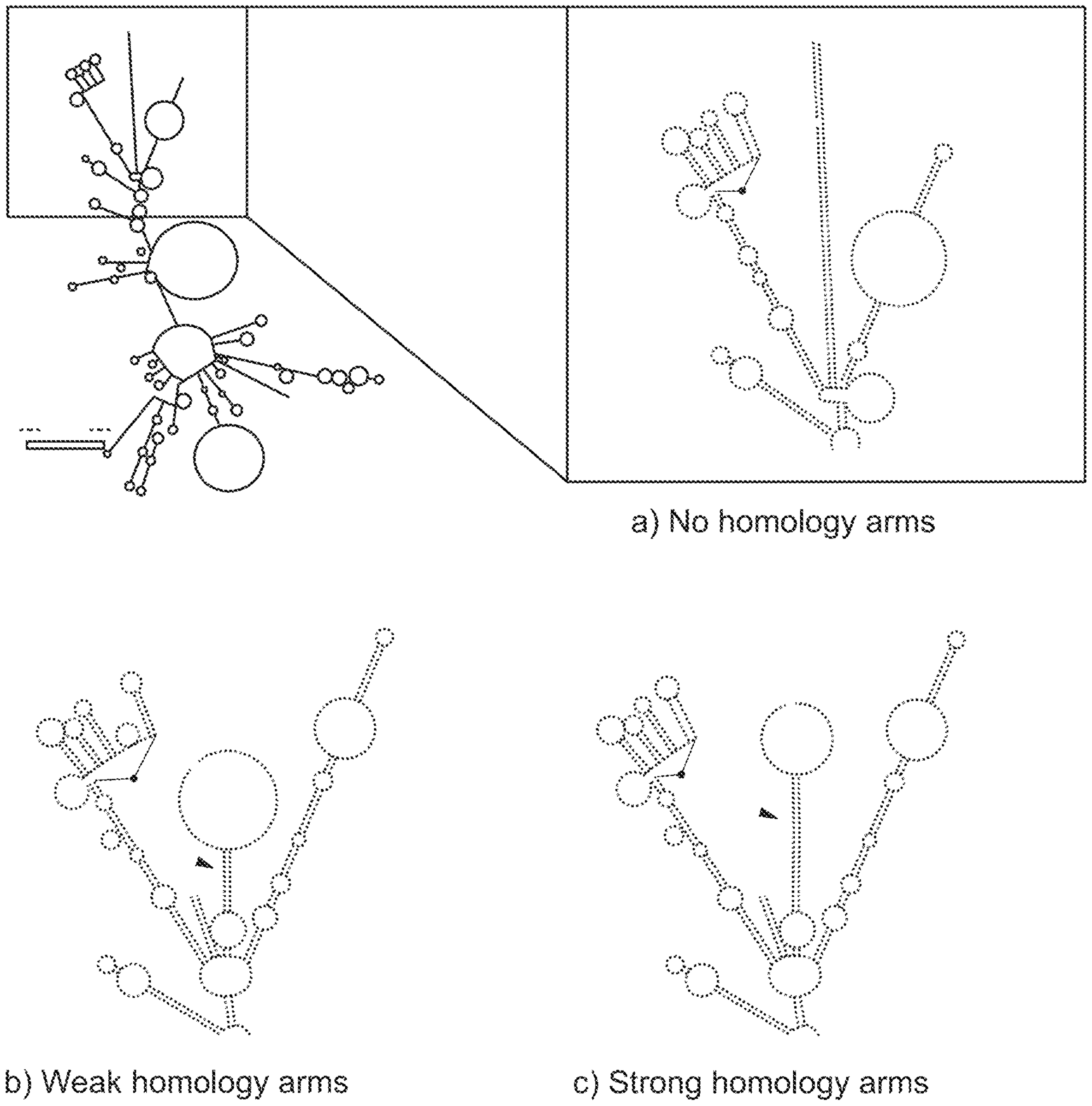
FIG. 25 depicts RNAFold predictions of precursor RNA secondary structure for homology arm design. Darker bases indicates higher base pairing probability. Without homology arms, no base pairing is predicted to occur between the ends of the precursor molecule.

In certain embodiments, the vectors, precursor RNA and circular RNA provided herein comprise a first (5') and/or a second (3') spacer. In some embodiments, including a spacer between the 3' group I intron fragment and the IRES may conserve secondary structures in those regions by preventing them from interacting, thus increasing splicing efficiency. In some embodiments, the first (between 3' group I intron fragment and IRES) and second (between the expression sequence and 5' group I intron fragment) spacers comprise additional base pairing regions that are predicted to base pair with each other and not to the first and second duplex forming regions. In some embodiments, such spacer base pairing brings the group I intron fragments in close proximity to each other, further increasing splicing efficiency. Additionally, in some embodiments, the combination of base pairing between the first and second duplex forming regions, and separately, base pairing between the first and second spacers, promotes the formation of a splicing bubble containing the group I intron fragments flanked by adjacent regions of base pairing (FIG. 25). Typical spacers are contiguous sequences with one or more of the following qualities: 1) is predicted to avoid interfering with proximal structures, for example, the IRES, expression sequence, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, a base pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the IRES. In an embodiment, this additional spacer prevents the structured regions of the IRES from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In certain embodiments, a 3' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. Typically, a 5' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. As described by Umekage et al. (2012), and illustrated in FIG. 33, external portions of the 3' group I intron fragment and 5' group I intron fragment are removed in circularization, causing the circular RNA provided herein to comprise only the portion of the 3' group I intron fragment formed by the optional exon sequence of at least 1 nt in length and 5' group I intron fragment formed by the optional exon sequence of at least 1 nt in length, if such sequences were present on the non-circularized precursor RNA. The part of the 3' group I intron fragment that is retained by a circular RNA is referred to herein as the post splicing 3' group I intron fragment. The part of the 5' group I intron fragment that is retained by a circular RNA is referred to herein as the post splicing 5' group I intron fragment.

In certain embodiments, the vectors, precursor RNA and circular RNA provided herein comprise an internal ribosome entry site (IRES). Inclusion of an IRES permits the translation of one or more open reading frames from a circular RNA (e.g., open reading frames that form the expression sequence). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161).

A multitude of IRES sequences are available and include sequences derived from a wide variety of viruses, such as from leader sequences of picornaviruses such as the encephalomyocarditis virus (EMCV) UTR (Jang et al. J. Virol. (1989) 63: 1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like.

In some embodiments, the IRES is an IRES sequence of Taura syndrome virus, Triatoma virus, Theiler's encephalomyelitis virus, Simian Virus 40, Solenopsis invicta virus 1, Rhopalosiphum padi virus, Reticuloendotheliosis virus, Human poliovirus 1, Plautia stali intestine virus, Kashmir bee virus, Human rhinovirus 2, Homalodisca coagulata virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, Drosophila C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, Drosophila antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BNS, Salivirus A BN2, Salivirus A 02394, Salivirus A GUT, Salivirus A CH, Salivirus A SZ1, Salivirus FHB, CVB3, CVB1, Echovirus 7, CVBS, EVA71, CVA3, CVA12, EV24 or an aptamer to eIF4G.

In some embodiments, the polynucleotides herein comprise an expression sequence. In some embodiments, the expression sequence encodes a CAR. In some embodiments, a polynucleotide comprises more than 1 expression sequence, e.g., 2, 3, 4, or 5 expression sequences. In some embodiments, one such expression sequence encodes a CAR and another encodes another therapeutic protein, such as a checkpoint inhibitor, e.g., an inhibitor of PD-1 inhibitor, a PD-L1 inhibitor, or a CTLA-4 inhibitor. In some embodiments, a polynucleotide comprises a first expression sequence encoding a CAR and a second expression sequence encoding an inhibitor of Programmed Death 1 (PD-1), PD-L1, PD-L2, Cytotoxic T-Lymphocyte Antigen 4 (CTLA-4), TIM-3, CEACAM (e.g., CEACAM-1, -3 and/or -5), VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, or LAGS. In some embodiments, an inhibitor is nivolumab, pembrolizumab, Ipilimumab, or atezolizumab. In some embodiments, an expression sequence encodes a protein that is cleaved into 2 or more functional units, e.g., a CAR and another therapeutic protein.

In certain embodiments, the polynucleotides provided herein comprise a CAR or TCR complex protein coding region. The CAR or TCR complex protein coding region is a sequence that encodes a chimeric antigen receptor (CAR) or any T cell receptor (TCR) complex protein. In some embodiments the CAR or TCR complex protein encodes a CAR. In some embodiments, the CAR or TCR complex protein coding region encodes two CARs in a bicistronic construct. In some embodiments, the CAR or TCR complex protein encodes TCRalpha, TCRbeta, TCRgamma, TCRdelta, CD3delta, CD3epsilon, CD3gamma, CD3zeta, CD4, and/or CD8. In some embodiments, the CAR or TCR complex protein encodes an artificial TCRalpha, TCRbeta, TCRgamma, TCRdelta, CD3delta, CD3epsilon, CD3gamma, CD3zeta, CD4, and/or CD8 variant. In some embodiments, the CAR or TCR complex protein encodes a natural TCRalpha, TCRbeta, TCRgamma, TCRdelta, CD3delta, CD3epsilon, CD3gamma, CD3zeta, CD4, and/or CD8 variant. In some embodiments, the CAR or TCR complex coding region concludes with a stop codon. In some embodiments, the CAR or TCR complex coding region concludes with a stop cassette.

In certain embodiments, the vectors provided herein comprise a 3' UTR. In some embodiments, the 3' UTR is from human beta globin, human alpha globin xenopus beta globin, xenopus alpha globin, human prolactin, human GAP-43, human eEFlal, human Tau, human TNFα, dengue virus, hantavirus small mRNA, bunyavirus small mRNA, turnip yellow mosaic virus, hepatitis C virus, rubella virus, tobacco mosaic virus, human IL-8, human actin, human GAPDH, human tubulin, hibiscus chlorotic rinsgspot virus, woodchuck hepatitis virus post translationally regulated element, sindbis virus, turnip crinkle virus, tobacco etch virus, or Venezuelan equine encephalitis virus.

In some embodiments, the vectors provided herein comprise a 5' UTR. In some embodiments, the 5' UTR is from human beta globin, Xenopus laevis beta globin, human alpha globin, Xenopus laevis alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

In some embodiments, the vector provided herein comprises a polyA region. In some embodiments the polyA region is at least 30 nucleotides long or at least 60 nucleotides long.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In certain embodiments, the polynucleotides provided herein are circular RNA polynucleotides or are useful for making circular RNA polynucleotides. Such polynucleotides comprise CAR or TCR complex protein encoding domains. Certain current CAR and recombinant TCR treatments engineer cells with DNA encoding the CAR or recombinant TCR, causing greater toxicity when compared to transitory forms of CAR or recombinant TCR expression, and introducing the risk of harmful mutagenesis. An alternative is a linear RNA encoding a CAR or recombinant TCR complex protein. However, linear RNA suffers from short half-lives in vivo, limiting treatment efficacy. In certain embodiments, circular RNA polynucleotides provided herein encoding CARs or recombinant TCR complex proteins provides the toxicity advantages of transitory expression, while increasing the therapeutic efficacy of the treatment when compared to linear RNA. The methods of circularizing RNA described herein, including the addition of homology regions adjacent to the group I intron fragments, allow for high circularization efficiency and for the circularization of large RNA polynucleotides.

In some embodiments, provided herein is a vector. In certain embodiments, the vector comprises, in the following order, a) a 5' homology region, b) a 3' group I intron fragment, c) optionally, a first spacer sequence, d) an IRES, e) an expression sequence (e.g., CAR or TCR complex protein coding region), f) optionally, a second spacer sequence, g) a 5' group I intron fragment, and h) a 3' homology region. In some embodiments, the vector comprises a transcriptional promoter upstream of the 5' homology region.

In some embodiments, provided herein is a precursor RNA. In certain embodiments, the precursor RNA is a linear RNA produced by in vitro transcription of a vector provided herein. In some embodiments, the precursor RNA comprises, in the following order, a) a 5' homology region, b) a 3' group I intron fragment, c) optionally, a first spacer sequence, d) an IRES, e) an expression sequence (e.g., CAR or TCR complex protein coding region), f) optionally, a second spacer sequence, g) a 5' group I intron fragment, and h) a 3' homology region. The precursor RNA can be unmodified, partially modified or completely modified.

In certain embodiments, provided herein is a circular RNA. In certain embodiments, the circular RNA is a circular RNA produced by a vector provided herein. In some embodiments, the circular RNA is circular RNA produced by circularization of a precursor RNA provided herein. In some embodiments, the circular RNA comprises, in the following sequence, a) a first spacer sequence, b) an IRES, c) an expression sequence (e.g., CAR or TCR complex protein coding region), and d) a second spacer sequence. In some embodiments, the circular RNA further comprises the portion of the 3' group I intron fragment that is 3' of the 3' splice site. In some embodiments, the circular RNA further comprises the portion of the 5' group I intron fragment that is 5' of the 5' splice site. In some embodiments, the circular RNA is at least 500, 600, 700, 800, 900, 1000, 1500, 2000, 2500, 3000, 3500, 4000 or 4500 nucleotides in size. The circular RNA can be unmodified, partially modified or completely modified.

In some embodiments, the circular RNA provided herein has higher functional stability than mRNA comprising the same expression sequence. In some embodiments, the circular RNA provided herein has higher functional stability than mRNA comprising the same expression sequence, 5moU modifications, an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, 5moU modifications, an optimized UTR, a cap, and/or a polyA tail. In some embodiments, the circular RNA provided herein may have higher stability than an equivalent linear mRNA. In some embodiments, this may be shown by measuring receptor presence and density in vitro or in vivo post electroporation, with time points measured over 1 week. In some embodiments, this may be shown by measuring RNA presence via qPCR or ISH.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, 5moU modifications, an optimized UTR, a cap, and/or a polyA tail. In certain embodiments, the circular RNA provided herein may result in lower toxicity than viral, e.g. lentiviral, engineering using DNA when expressing CARs or TCR complex proteins on immune cells, e.g., T cells, due to cytokine release syndrome (CRS). In some embodiments, this may be shown by measuring cytokine, e.g. IL6, release post infection/transfection in vitro, assessed by ELISA and/or qPCR.

In certain embodiments, the circular RNA provided herein may result in lower toxicity than viral, e.g., lentiviral, engineering using DNA when expressing CARs or TCR complex proteins on immune cells, e.g., T cells, due to cytokine release syndrome (CRS). In some embodiments, this may be shown by measuring cytokine, e.g., IL6, release post infection/transfection in vitro, assessed by ELISA and/or qPCR.

In some embodiments, the circular RNA provided herein may result in lower toxicity than viral, e.g., lentiviral, engineering using DNA when expressing CARs or TCR complex proteins on immune cells, e.g., T cells, due to a lack of insertional mutagenesis by circular RNA. In some embodiments, this may be shown by demonstrating that circular RNA does not integrate into the genome, while DNA delivered by lentiviruses does, by sequencing after administering circular RNA or DNA. In certain embodiments, the circular RNA provided herein can be transfected into a cell as is, or can be transfected in DNA vector form and transcribed in the cell. Transcription of circular RNA from a transfected DNA vector can be via added polymerases or polymerases encoded by nucleic acids transfected into the cell, or preferably via endogenous polymerases.

In certain embodiments, a circular RNA polynucleotide provided herein comprises modified RNA nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is Ψ (pseudouridine). In another embodiment, the modified nucleoside is Um (2'-O-methyluridine). In other embodiments, the modified nucleoside is $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2$i6A (2-methylthio-$N^6$ isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$- threonylcarbamoyladenosine); $hn^6A$($N^6$-hydroxynoryalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thio-cytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2{}_2G$ ($N^2$,$N^2$-dimethylguanosine); $m^2Gm$ ($N^2$,2'-O-dimethylguanosine); $m^2{}_2Gm$ ($N^2$,$N^2$,2'-O-trimethylguanosine); Gr(p) (2'-O-ribosylguanosine(phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6$, $N^6$-dimethyladenosine); Im (2'-O-methylinosine); $m^4C$ ($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6{}_2Am$ ($N^6$,$N^6$,O-2'-trimethyladenosine); $m^{2,7}G$ ($N^2$,7-dimethylguanosine); $m^{2,2,7}G$ ($N^2$,$N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-$N^6$-(cis-hydroxyisopentenyl) adenosine, N6-glycinylcarbamoyladenosine, N6-threonylcarbamoyladenosine, 2-methylthio-$N^6$-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methyl-pseudouridine, N6-methyladenosine, and/or pseudouridine. In some embodiments, such modified nucleosides provide additional stability and resistance to immune activation.

In particular embodiments, polynucleotides may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule (e.g., a CAR or TCR complex protein) is expressed inside the animal.

3. Payload

In some embodiments, the expression sequence encodes a therapeutic protein. In some embodiments, the therapeutic protein is selected from the proteins listed in Table 1.

TABLE 1

Protein Expression Sequences and Delivery Formulations

| Payload | Sequence | Target cell/ organ | Preferred delivery formulation |
|---|---|---|---|
| CD19 CAR | Any of SEQ ID NOs: 309-314 | T cells | 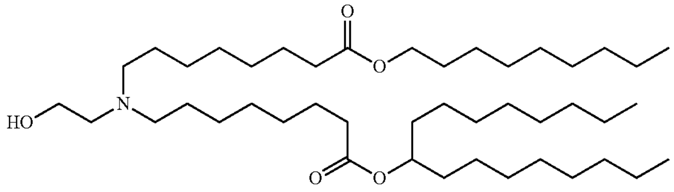<br>(50 mol %)<br>DSPC (10 mol %)<br>Beta-sitosterol (28.5 % mol %)<br>Cholesterol (10 mol %)<br>PEG DMG (1.5 mol %) |
| BCMA CAR | MALPVTALLLPLALLLHAAR<br>PDIVLTQSPASLAVSLGERAT<br>INCRASESVSVIGAHLIHWY<br>QQKPGQPPKLLIYLASNLET<br>GVPARFSGSGSGTDFTLTISS<br>LQAEDAAIYYCLQSRIFPRTF<br>GQGTKLEIKGSTSGSGKPGS<br>GEGSTKGQVQLVQSGSELK<br>KPGASVKVSCKASGYTFTDY<br>SINWVRQAPGQGLEWMGWI<br>NTETREPAYAYDFRGRFVFS<br>LDTSVSTAYLQISSLKAEDTA<br>VYYCARDYSYAMDYWGQG<br>TLVTVSSAAATTTPAPRPPTP<br>APTIASQPLSLRPEACRPAAG<br>GAVHTRGLDFACDIYIWAPL<br>AGTCGVLLLSLVITLYCKRG<br>RKKLLYIFKQPFMRPVQTTQ<br>EEDGCSCRFPEEEEGGCELR<br>VKFSRSADAPAYQQGQNQL<br>YNELNLGRREEYDVLDKRR<br>GRDPEMGGKPRRKNPQEGL<br>YNELQKDKMAEAYSEIGMK<br>GERRRGKGHDGLYQGLSTA<br>TKDTYDALHMQALPPR | T cells | 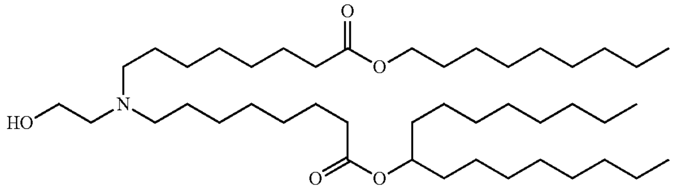<br>(50 mol %)<br>DSPC (10 mol %)<br>Beta-sitosterol (28.5 % mol %)<br>Cholesterol (10 mol %)<br>PEG DMG (1.5 mol %) |
| MAGE-A4 TCR | TCR alpha chain:<br>KNQVEQSPQSLIILEGKNCTL<br>QCNYTVSPFSNLRWYKQDT<br>GRGPVSLTIMTFSENTKSNG<br>RYTATLDADTKQSSLHITAS<br>QLSDSASYICVVNHSGGSYIP<br>TFGRGTSLIVHPYIQKPDPAV<br>YQLRDSKSSDKSVCLFTDFD<br>SQTNVSQSKDSDVYITDKTV<br>LDMRSMDFKSNSAVAWSNK<br>SDFACANAFNNSIIPEDTFFPS<br>PESS<br>TCR beta chain:<br>DVKVTQSSRYLVKRTGEKV<br>FLECVQDMDHENMFWYRQ<br>DPGLGLRLIYFSYDVKMKEK<br>GDIPEGYSVSREKKERFSLIL<br>ESASTNQTSMYLCASSFLMT<br>SGDPYEQYFGPGTRLTVTED<br>LKNVFPPEVAVFEPSEAEISH<br>TQKATLVCLATGFYPDHVEL<br>SWWVNGKEVHSGVSTDPQP<br>LKEQPALNDSRYCLSSRLRV<br>SATFWQNPRNHFRCQVQFY<br>GLSENDEWTQDRAKPVTQIV<br>SAEAWGRAD | T cells | 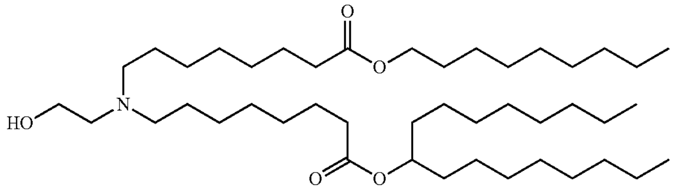<br>(50 mol %)<br>DSPC (10 mol %)<br>Beta-sitosterol (28.5 % mol %)<br>Cholesterol (10 mol %)<br>PEG DMG (1.5 mol %) |

TABLE 1-continued

Protein Expression Sequences and Delivery Formulations

| Payload | Sequence | Target cell/ organ | Preferred delivery formulation |
|---|---|---|---|
| NY-<br>ESO<br>TCR | TCRalpha extracellular sequence<br>MQEVTQIPAALSVPEGENLV<br>LNCSFTDSAIYNLQWFRQDP<br>GKGLTSLLLIQSSQREQTSGR<br>LNASLDKSSGRSTLYIAASQP<br>GDSATYLCAVRPTSGGSYIP<br>TFGRGTSLIVHPY<br>TCRbeta extracellular sequence<br>MGVTQTPKFQVLKTGQSMT<br>LQCAQDMNHEYMSWYRQD<br>PGMGLRLIHYSVGAGITDQG<br>EVPNGYNVSRSTTEDFPLRL<br>LSAAPSQTSVYFCASSYVGN<br>TGELFFGEGSRLTVL | T cells | 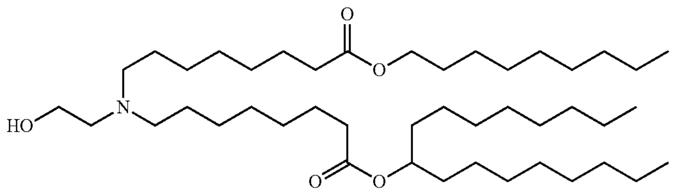<br>(50 mol %)<br>DSPC (10 mol %)<br>Beta-sitosterol (28.5 % mol %)<br>Cholesterol (10 mol %)<br>PEG DMG (1.5 mol %) |
| EPO | APPRLICDSRVLERYLLEAKE<br>AENITTGCAEHCSLNENITVP<br>DTKVNFYAWKRMEVGQQA<br>VEVWQGLALLSEAVLRGQA<br>LLVNSSQPWEPLQLHVDKA<br>VSGLRSLTTLLRALGAQKEA<br>ISPPDAASAAPLRTITADTFR<br>KLFRVYSNFLRGKLKLYTGE<br>ACRTGDR | Kidney or bone marrow | |
| PAH | MSTAVLENPGLGRKLSDFGQ<br>ETSYIEDNCNQNGAISLIFSL<br>KEEVGALAKVLRLFEENDV<br>NLTHIESRPSRLKKDEYEFFT<br>HLDKRSLPALTNIIKILRHDIG<br>ATVHELSRDKKKDTVPWFP<br>RTIQELDRFANQILSYGAELD<br>ADHPGFKDPVYRARRKQFA<br>DIAYNYRHGQPIPRVEYMEE<br>EKKTWGTVFKTLKSLYKTH<br>ACYEYNHIFPLLEKYCGFHE<br>DNIPQLEDVSQFLQTCTGFRL<br>RPVAGLLSSRDFLGGLAFRV<br>FHCTQYIRHGSKPMYTPEPDI<br>CHELLGHVPLFSDRSFAQFS<br>QEIGLASLGAPDEYIEKLATI<br>YWFTVEFGLCKQGDSIKAY<br>GAGLLSSFGELQYCLSEKPK<br>LLPLELEKTAIQNYTVTEFQP<br>LYYVAESFNDAKEKVRNFA<br>ATIPRPFSVRYDPYTQRIEVL<br><br>DNTQQLKILADSINSEIGILCS<br>ALQKIK | Hepatic cells | 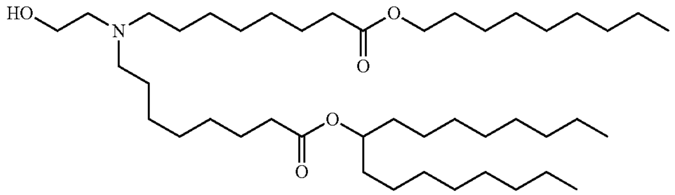<br>(50 mol %)<br>DSPC (10 mol %)<br>Cholesterol (38.5 mol %)<br>PEG DMG (1.5%)<br>OR<br>MC3 (50 mol %)<br>DSPC (10 mol %)<br>Cholesterol (38.5% mol %)<br>PEG-DMG (1.5%) |
| CPS1 | LSVKAQTAHIVLEDGTKMK<br>GYSFGHPSSVAGEVVFNTGL<br>GGYPEAITDPAYKGQILTMA<br>NPIIGNGGAPDTTALDELGLS<br>KYLESNGIKVSGLLVLDYSK<br>DYNHWLATKSLGQWLQEEK<br>VPAIYGVDTRMLTKIIRDKG<br>TMLGKIEFEGQPVDFVDPNK<br>QNLIAEVSTKDVKVYGKGN<br>PTKVVAVDCGIKNNVIRLLV<br>KRGAEVHLVPWNHDFTKME<br>YDGILIAGGPGNPALAEPLIQ<br>NVRKILESDRKEPLFGISTGN<br>LITGLAAGAKTYKMSMANR<br>GQNQPVLNITNKQAFITAQN<br>HGYALDNTLPAGWKPLFVN<br>VNDQTNEGIMHESKPFFAVQ<br>FHPEVTPGPIDTEYLFDSFFSL<br>IKKGKATTITSVLPKPALVAS<br>RVEVSKVLILGSGGLSIGQA<br>GEFDYSGSQAVKAMKEENV | Hepatic cells | 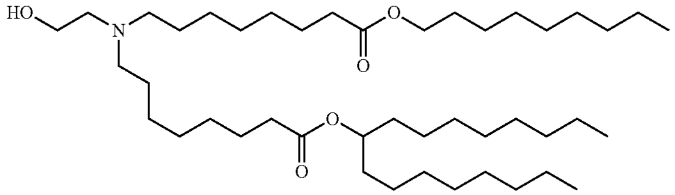<br>(50 mol %)<br>DSPC (10 mol %)<br>Cholesterol (38.5 mol %)<br>PEG DMG (1.5%)<br>OR<br>MC3 (50 mol %)<br>DSPC (10 mol %)<br>Cholesterol (38.5% mol %)<br>PEG-DMG (1.5%) |

TABLE 1-continued

| Protein Expression Sequences and Delivery Formulations | | | |
|---|---|---|---|
| Payload | Sequence | Target cell/ organ | Preferred delivery formulation |
| | KTVLMNPNIASVQTNEVGLK<br>QADTVYFLPITPQFVTEVIKA<br>EQPDGLILGMGGQTALNCG<br>VELFKRGVLKEYGVKVLGT<br>SVESIMATEDRQLFSDKLNEI<br>NEKIAPSFAVESIEDALKAAD<br>TIGYPVMIRSAYALGGLGSGI<br>CPNRETLMDLSTKAFAMTN<br>QILVEKSVTGWKEIEYEVVR<br>DADDNCVTVCNMENVDAM<br>GVHTGDSVVVAPAQTLSNA<br>EFQMLRRTSINVVRHLGIVG<br>ECNIQFALHPTSMEYCIIEVN<br>ARLSRSSALASKATGYPLAFI<br>AAKIALGIPLPEIKNVVSGKT<br>SACFEPSLDYMVTKIPRWDL<br>DRFHGTSSRIGSSMKSVGEV<br>MAIGRTFEESFQKALRMCHP<br>SIEGFTPRLPMNKEWPSNLD<br>LRKELSEPSSTRIYAIAKAID<br>DNMSLDEIEKLTYIDKWFLY<br>KMRDILNMEKTLKGLNSES<br>MTEETLKRAKEIGFSDKQISK<br>CLGLTEAQTRELRLKKNIHP<br>WVKQIDTLAAEYPSVTNYL<br>YVTYNGQEHDVNFDDHGM<br>MVLGCGPYHIGSSVEFDWC<br>AVSSIRTLRQLGKKTVVVNC<br>NPETVSTDFDECDKLYFEEL<br>SLERILDIYHQEACGGCIISV<br>GGQIPNNLAVPLYKNGVKIM<br>GTSPLQIDRAEDRSIFSAVLD<br>ELKVAQAPWKAVNTLNEAL<br>EFAKSVDYPCLLRPSYVLSG<br>SAMNVVFSEDEMKKFLEEA<br>TRVSQEHPVVLTKFVEGARE<br>VEMDAVGKDGRVISHAISEH<br>VEDAGVHSGDATLMLPTQTI<br>SQGAIEKVKDATRKIAKAFA<br>ISGPFNVQFLVKGNDVLVIEC<br>NLRASRSFPFVSKTLGVDFID<br>VATKVMIGENVDEKHLPTL<br>DHPIIPADYVAIKAPMFSWPR<br>LRDADPILRCEMASTGEVAC<br>FGEGIHTAFLKAMLSTGFKIP<br>QKGILIGIQQSFRPRFLGVAE<br>QLHNEGFKLFATEATSDWL<br>NANNVPATPVAWPSQEGQN<br>PSLSSIRKLIRDGSIDLVINLP<br>NNNTKFVHDNYVIRRTAVD<br>SGIPLLTNFQVTKLFAEAVQ<br>KSRKVDSKSLFHYRQYSAG<br>KAA | | |
| Cas9 | MKRNYILGLDIGITSVGYGII<br>DYETRDVIDAGVRLFKEANV<br>ENNEGRRSKRGARRLKRRR<br>RHRIQRVKKLLFDYNLLTDH<br>SELSGINPYEARVKGLSQKLS<br>EEEFSAALLHLAKRRGVHNV<br>NEVEEDTGNELSTKEQISRNS<br>KALEEKYVAELQLERLKKD<br>GEVRGSINRFKTSDYVKEAK<br>QLLKVQKAYHQLDQSFIDTY<br>IDLLETRRTYYEGPGEGSPFG<br>WKDIKEWYEMLMGHCTYFP<br>EELRSVKYAYNADLYNALN<br>DLNNLVITRDENEKLEYYEK<br>FQIIENVFKQKKKPTLKQIAK<br>EILVNEEDIKGYRVTSTGKPE<br>FTNLKVYHDIKDITARKEIIE<br>NAELLDQIAKILTIYQSSEDIQ<br>EELTNLNSELTQEEIEQISNL<br>KGYTGTHNLSLKAINLILDEL | Immune cells | 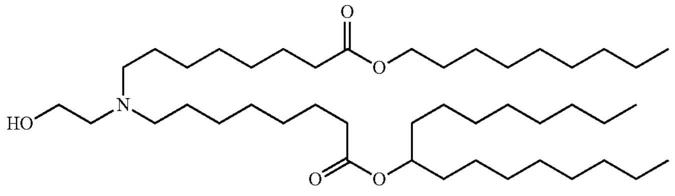<br>(50 mol %)<br>DSPC (10 mol %)<br>Beta-sitosterol (28.5 % mol %)<br>Cholesterol (10 mol %)<br>PEG DMG (1.5 mol %) |

TABLE 1-continued

| Protein Expression Sequences and Delivery Formulations | | | |
|---|---|---|---|
| Payload | Sequence | Target cell/ organ | Preferred delivery formulation |
| | WHTNDNQIAIFNRLKLVPKK VDLSQQKEIPTTLVDDFILSP VVKRSFIQSIKVINAIIKKYGL PNDIIIELAREKNSKDAQKMI NEMQKRNRQTNERIEEIIRTT GKENAKYLIEKIKLHDMQEG KCLYSLEAIPLEDLLNNPFNY EVDHIIPRSVSFDNSFNNKVL VKQEENSKKGNRTPFQYLSS SDSKISYETFKKHILNLAKGK GRISKTKKEYLLEERDINRFS VQKDFINRNLVDTRYATRGL MNLLRSYFRVNNLDVKVKSI NGGFTSFLRRKWKFKKERN KGYKHHAEDALITANADFIF KEWKKLDKAKKVMENQMF EEKQAESMPEIETEQEYKEIF ITPHQIKHIKDFKDYKYSHRV DKKPNRELINDTLYSTRKDD KGNTLIVNNLNGLYDKDND KLKKLINKSPEKLLMYHHDP QTYQKLKLIMEQYGDEKNP LYKYYEETGNYLTKYSKKD NGPVIKKIKYYGNKLNAHLD ITDDYPNSRNKVVKLSLKPY RFDVYLDNGVYKFVTVKNL DVIKKENYYEVNSKCYEEA KKLKKISNQAEFIASFYNND LIKINGELYRVIGVNNDLLNR IEVNMIDITYREYLENMNDK RPPRIIKTIASKTQSIKKYSTD ILGNLYEVKSKKHPQIIKKG | | |
| ADAM TS13 | AAGGILHLELLVAVGPDVFQ AHQEDTERYVLTNLNIGAEL LRDPSLGAQFRVHLVKMVIL TEPEGAPNITANLTSSLLSVC GWSQTINPEDDTDPGHADLV LYITRFDLELPDGNRQVRGV TQLGGACSPTWSCLITEDTG FDLGVTIAHEIGHSFGLEHDG APGSGCGPSGHVMASDGAA PRAGLAWSPCSRRQLLSLLS AGRARCVWDPPRPQPGSAG HPPDAQPGLYYSANEQCRV AFGPKAVACTFAREHLDMC QALSCHTDPLDQSSCSRLLV PLLDGTECGVEKWCSKGRC RSLVELTPIAAVHGRWSSWG PRSPCSRSCGGGVVTRRRQC NNPRPAFGGRACVGADLQA EMCNTQACEKTQLEFMSQQ CARTDGQPLRSSPGGASFYH WGAAVPHSQGDALCRHMC RAIGESFIMKRGDSFLDGTRC MPSGPREDGTLSLCVSGSCR TFGCDGRMDSQQVWDRCQ VCGGDNSTCSPRKGSFTAGR AREYVTFLTVTPNLTSVYIA NHRPLFTHLAVRIGGRYVVA GKMSISPNTTYPSLLEDGRV EYRVALTEDRLPRLEEIRIWG PLQEDADIQVYRRYGEEYGN LTRPDITFTYFQPKPRQAWV WAAVRGPCSVSCGAGLRWV NYSCLDQARKELVETVQCQ GSQQPPAWPEACVLEPCPPY | Hepatic cells | 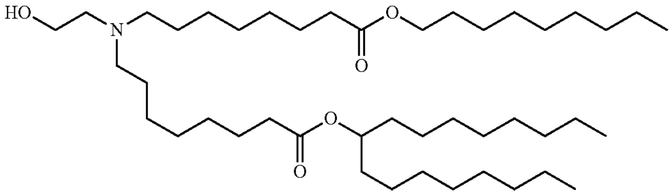 (50 mol %) DSPC (10 mol %) Cholesterol (38.5 mol %) PEG DMG (1.5%) OR MC3 (50 mol %) DSPC (10 mol %) Cholesterol (38.5% mol %) PEG-DMG (1.5%) |

TABLE 1-continued

Protein Expression Sequences and Delivery Formulations

| Payload | Sequence | Target cell/ organ | Preferred delivery formulation |
|---|---|---|---|
| | WAVGDFGPCSASCGGGLRE RPVRCVEAQGSLLKTLPPAR CRAGAQQPAVALETCNPQP CPARWEVSEPSSCTSAGGAG LALENETCVPGADGLEAPVT EGPGSVDEKLPAPEPCVGMS CPPGWGHLDATSAGEKAPSP WGSIRTGAQAAHVWTPAAG SCSVSCGRGLMELRFLCMDS ALRVPVQEELCGLASKPGSR REVCQAVPCPARWQYKLAA CSVSCGRGVVRRILYCARAH GEDDGEEILLDTQCQGLPRP EPQEACSLEPCPPRWKVMSL GPCSASCGLGTARRSVACVQ LDQGQDVEVDEAACAALVR PEASVPCLIADCTYRWHVGT WMECSVSCGDGIQRRRDTC LGPQAQAPVPADFCQHLPKP VTVRGCWAGPCVGQGTPSL VPHEEAAAPGRTTATPAGAS LEWSQARGLLFSPAPQPRRL LPGPQENSVQSSACGRQHLE PTGTIDMRGPGQADCAVAIG RPLGEVVTLRVLESSLNCSA GDMLLLWGRLTWRKMCRK LLDMTFSSKTNTLVVRQRCG RPGGGVLLRYGSQLAPETFY RECDMQLFGPWGEIVSPSLS PATSNAGGCRLFINVAPHARI AIHALATNMGAGTEGANAS YILIRDTHSLRTTAFHGQQVL YWESESSQAEMEFSEGFLKA QASLRGQYWTLQSWVPEMQ DPQSWKGKEGT | | |
| FOXP3 | MPNPRPGKPSAPSLALGPSP GASPSWRAAPKASDLLGAR GPGGTFQGRDLRGGAHASSS SLNPMPPSQLQLPTLPLVMV APSGARLGPLPHLQALLQDR PHFMHQLSTVDAHARTPVL QVHPLESPAMISLTPPTTATG VFSLKARPGLPPGINVASLE WVSREPALLCTFPNPSAPRK DSTLSAVPQSSYPLLANGVC KWPGCEKVFEEPEDFLKHCQ ADHLLDEKGRAQCLLQREM VQSLEQQLVLEKEKLSAMQ AHLAGKMALTKASSVASSD KGSCCIVAAGSQGPVVPAWS GPREAPDSLFAVRRHLWGSH GNSTFPEFLHNMDYFKFHN MRPPFTYATLIRWAILEAPEK QRTLNEIYHWFTRMFAFFRN HPATWKNAIRHNLSLHKCFV RVESEKGAVWTVDELEFRK KRSQRPSRCSNPTPGP | Immune cells | 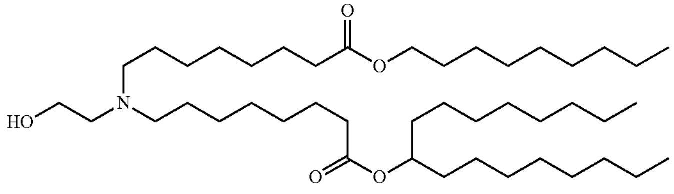 (50 mol %) DSPC (10 mol %) Beta-sitosterol (28.5 % mol %) Cholesterol (10 mol %) PEG DMG (1.5 mol %) |

TABLE 1-continued

| Protein Expression Sequences and Delivery Formulations | | | |
|---|---|---|---|
| Payload | Sequence | Target cell/ organ | Preferred delivery formulation |
| IL-10 | SPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENKSKAVEQVKNAFNKLQEKGIYKAMSEFDIFINYIEAYMTMKIRN | Immune cells | 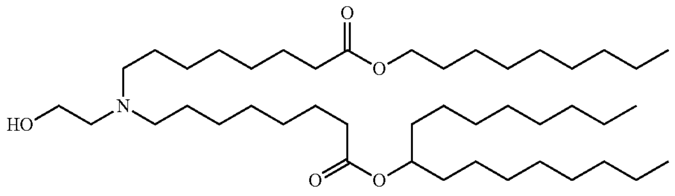<br>(50 mol %)<br>DSPC (10 mol %)<br>Beta-sitosterol (28.5 % mol %)<br>Cholesterol (10 mol %)<br>PEG DMG (1.5 mol %) |
| IL-2 | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT | Immune cells | 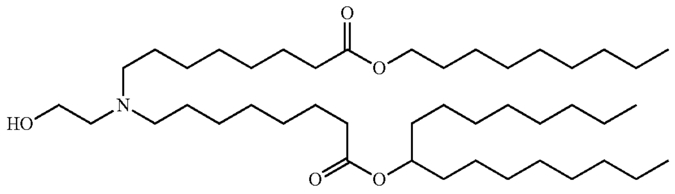<br>(50 mol %)<br>DSPC (10 mol %)<br>Beta-sitosterol (28.5 % mol %)<br>Cholesterol (10 mol %)<br>PEG DMG (1.5 mol %) |

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit. In certain embodiments, separate circRNA molecules encoding the individual subunits may be administered in separate transfer vehicles.

4. Ionizable Lipids

In certain embodiments disclosed herein are lipids that may be used as a component of a transfer vehicle to facilitate or enhance the delivery and release of circular RNA to one or more target cells (e.g., by permeating or fusing with the lipid membranes of such target cells).

In some embodiments, a lipid or transfer vehicle is a lipid as described in pages 32-55 of International Patent Application No. PCT/US2010/061058, paragraphs 86-117 of US Application Publication No. US2019/0314524, pages 43-146 of International Patent Application No. PCT/US2018/058555, pages 46-51 of International Patent Application No. PCT/US2018/053569, paragraphs 195-217 of International Patent Application No. PCT/US2017/028981, paragraphs 82-95 of US Application Publication No. US2019/0321489, paragraphs 5-19 and/or 38-77 of US Application Publication No. US2019/0314284, Tables 1-4 of International Patent Application No. PCT/US2019/025246, paragraphs 92-107 of US Application Publication No 20190091164, pages 78-97, 109-164, and/or 190-217 of International Patent Application No. PCT/US2019/015913, the contents of each of which are herein incorporated by reference in their entireties.

In some embodiments, a lipid or transfer vehicle is an ionizable lipid. In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells. In some embodiments, an ionizable lipid is a lipid as represented by formula 1 or as listed in Tables 1 or 2 of U.S. Pat. No. 9,708,628, the content of which is herein incorporated by reference in its entirety. In some embodiments, an ionizable lipid is as described in pages 7-13 of U.S. Pat. No. 9,765,022 or as represented by formula 1 of U.S. Pat. No. 9,765,022, the content of which is herein incorporated by reference in its entirety. In some embodiments, an ionizable lipid is described in pages 12-24 of International Patent Application No. PCT/US2019/016362 or as represented by formula 1 of International Patent Application PCT/US2019/016362, the contents of which are herein incorporated by reference in their entirety.

In some embodiments, a lipid or transfer vehicle is a lipid as described in International Patent Application Nos. PCT/US2010/061058, PCT/US2018/058555, PCT/US2018/053569, PCT/US2017/028981, PCT/US2019/025246, PCT/US2019/015913, PCT/US2019/016362, PCT/US2019/016362, US Application Publication Nos. US2019/0314524, US2019/0321489, US2019/0314284, and US2019/0091164, and U.S. Pat. Nos. 9,708,628 and 9,765,022, the contents of which are herein incorporated by reference in their entireties.

In some embodiments, a lipid that may be used as a component of a transfer vehicle to facilitate or enhance the delivery and release of circular RNA to one or more target cells may be one or more lipid listed in Table 2.

TABLE 2
| Exemplary Lipids | |
| --- | --- |
| Number | Lipid Structure |
| 1 | 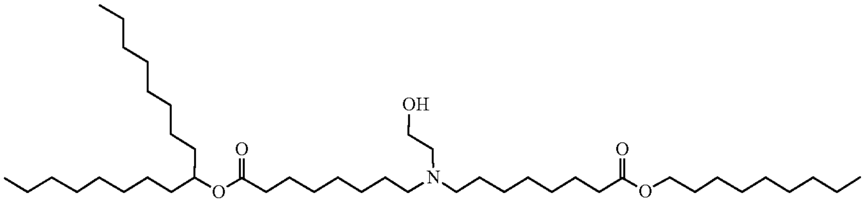 [SMILES: CCCCCCCCCOC(=O)CCCCCCCN(CCO)CCCCCCCC(=O)OC(CCCCCCCC)CCCCCCCC] |
| 2 | 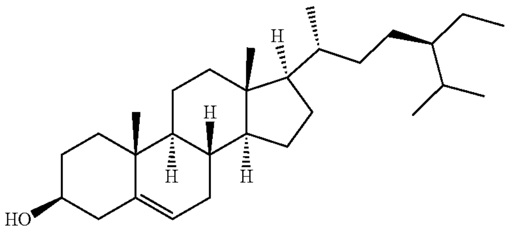 |
| 3 | 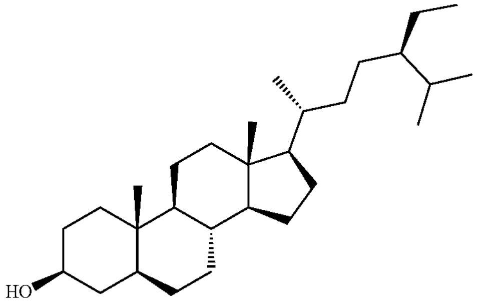 [SMILES: CC[C@H](CC[C@@H](C)[C@H]1CC[C@H]2[C@@H]3CC[C@H]4C[C@@H](O)CC[C@]4(C)[C@H]3CC[C@]12C)C(C)C] |
| 4 | 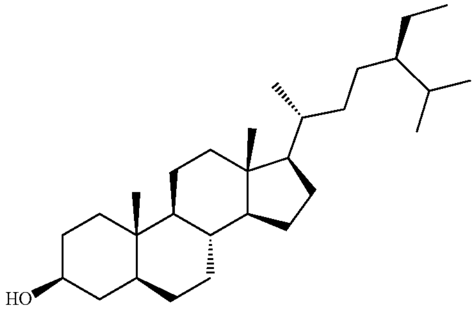 [SMILES: CC[C@H](CC[C@@H](C)[C@H]1CC[C@H]2[C@@H]3CC[C@H]4C[C@@H](O)CC[C@]4(C)[C@H]3CC[C@]12C)C(C)C] |
| 5 | 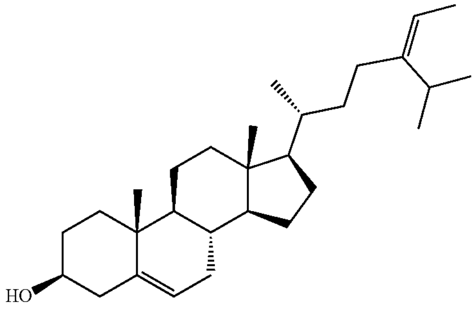 [SMILES: C/C=C(/CC[C@@H](C)[C@H]1CC[C@H]2[C@@H]3CC=C4C[C@@H](O)CC[C@]4(C)[C@H]3CC[C@]12C)C(C)C] |

TABLE 2-continued
| Exemplary Lipids | |
|---|---|
| Number | Lipid Structure |
| 6 | 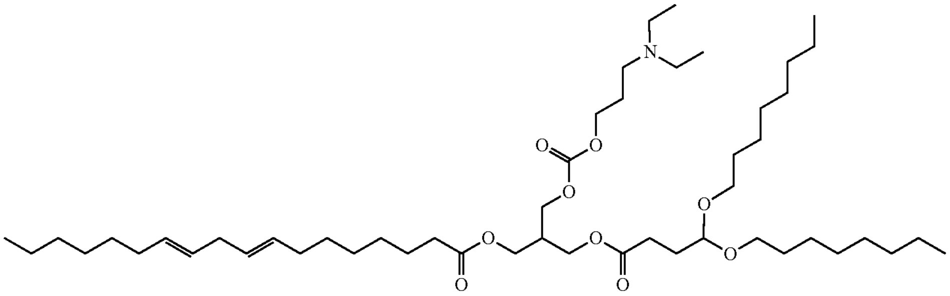 [SMILES: CCCCCC/C=C/C/C=C/CCCCCCC(=O)OCC(COC(=O)CCC(OCCCCCCCC)OCCCCCCCC)COC(=O)OCCCN(CC)CC] |
| 7 | 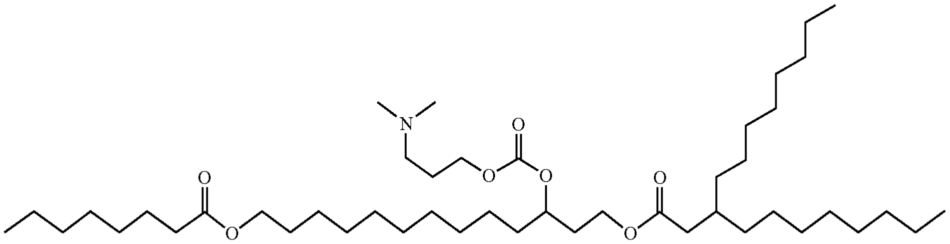 [SMILES: CCCCCCCCC(CCCCCCCC)CC(=O)OCCC(CCCCCCCCCCOC(=O)CCCCCCC)OC(=O)OCCCN(C)C] |
| 8 | 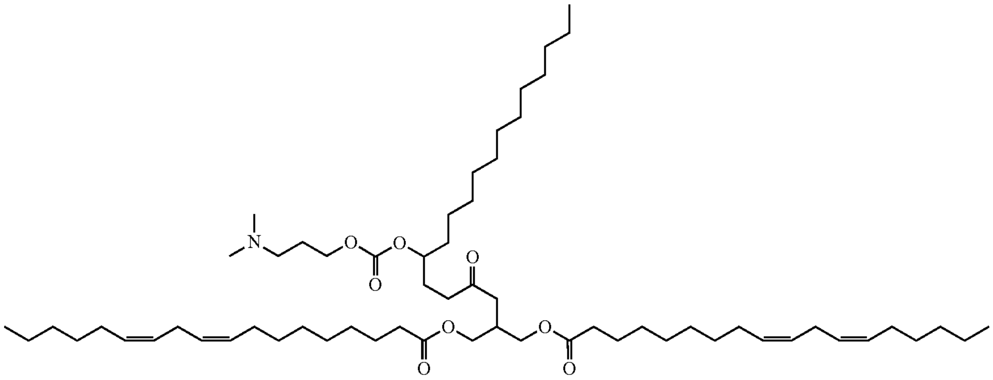 [SMILES: CCCCC/C=C\C/C=C\CCCCCCCC(=O)OCC(COC(=O)CCCCCCC/C=C\C/C=C\CCCCC)CC(=O)CCC(CCCCCCCCCCCC)OC(=O)OCCCN(C)C] |
| 9 | 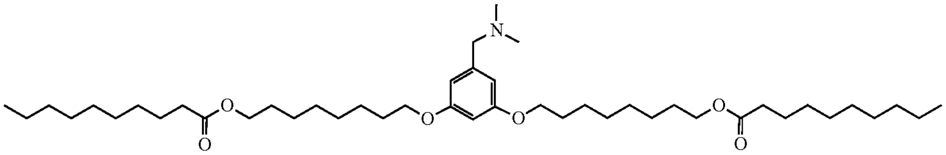 [SMILES: CCCCCCCCCC(=O)OCCCCCCCCOc1cc(CN(C)C)cc(OCCCCCCCCOC(=O)CCCCCCCCC)c1] |
| 10 | 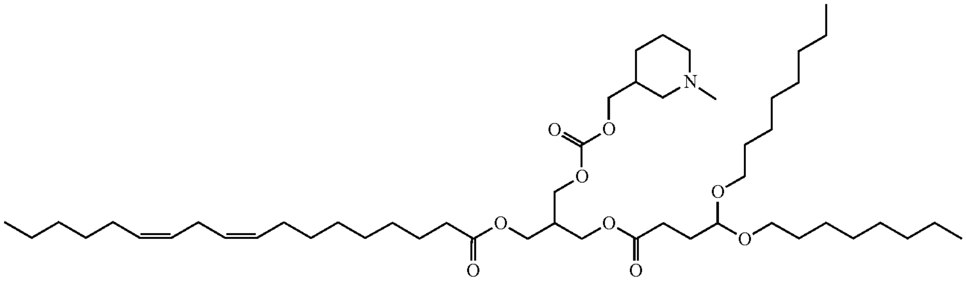 [SMILES: CCCCC/C=C\C/C=C\CCCCCCCC(=O)OCC(COC(=O)CCC(OCCCCCCCC)OCCCCCCCC)COC(=O)OCC1CCCN(C)C1] |

TABLE 2-continued
| Exemplary Lipids | |
|---|---|
| Number | Lipid Structure |
| 11 | 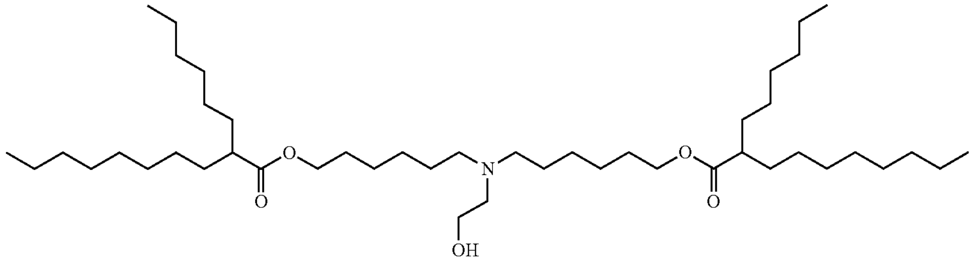 [SMILES: CCCCCCCCC(CCCCCC)C(=O)OCCCCCCN(CCO)CCCCCCOC(=O)C(CCCCCC)CCCCCCCC] |
| 12 | 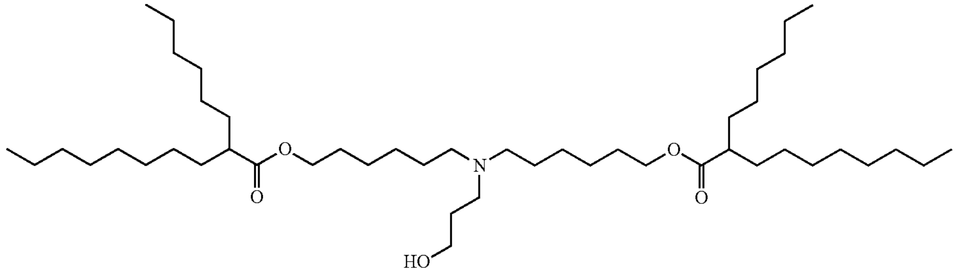 [SMILES: CCCCCCCCC(CCCCCC)C(=O)OCCCCCCN(CCCO)CCCCCCOC(=O)C(CCCCCC)CCCCCCCC] |
| 13 | 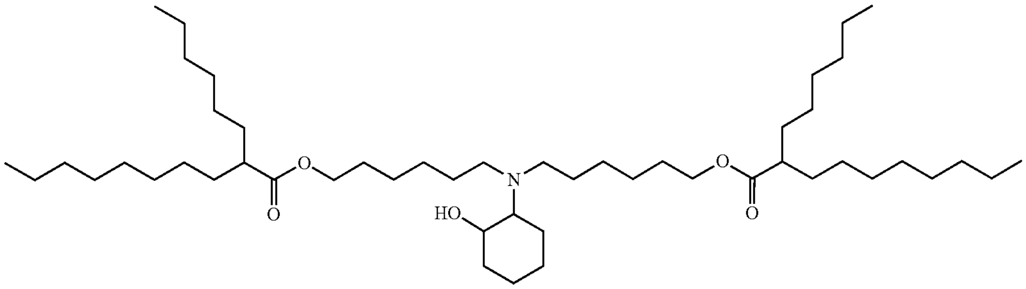 [SMILES: CCCCCCCCC(CCCCCC)C(=O)OCCCCCCN(CCCCCCOC(=O)C(CCCCCC)CCCCCCCC)C1CCCCC1O] |
| 14 | 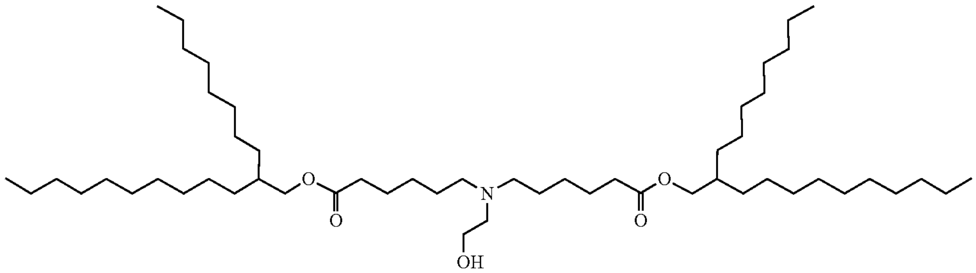 [SMILES: CCCCCCCCCCC(CCCCCCCC)COC(=O)CCCCCN(CCO)CCCCCC(=O)OCC(CCCCCCCC)CCCCCCCCCC] |
| 15 | 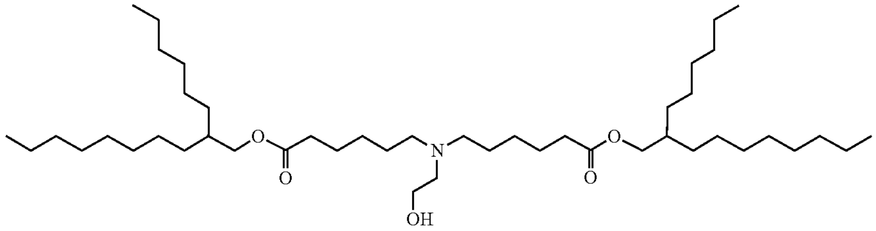 [SMILES: CCCCCCCCC(CCCCCC)COC(=O)CCCCCN(CCO)CCCCCC(=O)OCC(CCCCCC)CCCCCCCC] |
| 16 | 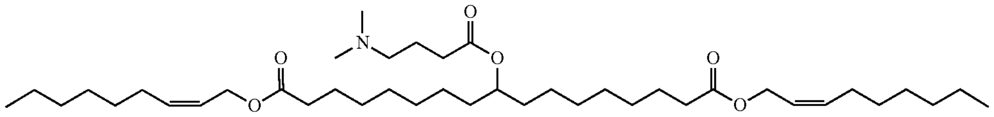 [SMILES: CCCCCC/C=C\COC(=O)CCCCCCCC(CCCCCCCC(=O)OC/C=C\CCCCCC)OC(=O)CCCN(C)C] |

TABLE 2-continued
| Exemplary Lipids | |
|---|---|
| Number | Lipid Structure |
| 17 | 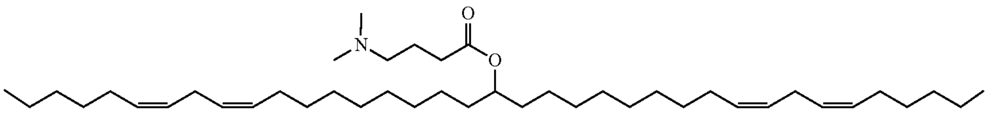 [SMILES: CCCCC/C=C\C/C=C\CCCCCCCCC(CCCCCCCC/C=C\C/C=C\CCCCC)OC(=O)CCCN(C)C] |
| 18 | 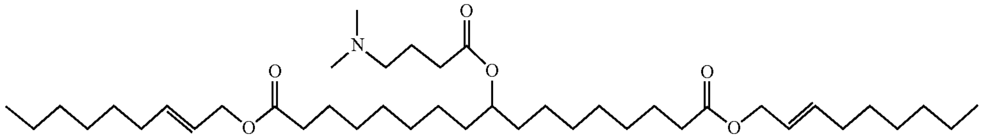 [SMILES: CCCCCC/C=C/COC(=O)CCCCCCCC(CCCCCCCC(=O)OC/C=C/CCCCCC)OC(=O)CCCN(C)C] |
| 19 | 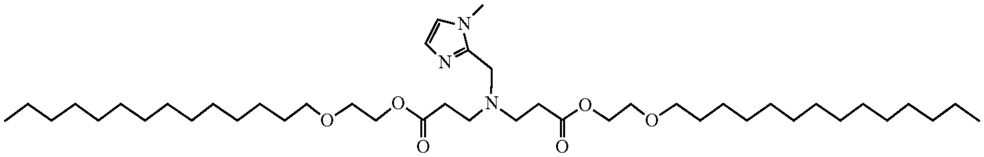 |
| 20 | 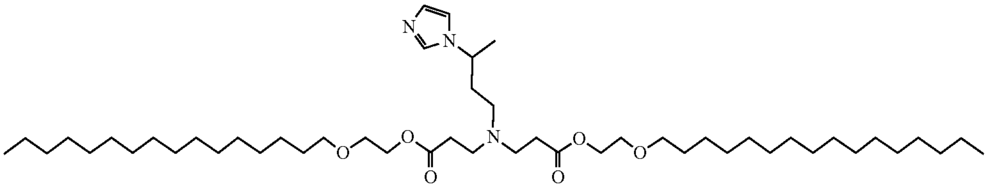 |
| 21 | 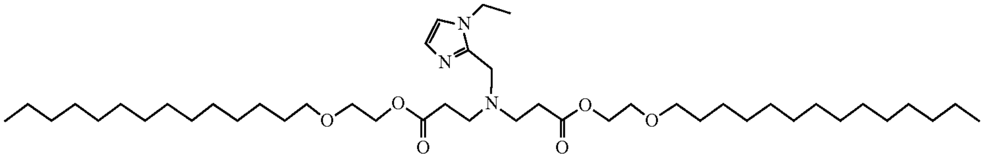 |
| 22 | 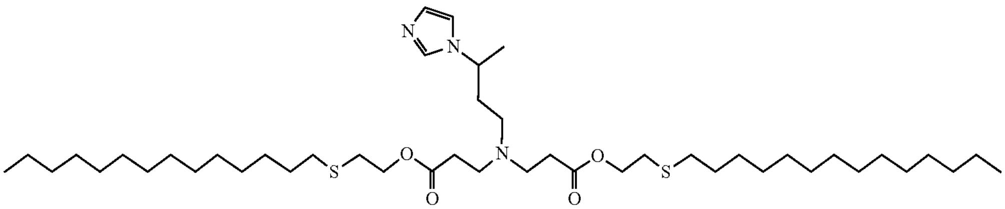 |
| 23 | 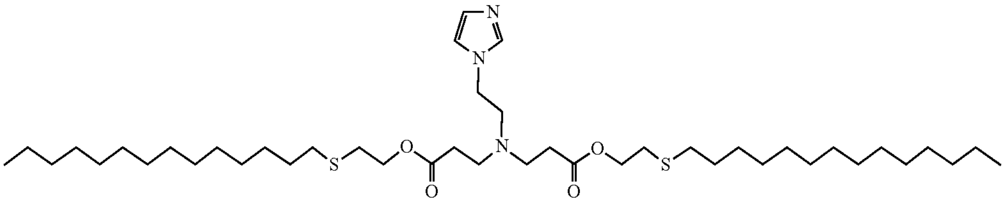 |
| 24 | 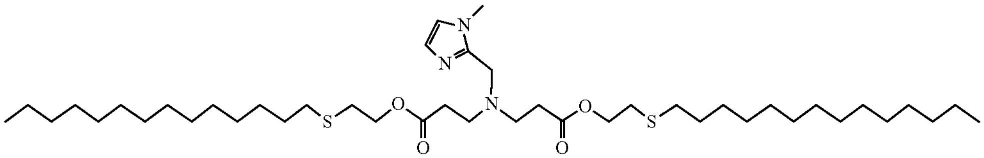 |

TABLE 2-continued
| Exemplary Lipids | |
|---|---|
| Number | Lipid Structure |
| 25 | 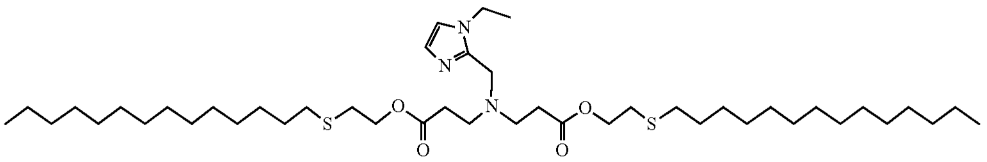 |
| 26 | 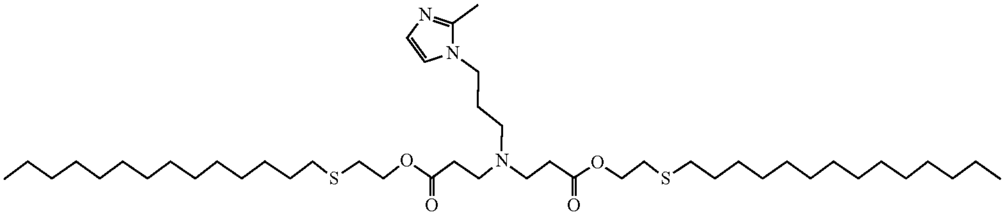 |
| 27 | 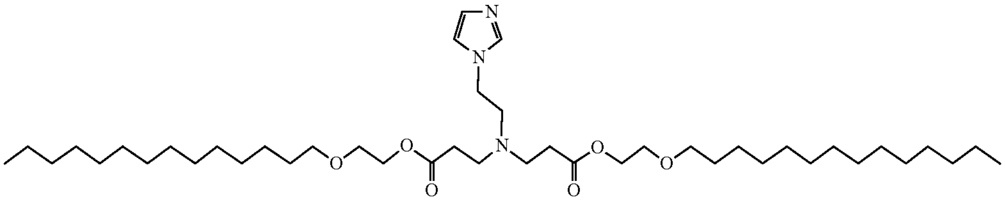 |
| 28 | 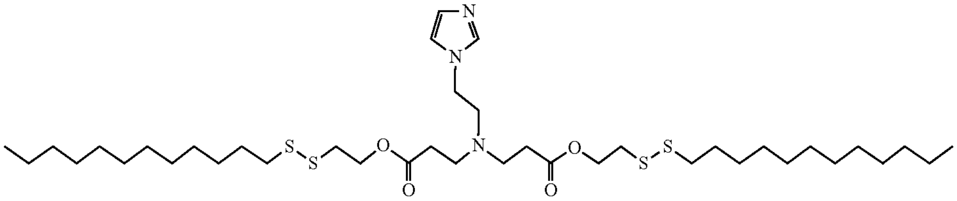 [SMILES: CCCCCCCCCCCCSSCCOC(=O)CCN(CCC(=O)OCCSSCCCCCCCCCCCC)CCn1ccnc1] |
| 29 | 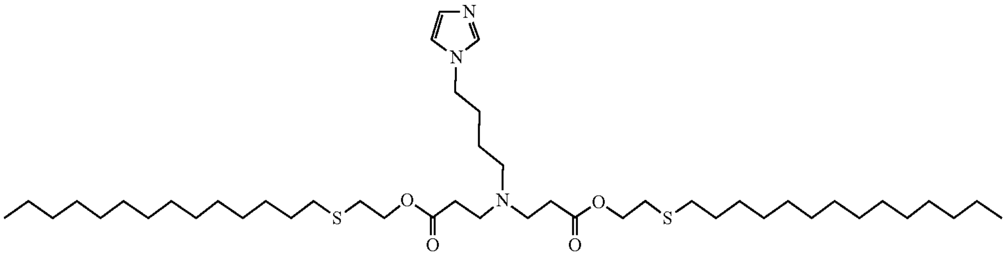 [SMILES: CCCCCCCCCCCCCCSCCOC(=O)CCN(CCCCn1ccnc1)CCC(=O)OCCSCCCCCCCCCCCCCC] |
| 30 | 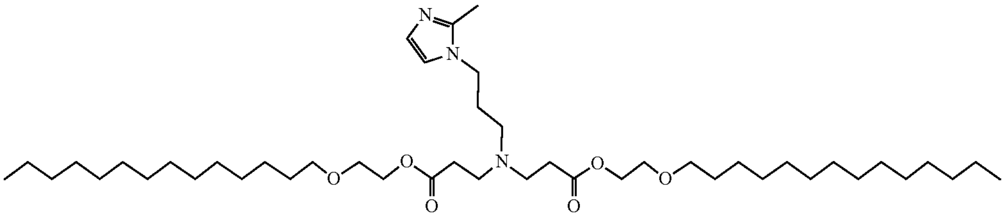 |
| 31 | 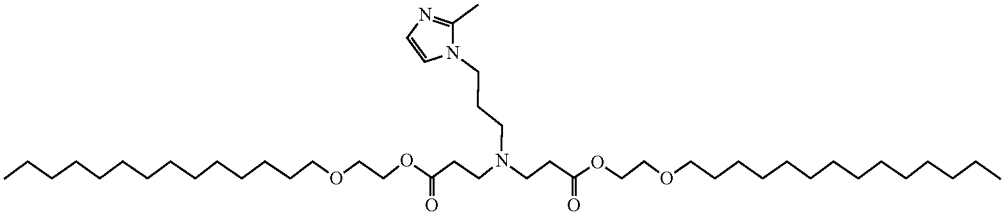 |

TABLE 2-continued
| Exemplary Lipids | |
|---|---|
| Number | Lipid Structure |
| 32 | 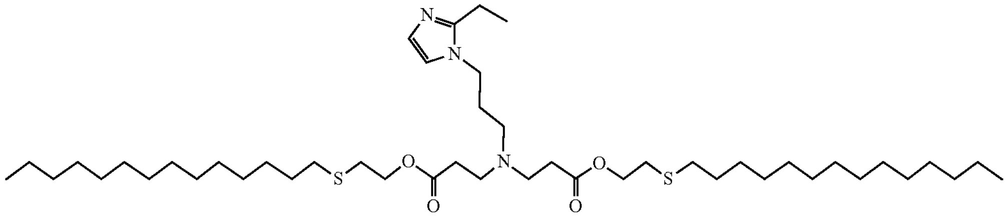 |
| 33 | 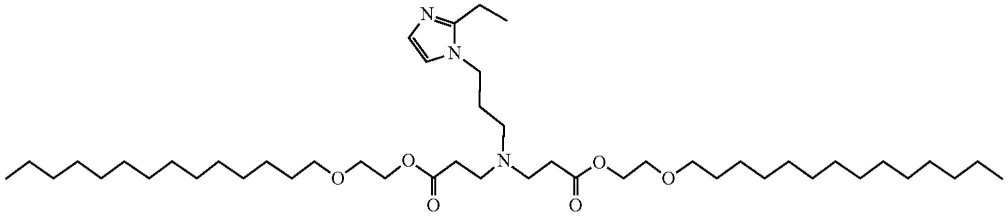 |
| 34 | 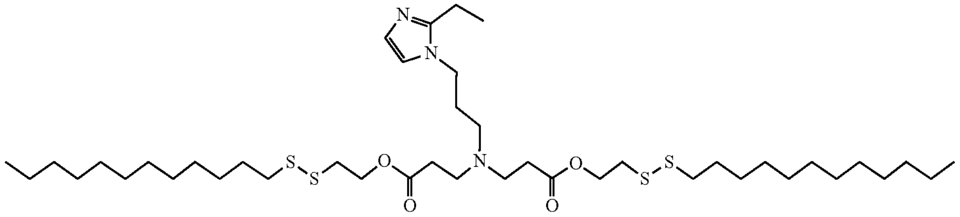 |
| 35 | 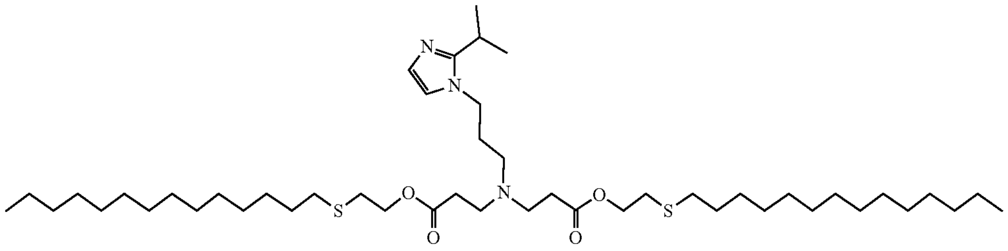 |
| 36 | 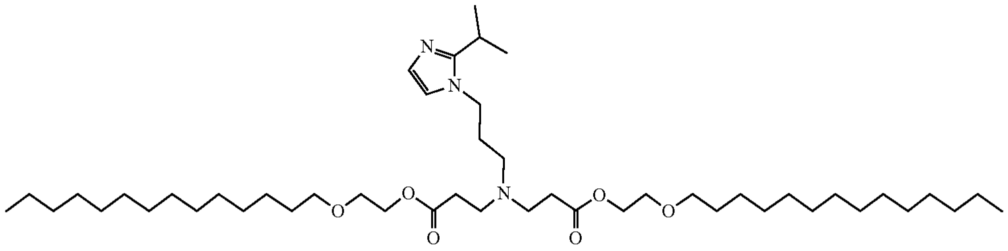 [SMILES: CCCCCCCCCCCCCCOCCOC(=O)CCN(CCCn1ccnc1C(C)C)CCC(=O)OCCOCCCCCCCCCCCCCC] |
| 37 | 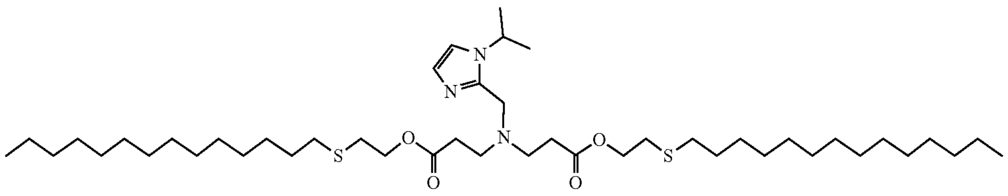 |

TABLE 2-continued
| Exemplary Lipids | |
|---|---|
| Number | Lipid Structure |
| 38 | 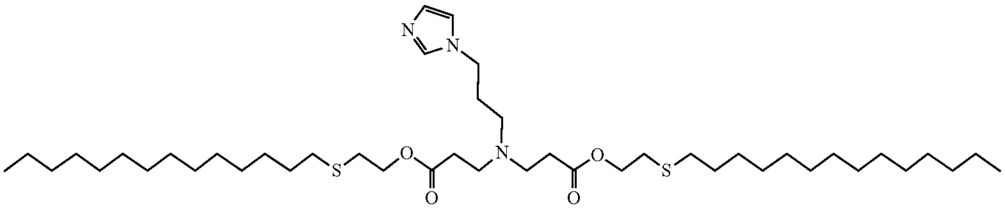 |
| 39 | 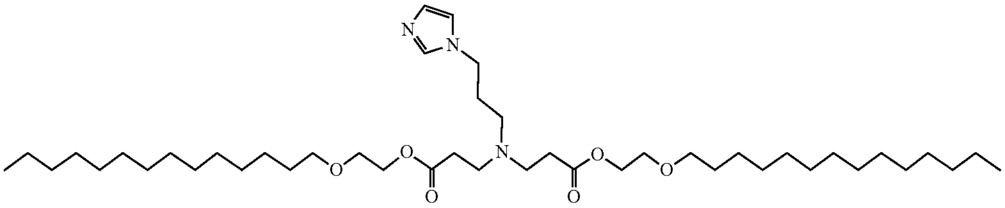 |
| 40 | 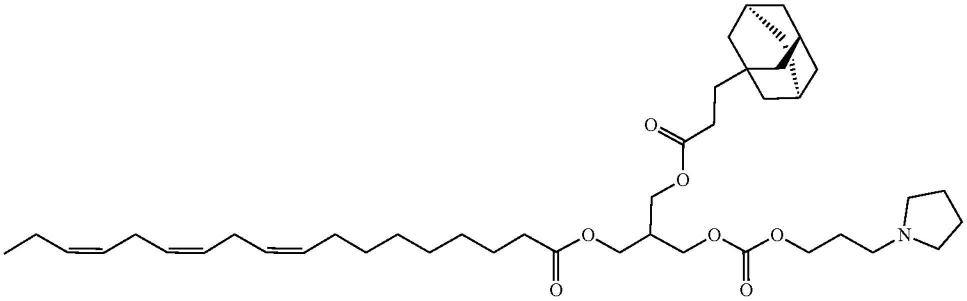 [SMILES: CC/C=C\C/C=C\C/C=C\CCCCCCCC(=O)OCC(COC(=O)CCC12C[C@H]3C[C@@H](C1)C[C@@H](C2)C3)COC(=O)OCCCN1CCCC1] |
| 41 | 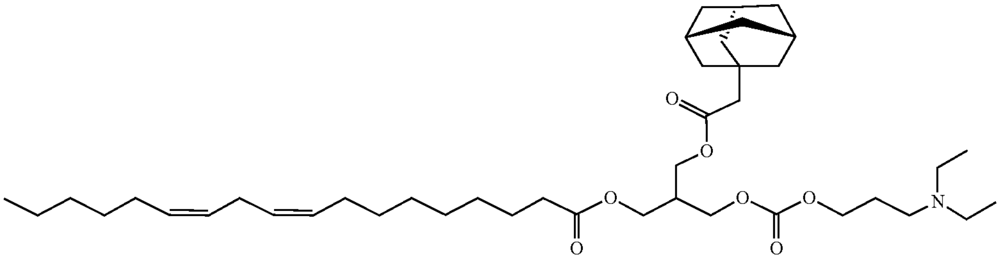 [SMILES: CCCCC/C=C\C/C=C\CCCCCCCC(=O)OCC(COC(=O)CC12C[C@H]3C[C@H](C1)C[C@@H](C2)C3)COC(=O)OCCCN(CC)CC] |
| 42 | 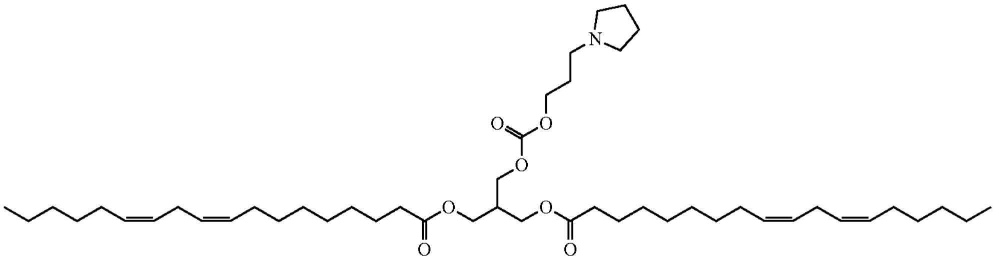 [SMILES: CCCCC/C=C\C/C=C\CCCCCCCC(=O)OCC(COC(=O)CCCCCCC/C=C\C/C=C\CCCCC)COC(=O)OCCCN1CCCC1] |
| 43 | 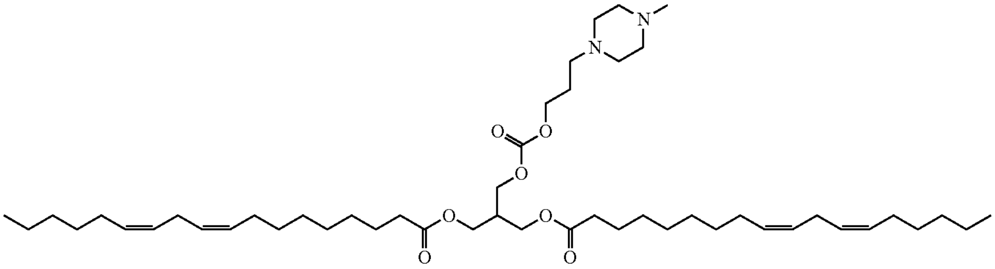 [SMILES: CCCCC/C=C\C/C=C\CCCCCCCC(=O)OCC(COC(=O)CCCCCCC/C=C\C/C=C\CCCCC)COC(=O)OCCCN1CCN(C)CC1] |

TABLE 2-continued
| Exemplary Lipids | |
|---|---|
| Number | Lipid Structure |
| 44 | 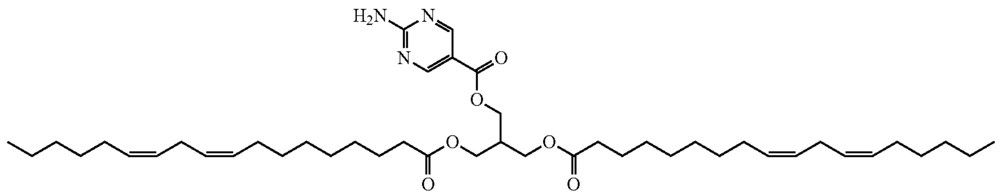 [SMILES: CCCCC/C=C\C/C=C\CCCCCCCC(=O)OCC(COC(=O)CCCCCCC/C=C\C/C=C\CCCCC)COC(=O)c1cnc(N)nc1] |
| 45 | 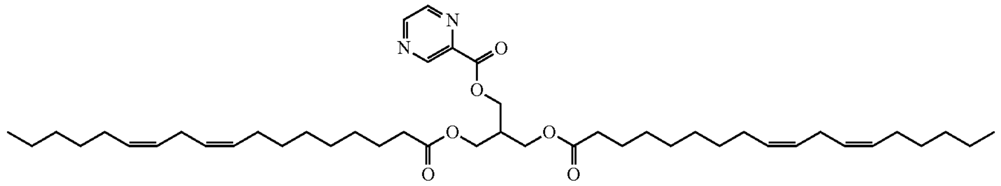 [SMILES: CCCCC/C=C\C/C=C\CCCCCCCC(=O)OCC(COC(=O)CCCCCCC/C=C\C/C=C\CCCCC)COC(=O)c1cnccn1] |
| 46 | 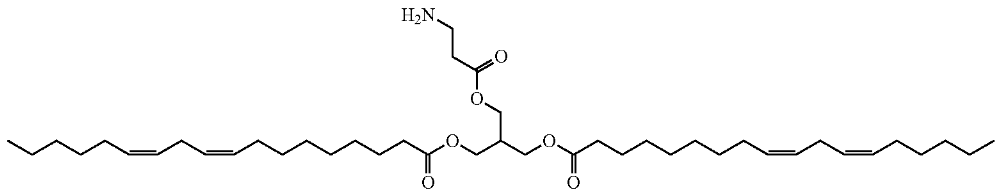 [SMILES: CCCCC/C=C\C/C=C\CCCCCCCC(=O)OCC(COC(=O)CCN)COC(=O)CCCCCCC/C=C\C/C=C\CCCCC] |
| 47 | 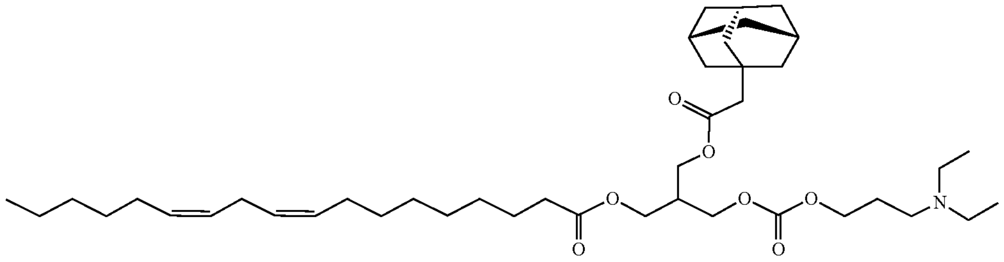 [SMILES: CCCCC/C=C\C/C=C\CCCCCCCC(=O)OCC(COC(=O)CC12C[C@H]3C[C@H](C1)C[C@@H](C2)C3)COC(=O)OCCCN(CC)CC] |
| 48 | 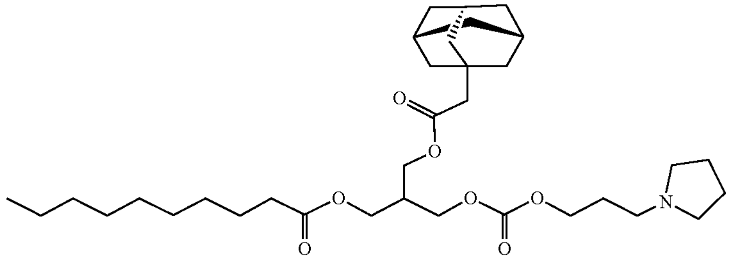 [SMILES: CCCCCCCCCC(=O)OCC(COC(=O)CC12C[C@H]3C[C@H](C1)C[C@@H](C2)C3)COC(=O)OCCCN1CCCC1] |
| 49 | 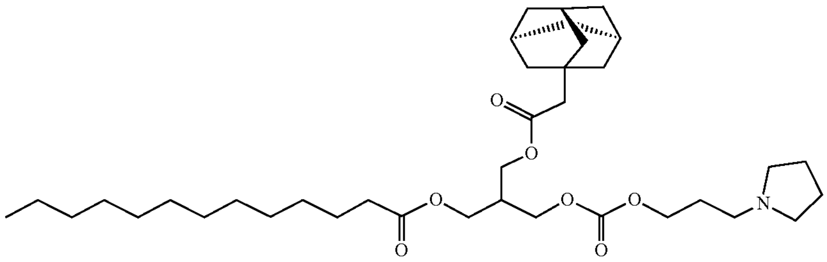 [SMILES: CCCCCCCCCCCCC(=O)OCC(COC(=O)CC12C[C@H]3C[C@H](C1)C[C@@H](C2)C3)COC(=O)OCCCN1CCCC1] |

TABLE 2-continued
| Exemplary Lipids | |
|---|---|
| Number | Lipid Structure |
| 50 | 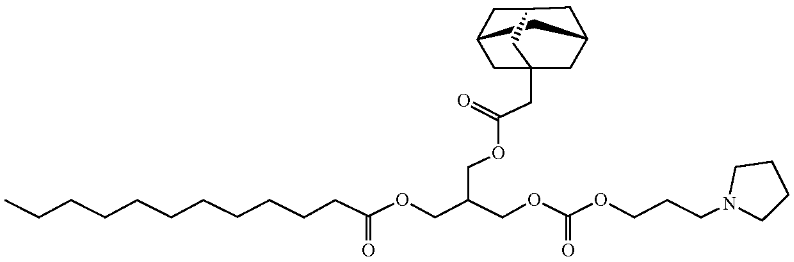 [SMILES: CCCCCCCCCCCC(=O)OCC(COC(=O)CC12C[C@H]3C[C@H](C1)C[C@@H](C2)C3)COC(=O)OCCCN1CCCC1] |
| 51 | 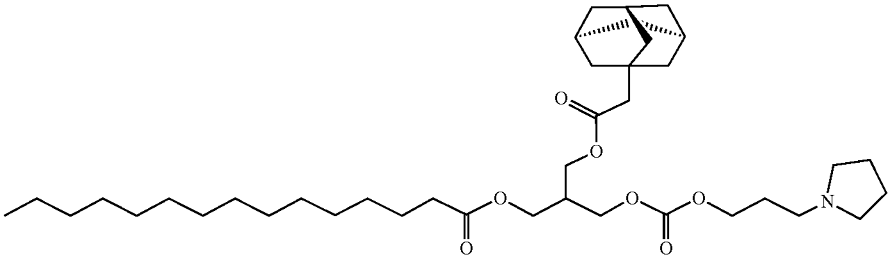 [SMILES: CCCCCCCCCCCCCCC(=O)OCC(COC(=O)CC12C[C@H]3C[C@H](C1)C[C@@H](C2)C3)COC(=O)OCCCN1CCCC1] |
| 52 | 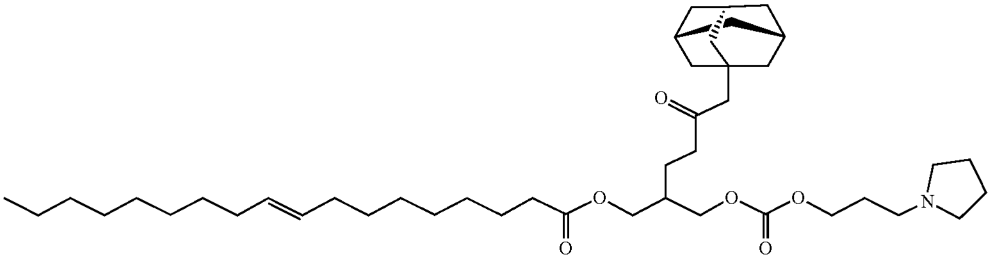 [SMILES: CCCCCCCC/C=C/CCCCCCCC(=O)OCC(CCC(=O)CC12C[C@H]3C[C@H](C1)C[C@@H](C2)C3)COC(=O)OCCCN1CCCC1] |
| 53 | 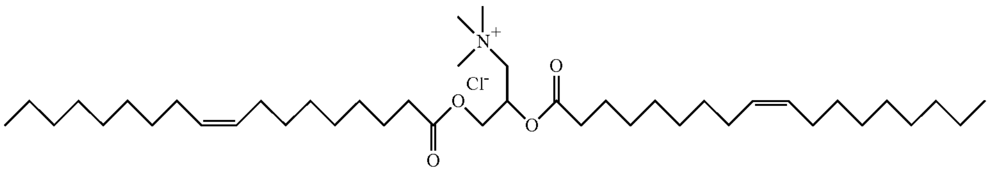 |
| 54 | 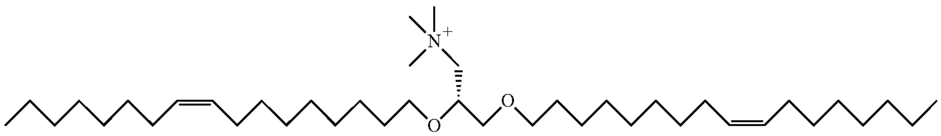 |
| 55 | 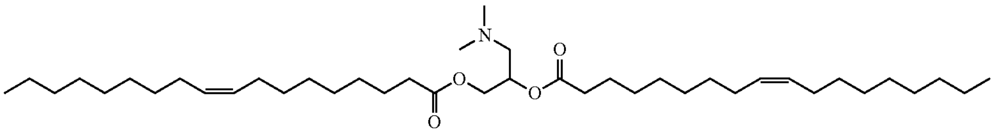 [SMILES: CCCCCCCC/C=C\CCCCCCCC(=O)OCC(CN(C)C)OC(=O)CCCCCCC/C=C\CCCCCCCC] |
| 56 | 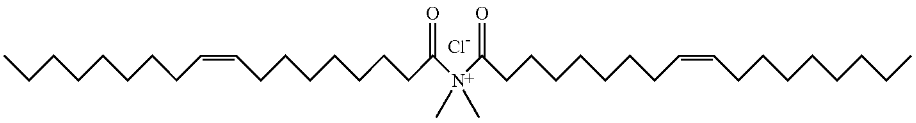 |
| 57 | 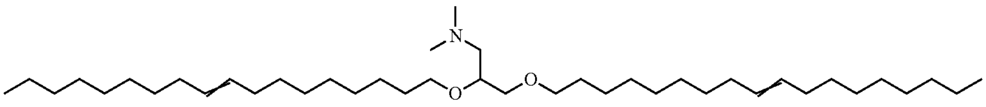 [SMILES: CCCCCCCCC=CCCCCCCCCOCC(CN(C)C)OCCCCCCCCC=CCCCCCCCC] |

TABLE 2-continued
| Exemplary Lipids | |
| --- | --- |
| Number | Lipid Structure |
| 58 | 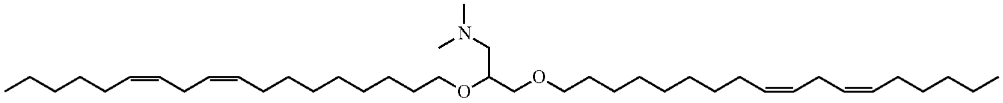 [SMILES: CCCCC/C=C\C/C=C\CCCCCCCCOCC(CN(C)C)OCCCCCCCC/C=C\C/C=C\CCCCC] |
| 59 | 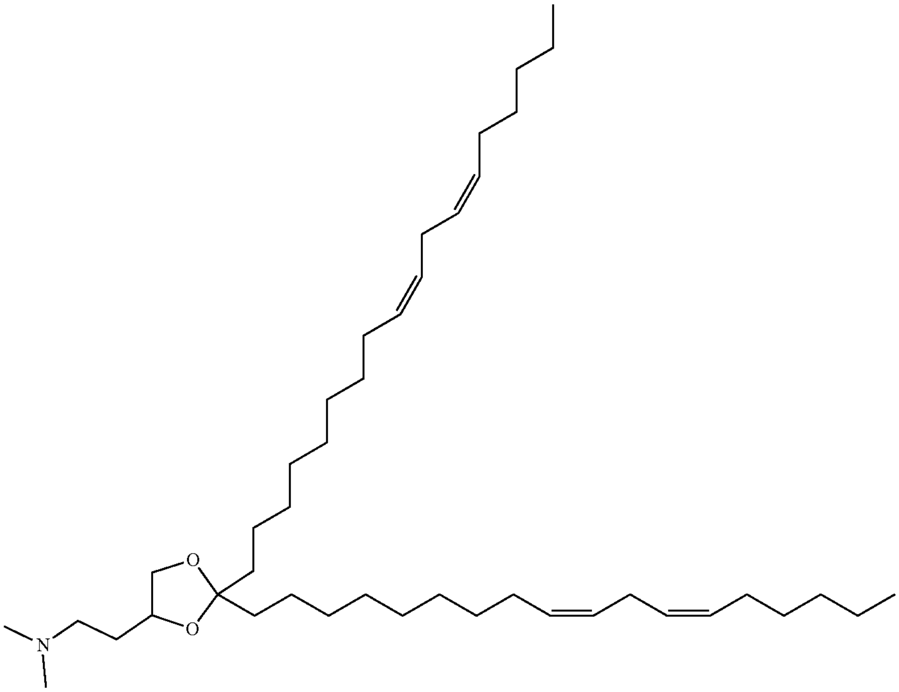 [SMILES: CCCCC/C=C\C/C=C\CCCCCCCCC1(CCCCCCCC/C=C\C/C=C\CCCCC)OCC(CCN(C)C)O1] |
| 60 | 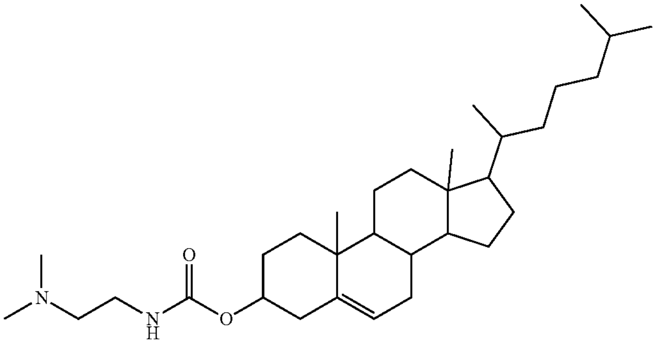 [SMILES: CC(C)CCCC(C)C1CCC2C3CC=C4CC(OC(=O)NCCN(C)C)CCC4(C)C3CCC12C] |
| 61 | 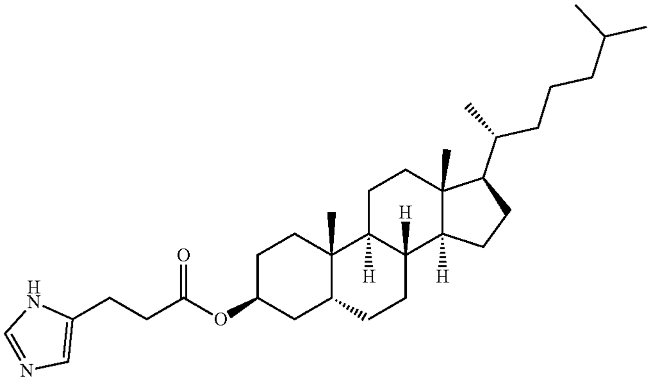 |

TABLE 2-continued
| Exemplary Lipids | |
|---|---|
| Number | Lipid Structure |
| 62 | 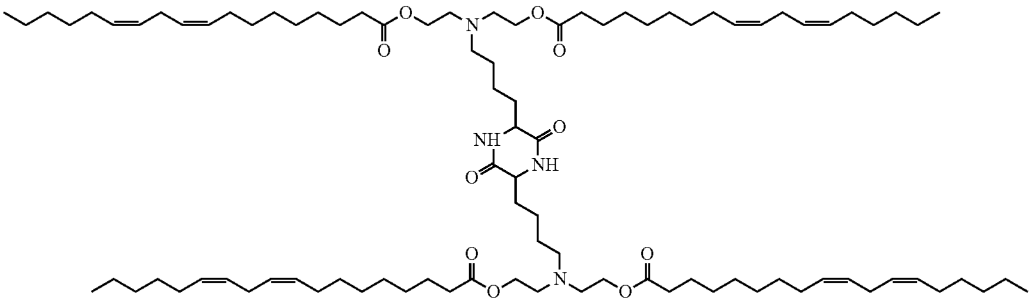 [SMILES: CCCCC/C=C\C/C=C\CCCCCCCC(=O)OCCN(CCCCC1NC(=O)C(CCCCN(CCOC(=O)CCCCCCC/C=C\C/C=C\CCCCC)CCOC(=O)CCCCCCC/C=C\C/C=C\CCCCC)NC1=O)CCOC(=O)CCCCCCC/C=C\C/C=C\CCCCC] |
| 63 | 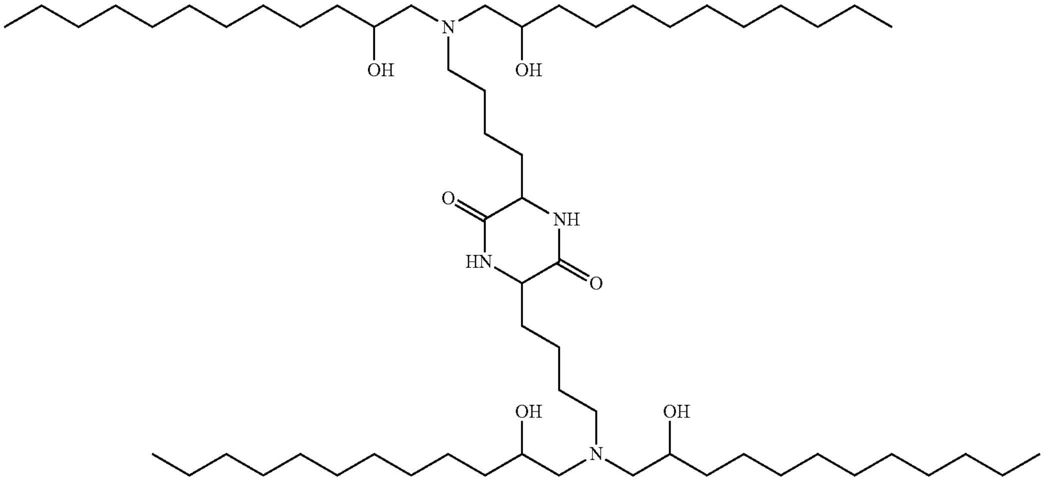 [SMILES: CCCCCCCCCCC(O)CN(CCCCC1NC(=O)C(CCCCN(CC(O)CCCCCCCCCC)CC(O)CCCCCCCCCC)NC1=O)CC(O)CCCCCCCCCC] |

TABLE 2-continued
| Exemplary Lipids | |
|---|---|
| Number | Lipid Structure |
| 64 | 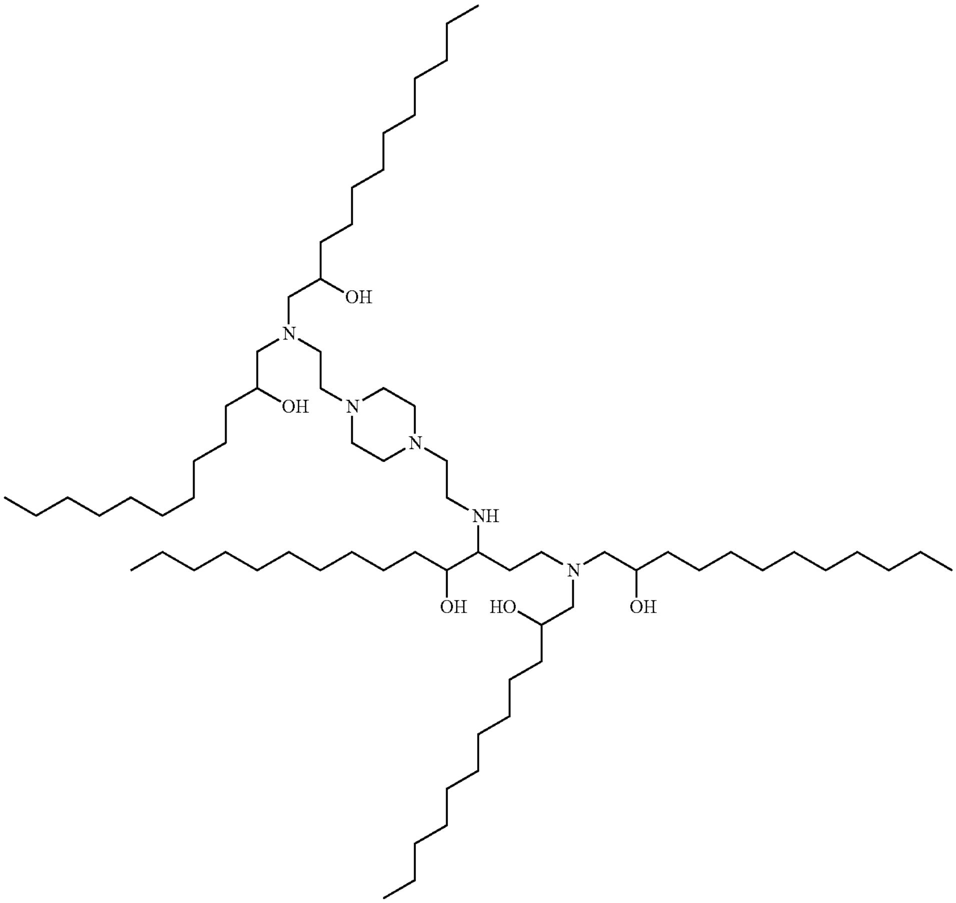 [SMILES: CCCCCCCCCCC(O)CN(CCC(NCCN1CCN(CCN(CC(O)CCCCCCCCCC)CC(O)CCCCCCCCCC)CC1)C(O)CCCCCCCCCC)CC(O)CCCCCCCCCC] |
| 65 | 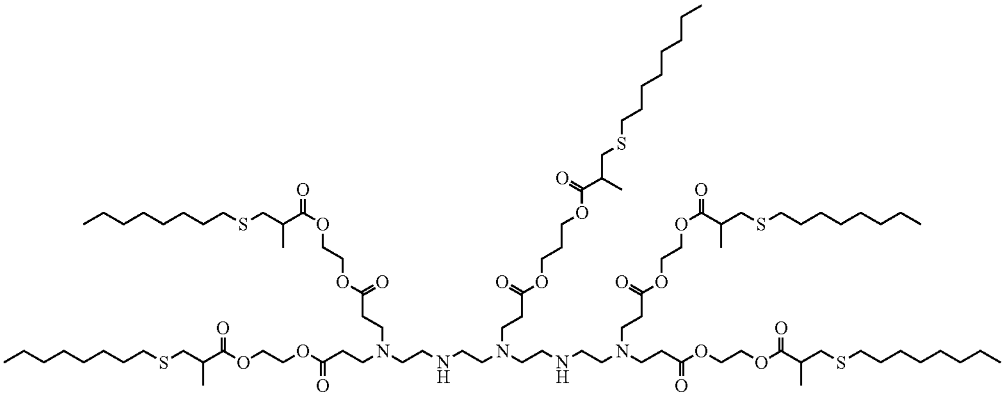 [SMILES: CCCCCCCCSCC(C)C(=O)OCCCOC(=O)CCN(CCNCCN(CCC(=O)OCCOC(=O)C(C)CSCCCCCCCC)CCC(=O)OCCOC(=O)C(C)CSCCCCCCCC)CCNCCN(CCC(=O)OCCOC(=O)C(C)CSCCCCCCCC)CCC(=O)OCCOC(=O)C(C)CSCCCCCCCC] |
| 66 | 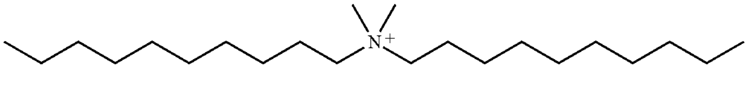 |

TABLE 2-continued
| Exemplary Lipids | |
|---|---|
| Number | Lipid Structure |
| 67 | 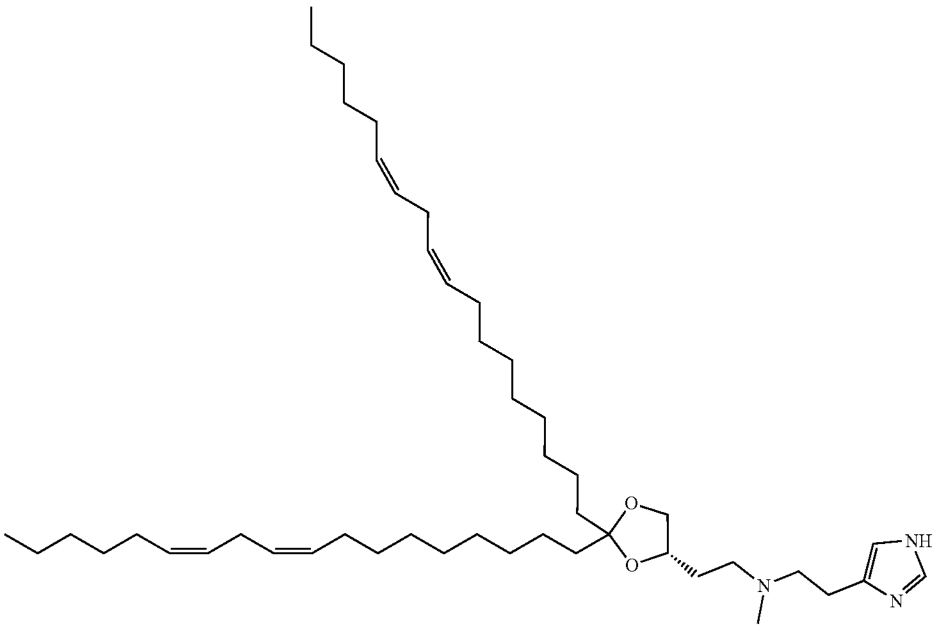 [SMILES: CCCCC/C=C\C/C=C\CCCCCCCCC1(CCCCCCCC/C=C\C/C=C\CCCCC)OC[C@H](CCN(C)CCc2c[nH]cn2)O1] |
| 68 | 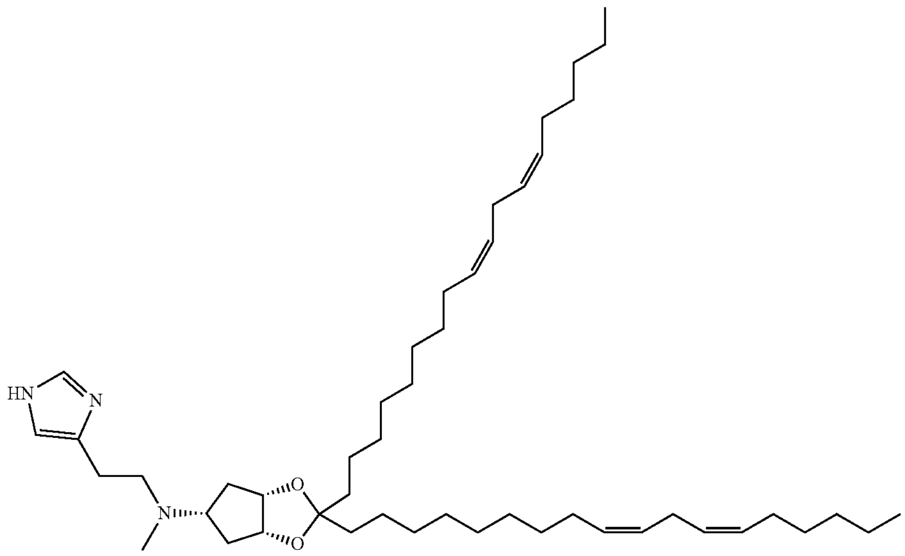 [SMILES: CCCCC/C=C\C/C=C\CCCCCCCCC1(CCCCCCCC/C=C\C/C=C\CCCCC)O[C@H]2C[C@@H](N(C)CCc3c[nH]cn3)C[C@H]2O1] |

TABLE 2-continued
| Exemplary Lipids | |
|---|---|
| Number | Lipid Structure |
| 69 | 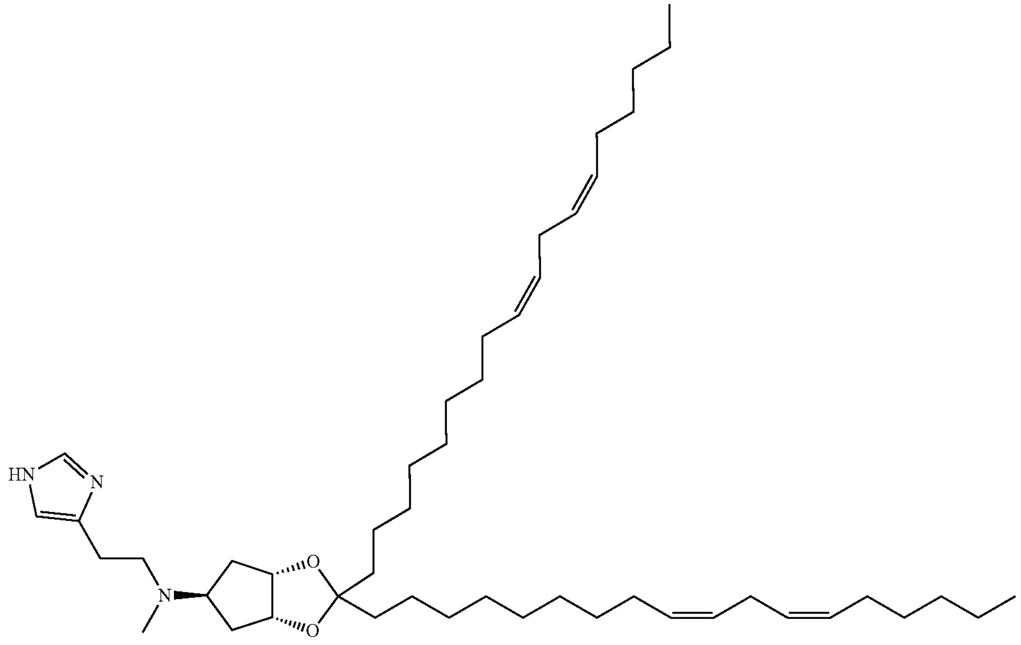 [SMILES: CCCCC/C=C\C/C=C\CCCCCCCCC1(CCCCCCCC/C=C\C/C=C\CCCCC)O[C@H]2C[C@H](N(C)CCc3c[nH]cn3)C[C@H]2O1] |
| 70 | 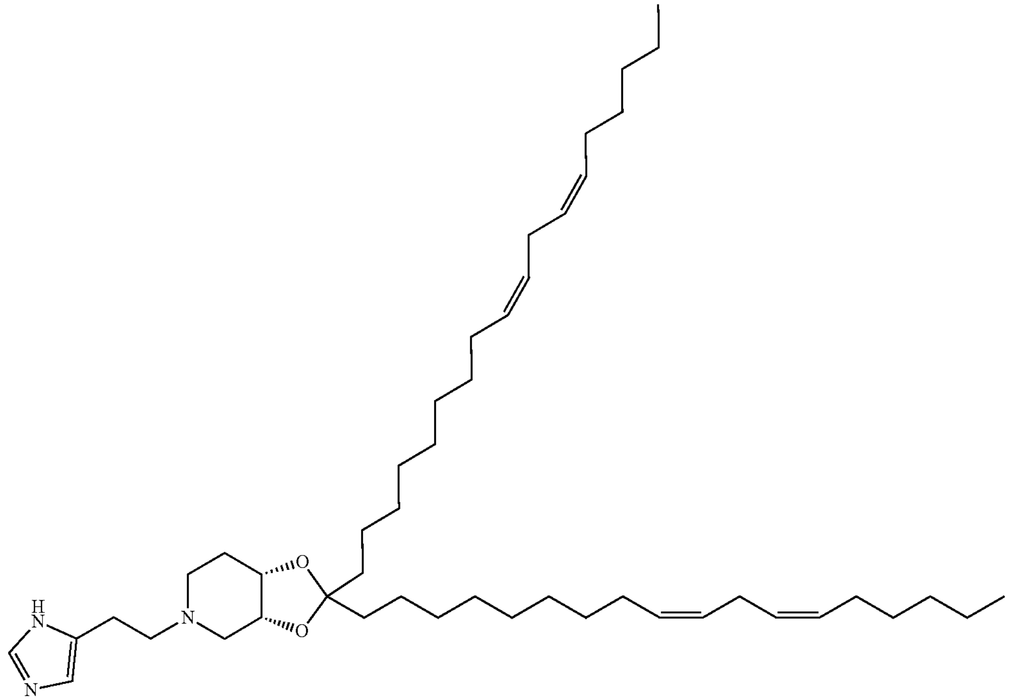 [SMILES: CCCCC/C=C\C/C=C\CCCCCCCCC1(CCCCCCCC/C=C\C/C=C\CCCCC)O[C@H]2CCN(CCc3cnc[nH]3)C[C@H]2O1] |

TABLE 2-continued

| Exemplary Lipids | |
|---|---|
| Number | Lipid Structure |
| 71 | 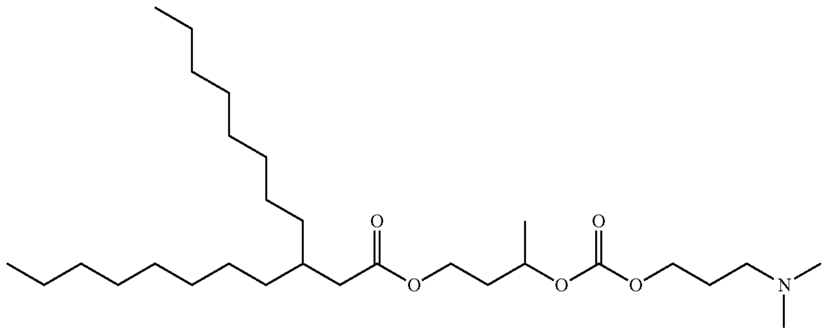 [SMILES: CCCCCCCCC(CCCCCCCC)CC(=O)OCCC(C)OC(=O)OCCCN(C)C] |

5. PEG Lipids

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of C6-C20 length. In some embodiments, the PEG-modified lipid employed in the compositions and methods of the invention is 1,2-dimyristoyl-sn-glycerol, methoxypolyethylene Glycol (2000 MW PEG) "DMG-PEG2000." The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

In an embodiment, a PEG-modified lipid is described in international patent application PCT/US2019/015913. In an embodiment, a transfer vehicle comprises one or more PEG-modified lipids.

Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but is not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DS G), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, such as from about $C_{14}$ to about $C_{16}$. In some embodiments, a PEG moiety, for example an mPEG-NH2, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG-DMG. PEG-DMG has the following structure:

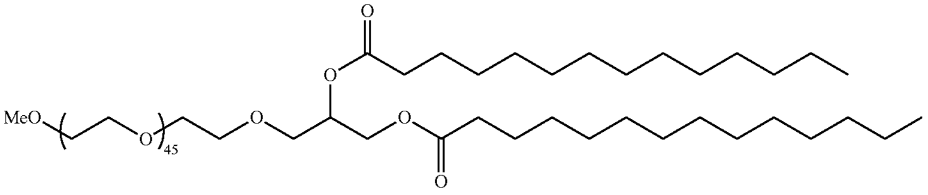

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In some embodiments, the PEG lipid is a compound of Formula (P1):

P1

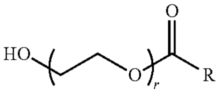

or a salt or isomer thereof, wherein:

r is an integer between 1 and 100;

R is $C_{10-40}$ alkyl, $C_{10-40}$ alkenyl, or $C_{10-40}$ alkynyl; and optionally one or more methylene groups of R are independently replaced with $C_{3-10}$ carbocyclylene, 4 to 10 membered heterocyclylene, $C_{6-10}$ arylene, 4 to 10 membered heteroarylene, —N($R^N$), —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$)S(O)—, —S(O)N($R^N$)—, —N($R^N$)S(O)N($R^N$)—, —OS(O)N($R^N$)—, —N($R^N$)S(O)O—, —S$(O)_2$—, —N($R^N$)S$(O)_2$—, —S$(O)_2$N($R^N$)—, —N($R^N$)S$(O)_2$N($R^N$)—, —OS$(O)_2$N($R^N$)—, or —N($R^N$)S$(O)_2$O—; and each instance of $R^N$ is independently hydrogen, $C_{1-6}$ alkyl, or a nitrogen protecting group.

For example, R is C17 alkyl. For example, the PEG lipid is a compound of Formula (P 1-a):

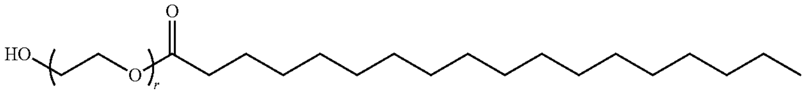

or a salt or isomer thereof, wherein r is an integer between 1 and 100.

For example, the PEG lipid is a compound of the following formula:

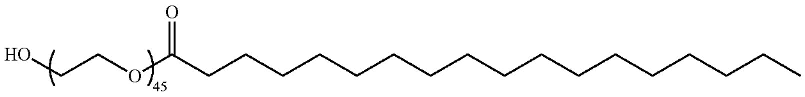

6. Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly)unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-paimitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE) dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

7. Structural Lipids

In an embodiment, a structural lipid is described in international patent application PCT/US2019/015913.

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. Structural lipids can include, but are not limited to, sterols (e.g., phytosterols or zoosterols).

In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol.

8. Chimeric Antigen Receptors

Chimeric antigen receptors (CARs or CAR-Ts) are genetically-engineered receptors. These engineered receptors may be inserted into and expressed by immune cells, including T cells via circular RNA as described herein. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. In some embodiments, the CAR encoded by the polynucleotide comprises (i) an antigen-binding molecule that specifically binds to a target antigen, (ii) a hinge domain, a transmembrane domain, and an intracellular domain, and (iii) an activating domain.

In certain aspects, provided herein are vectors, precursor RNAs and circular RNA polynucleotides that comprise a protein coding region that encodes a chimeric antigen receptor (CAR) or a T cell receptor (TCR) complex protein.

A CAR is an artificially constructed hybrid protein or polypeptide containing an antigen binding domain (e.g., single chain variable fragment (scFv)) linked to T-cell signaling domains. Characteristics of CARs include their ability to redirect T-cell specificity and reactivity toward at least one selected target (e.g., in a non-MHC-restricted manner), exploiting the antigen-binding properties of monoclonal antibodies. The ability CARs to recognize non-MHC-restricted antigen gives T cells expressing CARs the ability to recognize an antigen independent of antigen processing, thus bypassing a major mechanism of tumor escape. A bispecific CAR is specific to two different antigens. In an embodiment, certain polynucleotides provided herein encode bispecific CARs.

In some embodiments, the CAR comprises a transmembrane domain. In an embodiment, the transmembrane domain comprises a CD8 transmembrane domain. In some embodiments, the CAR comprises a CD8a (CD8 alpha) hinge and transmembrane domain. In a preferred embodiment, the CD8 is human. The CAR may comprise less than the whole CD8 protein. In an embodiment, the transmembrane domain comprises a CD28 transmembrane domain. In some embodiments, the CAR comprises a CD28 hinge and transmembrane domain. In a preferred embodiment, the CD28 is human. The CAR may comprise less than the whole CD28 protein.

In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

In some embodiments, the CAR comprises a CAR protein spacer. The CAR protein spacer may be between any aforementioned domains. In an embodiment, the CAR comprises an IgG heavy chain constant domain (CH2CH3) spacer. In a further embodiment, the CAR protein spacer can be between the scFv and the transmembrane domain. In a preferred embodiment, the sequence of the spacer, e.g., CH2CH3, is human.

In some embodiments, the CAR or TCR complex protein is a TCR complex protein (i.e., a protein that makes up part of the TCR complex). In some embodiments, the TCR complex protein is a recombinant, naturally occurring protein. In some embodiments, the TCR complex protein is an artificial version of a protein that makes up part of the TCR complex. In some embodiments, the TCR complex protein is TCRalpha, TCRbeta, TCRgamma, TCRdelta, CD3epsilon, CD3gamma, CD3delta, CD3zeta, CD4, or CD8. In some embodiments, the TCR complex protein comprises an artificial binding domain, and/or a costimulatory domain.

In certain embodiments, the TCR complex protein comprises a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a natural TCR Vα, Vβ, Cα, and/or Cβ. In some embodiments, each CDR or the TCR complex protein comprises zero changes or at most one, two, or three changes, from a TCR or fragment or derivative thereof that specifically binds to a target of interest.

Antigen Binding Domain

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest. In some embodiments, an antigen binding domain is an aptamer or nanobody specific for a target antigen.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the CAR or TCR comprises an antigen binding domain specific for an antigen selected from the group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRCSD), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), MUC16, 5T4, 8H9, αvβθ integrin, αvβ6 integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18, NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6 p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, haemagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, and Kaposi sarcoma-associated herpesvirus (KSHV) lytic nuclear antigen and KSHV latent nuclear antigen.

Hinge/Spacer Domain

In some embodiments, a CAR of the instant disclosure comprises a hinge or spacer domain. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD8[T CD11a (IT GAL), CD11b (IT GAM), CD11c (ITGAX), CD11d (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-IBB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, and IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e., comprise) a receptor tyrosine kinase (e.g., ErbB2), glycophorin A (GpA), 4-1BB/CD137, activating NK cell receptors, an Immunoglobulin protein, B7-H3, BAFFR, BFAME (SEAMF8), BTEA, CD100 (SEMA4D), CD103, CD160 (BY55), CD 18, CD 19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYR03 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta Q. The 4-1BB, CD28, CD3 zeta, or any of these may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

In some embodiments, a costimulatory domain comprises the amino acid sequence of SEQ ID NO: 318 or 320.

Intracellular Signaling Domain

The intracellular (signaling) domain of the engineered T cells disclosed herein may provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domains include (e.g., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD1 Id, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, IT GAD, ITGAE, ITGAL, IT GAM, ITGAX, ITGB2, ITGB7, ITGB1, KIRDS2, LAT, LFA-1, LFA-1, ligand that specifically binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta. In some embodiments, the activating domain comprises an amino acid sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of SEQ ID NO: 319.

9. Production of Polynucleotides

The vectors provided herein can be made using standard techniques of molecular biology. For example, the various elements of the vectors provided herein can be obtained using recombinant methods, such as by screening cDNA and genomic libraries from cells, or by deriving the polynucleotides from a vector known to include the same.

The various elements of the vectors provided herein can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223: 1299; and Jay et al., J. Biol. Chem. (1984) 259:631 1.

Thus, particular nucleotide sequences can be obtained from vectors harboring the desired sequences or synthesized completely, or in part, using various oligonucleotide synthesis techniques known in the art, such as site-directed mutagenesis and polymerase chain reaction (PCR) techniques where appropriate. One method of obtaining nucleotide sequences encoding the desired vector elements is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239: 1534-1536), and enzymatic filling-in of gapped oligonucleotides using T4 DNA polymerase (Queen et al., Proc. Natl. Acad. Sci. USA (1989) 86: 10029-10033) can be used.

The precursor RNA provided herein can be generated by incubating a vector provided herein under conditions permissive of transcription of the precursor RNA encoded by the vector. For example, in some embodiments a precursor RNA is synthesized by incubating a vector provided herein that comprises an RNA polymerase promoter upstream of its 5' duplex forming region and/or expression sequence with a compatible RNA polymerase enzyme under conditions permissive of in vitro transcription. In some embodiments, the vector is incubated inside of a cell by a bacteriophage RNA polymerase or in the nucleus of a cell by host RNA polymerase II.

In certain embodiments, provided herein is a method of generating precursor RNA by performing in vitro transcription using a vector provided herein as a template (e.g., a vector provided herein with a RNA polymerase promoter positioned upstream of the 5' homology region).

In certain embodiments, the resulting precursor RNA can be used to generate circular RNA (e.g., a circular RNA polynucleotide provided herein) by incubating it in the presence of magnesium ions and guanosine nucleotide or nucleoside at a temperature at which RNA circularization occurs (e.g., between 20° C. and 60° C.).

Thus, in certain embodiments provided herein is a method of making circular RNA. In certain embodiments, the method comprises synthesizing precursor RNA by transcription (e.g., run-off transcription) using a vector provided herein (e.g., a vector comprising, in the following order, a 5' homology region, a 3' group I intron fragment, a first spacer, an Internal Ribosome Entry Site (IRES), an expression sequence, a second spacer, a 5' group I intron fragment, and a 3' homology region) as a template, and incubating the resulting precursor RNA in the presence of divalent cations (e.g., magnesium ions) and GTP such that it circularizes to form circular RNA. In some embodiments, an inventive precursor RNA is capable of circularizing in the absence of magnesium ions and GTP and/or without the step of incubation with magnesium ions and GTP. In some embodiments, transcription is carried out in the presence of an excess of GMP.

In some embodiments, a composition comprising circular RNA has been purified. Circular RNA may be purified by any known method commonly used in the art, such as column chromatography, gel filtration chromatography, and size exclusion chromatography. In some embodiments, purification comprises one or more of the following steps: phosphatase treatment, HPLC size exclusion purification, and RNase R digestion. In some embodiments, purification comprises the following steps in order: RNase R digestion, phosphatase treatment, and HPLC size exclusion purification. In some embodiments, purification comprises reverse phase HPLC. In some embodiments, a purified composition contains less double stranded RNA, DNA splints, triphosphorylated RNA, phosphatase proteins, protein ligases, capping enzymes and/or nicked RNA than unpurified RNA. In some embodiments, a purified composition is less immunogenic than an unpurified composition. In some embodiments, immune cells exposed to a purified composition produce less IFN-β1, RIG-I, IL-2, IL-6, IFNγ, and/or TNFα than immune cells exposed to an unpurified composition.

10. Nanoparticles

In certain aspects, provided herein are pharmaceutical compositions comprising the circular RNA provided herein. In certain embodiments, such pharmaceutical compositions are formulated with nanoparticles to facilitate delivery.

In certain embodiments, the circular RNA provided herein may be delivered and/or targeted to a cell in a transfer vehicle, e.g., a nanoparticle, or a composition comprising a nanoparticle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a non-lipid polymeric core-shell nanoparticle, or a biodegradable nanoparticle. In some embodiments, the transfer vehicle comprises one or more cationic lipids, non-cationic lipids, ionizable lipids, PEG-modified lipids, polyglutamic acid lipids, Hyaluronic acid lipids, poly β-amino esters, poly beta amino peptides, or positively charged peptides.

In one embodiment, the transfer vehicle may be selected and/or prepared to optimize delivery of the circRNA to a target cell. For example, if the target cell is a hepatocyte the properties of the transfer vehicle (e.g., size, charge and/or pH) may be optimized to effectively deliver such transfer vehicle to the target cell, reduce immune clearance and/or promote retention in that target cell. Alternatively, if the target cell is the central nervous system (e.g., circRNA administered for the treatment of neurodegenerative diseases may specifically target brain or spinal tissue), selection and preparation of the transfer vehicle must consider penetration of; and retention within the blood brain barrier and/or the use of alternate means of directly delivering such transfer vehicle to such target cell. In one embodiment, the compositions of the present invention may be combined with agents that facilitate the transfer of exogenous circRNA (e.g., agents which disrupt or improve the permeability of the blood brain barrier and thereby enhance the transfer of exogenous circRNA to the target cells).

The use of transfer vehicles to facilitate the delivery of nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqueous space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a transfer vehicle typically serves to transport the circRNA to the target cell. For the purposes of the present invention, the transfer vehicles are prepared to contain the desired nucleic acids. The process of incorporation of a desired entity (e.g., a nucleic acid) into a liposome is often referred to as loading (Lasic, et al., FEBS Lett., 312: 255-258, 1992). The liposome-incorporated nucleic acids may be completely or partially located in the interior space of the liposome, within the bilayer membrane of the liposome, or associated with the exterior surface of the liposome membrane. The purpose of incorporating a circRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in an embodiment of the present invention, the selected transfer vehicle is capable of enhancing the stability of the circRNA contained therein. The liposome can allow the encapsulated circRNA to reach the target cell and/or may allow the encapsulated circRNA to reach the target cell, or alternatively limit the delivery of such circRNA to other sites or cells where the presence of the administered circRNA may be useless or undesirable. Furthermore, incorporating the circRNA into a transfer vehicle, such as for example, a cationic liposome, also facilitates the delivery of such circRNA into a target cell.

Ideally, transfer vehicles are prepared to encapsulate one or more desired circRNA such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N J. Caplen, et al., Gene Ther. 1995; 2: 603; S. Li, et al., Gene Ther. 1997; 4, 891.)

In an embodiment of the present invention, the transfer vehicle is formulated as a lipid nanoparticle. In an embodiment, the lipid nanoparticles are formulated to deliver one or more circRNA to one or more target cells. Examples of suitable lipids include the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In an embodiment, the transfer vehicle is formulated as a lipid as described in U.S. patent application Ser. No. 16/065,067, incorporated herein in its entirety. In one embodiment, the transfer vehicle is selected based upon its ability to facilitate the transfection of a circRNA to a target cell.

The invention contemplates the use of lipid nanoparticles as transfer vehicles comprising a cationic lipid to encapsulate and/or enhance the delivery of circRNA into the target cell that will act as a depot for protein production. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids for use in the compositions and methods of the invention include those described in international patent publication WO 2010/053572 and/or U.S. patent application Ser. No. 15/809,680, e.g., C12-200. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP," 1,2-Dioleoyl-3-Trimethylammonium-Propane or "DOTAP." Contemplated cationic lipids also include 1,2-distearyloxy-N,N-dimethyl-3-aminopropane or "DSDMA", 1,2-dioleyloxy-N,N-dimethyl-3-aminopropane or "DODMA," 1,2-dilinoleyloxy-N,N-dimethyl-3-aminopropane or "DLinDMA," 1,2-dilinolenyloxy-N,N-dimethyl-3-aminopropane or "DLenDMA," N-dioleyl-N,N-dimethylammonium chloride or "DODAC," N,N-distearyl-N,N-dimethylammonium bromide or "DDAB," N-(1,2-dimyristyloxyprop-3-yl)-N,N-dimethyl-N-hydroxyethyl ammonium bromide or "DMRIE," 3-dimethylamino-2-(cholest-5-en-3-beta-oxybutan-4-oxy)-1-(cis, cis-9,12-octadecadienoxy)propane or "CLinDMA," 2-[5'-(cholest-5-en-3-beta-oxy)-3'-oxapentoxy)-3-dimethyl-1-(cis,cis-9', 1-2'-octadecadienoxy)propane or "CpLinDMA," N,N-dimethyl-3,4-dioleyloxybenzylamine or "DMOBA," 1,2-N,N'-dioleylcarbamyl-3-dimethylaminopropane or "DOcarbDAP," 2,3-Dilinoleoyloxy-N,N-dimethylpropylamine or "DLinDAP," 1,2-N,N'-Dilinoleylcarbamyl-3-dimethylaminopropane or "DLincarbDAP," 1,2-Dilinoleoylcarbamyl-3-dimethylaminopropane or "DLinCDAP," 2,2-dilinoleyl-4-dimethylaminomethyl-[1,3]-dioxolane or "DLin-K-DMA," 2,2-dilinoleyl-4-dimethylaminoethyl[1,3]-dioxolane or "DLin-K-XTC2-DMA," and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, GL67, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, CA), LIPOFECTAMINE (DOSPA:DOPE) (Invitrogen), LIPOFECTAMINE2000. (Invitrogen), FUGENE (Promega, Madison, WI), TRANSFECTAM (DOGS) (Promega), and EFFECTENE (Qiagen, Valencia, CA).

Also contemplated are cationic lipids such as the dialkylamino-based, imidazole-based, and guanidinium-based lipids, such as those described in U.S. Pat. No. 10,413,618.

In other embodiments the compositions and methods described herein are directed to lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. 61/494,745, the entire teachings of which are incorporated herein by reference in their entirety.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or in combination with other lipids together which comprise the transfer vehicle (e.g., a lipid nanoparticle). Contemplated PEG-modified lipids include, but are not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the transfer vehicle.

The present invention also contemplates the use of non-cationic lipids including those described in U.S. patent application Ser. No. 15/809,680. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone or in combination with other excipients, for example, cationic lipids. When used in combination with a cationic lipid, the non-cationic lipid may comprise a molar ratio of 5% to about 90%, or about 10% to about 70% of the total lipid present in the transfer vehicle.

The transfer vehicle (e.g., a lipid nanoparticle) may be prepared by combining multiple lipid and/or polymer components. For example, a transfer vehicle may be prepared using C12-200, DOPE, cholesterol, DMG-PEG2K at a molar ratio of 40:30:25:5, or DODAP, DOPE, cholesterol, DMG-PEG2K at a molar ratio of 18:56:20:6, or HGT5000, DOPE, cholesterol, DMG-PEG2K at a molar ratio of 40:20:35:5, or HGT5001, DOPE, cholesterol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the circRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly. For example, in some embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

The transfer vehicles for use in the compositions of the invention can be prepared by various techniques which are presently known in the art. Multi-lamellar vesicles (MLV) may be prepared using conventional techniques, for example, by depositing a selected lipid on the inside wall of a suitable container or vessel, dissolving the lipid in an appropriate solvent, and then evaporating the solvent to leave a thin film on the inside of the vessel or by spray-drying. An aqueous phase may then be added to the vessel with a vortexing motion which results in the formation of MLVs. Uni-lamellar vesicles (ULV) can then be formed by homogenization, sonication or extrusion of the multi-lamellar vesicles. In addition, ULV can be formed by detergent removal techniques.

In certain embodiments of this invention, the compositions of the present invention comprise a transfer vehicle wherein the circRNA is associated on both the surface of the transfer vehicle and encapsulated within the same transfer vehicle. For example, during preparation of the compositions of the present invention, cationic transfer vehicles may associate with the circRNA through electrostatic interactions.

In certain embodiments, the compositions of the invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein circRNA (GFP circRNA), *Renilla* Luciferase circRNA and Firefly Luciferase circRNA.

In some embodiments, selection of the appropriate size of a transfer vehicle takes into consideration the site of the target cell or tissue and to some extent the application for which the liposome is being made. In some embodiments, it may be desirable to limit transfection of the circRNA to certain cells or tissues. For example, to target hepatocytes a transfer vehicle may be sized such that its dimensions are smaller than the fenestrations of the endothelial layer lining hepatic sinusoids in the liver. Accordingly, the appropriately-sized transfer vehicle can readily penetrate such endothelial fenestrations to reach the target hepatocytes. Alternatively, a transfer vehicle may be sized such that the dimensions of the liposome are of a sufficient diameter to limit or expressly avoid distribution into certain cells or tissues. For example, a transfer vehicle may be sized such that its dimensions are larger than the fenestrations of the endothelial layer lining hepatic sinusoids to thereby limit distribution of the transfer vehicle to hepatocytes. Generally, the size of the transfer vehicle is within the range of about 25 to 250 nm. In some embodiments, the size of the transfer vehicle is less than about 250 nm, 175 nm, 150 nm, 125 nm, 100 nm, 75 nm, 50 nm, 25 nm or 10 nm.

A variety of alternative methods known in the art are available for sizing of a population of transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-450 (1981), incorporated herein by reference. Average liposome diameter may be reduced by sonication of formed liposomes. Intermittent sonication cycles may be alternated with QELS assessment to guide efficient liposome synthesis.

Additionally, in certain embodiments, the circular RNA provided herein can be formulated using one or more liposomes, lipoplexes, or lipid nanoparticles. In one embodiment, the circular RNA may be formulated in a lipid nanoparticle such as those described in International Publication No. WO2012170930, herein incorporated by reference in its entirety. In one embodiment, the lipid may be a cleavable lipid such as those described in International Publication No. WO2012170889, herein incorporated by reference in its entirety. In one embodiment, the pharmaceutical compositions of the circular RNA may include at least one of the PEGylated lipids described in International Publication No. 2012099755, herein incorporated by reference. In one embodiment, a lipid nanoparticle formulation may be formulated by the methods described in International Publication Nos. WO2011127255 or WO2008103276, each of which is herein incorporated by reference in their entirety. A lipid nanoparticle may be coated or associated with a co-polymer such as, but not limited to, a block co-polymer, such as a branched polyether-polyamide block copolymer described in International Publication No. WO2013012476, herein incorporated by reference in its entirety. Liposomes, lipoplexes, or lipid nanoparticles may be used to improve the efficacy of circular RNA directed protein production as these formulations may be able to increase cell transfection by the circular RNA, increase the in vivo or in vitro half-life of the circular RNA, and/or allow for controlled release.

In embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit (e.g. in the case of a single-chain Fv antibody). In certain embodiments, separate circRNA molecules encoding the individual subunits may be administered in separate transfer vehicles.

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly, may provide a means to passively direct the delivery of the compositions to such target cells.

Alternatively, the present invention contemplates active targeting, which involves the use of targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagglutinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting moieties that have been conjugated to moieties present in the transfer vehicle (e.g., a lipid nanoparticle) therefore facilitate recognition and uptake of the compositions of the present invention in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, dendritic cell, or macrophage antigen. In some embodiments, the targeting moiety is capable of binding to a protein selected from the group CD3, CD4, CD8, PD-1, 4-1BB, CD5, CD7, C1q, and CD2. In some embodiments, the targeting moiety is an single chain Fv (scFv) fragment, nanobody, peptide, peptide-based macrocycle, minibody, heavy chain variable region, light chain variable region or fragment thereof. In some embodiments, the targeting moiety is selected from anti T-cell receptor motif antibodies, anti T-cell $\alpha$ chain antibodies, anti T-cell $\beta$ chain antibodies, anti T-cell $\gamma$ chain antibodies, anti T-cell $\delta$ chain antibodies, anti CCR7 antibodies, anti CD3 antibodies, anti CD4 antibodies, anti CD5 antibodies, anti CD7 antibodies, anti CD8 antibodies, anti CD11b antibodies, anti CD11c antibodies, anti CD16 antibodies, anti CD19 antibodies, anti CD20 antibodies, anti CD21 antibodies, anti CD22 antibodies, anti CD25 antibodies, anti CD28 antibodies, anti CD34 antibodies, anti CD35 antibodies, anti CD40 antibodies, anti CD45RA antibodies, anti CD45RO antibodies, anti CD52 antibodies, anti CD56 antibodies, anti CD62L antibodies, anti CD68 antibodies, anti CD80 antibodies, anti CD95 antibodies, anti CD117 antibodies, anti CD127 antibodies, anti CD133 antibodies, anti CD137 (4-1BB) antibodies, anti CD163 antibodies, anti C1q antibodies, anti F4/80 antibodies, anti IL-4Ra antibodies, anti Sca-1 antibodies, anti CTLA-4 antibodies, anti GITR antibodies anti GARP antibodies, anti LAP antibodies, anti granzyme B antibodies, anti LFA-1 antibodies, anti transferrin receptor antibodies, and fragments thereof.

In some embodiments, circular RNA is formulated according to a process described in U.S. patent application Ser. No. 15/809,680. In some embodiments, the present invention provides a process of encapsulating circular RNA in lipid nanoparticles comprising the steps of forming lipids into pre-formed lipid nanoparticles (i.e., formed in the absence of RNA) and then combining the pre-formed lipid nanoparticles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA). In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e., heating the separate components) as heating post-formulation (post-formation of nanoparticles) does not increase the encapsulation efficiency of the RNA in the lipid nanoparticles. In contrast, in some embodiments of the processes of the present invention, the order of heating of RNA does not appear to affect the RNA encapsulation percentage. In some embodiments, no heating (i.e. maintaining at ambient temperature) of one or more of the solution comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, ammonium sulfate, Tris, sodium bicarbonate, sodium citrate, sodium acetate, potassium phosphate or sodium phosphate. In some embodiments, a suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare an RNA solution suitable for the present invention. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present invention, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e. 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

Any desired lipids may be mixed at any ratios suitable for encapsulating RNAs. In some embodiments, a suitable lipid solution contains a mixture of desired lipids including cationic lipids, helper lipids (e.g., non cationic lipids and/or cholesterol lipids) and/or PEGylated lipids. In some embodiments, a suitable lipid solution contains a mixture of desired lipids including one or more cationic lipids, one or more helper lipids (e.g., non cationic lipids and/or cholesterol lipids) and one or more PEGylated lipids.

11. Target Cells

In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, dendritic cells, macrophages, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver to facilitate the delivery and the subsequent expression of the circRNA comprised therein by the cells of the liver (e.g., hepatocytes). The targeted cells may function as a biological "reservoir" or "depot" capable of producing, and systemically excreting a functional protein or enzyme. Accordingly, in one embodiment of the invention the transfer vehicle may target hepatocytes and/or preferentially distribute to the cells of the liver upon delivery. In an embodiment, following transfection of the target hepatocytes, the circRNA loaded in the vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes. In an embodiment of the present invention, the transfer vehicles comprise circRNA which encode a deficient protein or enzyme. Upon distribution of such compositions to the target tissues and the subsequent transfection of such target cells, the exogenous circRNA loaded into the transfer vehicle (e.g., a lipid nanoparticle) may be translated in vivo to produce a functional protein or enzyme encoded by the exogenously administered circRNA (e.g., a protein or enzyme in which the subject is deficient). Accordingly, the compositions of the present invention exploit a subject's ability to translate exogenously- or recombinantly-prepared circRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of circRNA encoding a deficient protein or enzyme avoids the need to deliver the nucleic acids to specific organelles within a target cell. Rather, upon transfection of a target cell and delivery of the nucleic acids to the cytoplasm of the target cell, the circRNA contents of a transfer vehicle may be translated and a functional protein or enzyme expressed.

In some embodiments, a circular RNA comprises one or more miRNA binding sites. In some embodiments, a circular RNA comprises one or more miRNA binding sites recognized by miRNA present in one or more non-target cells or non-target cell types (e.g., Kupffer cells) and not present in one or more target cells or target cell types (e.g., hepatocytes). In some embodiments, a circular RNA comprises one or more miRNA binding sites recognized by miRNA present in an increased concentration in one or more non-target cells or non-target cell types (e.g., Kupffer cells) compared to one or more target cells or target cell types (e.g., hepatocytes). miRNAs are thought to function by pairing with complementary sequences within RNA molecules, resulting in gene silencing.

12. Pharmaceutical Compositions

In certain embodiments, provided herein are compositions (e.g. pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab, chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises a cell provided herein or populations thereof.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions provided herein.

In certain embodiments, the pharmaceutical composition comprises a preservative. In certain embodiments, suitable preservatives may include, for example, methylparaben, propylparaben, sodium benzoate, and benzalkonium chloride. Optionally, a mixture of two or more preservatives may be used. The preservative or mixtures thereof are typically present in an amount of about 0.0001% to about 2% by weight of the total composition.

In some embodiments, the pharmaceutical composition comprises a buffering agent. In some embodiments, suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

The following formulations for oral, aerosol, parenteral (e.g., subcutaneous, intravenous, intraarterial, intramuscular, intradermal, intraperitoneal, and intrathecal), and topical administration are merely exemplary and are in no way limiting. More than one route can be used to administer the therapeutic agents provided herein, and in certain instances, a particular route can provide a more immediate and more effective response than another route.

Formulations suitable for oral administration can comprise or consist of (a) liquid solutions, such as an effective amount of the therapeutic agent dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent with a flavorant, usually sucrose, acacia or tragacanth. Pastilles can comprise the therapeutic agent with an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In some embodiments, the therapeutic agents provided herein can be administered in a physiologically acceptable diluent in a pharmaceutical carrier, such as a sterile liquid or mixture of liquids including water, saline, aqueous dextrose and related sugar solutions, an alcohol such as ethanol or hexadecyl alcohol, a glycol such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutical adjuvants.

Oils, which can be used in parenteral formulations in some embodiments, include petroleum, animal oils, vegetable oils, or synthetic oils. Specific examples of oils include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in certain embodiments of parenteral formulations include fatty alkali metal, ammonium, and triethanolamine salts, and suitable detergents include (a) cationic detergents such as, for example, dimethyl dialkyl ammonium halides. and alkyl pyridinium halides, (b) anionic detergents such as, for example, alkyl, aryl, and olefin sulfonates, alky, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In some embodiments, the parenteral formulations will contain, for example, from about 0.5% to about 25% by weight of the therapeutic agent in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol, sorbitan fatty acid esters such as sorbitan monooleate, and high molecular weight adducts of ethylene oxide with a hydrophobic base formed by the condensation of propylene oxide with propylene glycol. The parenteral formulations can be presented in unit-dose or multi-dose sealed containers, such as ampoules or vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In certain embodiments, injectable formulations are provided herein. The requirements for effective pharmaceutical carriers for injectable compositions are well-known to those of ordinary skill in the art (see, e.g., Pharmaceutics and Pharmacy Practice, J.B. Lippincott Company, Philadelphia, PA, Banker and Chalmers, eds., pages 238-250 (1982), and ASHP Handbook on Injectable Drugs, Toissel, 4th ed, pages 622-630 (1986)).

In some embodiments, topical formulations are provided herein. Topical formulations, including those that are useful for transdermal drug release, are suitable in the context of certain embodiments provided herein for application to skin. In some embodiments, the therapeutic agent alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

In certain embodiments, the therapeutic agents provided herein can be formulated as inclusion complexes, such as cyclodextrin inclusion complexes, or liposomes. Liposomes can serve to target the therapeutic agents to a particular tissue. Liposomes also can be used to increase the half-life of the therapeutic agents. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

In some embodiments, the therapeutic agents provided herein are formulated in time-released, delayed release, or sustained release delivery systems such that the delivery of the composition occurs prior to, and with sufficient time to cause, sensitization of the site to be treated. Such systems can avoid repeated administrations of the therapeutic agent, thereby increasing convenience to the subject and the physician, and may be particularly suitable for certain composition embodiments provided herein. In one embodiment, the compositions of the invention are formulated such that they are suitable for extended-release of the circRNA contained therein. Such extended-release compositions may be conveniently administered to a subject at extended dosing intervals. For example, in one embodiment, the compositions of the present invention are administered to a subject twice a day, daily or every other day. In an embodiment, the compositions of the present invention are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments the polypeptide is expressed at least at a therapeutic level for more than one, more than four, more than six, more than 12, more than 24, more than 48, or more than 72 hours after administration. In some embodiments, the polypeptide is detectable at a therapeutic level in patient serum or tissue (e.g., liver or lung). In some embodiments, the level of detectable polypeptide is from continuous expression from the circRNA composition over periods of time of more than one, more than four, more than six, more than 12, more than 24, more than 48, or more than 72 hours after administration.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments, the control can be the normal level of the relevant protein or polypeptide in the individual to whom the composition is administered. In other embodiments, the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of secreted protein may be observed in the serum and/or in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems: wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

In some embodiments, the therapeutic agent can be conjugated either directly or indirectly through a linking moiety to a targeting moiety. Methods for conjugating therapeutic agents to targeting moieties is known in the art. See, for instance, Wadwa et al., J, Drug Targeting 3:111 (1995) and U.S. Pat. No. 5,087,616.

In some embodiments, the therapeutic agents provided herein are formulated into a depot form, such that the manner in which the therapeutic agent is released into the body to which it is administered is controlled with respect to time and location within the body (see, for example, U.S. Pat. No. 4,450,150). Depot forms of therapeutic agents can be, for example, an implantable composition comprising the therapeutic agents and a porous or non-porous material, such as a polymer, wherein the therapeutic agents are encapsulated by or diffused throughout the material and/or degradation of the non-porous material. The depot is then implanted into the desired location within the body and the therapeutic agents are released from the implant at a predetermined rate.

13. Therapeutic Methods

In certain aspects, provided herein is a method of treating and/or preventing a condition, e.g., cancer, comprising introducing pharmaceutical composition provided herein into a subject in need thereof (e.g., a subject with cancer). In some embodiments, the pharmaceutical composition comprises a circular RNA polynucleotide provided herein. In some embodiments, the pharmaceutical composition comprises a vector provided herein. In some embodiments, the pharmaceutical composition comprises a cell (e.g., human cell, such as a human T cell) comprising a polynucleotide provided herein (e.g., a circular RNA or a vector provided herein).

Thus, in certain embodiments, provided herein are methods of treating and/or preventing a disease in a subject (e.g., mammalian subject, such as a human subject). Without being bound to a particular theory or mechanism, the CARs and TCR complex proteins have biological activity, e.g., ability to recognize an antigen, e.g., CD19, such that the CAR or TCR, when expressed by a cell, is able to mediate an immune response against the cell expressing the antigen, e.g., CD19, for which the CAR or TCR is specific. In this regard, an embodiment provided herein provides a method of treating or preventing cancer in a mammal, comprising administering to the mammal the therapeutic agents thereof, and/or the pharmaceutical compositions provided herein in an amount effective to treat or prevent cancer in the mammal.

In certain embodiments, the therapeutic agents provided herein are coadministered with one or more additional therapeutic agents (e.g., in the same pharmaceutical composition or in separate pharmaceutical compositions). In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously. In some embodiments, the additional therapeutic agent that can be co-administered with the therapeutic agents provided herein is a T cell active cytokine, such as IL-2, IL-7, IL-15 and/or IL-21.

In certain embodiments, the therapeutic agent is a cell or population of cells comprising a circular RNA or a vector provided herein that expresses a CAR or TCR complex protein encoded by the circular RNA or vector. In some embodiments, the administered cells are allogeneic to the subject being treated. In some embodiments, the administered cells are autologous to the subject being treated.

In certain embodiments, the methods further comprise lymphodepleting the subject prior to administering the therapeutic agent. Examples of lymphodepletion include, but may not be limited to, nonmyeloablative lymphodepleting chemotherapy, myeloablative lymphodepleting chemotherapy, total body irradiation, etc.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

14. Sequences

Table 3

Exemplary IRES sequences.

| SEQ ID NO: | IRES | Sequence |
|---|---|---|
| 1 | EMCV-A | cccccctctccctcccccccctaacgttact<br>ggccgaagccgcttggaataaggccggtgt<br>gcgtttgtctatatgttattttccaccata<br>ttgccgtcttttggcaatgtgagggcccgg<br>aaacctggccctgtcttcttgacgagcatt<br>cctaggggtctttcccctctcgccaaagga<br>atgcaaggtctgttgaatgtcgtgaaggaa<br>gcagttcctctggaagcttcttgaagacaa<br>acaacgtctgtagcgaccctttgcaggcag<br>cggaaccccccacctggcgacaggtgcctc<br>tgcggccaaaagccacgtgtataagataca<br>cctgcaaaggcggcacaaccccagtgccac<br>gttgtgagttggatagttgtggaaagagtc<br>aaatggctctcctcaagcgtattcaacaag<br>gggctgaaggatgcccagaaggtaccccat<br>tgtatgggatctgatctggggcctcggtgc<br>acatgctttacatgtgtttagtcgaggtta<br>aaaaacgtctaggccccccgaaccacgggg<br>acgtggttttcctttgaaaaacacgatgat<br>aatatggccacaacc |
| 2 | EMCV-B | ctcccccctcccccccccttactatactggcc<br>gaagccacttggaataaggccggtgtgcgt<br>ttgtctacatgctattttctaccgcattac<br>cgtcttatggtaatgtgagggtccagaacc<br>tgaccctgtcttcttgacgaacactcctag<br>gggtctttcccctctcgacaaaggagtgta<br>aggtctgttgaatgtcgtgaaggaagcagt<br>tcctctggaagcttcttaaagacaaacaac<br>gtctgtagcgaccctttgcaggcagcggaa<br>ccccccacctggtgacaggtgcctctgcgg<br>ccaaaagccacgtgtataagatacacctgc<br>aaaggcggcacaaccccagtgccacgttgt<br>gagttggatagttgtggaaagagtcaaatg<br>gctctcctcaagcgtattcaacaaggggct<br>gaaggatgcccagaaggtaccccattgtat<br>gggatctgatctggggcctcggtgcacgtg<br>ctttacacgtgttgagtcgaggtgaaaaaa<br>cgtctaggccccccgaaccacggggacgtg<br>gttttcctttgaaaccacgattacaat |
| 3 | EMCV-Bf | ttgccagtctgctcgatatcgcaggctggg<br>tccgtgactacccactcccccttcaacgt<br>gaaggctacgatagtgccagggcgggtact<br>gccgtaagtgccaccccaaacaacaacaac<br>aaaacaaactcccccctcccccccccttacta<br>tactggccgaagccacttggaataaggccg<br>gtgtgcgtttgtctacatgctattttctac<br>cgcattaccgtcttatggtaatgtgagggt<br>ccagaacctgaccctgtcttcttgacgaac<br>actcctaggggtctttcccctctcgacaaa<br>ggagtgtaaggtctgttgaatgtcgtgaag<br>gaagcagttcctctggaagcttcttaaaga<br>caaacaacgtctgtagcgaccctttgcagg<br>cagcggaaccccccacctggtgacaggtgc<br>ctctgcggccaaaagccacgtgtataagat<br>acacctgcaaaggcggcacaaccccagtgc<br>cacgttgtgagttggatagttgtggaaaga<br>gtcaaatggctctcctcaagcgtattcaac<br>aaggggctgaaggatgcccagaaggtaccc<br>cattgtatgggatctgatctggggcctcgg<br>tgcacgtgctttacacgtgttgagtcgagg<br>tgaaaaaacgtctaggccccccgaaccacg<br>gggacgtggttttcctttgaaaaccacgat<br>tacaat |
| 4 | EMCV-Cf | ttgccagtctgctcgatatcgcaggctggg<br>tccgtgactacccactcccccttcaacgt<br>gaaggctacgatagtgccagggcgggtact<br>gccgtaagtgccaccccaaaacaacaacaa<br>cccccccctctccctccTcccccccctaacgt<br>tactggccgaagccgcttggaataaggccg<br>gtgtgcgtttgtctatatgttattttccac<br>catattgccgtcttttggcaatgtgagggc<br>ccggaaacctggccctgtcttcttgacgag<br>cattcctaggggtctttcccctctcgccaa<br>aggaatgcaaggtctgttgaatgtcgtgaa<br>ggaagcagttcctctggaagcttcttgaag<br>acaaacaacgtctgtagcgaccctttgcag<br>gcagcggaaccccccacctggcgacaggtg<br>cctctgcggccaaaagccacgtgtataaga<br>tacacctgcaaaggcggcacaaccccagtg<br>ccacgttgtgagttggatagttgtggaaag<br>agtcaaatggctctcctcaagcgtattcaa<br>caaggggctgaaggatgcccagaaggtacc<br>ccattgtatgggatctgatctggggcctcg<br>gtgcacatgctttacatgtgtttagtcgag<br>gttaaaaaacgtctaggccccccgaaccac<br>ggggacgtggttttcctttgaaaaacacga<br>tgataat |
| 5 | EMCV pEC9 | cccccccccctaacgttactggccgaagccg<br>cttggaataaggccggtgtgcgtttgtcta<br>tatgttattttccaccatattgccgtcttt<br>tggcaatgtgagggcccggaaacctggccc<br>tgtcttcttgacgagcattcctaggggtct<br>ttcccctctcgccaaaggaatgcaaggtct<br>gttgaatgtcgtgaaggaagcagttcctct |

Table 3-continued

Exemplary IRES sequences.

| SEQ ID NO: | IRES | Sequence |
|---|---|---|
| | | ggaagcttcttgaagacaaacaacgtctgt<br>agcgaccctttgcaggcagcggaacccccc<br>acctggcgacaggtgcctctgcggccaaaa<br>gccacgtgtataagatacacctgcaaaggc<br>ggcacaaccccagtgccacgttgtgagttg<br>gatagttgtggaaagagtcaaatggctctc<br>ctcaagcgtattcaacaaggggctgaagga<br>tgcccagaaggtaccccattgtatgggatc<br>tgatctggggcctcggtgcacatgctttac<br>atgtgtttagtcgaggttaaaaaacgtcta<br>ggccccccgaaccacggggacgtggttttc<br>ctttgaaaaacacgatgataat |
| 6 | Picobirna-virus | gtaaattaaatgctatttacaaaatttaaa<br>cagaaaggagagatgttatgaaccggtttt<br>acaaggtttcatacatcgaaaatagcacta<br>cctggggcagccgacacactaacatcgtct<br>gtttaaccagaagtgttactgaaaggaggt<br>tattta |
| 7 | HCV QC64 | acctgcccctaataggggcgacactccgcc<br>atgaatcactcccctgtgaggaactactgt<br>cttcacgcagaaagcgtctagccatggcgt<br>tagtatgagtgtcgtacagcctccaggccc<br>ccccctcccgggagagccatagtggtctgc<br>ggaaccggtgagtacaccggaattgccggg<br>aagactgggtcctttcttggataaacccac<br>tctatgcccggacatttgggcgtgcccccg<br>caagactgctagccgagtagcgttgggttg<br>cgaaaggccttgtggtactgcctgataggg<br>tgcttgcgagtgccccgggaggtctcgtag<br>accgtgcatc |
| 8 | Human Cosavirus E/D | ctacaagctttgtgtaaacaaacttttgtt<br>tggcttttctcaagcttctctcacatcagg<br>ccccaaagatgtcctgaaggtaccccgtgt<br>atctgaggatgagcaccatcgactacccgg<br>acctgcaaaattttgcaaacgcatgtggta<br>tcccagcccctcctctcggggaggggggct<br>ttgctcactcagcacaggatctgatcagga<br>gatccacctccggtgctttacaccggggcg<br>tggatttaaaaattgcccaaggcctggcgc<br>acaacctaggggactaggttttccttatat<br>tttaaagctgtcaat |
| 9 | Human Cosavirus F | gtcttaggacgacgcatgtggtatcccagc<br>ccccgcctacattggcgggggcttttgaag<br>caccagacactggatctgatcaggaggagg<br>gtagctgctttacagcccctcttaaaaatt<br>gcccaaggtccggccacccaacctagggga<br>ctaggttttccttttatttttaaattgtca<br>tt |
| 10 | Human Cosavirus JMY | acatgggggagactgcatgtggcagtcttg<br>aaacgtgtggtttgacgtctaccttatatg<br>gcagtgggtggagtactgcaaagatgtcac<br>cgtgctttacacggtttttgaaccccacac<br>cggctgtttgacgctcgtagggcagcaggt<br>ttattttcattaaaattcttactttctagc<br>tgcatgagttctattcatgcagacggagtg<br>atactcccgttccttcttggacaggttgcc<br>tccacgccctttgtggatcttaaggtgacc<br>aagtcactggtgttggaggtgaagatagag<br>agtcctcttgggaatgtcatgtggctgtgc<br>caggggttgtagcgatgccattcgtgtgtg<br>cggatttcctctcgtggtgacacgagcctc<br>acaggccaaaagccccgtccgaaaggaccc<br>gaatggtggagtgaccctgactccccccctg<br>catagttttgtgattaggaacttgaggaat<br>ttctgtcataaatctctatcacatcaggcc<br>ccaaagatgtcctgaaggtaccctgtgtat<br>ctgaggatgagcaccaccgactacccggac<br>ttgcattagcagacacatgtggttgcccag<br>ccccacctcttcagaggtggggctttgctc<br>actcagcacaggatctgatcaggagccccg<br>ctcgtgtgctttacactcgacgcggggtta<br>aaaattgcccaaggcctggcacaacaacct<br>aggggactaggttttcctatttttgtaaat<br>tatgtcaat |
| 11 | Rhinovirus NAT001 | gtgacaatcagccagattgttaacggtcaa<br>gcacttctgtttccccggtacccttgtata<br>cgcttcacccgaggcgaaaagtgaggttat<br>cgttatccgcaaagtgcctacgagaagcct<br>agtagcacttttgaagcctatggctggtcg<br>ctcaactgtttacccagcagtagacctggc<br>agatgaggctagatgttccccaccagcgat<br>ggtgatctagcctgcgtggctgcctgcaca<br>ctctattgagtgtgaagccagaaagtggac<br>aaggtgtgaagagcctattgtgctcacttt<br>gagtcctccggcccctgaatgtggctaatc<br>ctaaccccgtagctgttgcatgtaatccaa<br>catgtctgcagtcgtaatgggcaactatgg<br>gatggaaccaactactttgggtgtccgtgt<br>ttcttgtttttctttatgcttgcttatggt<br>gacaactgtagttattacatttgttacc |
| 12 | HRV14 | ttaaaacagcggatgggtatcccaccattc<br>gacccattgggtgtagtactctggtactat<br>gtacctttgtacgcctgtttctccccaacc<br>acccttccttaaaattcccacccatgaaac<br>gttagaagcttgacattaaagtacaatagg<br>tggcgccatatccaatggtgtctatgtaca<br>agcacttctgtttcccaggagcgaggtata<br>ggctgtacccactgccaaaagcctttaacc<br>gttatccgccaaccaactacgtaacagtta<br>gtaccatcttgttcttgactggacgttcga<br>tcaggtggattttccctccactagtttggt<br>cgatgaggctaggaattccccacgggtgac<br>cgtgtcctagcctgcgtggcggccaaccca<br>gcttatgctgggacgccctttttaaggacat<br>ggtgtgaagactcgcatgtgcttggttgtg<br>agtcctccggcccctgaatgcggctaacct<br>taaccctagagccttatgccacgatccagt<br>ggttgtaaggtcgtaatgagcaattccggg<br>acgggaccgactactttgggtgtccgtgtt<br>tctcatttttcttcatattgtcttatggtc<br>acagcatatatatacatatactgtgatc |
| 13 | HRV89 | ttaaaactgggagtgggttgttcccactca<br>ctccacccatgcggtgttgtactctgttat<br>tacggtaactttgtacgccagtttttccca<br>cccttccccataatgtaacttagaagtttg<br>tacaatatgaccaataggtgacaatcatcc<br>agactgtcaaaggtcaagcacttctgtttc<br>cccggtcaatgaggatatgctttacccaag<br>gcaaaaaccttagagatcgttatccccaca<br>ctgcctacacagagcccagtaccattttttg<br>atataattgggttggtcgctccctgcaaac<br>ccagcagtagacctggcagatgaggctgga<br>cattccccactggcgacagtggtccagcct<br>gcgtggctgcctgctcacccttcttgggtg<br>agaagcctaattattgacaaggtgtgaaga<br>gccgcgtgtgctcagtgtgcttcctccggc<br>ccctgaatgtggctaaccttaaccctgcag<br>ccgttgcccataatccaatgggtttgcggt<br>cgtaatgcgtaagtgcgggatgggaccaac<br>tactttgggtgtccgtgtttcctgtttttc<br>ttttgattgcattttatggtgacaatttat<br>agtgtatagattgtcatc |
| 14 | HRVC-02 | ttaaaactgggtacaggttgttcccacctg<br>tatcacccacgtggtgtggtgctcttgtat<br>tccggtacacttgcacgccagtttgccacc<br>cctcacccgtcgtaacttagaagctaacaa<br>ctcgaccaacaggcggtggtaaaccatacc<br>acttacggtcaagcactcctgtttccccgg<br>tatgcgaggaatagactcctacagggttga |

Table 3-continued

Exemplary IRES sequences.

| SEQ ID NO: | IRES | Sequence |
|---|---|---|
| | | agcctcaagtatcgttatccgcattggtac<br>tacgcaaagcttagtagtgccttgaaagtc<br>ccttggttggtcgctccgctagtttcccct<br>agtagacctggcagatgaggcaggacactc<br>cccactggcgacagtggtcctgcctgcgtg<br>gctgcctgcgcacccttaggggtgcgaagc<br>caagtgacagacaaggtgtgaagagccccg<br>tgtgctaccaatgagtcctccggcccctga<br>atgcggctaatccaaccccacagctattgc<br>acacaagccagtgtgtatgtagtcgtaatg<br>agcaattgtgggacggaaccgactactttg<br>ggtgtccgtgtttccttttattcttatcat<br>tctgcttatggtgacaatactgtgaaatag<br>tgttgttacc |
| 15 | HRV-A21 | taaaactggatccaggttgttcccacctgg<br>atctcctattgggagttgtactctattatt<br>ccggtaattttgtacgccagttttatcttc<br>cccctccccaattgtaacttagaaggttat<br>caatacgaccaataggtggtagttagccaa<br>actaccaaaggtcaagcacttctgtttccc<br>cggtcaaagttgatatgctccaacagggca<br>aaaacaactgagatcgttatccgcaaagtg<br>cctacgcaaagcctagtaacacctttgaag<br>atttatggttggtcgttccgctatttccca<br>tagtagacctggcagatgaggctagaaatc<br>ccccactggcgacagtgctctagcctgcgt<br>ggctgcctgcgcaccccttgggtgcgaagc<br>catacattggacaaggtgtgaagagccccg<br>tgtgctcactttgagtcctccggcccctga<br>atgtggctaaccttaaccctgcagctagtg<br>catgtaatccaacatgttgctagtcgtaat<br>gagtaattgcgggacgggaccaactacttt<br>gggtgtccgtgtttcactttttccttttaa<br>tattgcttatggtgacaatatatatagcta<br>tatatattgacacc |
| 16 | Salivirus A SH1 | ttcccctgcaaccattacgcttactcgcat<br>gtgcattgagtggtgcatgtgttgaacaaa<br>cagctacactcacatgggggcgggttttcc<br>cgccctacggcttctcgcgaggcccacccc<br>tcccctttctcccataactacagtgctttg<br>gtaggtaagcatcctgatcccccgcggaag<br>ctgctcacgtggcaactgtggggacccaga<br>caggttatcaaaggcacccggtctttccgc<br>cttcaggagtatccctgctagcgaattcta<br>gtagggctctgcttggtgccaacctccccc<br>aaatgcgcgctgcgggagtgctcttcccca<br>actcaccctagtatcctctcatgtgtgtgc<br>ttggtcagcatatctgagacgatgttccgc<br>tgtcccagaccagtccagtaatggacgggc<br>cagtgtgcgtagtcgtcttccggcttgtcc<br>ggcgcatgtttggtgaaccggtggggtaag<br>gttggtgtgcccaacgcccgtactcagggg<br>atacctcaaggcacccaggaatgccaggga<br>ggtaccccgcttcacagcgggatctgaccc<br>tggggtaaatgtctgcgggggtcttcttg<br>gcccacttctcagtacttttcagg |
| 17 | Salivirus FHB | acatgggggtctgcggacggcttcggccc<br>acccgcgacaagaatgccgtcatctgtcct<br>cattacccgtattccttcccttcccccgca<br>accaccacgcttactcgcgcacgtgttgag<br>tggcacgtgcgttgtccaaacagctacacc<br>cacacccttcggggcgggtttgtcccgccc<br>tcgggttcctcgcggaacccccccctccct<br>ctctctctttctatccgccctcacttccca<br>taactacagtgctttggtaggtgagcaccc<br>tgacccccccgcggaagctgctaacgtggca<br>actgtggggatccaggcaggttatcaaagg<br>cacccggtctttccgccttcaggagtatct<br>ctgccggtgaattccggtagggctctgctt<br>ggtgccaacctcccccaaatgcgcgctgcg<br>ggagtgctcttccccaactcatcttagtaa |
| | | cctctcatgtgtgtgcttggtcagcatatc<br>tgaggcgacgttccgctgtcccagaccagt<br>ccagcaatggacgggccagtgtgcgtagtc<br>gctttccggttttccggcgcatgtttggcg<br>aaacgctgaggtaaggttggtgtgcccaac<br>gcccgtaatttggtgatacctcaagaccac<br>ccaggaatgccagggaggtaccccacttcg<br>gtgggatctgaccctgggctaattgtctac<br>ggtggttcttcttgcttccacttctctttt<br>ttctggcatg |
| 18 | Salivirus NG-J1 | tatggcaggcgggcttgtggacggcttcgg<br>cccacccacagcaagaatgccatcatctgt<br>cctcacccccaatttcccttttcttcccc<br>tgcaaccattacgcttactcgcatgtgcat<br>tgagtggtgcatgtgttgaacaaacagcta<br>cactcacatgggggcgggttttcccgccct<br>acggcctctcgcgaggcccaccccttccct<br>ccccttataactacagtgctttggtaggta<br>agcatcctgatcccccgcggaagctgctca<br>cgtggcaactgtggggacccagacaggtta<br>tcaaaggcacccggtctttccgccttcagg<br>agtatccctactagtgaattctagcggggc<br>tctgcttggtgccaacctcccccaaatgcg<br>cgctgcgggagtgctcttccccaactcacc<br>ctagtatcctctcatgtgtgtgcttggtca<br>gcatatctgagacgatgttccgctgtccca<br>gaccagtccagtaatggacgggccagtgcg<br>tgtagtcgtcttccggcttgtccggggcat<br>gtttggtgaaccggtggggtaaggttggtg<br>tgcccaacgcccgtactttggtgacacctc<br>aagaccacccaggaatgccagggaggtacc<br>ccacctcacggtgggatctgaccctgggct<br>aattgtctacggtggttcttcttgcttcca<br>cttctttcttctgttcacg |
| 19 | Human Parecho-virus 1 | tttgaaaggggtctcctagagagcttggcc<br>gtcgggccttataccccgacttgctgagtt<br>tctctaggagagcccttttcccagccctga<br>ggcggctggtcaataaaagcctcaaacgta<br>actaacacctaagaagatcatgtaaaccct<br>atgcctggtctccactattcgaaggcaact<br>tgcaataagaagagtgggatcaagacgctt<br>aaagcatagagacagttttcttttctaacc<br>cacatttgtgtggggtggcagatggcgtgc<br>cataactctaatagtgagataccacgcttg<br>tggaccttatgctcacacagccatcctcta<br>gtaagtttgtgagacgtctggtgacgtgtg<br>ggaacttattggaaacaacattttgctgca<br>aagcatcctactgccagcggaaaaacacct<br>ggtaacaggtgcctctggggccaaaagcca<br>aggtttaacagaccctttaggattggttct<br>aaacctgagatgttgtggaagatatttagt<br>acctgctgatctggtagttatgcaaacact<br>agttgtaaggcccatgaaggatgcccagaa<br>ggtacccgtaggtaacaagtgacactatgg<br>atctgatttggggccagatacctctatctt<br>ggtgatctggttaaaaaacatctaatgggc<br>caaacccgggggggatccccggtttcctct<br>tattctatcaatgccact |
| 20 | Crohivirus B | gtataagagacaggtgtttgccttgtcttc<br>ggactggcatcttgggaccaacccccctttt<br>tccccagccatgggttaaatggcaataaag<br>gacgtaacaactttgtaaccattaagcttt<br>gtaattttgtaaccactaagctttgtgcac<br>ataatgtaaccatcaagcttgttagtccca<br>gcaggaggtttgcatgcttgtagccgaaat<br>ggggctcgacccccccatagtaggatacttg<br>attttgcattccattgtggacctgcaaact<br>ctacacatagaggctttgtcttgcatctaa<br>acacctgagtacagtgtgtacctagaccct<br>atagtacgggaggaccgtttgtttcctcaa<br>taaccctacataataggctaggtgggcatg |

Table 3-continued

Exemplary IRES sequences.

| SEQ ID NO: | IRES | Sequence |
|---|---|---|
| | | cccaatttgcaagatcccagactgggggtc<br>ggtctgggcagggttagatccctgttagct<br>actgcctgatagggtggtgctcaaccatgt<br>gtagtttaaattgagctgttcatatacc |
| 21 | Yc-3 | actgaagatcctacagtaactactgcccca<br>atgaacgccacagatgggtctgctgatgac<br>tacctatcttagtgctagttgaggtttgaa<br>gtgagccggtttttagaagaaccagtttct<br>gaacattatcatccccagcatctattctat<br>acgcacaagatagatagtcatcagcagaca<br>catctgtgctactgcttgatagagttgcgg<br>ctggtcaacttagattggtataaccagttg<br>agtggcaa |
| 22 | Rosavirus M-7 | tatgcatcactggacggcctaacctcggtc<br>gtggcttcttgccgatttcagcgctaccag<br>gctttctggtctcgccaggcgttgattagt<br>aggtgcactgtctaagtgaagacagcagtg<br>ctctctgtgaaaagttgatgacactcttca<br>ggtttgtagcgatcactcaaggctagcgga<br>tttccccgtgtggtaacacacgcctctagg<br>cccagaaggcacggtgttgacagcacccct<br>tgagtggctggtcttccccaccagcacctg<br>atttgtggattcttcctagtaacggacaag<br>catggctgctcttaagcattcagtgcgtcc<br>ggggctgaaggatgcccagaaggtacccgc<br>aggtaacgataagctcactgtggatctgat<br>ctggggctgcgggctgggtgtctttccacc<br>cagccaaaacccgtaaaacggtagtcgcag<br>ttaaaaaacgtctaggccccacccccccag<br>ggatgggggggttcccttaaaccctcacaag<br>ttcaac |
| 23 | Shanbavirus A | tgaaaagggggcgcagggtggtggtggtta<br>ctaaatacccaccatcgccctgcacttccc<br>ttttcccctgtggctcagggtcacttagcc<br>ccctctttgggttaccagtagttttctacc<br>cctgggcacagggttaactatgcaagacgg<br>aacaacaatctcttagtccccctcgccgat<br>agtgggctcgacccccatgtgtaggagtgg<br>ataagggacggagtgagccgatacggggaa<br>gagtgtgcggtcacaccttaattccatgag<br>cgctgcgaagaaggaagctgtgaacaatgg<br>cgacctgaaccgtacacatggagctccaca<br>ggcatggtactcgttagactacgcagcctg<br>gttgggagtgggtataccctgggtgagccg<br>ccagtgaatgggagttcactggttaacaca<br>cactgcctgatagggtcagggcctcctgtc<br>cccgccgtaatgaggtagaccatatgcc |
| 24 | Pasivirus A | gcggctggatattctggccgtgcaactgct<br>tttgaccagtggctctgggtaacttagcca<br>aagtgtccttctccctttccctattatatg<br>ttttatggctttgtctggtcttgtttagtt<br>tatatataagatcctttccgccgatataga<br>cctcgacagtctagtgtaggaggattggtg<br>atattaatttgccccagaagagtgaccgtg<br>acacatagaaaccatgagtacatgtgtatc<br>cgtggaggatcgcccgggactggattccat<br>atcccattgccatcccaacaagcggagggt<br>atacccactatgtgcacgtctgcagtggga<br>gtctgcagatttagtcatactgcctgatag<br>ggtgtgggcctgcactctggggtactcagg<br>ctgtttatataat |
| 25 | Pasivirus A 2 | gctggactttctggctgcgcaactgctttt<br>aaccagtggctctgggttacttagccaaaa<br>ccccctttccccgtaccctagtttgtgtgt<br>gtattattattttgttgttgttttgtaaat<br>ttttatataagatcctttccgccgatatag<br>acctcgacagtctagtgtaggaggattggt<br>gatattaatatgccccagaagagtgaccgt<br>gacacatagaaaccatgagtacatgtgtat<br>ccgtggaggatcgcccgggactggattcca<br>tatcccattgccatcccaacaaacggaggg<br>tatacccgctatgtgcgcgtctacagtggg<br>aatctgtagatttagtcatactgcctgata<br>gggtgtgggcctgcactctggggtactcag<br>gctgtttatataat |
| 26 | Echovirus E14 | ttaaaacagcctgtgggttgttcccatcca<br>cagggcccactgggcgccagcactctggta<br>ttgcggtaccttagtgcgcctgttttatat<br>acccgtcccccaaacgtaacttagacgcat<br>gtcaacgaagaccaatagtaagcgcagcac<br>accagctgtgttccggtcaagcacttctgt<br>taccccggaccgagtatcaataagctactc<br>acgtggctgaaggagaaaacgttcgttacc<br>cgaccaattacttcaagaaacctagtaaca<br>ccatgaaggttgcgcagtgtttcgctccgc<br>acaaccccagtgtagatcaggtcgatgagt<br>caccgcattccccacgggtgaccgtggcgg<br>tggctgcgctggcggcctgcccatggggaa<br>acccatgggacgcttcaatactgacatggt<br>gcgaagagtctattgagctaattggtagtc<br>ctccggcccctgaatgcggctaatcctaac<br>tgcggagcagatacccacacaccagtgggc<br>agtctgtcgtaacgggcaactctgcagcgg<br>aaccgactactttgggtgtccgtgtttctc<br>tttatccttatactggctgcttatggtgac<br>aattgagagattgttaccatatagctattg<br>gattggccatccggtgacaaatagagcaat<br>tgtgtatttgtttgttggtttcgtgccatt<br>aaattacaaggttctaaacacccttaatct<br>tattatagcattcaacacaacaaa |
| 27 | Human Parechovirus 5 | gtacattagatgcgtcatctgcaactttag<br>tcaataaattacctccaatgtcattaccaa<br>cattccctaccttttcactaacacctaaga<br>caacaagtacctatgcctggtctccactat<br>tcgaaggcaacttgcaataagaagagtgga<br>attaagacgcttaaagcatagagctagtta<br>tcttttctaacccacaaagttttgtggggt<br>ggcagatggcgtgccataactctattagtg<br>agataccatgcttgtggatcttatgctcac<br>acagccatcctctagtaagttgataaggtg<br>tctggtgatatgtgggaactcacatgaacc<br>attaatttaccgtaaggtatcctatagcca<br>gcggaatcacatctggtgacagatgcctct<br>ggggccgaaagccaaggtttaacagaccct<br>ataggattggtttcaaaacctgaattgatg<br>tggattgtgtatagtacctgttgatctggt<br>aacagtgtcaacactagttgtaaggcccac<br>gaaggatgcccagaaggtacccgtaggtaa<br>caagtgacactatggatctgatctggggcc<br>agctacctctatcatggtgagttggttaaa<br>aaacgtctagtgggccaaacccaggggggga<br>tccctggtttccttttacctaatcaaagcc<br>act |
| 28 | Aichi Virus | tttgaaaaggggggtgggggggcctcggcccc<br>ctcaccctcttttccggtggtctggtcccg<br>gaccaccgttactccattcagcttcttcgg<br>aacctgttcggaggaattaaacgggcaccc<br>atactccccccacccccctttgtaactaa<br>gtatgtgtgctcgtgatcttgactcccacg<br>gaacggaccgatccgttggtgaacaaacag<br>ctaggtccacatcctcccttcccctgggag<br>ggcccccgccctcccacatcctccccccag<br>cctgacgtatcacaggctgtgtgaagcccc<br>cgcgaaagctgctcacgtggcaattgtggg<br>tccccccttcatcaagacaccaggtctttc<br>ctccttaaggctagccccggcgtgtgaatt<br>cacgttgggcaactagtggtgtcactgtgc<br>gctcccaatctcggccgcggagtgctgttc<br>cccaagccaaacccctggcccttcactatg<br>tgcctggcaagcatatctgagaaggtgttc |

Table 3-continued

Exemplary IRES sequences.

| SEQ ID NO: | IRES | Sequence |
|---|---|---|
| | | cgctgtggctgccaacctggtgacaggtgc<br>cccagtgtgcgtaaccttcttccgtctccg<br>gacggtagtgattggttaagatttggtgta<br>aggttcatgtgccaacgccctgtgcgggat<br>gaaacctctactgccctaggaatgccaggc<br>aggtaccccacctccgggtgggatctgagc<br>ctgggctaattgtctacgggtagtttcatt<br>tccaatccttttatgtcggagtc |
| 29 | Hepatitis A Virus HA 16 | ttcaagaggggtctccggagttttccggaa<br>cccctcttggaagtccatggtgaggga<br>cttgatacctcaccgccgtttgcctaggct<br>ataggctaaatttccctttccctgtccttc<br>ccttctatttccttttgttttgtttgtaaa<br>tattaattcctgcaggttcagggttcttta<br>atctgtttctctataagaacactcaatt<br>tttcacgctttctgtctcctttcttccagg<br>gctctccccttgccctaggctctggccg<br>ttgcgcccggcggggtcaactccatgatta<br>gcatggagctgtaggagtctaaattggg<br>gacgcagatgtttgggacgtcgccttgcag<br>tgttaacttggctttcatgaacctcttt<br>gatcttccacaaggggtaggctacgggtga<br>aacctcttaggctaatacttcaatgaag<br>agatgccttggatagggtaacagcggcgga<br>tattggtgagttgttaagacaaaaacca<br>ttcaacgccggaggactggctctcatccag<br>tggatgcattgagggaattgattgtcag<br>ggctgtctctaggtttaatctcagacctct<br>ctgtgcttagggcaaacactatttggcc<br>ttaaatgggatcctgtgagaggggtccct<br>ccattgacagctggactgttctttgggg<br>ccttatgtggtgtttgcctctgaggtactc<br>aggggcatttaggtttttcctcattctt<br>aaataata |
| 30 | Phopivirus | gggagtaaacctcaccaccgtttgccgtgg<br>tttacggctacctattttggatgtaaata<br>ttaattcctgcaggttcaggtctcttga<br>attatgtccacgctagtggcactctcttac<br>ccataagtgacgccttagcggaaccttt<br>ctacacttgatgtggttaggggttacatta<br>tttccctgggccttctttggccctttt<br>cccctgcactatcattctttcttccgggct<br>ctcagcatgccaatgttccgaccggtgc<br>gcccgccggggttaactccatggttagcat<br>ggagctgtaggccctaaaagtgctgaca<br>ctggaactggactattgaagcatacactgt<br>taactgaaacatgtaactccaatcgatc<br>ttctacaaggggtaggctacgggtgaaacc<br>ccttaggttaatactcatattgagagat<br>acttctgataggttaaggttgctggataat<br>ggtgagtttaacgacaaaaaccattcaa<br>cagctgtgggccaacctcatcaggtagatg<br>cttttggagccaagtgcgtaggggtgtg<br>tgtggaaatgcttcagtggaaggtgccctc<br>ccgaaaggtcgtaggggtaatcaggggc<br>agttaggtttccacaattacaatttgaa |
| 31 | CVA10 | gctcttccgatctgggttgttcccacccac<br>agggcccactgggcgccagcactctgat<br>tccacggaatctttgtgcgcctgttttaca<br>acccttcccaatttgtaacgtagaagcaat<br>acacactactgatcaatagtaggcatgg<br>cgcgccagtcatgtcatgatcaagcacttc<br>tgttcccccggactgagtatcaatagac<br>tgctcacgcggttgaaggagaaaacgttcg<br>ttacccggctaactacttcgagaaacct<br>agtagcaccatggaagctgcggagtgtttc<br>gctcagcactttccccgtgtagatcagg<br>tcgatgagtcactgcaatccccacgggcga<br>ccgtggcagtggctgcgttggcggcctg<br>cctatggggcaacccataggacgctctaat<br>gtggacatggtgcgaagagtctattgag<br>ctagttagtagtcctccggcccctgaatgc<br>ggctaatcctaactgcggagcacatgcc<br>ttcaacccaggaggtggtgtgtcgtaacgg<br>gtaactctgcagcggaaccgactacttt<br>gggtgtccgtgtttccttttatccttatat<br>tggctgcttatggtgacaatcacggaat<br>tgttgccatatagctattggattggccatc<br>cggtgtctaacagagctattgtatacct<br>atttgttggatttactcccctatcatacaa<br>atctctgaacactttgtgctttatactg<br>aacttaaacacacgaaa |
| 32 | Enterovirus C | ttaaaacagctctggggttgttcccacccc<br>agaggcccacgtggcggccagtacaccg<br>gtaccacggtacccttgtacgcctgtttta<br>tactcccctccccgtaaactagaagcac<br>gaaacacaagttcaatagaaggggggtacag<br>accagtaccaccacgaacaagcacttct<br>gttcccccggtgaggtcacatagactgtcc<br>ccacggtcaaaagtgactgatccgttat<br>ccgctcacgtacttcggaaagcctagtacc<br>accttggaatctacgatgcgttgcgctc<br>agcactcgaccccggagtgtagcttaggct<br>gatgagtctggacgttccccactggtga<br>cagtggtccaggctgcgttggcggcctacc<br>tgtggtccaaaaccacaggacgctagta<br>gtgaacaaggtgtgaagagcccactgagct<br>acctgagaatcctccggcccctgaatgc<br>ggctaatcccaaccacggagcaggtaatcg<br>caaaccagcggtcagcctgtcgtaacgc<br>gtaagtctgtggcggaaccgactactttgg<br>gtgtccgtgtttccttttattttttatgg<br>tggctgcttatggtgacaatcatagattgt<br>tatcataaagcaaattggattggccatccg<br>gagtgagctaaactatctatttctctgagt<br>gttggattcgtttcacccacattctgaaca<br>atcagcctcattagtgttaccctgttaa<br>taagacgatatcatcacg |
| 33 | Enterovirus D | ttaaaacagctctggggttgttcccacccc<br>agaggcccacgtggcggctagtactccg<br>gtaccccggtacccttgtacgcctgtttta<br>tactccctttcccaagtaactttagaagaa<br>ataaactaatgttcaacaggaggggggta<br>caaaccagtaccaccacgaacacacacttc<br>tgtttccccggtgaagttgcatagactg<br>tacccacggttgaaagcgatgaatccgtta<br>cccgcttaggtacttcgagaagcctagt<br>atcatcttggaatcttcgatgcgttgcgat<br>cagcactctaccccgagtgtagcttggg<br>tcgatgagtctggacaccccacaccggcga<br>cgtggtccaggctgcgttggcggcctac<br>ccatggctagcaccatgggacgctagttgt<br>gaacaaggtgcgaagagcctattgagct<br>acctgagagtcctccggcccctgaatgcgg<br>ctaatcccaaccacggagcaaatgctca<br>caatccagtgagtggtttgtcgtaatgcgc<br>aagtctgtggcggaaccgactactttgg<br>gtgtccgtgtttccttttatttttattatg<br>gctgcttatggtgacaatctgagattgt<br>tatcatatagctattggattagccatccgg<br>tgatatcttgaaattttgccataacttt<br>ttcacaaatcctacaacattacactacact<br>ttctcttgaataattgagacaactcata |
| 34 | Enterovirus J | ttaaaatagcctcagggttgttcccaccct<br>gagggcccacgtggtgtagtactctggtat<br>tacggtacctttgtacgcctattttata<br>ccccccttccccaagtaatttagaagcaagc<br>acaaaccagttcagtagtaagcagtaca<br>atccagtactgtaatgaacaagtacttctg<br>ttaccccggaagggtctatcggtaagct<br>gtacccacggctgaagaatgacctaccgtt<br>aaccggctacctacttcgagaagcctag |

Table 3-continued

Exemplary IRES sequences.

| SEQ ID NO: | IRES | Sequence |
|---|---|---|
| | | taatgccgttgaagttttattgacgttacg<br>ctcagcacactaccccgtgtgtagtttt<br>ggctgatgagtcacggcactccccacgggc<br>gaccgtggccgtggctgcgttggcggcc<br>aaccaaggagtgcaagctccttggacgtca<br>tattacagacatggtgtgaagagcctat<br>tgagctaggtggtagtcctccggcccctga<br>atgcggctaatcctaactccggagcata<br>tcggtgcgaaccagcacttggtgtgttgta<br>atacgtaagtctggagcggaaccgacta<br>ctttgggtgtccgtgtttcctgttttaact<br>tttatggctgcttatggtgacaatttaa<br>cattgttaccatatagctgttgggttggcc<br>atccggattttgttataaaaccatttcc<br>tcgtgccttgacctttaacacatttgtgaa<br>cttctttaaatcccttttattagtcctt<br>aaatactaaga |
| 35 | Human Pegivirus 2 | aactgttgttgtagcaatgcgcatattgct<br>acttcggtacgcctaattggtaggcgcccg<br>gccgaccggccccgcaagggcctagtag<br>gacgtgtgacaatgccatgagggatcat<br>gacactggggtgagcggaggcagcaccgaa<br>gtcgggtgaactcgactcccagtgcgac<br>cacctggcttggtcgttcatggagggcatg<br>cccacgggaacgctgatcgtgcaaaggg<br>atgggtccctgcactggtgccatgcgcggc<br>accactccgtacagcctgatagggtggc<br>ggcgggcccccccagtgtgacgtccgtgga<br>gcgcaac |
| 36 | GBV-C GT110 | tgacgtgggggggttgatTTTcccccccccg<br>gcactgggtgcaagccccagaaaccgacgc<br>ctatctaagtagacgcaatgactcggcgcc<br>gactcggcgaccggccaaaaggtggtggat<br>gggtgatgacagggttggtaggtcgtaaat<br>cccggtcatcctggtagccactataggtgg<br>gtcttaagagaaggtcaagattcctcttac<br>gcctgcggcgagaccgcgcacggtccacag<br>gtgttggccctaccggtgtgaataagggcc<br>cgacatcaggc |
| 37 | GBV-C K1737 | gacgtgggggggttgatcccccccccTTTgg<br>cactgggtgcaagccccagaaaccga<br>cgcctatttaaacagacgttaagaaccggc<br>gccgacccggcgaccggccaaaaggtgg<br>tggatgggtgatgccagggttggtaggtcg<br>taaatcccggtcatcttggtagccacta<br>taggtgggtcttaagggttggttaaggtcc<br>ctctggcgcttgtggcgagaaagcgcac<br>ggtccacaggtgttggccctaccggtgtga<br>ataagggcccgacgtcaggctcgtcgtt<br>aaaccgagcccactacccacctgggcaaac<br>aacgcccacgtacggtccacgtcgccct<br>tcaatgtctctcttgaccaataggcttagc<br>cggcgagttgacaaggaccagtgggggc<br>tgggcggtaggggaaggacccctgccgctg<br>cccttcccggtggagtgggaaatgc |
| 38 | GBV-C Iowa | tgacgtgggggggttgatccGccccccccccgg<br>cactCggtgcaagccccataaaccgacgc<br>ctatctaagtagacgcaatgactcggcgc<br>cgactcggcgaccggccaaaaggtggtgg<br>atgggtggtgacagggttggtaggtcgta<br>aatcccggtcatcctggtagccactatag<br>gtgggtcttaagagaaggtcaagactcct<br>cttgtgcctgcggcgagaccgcgcacggt<br>ccacaggtgctggccctaccggtgtgaat<br>aagggcccgacgtcaggctcgtcgttaaa<br>ccgagcccgtcacccacctgggcaaacga<br>cgcccacgtacggtccacgtcgcccttca |
| 39 | Pegivirus A 1220 | tgtagcaatgcgcatattgctacttcggta<br>cgcctaattggtaggcgcccggccgacc<br>ggccccgcaagggcctagtaggacgtgtga<br>caatgccatgcgggatcatgacactggg<br>gtgagcggaggcagcaccgaagtcgggtga<br>actcgactcccagtgcgaccacctggct<br>tggtcgttcatggagggcatgcccacggga<br>acgctgatcgtgcaaagggatgggtccc<br>tgcactggtgccatgcgcggcaccactccg<br>tacagcctgatagggtggcggcgggccc<br>ccccagtgtgacgtccgtggagcgcaac |
| 40 | Pasivirus A 3 | attttctggccgtgtagctgcttttgacca<br>gtggctctgggttacttagccaaatccccc<br>ttccttcaccctttaaatttgatggtc<br>tgtgttgtttgttttgtcttgtctaaataa<br>tatataagatccttcccgccgatacaga<br>cctcgacagtctggtgtaggagggttggtg<br>ttattaatttgctcccagaagagtgaccg<br>tgacacatagaaaccatgagtacatgtgta<br>tccgtggaggatcgcccgggactggatt<br>ccatatcccattgccatcccaacaagcgga<br>gggtatacccactatgtgcgcgtttgca<br>gtgggaatctgcaaatttagtcatactgcc<br>tgatagggtgtgggcctgcactctgggg<br>tactcaggctgttcatataat |
| 41 | Sapelovirus | cccctccacccttaaggtggttgtatccca<br>cataccccaccctcccttccaaagtggac<br>ggacaactggattttgactaacggcaagt<br>ctgaatggtatgatttggatacgtttaaac<br>ggcagtagcgtggcgagctatggaaaaa<br>tcgcaattgtcgatagccatgttagtgacg<br>cgcttcggcgtgctcctttggtgattcg<br>gcgactggttacaggagagtaggcagtgag<br>ctatgggcaaacctctacagtattactt<br>agagggaatgtgcaattgagacttgacgag<br>cgtctctttgagatgtggcgcatgctct<br>tggcattaccatagtgagcttccaggttgg<br>gaaacctggactgggcctatactacctg<br>atagggtcgcggctggccgcctgtaactag<br>tatagtcagttgaaaccccccc |
| 42 | Rosavirus B | gtctctttagtgtctatgcttcagagagcg<br>gtgaactgacaccgttgcttcttgcacagc<br>ccttcgtgccggtctttccggttctcga<br>cagcgttgggcatcatggctagttaggcta<br>agatagtggatgatctagtgaacagttt<br>tggattgtttggagttttgtagcgatgcta<br>gtagtgtgtgtggacctccccacgtggt<br>aacacgtgccccacaggccaaaagccaagg<br>tgttgaaagcacccctactagtcccaga<br>ctcacccatctgggaactcctctcatgaaa<br>aatcttagtaacttttgattcggctatt<br>catcaacctctctagtcaagggctgaagga<br>tgcccggaaggtacccgcaggtaacgat<br>aagctcactgtggatctgatccggggcttt<br>ggtgcgaccgtctgtccggcgtagccag<br>agttaaaaaacgtctaggcccttccacccc<br>aagggattggggtttccccaatcatttg<br>aaagttcact |
| 43 | Bakunsa Virus | ttttgaacgccacctcggagcgatatccgg<br>ggacccccctcccctttttccttcctacctt<br>cttcccaaatttccctcttcccttgtta<br>ttttggtttggatttcctggacatgactcg<br>gacggatctatctcatttgctttgtgtc<br>tgctccaccagtggcatggtcgaaagatca<br>tcaacactggacgtgtactgtaatggcc<br>aaacgtgcccacaggggaaaccatgccggt<br>cgctgtagcggcgggtggacgtggtgga<br>cccctctccctgctcataaactttgggtag<br>gtgaagggttcaagcgacgcttgccgtg<br>agggcgcatccggatggtgggaaccaacaa<br>actaggctgtaatggccgacctcaggtg<br>gatgagctagggctgctgcaccaaaaggga |

Table 3-continued

Exemplary IRES sequences.

| SEQ ID NO: | IRES | Sequence |
|---|---|---|
| | | ctcgattcgatatcccggcctggtagcc<br>tagtgcagtggactcgtagttgggaatcta<br>cgactggcctagtacagggtgatagccc<br>cgtttcccacgcccacctgttgtagggaca<br>cccccccc |
| 44 | Tremovirus A | tttgaaagaggcctccggagtgtccggagg<br>ctctctttcgacccaacccatactgggg<br>ggtgtgtgggaccgtacctggagtgcacgg<br>tatatatgcattcccgcatggcaagggc<br>gtgctaccttgccccttgacgcatggtatg<br>cgtcatcatttgccttggttaagccccata<br>gaaacgaggcgtcacgtgccgaaaatcc<br>ctttgcgtttcacagaaccatcctaaccat<br>gggtgtagtatgggaatcgtgtatgggg<br>atgattaggatctctcgtagagggataggt<br>gtgccattcaaatccagggagtactctg<br>gctctgacattgggacatttgatgtaaccg<br>gacctggttcagtatccgggttgtcctg<br>tattgttacggtgtatccgtcttggcacac<br>tgaaagggtatttttgggtaatcctttc<br>ctactgcctgatagggtggcgtgcccggcc<br>acgagagattaagggtagcaatttaaac |
| 45 | Swine Pasivirus 1 | gcttttgaccagtggctctgggttacttag<br>ccaagtccctttctcttattttcactagtt<br>tatgttgtgtgttgtctgttttgttttg<br>tttaaattgtatacaagatccttcccgccg<br>acacagacctcgacagtctggtgtagga<br>gggttggtgatattaatttgccccaaaaga<br>gtgaccgtgatacgtggaaaccatgagt<br>acatgtgtatccgtggaggatcgcccggga<br>ctggattccatatcccattgccatccca<br>acaaacggagggtatacccaccacgtgcgc<br>gtttgcagtgggaatctgcaaatttagt<br>catactgcctgatagggtgtgggcctgcac<br>tttggggtactcaggctgttcatataat |
| 46 | PLV-CHN | acatggggtatgttgtctgtcctgttttgt<br>tgaaacaatatataagatcctttccgccga<br>tatagacctcgacagtctagtgtaggag<br>gattggtgatagtaacttgccccagaagag<br>tgaccgtgacacatagaaaccatgagta<br>catgtgtatccgtggaggatcgcccgggac<br>tggattccatatcccattgccatcccaa<br>caaacggagggtatacccactatgtgcgcg<br>tttgcagtgggagcctgcaaatttagtc<br>atactgcctgatagggtgtgggcctgcact<br>ctggggtactcaggctgtttatataat |
| 47 | Pasivirus A (longer) | tgaaaaagtggttgtgcagctggattttcc<br>ggctgtgcaactgcttttgaccagtggctc<br>tgggttacttagccaaattcctttccct<br>tatccctattggtttgtgttgtgtgttgtt<br>tgttttgttttgtcttaactatatacaa<br>gatccttcccgccgatacagacctcgacag<br>tctggtgtaggagggttggtgttattaa<br>tttgccccaaaagagtgaccgtgacacgtg<br>gaaaccatgagtacatgtgtatccgtgg<br>aggatcgcccgggactggattccatatccc<br>attgccatcccaacaaacggagggtata<br>cccaccacgtgcgcgtttgcagtgggaatc<br>tgcaaatttagtcatactgcctgatagg<br>gtgtgggcctgcactttggggtactcaggc<br>tgtttatataat |
| 48 | Sicinivirus | gtgtcattaaggtgtgtttggaagttcgaa<br>ttagctggtttgtggtgattagtagacccc<br>ctggaggtacccaattcggatctgacca<br>gggacccgtgactataccgctccggtaatt<br>cgggtttaaaacaatgaacgtcaccaca<br>caattacttttctcattttattttcatcat<br>tgtcttcctatttaccgattacactcga<br>tttccttggatgttcctggagatttccctg |

Table 3-continued

Exemplary IRES sequences.

| SEQ ID NO: | IRES | Sequence |
|---|---|---|
| | | gttacctggaccctcattattgttgttg<br>tttcacccagcgagctgtcccaattgctta<br>ttatttgcgcttacaacttcgtcctaat<br>atttttctggttgatcgggttgattgagct<br>cccgggctatcctgccattcaac |
| 49 | Hepacivirus K | gggaacaatggtccgtccgcggaacgactc<br>tagccatgagtctagtacgagtgcgtgc<br>cacccattagcacaaaaaccactgactgag<br>ccacacccctcccggaatcctgagtaca<br>ggacattcgctcggacgacgcatgagcctc<br>catgccgagaaaattgggtatacccacg<br>ggtaaggggtggccacccagcgggaatctg<br>ggggctggtcactgactatggtacagcc<br>tgatagggtgctgccgcagcgtcagtggta<br>tgcggctgttcatggaac |
| 50 | Hepacivirus A | acctccgtgctaggcacggtgcgttgtcag<br>cgttttgcgcttgcatgcgctacacgcg<br>tcgtccaacgcggagggaacttcacatcac<br>catgtgtcactcccccctatggagggttcc<br>accccgcttacacggaaatgggttaacca<br>tacccaaagtacgggtatgcgggtcctc<br>ctagggcccccccggcaggtcgagggagct<br>ggaattcgtgaattcgtgagtacacgaa<br>aatcgcggcttgaacgtctttgaccttcgg<br>agccgaaatttgggcgtgccccacgaag<br>gaaggcgggggcggtgttgggccgccgccc<br>cctttatcccacggtctgataggatgct<br>tgcgagggcacctgccggtctcgtagacca<br>taggac |
| 51 | BVDV1 | gtatacgagaatttgcctaggacctcgttt<br>acaatatgggcaatctaaaattataattag<br>gcctaagggacaaatcctcctcagcgaagg<br>ccgaaaagaggctagccatgcccttagtag<br>gactagcaaaataagggggtagcaacagt<br>ggtgagttcgttggatggctgaagccctga<br>gtacagggtagtcgtcagtggttcgacgct<br>tcggaggacaagcctcgagataccacgtgg<br>acgagggcatgcccacagcacatcttaacc<br>tggacgggggtcgttcaggtgaaaacggtt<br>taaccaaccgctacgaatacagcctgatag<br>ggtgctgcagaggcccactgtattgctact<br>gaaaatctctgctgtacatggcac |
| 52 | Border Disease Virus | gtatacgggagtagctcatgcccgtataca<br>aaattggatattccaaaactcgattgggtt<br>agggagccctcctagcgacggccgaaccgt<br>gttaaccatacacgtagtaggactagcaga<br>cgggaggactagccatcgtggtgagatccc<br>tgagcagtctaaatcctgagtacaggatag<br>tcgtcagtagttcaacgcaggcacggttct<br>gccttgagatgctacgtggacgagggcatg<br>cccaagacttgctttaatctcggcgggggt<br>cgccgaggtgaaaacacctaacggtgttgg<br>ggttacagcctgatagggtgctgcagaggc<br>ccacgaataggctagtataaaaatctctgc<br>tgtacatggcac |
| 53 | BVDV2 | gtatacgagattagctaaagtactcgtata<br>tggattggacgtcaacaaatttttaattgg<br>caacgtagggaaccttcccctcagcgaagg<br>ccgaaaagaggctagccatgccctttagta<br>ggactagcaaaagtaggggactagcggta<br>gcagtgagttcgttggatggccgaacccct<br>gagtacaggggagtcgtcaatggttcgaca<br>ctccattagtcgaggagtctcgagatgcca<br>tgtggacgagggcatgcccacggcacatct<br>taacccatgcgggggttgcatgggtgaaag<br>cgctaatcgtggcgttatggacacagcctg<br>atagggtgtagcagagacctgctattccgc<br>tagtaaaaaactctgctgtacatggcac |

Table 3-continued

Exemplary IRES sequences.

| SEQ ID NO: | IRES | Sequence |
|---|---|---|
| 54 | CSFV-PK15C | gtatacgaggttagttcattctcgtatgcattattggacaaatcaaaatttcaatttggttcagggcctccctccagcgacggccgaactgggctagccatgcccatagtaggactagcaaacggagggactagccgtagtggcgagctccctgggtgttctaagtcctgagtacaggacagtcgtcagtagttcgacgtgagcagaagcccacctcgagatgctatgtggacgagggcatgcccaagacgcaccttaaccctagcgggg
gtcgctagggtgaaatcacaccacgtgatgggagtccgacctgatagggtgctgcagaggctcactattaggctagtataaaaatctctgctgtacatggcac |
| 55 | SF573 Dicistro-virus | aaaaccgaccccagagatcagaaagtcgttgacgcgatcttttattagaggacgttgcgctggcgcgagctttaattagcagacgccaaaaataaacaacaaaatgctgatcgcgagacttaattgtcagacgattggccaaatccgatgtgatctttgctgctcccagattgccgaaataggagtagtag |
| 56 | Hubei Picorna-like Virus | ccccaaaacccccccccttaaactcaacactgtagtggattcattttccgttgcaaaacaaaacattactacccgcatttatgtaggctctgtgttttctatgcgaccgttacattaatctctactctgacccactagtttataaaaccgaagacctgaatgaaacgattttccttcttttcaacctctaacgaacctctgacggcttgagaaacctgaagttagtaattatgtttaaaagaaaggaaagtcaaacgcgatgactcttacatccctattccataccgttgctccacaatgtgagcgatgcgaggtcgggactgcagtattaggggaacgagctacatggagagttaattatctctcccctcctacgggagtctcatgtgagctgtagaaagcggttggcacctctcgttacctcgcctgtacatgatcc |
| 57 | CRPV | aaaagcaaaaatgtgatcttgcttgtaaatacaattttgagaggttaataaattacaagtagtgctatttttgtatttaggttagctatttagctttacgttccaggatgcctagtggcagccccacaatatccaggaagccctctctgcggtttttcagattaggtagtcgaaaaacctaagaaatttacct |
| 58 | Salivirus A BN5 | tttcctcctttcgaccgccttacggcaggcgggtccgcggacggcttcggcctacccgcgacaagaatgccgtcatctgtccttatcacccatattctttcccttcccccgcaaccatcacgcttactcgcgcacgtgttgagtggcacgtgcgttgtccaaacagttacactcacacccttggggcgggtttgtcccgccctcgggttcctcgcggaaccctccctcttctctctccctttctatccgccttcactttccataactacagtgctttggtaggtaagcatcctgaccccccgcggaagctgccaacgtggcaactgtggggatccaggcaggttatcaaaggcacccggtctttccgccttcaggagtatccctgccggtgaattccgacagggctctgcttggtgccaacctcccccaaatgcgcgctgcgggagtgctcttccccaactcatcttagtaacctctcatgtgtgtgcttggtcagcatatctgaggcgacgttccgctgtcccagaccagtccagcaatggacgggccagtgtgcgtagtcgctttccggtttcccggcgcatgtttggcgaaacgctgaggtaaggttggtgtgcccaatgcccgtaatttggtgacacctcaagaccacccaggaatgccagggaggtaccccacttcggtgggatctgaccctgggctaattgtctacggtggttcttcttgcttccacttctctttttttctggcatg |
| 59 | Salivirus A BN2 | tatggcaggcgggcttgtggacggcttcggcccacccacagcaagaatgccatcatctgtcctcacccccatgtttccccttttctttccctgcaaccgttacgcttactcgcaggtgcatttgagtggtgcacgtgttgaataaacagctacactcacatgggggcgggttttcccgccctgcggcctctcgcgaggcccacccctccccttcctcccataactacagtgctttggtaggtaagcatcctgatcccccgcggaagctgctcacgtggcaactgtggggacccagacaggttatcaaaggcacccggtctttccgccttcaggagtatccctgctagtgaattctagtagggctctgcttggtgccaacctcccccaaatgcgcgctgcgggagtgctcttccccaactcaccctagtatcctctcatgtgtgtgcttggtcagcatatctgagacgatgttccgctgtcccagaccagtccagtaatggacgggccagtgtgcgtagtcgtcttccggcttttccggcgcatgtttggtgaaccggtggggtaaggttggtgtgcccaacgcccgtactttggtgatacctcaagaccacccaggaatgccagggaggtaccccgcttcacagcgggatctgaccctgggctaattgtctacggtggttcttcttgcttccacttctttctactgttc |
| 60 | Salivirus A 02394 | tttcgaccgccttatggcaggcgggcttgtggacggcttcggcccacccacagcaagaatgccatcatctgtcctcacccccatttctcccctccttcccctgcaaccattacgcttactcgcatgtgcattgagtggtgcacgtgttgaacaaacagctacactcacgtgggggcgggttttcccgcccttcggcctctcgcgaggcccacccttccccttcctcccataactacagtgctttggtaggtaagcatcctgatcccccgcggaagctgctcgcgtggcaactgtggggacccagacaggttatcaaaggcacccggtctttccgcctccaggagtatccctgctagtgaattctagtggggctctgcttggtgccaacctcccccaaatgcgcgctgcgggagtgctcttccccaactcaccctagtatcctctcatgtgtgtgcttggtcagcatatctgagacgatgttccgctgtcccagaccagtccagcaatggacgggccagtgtgcgtagtcgtcttccggcttgtccggcgcatgtttggtgaaccggtggggtaaggttggtgtgcccaacgcccgtactttggtgacaactcaagaccacccaggaatgccagggaggtaccccgcctcacggcgggatctgaccctgggctaattgtctacggtggttcttcttgcttccatttctttcttctgttc |
| 61 | Salivirus A GUT | tatggcaggcgggcttgtggacggtttcggcccacccacagcaagaatgccatcatctgtcctcacccccaatttcccctttcttcccctgcaatcatcacgcttactcgcatgtgcattgagtggtgcatgtgttgaacaaacagctacactcacatgggggcgggttttcccgccctacggcctctcgcgaggcccacccttcccctccccttataactacagtgctttggcaggtaagcatcctgatcccccgcggaagctgctcacgtggcaactgtggggacccagacaggttatcaaaggcacccggtctttccgccttcaggagcatccccactagtgaattctagtggggctctgcttggtgccaacctcccccaaatgcgcgctgcgggagtgctcttccccaacccatcctagtatcctctcatgtgtgtgcttggtcagcatatctgagacgacgttccgctgtcccagaccagtccagtaatggacgggccagtgtgcgtagtcgtcttccggcttgtccggcgcatgtttggtgaaccggtggggtaaggttggtgtgcccaacgcccgtactttggtgacacctcaagaccacccaggaatgccagggaggtaccc |

Table 3-continued

Exemplary IRES sequences.

| SEQ ID NO: | IRES | Sequence |
|---|---|---|
| | | cgcctcacggcgggatctgaccctgggcta attgtctacggtggttcttcttgcttccac ttctttctt |
| 62 | Salivirus A CH | ttctcctgcaaccattacgcttaatcgcat gtgcattgagtggtgcatgtgttgaacaaa cagctacaatcacatgggggcgggttttcc cgccccacggcttctcgcgaggcccatc cctccctttctcccataactacagtgctt tggtaggtaagcatcccgatctcccgcgga agctgctcacgtggcaactgtggggaccca gacaggttatcaaaggcacccggtctttcc gccttcaggagtatccctgctagcgaattc tagtagggctctgcttggtgccaacctctc ccaaatgcgcgctgcgggagtgctcttccc caaatcaccccagtatcctctcatgtgtgt gcctggtcagcatatctgagacgatgttcc gctgtcccagaccagtccagtaatggacgg gccagtgtgcgtagtcgtcctccggcttgt ccggcgcatgtttggtgaaccggtggggta aggttggtgtgcccaacgcccgtaatcagg ggatacctcaaggcacccaggaatgccagg gaggtatcccgcctcacagcgggatctgac cctggggtaaatgtctgcggggggtcctct tggcccaattctcagtaattttcagg |
| 63 | Salivirus A SZ1 | tctgtcctcaccccatcttcccttctttcc tgcaccgttacgcttactcgcatgtgcatt gagtggtgcacgtgcttgaacaaacagcta cactcacatgggggcgggttttcccgccct gcggcctctcgcgaggcccacccctcccct tcctcccataactacagtgctttggtaggt aagcatcctgatccccgcggaagctgctc acgtggcaactgtggggacccagacaggtt atcaaaggcacccggtctttccgccttcag gagtatccctgctagtgaattctagtaggg ctctgcttggtgccaacctcccccaaatgc gcgctgcgggagtgctcttccccaactcac cctagtatcctctcatgtgtgtgcttggtc agcatatctgagacgatgttccgctgtccc agaccagtccagtaatggacgggccagtgt gcgtagtcgtcttccggcttgtccggcgca tgtttggtgaaccggtggggtaaggttggt gtgcccaacgcccgtactttggtgatacct caagaccacccaggaatgccagggaggtac cccgcttcacagcgggatctgaccctgggc taattgtctacggtggttcttcttgcttcc acttctttctactgttcatg |
| 64 | Salivirus FHB | acatggggggtctgcggacggcttcggccc acccgcgacaagaatgccgtcatctgtcct cattacccgtattccttcccttcccccgca accaccacgcttactcgcgcacgtgttgag tggcacgtgcgttgtccaaacagctacacc cacacccttcggggcgggtttgtcccgccc tcgggttcctcgcggaacccccccctccct ctctctctttctatccgccctcacttccca taactacagtgctttggtaggtgagcaccc tgaccccccgcggaagctgctaacgtggca actgtggggatccaggcaggttatcaaagg cacccggtctttccgccttcaggagtatct ctgccggtgaattccggtagggctctgctt ggtgccaacctcccccaaatgcgcgctgcg ggagtgctcttccccaactcatcttagtaa cctctcatgtgtgtgcttggtcagcatatc tgaggcgacgttccgctgtcccagaccagt ccagcaatggacgggccagtgtgcgtagtc gctttccggttttccggcgcatgtttggcg aaacgctgaggtaaggttggtgtgcccaac gcccgtaatttggtgatacctcaagaccac ccaggaatgccagggaggtaccccacttcg gtgggatctgaccctgggctaattgtctac ggtggttcttcttgcttccacttctctttt ttctggcatg |
| 65 | CVB3 | ttaaaacagcctgtgggttgatcccaccca caggcccattgggcgctagcactctggtat cacggtacctttgtgcgcctgttttatacc ccctcccccaactgtaacttagaagtaaca cacaccgatcaacagtcagcgtggcacacc agccacgttttgatcaagcacttctgttac cccggactgagtatcaatagactgctcacg cggttgaaggagaaagcgttcgttatccgg ccaactacttcgaaaaacctagtaacaccg tggaagttgcagagtgtttcgctcagcact accccagtgtagatcaggtcgatgagtcac cgcattccccacgggcgaccgtggcggtgg ctgcgttggcggcctgcccatggggaaacc catgggacgctctaatacagacatggtgcg aagagtctattgagctagttggtagtcctc cggcccctgaatgcggctaatcctaactgc ggagcacacaccctcaagccagagggcagt gtgtcgtaacgggcaactctgcagcggaac cgactactttgggtgtccgtgtttcatttt attcctatactggctgcttatggtgacaat tgagagatcgttaccatatagctattggat tggccatccggtgactaatagagctattat atatccctttgttgggtttataccacttag cttgaaagaggttaaaacattacaattcat tgttaagttgaatacagcaaa |
| 66 | CVB1 | ttaaaacagcctgtgggttgttcccaccca caggcccattgggcgctagcactctggt atcacggtacctttgtgcgcctgttttaca tcccctccccaaattgtaatttagaagttt cacacaccgatcattagcaagcgtggcaca ccagccatgttttgatcaagcacttctgtt accccggactgagtatcaatagaccgctaa cgcggttgaaggagaaaacgttcgttaccc ggccaactacttcgaaaaacctagtaacac catggaagttgcggagtgtttcgctcagca ctaccccagtgtagatcaggtcgatgagtc accgcgttccccacgggcgaccgtggcggt ggctgcgttggcggcctgcctacggggaaa cccgtaggacgctctaatacagacatggtg cgaagagtctattgagctagttggtaatcc tccggcccctgaatgcggctaatcctaact gcggagcacataccctcaaaccagggggca gtgtgtcgtaacgggcaactctgcagcgga accgactactttgggtgtccgtgtttcatt ttattcctatactggctgcttatggtgaca attgacaggttgttaccatatagttattgg attggccatccggtgactaacagagcaatt atatatctctttgttgggtttataccactt agcttgaaagaggttaaaacactacatctc atcattaaactaaatacaacaaa |
| 67 | Echovirus 7 | ttaaaacagcctgtgggttgttcccaccca cagggcccattgggcgtcagcaccctggta tcacggtacctttgtgcgcctgttttatat cccttcccccaattgtaacttagaagaaac acacaccgatcaacagcaagcgtggcacac cagccatgttttggtcaagcacttctgtta ccccggactgagtatcaatagactgctcac gcggttgaaggagaaagcgtccgttatccg gccagctacttcgagaaacctagtaacacc atggaagttgcggagtgtttcgctcagcac taccccagtgtagatcaggtcgatgagtca ccgctttccccacgggcgaccgtggcggtg gctgcgttggcggcctgcctatgggggaac ccataggacgctctaatacagacatggtgc gaagagtctattgagctagctggtattcct ccggcccctgaatgcggctaatcctaactg tggagcacatgcccctaatccaaggggtag tgtgtcgtaatgagcaattccgcagcggaa ccgactactttgggtgtccgtgtttcctct tattcttgtactggctgcttatggtgacaa ttgagagattgttaccatatagctattgga |

Table 3-continued

Exemplary IRES sequences.

| SEQ ID NO: | IRES | Sequence |
|---|---|---|
| | | ttggccatccggtgactaatagagctattg<br>tgtatctctttgttggatttgtaccactta<br>atttgaaagaaatcaggacactacgctaca<br>ttttactattgaacaccgcaaa |
| 68 | CVB5 | ttaaaacagcctgtgggttgtacccaccca<br>cagggcccactgggcgctagcactctggta<br>tcacggtacctttgtgcgcctgttttatgc<br>cccccttcccccaattgaaacttagaagtta<br>cacacaccgatcaacagcgggcgtggcata<br>ccagccgcgtcttgatcaagcactcctgtt<br>tccccggaccgagtatcaatagactgctca<br>cgcggttgaaggagaaaacgttcgttaccc<br>ggctaactacttcgagaaacctagtagcat<br>catgaaagttgcgaagcgtttcgctcagca<br>catccccagtgtagatcaggtcgatgagtc<br>accgcattccccacgggcgaccgtggcggt<br>ggctgcgttggcggcctgcctacggggcaa<br>cccgtaggacgcttcaatacagacatggtg<br>cgaagagtcgattgagctagttagtagtcc<br>tccggcccctgaatccggctaatcctaact<br>gcggagcacataccctcaacccagggggca<br>ttgtgtcgtaacgggtaactctgcagcgga<br>accgactactttgggtgtccgtgtttcctt<br>ttattcttataatggctgcttatggtgaca<br>attgaaagattgttaccatatagctattgg<br>attggccatccggtgtctaacagagctatt<br>atatacctctttgttggatttgtaccactt<br>gatctaaaggaagtcaagacactacaattc<br>atcatacaattgaacacagcaaa |
| 69 | EVA71 | ttaaaacagcctgtgggttgcacccactca<br>cagggcccactgggcgcaagcactctggca<br>cttcggtacctttgtgcgcctgttttatat<br>cccctcccccaatgaaatttagaagcagca<br>aaccccgatcaatagcaggcataacgctcc<br>agttatgtcttgatcaagcacttctgtttc<br>cccggactgagtatcaatagactgctcacg<br>cggttgaaggagaaaacgttcgttatccgg<br>ctaactacttcggaaagcctagtaacacca<br>tggaagttgcggagagtttcgttcagcact<br>tccccagtgtagatcaggtcgatgagtcac<br>cgcattccccacgggcgaccgtggcggtgg<br>ctgcgttggcggcctgcccatggggtaacc<br>catgggacgctctaatacggacatggtgtg<br>aagagtctactgagctagttagtagtcctc<br>cggcccctgaatgcggctaatcccaactgc<br>ggagcacacgcccacaagccagtgggtagt<br>gtgtcgtaacgggcaactctgcagcggaac<br>cgactactttgggtgtccgtgtttcctttt<br>attcttatgttggctgcttatggtgacaat<br>taaagagttgttaccatatagctattggat<br>tggccatccggtgtgcaacagagcgatcgt<br>ttacctatttattggttttgtaccattgac<br>actgaagtctgtgatcacccttaattttat<br>cttaaccctcaacacagccaaac |
| 70 | CVA3 | ttaaaacagcctgtgggttgtacccaccca<br>cagggcccactgggcgctagcacactggta<br>ttacggtacctttgtgcgcctgttttatac<br>cccccccaacctcgaaacttagaagtaaag<br>caaacccgatcaatagcaggtgcggcgcac<br>cagtcgcatcttgatcaagcacttctgtaa<br>ccccggaccgagtatcaatagactgctcac<br>gcggttgaaggagaaaacgttcgttacccg<br>gctaactacttcgagaaacccagtagcatc<br>atgaaagttgcagagtgtttcgctcagcac<br>taccccgtgtagatcaggccgatgagtca<br>ccgcacttccccacgggcgaccgtggcggt<br>ggctgcgttggcggcctgcctatggggcaa<br>cccataggacgctctaatacggacatggtg<br>cgaagagtctattgagctagttagtagtcc<br>tccggcccctgaatgcggctaatcctaact<br>gcggagcacatacccttaatccaaagggca<br>gtgtgtcgtaacgggtaactctgcagcgga<br>accgactactttgggtgtccgtgtttcctt<br>ttaatttttactggctgcttatggtgacaa<br>ttgaggaattgttgccatatagctattgga<br>ttggccatccggtgactaacagagctattg<br>tgttccaatttgttggatttaccccgctca<br>cactcacagtcgtaagaacccttcattacg<br>tgttatttctcaactcaagaaa |
| 71 | CVA12 | ttaaaacagcctgtgggttgtacccaccca<br>cagggcccactgggcgctagcactctggta<br>ctacggtacctttgtgtgcctgttttaagc<br>ccctacccccccactcgtaacttagaaggct<br>tctcacactcgatcaatagtaggtgtggca<br>cgccagtcacaccgtgatcaagcacttctg<br>ttaccccggtctgagtaccaataagctgct<br>aacgcggctgaaggggaaaacgatcgttat<br>ccggctaactacttcgagaaacccagtacc<br>accatgaacgttgcagggtgtttcgctcgg<br>cacaaccccagtgtagatcaggtcgatgag<br>tcaccgtattccccacgggcgaccgtggcg<br>gtggctgcgttggcggcctgcccatggggt<br>gacccatgggacgctctaatactgacatgg<br>tgcgaagagtctattgagctagttagtagt<br>cctccggcccctgaatgcggctaatcctaa<br>ctgcggagcacatacccttaatccaaaggg<br>cagtgtgtcgtaacgggcaactctgcagcg<br>gaaccgactactttgggtgtccgtgtttcc<br>ttttattcttacattggctgcttatggtga<br>caattgaaaagttgttaccatatagctatt<br>ggattggccatccggtgacaaatagagcta<br>ttgtatatctttttgttggttacgtacccc<br>ttaattacaaagtggtttcaactttgaaat<br>acatcctaacactaaattgtagaaa |
| 72 | EV24 | ttaaaacagcctgtgggttgcacccaccca<br>cagggcccacagggcgctagcactctggta<br>tcacggtacctttgtgcgcctgttttatta<br>ccccttccccaattgaaaattagaagcaat<br>gcacaccgatcaacagcaggcgtggcgcac<br>cagtcacgtctcgatcaagcacttctgttt<br>ccccggaccgagtatcaatagactgctcac<br>gcggttgaaggagaaagtgttcgttatccg<br>gctaaccacttcgagaaacccagtaacacc<br>atgaaagttgcagggtgtttcgctcagcac<br>ttccccagtgtagatcaggtcgatgagtca<br>ccgcgttccccacgggcgaccgtggcggtg<br>gctgcgttggcggcctgcctatgggttaac<br>ccataggacgctctaatacagacatggtgc<br>gaagagtttattgagctggttagtatccct<br>ccggcccctgaatgcggctaatcctaactg<br>cggagcacgtgcctccaatccaggggggttg<br>catgtcgtaacgggtaactctgcagcggaa<br>ccgactactttgggtgtccgtgtttccttt<br>tattcttatactggctgcttatggtgacaa<br>tcgaggaattgttaccatatagctattgga<br>ttggccatccggtgtctaacagagcgatta<br>tatacctctttgttggatttatgcagctca<br>ataccaccaactttaacacattgaaatata<br>tcttaaagttaaacacagcaaa |

In some embodiments, an IRES of the invention is an IRES having a sequence as listed in Table 3 (SEQ ID NO: 1-72). In some embodiments, an IRES is a Salivirus IRES. In some embodiments, an IRES is a Salivirus SZ1 IRES.

TABLE 4

*Anabaena* permutation site 5' intron fragment sequences.

| SEQ ID NO. | Permutation site | Sequence |
|---|---|---|
| 73 | L2-1 | GAAGAAATTCTTTAAGTGGATGCTC<br>TCAAACTCAGGGAAACCTAAATCTA<br>GTTATAGACAAGGCAATCCTGAGCC<br>AAGCCGAAGTAGTAATTAGTAAGTT<br>AACAATAGATGACTTACAACTAATC<br>GGAAGGTGCAGAGACTCGACGGGAG<br>CTACCCTAACGTCAAGACGAGGGTA<br>AAGAGAGAGTCCAATTCTCAAAGCC<br>AATAGGCAGTAGCGAAAGCTGCAAG<br>AGAATGAAAATCCGT |
| 74 | L2-2 | AAGAAATTCTTTAAGTGGATGCTCT<br>CAAACTCAGGGAAACCTAAATCTAG<br>TTATAGACAAGGCAATCCTGAGCCA<br>AGCCGAAGTAGTAATTAGTAAGTTA<br>ACAATAGATGACTTACAACTAATCG<br>GAAGGTGCAGAGACTCGACGGGAGC<br>TACCCTAACGTCAAGACGAGGGTAA<br>AGAGAGAGTCCAATTCTCAAAGCCA<br>ATAGGCAGTAGCGAAAGCTGCAAGA<br>GAATGAAAATCCGT |
| 75 | L2-3 | AGAAATTCTTTAAGTGGATGCTCTC<br>AAACTCAGGGAAACCTAAATCTAGT<br>TATAGACAAGGCAATCCTGAGCCAA<br>GCCGAAGTAGTAATTAGTAAGTTAA<br>CAATAGATGACTTACAACTAATCGG<br>AAGGTGCAGAGACTCGACGGGAGCT<br>ACCCTAACGTCAAGACGAGGGTAAA<br>GAGAGAGTCCAATTCTCAAAGCCAA<br>TAGGCAGTAGCGAAAGCTGCAAGAG<br>AATGAAAATCCGT |
| 76 | L5-1 | GTTATAGACAAGGCAATCCTGAGCC<br>AAGCCGAAGTAGTAATTAGTAAGTT<br>AACAATAGATGACTTACAACTAATC<br>GGAAGGTGCAGAGACTCGACGGGAG<br>CTACCCTAACGTCAAGACGAGGGTA<br>AAGAGAGAGTCCAATTCTCAAAGCC<br>AATAGGCAGTAGCGAAAGCTGCAAG<br>AGAATGAAAATCCGT |
| 77 | L5-2 | TTATAGACAAGGCAATCCTGAGCCA<br>AGCCGAAGTAGTAATTAGTAAGTTA<br>ACAATAGATGACTTACAACTAATCG<br>GAAGGTGCAGAGACTCGACGGGAGC<br>TACCCTAACGTCAAGACGAGGGTAA<br>AGAGAGAGTCCAATTCTCAAAGCCA<br>ATAGGCAGTAGCGAAAGCTGCAAGA<br>GAATGAAAATCCGT |
| 78 | L5-3 | TATAGACAAGGCAATCCTGAGCCAA<br>GCCGAAGTAGTAATTAGTAAGTTAA<br>CAATAGATGACTTACAACTAATCGG<br>AAGGTGCAGAGACTCGACGGGAGCT<br>ACCCTAACGTCAAGACGAGGGTAAA<br>GAGAGAGTCCAATTCTCAAAGCCAA<br>TAGGCAGTAGCGAAAGCTGCAAGAG<br>AATGAAAATCCGT |
| 79 | L5-4 | ATAGACAAGGCAATCCTGAGCCAAG<br>CCGAAGTAGTAATTAGTAAGTTAAC<br>AATAGATGACTTACAACTAATCGGA<br>AGGTGCAGAGACTCGACGGGAGCTA<br>CCCTAACGTCAAGACGAGGGTAAAG<br>AGAGAGTCCAATTCTCAAAGCCAAT<br>AGGCAGTAGCGAAAGCTGCAAGAGA<br>ATGAAAATCCGT |
| 80 | L5-5 | TAGACAAGGCAATCCTGAGCCAAGC<br>CGAAGTAGTAATTAGTAAGTTAACA<br>ATAGATGACTTACAACTAATCGGAA<br>GGTGCAGAGACTCGACGGGAGCTAC |

TABLE 4-continued

*Anabaena* permutation site 5' intron fragment sequences.

| SEQ ID NO. | Permutation site | Sequence |
|---|---|---|
| | | CCTAACGTCAAGACGAGGGTAAAGA<br>GAGAGTCCAATTCTCAAAGCCAATA<br>GGCAGTAGCGAAAGCTGCAAGAGAA<br>TGAAAATCCGT |
| 81 | L6-1 | ACAATAGATGACTTACAACTAATCG<br>GAAGGTGCAGAGACTCGACGGGAGC<br>TACCCTAACGTCAAGACGAGGGTAA<br>AGAGAGAGTCCAATTCTCAAAGCCA<br>ATAGGCAGTAGCGAAAGCTGCAAGA<br>GAATGAAAATCCGT |
| 82 | L6-2 | CAATAGATGACTTACAACTAATCGG<br>AAGGTGCAGAGACTCGACGGGAGCT<br>ACCCTAACGTCAAGACGAGGGTAAA<br>GAGAGAGTCCAATTCTCAAAGCCAA<br>TAGGCAGTAGCGAAAGCTGCAAGAG<br>AATGAAAATCCGT |
| 83 | L6-3 | AATAGATGACTTACAACTAATCGGA<br>AGGTGCAGAGACTCGACGGGAGCTA<br>CCCTAACGTCAAGACGAGGGTAAAG<br>AGAGAGTCCAATTCTCAAAGCCAAT<br>AGGCAGTAGCGAAAGCTGCAAGAGA<br>ATGAAAATCCGT |
| 84 | L6-4 | ATAGATGACTTACAACTAATCGGAA<br>GGTGCAGAGACTCGACGGGAGCTAC<br>CCTAACGTCAAGACGAGGGTAAAGA<br>GAGAGTCCAATTCTCAAAGCCAATA<br>GGCAGTAGCGAAAGCTGCAAGAGAA<br>TGAAAATCCGT |
| 85 | L6-5 | TAGATGACTTACAACTAATCGGAAG<br>GTGCAGAGACTCGACGGGAGCTACC<br>CTAACGTCAAGACGAGGGTAAAGAG<br>AGAGTCCAATTCTCAAAGCCAATAG<br>GCAGTAGCGAAAGCTGCAAGAGAAT<br>GAAAATCCGT |
| 86 | L6-6 | AGATGACTTACAACTAATCGGAAGG<br>TGCAGAGACTCGACGGGAGCTACCC<br>TAACGTCAAGACGAGGGTAAAGAGA<br>GAGTCCAATTCTCAAAGCCAATAGG<br>CAGTAGCGAAAGCTGCAAGAGAATG<br>AAAATCCGT |
| 87 | L6-7 | GATGACTTACAACTAATCGGAAGGT<br>GCAGAGACTCGACGGGAGCTACCCT<br>AACGTCAAGACGAGGGTAAAGAGAG<br>AGTCCAATTCTCAAAGCCAATAGGC<br>AGTAGCGAAAGCTGCAAGAGAATGA<br>AAATCCGT |
| 88 | L6-8 | ATGACTTACAACTAATCGGAAGGTG<br>CAGAGACTCGACGGGAGCTACCCTA<br>ACGTCAAGACGAGGGTAAAGAGAGA<br>GTCCAATTCTCAAAGCCAATAGGCA<br>GTAGCGAAAGCTGCAAGAGAATGAA<br>AATCCGT |
| 89 | L6-9 | TGACTTACAACTAATCGGAAGGTGC<br>AGAGACTCGACGGGAGCTACCCTAA<br>CGTCAAGACGAGGGTAAAGAGAGAG<br>TCCAATTCTCAAAGCCAATAGGCAG<br>TAGCGAAAGCTGCAAGAGAATGAAA<br>ATCCGT |
| 90 | L8-1 | CAAGACGAGGGTAAAGAGAGAGTCC<br>AATTCTCAAAGCCAATAGGCAGTAG<br>CGAAAGCTGCAAGAGAATGAAAATC<br>CGT |

TABLE 4-continued

*Anabaena* permutation site 5' intron fragment sequences.

| SEQ ID NO. | Permutation site | Sequence |
|---|---|---|
| 91 | L8-2 | AAGACGAGGGTAAAGAGAGAGTCCAATTCTCAAAGCCAATAGGCAGTAGCGAAAGCTGCAAGAGAATGAAAATCCGT |
| 92 | L8-3 | AGACGAGGGTAAAGAGAGAGTCCAATTCTCAAAGCCAATAGGCAGTAGCGAAAGCTGCAAGAGAATGAAAATCCGT |
| 93 | L8-4 | GACGAGGGTAAAGAGAGAGTCCAATTCTCAAAGCCAATAGGCAGTAGCGAAAGCTGCAAGAGAATGAAAATCCGT |
| 94 | L8-5 | ACGAGGGTAAAGAGAGAGTCCAATTCTCAAAGCCAATAGGCAGTAGCGAAAGCTGCAAGAGAATGAAAATCCGT |
| 95 | L9a-1 | AATAGGCAGTAGCGAAAGCTGCAAGAGAATGAAAATCCGT |
| 96 | L9a-2 | ATAGGCAGTAGCGAAAGCTGCAAGAGAATGAAAATCCGT |
| 97 | L9a-3 | TAGGCAGTAGCGAAAGCTGCAAGAGAATGAAAATCCGT |
| 98 | L9a-4 | AGGCAGTAGCGAAAGCTGCAAGAGAATGAAAATCCGT |
| 99 | L9a-5 | GGCAGTAGCGAAAGCTGCAAGAGAATGAAAATCCGT |
| 100 | L9-1 | GAAAGCTGCAAGAGAATGAAAATCCGT |
| 101 | L9-2 | AAAGCTGCAAGAGAATGAAAATCCGT |
| 102 | L9-3 | AAGCTGCAAGAGAATGAAAATCCGT |
| 103 | L9-4 | AGCTGCAAGAGAATGAAAATCCGT |
| 104 | L9-5 | GCTGCAAGAGAATGAAAATCCGT |
| 105 | L9-6 | CTGCAAGAGAATGAAAATCCGT |
| 106 | L9-7 | AAGAGAATGAAAATCCGT |
| 107 | L9-8 | AGAGAATGAAAATCCGT |
| 108 | L9-9 | GAGAATGAAAATCCGT |
| 109 | L9a-6 | GCAGTAGCGAAAGCTGCAAGAGAATGAAAATCCGT |
| 110 | L9a-7 | AGTAGCGAAAGCTGCAAGAGAATGAAAATCCGT |
| 111 | L9a-8 | GTAGCGAAAGCTGCAAGAGAATGAAAATCCGT |

In some embodiments, a 5' intron fragment is a fragment having a sequence listed in Table 4. Typically, a construct containing a 5' intron fragment listed in Table 4 will contain a corresponding 3' intron fragment as listed in Table 5 (e.g., both representing fragments with the L9a-8 permutation site).

TABLE 5

Anabaena permutation site 3' intron fragment sequences.

| SEQ ID NO. | Permutation site | Sequence |
|---|---|---|
| 112 | L2-1 | ACGGACTTAAATAATTGAGCCTTAAA |
| 113 | L2-2 | ACGGACTTAAATAATTGAGCCTTAAAG |
| 114 | L2-3 | ACGGACTTAAATAATTGAGCCTTAAAGA |
| 115 | L5-1 | ACGGACTTAAATAATTGAGCCTTAAAGAAGAAATTCTTTAAGTGGATGCTCTCAAACTCAGGGAAACCTAAATCTA |
| 116 | L5-2 | ACGGACTTAAATAATTGAGCCTTAAAGAAGAAATTCTTTAAGTGGATGCTCTCAAACTCAGGGAAACCTAAATCTAG |
| 117 | L5-3 | ACGGACTTAAATAATTGAGCCTTAAAGAAGAAATTCTTTAAGTGGATGCTCTCAAACTCAGGGAAACCTAAATCTAGT |
| 118 | L5-4 | ACGGACTTAAATAATTGAGCCTTAAAGAAGAAATTCTTTAAGTGGATGCTCTCAAACTCAGGGAAACCTAAATCTAGTT |
| 119 | L5-5 | ACGGACTTAAATAATTGAGCCTTAAAGAAGAAATTCTTTAAGTGGATGCTCTCAAACTCAGGGAAACCTAAATCTAGTTA |
| 120 | L6-1 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTA |
| 121 | L6-2 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAA |
| 122 | L6-3 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAAC |
| 123 | L6-4 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACA |
| 124 | L6-5 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAA |
| 125 | L6-6 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAAT |
| 126 | L6-7 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACA |

TABLE 5-continued

Anabaena permutation site 3' intron fragment sequences.

| SEQ ID NO. | Permutation site | Sequence |
|---|---|---|
| | | ATA |
| 127 | L6-8 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAG |
| 128 | L6-9 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGA |
| 129 | L8-1 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGT |
| 130 | L8-2 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTC |
| 131 | L8-3 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCA |
| 132 | L8-4 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAA |
| 133 | L8-5 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAG |
| 134 | L9a-1 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCC |
| 135 | L9a-2 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCA |
| 136 | L9a-3 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAA |
| 137 | L9a-4 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAAT |
| 138 | L9a-5 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATA |
| 139 | L9-1 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGC |
| 140 | L9-2 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCG |
| 141 | L9-3 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGA |
| 142 | L9-4 | ACGGACTTAAATAATTGAGCCTTAAAGAAGAAATTCTTTAAGTGGATGCTCT |

TABLE 5-continued

Anabaena permutation site 3' intron fragment sequences.

| SEQ ID NO. | Permutation site | Sequence |
|---|---|---|
| | | CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAC<br>AGTCCAATTCTCAAAGCCAATAGGCA<br>GTAGCGAA |
| 143 | L9-5 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA<br>GTAGCGAAA |
| 144 | L9-6 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA<br>GTAGCGAAAG |
| 145 | L9-7 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA<br>GTAGCGAAAGCTGC |
| 146 | L9-8 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA<br>GTAGCGAAAGCTGCA |
| 147 | L9-9 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA<br>GTAGCGAAAGCTGCAA |
| 148 | L9a-6 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAG |
| 149 | L9a-7 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGC |
| 150 | L9a-8 | ACGGACTTAAATAATTGAGCCTTAAA<br>GAAGAAATTCTTTAAGTGGATGCTCT<br>CAAACTCAGGGAAACCTAAATCTAGT<br>TATAGACAAGGCAATCCTGAGCCAAG<br>CCGAAGTAGTAATTAGTAAGTTAACA<br>ATAGATGACTTACAACTAATCGGAAG<br>GTGCAGAGACTCGACGGGAGCTACCC<br>TAACGTCAAGACGAGGGTAAAGAGAG<br>AGTCCAATTCTCAAAGCCAATAGGCA |

In some embodiments, a 3' intron fragment is a fragment having a sequence listed in Table 5. In some embodiments, a construct containing a 3' intron fragment listed in Table 5 will contain a corresponding 5' intron fragment as listed in Table 4 (e.g., both representing fragments with the L9a-8 permutation site).

TABLE 6

Non-anabaena permutation site 5' intron fragment sequences.

| SEQ ID NO. | Intron | Sequence |
|---|---|---|
| 151 | Azop1 | tgcgccgatgaaggtgtagagacta<br>gacggcacccacctaaggcaaacgc<br>tatggtgaaggcatagtccagggag<br>tggcgaaagtcacacaaaccggaat<br>ccgt |
| 152 | Azop2 | ccgggcgtatggcaacgccgagcca<br>agcttcggcgcctgcgccgatgaag<br>gtgtagagactagacggcacccacc<br>taaggcaaacgctatggtgaaggca<br>tagtccagggagtggcgaaagtcac<br>acaaaccggaatccgt |
| 153 | Azop3 | acggcacccacctaaggcaaacgct<br>atggtgaaggcatagtccagggagt<br>ggcgaaagtcacacaaaccggaatc<br>cgt |
| 154 | Azop4 | acgctatggtgaaggcatagtccag<br>ggagtggcgaaagtcacacaaaccg<br>gaatccgt |
| 155 | S795p1 | attaaagttatagaattatcagaga<br>atgatatagtccaagccttatggta<br>acatgagggcacttgaccctggtag |
| 156 | Twortp1 | aagatgtaggcaatcctgagctaag<br>ctcttagtaataagagaaagtgcaa<br>cgactattccgataggaagtagggt<br>caagtgactcgaaatggggattacc<br>cttctagggtagtgatatagtctga<br>acatatatggaaacatatagaagga<br>taggagtaacgaacctattcgtaac |

TABLE 6-continued

Non-anabaena permutation site 5' intron fragment sequences.

| SEQ ID NO. | Intron | Sequence |
|---|---|---|
| | | ataattgaacttttagttat |
| 157 | Twortp2 | taataagagaaagtgcaacgactat<br>tccgataggaagtagggtcaagtga<br>ctcgaaatggggattacccttctag<br>ggtagtgatatagtctgaacatata<br>tggaaacatatagaaggataggagt<br>aacgaacctattcgtaacataattg<br>aacttttagttat |
| 158 | Twortp3 | taggaagtagggtcaagtgactcga<br>aatggggattacccttctagggtag<br>tgatatagtctgaacatatatggaa<br>acatatagaaggataggagtaacga<br>acctattcgtaacataattgaactt<br>ttagttat |
| 159 | Twortp4 | ctagggtagtgatatagtctgaaca<br>tatatggaaacatatagaaggatag<br>gagtaacgaacctattcgtaacata<br>attgaacttttagttat |
| 160 | LSUp1 | agttaataaagatgatgaaatagtc<br>tgaaccattttgagaaaagtggaaa<br>taaaagaaaatcttttatgataaca<br>taaattgaacaggctaa |
| 161 | Phip1 | caaagactgatgatatagtccgacac<br>tcctagtaataggagaatacagaaag<br>gatgaaatcc |
| 162 | Nostoc | agtcgagggtaaagggagagtccaat<br>tctcaaagcctattggcagtagcgaa<br>agctgcgggagaatgaaaatccgt |
| 163 | Nostoc | agccgagggtaaagggagagtccaat<br>tctcaaagccaataggcagtagcgaa<br>agctgcgggagaatgaaaatccgt |
| 164 | Nodularia | agccgagggtaaagggagagtccaat<br>tctcaaagccgaaggttattaaaacc<br>tggcagcagtgaaagctgcgggagaa<br>tgaaaatccgt |
| 165 | Pleurocapsa | agctgagggtaaagagagagtccaat<br>tctcaaagccagcagatggcagtagc<br>gaaagctgcgggagaatgaaaatccg<br>t |
| 166 | Planktothrix | agccgagggtaaagagagagtccaat<br>tctcaaagccaattggtagtagcgaa<br>agctacgggagaatgaaaatccgt |

In some embodiments, a 5' intron fragment is a fragment having a sequence listed in Table 6. A construct containing a 5' intron fragment listed in Table 6 will contain a corresponding 3' intron fragment as listed in Table 7 (e.g., both representing fragments with the Azop1 intron).

TABLE 7

Non-anabaena permutation site 3' intron fragment sequences.

| SEQ ID NO. | Intron | Sequence |
|---|---|---|
| 167 | Azop1 | gcggactcatatttcgatgtgccttg<br>cgccgggaaaccacgcaagggatggt<br>gtcaaattcggcgaaacctaagcgcc<br>cgcccgggcgtatggcaacgccgagc<br>caagcttcggcgcc |
| 168 | Azop2 | gcggactcatatttcgatgtgccttg<br>cgccgggaaaccacgcaagggatggt<br>gtcaaattcggcgaaacctaagcgcc<br>cgc |
| 169 | Azop3 | gcggactcatatttcgatgtgccttg<br>cgccgggaaaccacgcaagggatggt<br>gtcaaattcggcgaaacctaagcgcc<br>cgcccgggcgtatggcaacgccgagc<br>caagcttcggcgcctgcgccgatgaa<br>ggtgtagagactag |
| 170 | Azop4 | gcggactcatatttcgatgtgccttg<br>cgccgggaaaccacgcaagggatggt<br>gtcaaattcggcgaaacctaagcgcc<br>cgcccgggcgtatggcaacgccgagc<br>caagcttcggcgcctgcgccgatgaa<br>ggtgtagagactagacggcacccacc<br>taaggcaa |
| 171 | S795p1 | aggattagatactacactaagtgtcc<br>cccagactggtgacagtctggtgtgc<br>atccagctatatcggtgaaaccccat<br>tggggtaataccgagggaagctatat<br>tatatatatattaataaatagccccg<br>tagagactatgtaggtaaggagatag<br>aagatgataaaatcaaaatcatc |
| 172 | Twortp1 | actactgaaagcataaataattgtgc<br>ctttatacagtaatgtatatcgaaaa<br>atcctctaattcagggaacacctaaa<br>caaact |
| 173 | Twortp2 | actactgaaagcataaataattgtgc<br>ctttatacagtaatgtatatcgaaaa<br>atcctctaattcagggaacacctaaa<br>caaactaagatgtaggcaatcctgag<br>ctaagctcttag |
| 174 | Twortp3 | actactgaaagcataaataattgtgc<br>ctttatacagtaatgtatatcgaaaa<br>atcctctaattcagggaacacctaaa<br>caaactaagatgtaggcaatcctgag<br>ctaagctcttagtaataagagaaagt<br>gcaacgactattccga |
| 175 | Twortp4 | actactgaaagcataaataattgtgc<br>ctttatacagtaatgtatatcgaaaa<br>atcctctaattcagggaacacctaaa<br>caaactaagatgtaggcaatcctgag<br>ctaagctcttagtaataagagaaagt<br>gcaacgactattccgataggaagtag<br>ggtcaagtgactcgaaatggggatta<br>ccctt |
| 176 | LSUp1 | cgctagggatttataactgtgagtc<br>ctccaatattataaaatgttggtaa<br>tatattgggtaaatttcaaagacaa<br>cttttctccacgtcaggatatagtg<br>tatttgaagcgaaacttattttagc<br>agtgaaaaagcaaataaggacgttc<br>aacgactaaaaggtgagtattgcta<br>acaataatcctttttttttaatgccc<br>aacatctttattaact |
| 177 | Phip1 | gtgggtgcataaactatttcattgt<br>gcacattaaatctggtgaactcggt<br>gaaaccctaatggggcaataccgag<br>ccaagccatagggaggatatatgag |

TABLE 7-continued

| Non-anabaena permutation site 3' intron fragment sequences. | | |
|---|---|---|
| SEQ ID NO. | Intron | Sequence |
| | | aggcaagaagttaattcttgaggccactgagactggctgtatcatccctacgtcacacaaacttaatgccgatggttatttcagaaagaaaaccaatggcgtcttagagatgtatcacagaacggtgtggaaggagcataacggagacatacctgatggcttcgagatagaccataagtgtcgcaatagggcttgctgtaatatagagcatttacagatgcttgagggtacagcccacactgttaagaccaatcgtgaacgctacgcagacagaaaggaaacagctagggaatactggctggagactggatgtaccggcctagcactcggtgagaagtttggtgtgtcgttctcttctgcttgtaagtggattagagaatggaaggcgtagagactatccgaaaggagtagggccgagggtgagactccctcgtaacccgaagcgccagacagtcaact |
| 178 | Nostoc | acggacttaagtaattgagccttaaagaagaaattctttaagtggcagctctcaaactcagggaaacctaaatctgttcacagacaaggcaatcctgagccaagccgaaagagtcatgagtgctgagtagtgagtaaaataaaagctcacaactcagaggttgtaactctaagctagtcggaaggtgcagagactcgacgggagctaccctaacgtaa |
| 179 | Nostoc | acggacttaaactgaattgagccttagagaagaaattctttaagtgtcagctctcaaactcagggaaacctaaatctgttgacagacaaggcaatcctgagccaagccgagaactctaagttattcggaaggtgcagagactcgacgggagctaccctaacgtca |
| 180 | Nodularia | acggacttagaaaactgagccttgatcgagaaatctttcaagtggaagctctcaaattcagggaaacctaaatctgtttacagatatggcaatcctgagccaagccgaaacaagtcctgagtgttaaagctcataactcatcggaaggtgcagagactcgacgggagctaccctaacgtta |
| 181 | Pleurocapsa | acggacttaaaaaaattgagccttggcagagaaatctgtcatgcgaacgctctcaaattcagggaaacctaagtctggcaacagatatggcaatcctgagccaagccttaatcaaggaaaaaaacatttttaccttttaccttgaaaggaaggtgcagagactcaacgggagctaccctaacaggtca |
| 182 | Planktothrix | acggacttaaagataaattgagccttgaggcgagaaatctctcaagtgtaagctgtcaaattcagggaaacctaaatctgtaaattcagacaaggcaatcctgagccaagcctaggggtattagaaatgagggagtttccccaatctaagatcaatacctaggaaggtgcagagactcgacgggagctaccctaacgtta |

In some embodiments, a 3' intron fragment is a fragment having a sequence listed in Table 7. A construct containing a 3' intron fragment listed in Table 7 will contain the corresponding 5' intron fragment as listed in Table 6 (e.g., both representing fragments with the Azop1 intron).

TABLE 8

| Spacer and *Anabaena* 5' intron fragment sequences. | | |
|---|---|---|
| SEQ ID NO. | Spacer | Sequence |
| 183 | T25 L10 | agtatataagaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 184 | T25 L20 | ctgaaattatacttatactcaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 185 | T25 L30 (180-10) [Control] | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 186 | T25 L40 | catcaacaatatgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 187 | T25 L50 | catcaacaatatgaaactatacttatactcagtatatgaagcattatcgcaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 188 | T50 L10 | tagcgtcagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 189 | T50 L20 | atactcatactagcgtcagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 190 | T50 L30 | gtgtgaagctatactcatactagcgtcagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 191 | T50 L40 | cctcacctgagtgtgaagctatactcatactagcgtcagcaaacaaacaaaTAGATGACTTACAACTAATCGGAAGGTGCAGAGACTCGACGGGAGCTACCCTAACGTCAAGACGAGGGTAAAGAGAGAG |

TABLE 8-continued

Spacer and *Anabaena* 5' intron fragment sequences.

| SEQ ID NO. | Spacer | Sequence |
| --- | --- | --- |
| | | TCCAATTCTCAAAGCCAATAGGCAGTAGCGAAAGCTGCAAGAGAATGAAAATCCGTggctcgcagc |
| 192 | T50 L50 | ccgaatgatgcctcacctgagtgtgaagctatactcatactagcgtcagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 193 | T75 L10 | cggtgcgagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 194 | T75 L20 | cgctccgacccagtgcgagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 195 | T25 L301MM | ctgaaattatactAatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 196 | T25 L303MM | ctgaaaAtatactAatactcaCtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 197 | T25 L305MM | ctgaTaAtataGtAatactcaCtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 198 | T25 L308MM | ctgaTaAtaAaGtAatacAcaCtataAgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 199 | T25 L30 OffTarget 10 | ctgaaattatacttatactctctaagttacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 200 | T25 L30 OffTarget 20 | ctgaaattatgtgtgttacAtctaagttacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 201 | T25 L30 OffTarget 30 | gttgatcggtgtgtgttacAtctaagttacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 202 | T25 L30125-10 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTgattaaacag |
| 203 | T25 L30 I25-20 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTgattcacaatataaattacg |
| 204 | T25 L30 I50-10 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggatcatagc |
| 205 | T25 L30 I50-20 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggatcgcagcataatatccg |
| 206 | T25 L30 I80-20 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagcgcgcctaccg |
| 207 | T25 L30 I80-20x2 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagcgcgcctaccgaaagccggcgtcgacgttagcgc |

TABLE 8-continued

Spacer and *Anabaena* 5' intron fragment sequences.

| SEQ ID NO. | Spacer | Sequence |
|---|---|---|
| 208 | T25 L30 I50-20x2 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggatcgcagcataatatccgaaacgaggatacaagtgacatgc |
| 209 | T25 L30 I25-20x2 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTgattcacaatctaaattacgaaacgataaatgataactctaac |
| 210 | T0 L0 | aaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 211 | T100 L5 | cgggcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 212 | T75 L30 | cgctccgacgagcttccggccagtgcgagcaaacaaacaaaTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGTggctcgcagc |
| 213 | T0 L0a | aaacaaaccacGGCAGTAGCGAAAGCTGCAAGAGAATGAAAATCCGTggctcgcagc |
| 214 | T25 L10a | agtatataagaaacaaaccacGGCAGTAGCGAAAGCTGCAAGAGAATGAAAATCCGTggctcgcagc |
| 215 | T25 L20a | ctgaaattatacttatactcaaacaaaccacGGCAGTAGCGAAAGCTGCAAGAGAATGAAAATCCGTggctcgcagc |
| 216 | T25 L30a (I80-10) [Control] | ctgaaattatacttatactcagtatatgacaaacaaaccacGGCAGTAGCGAAAGCTGCAAGAGAATGAAAATCCGTggctcgcagc |
| 217 | T50 L10a | tagcgtcagcaaacaaacaaaGGCAGTAGCGAAAGCTGCAAGAGAATGAAAATCCGTggctcgcagc |
| 218 | T50 L20a | atactcatactagcgtcagcaaacaaacaaaGGCAGTAGCGAAAGCTGCAAGAGAATGAAAATCCGTggctcgcagc |
| 219 | T50 L30a | gtgtgaagctatactcatactagcgtcagcaaacaaacaaaGGCAGTAGCGAAAGCTGCAAGAGAATGAAAATCCGTggctcgcagc |
| 220 | T75 L10a | cggtgcgagcaaacaaacaaaGGCAGTAGCGAAAGCTGCAAGAGAATGAAAATCCGTggctcgcagc |
| 221 | T75 L20a | cgctccgacccagtgcgagcaaacaaacaaaGGCAGTAGCGAAAGCTGCAAGAGAATGAAAATCCGTggctcgcagc |
| 222 | T75 L30a | cgctccgacgagcttccggccagtgcgagcaaacaaacaaaGGCAGTAGCGAAAGCTGCAAGAGAATGAAAATCCGTggctcgcagc |
| 223 | T0 L0b | aaacaaaccacAAGACGAGGGTAAAGAGAGAGTCCAATTCTCAAAGCCAATAGGCAGTAGCGAAAGCTGCAAGAGAATGAAAATCCGTggctcgcagc |
| 224 | T25 L10b | agtatataagaaacaaaccacAAGACGAGGGTAAAGAGAGAGTCCAATTCTCAAAGCCAATAGGCAGTAGCGAAAGCTGCAAGAGAATGAAAATCCGTggctcgcagc |
| 225 | T25 L20b | ctgaaattatacttatactcaaacaaaccacAAGACGAGGGTAAAGAGAGAGTCCAATTCTCAAAGCCAATAGGCAGTAGCGAAAGCTGCAAGAGAATGAAAATCCGTggctcgcagc |
| 226 | T25 L30b (I80-10) [Control] | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTggctcgcagc |
| 227 | T50 L10b | tagcgtcagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |
| 228 | T50 L20b | atactcatactagcgtcagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |
| 229 | T50 L30b | gtgtgaagctatactcatactagcgtcagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |
| 230 | T75 L10b | cggtgcgagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |
| 231 | T75 L20b | cgctccgacccagtgcgagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |

TABLE 8-continued

| Spacer and *Anabaena* 5' intron fragment sequences. | | |
|---|---|---|
| SEQ ID NO. | Spacer | Sequence |
| 232 | T75 L30b | cgctccgacgagcttccggccagtgcgagcaaacaaacaaaAAGACGAGGGTAAAGAGAGAGTCCAATTCTCAAAGCCAATAGGCAGTAGCGAAAGCTGCAAGAGAATGAAAATCCGTggctcgcagc |
| 233 | T25 L30 I0-0 | ctgaaattatacttatactcagtatatgacaaacaaaccacTAGATGACTTACAACTAATCGGAAGGTGCAGAGACTCGACGGGAGCTACCCTAACGTCAAGACGAGGGTAAAGAGAGAGTCCAATTCTCAAAGCCAATAGGCAGTAGCGAAAGCTGCAAGAGAATGAAAATCCGT |
| 234 | T25 L30a I0-0 | ctgaaattatacttatactcagtatatgacaaacaaaccacGGCAGTAGCGAAAGCTGCAAGAGAATGAAAATCCGT |
| 235 | T25 L30a I25-10 | ctgaaattatacttatactcagtatatgacaaacaaaccacGGCAGTAGCGAAAGCTGCAAGAGAATGAAAATCCGTgattaaacag |
| 236 | T25 L30a I25-20 | ctgaaattatacttatactcagtatatgacaaacaaaccacGGCAGTAGCGAAAGCTGCAAGAGAATGAAAATCCGTgattcacaatataaattacg |
| 237 | T25 L30a I50-10 | ctgaaattatacttatactcagtatatgacaaacaaaccacGGCAGTAGCGAAAGCTGCAAGAGAATGAAAATCCGTggatcatagc |
| 238 | T25 L30a I50-20 | ctgaaattatacttatactcagtatatgacaaacaaaccacGGCAGTAGCGAAAGCTGCAAGAGAATGAAAATCCGTggatcgcagcataatatccg |
| 239 | T25 L30a I80-20 | ctgaaattatacttatactcagtatatgacaaacaaaccacGGCAGTAGCGAAAGCTGCAAGAGAATGAAAATCCGTggctcgcagcgcgcctaccg |
| 240 | T25 L30b I0-0 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGT |
| 241 | T25 L30b I25-10 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTgattaaacag |
| 242 | T25 L30b I25-20 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTgattcacaatataaattacg |
| 243 | T25 L30b I50-10 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTggatcatagc |
| 244 | T25 L30b I50-20 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTggatcgcagcataatatccg |
| 245 | T25 L30b I80-20 | ctgaaattatacttatactcagtatatgacaaacaaaccacAAGACGAGGGTAAAGAGAGAGTCCAATTCTCAAAGCCAATAGGCAGTAGCGAAAGCTGCAAGAGAATGAAAATCCGTggctcgcagcgcgcctaccg |

In some embodiments, a spacer and 5' intron fragment are spacers and fragments having sequences as listed in Table 8.

TABLE 9

| Spacer and Anabaena 3' intron fragment sequences. | | |
|---|---|---|
| SEQ ID NO. | Spacer | Sequence |
| 246 | T25 L10 | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAAcacaaacacaacttatatact |
| 247 | T25 L20 | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAAcacaaacacaagagtataagtataatttcag |
| 248 | T25 L30 (I80-10) [Control] | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAAcacaaacacaagtcatatactgagtataagtataatttcag |

TABLE 9-continued

| Spacer and Anabaena 3' intron fragment sequences. | | |
|---|---|---|
| SEQ ID NO. | Spacer | Sequence |
| 249 | T25 L40 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcatattgttgatg |
| 250 | T25 L50 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagcgataatgcttcatatactgagtataagtatagtttcatattgttgatg |
| 251 | T50 L10 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctgacgcta |
| 252 | T50 L20 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctgacgctagtatgagtat |
| 253 | T50 L30 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctgacgctagtatgagtatagcttcacac |
| 254 | T50 L40 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctgacgctagtatgagtatagcttcacactcaggtgagg |
| 255 | T50 L50 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctgacgctagtatgagtatagcttcacactcaggtgaggcatcattcgg |
| 256 | T75 L10 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctcgcaccg |
| 257 | T75 L20 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctcgcactgggtcggagcg |
| 258 | T25 L30 1MM | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcag |
| 259 | T25 L30 3MM | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcag |
| 260 | T25 L30 5MM | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcag |

TABLE 9-continued

Spacer and Anabaena 3' intron fragment sequences.

| SEQ ID NO. | Spacer | Sequence |
|---|---|---|
| 261 | T25 L30 8MM | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcag |
| 262 | T25 L30 OffTarget 10 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtaacttagagagtataagtataatttcag |
| 263 | T25 L30 OffTarget 20 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtaacttagaTgtaacacacataatttcag |
| 264 | T25 L30 OffTarget 30 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtaacttagaTgtaacacacaccgatcaac |
| 265 | T25 L30 I25-10 | ctgtttaatcACGGACTTAAATAATTGAGCCTTAAAGAAG AAATTCTTTAAGTGGATGCTCTCAAACTCAGGGAAA CCTAAATCTAGTTATAGACAAGGCAATCCTGAGCCA AGCCGAAGTAGTAATTAGTAAGTTAACAAcacaaacaca agtcatatactgagtataagtataatttcag |
| 266 | T25 L30 I25-20 | cgtaatttatattgtgaatcACGGACTTAAATAATTGAGCCTTAA AGAAGAAATTCTTTAAGTGGATGCTCTCAAACTCAG GGAAACCTAAATCTAGTTATAGACAAGGCAATCCT GAGCCAAGCCGAAGTAGTAATTAGTAAGTTAACAAc acaaacacaagtcatatactgagtataagtataatttcag |
| 267 | T25 L30 I50-10 | gctatgatccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caagtcatatactgagtataagtataatttcag |
| 268 | T25 L30 I50-20 | cggatattatgctgcgatccACGGACTTAAATAATTGAGCCTTA AAGAAGAAATTCTTTAAGTGGATGCTCTCAAACTCA GGGAAACCTAAATCTAGTTATAGACAAGGCAATCC TGAGCCAAGCCGAAGTAGTAATTAGTAAGTTAACA Acacaaacacaagtcatatactgagtataagtataatttcag |
| 269 | T25 L30 I80-20 | cggtaggcgcgctgcgagccACGGACTTAAATAATTGAGCCTT AAAGAAGAAATTCTTTAAGTGGATGCTCTCAAACTC AGGGAAACCTAAATCTAGTTATAGACAAGGCAATC CTGAGCCAAGCCGAAGTAGTAATTAGTAAGTTAAC AAcacaaacacaagtcatatactgagtataagtataatttcag |
| 270 | T25 L30 I80-20x2 | gcgctaacgtcgacgccggcaaacggtaggcgcgctgcgagccACGGACT TAAATAATTGAGCCTTAAAGAAGAAATTCTTTAAGT GGATGCTCTCAAACTCAGGGAAACCTAAATCTAGTT ATAGACAAGGCAATCCTGAGCCAAGCCGAAGTAGT AATTAGTAAGTTAACAAcacaaacacaagtcatatactgagtataagt ataatttcag |
| 271 | T25 L30 I50-20x2 | gcatgtcacttgtatcctcgaaacggatattatgctgcgatccACGGACTTAA ATAATTGAGCCTTAAAGAAGAAATTCTTTAAGTGGA TGCTCTCAAACTCAGGGAAACCTAAATCTAGTTATA GACAAGGCAATCCTGAGCCAAGCCGAAGTAGTAAT TAGTAAGTTAACAAcacaaacacaagtcatatactgagtataagtataatt tcag |
| 272 | T25 L30 I25-20x2 | gttagagttatcatttatcgaaacgtaatttagattgtgaatcACGGACTTAAA TAATTGAGCCTTAAAGAAGAAATTCTTTAAGTGGAT GCTCTCAAACTCAGGGAAACCTAAATCTAGTTATAG |

TABLE 9-continued

| Spacer and Anabaena 3' intron fragment sequences. | | |
|---|---|---|
| SEQ ID NO. | Spacer | Sequence |
| | | ACAAGGCAATCCTGAGCCAAGCCGAAGTAGTAATT AGTAAGTTAACAAcacaaacacaagtcatatactgagtataagtataattt cag |
| 273 | T0 L0 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAcacaaaca caa |
| 274 | T100 L5 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagcccg |
| 275 | T75 L30 | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAAaacaaaaa caagctcgcactggccggaagctcgtcggagcg |
| 276 | T0 L0a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAcacaaacacaa |
| 277 | T25 L10a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAcacaaacacaacttatatac t |
| 278 | T25 L20a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAcacaaacacaagagtataa gtataatttcag |
| 279 | T25 L30 (I80-10) [Control] | agctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAcacaaacacaagtcatata ctgagtataagtataatttcag |
| 280 | T50 L10a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctgacg cta |
| 281 | T50 L20a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctgacg ctagtatgagtat |

TABLE 9-continued

Spacer and Anabaena 3' intron fragment sequences.

| SEQ ID NO. | Spacer | Sequence |
|---|---|---|
| 282 | T50 L30a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctgacg ctagtatgagtatagcttcacac |
| 283 | T75 L10a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctcgca ccg |
| 284 | T75 L20a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctcgca ctgggtcggagcg |
| 285 | T75 L30a | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAaacaaaaacaagctcgca ctggccggaagctcgtcggagcg |
| 286 | T0 L0b | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCcacaaacacaa |
| 287 | T25 L10b | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCcacaaacacaacttatatact |
| 288 | T25 L20b | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCcacaaacacaagagtataagtataatttca g |
| 289 | T25 L30b (I80-10) [Control] | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCcacaaacacaagtcatatactgagtataa gtataatttcag |
| 290 | T50 L10b | gctgcgagccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCaacaaaaacaagctgacgcta |

TABLE 9-continued

Spacer and Anabaena 3' intron fragment sequences.

| SEQ ID NO. | Spacer | Sequence |
|---|---|---|
| 291 | T50 L20b | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCaacaaaaacaagctgacgctagtatgagtat |
| 292 | T50 L30b | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCaacaaaaacaagctgacgctagtatgagtatagcttcacac |
| 293 | T75 L10b | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCaacaaaaacaagctcgcaccg |
| 294 | T75 L20b | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCaacaaaaacaagctcgcactgggtcggagcg |
| 295 | T75 L30b | gctgcgagccACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCaacaaaaacaagctcgcactggccggaagctcgtcggagcg |
| 296 | T25 L30 I0-0 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAAcacaaacacaagtcatatactgagtataagtataatttcag |
| 297 | T25 L30a I0-0 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAcacaaacacaagtcatatactgagtataagtataatttcag |
| 298 | T25 L30a I25-10 | ctgtttaatcACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAcacaaacacaagtcatatactgagtataagtataatttcag |
| 299 | T25 L30a I25-20 | cgtaatttatattgtgaatcACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAACAATAGATGACTTACAACTAATCGGAAGGTGCAGAGACTCGACGGGAGCTACCCTAACGTCAAGACGAGGGTAAAGAGAGAGTCCAATTCTCAAAGCCAATAcacaaacacaagtcatatactgagtataagtataatttcag |
| 300 | T25 L30a I50-10 | gctatgatccACGGACTTAAATAATTGAGCCTTAAAGAAGAAATTCTTTAAGTGGATGCTCTCAAACTCAGGGAA |

TABLE 9-continued

Spacer and Anabaena 3' intron fragment sequences.

| SEQ ID NO. | Spacer | Sequence |
|---|---|---|
| | | ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCAAGACGAGGGTAAAGAG AGAGTCCAATTCTCAAAGCCAATAcacaaacacaagtcatata ctgagtataagtataatttcag |
| 301 | T25 L30a I50-20 | cggatattatgctgcgatccACGGACTTAAATAATTGAGCCTTA AAGAAGAAATTCTTTAAGTGGATGCTCTCAAACTCA GGGAAACCTAAATCTAGTTATAGACAAGGCAATCC TGAGCCAAGCCGAAGTAGTAATTAGTAAGTTAACA ATAGATGACTTACAACTAATCGGAAGGTGCAGAGA CTCGACGGGAGCTACCCTAACGTCAAGACGAGGGT AAAGAGAGAGTCCAATTCTCAAAGCCAATAcacaaaca caagtcatatactgagtataagtataatttcag |
| 302 | T25 L30a I80-20 | cggtaggcgcgctgcgagccACGGACTTAAATAATTGAGCCTT AAAGAAGAAATTCTTTAAGTGGATGCTCTCAAACTC AGGGAAACCTAAATCTAGTTATAGACAAGGCAATC CTGAGCCAAGCCGAAGTAGTAATTAGTAAGTTAAC AATAGATGACTTACAACTAATCGGAAGGTGCAGAG ACTCGACGGGAGCTACCCTAACGTCAAGACGAGGG TAAAGAGAGAGTCCAATTCTCAAAGCCAATAcacaaac acaagtcatatactgagtataagtataatttcag |
| 303 | T25 L30b I0-0 | ACGGACTTAAATAATTGAGCCTTAAAGAAGAAATT CTTTAAGTGGATGCTCTCAAACTCAGGGAAACCTAA ATCTAGTTATAGACAAGGCAATCCTGAGCCAAGCC GAAGTAGTAATTAGTAAGTTAACAATAGATGACTTA CAACTAATCGGAAGGTGCAGAGACTCGACGGGAGC TACCCTAACGTCcacaaacacaagtcatatactgagtataagtataatttca g |
| 304 | T25 L30b I25-10 | ctgtttaatcACGGACTTAAATAATTGAGCCTTAAAGAAG AAATTCTTTAAGTGGATGCTCTCAAACTCAGGGAAA CCTAAATCTAGTTATAGACAAGGCAATCCTGAGCCA AGCCGAAGTAGTAATTAGTAAGTTAACAATAGATG ACTTACAACTAATCGGAAGGTGCAGAGACTCGACG GGAGCTACCCTAACGTCcacaaacacaagtcatatactgagtataagt ataatttcag |
| 305 | T25 L30b I25-20 | cgtaatttatattgtgaatcACGGACTTAAATAATTGAGCCTTAA AGAAGAAATTCTTTAAGTGGATGCTCTCAAACTCAG GGAAACCTAAATCTAGTTATAGACAAGGCAATCCT GAGCCAAGCCGAAGTAGTAATTAGTAAGTTAACAA TAGATGACTTACAACTAATCGGAAGGTGCAGAGAC TCGACGGGAGCTACCCTAACGTCcacaaacacaagtcatatact gagtataagtataatttcag |
| 306 | T25 L30b I50-10 | gctatgatccACGGACTTAAATAATTGAGCCTTAAAGAA GAAATTCTTTAAGTGGATGCTCTCAAACTCAGGGAA ACCTAAATCTAGTTATAGACAAGGCAATCCTGAGCC AAGCCGAAGTAGTAATTAGTAAGTTAACAATAGAT GACTTACAACTAATCGGAAGGTGCAGAGACTCGAC GGGAGCTACCCTAACGTCcacaaacacaagtcatatactgagtataa gtataatttcag |
| 307 | T25 L30b I50-20 | cggatattatgctgcgatccACGGACTTAAATAATTGAGCCTTA AAGAAGAAATTCTTTAAGTGGATGCTCTCAAACTCA GGGAAACCTAAATCTAGTTATAGACAAGGCAATCC TGAGCCAAGCCGAAGTAGTAATTAGTAAGTTAACA ATAGATGACTTACAACTAATCGGAAGGTGCAGAGA CTCGACGGGAGCTACCCTAACGTCcacaaacacaagtcatata ctgagtataagtataatttcag |
| 308 | T25 L30b I80-20 | cggtaggcgcgctgcgagccACGGACTTAAATAATTGAGCCTT AAAGAAGAAATTCTTTAAGTGGATGCTCTCAAACTC AGGGAAACCTAAATCTAGTTATAGACAAGGCAATC CTGAGCCAAGCCGAAGTAGTAATTAGTAAGTTAAC AATAGATGACTTACAACTAATCGGAAGGTGCAGAG ACTCGACGGGAGCTACCCTAACGTCcacaaacacaagtcatat actgagtataagtataatttcag |

In some embodiments, a spacer and 3' intron fragment is a spacer and intron fragment having sequences as listed in Table 9.

TABLE 10

CAR sequences.

| SEQ ID NO. | CAR | Sequence |
|---|---|---|
| 309 | FMC63-4-1BB | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC<br>AAAAGCCCGACGGCACCGTGAAGCTGCTGATCTAC<br>CACACCAGCAGACTGCACAGCGGCGTGCCAAGCAG<br>ATTTTCTGGCAGCGGCTCTGGCACCGACTACAGCCT<br>GACAATCAGCAACCTGGAACAAGAGGATATCGCTA<br>CCTACTTCTGCCAGCAAGGCAACACCCTGCCTTACA<br>CCTTTGGCGGAGGCACCAAGCTGGAAATCACCGGC<br>TCTACAAGCGGCAGCGGCAAACCTGGATCTGGCGA<br>GGGATCTACCAAGGGCGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTGCCGCCGCTATCGA<br>AGTGATGTACCCTCCTCCTTACCTGGACAACGAGAA<br>GTCCAACGGCACCATCATCCACGTGAAGGGCAAGC<br>ACCTGTGTCCTTCTCCACTGTTCCCCGGACCTAGCA<br>AGCCTTTCTGGGTGCTCGTTGTTGTTGGCGGCGTGC<br>TGGCCTGTTACAGCCTGCTGGTTACCGTGGCCTTCA<br>TCATCTTTTGGGTCAAGAGAGGCCGGAAGAAACTTC<br>TTTATATATTCAAGCAGCCCTTTATGCGACCCGTTC<br>AGACTACCCAAGAGGAAGATGGATGCAGTTGCCGC<br>TTTCCAGAAGAGGAGGAGGGCGGGTGCGAACTGtaa |
| 310 | FMC63-CD28 | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC<br>AAAAGCCCGACGGCACCGTGAAGCTGCTGATCTAC<br>CACACCAGCAGACTGCACAGCGGCGTGCCAAGCAG<br>ATTTTCTGGCAGCGGCTCTGGCACCGACTACAGCCT<br>GACAATCAGCAACCTGGAACAAGAGGATATCGCTA<br>CCTACTTCTGCCAGCAAGGCAACACCCTGCCTTACA<br>CCTTTGGCGGAGGCACCAAGCTGGAAATCACCGGC<br>TCTACAAGCGGCAGCGGCAAACCTGGATCTGGCGA<br>GGGATCTACCAAGGGCGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTGCCGCCGCTATCGA<br>AGTGATGTACCCTCCTCCTTACCTGGACAACGAGAA<br>GTCCAACGGCACCATCATCCACGTGAAGGGCAAGC<br>ACCTGTGTCCTTCTCCACTGTTCCCCGGACCTAGCA<br>AGCCTTTCTGGGTGCTCGTTGTTGTTGGCGGCGTGC<br>TGGCCTGTTACAGCCTGCTGGTTACCGTGGCCTTCA<br>TCATCTTTTGGGTCCGAAGCAAGCGGAGCCGGCTGC<br>TGCACTCCGACTACATGAACATGACCCCTAGACGGC<br>CCGGACCAACCAGAAAGCACTACCAGCCTTACGCT<br>CCTCCTAGAGACTTCGCCGCCTACCGGTCCtaa |
| 311 | FMC63-CD28-zeta | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC |

TABLE 10-continued

CAR sequences.

| SEQ ID NO. | CAR | Sequence |
|---|---|---|
| | | AAAAGCCCGACGGCACCGTGAAGCTGCTGATCTAC CACACCAGCAGACTGCACAGCGGCGTGCCAAGCAG ATTTTCTGGCAGCGGCTCTGGCACCGACTACAGCCT GACAATCAGCAACCTGGAACAAGAGGATATCGCTA CCTACTTCTGCCAGCAAGGCAACACCCTGCCTTACA CCTTTGGCGGAGGCACCAAGCTGGAAATCACCGGC TCTACAAGCGGCAGCGGCAAACCTGGATCTGGCGA GGGATCTACCAAGGGCGAAGTGAAACTGCAAGAGT CTGGCCCTGGACTGGTGGCCCCATCTCAGTCTCTGA GCGTGACCTGTACAGTCAGCGGAGTGTCCCTGCCTG ATTACGGCGTGTCCTGGATCAGACAGCCTCCTCGGA AAGGCCTGGAATGGCTGGGAGTGATCTGGGGCAGC GAGACAACCTACTACAACAGCGCCCTGAAGTCCCG GCTGACCATCATCAAGGACAACTCCAAGAGCCAGG TGTTCCTGAAGATGAACAGCCTGCAGACCGACGAC ACCGCCATCTACTATTGCGCCAAGCACTACTACTAC GGCGGCAGCTACGCCATGGATTATTGGGGCCAGGG CACCAGCGTGACCGTTTCTTCTGCCGCCGCTATCGA AGTGATGTACCCTCCTCCTTACCTGGACAACGAGAA GTCCAACGGCACCATCATCCACGTGAAGGGCAAGC ACCTGTGTCCTTCTCCACTGTTCCCCGGACCTAGCA AGCCTTTCTGGGTGCTCGTTGTTGTTGGCGGCGTGC TGGCCTGTTACAGCCTGCTGGTTACCGTGGCCTTCA TCATCTTTTGGGTCCGAAGCAAGCGGAGCCGGCTGC TGCACTCCGACTACATGAACATGACCCCTAGACGGC CCGGACCAACCAGAAAGCACTACCAGCCTTACGCT CCTCCTAGAGACTTCGCCGCCTACCGGTCCAGAGTG AAGTTCAGCAGATCCGCCGATGCTCCCGCCTATCAG CAGGGCCAAAACCAGCTGTACAACGAGCTGAACCT GGGGAGAAGAGAAGAGTACGACGTGCTGGACAAGC GGAGAGGCAGAGATCCTGAAATGGGCGGCAAGCCC AGACGGAAGAATCCTCAAGAGGGCCTGTATAATGA GCTGCAGAAAGACAAGATGGCCGAGGCCTACAGCG AGATCGGAATGAAGGGCGAGCGCAGAAGAGGCAA GGGACACGATGGACTGTACCAGGGACTGAGCACCG CCACCAAGGATACCTATGACGCCCTGCACATGCAG GCCCTGCCTCCAAGAtaa |
| 312 | FMC63-zeta | ATGCTGCTGCTGGTCACATCTCTGCTGCTGTGCGAG CTGCCCCATCCTGCCTTTCTGCTGATCCCCGACATCC AGATGACCCAGACCACAAGCAGCCTGTCTGCCAGC CTGGGCGATAGAGTGACCATCAGCTGTAGAGCCAG CCAGGACATCAGCAAGTACCTGAACTGGTATCAGC AAAAGCCCGACGGCACCGTGAAGCTGCTGATCTAC CACACCAGCAGACTGCACAGCGGCGTGCCAAGCAG ATTTTCTGGCAGCGGCTCTGGCACCGACTACAGCCT GACAATCAGCAACCTGGAACAAGAGGATATCGCTA CCTACTTCTGCCAGCAAGGCAACACCCTGCCTTACA CCTTTGGCGGAGGCACCAAGCTGGAAATCACCGGC TCTACAAGCGGCAGCGGCAAACCTGGATCTGGCGA GGGATCTACCAAGGGCGAAGTGAAACTGCAAGAGT CTGGCCCTGGACTGGTGGCCCCATCTCAGTCTCTGA GCGTGACCTGTACAGTCAGCGGAGTGTCCCTGCCTG ATTACGGCGTGTCCTGGATCAGACAGCCTCCTCGGA AAGGCCTGGAATGGCTGGGAGTGATCTGGGGCAGC GAGACAACCTACTACAACAGCGCCCTGAAGTCCCG GCTGACCATCATCAAGGACAACTCCAAGAGCCAGG TGTTCCTGAAGATGAACAGCCTGCAGACCGACGAC ACCGCCATCTACTATTGCGCCAAGCACTACTACTAC GGCGGCAGCTACGCCATGGATTATTGGGGCCAGGG CACCAGCGTGACCGTTTCTTCTGCCGCCGCTATCGA AGTGATGTACCCTCCTCCTTACCTGGACAACGAGAA GTCCAACGGCACCATCATCCACGTGAAGGGCAAGC ACCTGTGTCCTTCTCCACTGTTCCCCGGACCTAGCA AGCCTTTCTGGGTGCTCGTTGTTGTTGGCGGCGTGC TGGCCTGTTACAGCCTGCTGGTTACCGTGGCCTTCA TCATCTTTTGGGTCAGAGTGAAGTTCAGCAGATCCG CCGATGCTCCCGCCTATCAGCAGGGCCAAAACCAG CTGTACAACGAGCTGAACCTGGGGAGAAGAGAAGA GTACGACGTGCTGGACAAGCGGAGAGGCAGAGATC CTGAAATGGGCGGCAAGCCCAGACGGAAGAATCCT CAAGAGGGCCTGTATAATGAGCTGCAGAAAGACAA GATGGCCGAGGCCTACAGCGAGATCGGAATGAAGG GCGAGCGCAGAAGAGGCAAGGGACACGATGGACTG TACCAGGGACTGAGCACCGCCACCAAGGATACCTA TGACGCCCTGCACATGCAGGCCCTGCCTCCAAGAtaa |

TABLE 10-continued

CAR sequences.

| SEQ ID NO. | CAR | Sequence |
|---|---|---|
| 313 | CircKymriah - Q388 | ATGGCTCTCCCGGTCACAGCCCTTCTCCTGCCCCTG GCACTCTTGCTGCATGCGGCACGACCCGACATCCAG ATGACCCAGACCACAAGCAGCCTGTCTGCCAGCCTG GGCGATAGAGTGACCATCAGCTGTAGAGCCAGCCA GGACATCAGCAAGTACCTGAACTGGTATCAGCAAA AGCCCGACGGCACCGTGAAGCTGCTGATCTACCAC ACCAGCAGACTGCACAGCGGCGTGCCAAGCAGATT TTCTGGCAGCGGCTCTGGCACCGACTACAGCCTGAC AATCAGCAACCTGGAACAAGAGGATATCGCTACCT ACTTCTGCCAGCAAGGCAACACCCTGCCTTACACCT TTGGCGGAGGCACCAAGCTGGAAATCACCGGTGGA GGTGGTTCTGGCGGAGGGGGATCTGGTGGAGGCGG TTCAGAAGTGAAACTGCAAGAGTCTGGCCCTGGACT GGTGGCCCCATCTCAGTCTCTGAGCGTGACCTGTAC AGTCAGCGGAGTGTCCCTGCCTGATTACGGCGTGTC CTGGATCAGACAGCCTCCTCGGAAAGGCCTGGAAT GGCTGGGAGTGATCTGGGGCAGCGAGACAACCTAC TACAACAGCGCCCTGAAGTCCCGGCTGACCATCATC AAGGACAACTCCAAGAGCCAGGTGTTCCTGAAGAT GAACAGCCTGCAGACCGACGACACCGCCATCTACT ATTGCGCCAAGCACTACTACTACGGCGGCAGCTACG CCATGGATTATTGGGGCCAGGGCACCAGCGTGACC GTTTCTTCTACCACAACGCCCGCCCCGCGACCGCCT ACTCCCGCTCCCACAATTGCATCACAACCCCTGTCT TTGAGACCCGAAGCTTGTCGACCAGCTGCCGGTGGC GCGGTTCACACGCGGGGGCTCGATTTCGCCTGTGAT ATATATATATGGGCCCCATTGGCTGGAACATGCGGA GTATTGCTTCTGAGCCTGGTGATTACCCTCTACTGTA AGAGAGGCCGGAAGAAACTTCTTTATATATTCAAGC AGCCCTTTATGCGACCCGTTCAGACTACCCAAGAGG AAGATGGATGCAGTTGCCGCTTTCCAGAAGAGGAG GAGGGCGGGTGCGAACTGAGAGTGAAGTTCAGCAG ATCCGCCGATGCTCCCGCCTATCAGCAGGGCCAAAA CCAGCTGTACAACGAGCTGAACCTGGGGAGAAGAG AAGAGTACGACGTGCTGGACAAGCGGAGAGGCAGA GATCCTGAAATGGGCGGCAAGCCCAGACGGAAGAA TCCTCAAGAGGGCCTGTATAATGAGCTGCAGAAAG ACAAGATGGCCGAGGCCTACAGCGAGATCGGAATG AAGGGCGAGCGCAGAAGAGGCAAGGGACACGATG GACTGTACCAGGGACTGAGCACCGCCACCAAGGAT ACCTATGACGCCCTGCACATGCAGGCCCTGCCTCCA AGAtaa |
| 314 | CircKymriah - K388 | ATGGCTCTCCCGGTCACAGCCCTTCTCCTGCCCCTG GCACTCTTGCTGCATGCGGCACGACCCGACATCCAG ATGACCCAGACCACAAGCAGCCTGTCTGCCAGCCTG GGCGATAGAGTGACCATCAGCTGTAGAGCCAGCCA GGACATCAGCAAGTACCTGAACTGGTATCAGCAAA AGCCCGACGGCACCGTGAAGCTGCTGATCTACCAC ACCAGCAGACTGCACAGCGGCGTGCCAAGCAGATT TTCTGGCAGCGGCTCTGGCACCGACTACAGCCTGAC AATCAGCAACCTGGAACAAGAGGATATCGCTACCT ACTTCTGCCAGCAAGGCAACACCCTGCCTTACACCT TTGGCGGAGGCACCAAGCTGGAAATCACCGGTGGA GGTGGTTCTGGCGGAGGGGGATCTGGTGGAGGCGG TTCAGAAGTGAAACTGCAAGAGTCTGGCCCTGGACT GGTGGCCCCATCTCAGTCTCTGAGCGTGACCTGTAC AGTCAGCGGAGTGTCCCTGCCTGATTACGGCGTGTC CTGGATCAGACAGCCTCCTCGGAAAGGCCTGGAAT GGCTGGGAGTGATCTGGGGCAGCGAGACAACCTAC TACAACAGCGCCCTGAAGTCCCGGCTGACCATCATC AAGGACAACTCCAAGAGCCAGGTGTTCCTGAAGAT GAACAGCCTGCAGACCGACGACACCGCCATCTACT ATTGCGCCAAGCACTACTACTACGGCGGCAGCTACG CCATGGATTATTGGGGCCAGGGCACCAGCGTGACC GTTTCTTCTACCACAACGCCCGCCCCGCGACCGCCT ACTCCCGCTCCCACAATTGCATCACAACCCCTGTCT TTGAGACCCGAAGCTTGTCGACCAGCTGCCGGTGGC GCGGTTCACACGCGGGGGCTCGATTTCGCCTGTGAT ATATATATATGGGCCCCATTGGCTGGAACATGCGGA GTATTGCTTCTGAGCCTGGTGATTACCCTCTACTGTA AGAGAGGCCGGAAGAAACTTCTTTATATATTCAAGC AGCCCTTTATGCGACCCGTTCAGACTACCCAAGAGG AAGATGGATGCAGTTGCCGCTTTCCAGAAGAGGAG GAGGGCGGGTGCGAACTGAGAGTGAAGTTCAGCAG |

TABLE 10-continued

CAR sequences.

| SEQ ID NO. | CAR | Sequence |
|---|---|---|
| | | ATCCGCCGATGCTCCCGCCTATAAGCAGGGCCAAA ACCAGCTGTACAACGAGCTGAACCTGGGGAGAAGA GAAGAGTACGACGTGCTGGACAAGCGGAGAGGCAG AGATCCTGAAATGGGCGGCAAGCCCAGACGGAAGA ATCCTCAAGAGGGCCTGTATAATGAGCTGCAGAAA GACAAGATGGCCGAGGCCTACAGCGAGATCGGAAT GAAGGGCGAGCGCAGAAGAGGCAAGGGACACGAT GGACTGTACCAGGGACTGAGCACCGCCACCAAGGA TACCTATGACGCCCTGCACATGCAGGCCCTGCCTCC AAGAtaa |
| 315 | CircM971-CD22 | ATGCTGCTGCTGGTCACATCTCTGCTGCTGTGCGAG CTGCCCCATCCTGCCTTTCTGCTGATCCCCCAGGTTC AACTCCAGCAGTCTGGTCCCGGCCTCGTTAAACCAA GCCAGACTTTGTCTCTTACCTGTGCTATCAGTGGCG ATAGCGTGTCTAGTAATTCAGCCGCATGGAACTGGA TCCGACAATCACCGAGTAGGGGACTTGAATGGCTG GGTAGAACCTATTACCGGTCCAAATGGTACAATGAC TATGCAGTGTCTGTAAAAAGCAGGATCACGATCAA CCCTGATACGTCTAAAAACCAGTTTTCTCTGCAACT TAATAGTGTGACCCCTGAAGACACCGCTGTGTATTA CTGTGCACGGGAGGTTACCGGTGATCTTGAAGATGC TTTTGATATATGGGGCCAAGGTACGATGGTCACGGT GTCTAGTgggggaggcggcagcGACATACAGATGACGCAG AGCCCATCCAGTCTCTCCGCGTCTGTTGGTGACAGA GTGACTATTACATGTAGGGCGTCTCAGACCATTTGG TCTTACCTCAATTGGTATCAACAGCGACCAGGCAAA GCACCGAACTTGCTCATTTACGCTGCCAGCTCACTC CAAAGTGGTGTGCCGTCCAGATTTAGTGGTAGGGGC AGTGGCACTGATTTCACTCTGACTATTTCAAGTCTTC AAGCTGAGGATTTTGCCACATACTACTGCCAGCAAA GTTACTCAATACCTCAGACTTTTGGACAGGGGACAA AATTGGAGATTAAAtccggaACCACAACGCCCGCCCCG CGACCGCCTACTCCCGCTCCCACAATTGCATCACAA CCCCTGTCTTTGAGACCCGAAGCTTGTCGACCAGCT GCCGGTGGCGCGGTTCACACGCGGGGGCTCGATTTC GCCTGTGATATATATATATGGGCCCCATTGGCTGGA ACATGCGGAGTATTGCTTCTGAGCCTGGTGATTACC CTCTACTGTAAGAGAGGCCGGAAGAAACTTCTTTAT ATATTCAAGCAGCCCTTTATGCGACCCGTTCAGACT ACCCAAGAGGAAGATGGATGCAGTTGCCGCTTTCC AGAAGAGGAGGAGGGCGGGTGCGAACTGAGAGTG AAGTTCAGCAGATCCGCCGATGCTCCCGCCTATAAG CAGGGCCAAAACCAGCTGTACAACGAGCTGAACCT GGGGAGAAGAGAAGAGTACGACGTGCTGGACAAGC GGAGAGGCAGAGATCCTGAAATGGGCGGCAAGCCC AGACGGAAGAATCCTCAAGAGGGCCTGTATAATGA GCTGCAGAAAGACAAGATGGCCGAGGCCTACAGCG AGATCGGAATGAAGGGCGAGCGCAGAAGAGGCAA GGGACACGATGGACTGTACCAGGGACTGAGCACCG CCACCAAGGATACCTATGACGCCCTGCACATGCAG GCCCTGCCTCCAAGAtaa |
| 316 | CircCD19_22 Bispecific 29 | ATGCTGCTGCTGGTCACATCTCTGCTGCTGTGCGAG CTGCCCCATCCTGCCTTTCTGCTGATCCCCGACATCC AGATGACCCAGACCACAAGCAGCCTGTCTGCCAGC CTGGGCGATAGAGTGACCATCAGCTGTAGAGCCAG CCAGGACATCAGCAAGTACCTGAACTGGTATCAGC AAAAGCCCGACGGCACCGTGAAGCTGCTGATCTAC CACACCAGCAGACTGCACAGCGGCGTGCCAAGCAG ATTTTCTGGCAGCGGCTCTGGCACCGACTACAGCCT GACAATCAGCAACCTGGAACAAGAGGATATCGCTA CCTACTTCTGCCAGCAAGGCAACACCCTGCCTTACA CCTTTGGCGGAGGCACCAAGCTGGAAATCACCggcgg cggaggatccCAGGTTCAACTCCAGCAGTCTGGTCCCGG CCTCGTTAAACCAAGCCAGACTTTGTCTCTTACCTG TGCTATCAGTGGCGATAGCGTGTCTAGTAATTCAGC CGCATGGAACTGGATCCGACAATCACCGAGTAGGG GACTTGAATGGCTGGGTAGAACCTATTACCGGTCCA AATGGTACAATGACTATGCAGTGTCTGTAAAAAGC AGGATCACGATCAACCCTGATACGTCTAAAAACCA GTTTTCTCTGCAACTTAATAGTGTGACCCCTGAAGA CACCGCTGTGTATTACTGTGCACGGGAGGTTACCGG TGATCTTGAAGATGCTTTTGATATATGGGGCCAAGG TACGATGGTCACGGTGTCTAGTGGCTCTACAAGCGG CAGCGGCAAACCTGGATCTGGCGAGGGATCTACCA |

TABLE 10-continued

CAR sequences.

| SEQ ID NO. | CAR | Sequence |
|---|---|---|
| | | AGGGCGACATACAGATGACGCAGAGCCCATCCAGT<br>CTCTCCGCGTCTGTTGGTGACAGAGTGACTATTACA<br>TGTAGGGCGTCTCAGACCATTTGGTCTTACCTCAAT<br>TGGTATCAACAGCGACCAGGCAAAGCACCGAACTT<br>GCTCATTTACGCTGCCAGCTCACTCCAAAGTGGTGT<br>GCCGTCCAGATTTAGTGGTAGGGGCAGTGGCACTG<br>ATTTCACTCTGACTATTTCAAGTCTTCAAGCTGAGG<br>ATTTTGCCACATACTACTGCCAGCAAAGTTACTCAA<br>TACCTCAGACTTTTGGACAGGGGACAAAATTGGAG<br>ATTAAAgggggaggcggcagcGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTtccggaACCACAACGC<br>CCGCCCCGCGACCGCCTACTCCCGCTCCCACAATTG<br>CATCACAACCCCTGTCTTTGAGACCCGAAGCTTGTC<br>GACCAGCTGCCGGTGGCGCGGTTCACACGCGGGGG<br>CTCGATTTCGCCTGTGATATATATATATGGGCCCCA<br>TTGGCTGGAACATGCGGAGTATTGCTTCTGAGCCTG<br>GTGATTACCCTCTACTGTAAGAGAGGCCGGAAGAA<br>ACTTCTTTATATATTCAAGCAGCCCTTTATGCGACCC<br>GTTCAGACTACCCAAGAGGAAGATGGATGCAGTTG<br>CCGCTTTCCAGAAGAGGAGGAGGGCGGGTGCGAAC<br>TGAGAGTGAAGTTCAGCAGATCCGCCGATGCTCCCG<br>CCTATAAGCAGGGCCAAAACCAGCTGTACAACGAG<br>CTGAACCTGGGGAGAAGAGAAGAGTACGACGTGCT<br>GGACAAGCGGAGAGGCAGAGATCCTGAAATGGGCG<br>GCAAGCCCAGACGGAAGAATCCTCAAGAGGGCCTG<br>TATAATGAGCTGCAGAAAGACAAGATGGCCGAGGC<br>CTACAGCGAGATCGGAATGAAGGGCGAGCGCAGAA<br>GAGGCAAGGGACACGATGGACTGTACCAGGGACTG<br>AGCACCGCCACCAAGGATACCTATGACGCCCTGCA<br>CATGCAGGCCCTGCCTCCAAGAtaa |
| 317 | CircCD19_<br>22<br>Bispecific<br>30 | ATGCTGCTGCTGGTCACATCTCTGCTGCTGTGCGAG<br>CTGCCCCATCCTGCCTTTCTGCTGATCCCCCAGGTTC<br>AACTCCAGCAGTCTGGTCCCGGCCTCGTTAAACCAA<br>GCCAGACTTTGTCTCTTACCTGTGCTATCAGTGGCG<br>ATAGCGTGTCTAGTAATTCAGCCGCATGGAACTGGA<br>TCCGACAATCACCGAGTAGGGGACTTGAATGGCTG<br>GGTAGAACCTATTACCGGTCCAAATGGTACAATGAC<br>TATGCAGTGTCTGTAAAAAGCAGGATCACGATCAA<br>CCCTGATACGTCTAAAAACCAGTTTTCTCTGCAACT<br>TAATAGTGTGACCCCTGAAGACACCGCTGTGTATTA<br>CTGTGCACGGGAGGTTACCGGTGATCTTGAAGATGC<br>TTTTGATATATGGGGCCAAGGTACGATGGTCACGGT<br>GTCTAGTgggggaggcggcagcGACATACAGATGACGCAG<br>AGCCCATCCAGTCTCTCCGCGTCTGTTGGTGACAGA<br>GTGACTATTACATGTAGGGCGTCTCAGACCATTTGG<br>TCTTACCTCAATTGGTATCAACAGCGACCAGGCAAA<br>GCACCGAACTTGCTCATTTACGCTGCCAGCTCACTC<br>CAAAGTGGTGTGCCGTCCAGATTTAGTGGTAGGGGC<br>AGTGGCACTGATTTCACTCTGACTATTTCAAGTCTTC<br>AAGCTGAGGATTTTGCCACATACTACTGCCAGCAAA<br>GTTACTCAATACCTCAGACTTTTGGACAGGGGACAA<br>AATTGGAGATTAAAGGGGGAGGCGGATCCGGCGGT<br>GGTGGCTCCGGCGGTGGTGGTTCTGGAGGCGGCGG<br>AAGCGGTGGGGGTGGTAGCGACATCCAGATGACCC<br>AGACCACAAGCAGCCTGTCTGCCAGCCTGGGCGAT<br>AGAGTGACCATCAGCTGTAGAGCCAGCCAGGACAT<br>CAGCAAGTACCTGAACTGGTATCAGCAAAAGCCCG<br>ACGGCACCGTGAAGCTGCTGATCTACCACACCAGC<br>AGACTGCACAGCGGCGTGCCAAGCAGATTTTCTGGC<br>AGCGGCTCTGGCACCGACTACAGCCTGACAATCAG<br>CAACCTGGAACAAGAGGATATCGCTACCTACTTCTG<br>CCAGCAAGGCAACACCCTGCCTTACACCTTTGGCGG<br>AGGCACCAAGCTGGAAATCACCGGCTCTACAAGCG<br>GCAGCGGCAAACCTGGATCTGGCGAGGGATCTACC<br>AAGGGCGAAGTGAAACTGCAAGAGTCTGGCCCTGG<br>ACTGGTGGCCCCATCTCAGTCTCTGAGCGTGACCTG |

TABLE 10-continued

| CAR sequences. | |
|---|---|
| SEQ ID NO. CAR | Sequence |
| | TACAGTCAGCGGAGTGTCCCTGCCTGATTACGGCGT GTCCTGGATCAGACAGCCTCCTCGGAAAGGCCTGG AATGGCTGGGAGTGATCTGGGGCAGCGAGACAACC TACTACAACAGCGCCCTGAAGTCCCGGCTGACCATC ATCAAGGACAACTCCAAGAGCCAGGTGTTCCTGAA GATGAACAGCCTGCAGACCGACGACACCGCCATCT ACTATTGCGCCAAGCACTACTACTACGGCGGCAGCT ACGCCATGGATTATTGGGGCCAGGGCACCAGCGTG ACCGTTTCTTCTtccggaACCACAACGCCCGCCCCGCG ACCGCCTACTCCCGCTCCCACAATTGCATCACAACC CCTGTCTTTGAGACCCGAAGCTTGTCGACCAGCTGC CGGTGGCGCGGTTCACACGCGGGGGCTCGATTTCGC CTGTGATATATATATATGGGCCCCATTGGCTGGAAC ATGCGGAGTATTGCTTCTGAGCCTGGTGATTACCCT CTACTGTAAGAGAGGCCGGAAGAAACTTCTTTATAT ATTCAAGCAGCCCTTTATGCGACCCGTTCAGACTAC CCAAGAGGAAGATGGATGCAGTTGCCGCTTTCCAG AAGAGGAGGAGGGCGGGTGCGAACTGAGAGTGAA GTTCAGCAGATCCGCCGATGCTCCCGCCTATAAGCA GGGCCAAAACCAGCTGTACAACGAGCTGAACCTGG GGAGAAGAGAAGAGTACGACGTGCTGGACAAGCGG AGAGGCAGAGATCCTGAAATGGGCGGCAAGCCCAG ACGGAAGAATCCTCAAGAGGGCCTGTATAATGAGC TGCAGAAAGACAAGATGGCCGAGGCCTACAGCGAG ATCGGAATGAAGGGCGAGCGCAGAAGAGGCAAGG GACACGATGGACTGTACCAGGGACTGAGCACCGCC ACCAAGGATACCTATGACGCCCTGCACATGCAGGC CCTGCCTCCAAGAtaa |

In some embodiments, a CAR has a sequence as listed in Table 10.

TABLE 11

| CAR domain sequences. | | |
|---|---|---|
| SEQ ID NO. | Protein | Sequence |
| 318 | 4-1BB | KRGRKKLLYIFKQPFMRPVQTTQEEDGCSCRFPEEE EGGCEL |
| 319 | CD3ζ intracellular domain | RVKFSRSADAPAYKQGQNQLYNELNLGRREEYDVLD KRRGRDPEMGGKPRRKNPQEGLYNELQKDKMAEAY SEIGMKGERRRGKGHDGLYQGLSTATKDTYDALHMQ ALPPR |
| 320 | CD28 intracellular signaling domain | QVQLVQSGAEVEKPGASVKVSCKASGYTFTDYYMH WVRQAPGQGLEWMGWINPNSGGTNYAQKFQGRVTM TRDTSISTAYMELSRLRSDDTAVYYCASGWDFDYWG QGTLVTVSSGGGGSGGGGSGGGGSGGGGSDIVMTQS PSSLSASVGDRVTITCRASQSIRYYLSWYQQKPGKA PKLLIYTASILQNGVPSRFSGSGSGTDFTLTIS SLQPEDFATYYCLQTYTTPDFGPGTKVEIK |
| 321 | FMC63 VH | EVKLQESGPGLVAPSQSLSVTCTVSGVSLPDYGVSW IRQPPRKGLEWLGVIWGSETTYYNSALKSRLTIIKD NSKSQVFLKMNSLQTDDTAIYYCAKHYYYGGSYAMD YWGQGTSVTVSS |
| 322 | FMC63 VL | DIQMTQTTSSLSASLGDRVTISCRASQDISKYLNWY QQKPDGTVKLLIYHTSRLHSGVPSRFSGSGSGTDYS LTISNLEQEDIATYFCQQGNTLPYTFGGGTKLEIT |

In some embodiments, a CAR domain encoded by an inventive polynucleotide has a sequence as listed in Table 11.

Preferred embodiments are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Wesselhoeft et al. (2019) RNA Circularization Diminishes Immunogenicity and Can Extend Translation Duration In Vivo. Molecular Cell. 74(3), 508-520 and Wesselhoeft et al. (2018) Engineering circular RNA for Potent and Stable Translation in Eukaryotic Cells. Nature Communications. 9, 2629 are incorporated by reference in their entirety.

The invention is further described in detail by reference to the following examples but are not intended to be limited to the following examples. These examples encompass any and all variations of the illustrations with the intention of providing those of ordinary skill in the art with complete disclosure and description of how to make and use the subject invention and are not intended to limit the scope of what is regarded as the invention.

Example 1

Example 1A: External Homology Regions Allow for Circularization of Long Precursor RNA Using the Permuted Intron Exon (PIE) Circularization Strategy A 1.1 kb sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained.

Perfectly complementary 9 nucleotide and 19 nucleotide long homology regions were designed and added at the 5' and 3' ends of the precursor RNA. Addition of these homology arms increased splicing efficiency from 0 to 16% for 9 nucleotide homology regions and to 48% for 19 nucleotide homology regions as assessed by disappearance of the precursor RNA band.

The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. This shows that circular RNA is a major product of the splicing reactions of precursor RNA containing the 9 or 19 nucleotide long external homology regions.

Example 1B: Spacers that Conserve Secondary Structures of IRES and PIE Splice Sites Increase Circularization Efficiency A series of spacers was designed and inserted between the 3' PIE splice site and the IRES. These spacers were designed to either conserve or disrupt secondary structures within intron sequences in the IRES, 3' PIE splice site, and/or 5' splice site. The addition of spacer sequences designed to conserve secondary structures resulted in 87% splicing efficiency, while the addition of a disruptive spacer sequences resulted in no detectable splicing.

Example 2

Example 2A: Internal Homology Regions in Addition to External Homology Regions Creates a Splicing Bubble and Allows for Translation of Several Expression Sequences Spacers were designed to be unstructured, non-homologous to the intron and IRES sequences, and to contain spacer-spacer homology regions. These were inserted between the 5' exon and IRES and between the 3' exon and expression sequence in constructs containing external homology regions, EMCV IRES, and expression sequences for *Gaussia* luciferase (total length: 1289 nt), Firefly luciferase (2384 nt), eGFP (1451 nt), human erythropoietin (1313 nt), and Cas9 endonuclease (4934 nt). Circularization of all 5 constructs was achieved. Circularization of constructs utilizing T4 phage and Anabaena introns were roughly equal. Circularization efficiency was higher for shorter sequences. To measure translation, each construct was transfected into HEK293 cells. *Gaussia* and Firefly luciferase transfected cells produced a robust response as measured by luminescence, human erythropoietin was detectable in the media of cells transfected with erythropoietin circRNA, and EGFP fluorescence was observed from cells transfected with EGFP circRNA. Co-transfection of Cas9 circRNA with sgRNA directed against GFP into cells constitutively expressing GFP resulted in ablated fluorescence in up to 97% of cells in comparison to an sgRNA-only control.

Example 2B: Use of CVB3 IRES Increases Protein Production

Constructs with internal and external homology regions and differing IRES containing either *Gaussia* luciferase or Firefly luciferase expression sequences were made. Protein production was measured by luminescence in the supernatant of HEK293 cells 24 hours after transfection. The Coxsackievirus B3 (CVB3) IRES construct produced the most protein in both cases.

Example 2C: Use of polyA or polyAC Spacers Increases Protein Production

Thirty nucleotide long polyA or polyAC spacers were added between the IRES and splice junction in a construct with each IRES that produced protein in example 2B. *Gaussia* luciferase activity was measured by luminescence in the supernatant of HEK293 cells 24 hours after transfection. Both spacers improved expression in every construct over control constructs without spacers.

Example 3

HEK293 or HeLa Cells Transfected with Circular RNA Produce More Protein than Those Transfected with Comparable Unmodified or Modified Linear RNA.

HPLC-purified *Gaussia* luciferase-coding circRNA (CVB3-GLuc-pAC) was compared with a canonical unmodified 5' methylguanosine-capped and 3' polyA-tailed linear GLuc mRNA, and a commercially available nucleoside-modified (pseudouridine, 5-methylcytosine) linear GLuc mRNA (from Trilink). Luminescence was measured 24 h post-transfection, revealing that circRNA produced 811.2% more protein than the unmodified linear mRNA in HEK293 cells and 54.5% more protein than the modified mRNA. Similar results were obtained in HeLa cells and a comparison of optimized circRNA coding for human erythropoietin with linear mRNA modified with 5-methoxyuridine.

Luminescence data was collected over 6 days. In HEK293 cells, circRNA transfection resulted in a protein production half-life of 80 hours, in comparison with the 43 hours of unmodified linear mRNA and 45 hours of modified linear mRNA. In HeLa cells, circRNA transfection resulted in a protein production half-life of 116 hours, in comparison with the 44 hours of unmodified linear mRNA and 49 hours of modified linear mRNA. CircRNA produced substantially more protein than both the unmodified and modified linear mRNAs over its lifetime in both cell types.

Example 4

Example 4A: Purification of circRNA by RNase Digestion, HPLC Purification, and Phosphatase Treatment Decreases Immunogenicity. Completely Purified Circular RNA is Significantly Less Immunogenic than Unpurified or Partially Purified Circular RNA. Protein Expression Stability and Cell Viability are Dependent on Cell Type and Circular RNA Purity Human embryonic kidney 293 (HEK293) and human lung carcinoma A549 cells were transfected with:

a. products of an unpurified GLuc circular RNA splicing reaction, b. products of RNase R digestion of the splicing reaction, c. products of RNase R digestion and HPLC purification of the splicing reaction, or d. products of RNase digestion, HPLC purification, and phosphatase treatment of the splicing reaction.

RNase R digestion of splicing reactions was insufficient to prevent cytokine release in A549 cells in comparison to untransfected controls.

The addition of HPLC purification was also insufficient to prevent cytokine release, although there was a significant reduction in interleukin-6 (IL-6) and a significant increase in interferon-α1 (IFN-α1) compared to the unpurified splicing reaction.

The addition of a phosphatase treatment after HPLC purification and before RNase R digestion dramatically reduced the expression of all unregulated cytokines assessed in A549 cells. Secreted monocyte chemoattractant protein 1 (MCP1), IL-6, IFN-α1, tumor necrosis factor α (TNFα), and IFNγ inducible protein-10 (IP-10) fell to undetectable or un-transfected baseline levels.

There was no substantial cytokine release in HEK293 cells. A549 cells had increased GLuc expression stability and cell viability when transfected with higher purity circular RNA. Completely purified circular RNA had a stability phenotype similar to that of transfected 293 cells.

Example 4B: Circular RNA does not Cause Significant Immunogenicity and is not a RIG-I Ligand A549 cells were transfected with the products of a splicing reaction.

A549 cells were transfected with:

a. unpurified circular RNA, b. high molecular weight (linear and circular concatenations) RNA, c. circular (nicked) RNA, d. an early fraction of purified circular RNA (more overlap with nicked RNA peak), e. a late fraction of purified circular RNA (less overlap with nicked RNA peak), f. introns excised during circularization, or g. vehicle (i.e. untransfected control).

Precursor RNA was separately synthesized and purified in the form of the splice site deletion mutant (DS) due to difficulties in obtaining suitably pure linear precursor RNA from the splicing reaction. Cytokine release and cell viability was measured in each case.

Robust IL-6, RANTES, and IP-10 release was observed in response to most of the species present within the splicing reaction, as well as precursor RNA. Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. A549 cell viability 36 hours post-transfection was significantly greater for late circRNA fractions compared with all of the other fractions.

RIG-I and IFN-β1 transcript induction upon transfection of A549 cells with late circRNA HPLC fractions, precursor RNA or unpurified splicing reactions were analyzed. Induction of both RIG-I and IFN-β1 transcripts were weaker for late circRNA fractions than precursor RNA and unpurified splicing reactions. RNase R treatment of splicing reactions alone was not sufficient to ablate this effect. Addition of very small quantities of the RIG-I ligand 3p-hpRNA to circular RNA induced substantial RIG-I transcription. In HeLa cells, transfection of RNase R-digested splicing reactions induced RIG-I and IFN-β1, but purified circRNA did not. Overall, HeLa cells were less sensitive to contaminating RNA species than A549 cells.

A time course experiment monitoring RIG-I, IFN-β1, IL-6, and RANTES transcript induction within the first 8 hours after transfection of A549 cells with splicing reactions or fully purified circRNA did not reveal a transient response to circRNA. Purified circRNA similarly failed to induce pro-inflammatory transcripts in RAW264.7 murine macrophages.

A549 cells were transfected with purified circRNA containing an EMCV IRES and EGFP expression sequence. This failed to produce substantial induction of pro-inflammatory transcripts. These data demonstrate that non-circular components of the splicing reaction are responsible for the immunogenicity observed in previous studies and that circRNA is not a natural ligand for RIG-I.

Example 5

Circular RNA Avoids Detection by TLRs.

TLR 3, 7, and 8 reporter cell lines were transfected with multiple linear or circular RNA constructs and secreted embryonic alkaline phosphatase (SEAP) was measured.

Linearized RNA was constructed by deleting the intron and homology arm sequences. The linear RNA constructs were then treated with phosphatase (in the case of capped RNAs, after capping) and purified by HPLC.

None of the attempted transfections produced a response in TLR7 reporter cells. TLR3 and TLR8 reporter cells were activated by capped linearized RNA, polyadenylated linearized RNA, the nicked circRNA HPLC fraction, and the early circRNA fraction. The late circRNA fraction and m1ψ-mRNA did not provoke TLR-mediated response in any cell line.

In a second experiment, circRNA was linearized using two methods: treatment of circRNA with heat in the presence of magnesium ions and DNA oligonucleotide-guided RNase H digestion. Both methods yielded a majority of full-length linear RNA with small amounts of intact circRNA. TLR3, 7, and 8 reporter cells were transfected with circular RNA, circular RNA degraded by heat, or circular RNA degraded by RNase H, and SEAP secretion was measured 36 hours after transfection. TLR8 reporter cells secreted SEAP in response to both forms of degraded circular RNA, but did not produce a greater response to circular RNA transfection than mock transfection. No activation was observed in TLR3 and TLR7 reporter cells for degraded or intact conditions, despite the activation of TLR3 by in vitro transcribed linearized RNA.

Example 6

Unmodified Circular RNA Produces Increased Sustained In Vivo Protein Expression than Linear RNA.

Mice were injected and HEK293 cells were transfected with unmodified and m1ψ-modified human erythropoietin (hEpo) linear mRNAs and circRNAs. Equimolar transfection of m1ψ-mRNA and unmodified circRNA resulted in robust protein expression in HEK293 cells. hEpo linear mRNA and circRNA displayed similar relative protein expression patterns and cell viabilities in comparison to GLuc linear mRNA and circRNA upon equal weight transfection of HEK293 and A549 cells.

In mice, hEpo was detected in serum after the injection of hEpo circRNA or linear mRNA into visceral adipose. hEpo detected after the injection of unmodified circRNA decayed more slowly than that from unmodified or m1ψ-mRNA and was still present 42 hours post-injection. Serum hEpo rapidly declined upon the injection of unpurified circRNA splicing reactions or unmodified linear mRNA. Injection of unpurified splicing reactions produced a cytokine response detectable in serum that was not observed for the other RNAs, including purified circRNA.

Example 7

Circular RNA can be Effectively Delivered In Vivo or In Vitro Via Lipid Nanoparticles.

Purified circular RNA was formulated into lipid nanoparticles (LNPs) with the ionizable lipidoid cKK-E12 (Dong et al., 2014; Kauffman et al., 2015). The particles formed uniform multilamellar structures with an average size, polydispersity index, and encapsulation efficiency similar to that of particles containing commercially available control linear mRNA modified with 5moU.

Purified hEpo circRNA displayed greater expression than 5moU-mRNA when encapsulated in LNPs and added to HEK293 cells. Expression stability from LNP-RNA in HEK293 cells was similar to that of RNA delivered by transfection reagent, with the exception of a slight delay in decay for both 5moU-mRNA and circRNA. Both unmodified circRNA and 5moU-mRNA failed to activate RIG-I/IFN-β1 in vitro.

In mice, LNP-RNA was delivered by local injection into visceral adipose tissue or intravenous delivery to the liver. Serum hEpo expression from circRNA was lower but comparable with that from 5moU-mRNA 6 hours after delivery in both cases. Serum hEpo detected after adipose injection of unmodified LNP-circRNA decayed more slowly than that from LNP-5moU-mRNA, with a delay in expression decay present in serum that was similar to that noted in vitro, but serum hEpo after intravenous injection of LNP-circRNA or LNP-5moU-mRNA decayed at approximately the same rate. There was no increase in serum cytokines or local RIG-I, TNFα, or IL-6 transcript induction in any of these cases.

Example 8

Expression and Functional Stability by IRES in HEK293, HepG2, and 1C1C7 Cells.

Figure 1B:
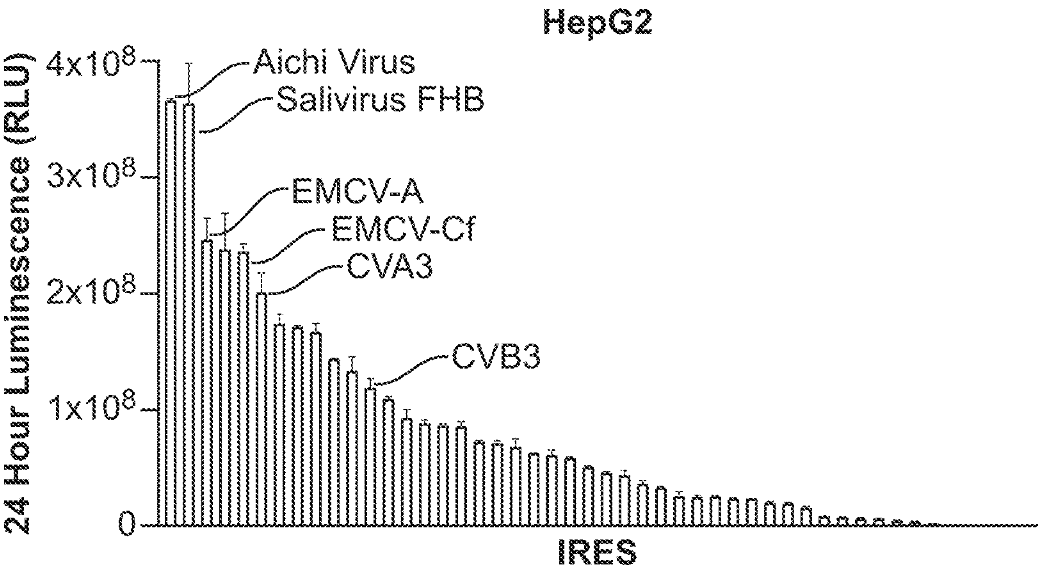
Figure 1C:
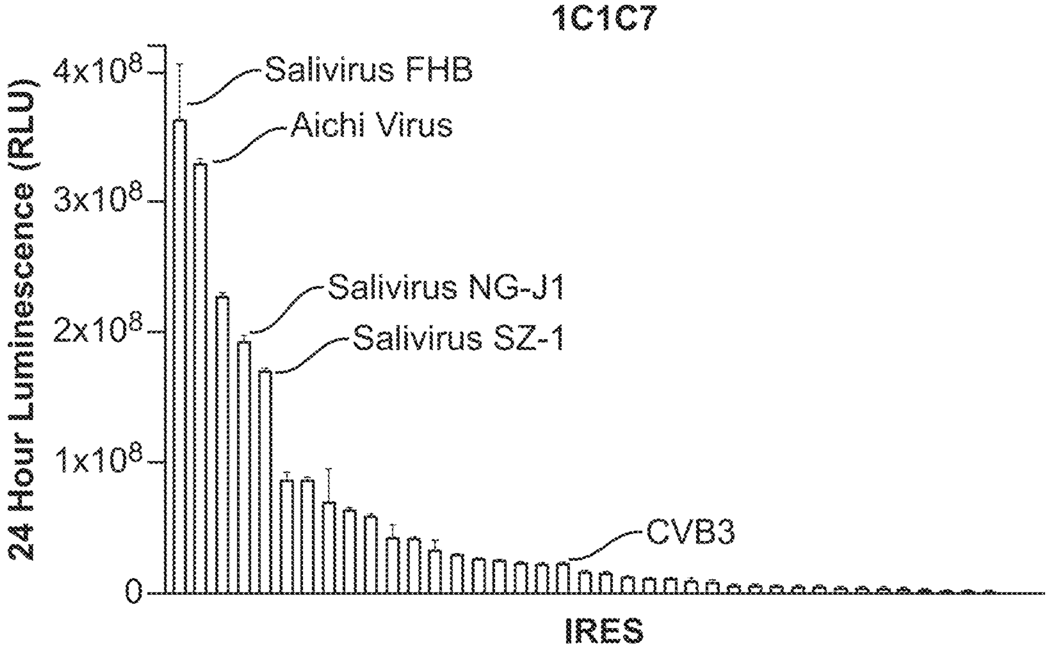

Constructs including anabaena intron/exon regions, a *Gaussia* luciferase expression sequence, and varying IRES were circularized. 100 ng of each circularization reaction was separately transfected into 20,000 HEK293 cells, HepG2 cells, and 1C1C7 cells using Lipofectamine MessengerMax. Luminescence in each supernatant was assessed after 24 hours as a measure of protein expression. In HEK293 cells, constructs including Crohivirus B, Salivirus FHB, Aichi Virus, Salivirus HG-J1, and Enterovirus J IRES produced the most luminescence at 24 hours (FIG. 1A). In HepG2 cells, constructs including Aichi Virus, Salivirus FHB, EMCV-Cf, and CVA3 IRES produced high luminescence at 24 hours (FIG. 1B). In 1C1C7 cells, constructs including Salivirus FHB, Aichi Virus, Salivirus NG-J1, and Salivirus A SZ-1 IRES produced high luminescence at 24 hours (FIG. 1C).

Figure 2A:
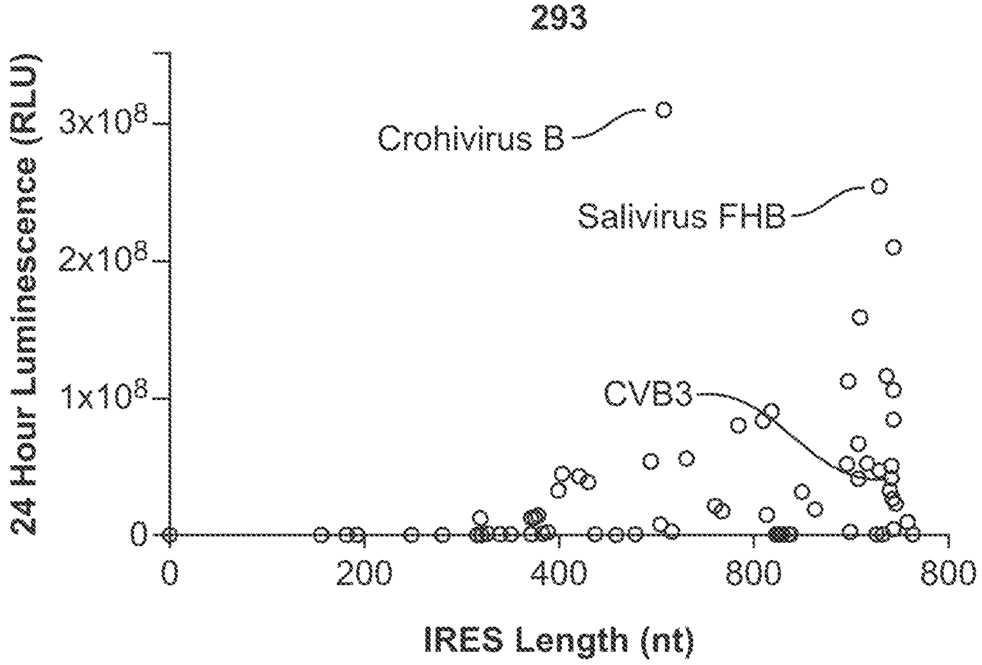
FIGS. 2A-2C depict luminescence in supernatants of HEK293 (FIG. 2A), HepG2 (FIG. 2B), or 1C1C7 (FIG. 2C) cells 24 hours after transfection with circular RNA comprising a *Gaussia* luciferase expression sequence and various IRES sequences having different lengths.
Figure 2B:
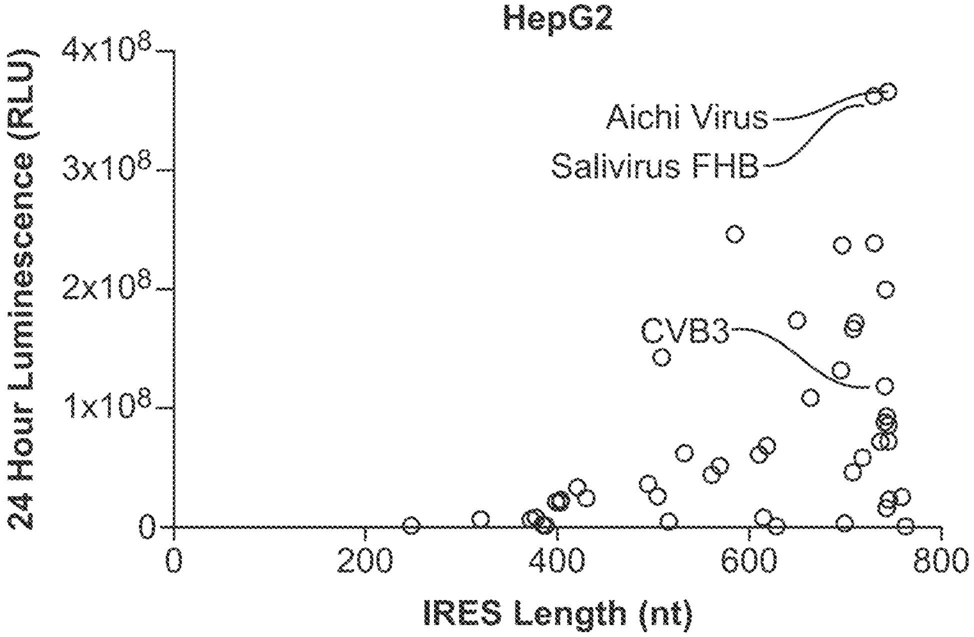
Figure 2C:
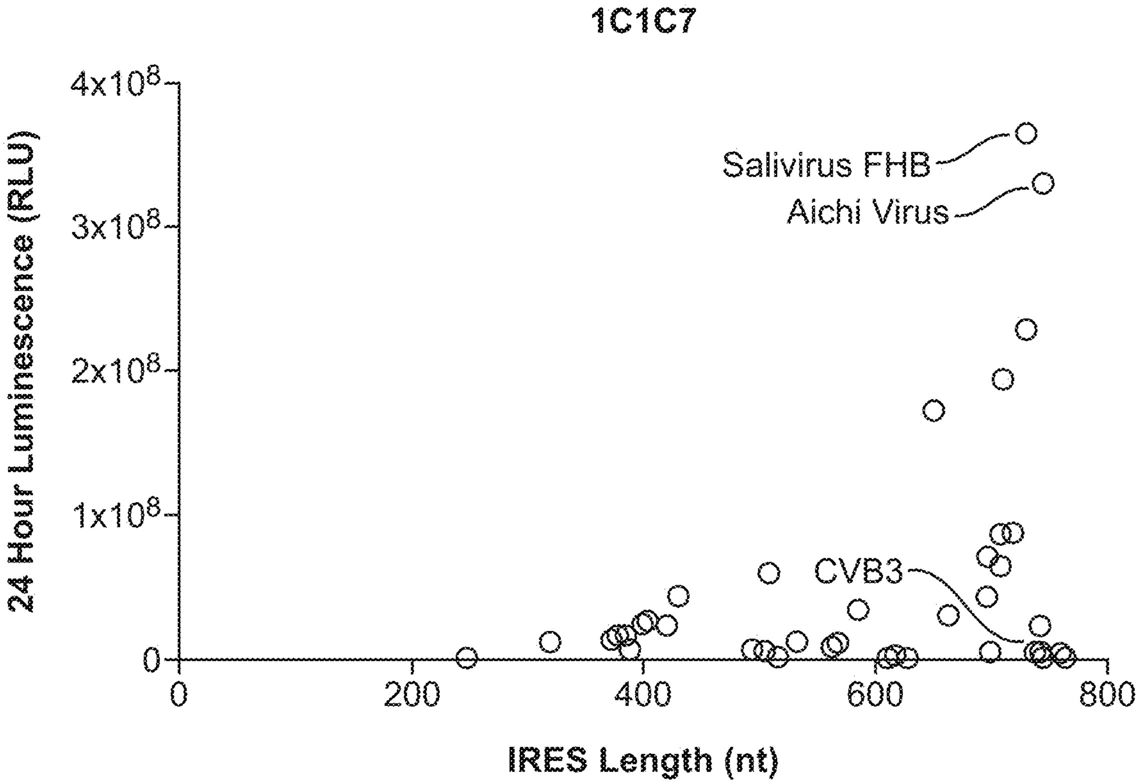

A trend of larger IRES producing greater luminescence at 24 hours was observed. Shorter total sequence length tends to increase circularization efficiency, so selecting a high expression and relatively short IRES may result in an improved construct. In HEK293 cells, a construct using the Crohivirus B IRES produced the highest luminescence, especially in comparison to other IRES of similar length (FIG. 2A). Expression from IRES constructs in HepG2 and 1C1C7 cells plotted against IRES size are in FIGS. 2B and 2C.

Figure 3A:
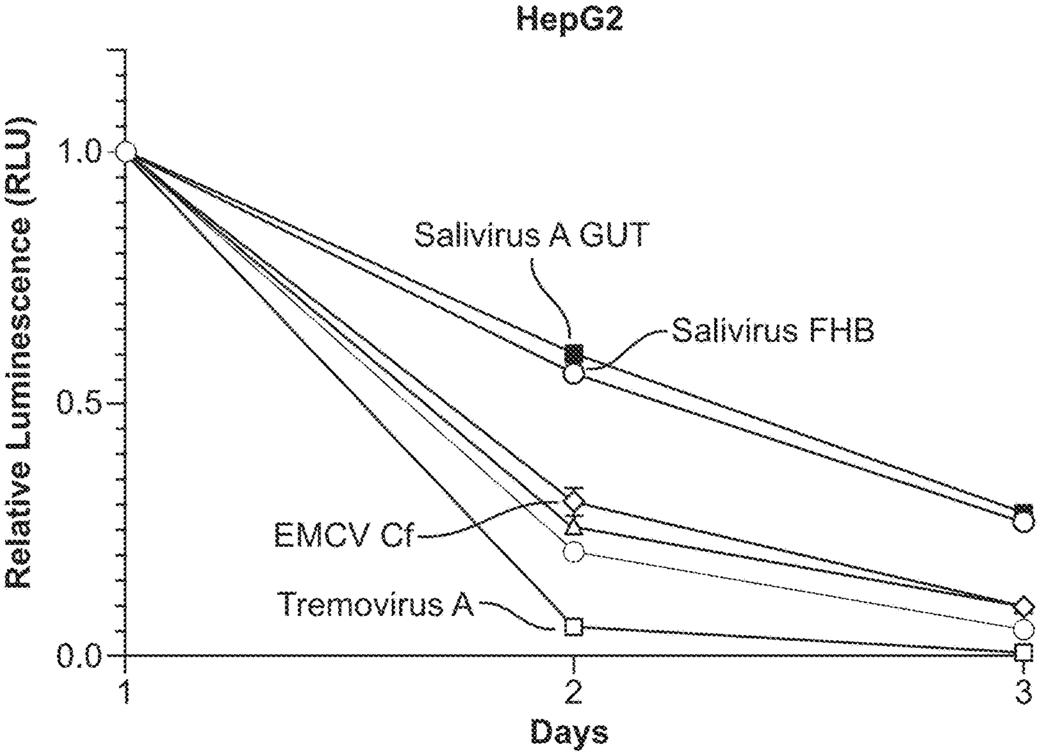
FIGS. 3A and 3B depict stability of select IRES constructs in HepG2 (FIG. 3A) or 1C1C7 (FIG. 3B) cells over 3 days as measured by luminescence.
Figure 3B:
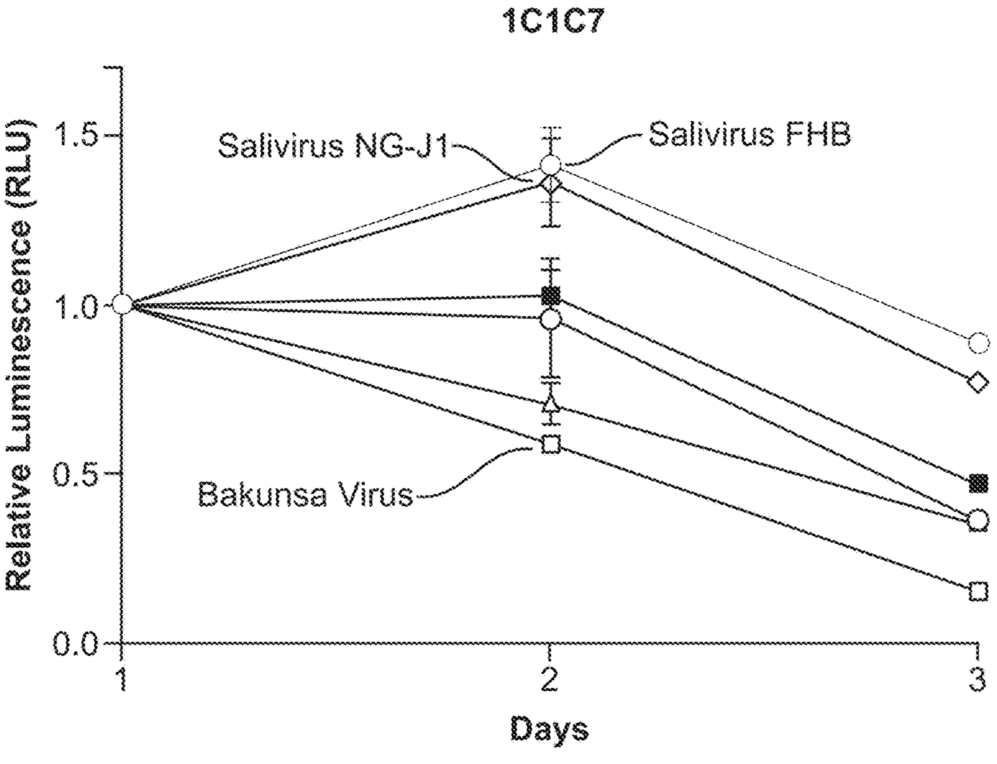

Functional stability of select IRES constructs in HepG2 and 1C1C7 cells were measured over 3 days. Luminescence from secreted *Gaussia* luciferase in supernatant was measured every 24 hours after transfection of 20,000 cells with 100 ng of each circularization reaction, followed by complete media replacement. Salivirus A GUT and Salivirus FHB exhibited the highest functional stability in HepG2 cells, and Salivirus N-J1 and Salivirus FHB produced the most stable expression in 1C1C7 cells (FIGS. 3A and 3B).

Example 9

Expression and Functional Stability by IRES in Jurkat Cells.

Figure 4A:
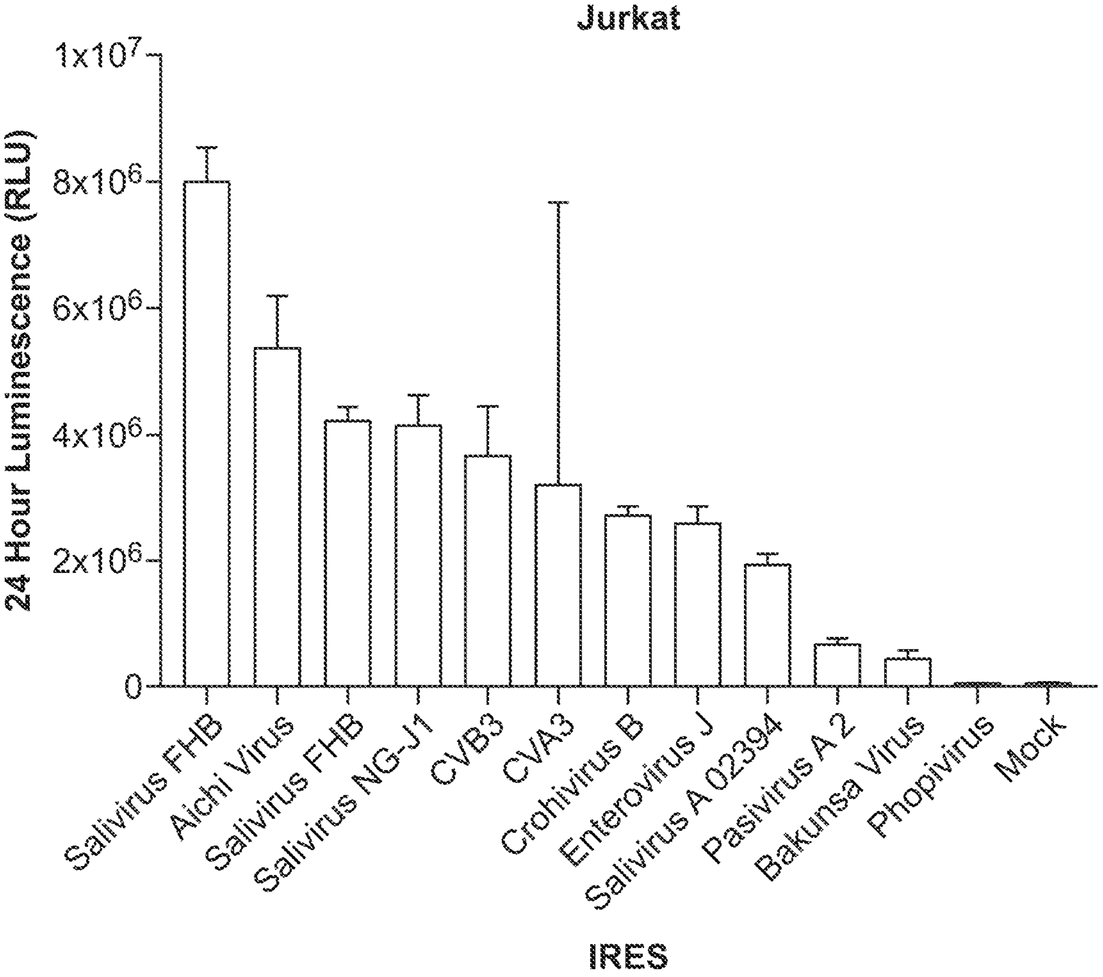
FIGS. 4A and 4B depict protein expression from select IRES constructs in Jurkat cells, as measured by luminescence from secreted *Gaussia* luciferase in cell supernatants.
Figure 4B:
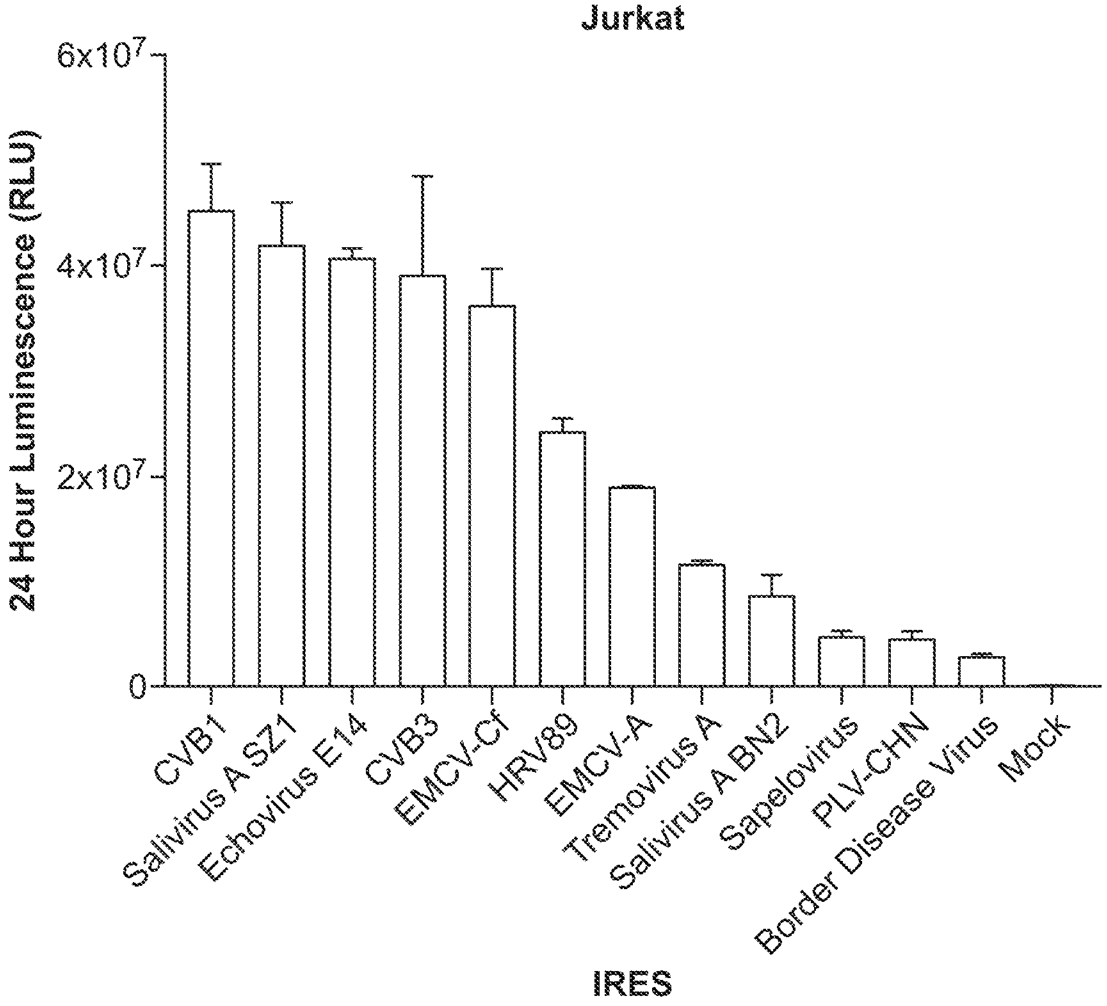

2 sets of constructs including anabaena intron/exon regions, a *Gaussia* luciferase expression sequence, and a subset of previously tested IRES were circularized. 60,000 Jurkat cells were electroporated with 1 μg of each circularization reaction. Luminescence from secreted *Gaussia* luciferase in supernatant was measured 24 hours after electroporation. A CVB3 IRES construct was included in both sets for comparison between sets and to previously defined IRES efficacy. CVB1 and Salivirus A SZ1 IRES constructs produced the most expression at 24 h. Data can be found in FIGS. 4A and 4B.

Figure 5A:
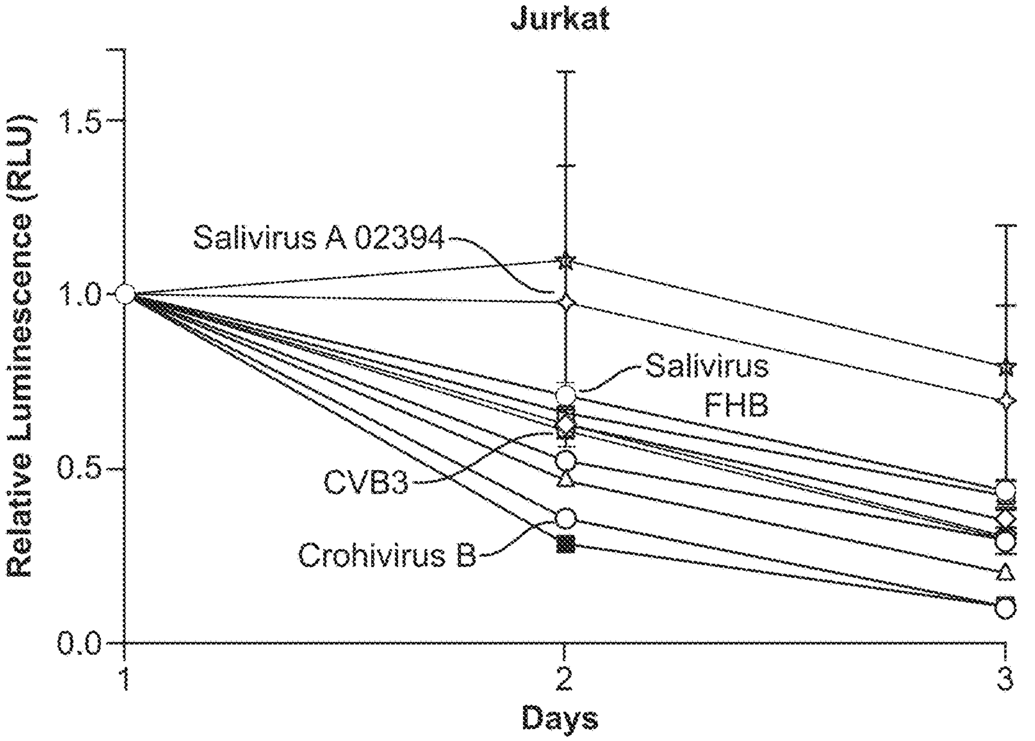
FIGS. 5A and 5B depict stability of select IRES constructs in Jurkat cells over 3 days as measured by luminescence.
Figure 5B:
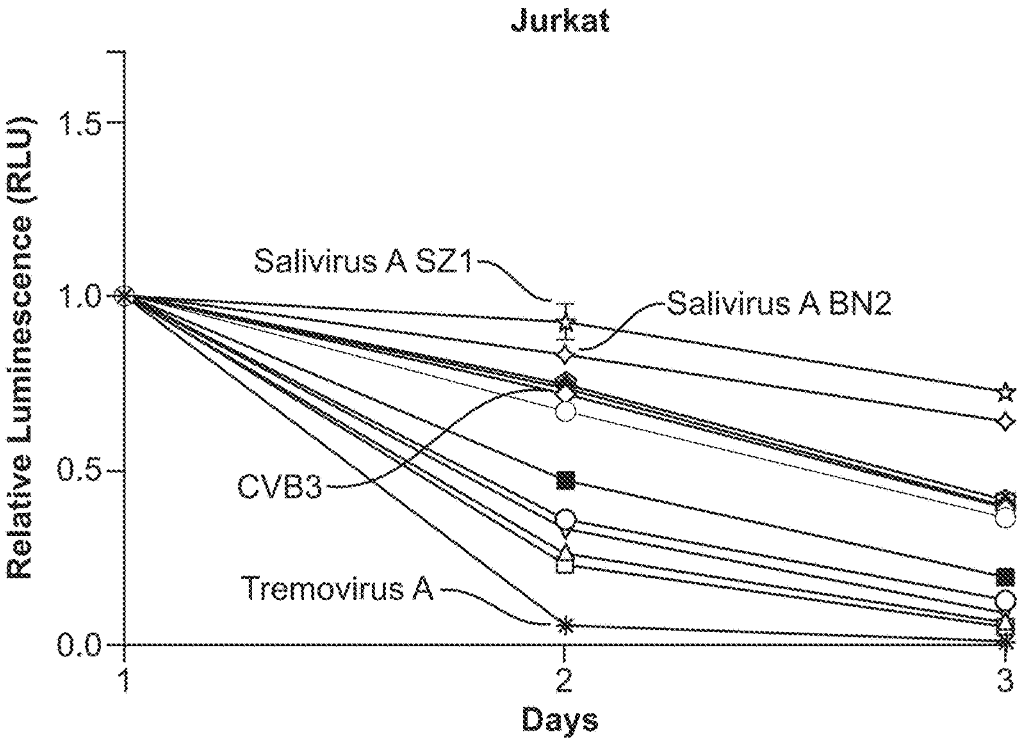

Functional stability of the IRES constructs in each round of electroporated Jurkat cells was measured over 3 days. Luminescence from secreted *Gaussia* luciferase in supernatant was measured every 24 hours after electroporation of 60,000 cells with 1 μg of each circularization reaction, followed by complete media replacement (FIGS. 5A and 5B).

Salivirus A SZ1 and Salivirus A BN2 IRES constructs had high functional stability compared to other constructs.

Example 10

Expression, Functional Stability, and Cytokine Release of Circular and Linear RNA in Jurkat Cells.

Figure 6A:
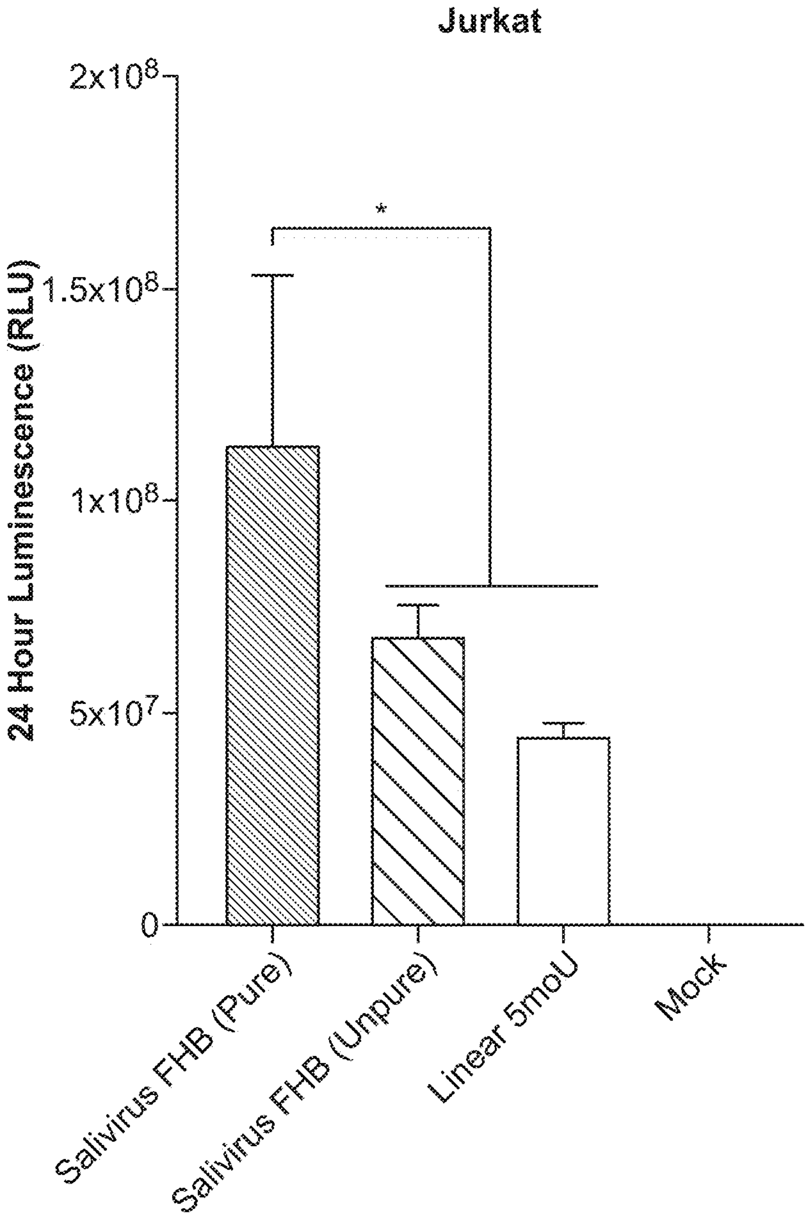
FIGS. 6A and 6B depict comparisons of 24 hour luminescence (FIG. 6A) or relative luminescence over 3 days (FIG. 6B) of modified linear, unpurified circular, or purified circular RNA encoding *Gaussia* luciferase.

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) is commercially available and was purchased from Trilink. 5moU nucleotide modifications have been shown to improve mRNA stability and expression (Bioconjug Chem. 2016 Mar. 16; 27(3):849-53). Expression of modified mRNA, circularization reactions (unpure), and circRNA purified by size exclusion HPLC (pure) in Jurkat cells were measured and compared (FIG. 6A). Luminescence from secreted *Gaussia* luciferase in supernatant was measured 24 hours after electroporation of 60,000 cells with 1 μg of each RNA species.

Figure 6B:
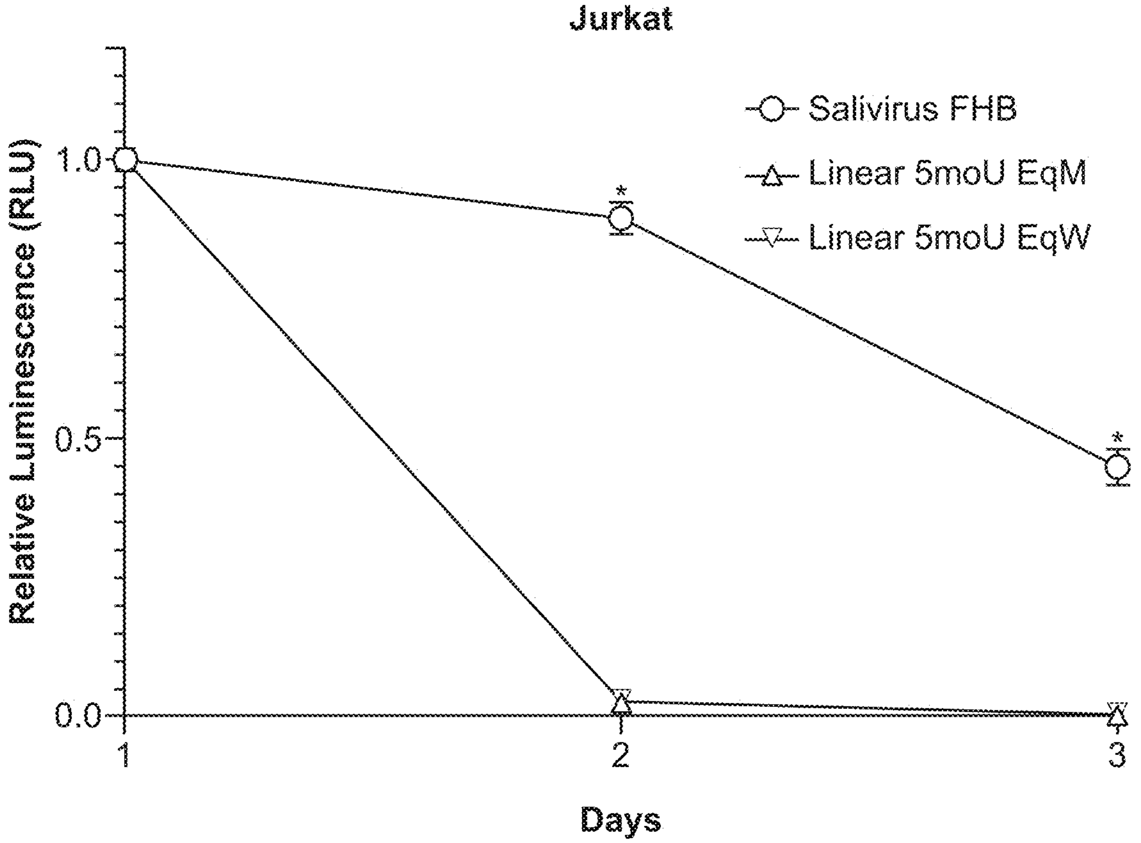

Luminescence from secreted *Gaussia* luciferase in supernatant was measured every 24 hours after electroporation of 60,000 cells with lug of each RNA species, followed by complete media replacement. A comparison of functional stability data of modified mRNA and circRNA in Jurkat cells over 3 days is in FIG. 6B.

Figure 7A:
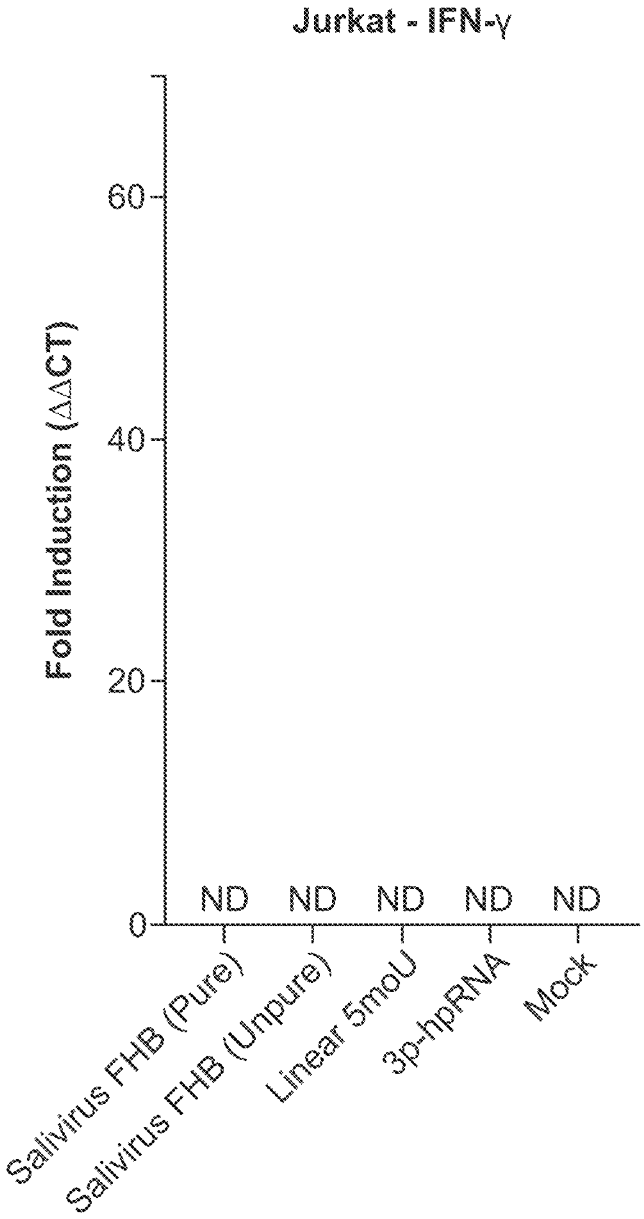
FIGS. 7A-7F depict transcript induction of IFNγ (FIG. 7A), IL-6 (FIG. 7B), IL-2 (FIG. 7C), RIG-I (FIG. 7D), IFN-β1 (FIG. 7E), and TNFα (FIG. 7F) after electroporation of Jurkat cells with modified linear, unpurified circular, or purified circular RNA.
Figure 7B:
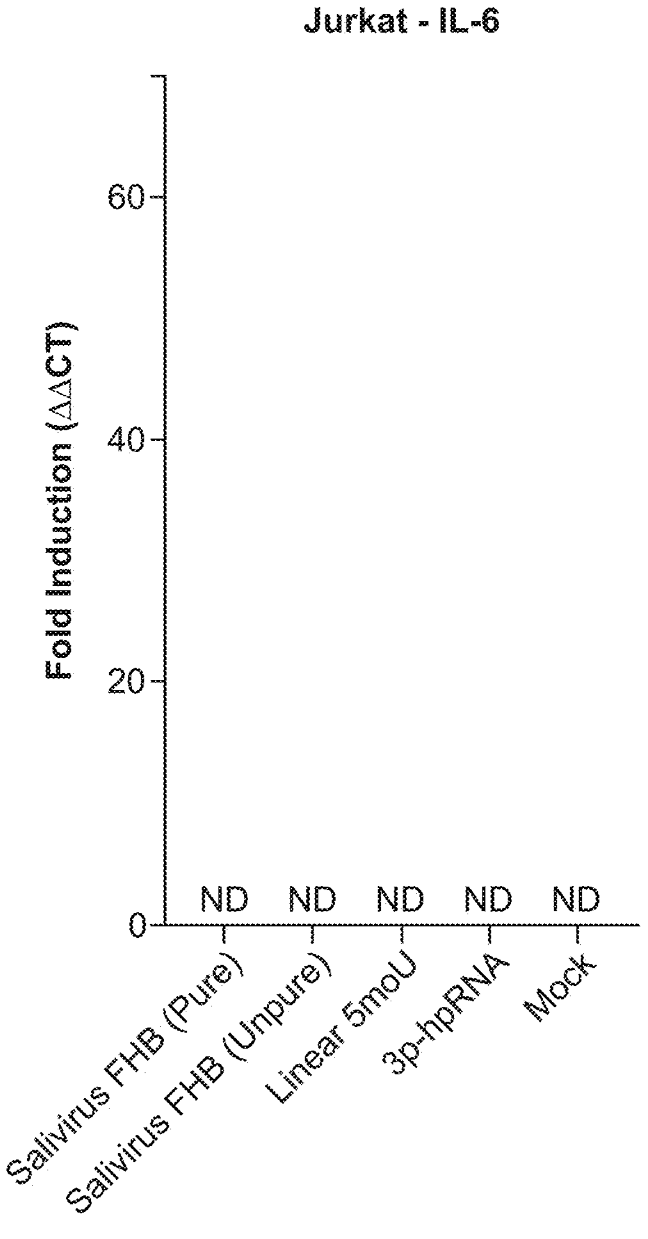
Figure 7C:
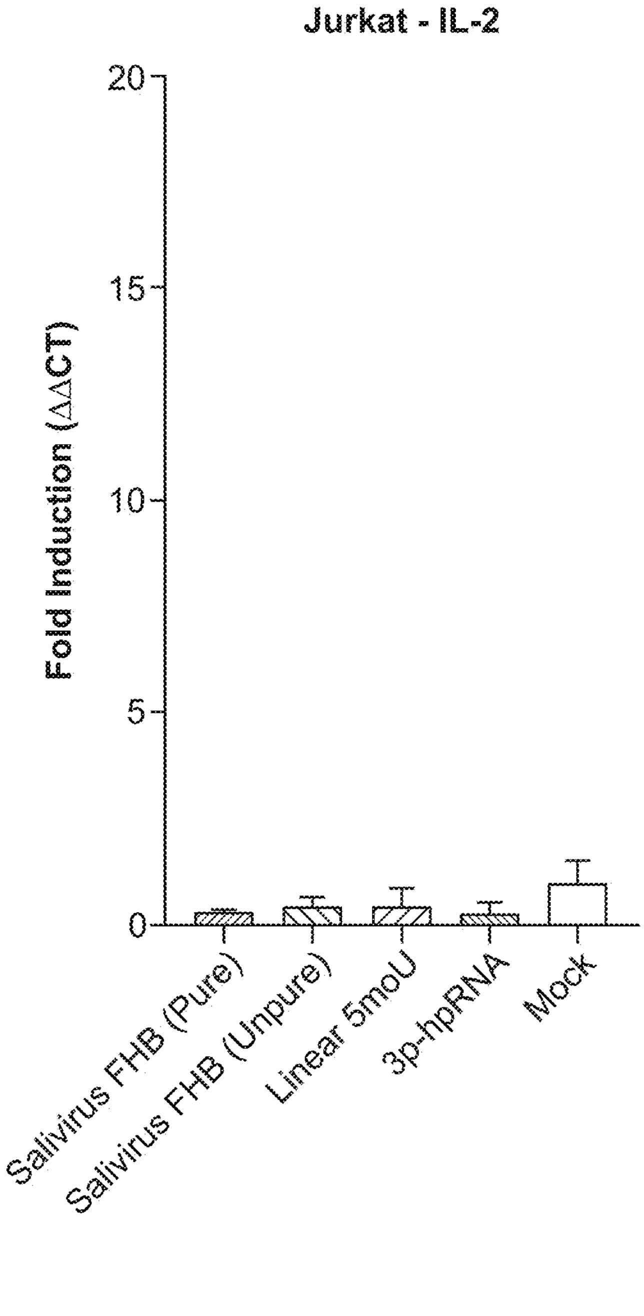
Figure 7D:
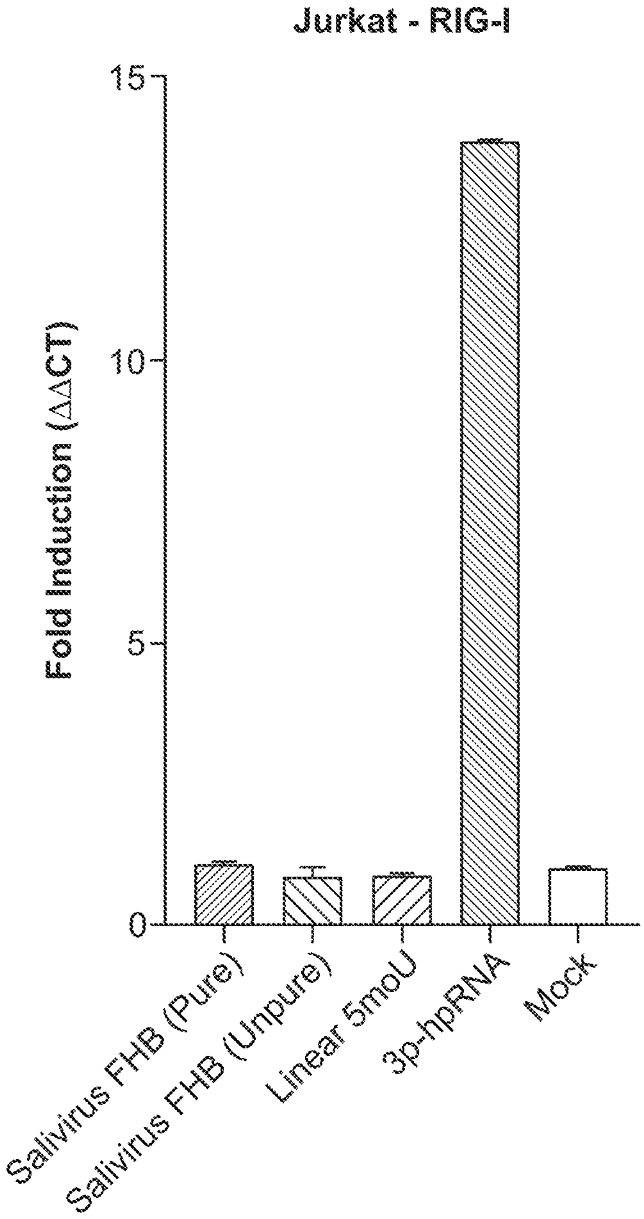
Figure 7E:
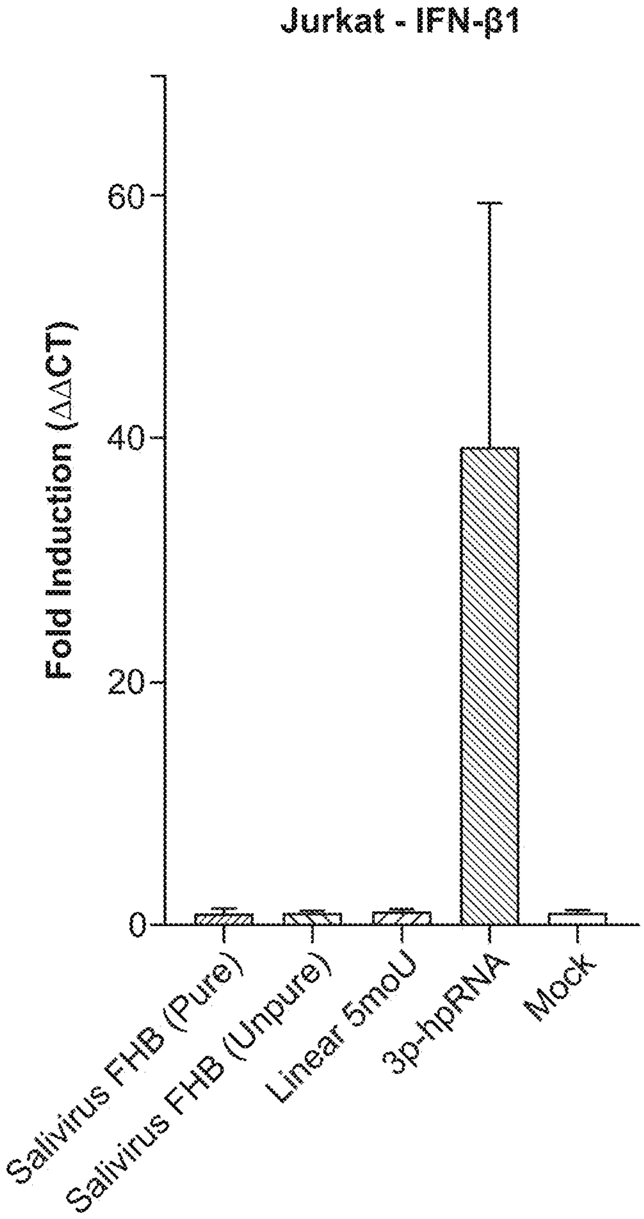
Figure 7F:
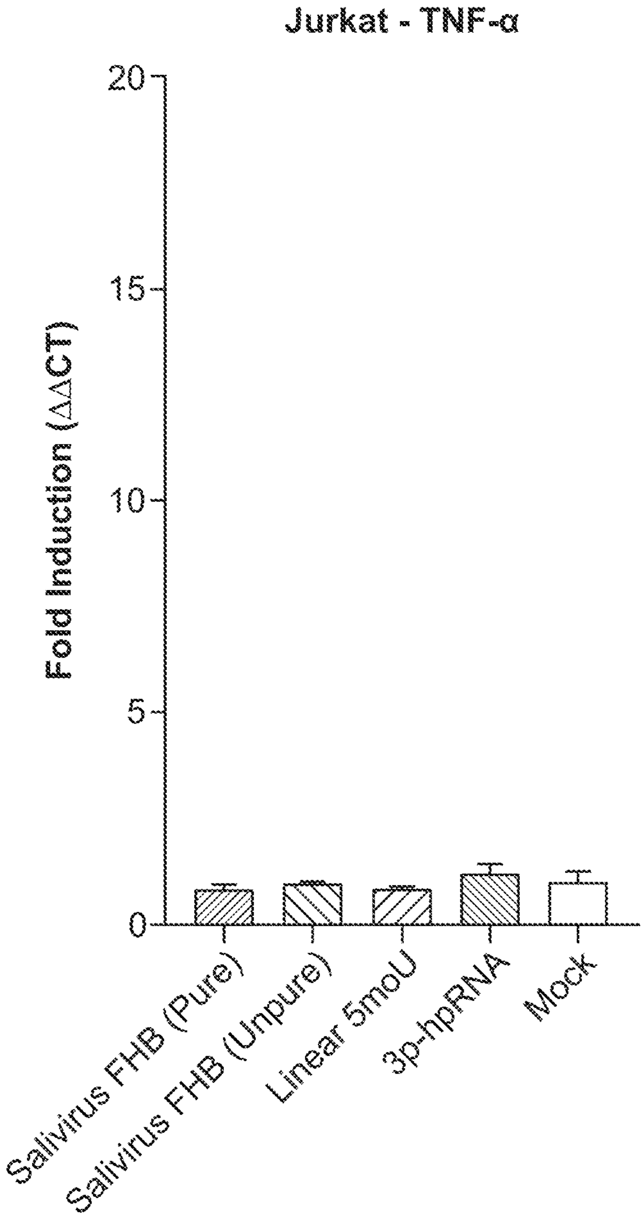

IFNγ (FIG. 7A), IL-6 (FIG. 7B), IL-2 (FIG. 7C), RIG-I (FIG. 7D), IFN-β1 (FIG. 7E), and TNFα (FIG. 7F) transcript induction was measured 18 hours after electroporation of 60,000 Jurkat cells with 1 μg of each RNA species described above and 3p-hpRNA (5' triphosphate hairpin RNA, which is a known RIG-I agonist).

Example 11

Expression of Circular and Linear RNA in Monocytes and Macrophages.

Figure 8A:
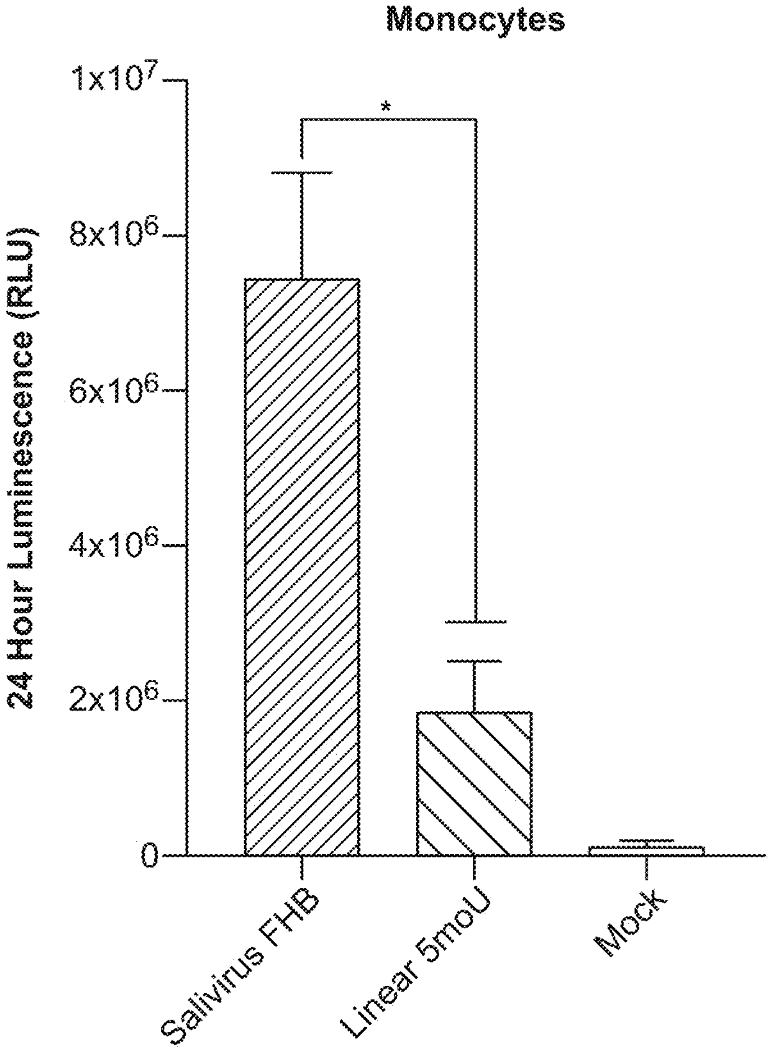
FIGS. 8A-8C depict a comparison of luminescence of circular RNA and modified linear RNA encoding *Gaussia* luciferase in human primary monocytes (FIG. 8A) and macrophages (FIG. 8B and FIG. 8C).
Figure 8B:
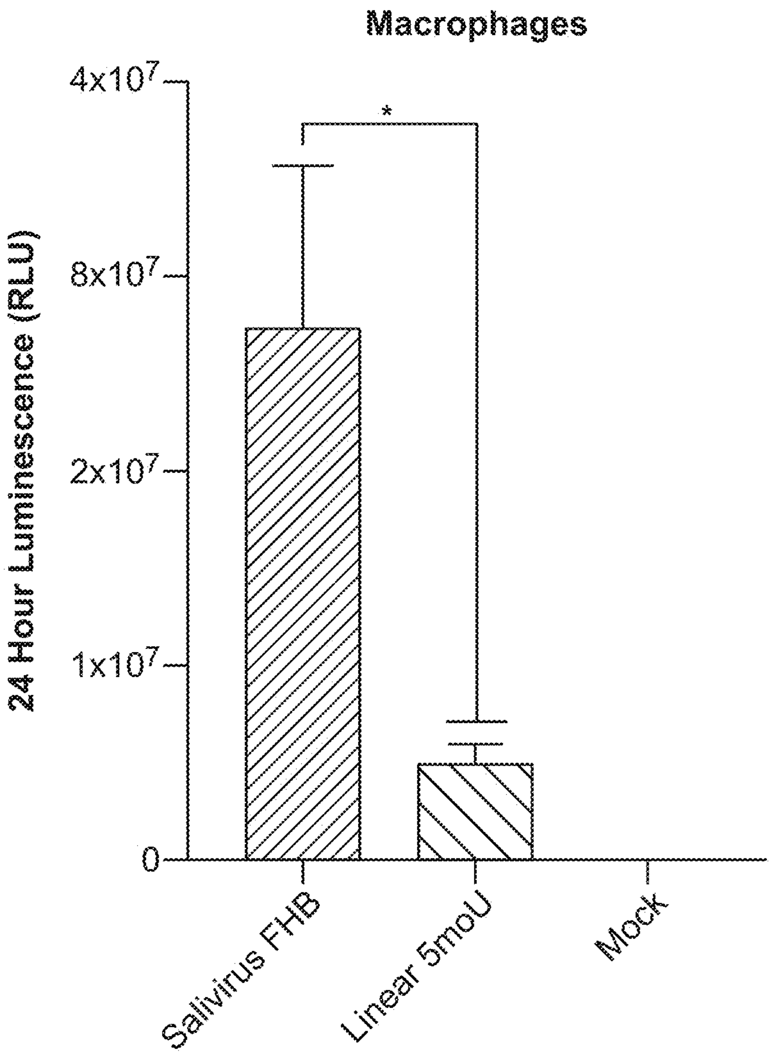
Figure 8C:
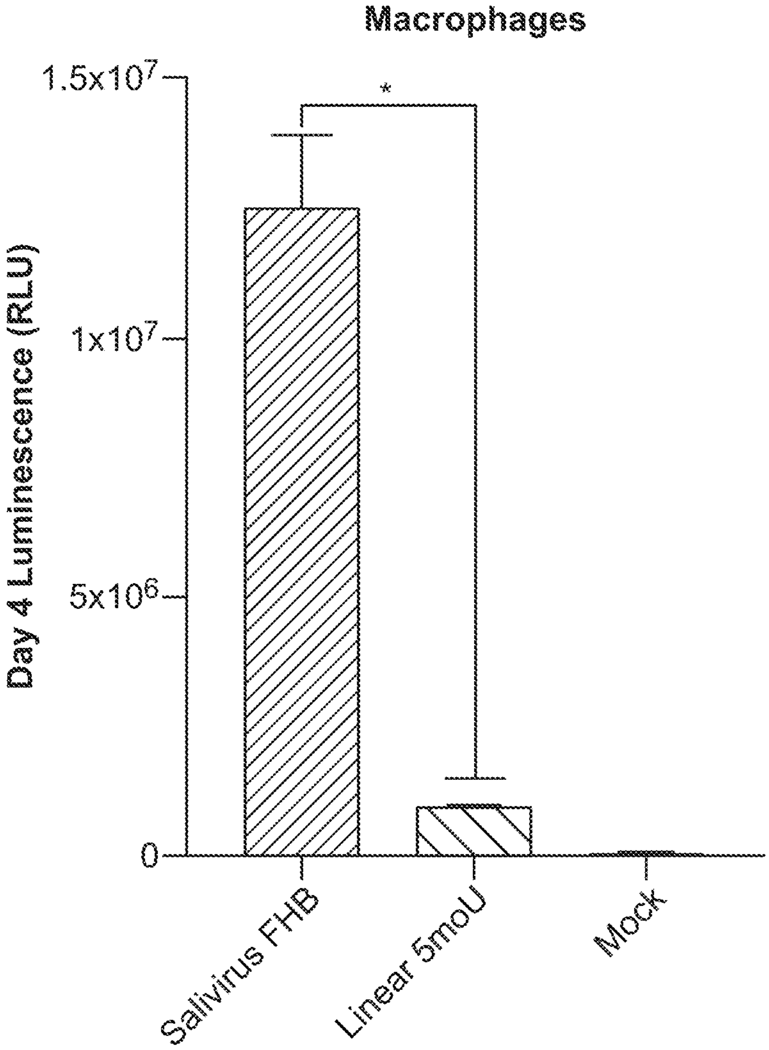

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) was purchased from Trilink. Expression of circular and modified mRNA was measured in human primary monocytes (FIG. 8A) and human primary macrophages (FIG. 8B). Luminescence from secreted *Gaussia* luciferase in supernatant was measured 24 hours after electroporation of 60,000 cells with 1 μg of each RNA species. Luminescence was also measured 4 days after electroporation of human primary macrophages with media changes every 24 hours (FIG. 8C). The difference in luminescence was statistically significant in each case ($p<0.05$).

Example 12

Expression and Functional Stability by IRES in Primary T Cells.

Figure 9A:
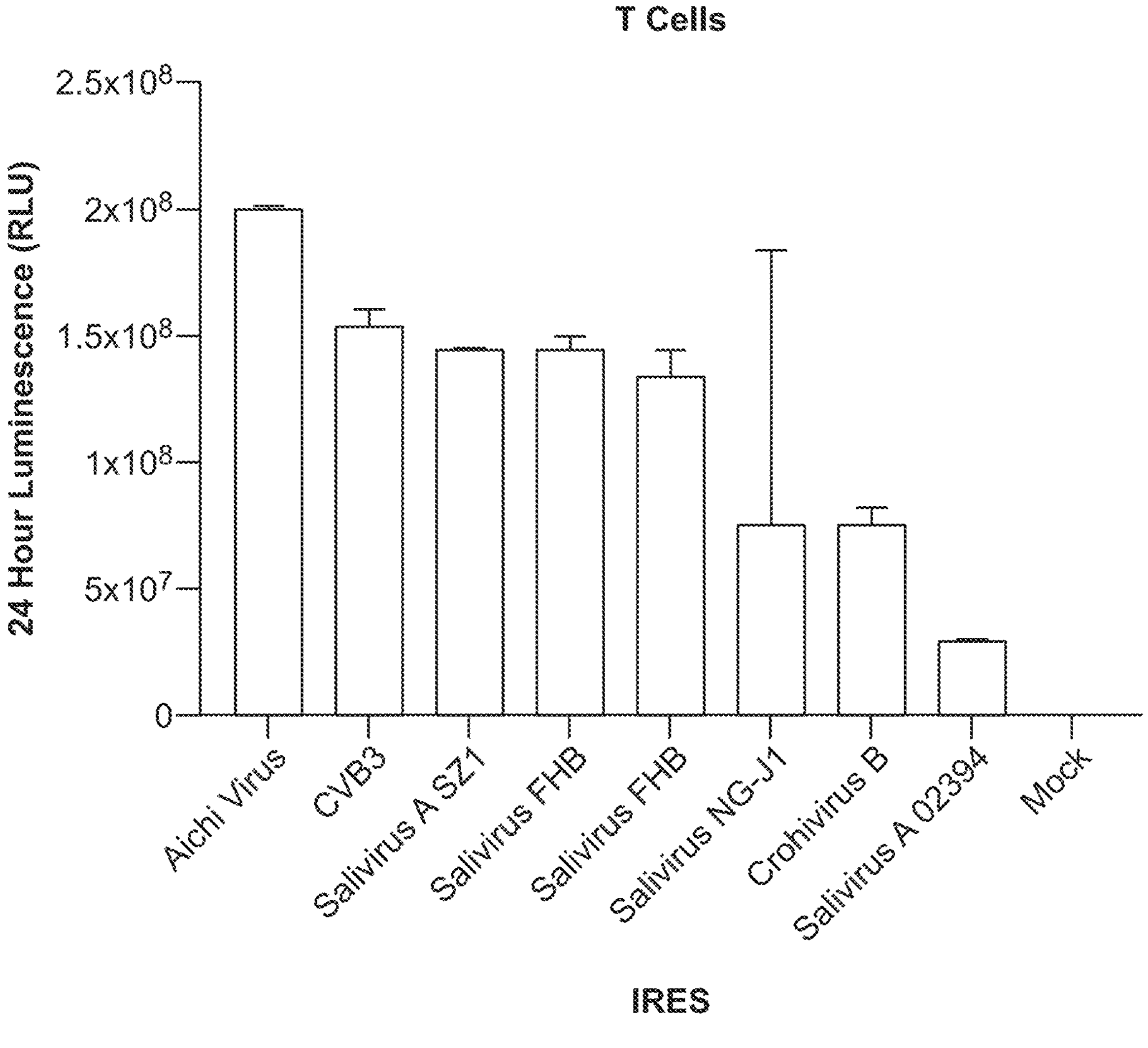
FIGS. 9A and 9B depict relative luminescence over 3 days (FIG. 9A) in supernatant of primary T cells after transduction with circular RNA comprising a *Gaussia* luciferase expression sequence and varying IRES sequences or 24 hour luminescence (FIG. 9B).

Constructs including anabaena intron/exon regions, a *Gaussia* luciferase expression sequence, and a subset of previously tested IRES were circularized and reaction products were purified by size exclusion HPLC. 150,000 primary human CD3+ T cells were electroporated with 1 μg of each circRNA. Luminescence from secreted *Gaussia* luciferase in supernatant was measured 24 hours after electroporation (FIG. 9A). Aichi Virus and CVB3 IRES constructs had the most expression at 24 hours.

Figure 9B:
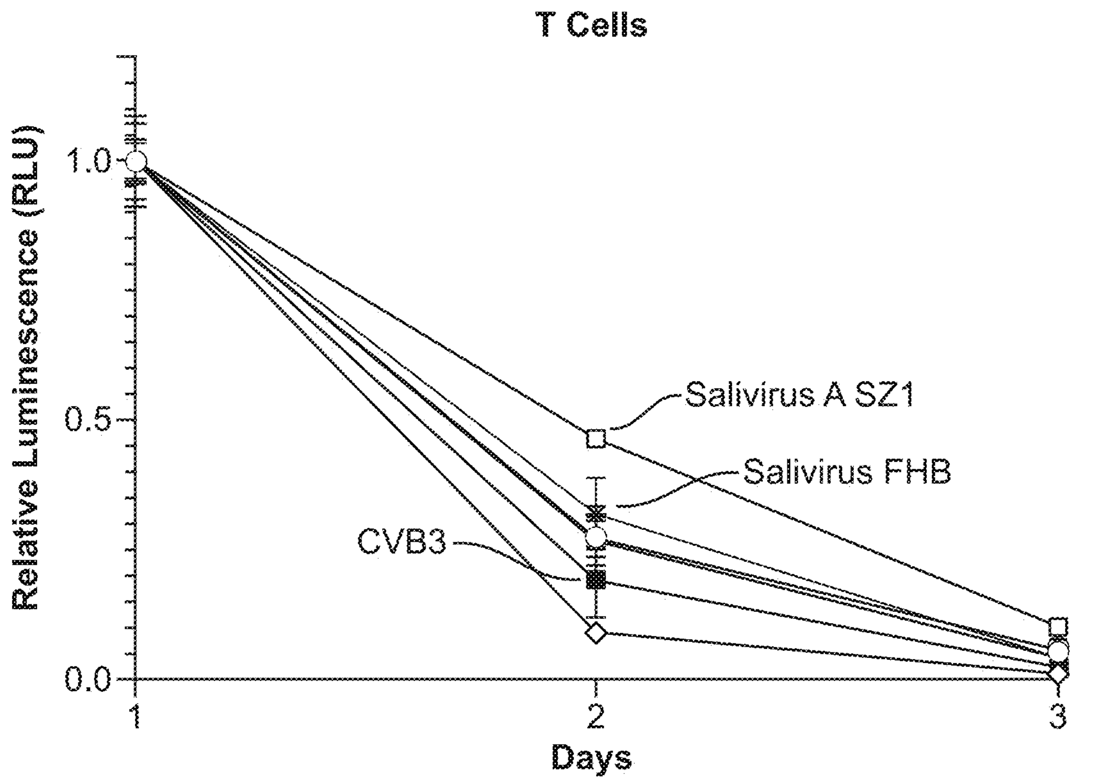

Luminescence was also measured every 24 hours after electroporation for 3 days in order to compare functional stability of each construct (FIG. 9B). The construct with a Salivirus A SZ1 IRES was the most stable.

Example 13

Expression and Functional Stability of Circular and Linear RNA in Primary T Cells and PBMCs.

Figure 10A:
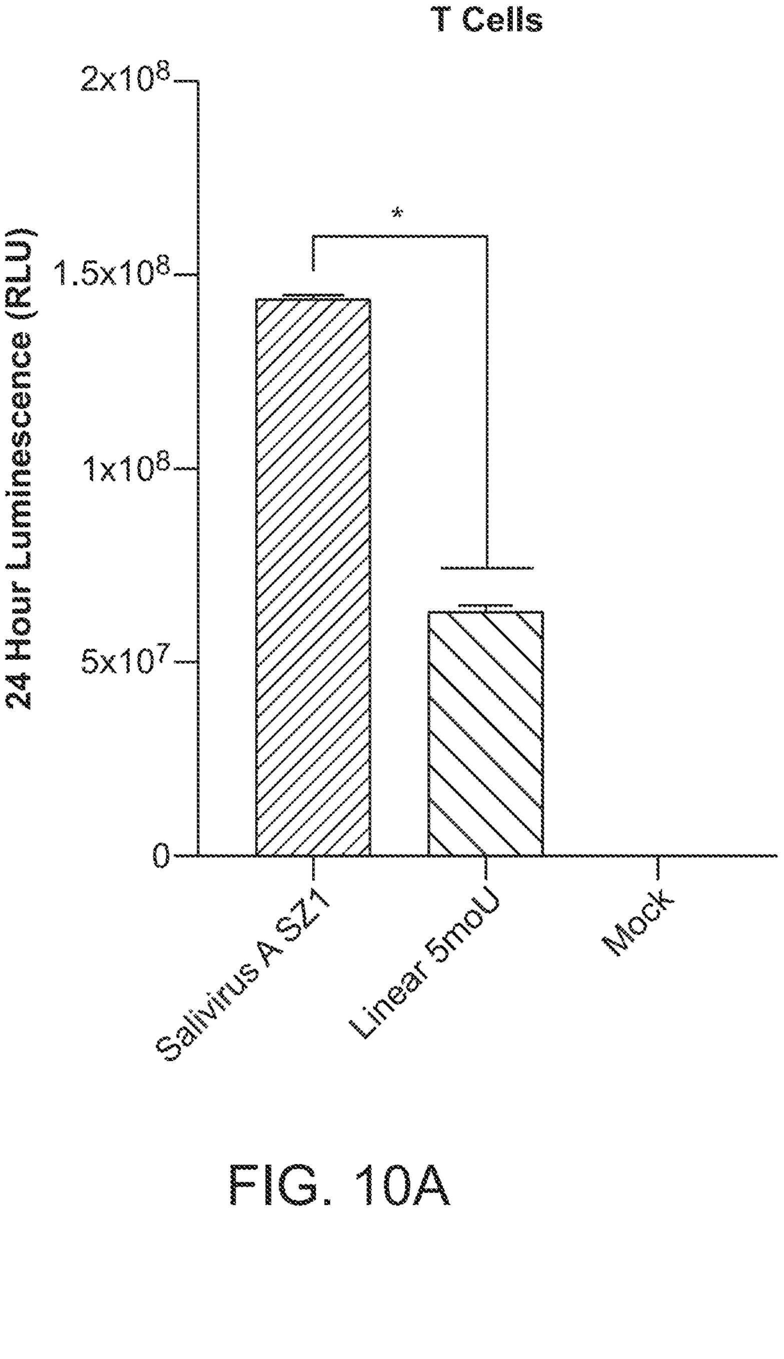
FIGS. 10A-10C depict 24 hour luminescence in supernatant of primary T cells (FIG. 10A) after transduction with circular RNA or modified linear RNA comprising a *Gaussia* luciferase expression sequence, or relative luminescence over 3 days (FIG. 10B), and 24 hour luminescence in PBMCs (FIG. 10C).
Figure 10B:
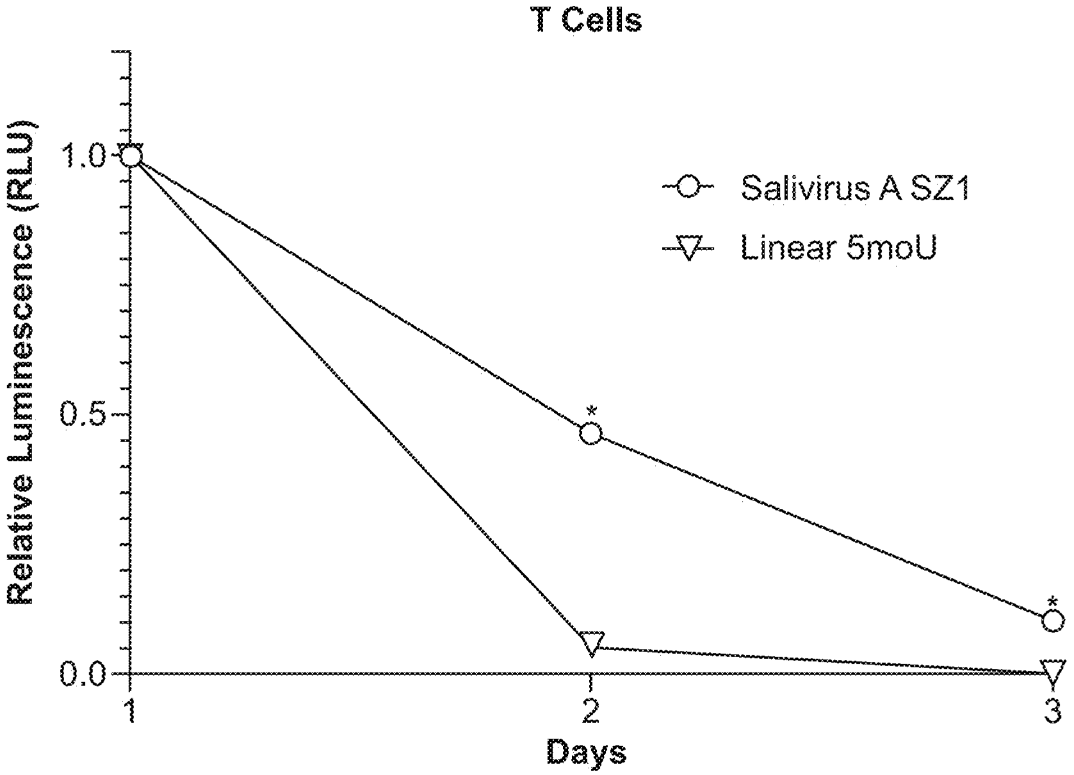
Figure 10C:
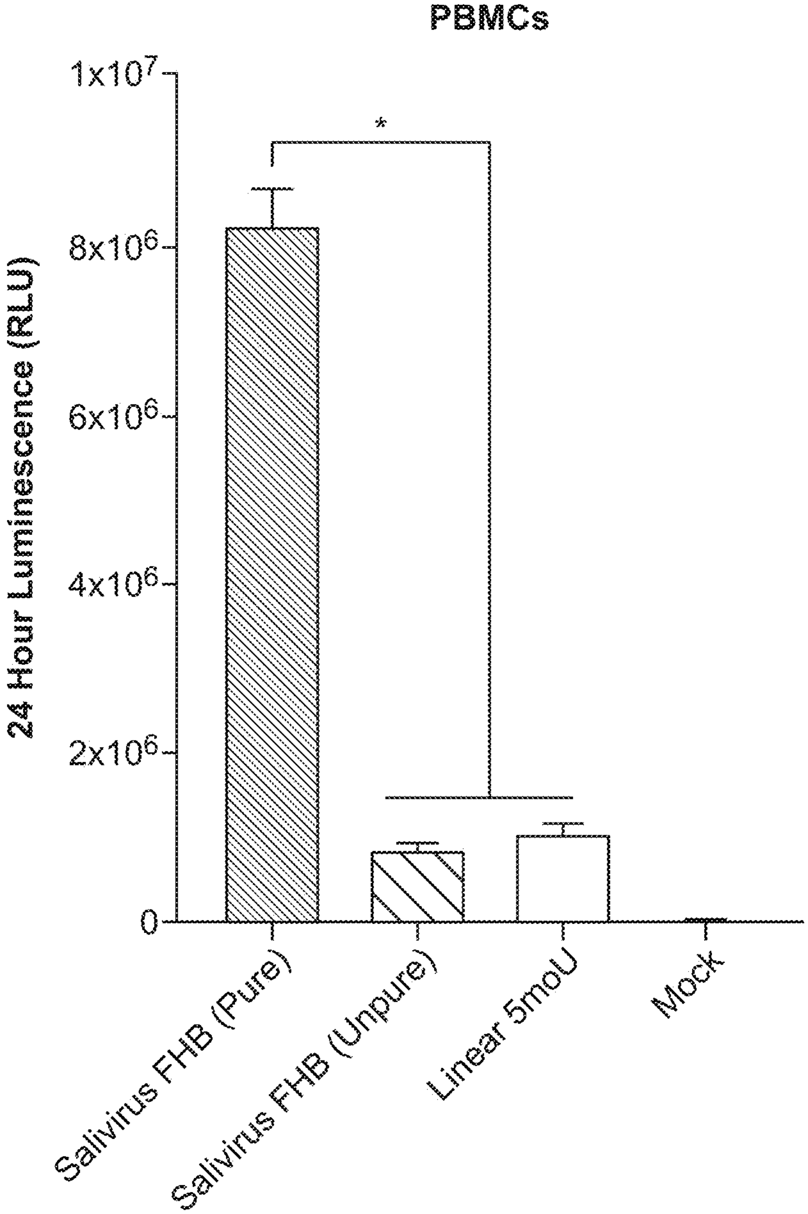

Constructs including anabaena intron/exon regions, a *Gaussia* luciferase expression sequence, and a Salivirus A SZ1 IRES or Salivirus FHB IRES were circularized. mRNA including a *Gaussia* luciferase expression sequence and a ~150 nt polyA tail, and modified to replace 100% of uridine with 5-methoxy uridine (5moU) and was purchased from Trilink. Expression of Salivirus A SZ1 IRES HPLC purified circular and modified mRNA was measured in human primary CD3+ T cells. Expression of Salivirus FHB HPLC purified circular, unpurified circular and modified mRNA was measured in human PBMCs. Luminescence from secreted *Gaussia* luciferase in supernatant was measured 24 hours after electroporation of 150,000 cells with 1 μg of each RNA species. Data for primary human T cells is shown in FIGS. 10A and 10B, and data for PBMCs is shown in FIG. 10C. The difference in expression between the purified circular RNA and unpurified circular RNA or linear RNA was significant in each case ($p<0.05$).

Luminescence from secreted *Gaussia* luciferase in primary T cell supernatant was measured every 24 hours after electroporation over 3 days in order to compare construct functional stability. Data is shown in FIG. 10B. The difference in relative luminescence from the day 1 measurement between purified circular RNA and linear RNA was significant at both day 2 and day 3 for primary T cells.

Example 14

Circularization Efficiency by Permutation Site in Anabaena Intron.

Figure 11A:
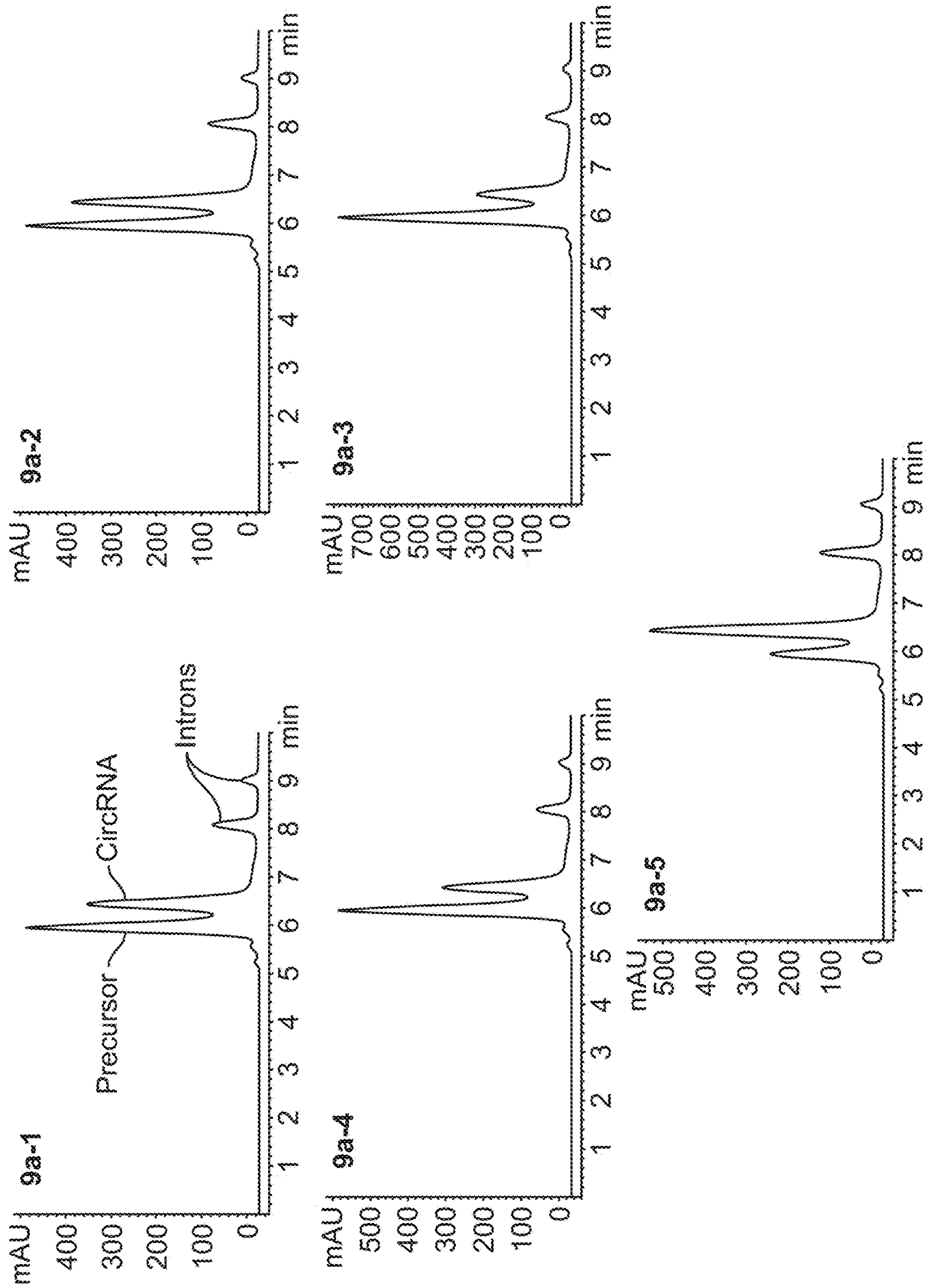
FIGS. 11A and 11B depict HPLC chromatograms (FIG. 11A) and circularization efficiencies (FIG. 11B) of RNA constructs having different permutation sites.

RNA constructs including a CVB3 IRES, a *Gaussia* luciferase expression sequence, anabaena intron/exon regions, spacers, internal homology regions, and homology arms were produced. Circularization efficiency of constructs using the traditional anabaena intron permutation site and 5 consecutive permutations sites in P9 was measured by HPLC. HPLC chromatograms for the 5 consecutive permutation sites in P9 are shown in FIG. 11A.

Figure 11B:
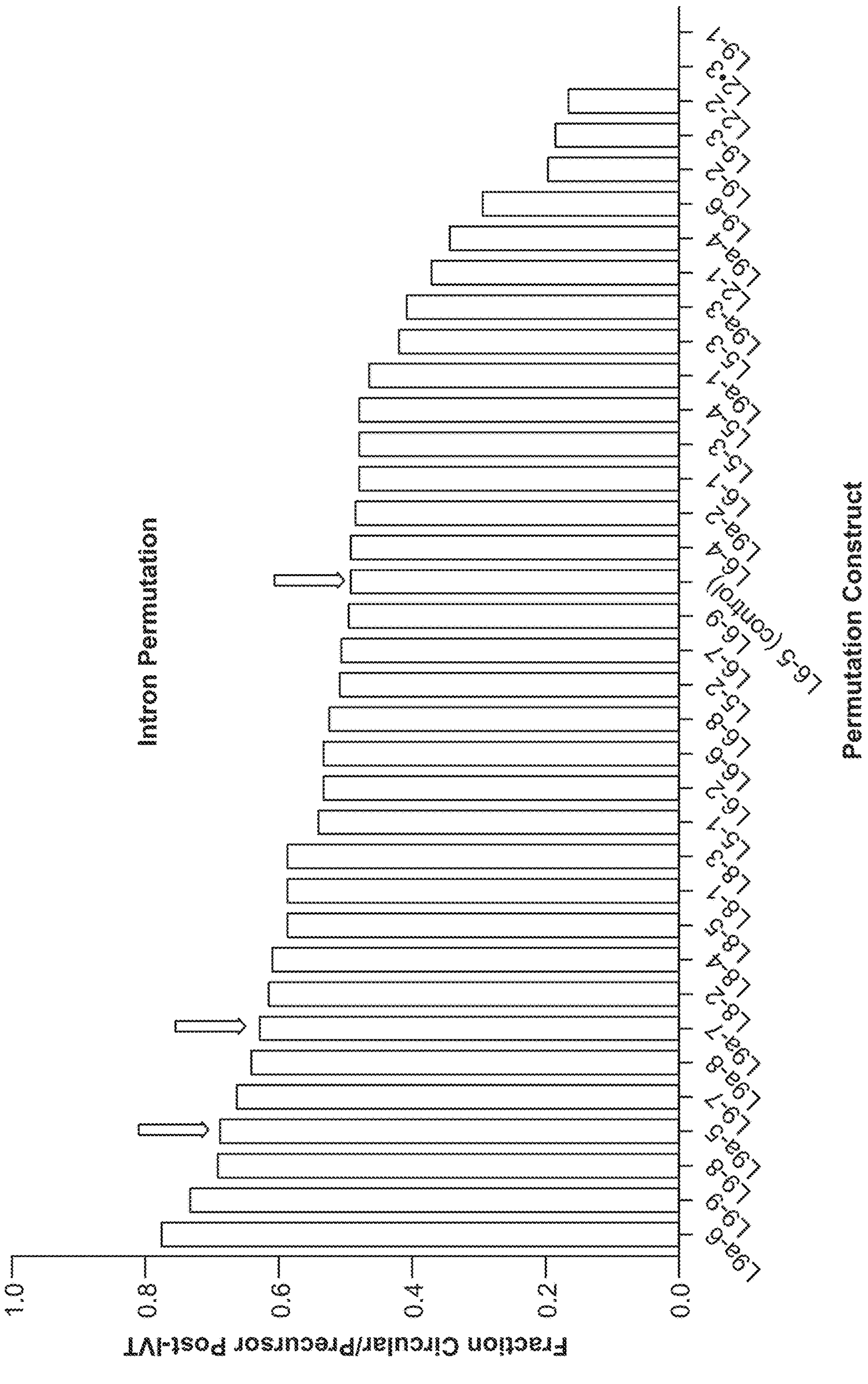

Circularization efficiency was measured at a variety of permutation sites. Circularization efficiency is defined as the area under the HPLC chromatogram curve for each of: circRNA/(circRNA+ precursor RNA). Ranked quantification of circularization efficiency at each permutation site is in FIG. 11B. 3 permutation sites (indicated in FIG. 11B) were selected for further investigation.

Circular RNA in this example was circularized by in vitro transcription (IVT) then purified via spin column. Circularization efficiency for all constructs would likely be higher if the additional step of incubation with $Mg^{2+}$ and guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 15

Circularization Efficiency of Alternative Introns.

Figure 12A:
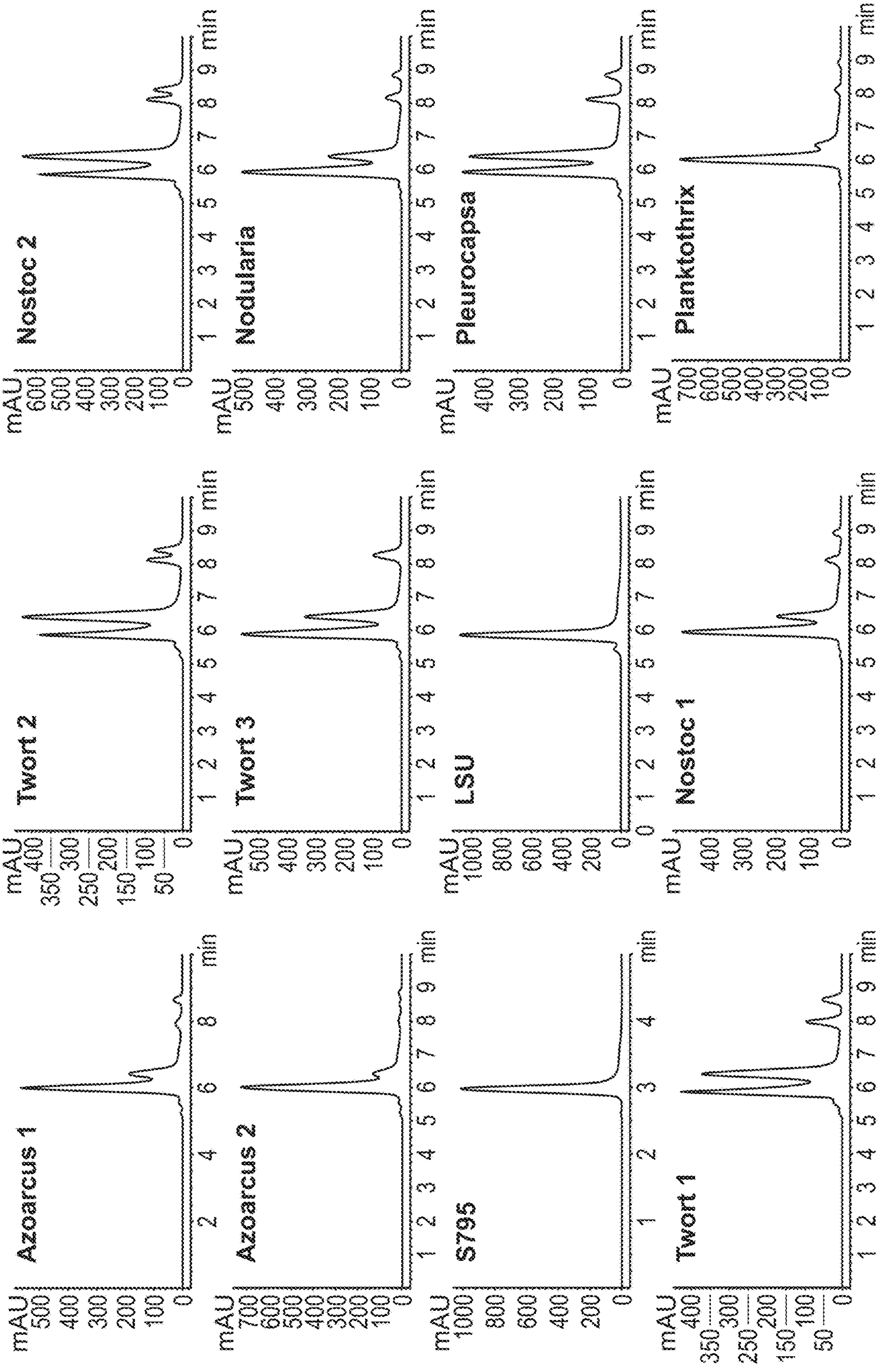
FIGS. 12A and 12B depict HPLC chromatograms (FIG. 12A) and circularization efficiencies (FIG. 12B) of RNA constructs having different introns and/or permutation sites.
Figure 12B:
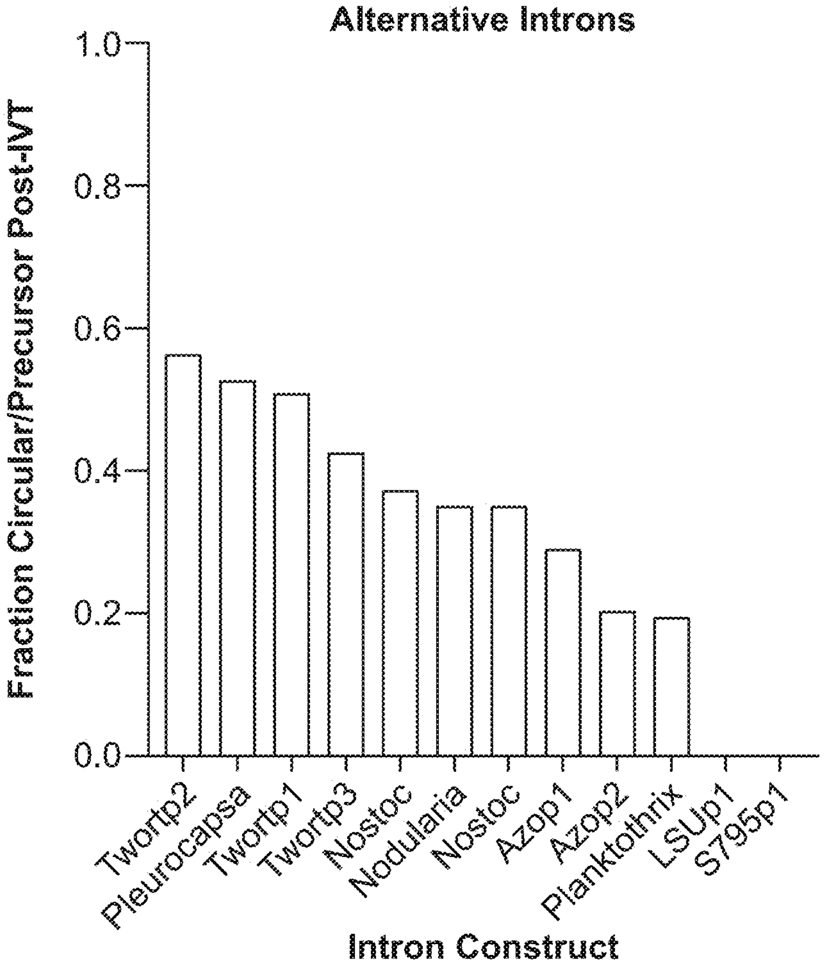

Precursor RNA containing a permuted group 1 intron of variable species origin or permutation site and several constant elements including: a CVB3 IRES, a *Gaussia* luciferase expression sequence, spacers, internal homology regions, and homology arms were created. Circularization data can be found in FIGS. 12A and 12B. FIG. 12A shows chromatograms resolving precursor, CircRNA and introns. FIG. 12B provides ranked quantification of circularization efficiency, based on the chromatograms shown in FIG. 12A, as a function of intron construct.

Circular RNA in this example was circularized by in vitro transcription (IVT) then spin column purification. Circularization efficiency for all constructs would likely be higher if the additional step of incubation with Mg' and guanosine nucleotide were included; however, removing this step allows for comparison between, and optimization of, circular RNA constructs. This level of optimization is especially useful for maintaining high circularization efficiency with large RNA constructs, such as those encoding chimeric antigen receptors.

Example 16

Circularization Efficiency by Homology Arm Presence or Length.

Figure 13A:
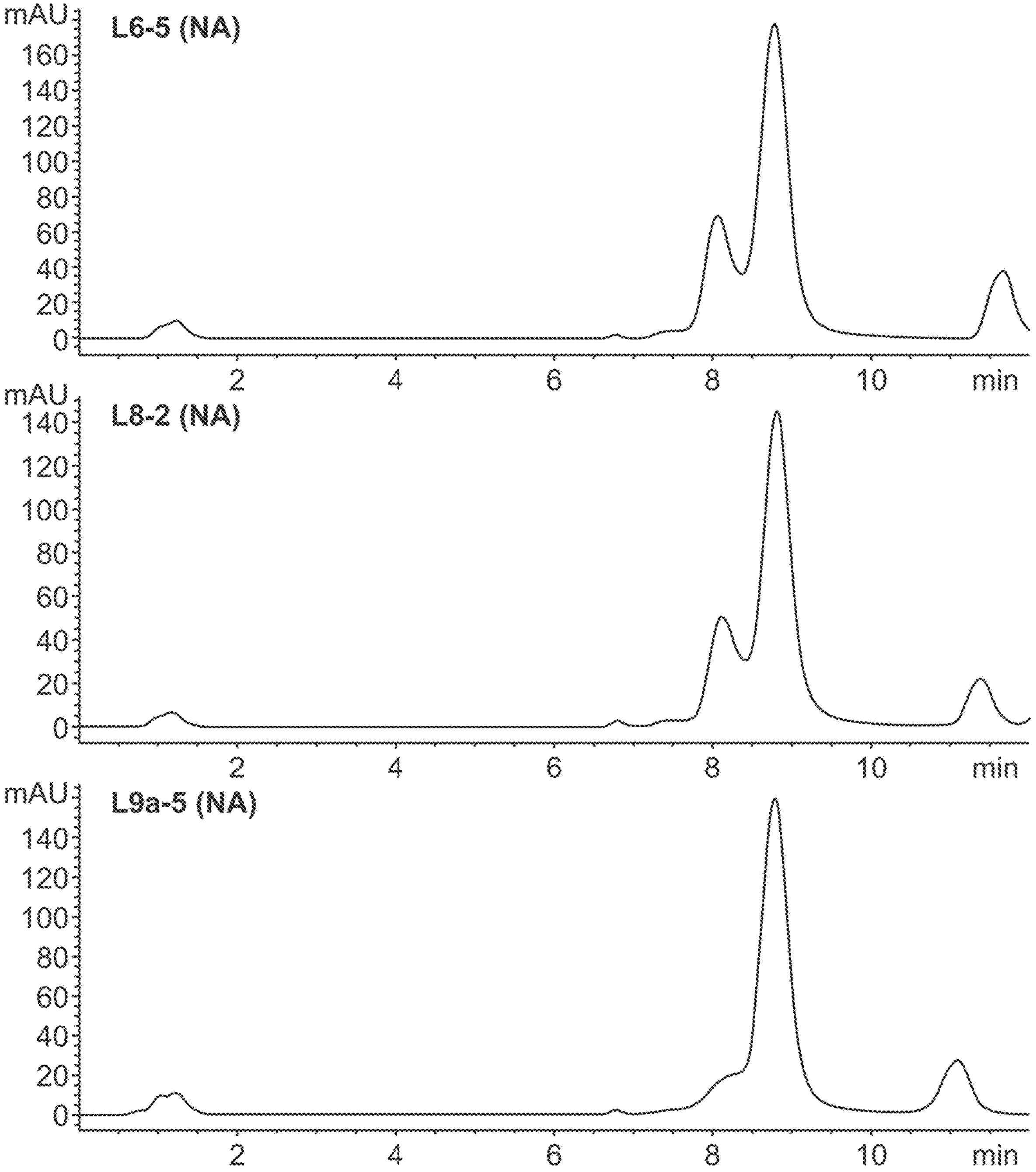
FIGS. 13A and 13B depict HPLC chromatograms (FIG. 13A) and circularization efficiencies (FIG. 13B) of 3 RNA constructs with or without homology arms.
Figure 13B:
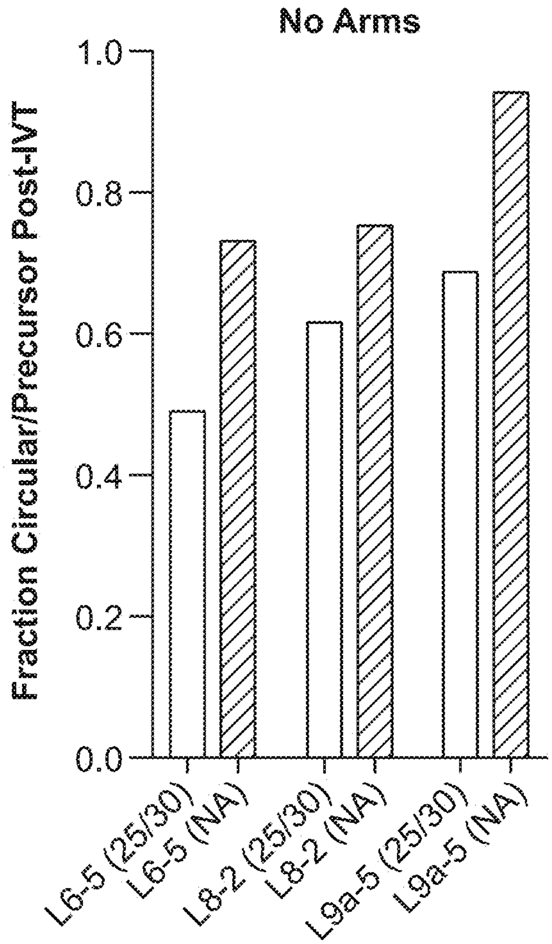

RNA constructs including a CVB3 IRES, a *Gaussia* luciferase expression sequence, anabaena intron/exon regions, spacers, and internal homology regions were produced. Constructs representing 3 Anabaena intron permutation sites were tested with 30 nt, 25% GC homology arms or without homology arms ("NA"). These constructs were allowed to circularize without an Mg' incubation step. Circularization efficiency was measured and compared. Data can be found in FIGS. 13A and 13B. Circularization efficiency was higher for each construct lacking homology arms. FIG. 13A provides ranked quantification of circularization efficiency; FIG. 13B provides chromatograms resolving precursor, circRNA and introns.

Figure 14:
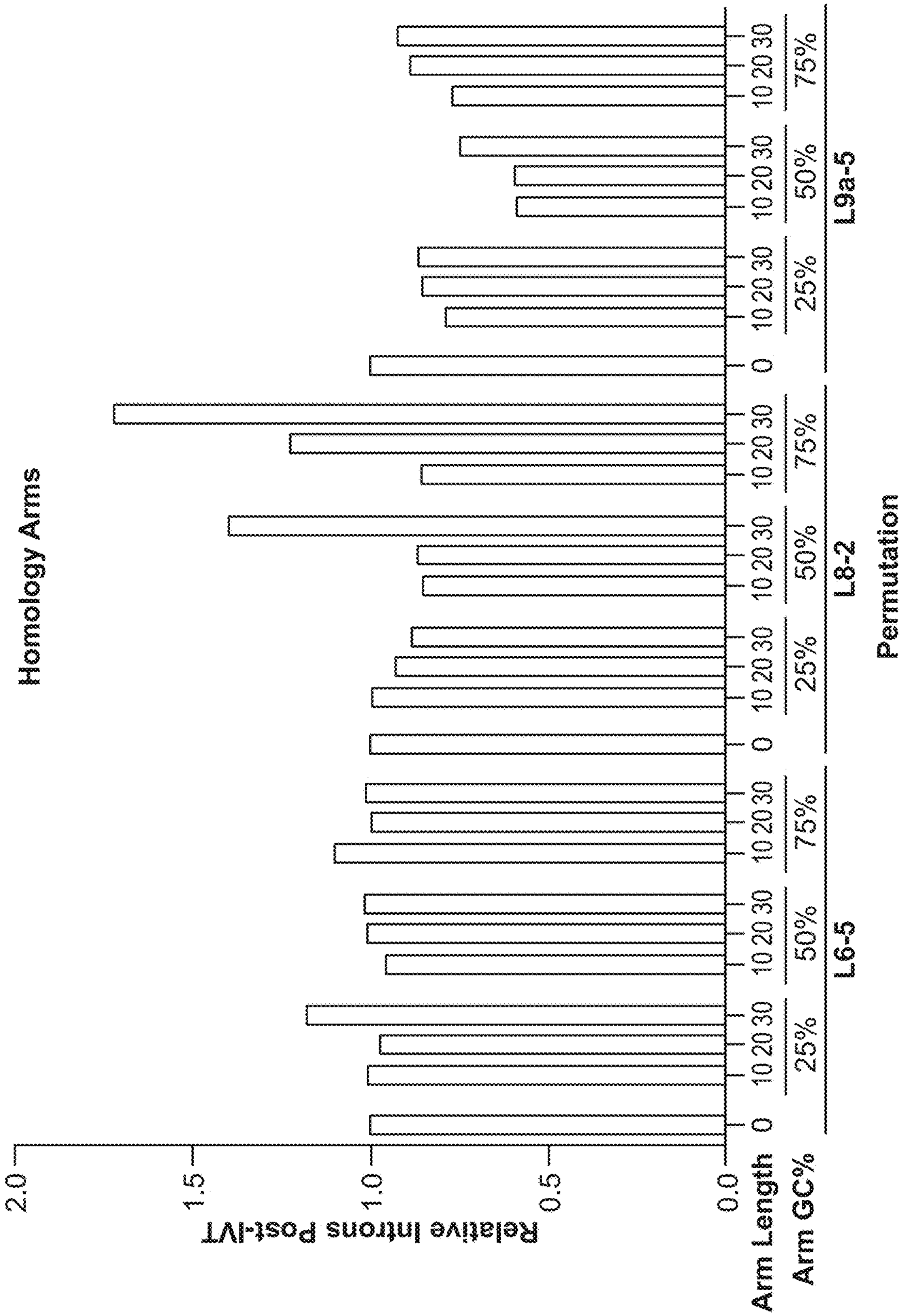
FIG. 14 depicts circularization efficiencies of 3 RNA constructs without homology arms or with homology arms having various lengths and GC content.

For each of the 3 permutation sites, constructs were created with 10 nt, 20 nt, and 30 nt arm lengths and 25%, 50%, and 75% GC content. Splicing efficiency of these constructs was measured and compared to constructs without homology arms (FIG. 14). Splicing efficiency is defined as the proportion of free introns relative to the total RNA in the splicing reaction.

Figure 15A:
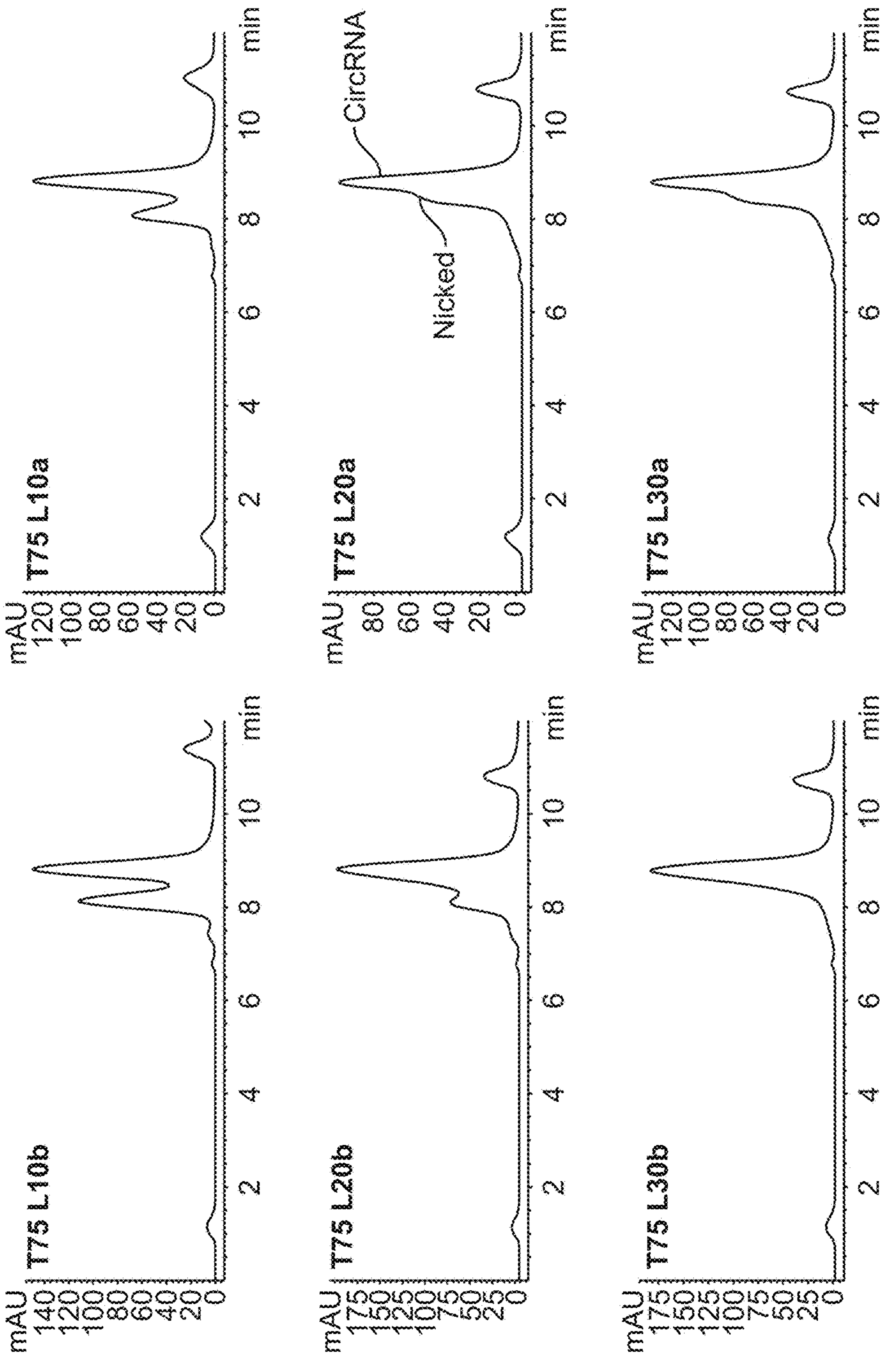
FIGS. 15A and 15B depict HPLC HPLC chromatograms showing the contribution of strong homology arms to improved splicing efficiency, the relationship between circularization efficiency and nicking in select constructs, and combinations of permutations sites and homology arms hypothesized to demonstrate improved circularization efficiency.

FIG. 15A (left) shows HPLC chromatograms indicating the contribution of strong homology arms to improved splicing efficiency. Top left: 75% GC content, 10 nt homology arms. Center left: 75% GC content, 20 nt homology arms. Bottom left: 75% GC content, 30 nt homology arms.

FIG. 15A (right) shows HPLC chromatograms showing increased splicing efficiency paired with increased nicking, appearing as a shoulder on the circRNA peak. Top right: 75% GC content, 10 nt homology arms. Center right: 75% GC content, 20 nt homology arms. Bottom right: 75% GC content, 30 nt homology arms.

Figure 15B:
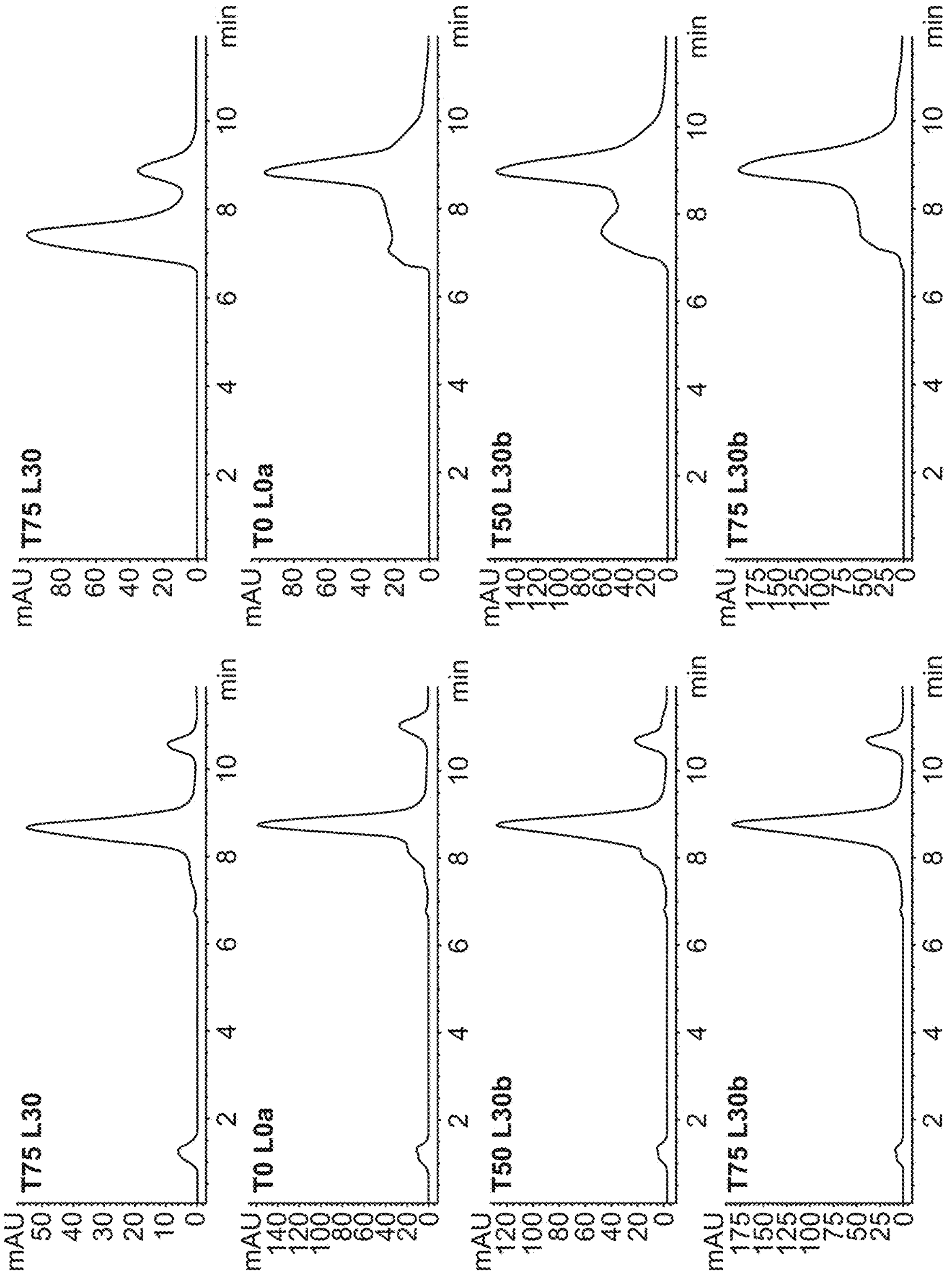

FIG. 15 B (left) shows select combinations of permutation sites and homology arms hypothesized to demonstrate improved circularization efficiency.

FIG. 15 B (right) shows select combinations of permutation sites and homology arms hypothesized to demonstrate improved circularization efficiency, treated with *E. coli* polyA polymerase.

Circular RNA in this example was circularized by in vitro transcription (IVT) then spin-column purified. Circularization efficiency for all constructs would likely be higher if an additional $Mg^{2+}$ incubation step with guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 17

Circular RNA Encoding a CAR

Figure 16:
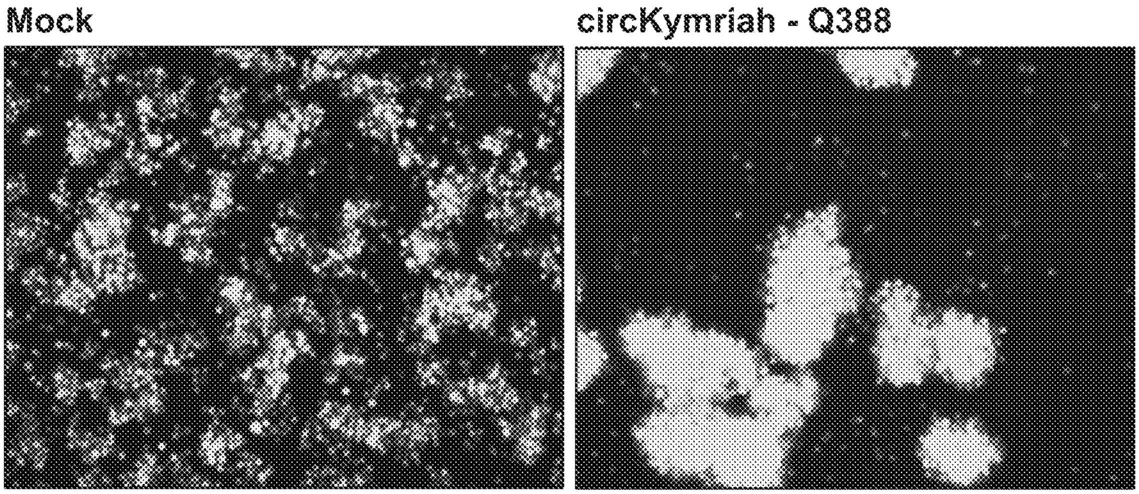
FIG. 16 shows fluorescent images of T cells mock electroporated (left) or electroporated with circular RNA encoding a CAR (right) and co-cultured with Raji cells expressing GFP and firefly luciferase.

Constructs including anabaena intron/exon regions, a Kymriah chimeric antigen receptor (CAR) expression sequence, and a CVB3 IRES were circularized. 100,000 human primary CD3+ T cells were electroporated with 500 ng of circRNA and co-cultured for 24 hours with Raji cells stably expressing GFP and firefly luciferase. Effector to target ratio (E:T ratio) 0.75:1. 100,000 human primary CD3+ T cells were mock electroporated and co-cultured as a control (FIG. 16).

Figure 17:
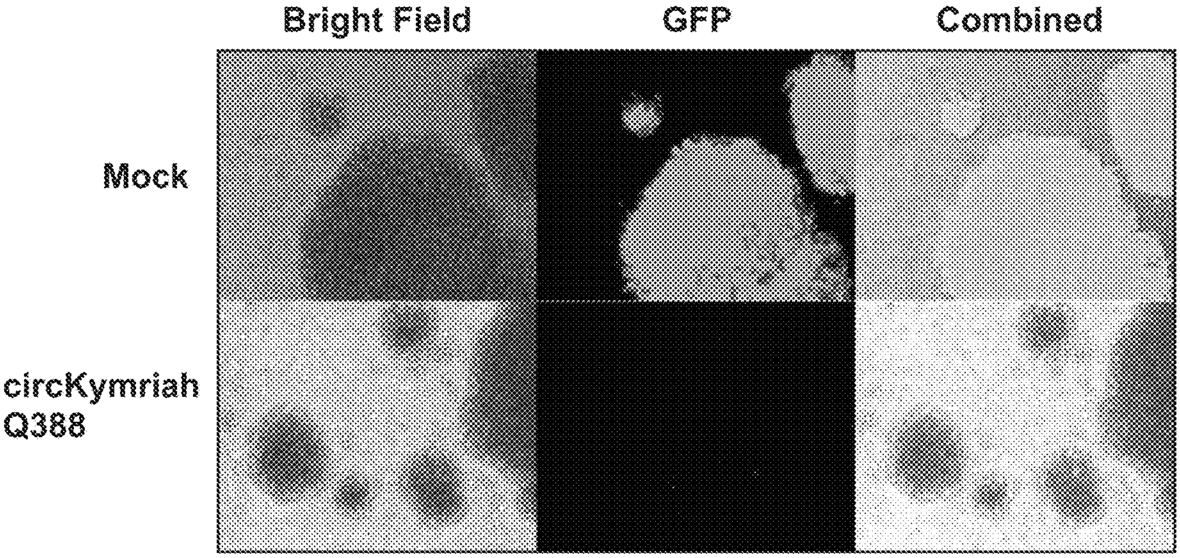
FIG. 17 shows bright field (left), fluorescent (center), and overlay (right) images of T cells mock electroporated (top) or electroporated with circular RNA encoding a CAR (bottom) and co-cultured with Raji cells expressing GFP and firefly luciferase.

Sets of 100,000 human primary CD3+ T cells were mock electroporated or electroporated with 1 μg of circRNA then co-cultured for 48 hours with Raji cells stably expressing GFP and firefly luciferase. E:T ratio 10:1 (FIG. 17).

Figure 18:
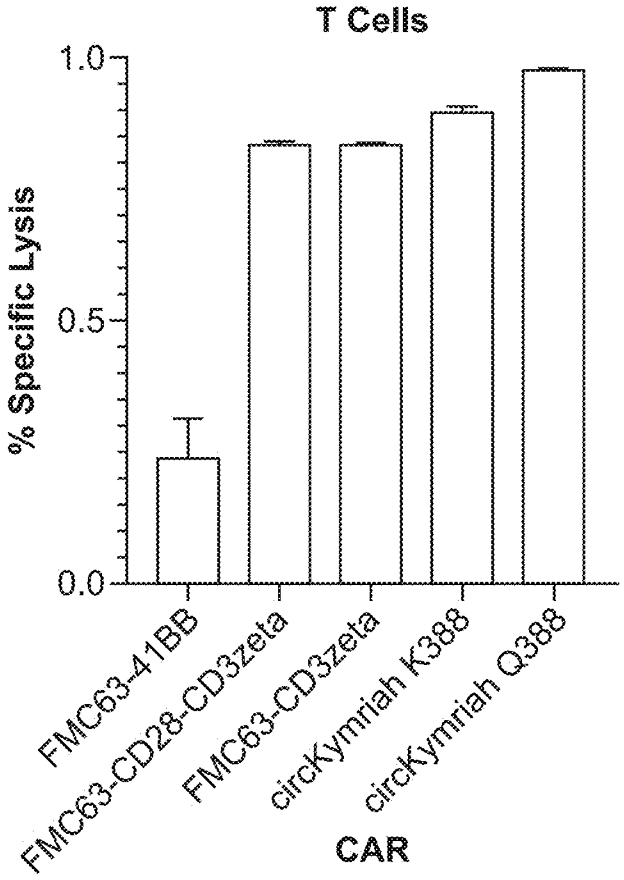
FIG. 18 depicts specific lysis of Raji target cells by T cells mock electroporated or electroporated with circular RNA encoding different CAR sequences.

Quantification of specific lysis of Raji target cells was determined by detection of firefly luminescence (FIG. 18). 100,000 human primary CD3+ T cells either mock electroporated or electroporated with circRNA encoding different CAR sequences were co-cultured for 48 hours with Raji cells stably expressing GFP and firefly luciferase. % Specific lysis defined as 1-[CAR condition luminescence]/[mock condition luminescence]. E:T ratio 10:1.

Example 18

Expression and Functional Stability of Circular and Linear RNA in Jurkat Cells and Resting Human T Cells.

Figure 19A:
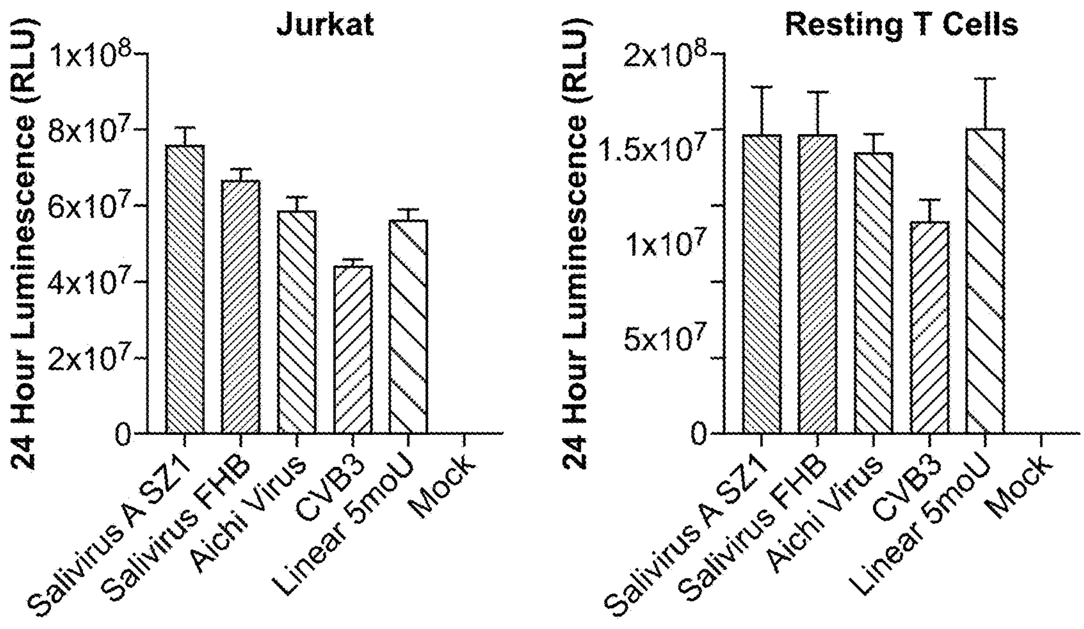
FIGS. 19A and 19B depict luminescence in supernatants of Jurkat cells (left) or resting primary human CD3+ T cells (right) 24 hours after transduction with linear or circular RNA comprising a *Gaussia* luciferase expression sequence and varying IRES sequences (FIG. 19A), and relative luminescence over 3 days (FIG. 19B).

Constructs including anabaena intron/exon regions, a *Gaussia* luciferase expression sequence, and a subset of previously tested IRES were circularized and reaction products were purified by size exclusion HPLC. 150,000 Jurkat cells were electroporated with 1 μg of circular RNA or 5moU-mRNA. Luminescence from secreted *Gaussia* luciferase in supernatant was measured 24 hours after electroporation (FIG. 19A left). 150,000 resting primary human CD3+ T cells (10 days post-stimulation) were electroporated with 1 μg of circular RNA or 5moU-mRNA. Luminescence from secreted *Gaussia* luciferase in supernatant was measured 24 hours after electroporation (FIG. 19A right).

Figure 19B:
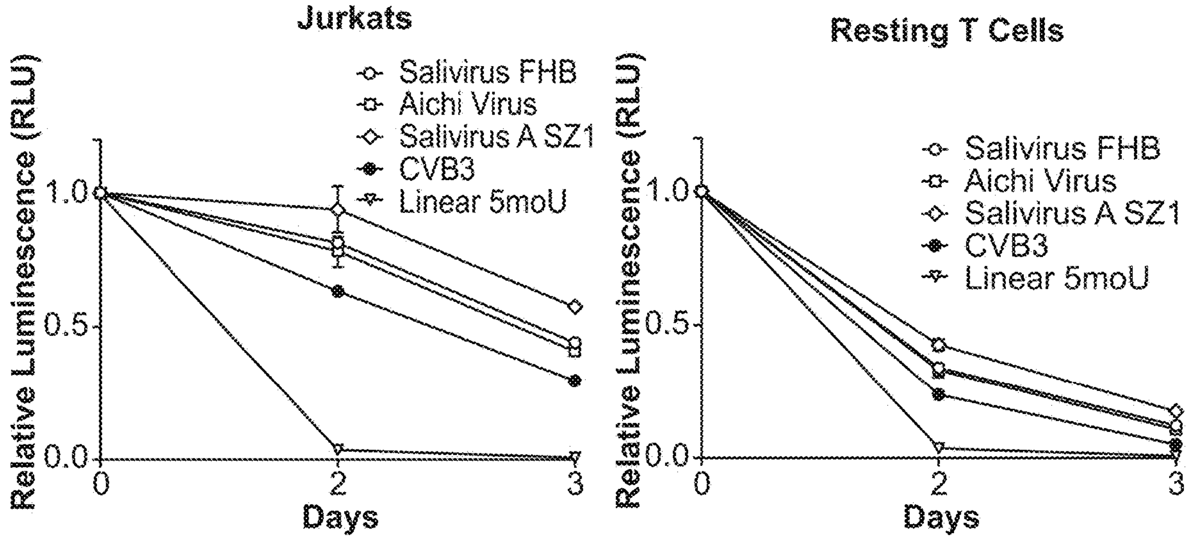

Luminescence from secreted *Gaussia* luciferase in supernatant was measured every 24 hours after electroporation, followed by complete media replacement. Functional stability data is shown in FIG. 19B. Circular RNA had more functional stability than linear RNA in each case, with a more pronounced difference in Jurkat cells.

Example 19

IFN-β1, RIG-I, IL-2, IL-6, IFNγ, and TNFα Transcript Induction of Cells Electroporated with Linear RNA or Varying Circular RNA Constructs.

Figure 20A:
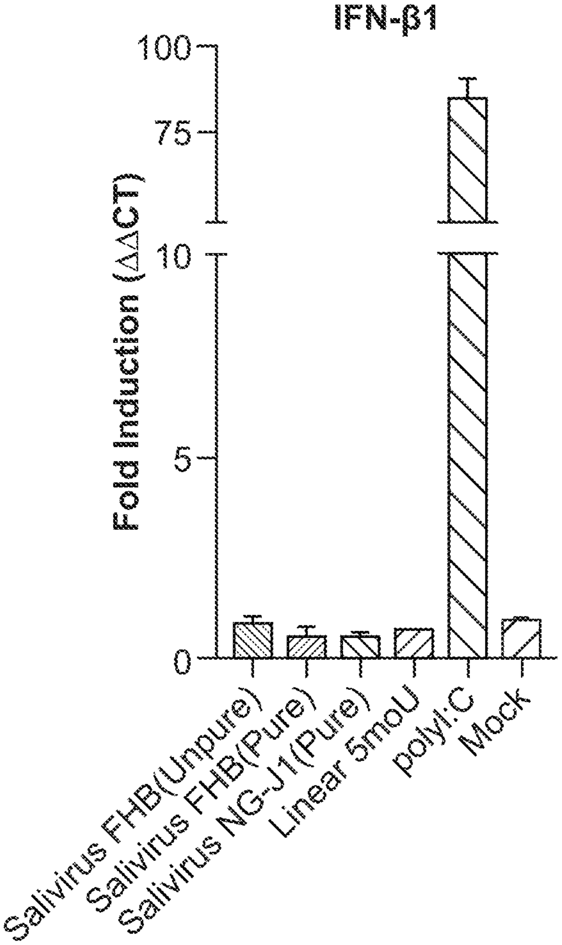
FIGS. 20A-20F depict transcript induction of IFN-β1 (FIG. 20A), RIG-I (FIG. 20B), IL-2 (FIG. 20C), IL-6 (FIG. 20D), IFNγ (FIG. 20E), and TNFα (FIG. 20F) after electroporation of human CD3+ T cells with modified linear, unpurified circular, or purified circular RNA.
Figure 20B:
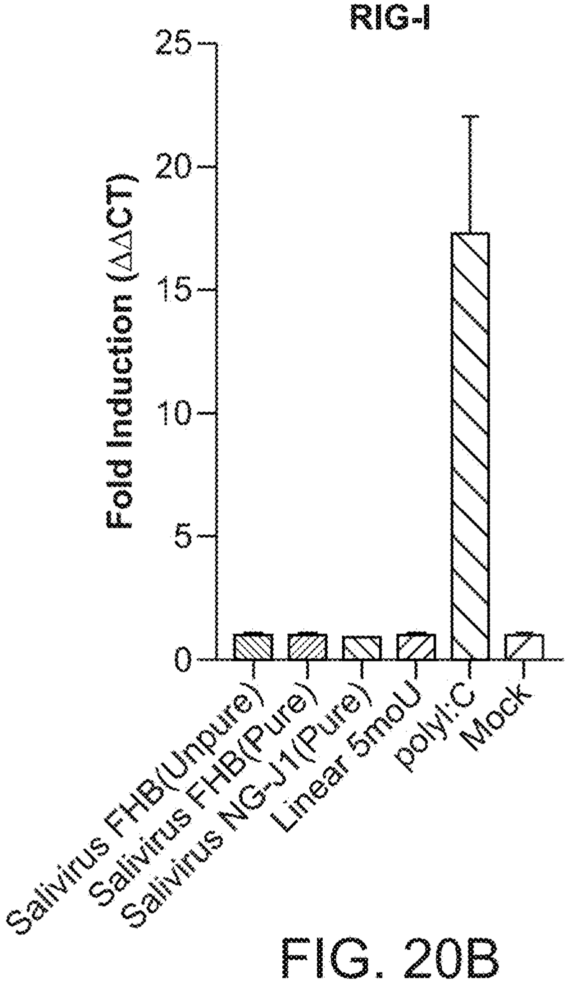
Figure 20C:
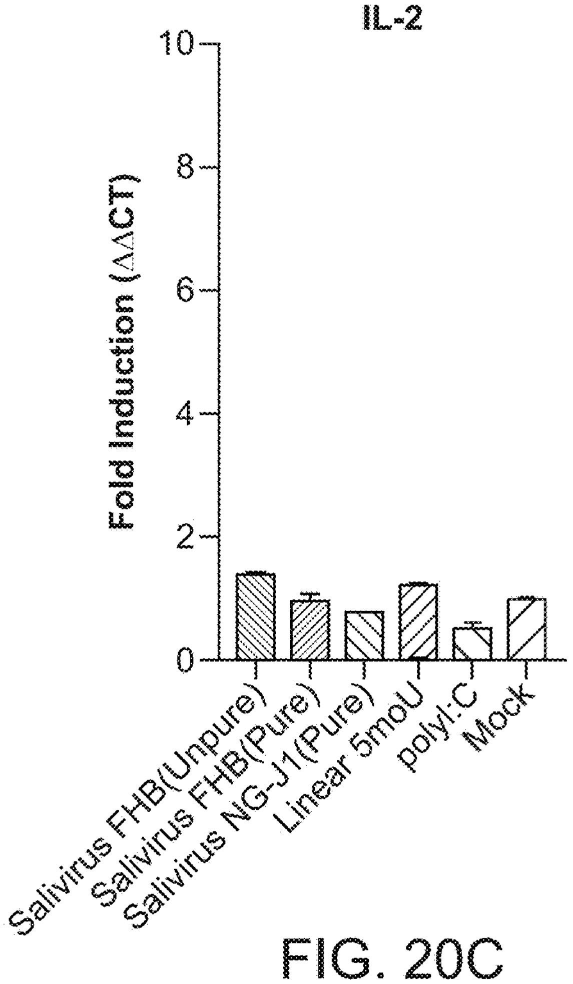
Figure 20D:
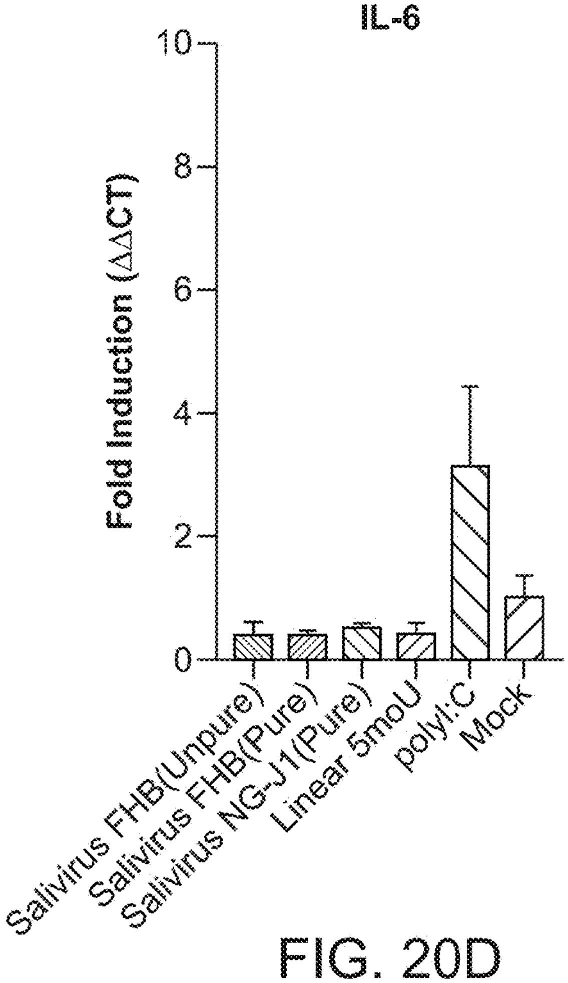
Figure 20E:
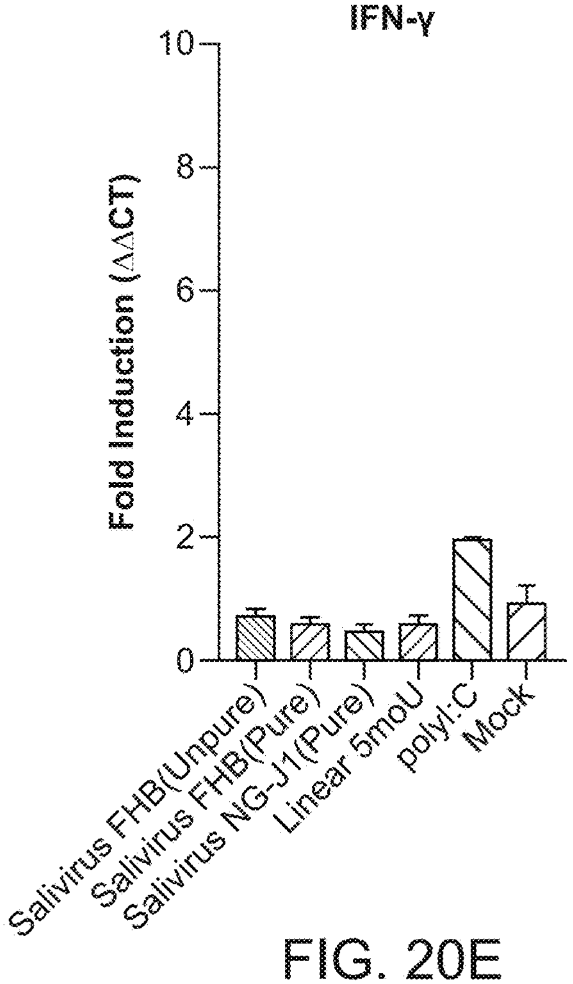
Figure 20F:
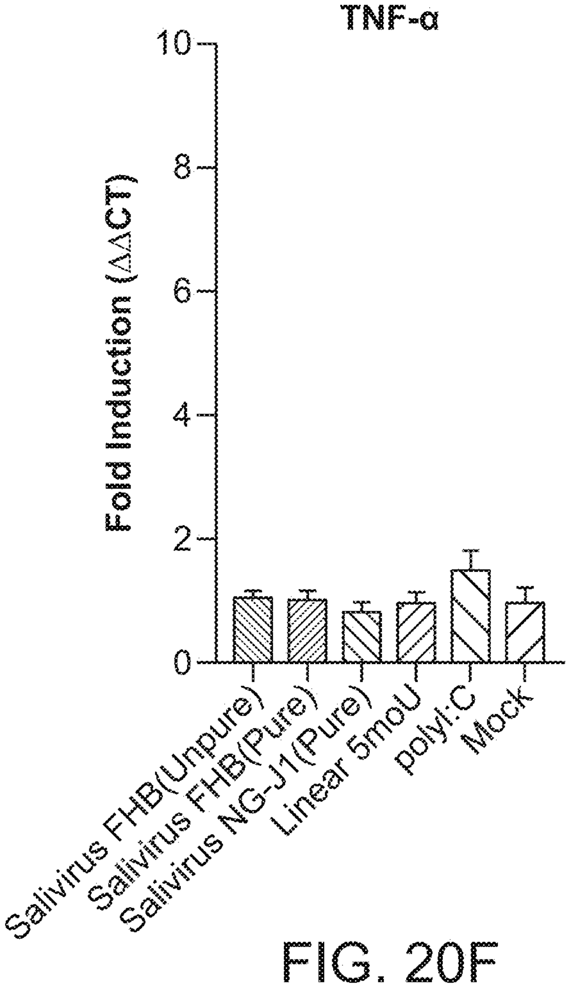

Constructs including anabaena intron/exon regions, a *Gaussia* luciferase expression sequence, and a subset of previously tested IRES were circularized and reaction products were purified by size exclusion HPLC. 150,000 CD3+ human T cells were electroporated with 1 μg of circular RNA, 5moU-mRNA, or immunostimulatory positive control poly inosine: cytosine. IFN-β1 (FIG. 20A), RIG-I (FIG. 20B), IL-2 (FIG. 20C), IL-6 (FIG. 20D), IFN-γ (FIG. 20E), and TNF-α (FIG. 20F) transcript induction was measured 18 hours after electroporation.

Example 20

Specific Lysis of Target Cells and IFNγ Transcript Induction by CAR Expressing Cells Electroporated with Different Amounts of Circular or Linear RNA; Specific Lysis of Target and Non-Target Cells by CAR Expressing Cells at Different E:T Ratios.

Figure 21A:
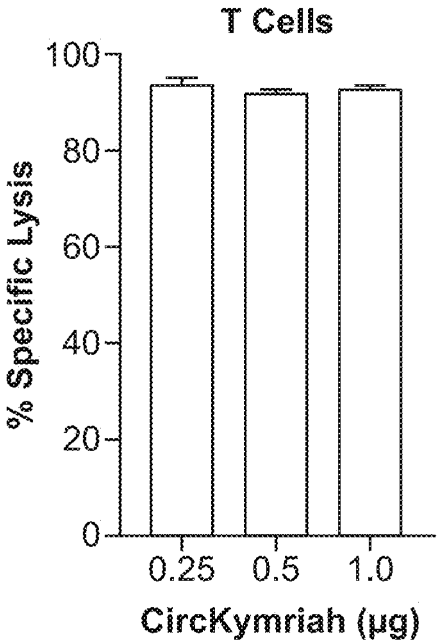
FIGS. 21A and 21B depict specific lysis of Raji target cells by human primary CD3+ T cells electroporated with circRNA encoding a CAR as determined by detection of firefly luminescence (FIG. 21A), and IFNγ transcript induction 24 hours after electroporation with different quantities of circular or linear RNA encoding a CAR sequence (FIG. 21B).
Figure 21B:
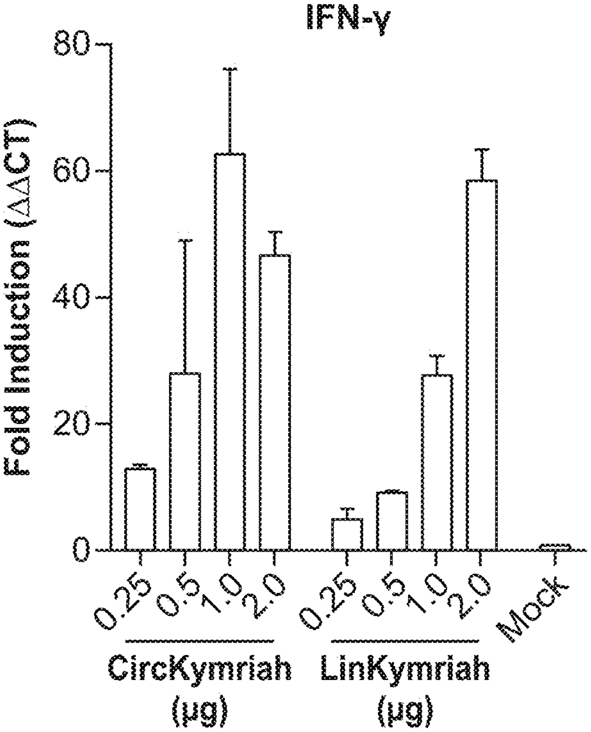

Constructs including anabaena intron/exon regions, an anti-CD19 CAR expression sequence, and a CVB3 IRES were circularized and reaction products were purified by size exclusion HPLC. 150,000 human primary CD3+ T cells either mock electroporated or electroporated with different quantities of circRNA encoding an anti-CD19 CAR sequence were co-cultured for 12 hours with Raji cells stably expressing GFP and firefly luciferase at an E:T ratio of 2:1. % Specific lysis of Raji target cells was determined by detection of firefly luminescence (FIG. 21A). % Specific lysis was defined as 1-[CAR condition luminescence]/[mock condition luminescence]. IFNγ transcript induction was measured 24 hours after electroporation (FIG. 21B).

Figure 22A:
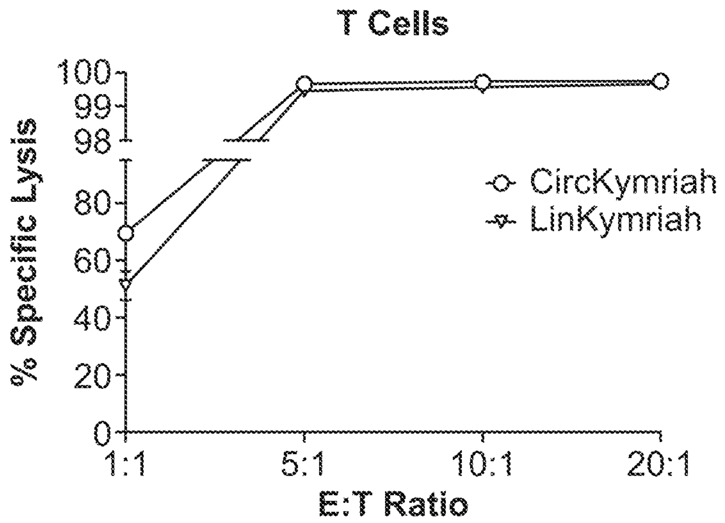
FIGS. 22A and 22B depict specific lysis of target or non-target cells by human primary CD3+ T cells electroporated with circular or linear RNA encoding a CAR at different E:T ratios (FIG. 22A and FIG. 22B) as determined by detection of firefly luminescence.

150,000 human primary CD3+ T cells were either mock electroporated or electroporated with 500 ng circRNA or m1ψ-mRNA encoding an anti-CD19 CAR sequence, then co-cultured for 24 hours with Raji cells stably expressing firefly luciferase at different E:T ratios. Specific lysis of Raji target cells was determined by detection of firefly luminescence (FIG. 22A). Specific lysis was defined as 1-[CAR condition luminescence]/[mock condition luminescence].

Figure 22B:
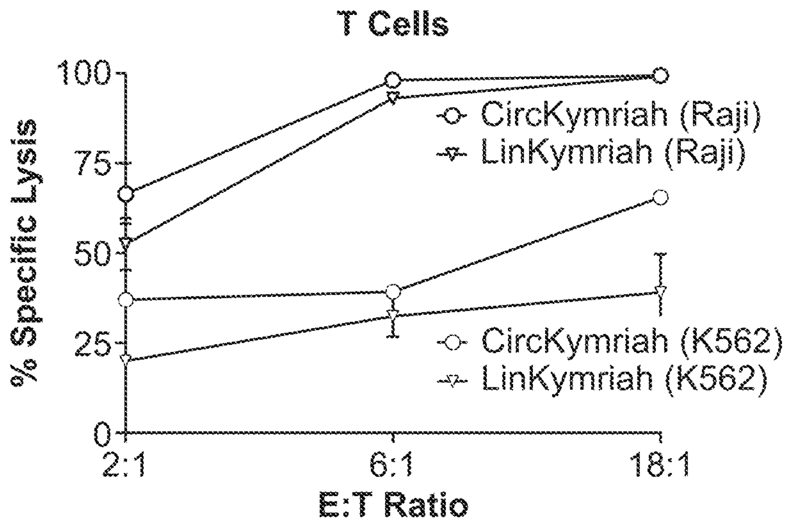

CAR expressing T cells were also co-cultured for 24 hours with Raji or K562 cells stably expressing firefly luciferase at different E:T ratios. Specific lysis of Raji target cells or K562 non-target cells was determined by detection of firefly luminescence (FIG. 22B). % Specific lysis is defined as 1-[CAR condition luminescence]/[mock condition luminescence].

Example 21

Specific Lysis of Target Cells by T Cells Electroporated with Circular RNA or Linear RNA Encoding a CAR.

Figure 23:
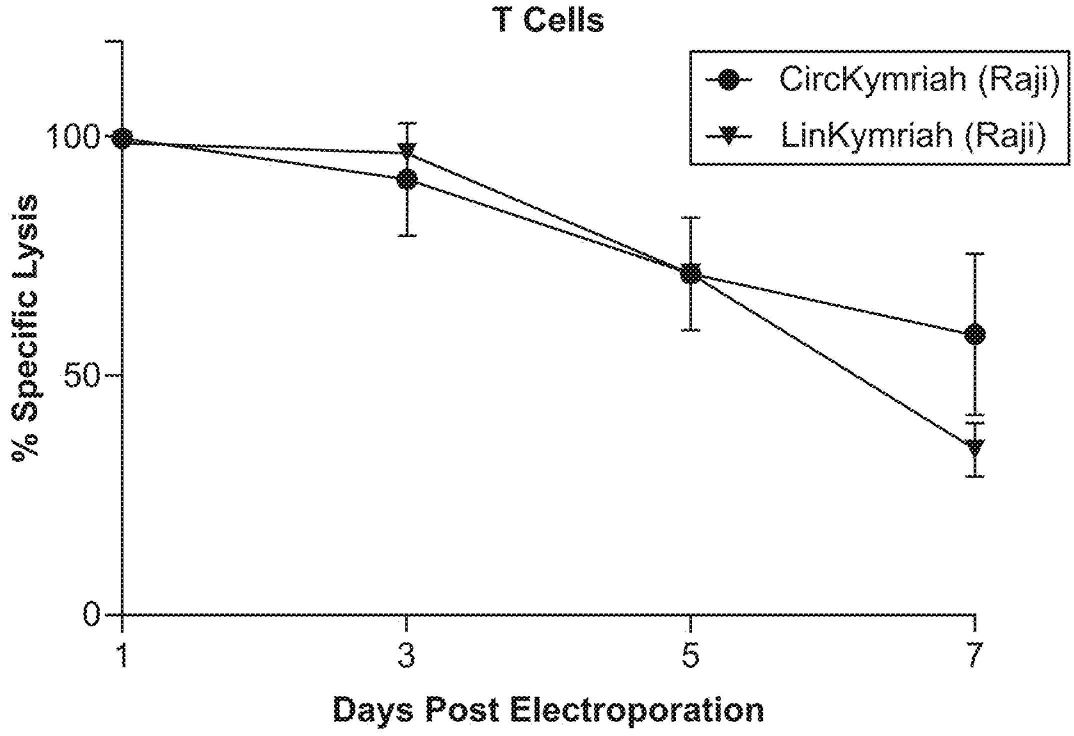
FIG. 23 depicts specific lysis of target cells by human CD3+ T cells electroporated with RNA encoding a CAR at 1, 3, 5, and 7 days post electroporation.

Constructs including anabaena intron/exon regions, an anti-CD19 CAR expression sequence, and a CVB3 IRES were circularized and reaction products were purified by size exclusion HPLC. Human primary CD3+ T cells were electroporated with 500 ng of circular RNA or an equimolar quantity of m1ψ-mRNA, each encoding a CD19-targeted CAR. Raji cells were added to CAR-T cell cultures over 7 days at an E:T ratio of 10:1. % Specific lysis was measured for both constructs at 1, 3, 5, and 7 days (FIG. 23).

Example 22

Specific Lysis of Raji Cells by T Cells Expressing an Anti-CD19 CAR or an Anti-BCMA CAR.

Figure 24:
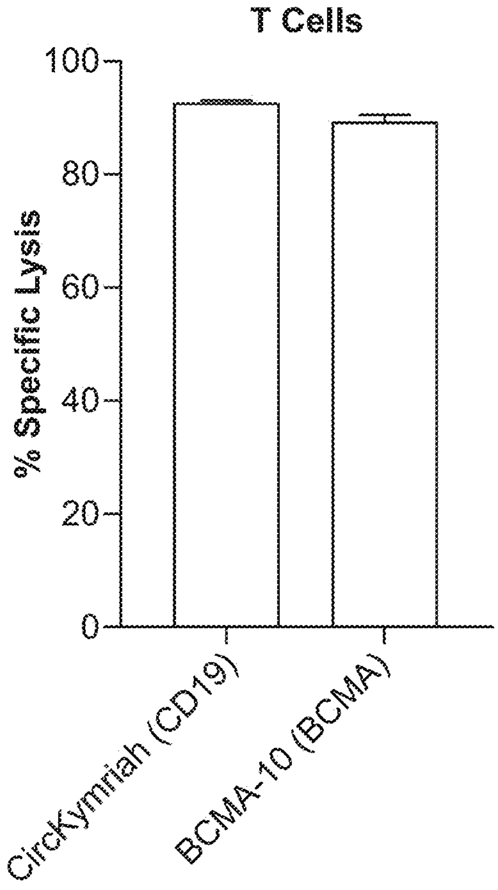
FIG. 24 depicts specific lysis of target cells by human CD3+ T cells electroporated with circular RNA encoding a CD19 or BCMA targeted CAR.

Constructs including Anabaena intron/exon regions, anti-CD19 or anti-BCMA CAR expression sequence, and a CVB3 IRES were circularized and reaction products were purified by size exclusion HPLC. 150,000 primary human CD3+ T cells were electroporated with 500 ng of circRNA, then were co-cultured with Raji cells at an E:T ratio of 2:1. % Specific lysis was measured 12 hours after electroporation (FIG. 24).

Example 23

Synthesis of Compounds

Synthesis of representative ionizable lipids of the invention are described in PCT applications PCT/US2016/052352, PCT/US2016/068300, PCT/US2010/061058, PCT/US2018/058555, PCT/US2018/053569, PCT/US2017/028981, PCT/US2019/025246, PCT/US2018/035419, PCT/US2019/015913, and US applications with publication numbers 20190314524, 20190321489, and 20190314284, the contents of each of which are incorporated herein by reference in their entireties.

Example 24

Production of Nanoparticle Compositions

In order to investigate safe and efficacious nanoparticle compositions for use in the delivery of circular RNA to cells, a range of formulations are prepared and tested. Specifically, the particular elements and ratios thereof in the lipid component of nanoparticle compositions are optimized.

Nanoparticles can be made with mixing processes such as microfluidics and T-junction mixing of two fluid streams, one of which contains the circular RNA and the other has the lipid components.

Lipid compositions are prepared by combining an ionizable lipid, optionally a helper lipid (such as DOPE, DSPC, or oleic acid obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid such as cholesterol at concentrations of about, e.g., 50 mM in a solvent, e.g., ethanol. Solutions should be refrigerated for storage at, for example, −20° C. Lipids are combined to yield desired molar ratios (see, for example, Tables 12 and 13 below) and diluted with water and ethanol to a final lipid concentration of e.g., between about 5.5 mM and about 25 mM.

TABLE 12

| Formulation number | Description |
|---|---|
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 2 | Aliquots of 50 mg/mL ethanolic solutions of DODAP, DOPE, cholesterol and DMG-PEG2K (18:56:20:6) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9 nm (Dv(50) = 57.3 nm; Dv(90) = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/ |

TABLE 12-continued

| Formulation number | Description |
|---|---|
| | 150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |
| 6 | Aliquots of 50 mg/mL ethanolic solutions of HGT5001, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |

In some embodiments, transfer vehicle has a formulation as described in Table 12.

TABLE 13

| Composition (mol %) | Components |
|---|---|
| 40:20:38.5:1.5 | Compound:Phospholipid:Phytosterol*:PEG-DMG |
| 45:15:38.5:1.5 | Compound:Phospholipid:Phytosterol*:PEG-DMG |
| 50:10:38.5:1.5 | Compound:Phospholipid:Phytosterol*:PEG-DMG |
| 55:5:38.5:1.5 | Compound:Phospholipid:Phytosterol*:PEG-DMG |
| 60:5:33.5:1.5 | Compound:Phospholipid:Phytosterol*:PEG-DMG |
| 45:20:33.5:1.5 | Compound:Phospholipid:Phytosterol*:PEG-DMG |
| 50:20:28.5:1.5 | Compound:Phospholipid:Phytosterol*:PEG-DMG |
| 55:20:23.5:1.5 | Compound:Phospholipid:Phytosterol*:PEG-DMG |
| 60:20:18.5:1.5 | Compound:Phospholipid:Phytosterol*:PEG-DMG |
| 40:15:43.5:1.5 | Compound:Phospholipid:Phytosterol*:PEG-DMG |
| 50:15:33.5:1.5 | Compound:Phospholipid:Phytosterol*:PEG-DMG |
| 55:15:28.5:1.5 | Compound:Phospholipid:Phytosterol*:PEG-DMG |
| 60:15:23.5:1.5 | Compound:Phospholipid:Phytosterol*:PEG-DMG |
| 40:10:48.5:1.5 | Compound:Phospholipid:Phytosterol*:PEG-DMG |
| 45:10:43.5:1.5 | Compound:Phospholipid:Phytosterol*:PEG-DMG |
| 55:10:33.5:1.5 | Compound:Phospholipid:Phytosterol*:PEG-DMG |
| 60:10:28.5:1.5 | Compound:Phospholipid:Phytosterol*:PEG-DMG |
| 40:5:53.5:1.5 | Compound:Phospholipid:Phytosterol*:PEG-DMG |
| 45:5:48.5:1.5 | Compound:Phospholipid:Phytosterol*:PEG-DMG |
| 50:5:43.5:1.5 | Compound:Phospholipid:Phytosterol*:PEG-DMG |
| 40:20:40:0 | Compound:Phospholipid:Phytosterol*:PEG-DMG |
| 45:20:35:0 | Compound:Phospholipid:Phytosterol*:PEG-DMG |
| 50:20:30:0 | Compound:Phospholipid:Phytosterol*:PEG-DMG |
| 55:20:25:0 | Compound:Phospholipid:Phytosterol*:PEG-DMG |
| 60:20:20:0 | Compound:Phospholipid:Phytosterol*:PEG-DMG |
| 40:15:45:0 | Compound:Phospholipid:Phytosterol*:PEG-DMG |

In some embodiments, transfer vehicle has a formulation as described in Table 13, where Compound refers to a circular RNA as described herein.

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kDa. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation.

Alternative processes including, but not limited to, T-junction and direct injection, may be used to achieve the same nano-precipitation. B. Characterization of nanoparticle compositions A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, CA) can be used to evaluate the encapsulation of circRNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilabel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100).

C.

In Vivo Formulation Studies:

In order to monitor how effectively various nanoparticle compositions deliver circRNA to targeted cells, different nanoparticle compositions including circRNA are prepared and administered to rodent populations. Mice are intravenously, intramuscularly, intraarterially, or intratumorally administered a single dose including a nanoparticle composition with a lipid nanoparticle formulation. In some instances, mice may be made to inhale doses. Dose sizes may range from 0.001 mg/kg to 10 mg/kg, where 10 mg/kg describes a dose including 10 mg of a circRNA in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. Time courses of protein expression can also be evaluated. Samples collected from the rodents for evaluation may include blood and tissue (for example, muscle tissue from the site of an intramuscular injection and internal tissue); sample collection may involve sacrifice of the animals.

Higher levels of protein expression induced by administration of a composition including a circRNA will be indicative of higher circRNA translation and/or nanoparticle composition circRNA delivery efficiencies. As the non-RNA components are not thought to affect translational machineries themselves, a higher level of protein expression is likely indicative of a higher efficiency of delivery of the circRNA by a given nanoparticle composition relative to other nanoparticle compositions or the absence thereof.

Example 25

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the transfer vehicle compositions in 1×PBS in determining particle size and 15 mM PBS in determining zeta potential.

Ultraviolet-visible spectroscopy can be used to determine the concentration of a therapeutic and/or prophylactic (e.g., RNA) in transfer vehicle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of therapeutic and/or prophylactic in the transfer vehicle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For transfer vehicle compositions including RNA, a QUANT-IT™ RIBOGREEN® RNA assay (Invitrogen Corporation Carlsbad, CA) can be used to evaluate the encapsulation of RNA by the transfer vehicle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Example 26

T Cell Targeting

To target transfer vehicles to T-cells, T cell antigen binders, e.g., anti-CD8 antibodies, are coupled to the surface of the transfer vehicle. Anti-T cell antigen antibodies are mildly reduced with an excess of DTT in the presence of EDTA in PBS to expose free hinge region thiols. To remove DTT, antibodies are passed through a desalting column. The heterobifunctional cross-linker SM(PEG)24 is used to anchor antibodies to the surface of circRNA-loaded transfer vehicles (Amine groups are present in the head groups of PEG lipids, free thiol groups on antibodies were created by DTT, SM(PEG)24 cross-links between amines and thiol groups). Transfer vehicles are first incubated with an excess of SM(PEG)24 and centrifuged to remove unreacted cross-linker. Activated transfer vehicles are then incubated with an excess of reduced anti-T cell antigen antibody. Unbound antibody is removed using a centrifugal filtration device.

Example 27

RNA Containing Transfer Vehicle Using RV88.

In this example RNA containing transfer vehicles are synthesized using the 2-D vortex microfluidic chip with the cationic lipid RV88 for delivery of circRNA.

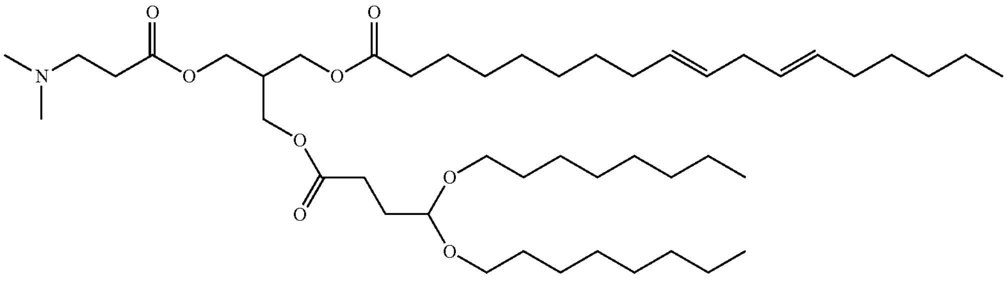

RV88

TABLE 14

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV88 | GVK bio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

RV88, DSPC, and cholesterol all being prepared in ethanol at a concentration of 10 mg/ml in borosilica vials. The lipid 14:0-PEG2K PE is prepared at a concentration of 4 mg/ml also in a borosilica glass vial. Dissolution of lipids at stock concentrations is attained by sonication of the lipids in ethanol for 2 min. The solutions are then heated on an orbital tilting shaker set at 170 rpm at 37° C. for 10 min. Vials are then equilibrated at 26° C. for a minimum of 45 min. The lipids are then mixed by adding volumes of stock lipid as shown in Table 15. The solution is then adjusted with ethanol such that the final lipid concentration was 7.92 mg/ml

TABLE 15

| Composition | MW | % | nmoles | mg | Stock (mg/ml) | ul | Ethanol (ul) |
|---|---|---|---|---|---|---|---|
| RV88 | 794.2 | 40% | 7200 | 5.72 | 10 | 571.8 | 155.3 |
| DSPC | 790.15 | 10% | 1800 | 1.42 | 10 | 142.2 | |

TABLE 15-continued

| Composition | MW | % | nmoles | mg | Stock (mg/ml) | ul | Ethanol (ul) |
|---|---|---|---|---|---|---|---|
| Cholesterol | 386.67 | 48% | 8640 | 3.34 | 10 | 334.1 | |
| PEG2K | 2693.3 | 2% | 360 | 0.97 | 4 | 242.4 | |

RNA is prepared as a stock solution with 75 mM Citrate buffer at pH 6.0 and a concentration of RNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the RNA-liposomes is exchanged by using G-25 mini desalting columns to 10 mM Tris-HCl, 1 mM EDTA, at pH 7.5. Following buffer exchange, the materials are characterized for size, and RNA entrapment through DLS analysis and Ribogreen assays, respectively.

Example 28

RNA Containing Transfer Vehicle Using RV94.

In this example, RNA containing liposome are synthesized using the 2-D vortex microfluidic chip with the cationic lipid RV94 for delivery of circRNA.

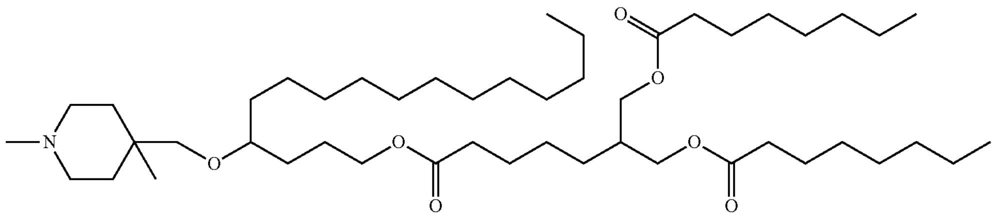

RV94

TABLE 16

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV94 | GVKbio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

The lipids were prepared as in Example 27 using the material amounts named in Table 17 to a final lipid concentration of 7.92 mg/ml.

TABLE 17

| Composition | MW | % | nmoles | mg | Stock (mg/ml) | ul | Ethanol (ul) |
|---|---|---|---|---|---|---|---|
| RV94 | 808.22 | 40% | 28800 | 2.3 | 10 | 232.8 | 155.3 |
| DSPC | 790.15 | 10% | 720 | 0.57 | 10 | 56.9 | |
| Cholesterol | 386.67 | 48% | 3456 | 1.34 | 10 | 133.6 | |
| PEG2K | 2693.3 | 2% | 144 | 0.39 | 4 | 97.0 | |

The aqueous solution of circRNA is prepared as a stock solution with 75 mM Citrate buffer at pH 6.0 the circRNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the circRNA-transfer vehicles is exchanged by using G-25 mini desalting columns to 10 mM Tris-HCl, 1 mM EDTA, at pH 7.5, as described above. Following buffer exchange, the materials are characterized for size, and RNA entrapment through DLS analysis and Ribogreen assays, respectively. The biophysical analysis of the liposomes is shown in Table 18.

TABLE 18

| Sample | N:P | TFR | Ratio (aqueous/ | RNA encapsulation amount | RNA encapsulation yield | size | |
|---|---|---|---|---|---|---|---|
| Name | Ratio | nl/mn | org phase) | (μg/ml) | % | d · nm | PDI |
| SAM-RV94 | 8 | 22 | 2 | 31.46 | 86.9 | 113.1 | 0.12 |

Example 29

General Protocol for in Line Mixing.

Individual and separate stock solutions are prepared—one containing lipid and the other circRNA. Lipid stock containing a desired lipid or lipid mixture, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3 and pH 5, depending on the type of lipid employed. The circRNA is also solubilized in citrate buffer at a concentration of 4 mg/mL. 5 mL of each stock solution is prepared.

Stock solutions are completely clear and lipids are ensured to be completely solubilized before combining with circRNA. Stock solutions may be heated to completely solubilize the lipids. The circRNAs used in the process may be unmodified or modified oligonucleotides and may be conjugated with lipophilic moieties such as cholesterol.

The individual stocks are combined by pumping each solution to a T-junction. A dual-head Watson-Marlow pump was used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 $mm^3$. Each of the large ends (1.6 mm) of polypropylene line is placed into test tubes containing either solubilized lipid stock or solubilized circRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated circRNA via tail vein injection. At various time points after administration, serum samples are collected by retroorbital bleed. Serum levels of Factor VII protein are determined in samples using a chromogenic assay (Biophen FVTI, Aniara Corporation, OH). To determine liver RNA levels of Factor VII, animals are sacrificed and livers are harvested and snap frozen in liquid nitrogen. Tissue lysates are prepared from the frozen tissues and liver RNA levels of Factor VII are quantified using a branched DNA assay (QuantiGene Assay, Panomics, CA).

FVII activity is evaluated in FVTI siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 30 circRNA Formulation Using Preformed Vesicles.

Cationic lipid containing transfer vehicles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. For cationic lipid mixtures which do not form small vesicles, hydrating the lipid mixture with a lower pH buffer (50 mM citrate, pH 3) to protonate the phosphate group on the DSPC headgroup helps form stable 70-90 nm vesicles.

The FVII circRNA (solubilised in a 50 mM citrate, pH 4 aqueous solution containing 30% ethanol) is added to the vesicles, pre-equilibrated to 35° C., at a rate of ~5 mL/min with mixing. After a final target circRNA/lipid ratio of 0.06 (wt wt) is achieved, the mixture is incubated for a further 30 min at 35° C. to allow vesicle re-organization and encapsulation of the FVII RNA. The ethanol is then removed and the external buffer replaced with PBS (155 mM NaCl, 3 mM Na2HPO4, ImM KH2P04, pH 7.5) by either dialysis or tangential flow diafiltration. The final encapsulated circRNA-to-lipid ratio is determined after removal of unencapsulated RNA using size-exclusion spin columns or ion exchange spin columns.

Example 31

Homology Regions Improves Precursor RNA Circularization

The engineered circular RNA was designed to optimize stability and is comparably more efficient in expressing proteins than linear mRNA (R. Wesselhoeft et al., 2018). This circular RNA was derived from a vector containing in the following order: a 5' homology region, a 3' group I intron fragment, a first spacer, an Internal Ribosome Entry Site (IRES), a protein coding region, a second spacer, a 5' group I intron fragment, and a 3' homology region.

Figure 26:
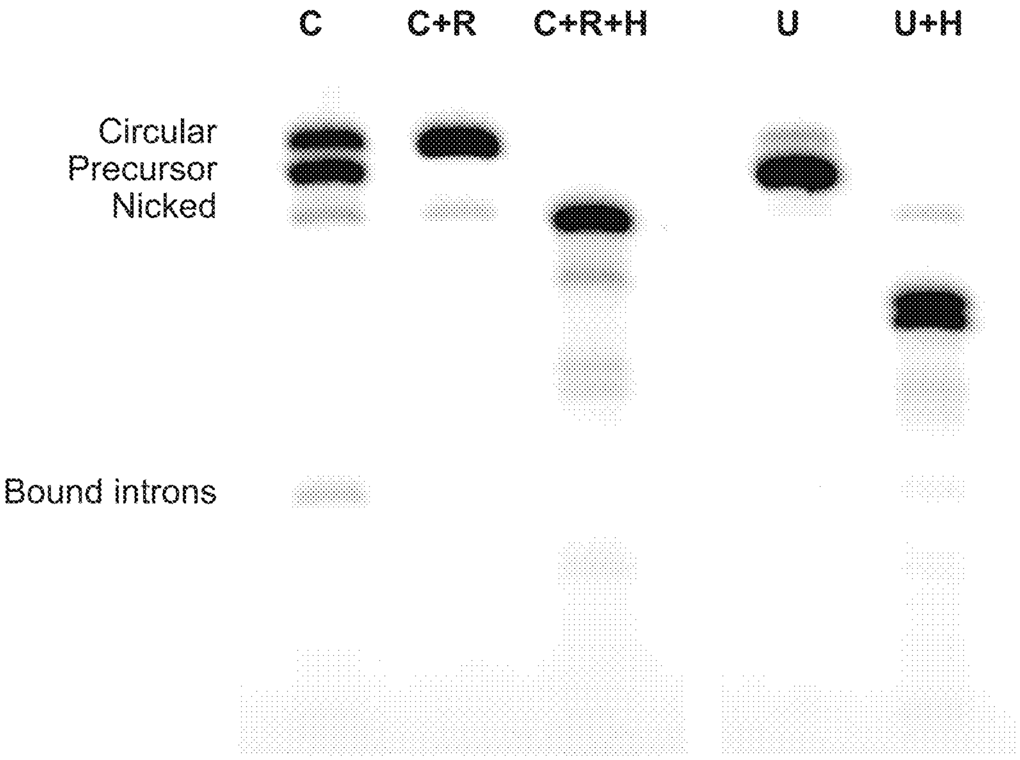
FIG. 26 depicts agarose gel confirmation of precursor RNA circularization. C: precursor RNA (with strong homology arms) subjected to circularization conditions. C+R: Lane C, digested with RNase R. C+R+H: Lane C+R, digested with oligonucleotide-guided RNase H. U: precursor RNA not subjected to circularization conditions. U+H: Lane U, digested with oligonucleotide-guided RNase H.
Figure 27:
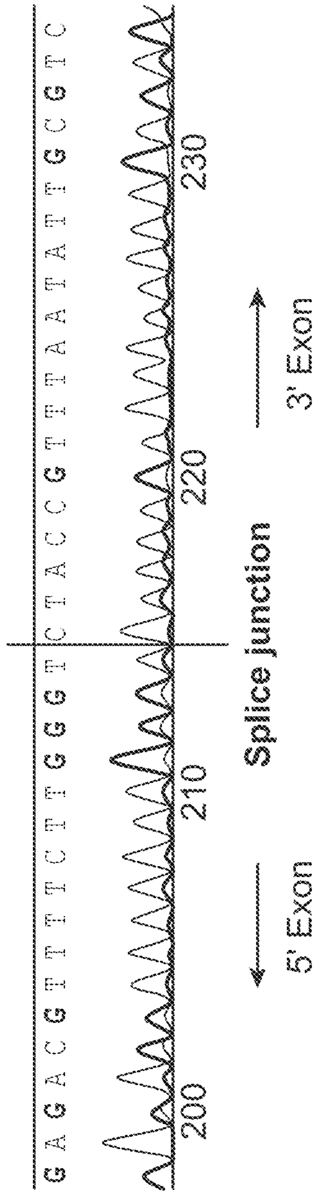
FIG. 27 depicts Sanger sequencing output of RT-PCR across the splice junction of the sample depicted in lane C+R from FIG. 26.

Both homology regions were created using the permuted intron exon method, which utilizes self-splicing group I catalytic introns, such as those from the T4 phage Td gene, to promote RNA circularization with only the addition of a guanosine nucleotide or nucleoside and Mg2+(Petkovic S. and Muller S. (2015) RNA circularization strategies in vivo and in vitro. Nucleic Acids Research. 43, 2454-2465, which is incorporated by reference in its entirety). The resulting permuted intron-exon (PIE) regions allow for 5' and 3' ends of the RNA to covalently link and form a circular RNA. These PIE regions were engineered to have 5' and 3' ends that perfectly complement each other to form "homology regions." Nine nucleotide-long weak homology regions and 19 nucleotide-long strong homology regions were designed, and RNAFold was used to predict secondary structure (FIG. 25). Addition of these homology regions increased splicing efficiency of a construct containing a EMCV IRES and encoding *Gaussia* luciferase from 0% to 16% for weak homology regions and to 48% for strong homology regions. Effective circularization was confirmed by the presence of splicing products on an agarose gel (FIG. 26). In comparison, when the linear mRNA was treated with the same RNase H, the result comprises two products that did not effectively separate out circularized RNA (FIG. 27).

Figure 28:
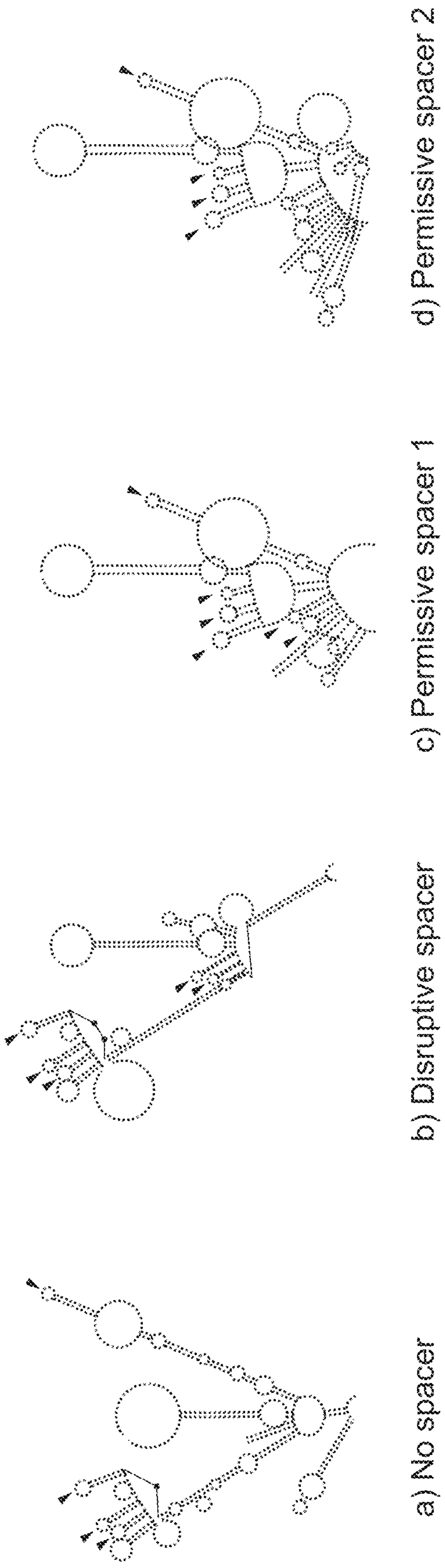
FIG. 28 depicts RNAFold predictions of precursor RNA secondary structure in the context of designed spacers. Secondary structures potentially important for ribozyme function are identified by black arrows.
Figure 29:
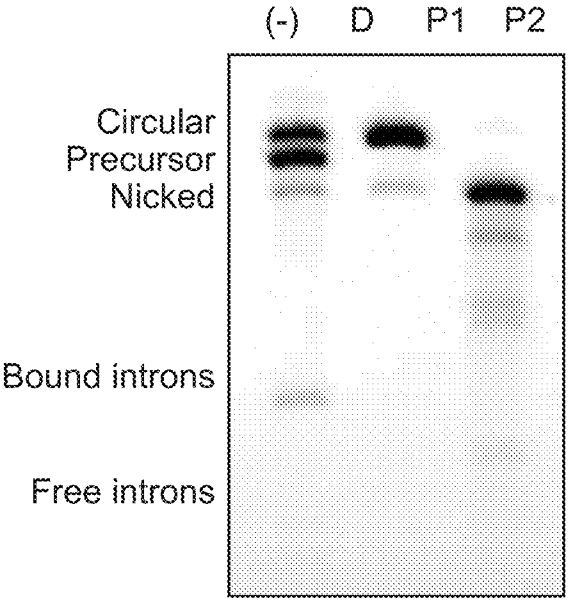
FIG. 29 depicts an agarose gel demonstrating the effect of spacers on splicing. (—): no spacer. D: disruptive spacer. P1: permissive spacer 1. P2: permissive spacer 2. c RNAFold predictions of precursor RNA secondary structure for internal homology region design. Lack of significant internal homology (Anabaena 1.0) and introduced internal homology (Anabaena 2.0) indicated by black arrows. Splicing bubble indicated as the region between homology arms and internal homology regions that contains the splicing ribozyme.
Figure 30:
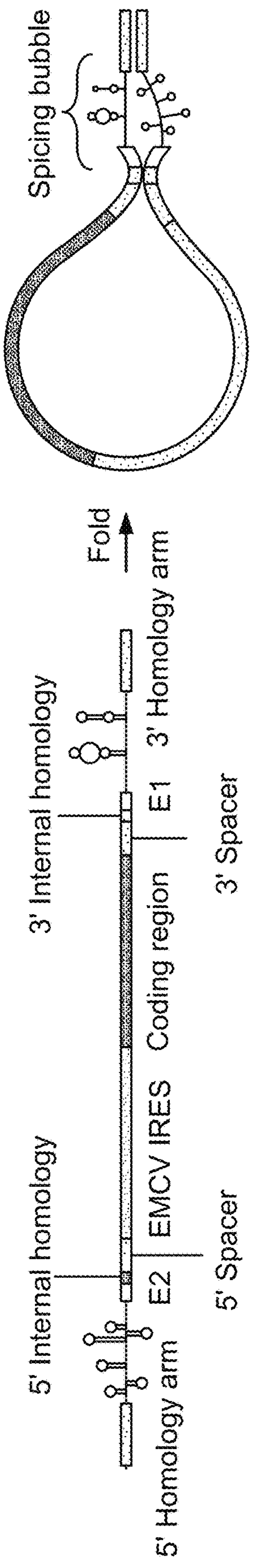
FIG. 30 is a schematic diagram showing elements of the engineered self-splicing precursor RNA design.

The two spacer regions were included to ensure that the structure will fold independently to form the circular RNA (FIG. 28). These spacer sequences were established to: (1) be unstructured and non-homologous to the proximal intron and IRES sequences; (2) separate intron and IRES secondary structures to allow each to independently fold from one another; and (3) contain a region of spacer-spacer complementary allowing formation of a sheltered splicing bubble (FIG. 30). The addition of spacer sequences that permit splicing increases splicing efficiency from 46 to 87%, while the disruptive spacer sequence completely abrogates splicing (FIG. 29). When the precursor RNA was tested with the homology regions, spacers, EMCV IRES, and coding regions, the sequences achieved circularization.

Example 32

Engineered Circular RNA Provides More Stability than Linear RNA

Figure 31:
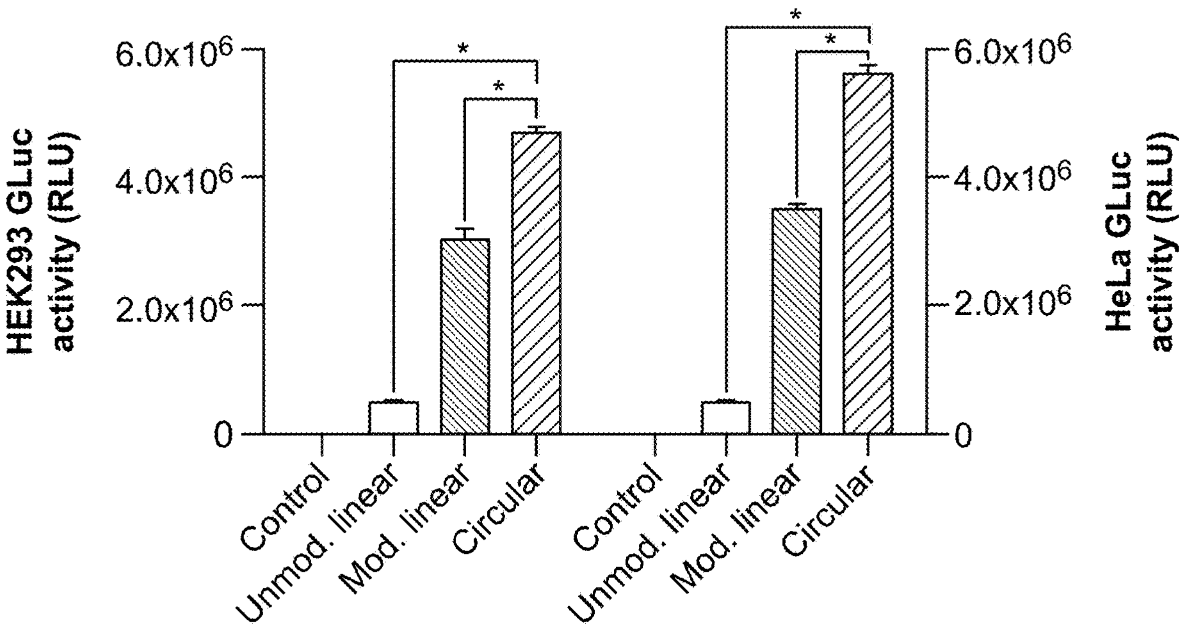
FIG. 31 shows luminescence in the supernatant of HEK293 (left, black outline) and HeLa (right, gray outline) cells 24 h after transfection with CVB3-GLuc-pAC circRNA or modified or unmodified linear GLuc mRNA (n=4 HEK293, n=3 HeLa).
Figure 32:
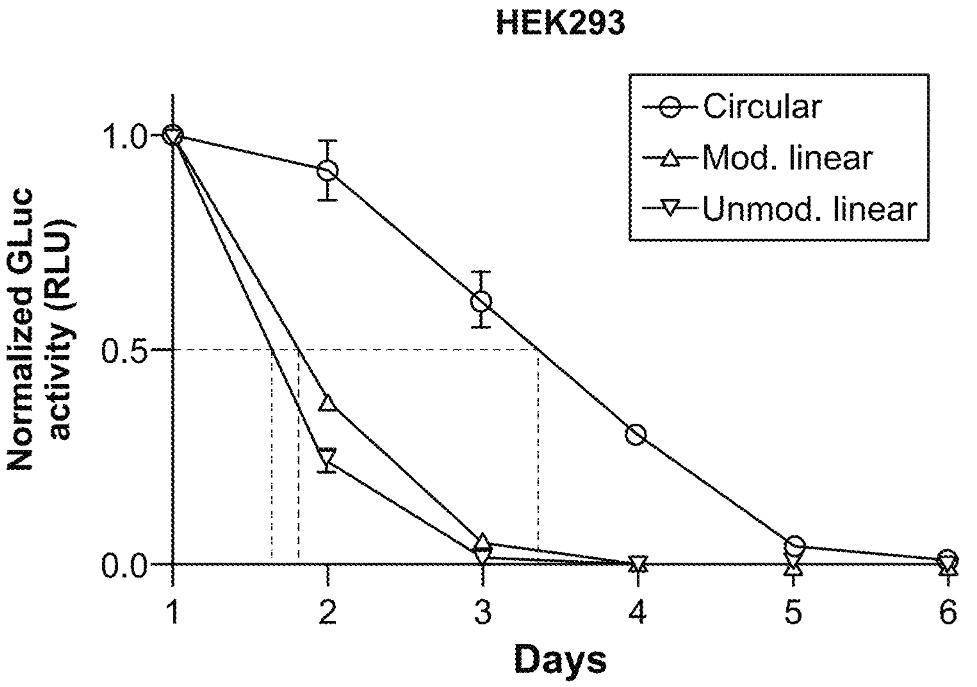
FIG. 32 shows luminescence in the supernatant of HEK293 cells starting 24 h after transfection with CVB3-GLuc-pAC circRNA or modified or unmodified linear GLuc mRNA and continuing for 6 days (n=4).

Stability of the circular RNA was determined using HPLC-purified engineered circular RNA (A. Wesselhoef, 2018). The circular RNA was a *Gaussia* luciferase-coding circular RNA (CVB3-GLuc-pAC). A canonical unmodified 5' methyl guanosine-capped and 3' polyA-tailed linear GLuc mRNA as well as a nucleoside-modified (pseudouridine, 5-methylcytosine) linear GLuc mRNA was as a linear comparison to the circular construct. Luminescence was performed in a supernatant of HEK293 and HeLa cells for 24 hours of transfection and then continuously monitored each day for 6 days for GLuc activity. Exogenous circular RNA produced 811.2% more protein than linear unmodified mRNA after 24 hours of transfection (FIG. 31). Within 24 hours, the circular RNA also produced more 54.5% more protein than the modified linear mRNA (FIG. 31). During the span of 6 days, circular RNA in HEK293 cells exhibited a protein production half-life of 80 hours, while the unmodified and modified linear mRNA performed half-lives of 43 and 45 hours respectively (FIG. 32). Since the circular RNA had a greater production of protein and a longer protein production half-life, circular RNA provides more stability than linear mRNA.

Example 33

Figure 33:
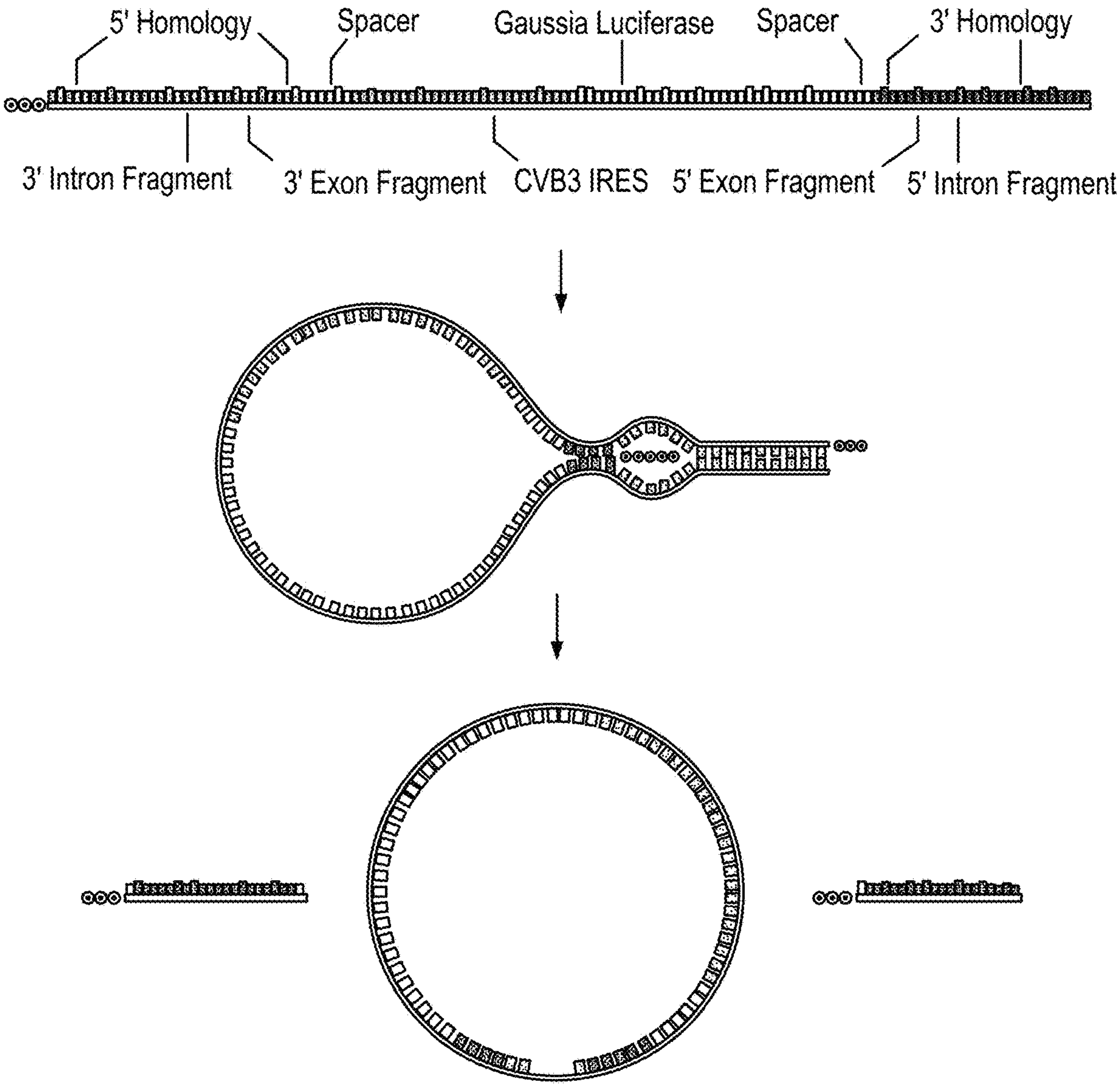
FIG. 33 gives an overview of precursor RNA design and self-splicing. Shading denotes different regions of RNAs described herein.
Figure 34:
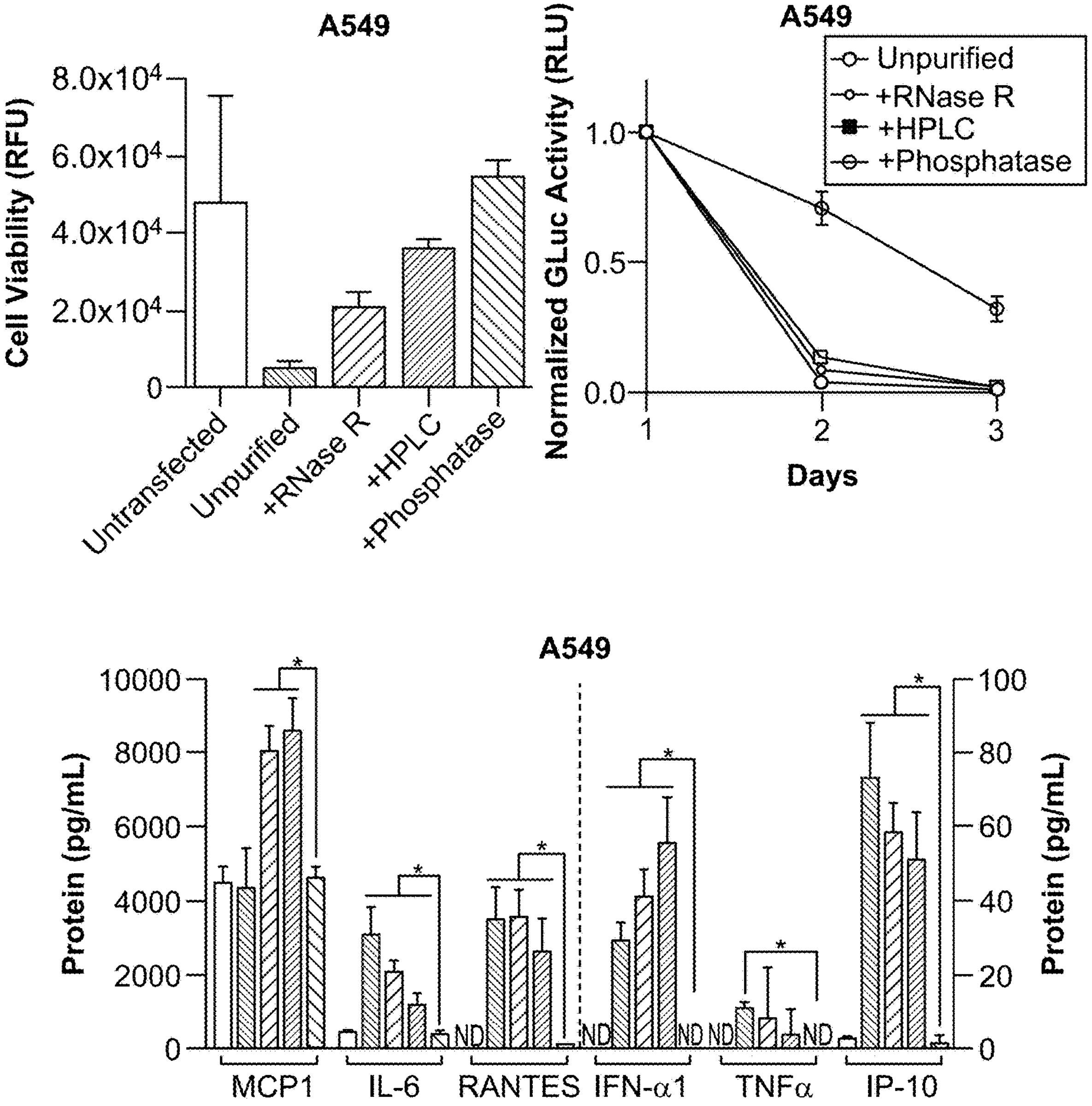
FIG. 34 depicts cell viability, circRNA expression stability, and cytokine release from A549 cells transfected with different circRNA preparations (+RNase R, unpurified circRNA digested with RNase R only; +HPLC, unpurified circRNA HPLC purified, and then digested with RNase R; +Phos, unpurified circRNA HPLC purified, treated with a phosphatase, and then digested with RNase R). Cell viability was assessed 3 days after transfection. Cytokine release was assessed 24 h after transfection (data presented as means+SDs; n=3; *p<0.05; ND, not detected).
Figure 35:
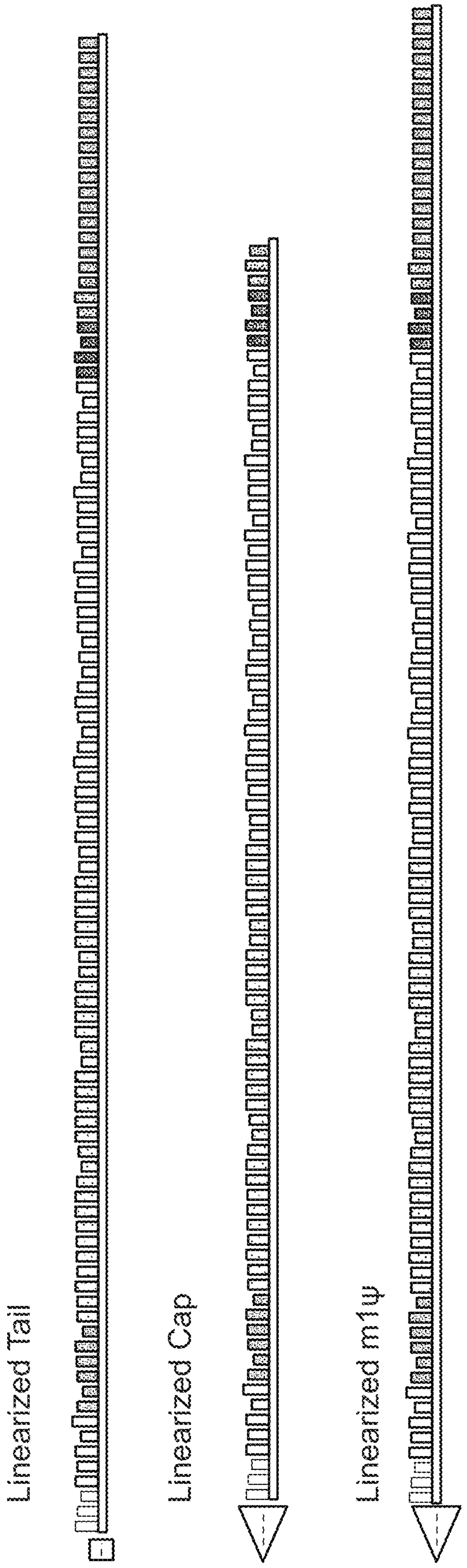
FIG. 35 depicts schematics of RNAs introduced and used for TLR experiments. Linearized circRNAs contain all of the same sequence elements as spliced circRNA due to deletions encompassing both the introns and the homology arms.

Purification of Circular RNA Encoding CARS Promotes an Effective Removal of Immunogenicity Using the engineered circular RNA, further steps of purification from the translation from the precursor RNA molecule diminishes immunogenicity (R. Wesselhoeft et al., 2019). Optimal purification during the splicing reaction included RNAse R, high-performance liquid chromatography (HPLC), digestion with oligonucleotide targeted RNAse H, and phosphatase to remove residual triphosphates. The effectiveness of circular RNA's immunogenicity, two cell lines (human embryotic kidney, 293; human lung carcinoma, A549) are observed for differential cell viability and CAR expression stability responses in circular RNA precursors containing a coxsackievirus B3 internal ribosome entry site (CVB3 IRES), a protein coding message, two designed spacer sequences, two short exon fragments from the PIE construct, and 3' and 5' intron segments of permuted Anabaena pre-tRNA group I intron (FIG. 33). For human lung carcinoma cell lines treatment, RNAse R and HPLC individually are not enough to reduce cytokine release of interleukin-6 (IL-6) (FIG. 34) and further lead to the significant increase of interferon-α1 (IFN-α1). Phosphatase treatment after HPLC and before RNAse digestion shows increased cell viability, greater normalized GLuc Activity and undetectable or un-transfected base line levels of monocyte chemoattractant protein 1 (MCP1), IL-6, IF-α, tumor necrosis factor α (TNF-α), and IFN-γ inducible protein-10 (IP-10) compared to a unpurified circular RNA.

Example 34

Engineered Circular RNA Encoding CAR Avoids Toll-Like Receptor Degradation

Circular RNA can avoid Toll-Like Receptor (TLR) detection. When TLRs 3, 7, and 8 detect RNAs in endosomes, they bind to the RNA and lead to an inflammatory response (T. Kawasaki & T. Kawai, 2014). Linearized versions of circular RNA lacking the intron and homology arm sequences are treated with phosphatase and HPLC. TLRs 3 and 8 show a largely reduced relative SEAP activity when the RNA is circular instead of linear.

Example 35

Example 35A—Circular RNA Delivery Through Lipid Nanoparticles Provide Effective Expression of Proteins In Vivo or In Vitro LNPs are synthesized by mixing 1 volume lipid mixture of MC3, DSPC (Avanti Polar Lipids, Alabaster, Ala.), Cholesterol (Sigma-Aldrich, Taufkirchen, Germany), DMG-PEG (NOF, Bouwelven, Belgium), and DSPE-PEG (50:10.5:38:1.4:0.5 mol ratio) in ethanol with 3 volumes of circular RNA (1:16 w/w circular RNA to lipid) in acetate buffer via injection in the micro fluidic mixing device Nanoassemblr® (Precision Nanosystems, Vancouver BC) at a combined flow rate of 2 mL/min (0.5 mL/min for ethanol and 1.5 mL/min for aqueous buffer). The resultant mixture is dialyzed against phosphate buffered saline (PBS) (pH 7.4) twice for 16 h at 200 times the primary volume with a Slide-A-Lyzer cassettes (10 kda cutoff, Thermo Fisher Scientific Inc. Rockford, Ill.) to remove ethanol. The resulting nanoparticle suspension was filtered through 0.2 μm sterile filter (Sarstedt, Numbrecht, Germany) into glass vials and sealed with a crimp closure.

Characterization of Formulations

A Zetasizer Nano ZS (Malvern Instruments Ltd, Malvern, Worcestershire, UK) is used to determine the particle size, the polydispersity index (PDI) and the zeta potential of the circular RNA nanoparticles in PBS in determining particle size and 15 mM PBS in determining zeta potential.

Ultraviolet-visible spectroscopy is used to determine the concentration of circular RNA nanoparticle formulation. LNPs are diluted 10 to 1 in 4:1 (v/v) mixture of methanol and chloroform solution. After mixing, the absorbance spectrum of the solution is recorded between 230 nm and 330 nm on a DU 800 spectrophotometer (Beckman Coulter, Beckman Coulter, Inc., Brea, Calif.). The circular RNA in the nanoparticle formulation is calculated based on the extinction coefficient of circular RNA used in the formulation and with the baseline subtracted out from the difference between the value of 260 nm wavelength and the baseline at 330 nm.

QUANT-IT™ RIBOGREEN® RNA assay (Invitrogen Corporation Carlsbad, Calif) is used to evaluate the encapsulation of circular RNA by the nanoparticle. Samples are prepared per the manufacturer's instructions. The fluorescence intensity is measured using a fluorescence plate reader (Wallac Victor 1420 Multilabel Counter; Perkin Elmer, Waltham, Mass.) at an excitation wavelength of ~480 nm and an emission wavelength of ~520 nm. The fluorescence values of the reagent blank are subtracted from that of each of the samples and the percentage of free circular RNA is determined by dividing the fluorescence intensity of the intact sample (without addition of Triton X-100) by the fluorescence value of the disrupted sample (caused by the addition of Triton X-100).

Attaching a Targeting Ligand to the LNP.

First, nanobodies are selected for their binding capacity to CD3, CD4, or CD8. Preferably CD3 antibodies are used which bind, induce rapid internalization, but do not over stimulate T cells. Once a nanobody is selected, site directed mutagenesis using techniques known to one of ordinary skill in the art are used to generate a nanobody with a single surface exposed cysteine.

Nanobodies are first conjugated to an alkyne group for Click chemistry via the reactive cysteine. By mixing alkyne-maleimide with the nanobody devoid of reducing agent (no DTT or BME) of choice in a 10× molar ratio of alkyne-maleimide to nanobody, the single free cysteine is labeled (Hermanson, Bioconjugation techniques, 3rd addition, 2013, incorporated by reference). Free alkyne linker groups are dialyzed away with amicon filters with 2×100 volumes of PBS.

The purified nanobody alkyne is reacted with DSPE-PEG-azide via click chemistry and the addition of copper as a catalyst and is described in Presolski et al (Presolski et al 2011, Current protocols in chemical biology 3: 153-162). Once the nanobody is modified, 250 nm cholesterol is added to produce a micellar formulation of the lipid modified nanobody.

To incorporate the lipid modified nanobody micelles into the LNP, the lipid nanobody is incubated with LNPs for 48 hour at 4C at a ratio of 1:1 nanobody to circular RNA weight. The nanobody Labeled LNP is separated from free nanobody lipid via dialysis with a 1MDa cutoff membrane (BioLabs, LTS). Nanobody incorporation is also measured via ELISA or western blot compared to a standard.

Example 35B—Formulation of Circular RNA into a Polymeric Nanoparticle for Delivery to T Cells PBAE Polymer Synthesis PBAE polymer is synthesized using methods previously (Mangraviti et al., ACS Nano 9, 1236-1249 (2015)). Briefly, 1,4-butanediol diacrylate was combined with 4-amino-1-butanol in a 1.1:1 molar ratio of diacrylate to amine monomer. After mixing, the reaction is at 90° C. for 24 h with stirring to produce acrylate-terminated poly(4-amino-1-butanol-co-1,4-butanediol diacrylate). The polymer is dissolved at a ratio of 1.15 g per ml tetrahydrofuran (THF). To form the piperazine-capped 447 polymer, 786 mg of 1-(3-aminopropyl)-4-methylpiperazine dissolved in 13 ml THF was added to the polymer/THF solution. The resulting mixture is incubated for 2 hours with stirring, then precipitated with 5 volumes of diethyl ether. After the solvent is decanted, the polymer is washed with 2 volumes of ether, and dried under vacuum for 2 days before used to form a stock of 100 mg/ml in DMSO. Polymer is stored at −20° C.

PGA-Antibody Conjugation.

15 kD poly-glutamic acid (from Alamanda Polymers) is dissolved in water to form 20 mg/ml and sonicated for 10 min. An equal volume of 4 mg/ml 1-ethyl-3-(3-dimethylaminopropyl) carbodiimide hydrochloride (Thermo Fisher) in water is added, mixed for 5 min at room temperature. The resulting activated PGA was then combined with antibodies at a 4:1 molar ratio in phosphate buffered saline (PBS) and mixed for 6 hrs at room temperature. To remove unlinked PGA, the solution was exchanged 3 times against PBS across a 50,000 NMWCO membrane (Millipore). Antibody concentrations are determined using a NanoDrop 2000 spectrophotometer (Thermo Scientific). The antibodies used for T cell experiments are anti-CD3 (clone OKT3), anti-CD4 (clone OKT4), anti-CD8 (clone OKT8), and anti-CD28

(clone 9.3, all from BioXCell). Clone C1.18.4 is used as a control antibody. For HSC transduction, polyclonal goat anti-mouse IgG and polyclonal goat anti-mouse CD105 antibodies (Fisher) are used.

Nanoparticle (NP) Preparation

Circular RNA stocks are diluted to 100 μg/ml in sterile, nuclease-free 25 mM sodium acetate buffer, pH 5.2 (NaOAc). PBAE-447 polymer in DMSO is diluted to 6 mg/ml in NaOAc, and added to circular RNA at a 60:1 (w:w) ratio. The Mixture is vortexed for 15 sec and incubated for 5 min at room temperature to form NPs. To add targeting elements to the nanoparticles, PGA-linked antibodies are diluted to 250 μg/ml in NaOAc and added at a 2.5:1 (w:w) ratio to the circular RNA. The mixture is vortexed for 15 sec and incubated for 5 min at room temperature to form NPs coated in PGA—antibody. PGA-PEG and other blocking agents can be mixed in as well to generate NP particles with greater half lives in serum.

The nanoparticles are lyophilized by mixing them with 60 mg/ml D-sucrose as a cryoprotectant, and flash-freezing them in liquid nitrogen, before processing them in a FreeZone 2.5 L Freeze Dry System (Labconco). The lyophilized NPs are stored at −80° C. until use. For application, lyophilized NPs are re-suspended in a volume of sterile water to restore their original concentration.

Example 36

Introducing CAR Circular RNA into Cells In Vitro

Circular RNA can be introduced to the cytoplasm of eukaryotic cells using a lipid-polymeric transfection reagent. For example, 100 ng of circRNA in <5 uL water or storage buffer (pH 5-7) can be mixed with OptiMem (Gibco) to a final volume of 5 uL. Separately, 0.2 uL MessengerMax transfection reagent (Thermo Fisher) can be mixed with OptiMem (Gibco) to a final volume of 5 uL. This second mixture can then be added to the first mixture to produce a mixture of circRNA, OptiMem, and MessengerMax transfection reagent that can then be added to the culture medium of 10,000-50,000 eukaryotic cells after a short incubation (5-30 minutes) in order to promote cellular internalization of the circRNA. Alternatively, circRNA can be electroporated into eukaryotic cells using, for example, the Neon electroporation system (Thermo Fisher). lug of circRNA can be electroporated into 200,000 T cells at 1,600V for 10 ms with 3 pulses in a volume of up to 100 uL. Alternatively, circRNA can be introduced into eukaryotic cells using a lipid nanoparticle or polymer complexed with circRNA.

Example 37

Expression of CAR on T-Cells Transduced with Circular RNA

The engineered circular RNA encoding CAR are delivered by lipid nanoparticles to T-cells to generate CAR expressing T-Cells. To determine the efficiency of translation, the engineered circular RNA includes a CAR coding region. T cells are then transfected with CAR-coding circRNA. Flow cytometry is then used to analyze CAR expression on the cell surface (S. De Olivera et al., 2013). Fluorescein isothiocyanate conjugated polyclonal F(Ab')2 fragment goat antihuman IgG1Fcγ (Jackson ImmunoResearch Laboratories, West Grove, PA) (55.5 ng per 105 cells) is used to detect the presence of human IgG spacer in the CAR constructs located on the cell surface. Jurkat cells are stably transduced with the CD19-CAR, with an expression rate of above 96% to compare with the control T-Cells. The CAR expressing T-Cells are further washed with PBS. The flow cytometer results show the expression of CARs by the T cells.

Example 38

Example 38A—Transfection of circRNA Encoding a CAR Results in Minimal Cytokine Release from T Cells Use of engineered circular RNA to express CARs produces less cytokine release than when lentiviruses are used. One of the main downfalls of using lentiviruses as a vector in gene therapy is the cytokine release that results from unstable packaging cells or expression of gag or pol genes of HIV that results in cascading cytotoxic effects (O. Merten, 2016). CAR-Transduced T-Cells generated using circular RNAs exert little to no cytokine release in comparison to lentiviral delivery of CARs.

Cytokine release can be determined through cytokine release assays. For example, a CRA is performed using therapeutic mAbs (S. Vessillier et al., 2015). Purified human IgG4κ and IgG1 are used as isotype controls (AMS Biotechnology Ltd, UK) and anti-CD28 agonist (Biolegend, UK) is used as a control to assess specificity for a CD28 superagonist. Sodium azide is removed from control mAbs using Amicon® Ultra-4 centrifugal filter units (Millipore Ltd, UK) and confirmed endotoxin-free using the limulus amebocyte lysate gel clot test. Since human FcγRI and FcγRIIIa bind murine IgG2a as per human IgG1, muromonab-CD3 responses are compared to human IgG1 isotype control. Phytohaemagglutinin (PHA; Sigma-Aldrich Ltd, UK) at 10 μg ml-1 is used as a positive control. PBMC SP CRAs are performed by wet coating wells of microtitre plates at a mAb concentration of 1 μg well-1 for 1 hour, followed by washing to remove unbound mAb and then the addition of PBMC for 48 hours (Eastwood et al., 2010, Eastwood et al., 2013). PBMC HDC CRAs are performed by addition of mAb at 1 μg ml-1, to PBMC pre-incubated at high density for 48 hours, and 24 hour-stimulation (Romer et al., 2011, Bartholomaeus et al., 2014). WB and 10% (v/v) WB CRAs are performed at a mAb concentration of 5 μg ml-1 and 48-hour stimulation, as previously described (Wolf et al., 2012, Bailey et al., 2013). All concentrations are chosen for comparability with previously published findings on cytokine release using these methods. Although not a published method, WB SP and 10% (v/v) WB SP CRAs are performed as per the PBMC SP CRA with a mAb coating concentration of 1 μg well-1, as controls. All assays are carried out in 96-well round bottom microtitre plates (Sigma Aldrich Ltd), PBMC SP and HDC CRA utilized 2×105 PBMC in 200 μl of complete media per well, the WB CRA utilized 200 μl of WB per well containing 0.7-2.0×106 WBCs and the 10% (v/v) WB CRA utilized a tenth of the latter in complete media at 200 μl well-1. CRA comparisons are performed using the same set of donors, except for the PBMC HDC CRA which utilized a different set of 8 donors. The effect of selective depletion of RBCs from heparinized WB are assessed, using EasySep™ glycophorin A positive cell depletion cocktail (Stemcell Technologies, UK) according to the manufacturer's instructions. Buffy coats are prepared from whole blood by centrifugation and incubated with anti-glycophorin A reagent for 15 minutes at room temperature before addition of magnetic nanoparticles added and a further incubation for 10 minutes. RBCs are then removed by immuno-magnetic separation. Depletion of 95-99% of RBCs are confirmed by visual assessment. The resultant white blood cell (WBC) suspension consisting almost entirely of plasma depleted polymorphonuclear leukocytes, lymphocytes and monocytes is adjusted to 1×106 ml-1 in complete media and used in a WBC SP CRA at 200 μl well-1 and a mAb coating concentration of 1 μg well-1 TGN1412. To investigate inhibition of TGN1412-associated cytokine release, WBCs are resuspended in autologous WB or 10-200 μg well-1 of GYPA (Sigma-Aldrich Ltd) is added. To assess the effect of IL-2 on TGN1412-associated cytokine release, daclizumab (IL-2R antagonist) at a concentration of 5 μg ml-1 is added to cells and pre-incubated for 10 min prior to plating in a PBMC SP CRA as described above. Concentrations of IFNγ, IL-2, IL-13 and IL-8 in culture supernatants are measured using custom made MSD plates, according to the manufacturer's instructions (Meso Scale Discovery, USA). TNFα and IL-17 concentrations are quantified by ELISA as previously described (Eastwood et al., 2010, Eastwood et al., 2013).

The cytokine release assay is completed for T cells engineered using the lentiviruses as well as using the engineered circular RNA in establishing CAR-Transduced T-cells. The T cells engineered circular RNA produces significantly less cytokines.

Example 38B—CAR-Transduced T-Cells Derived from Engineered Circular RNA Kill Tumor Cells CAR transduced T-cells created using engineered circular RNA are capable of killing tumor cells. Newborn mice, which are transgenic for human IL-3, SCF, and GM-CSF, are given an injection of fetal liver CD34+ or other hematopoietic stem cell to create humanized immune system (HIS) mice. After 5-6 weeks, engraftment of human hematopoiesis is confirmed. A killing assay is then performed to determine the effectiveness of these CAR transduced T cells. For example, UPN035, an oligoclonal population of primary CD3+ and CD8+ T cells is transfected to express a chimeric ScFv immunoreceptor that directs specific cytolysis of CD19+ target cells (L. Cao et al, "Development and application of a multiplexable flow-cytometry-based assay to quantify cell-mediated cytolysis," Cytometry Part A 77A(6): 534-545 (2010)). 4-h51Cr release assays are performed, for example, where 90-95% confluent U251T cells is labeled overnight in Dulbecco's Modified Eagle Medium (DMEM) solution with Na51CrO4 (C. Brown et al., "Biophotonic cytotoxicity assay for high-throughput screening of cytolytic killing," J. Immunol. Methods 297(1-2): 39-52 (2005)). The next day, the U251T cells are washed with EDTA solution, tyrpsinized, resuspended in DMEM, incubated for 60 minutes at 37° C., and then washed again with DMEM. The target cells are co-cultured with increasing numbers of CD8+ effector CTL in V-bottom 96-well micro-plates at 5% CO2 at 37° C. After 1-4 hours, 50% of the supernatant is removed and released 51Cr is counted with Cobra II auto-gamma (Packard). The percent lyse is calculated based on the combined positive score in comparison to the 100% lysed control determined by plating target cells in 1% SDS as well as the 0% lysed control determined by plating target cells in media without effector cells. The CAR transduced T-cells effectively kill tumor cells.

Example 38C—CAR-Transduced T-Cells Derived from Engineered Circular RNA Kill Tumor Cells A hematological cancer system is produced by injecting luciferase-expressing Eu-ALL01 leukemia cells into 4-6 week old female albino C57BL.6J-Tyr mice. One week following injection, mice are randomized into three groups. The mice in group 1 are treated with a control nanoparticle formulation containing circular RNA expressing eGFP. The mice in group 2 are treated with a test nanoparticle formulation containing circular RNA encoding a CD19-specific CAR. The mice in group 3 are treated with a test nanoparticle formulation containing linear modified RNA encoding a CD19-specific CAR.

Over time, luciferase-expressing leukemia is detected in the mice by intravenously administering D-luciferin and mice are imaged on a Xenogen IVIS spectrum imaging system (Xenogen) 10 min post injection of D-Luciferin. The mice in group 1 show rapid leukemia spread. The mice in group 2 show decreased amounts of leukemia luminescence at early time points and later time points compared to the mice in group 3. The mice in group 3 mice show leukemia rebound and an increase in the number of cancer cells sooner than group 2 mice due to the lower stability of the linear modified RNA construct compared to the circular RNA construct.

Example 39

Detection of TCR Complex Protein Expression

Following delivery of circular RNA encoding a TCR complex protein using nanoparticles or electroporation, expression of the TCR complex protein is confirmed by flow cytometry. TCR complex protein may be detected by using the appropriate anti-target antibody (e.g., expression of a CD19-specific TCR complex protein may be detected with an anti-CD19 scFv antibody). T cells are washed in staining buffer and re-suspended in PBS. For dead cell exclusion, cells are incubated, for example, with LIVE/DEAD® Fixable Aqua Dead Cell Stain (Invitrogen) for 30 minutes on ice. Cells are washed with PBS and re-suspended in staining buffer. FACS buffer is added to each tube, and cells are pelleted by centrifugation. Surface expression of TCR complex proteins is detected by, for example, Zenon® R-Phycoerythrin-labeled human anti-tumor antigen IgG1 Fc or tumor antigen-Fc. Antibodies or soluble tumor antigen is added to the respective samples and incubated. Cells are then washed, and T cells stained for surface markers.

Example 40

Recombinant TCR Complex Protein Expressing T Cell Treatment in an In Vivo Solid Tumor Xenograft Mouse Model T-cells expressing recombinant TCR that are created using engineered circular RNA. Primary human solid tumor cells are grown in immune compromised mice. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from lung cancer, ovarian cancer, melanoma, colon cancer, gastric cancer, renal cell carcinoma, esophageal carcinoma, glioma, urothelial cancer, retinoblastoma, breast cancer, Non-Hodgkin lymphoma, pancreatic carcinoma, Hodgkin's lymphoma, myeloma, hepatocellular carcinoma, leukemia, cervical carcinoma, cholangiocarcinoma, oral cancer, head and neck cancer, or mesothelioma. These mice are used to test the efficacy of T cells expressing the recombinant TCR complex protein in the human tumor xenograft models. Following an implant or injection of $1\times10^5$-$1\times10^7$ tumor cells subcutaneously, tumors are allowed to grow to 200-500 $mm^3$ prior to initiation of treatment. The T-Cells expressing recombinant TCR are then introduced into the mice. Tumor shrinkage in response to treatment with human T cells comprising the inventive TCR complex proteins can be either assessed by caliper measurement of tumor size or by following the intensity of a luciferase protein (ffluc) signal emitted by ffluc-expressing tumor cells.

Example 41

Engineering CAR Expression Using Circular RNA Results in Less Cytokine Release Syndrome Compared to Lentivirus The use of the engineered circular RNA to generate CAR expression is less susceptible to cytokine release syndrome than when lentivirus is used as a vector. Cells engineered to express a CD19-specific CAR using are compared to cells engineered to express CD19-specific CAR using lentivirus. Each type of vectors are transfected into T cells, which are then delivered to a mice to which a cell line expressing CD19 has been also administered. IL-6 expression by the mice is monitored over time by ELISA. Mice administered the CAR-T cells generated using circular RNA produce less IL-6 than mice administered CAR-T cells generated using lentivirus.

Example 42

Example 42A—CAR-Expressing T Cells Produced Using Circular RNA Exhibit Functional Killing for Longer In Vitro than CAR-Expressing T Cells Produced Using Modified mRNA Eμ-ALL01 leukemia cells (or B16F10 melanoma tumor cells as controls) are labelled with the membrane dye PKH-26 (Sigma-Aldrich), washed with RPMI containing 10% fetal calf serum, and resuspended in the same medium at a concentration of $1\times10^5$ tumor cells per ml. T cells that have been transfected with either circular RNA CAR-T constructs encoding CD19 targeting CARs or modified mRNA constructs encoding CD19 targeting CARs are added to the suspension at varying effector-to-target cell ratios in 96-well plates (final volume, 200 μl) and incubated for 3 h at 37° C. Cells are transferred to V-bottom 96-well plates. The transduced T cells are tested for their ability to kill the CD19-expressing Eμ-ALL01 leukemia cells on days 1, 2, 3, 4, 6, 8, and 10 after transduction. CAR-expressing T cells produced using circular RNA functional in the cell killing of the CD19-expressing cells for longer compared to CAR-expressing T cells produced using modified mRNA.

Example 42B—CAR-Expressing T Cells Produced Using Circular RNA Exhibit Cytokine Secretion Longer In Vitro than CAR-Expressing T Cells Produced Using Modified mRNA CAR-T Cells are produced by transducing either a CD19-specific CAR-encoding circular RNA or a CD19-specific CAR-encoding modified mRNA. T-cell cytokine release is measured with ELISA (R&D Systems) 24 h (IL-2) or 48 h (IFN-μ and TNF-α) after stimulation on irradiated En-ALL01 leukemia cells or B16F10 melanoma controls. T cells are stimulated and tested for cytokine release on day 1, 2, 3, 4, 6, 8, 10 after transduction to demonstrate that CAR-T cells generated using circular RNA produce more cytokines for longer periods of time compared to CAR-T cells produced using modified mRNA.

Furthermore expression of the CD19 CAR construct is measured by labeling the CAR-T transduced cells with an soluble CD19 fluorescently labeled protein. The cells are then washed in media and flow cytometry is used to assess the functional expression of the CD19 CAR. Circular RNA transduced CD19 CAR cells show functional expression for longer at later time points compared to modified mRNA transduced T cells.

Example 43

Electroporation of Primary Human T-Cells with circRNA Encoding a CAR 150,000 primary human T-cell isolated from four different donors were electroporated with 250 ng of circRNA having anabaena intron/exon regions, an anti-CD19 CAR expression sequence, and a CVB3 IRES. After 24 hours of incubation, cells were analyzed for surface expression of anti-CD19 CAR by flow cytometry analysis using standard techniques and reagents known to persons of ordinary skill in the art.

Figure 36:
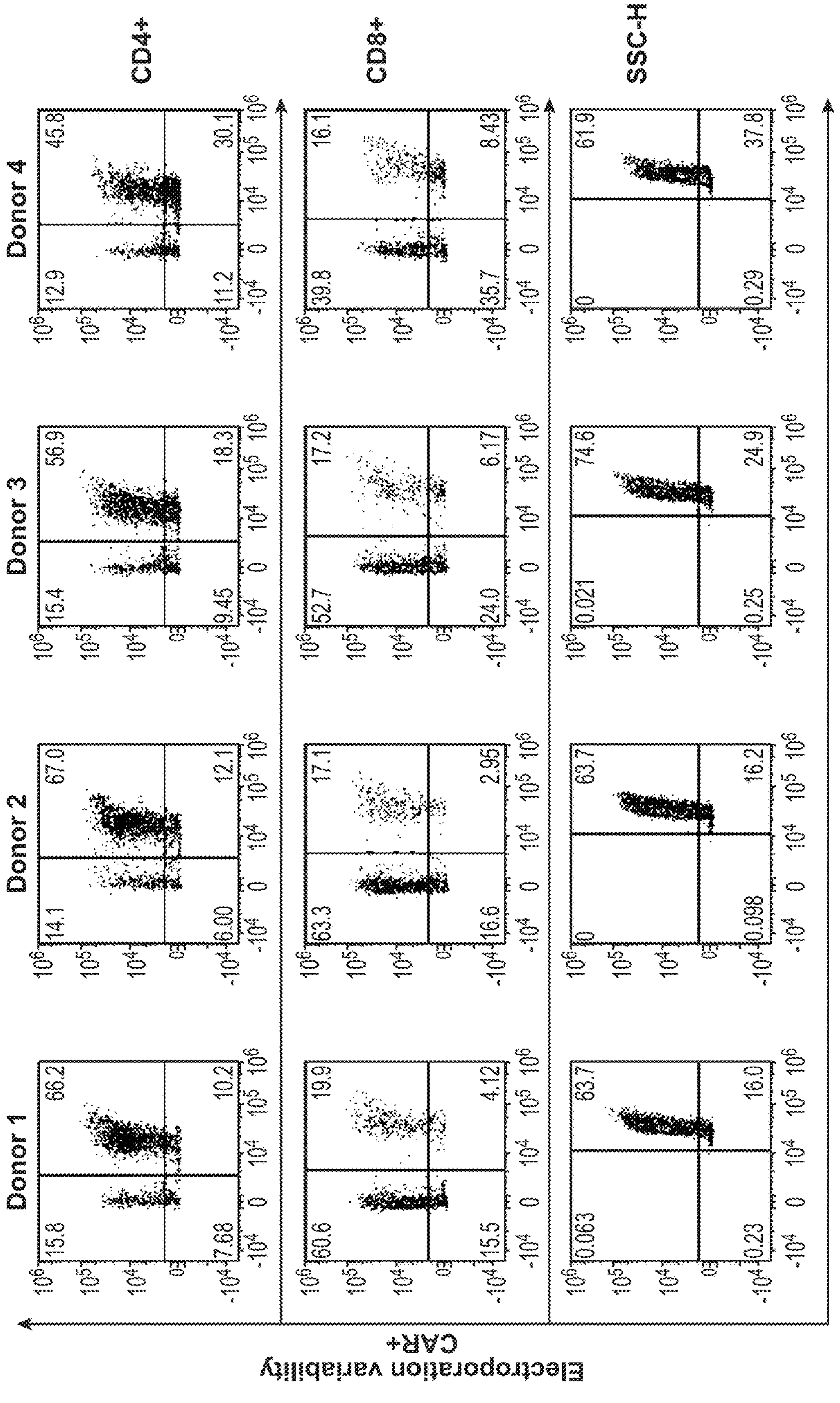
FIG. 36 shows the surface expression of anti-CD19 CAR on primary human T-cells isolated from four donors and electroporated with circRNA.
Figure 37B:
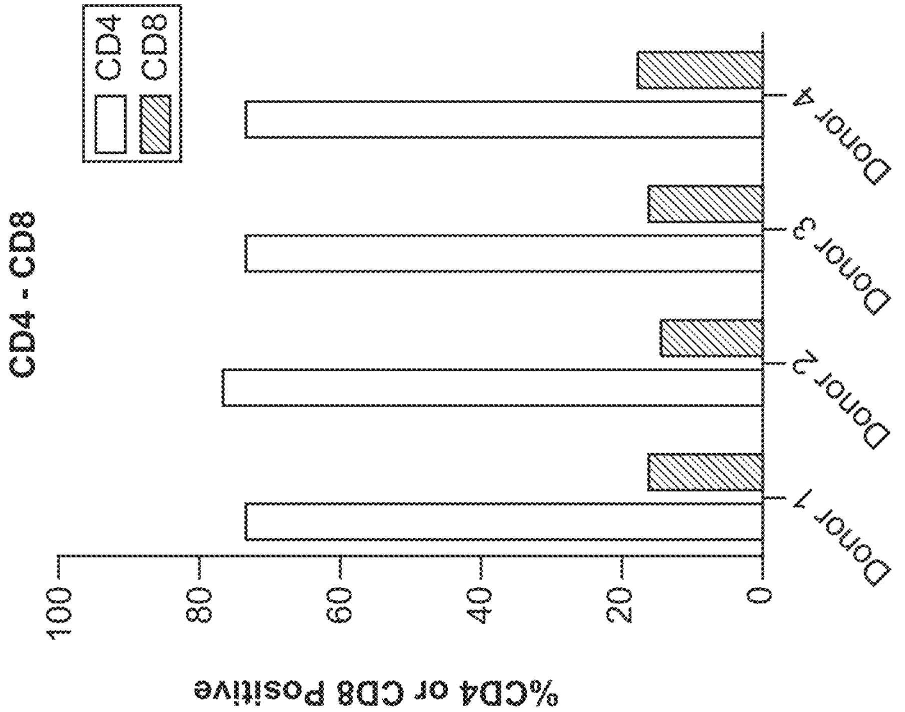
FIGS. 37A and 37B show the proportion of CAR+ of live T cells electroporated with circRNA (FIG. 37A) and the proportion of CD4 and CD8 positive T cells in the 4 human donors in FIG. 36 (FIG. 37B).
Figure 37A:
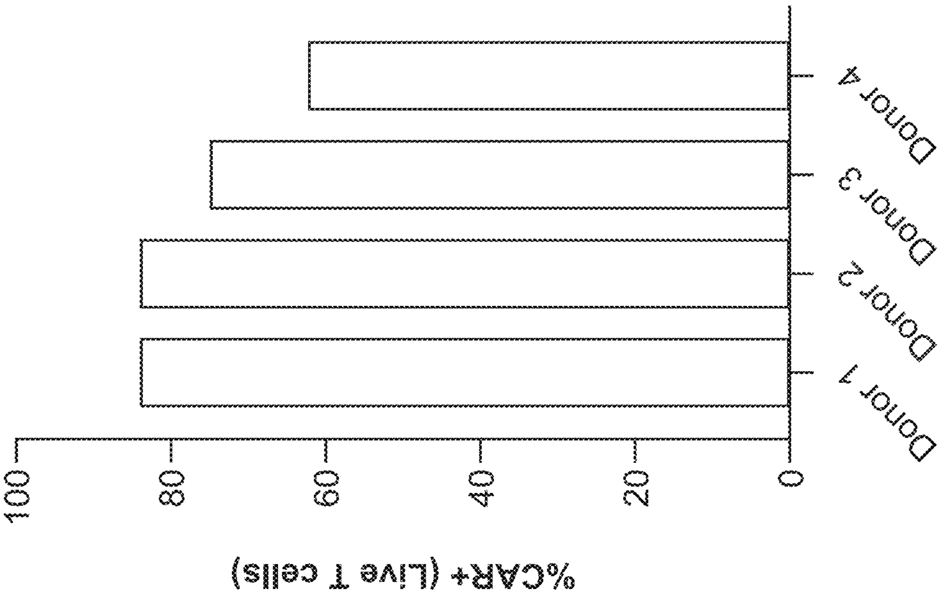

As shown in FIGS. 36 and 37, primary human T-cells can be electroporated to achieve significant surface CAR expression in the live T-cell population.

Example 44

Efficacy of circRNA CAR T-Cell Against CD19+ Target Cells

Figure 38:
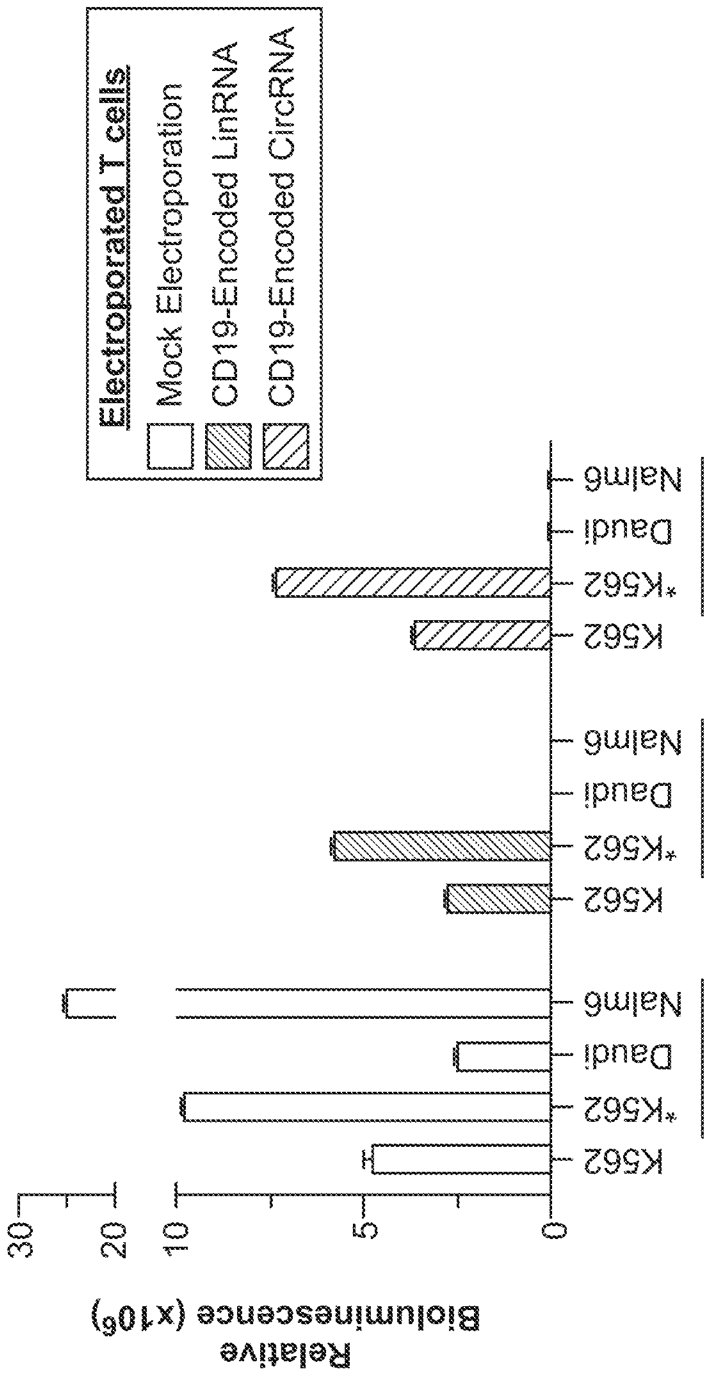
FIG. 38 shows the efficacy of T cells mock electroporated, or electroporated with anti-CD19 CAR-encoding circRNA or linear RNA, in reducing the bioluminescence of luciferase-expressing CD19+ target cells and CD19− non-target cells.

Constructs including anabaena intron/exon regions, and an anti-CD19 CAR expression sequence were circularized. 150,000 human primary CD3+ T cells were either mock electroporated or electroporated with 250 ng circRNA encoding a CAR against CD19. 1 day after electroporation, 10,000 T cells were cocultured with 10,000 target or non-target cells stably expressing firefly luciferase for 24 hours. Quantification of remaining cells of Daudi or Nalm6 target cells, or K562 non-target cells was determined by detection of firefly luminescence (FIG. 38).

Example 45

Figure 39A:
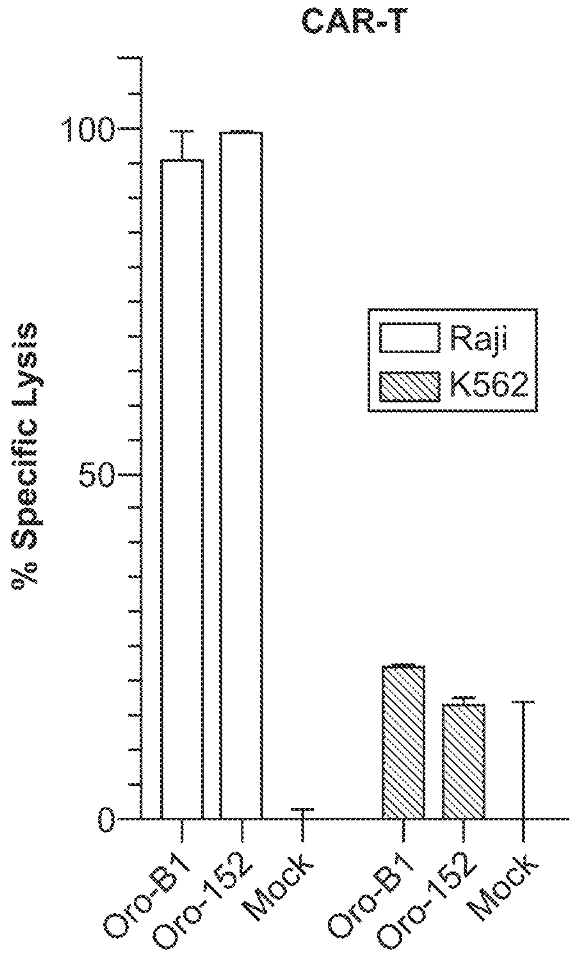
FIGS. 39A and 39B show the efficacy of T-cells electroporated with anti-CD19 CAR-encoding circRNAs having different IRES and co-cultured with luciferase-expressing Raji or K562 cells 5 days (FIG. 39A) or 1 day (FIG. 39B) after electroporation. (Oro-B1=circKymriah; CVB3 IRES, Oro-152=circKymriah; Salivirus SZ1 IRES, L9a-5 permutation site)

Example 45A—Efficacy of circRNA CAR T Cells Having Different IRES Sequences 5 Days after Electroporation Constructs including anabaena intron/exon regions, an anti-CD19 CAR expression sequence, and a CVB3 IRES or a Salivirus SZ1 IRES were circularized. 150,000 human primary CD3+ T cells were either mock electroporated or electroporated with 250 ng circRNA. 10,000 cells were seeded for coculture experiments. 5 days after electroporation, 10,000 Raji or K562 cells stably expressing firefly luciferase were cocultured with seeded T cells for 24 hours. Specific lysis was defined as (1-[CAR condition luminescence]/[mock condition luminescence])*100 (FIG. 39A).

Example 45B—Efficacy of circRNA CAR T Cells 1 Day after Electroporation

Figure 39B:
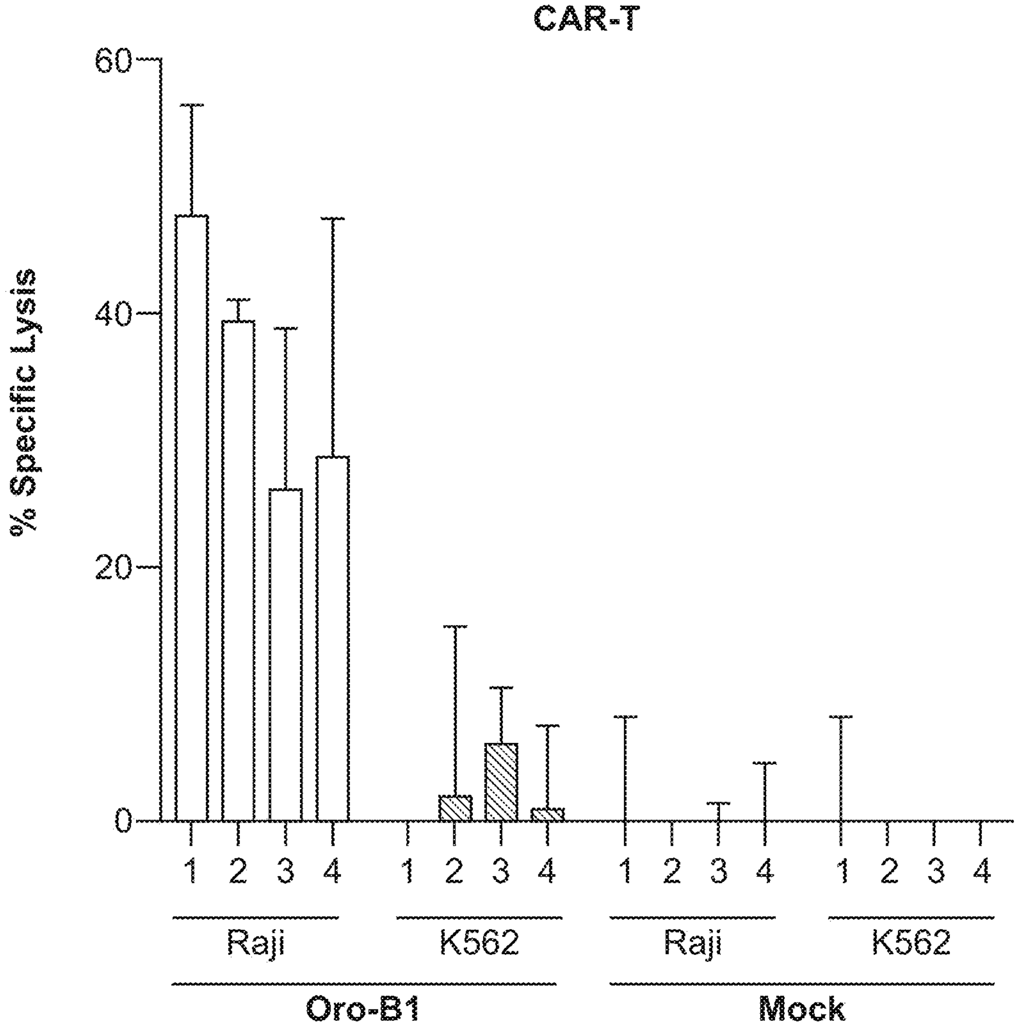

Constructs including anabaena intron/exon regions, an anti-CD19 CAR expression sequence, and a CVB3 IRES were circularized. 150,000 human primary CD3+ T cells from 4 different donors were either mock electroporated or electroporated with 250 ng circRNA. 10,000 cells were seeded for coculture experiments. 1 day after electroporation, 10,000 Raji (target) or K562 (non-target) cells stably expressing firefly luciferase were cocultured with seeded T cells for 24 hours. Specific lysis was defined as (1-[CAR condition luminescence]/[mock condition luminescence]) *100 (FIG. 39B)

Example 46

Example 46A—Lysis Kinetics of circRNA CAR T Cells

Figure 40A:
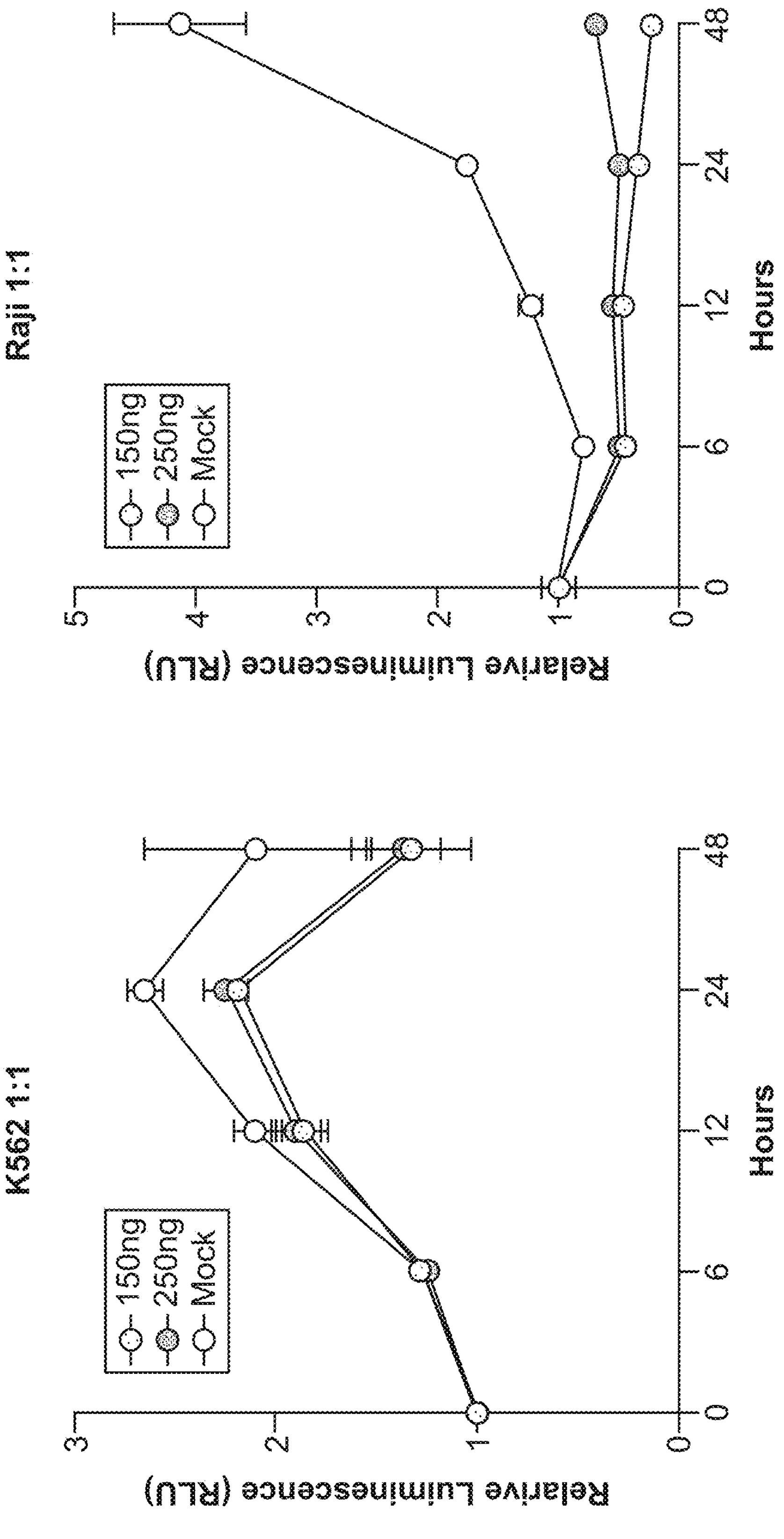
FIGS. 40A-40C show the lysis of target and non-target cells by T cells electroporated with circRNA encoding anti-CD19 CAR.

Constructs including anabaena intron/exon regions, an anti-CD19 CAR expression sequence, and a CVB3 IRES or a Salivirus SZ1 IRES were circularized. Human primary CD3+ T cells were electroporated with 150 ng or 250 ng of circRNA over 48 hours. Raji-luc on-target or K562-luc off-target cells were cocultured with the modified CD3+ T cells at a 1:1 ratio. Luminescence of Raji-luc and K562-luc cells was measured (FIG. 40A).

Example 46B—Lysis Kinetics of circRNA CAR T Cells

Figure 40B:
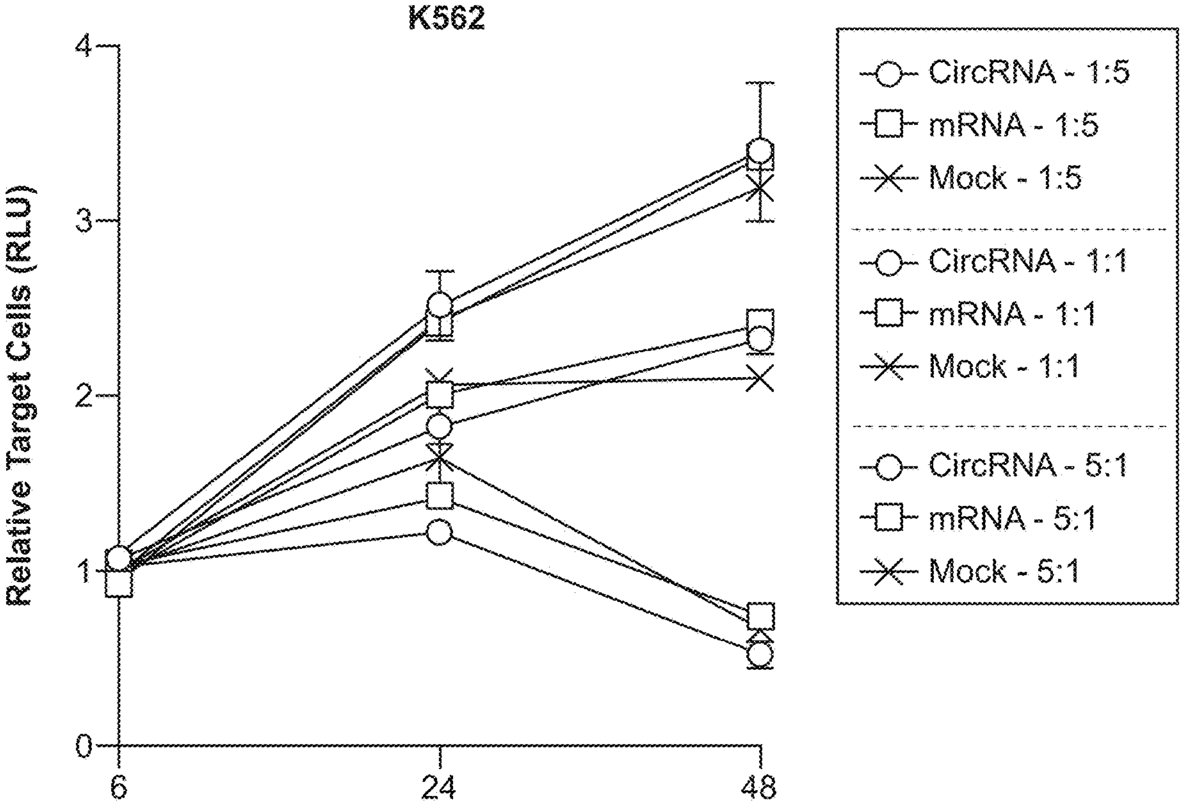

Quantification of specific lysis of K562 target cells was determined by detection of firefly luminescence. 150,000 human primary CD3+ T cells were either mock electroporated or electroporated with 250 ng circRNA. 10,000 cells were seeded for coculture experiments. 1 day after electroporation, 2,000, 10,000, or 50,000 K562 cells stably expressing firefly luciferase were cocultured with seeded T cells for 24 hours. Specific lysis defined as (1-[CAR condition luminescence]/[mock condition luminescence])*100 (FIG. 40B).

Figure 40C:
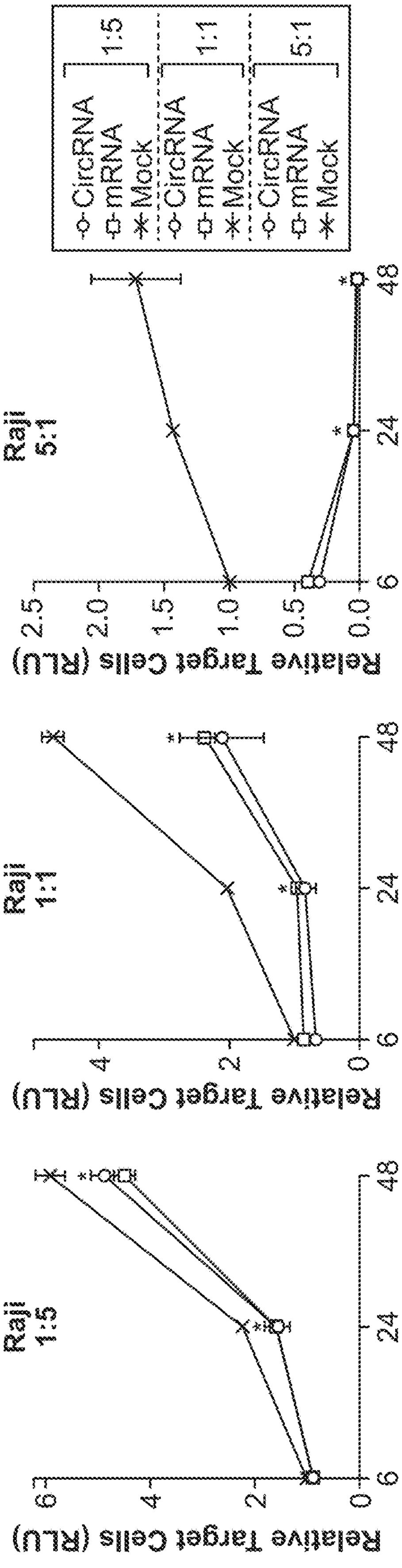

Example 46C—Effect of Co-Culture Ration on Lysis Kinetics of circRNA CAR T Cells Quantification of specific lysis of Raji target cells was determined by detection of firefly luminescence. 150,000 human primary CD3+ T cells were either mock electroporated or electroporated with 250 ng circRNA. 10,000 cells were seeded for coculture experiments. 1 day after electroporation, 2,000, 10,000, or 50,000 Raji cells stably expressing firefly luciferase were cocultured with seeded T cells for 24 hours. Specific lysis was defined as (1-[CAR condition luminescence]/[mock condition luminescence]) *100 (FIG. 40C).

Example 47

Figure 41A:
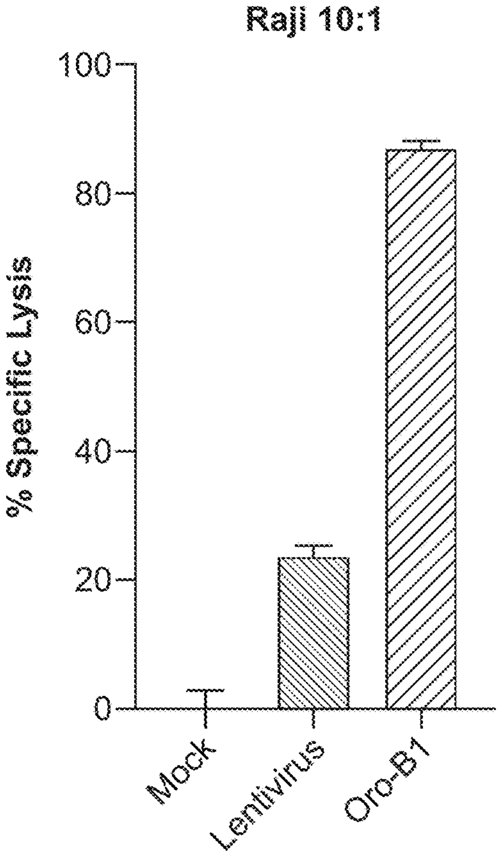
FIGS. 41A-41C shows the efficacy of T-cells electroporated with anti-CD19 CAR-encoding circRNAs in lysing CD19+ Raji cells as compared to T-cells transduced with anti-CD19 CAR-encoding lentivirus.
Figure 41B:
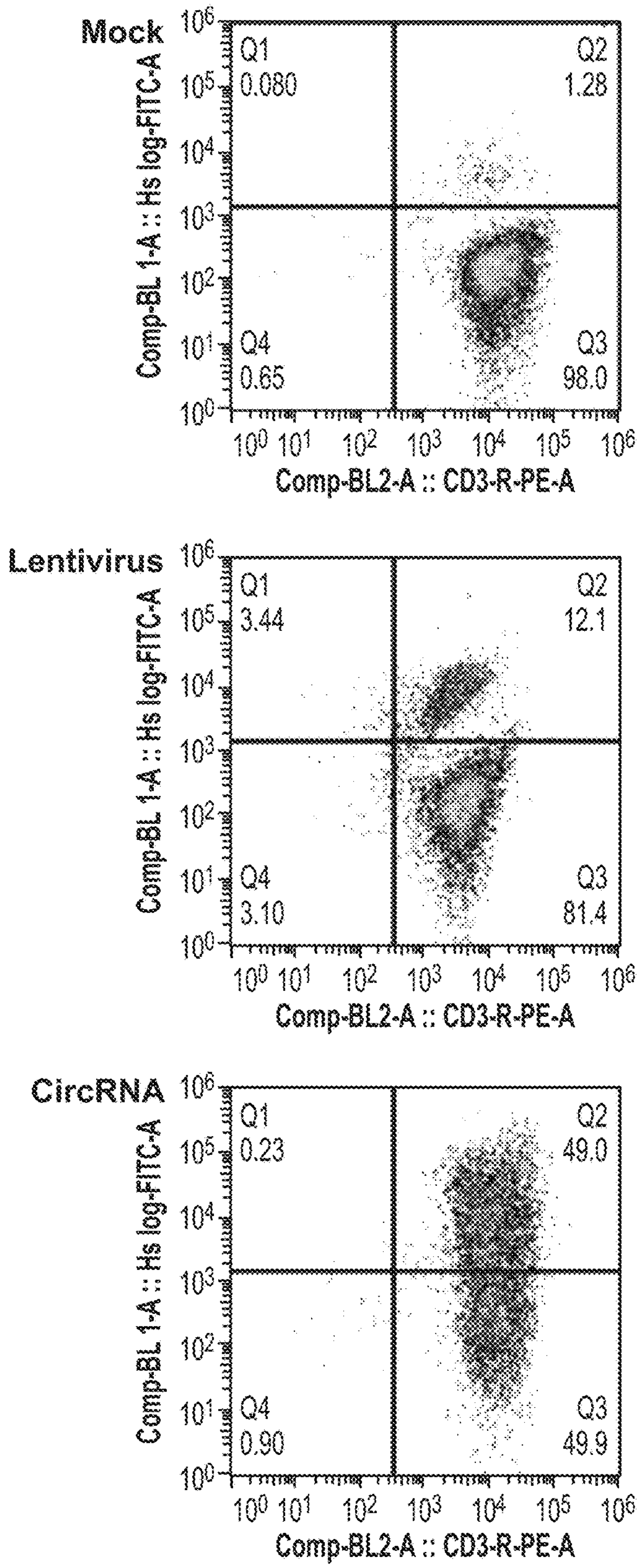
Figure 41C:
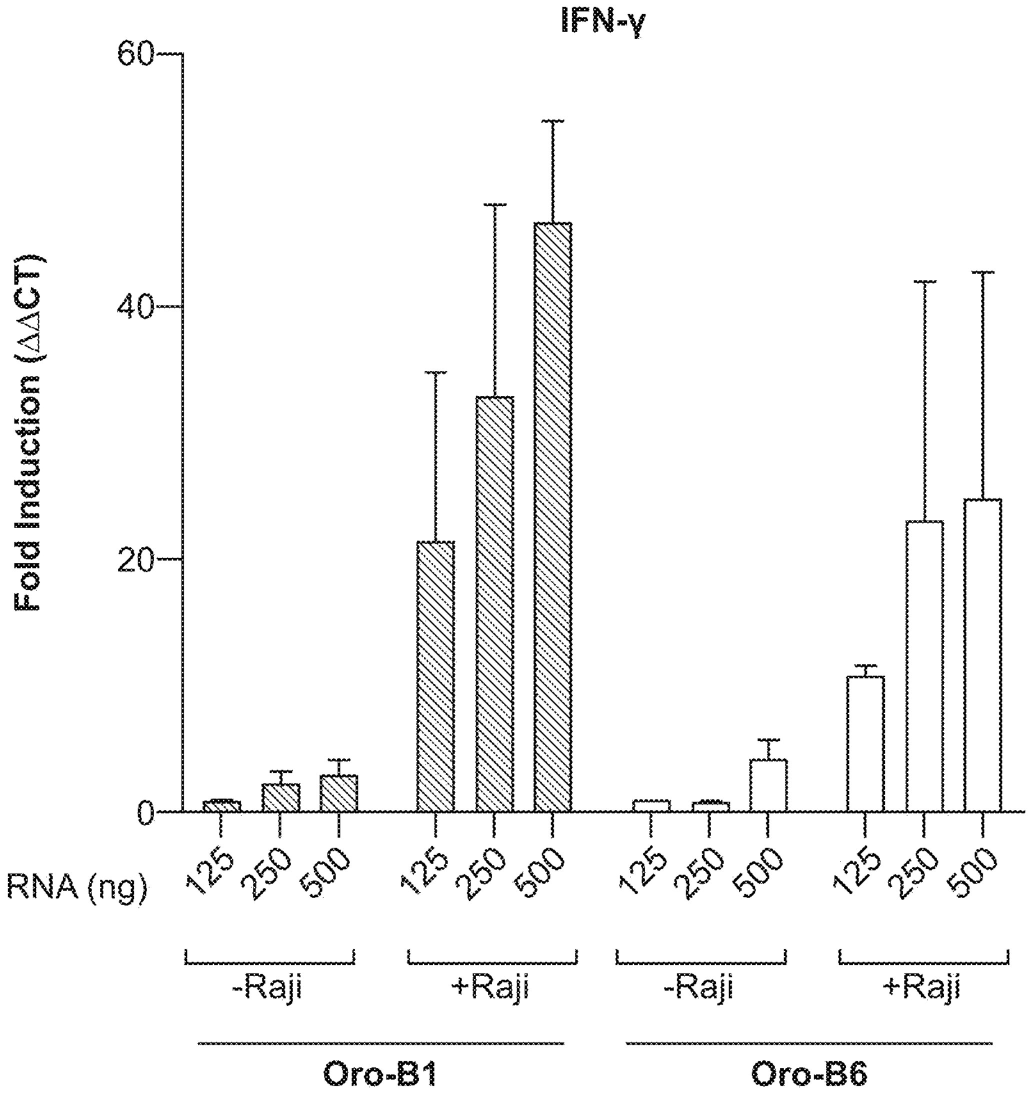
Figure 42:
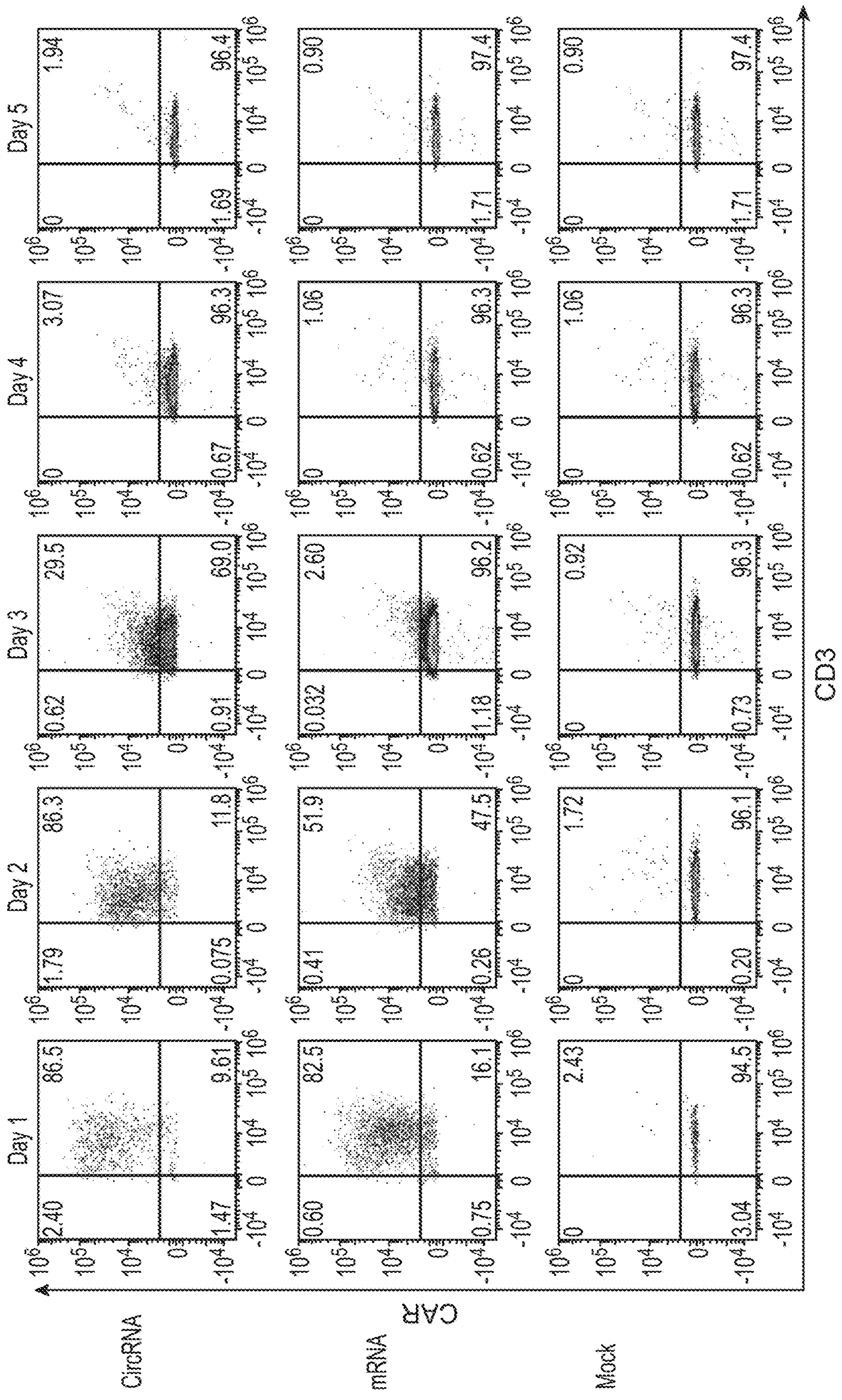
FIG. 42 shows the stability of anti-CD19 CAR expression in primary human CD3+ T cells electroporated with anti-CD19CAR-encoding circRNA or linear mRNA.

Comparison of circRNA CAR T Cells to Cells Electroporated with Linear CAR RNA or Transduced with CAR Lentivirus Constructs including anabaena intron/exon regions, an anti-CD19 CAR expression sequence, and a Salivirus SZ1 IRES were circularized. CD3+ primary human T cells were electroporated with circRNA or were infected with lentivirus encoding anti-CD19 CAR. Interferon gamma transcript induction was measured after 24 hours of culture with or without Raji target cells (FIG. 41A). Proportion of CAR+ T cells was also measured (FIG. 41B). Specific lysis of Raji target cells by human primary CD3+ T cells mock electroporated, electroporated with circRNA encoding a CAR against CD19, or infected with lentivirus encoding a CAR against CD19 was measured (FIG. 41C).

Example 48

Stability of CircRNA

Constructs including anabaena intron/exon regions, an anti-CD19 CAR expression sequence, and a Salivirus SZ1 IRES were circularized. CAR surface expression was measured 1-5 days after electroporation of 150,000 primary human CD3+ T cells with 250 ng of linear mRNA or circRNA encoding an anti-CD19 CAR. T cells were electroporated 5 days after stimulation. Cell viability was assessed with DAPI. Live cells were analyzed for CD3 and CAR expression (FIG. 48).

Example 49

CAR Expression in Human Monocytes

Figure 43:
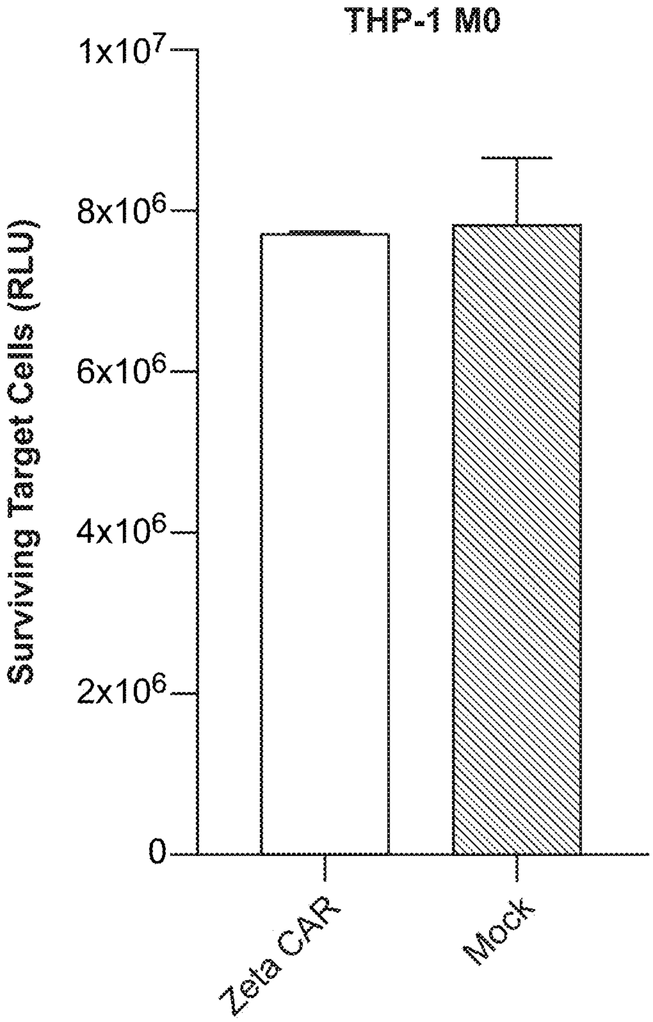
FIG. 43 shows the efficacy of THP-1 monocytes electroporated with a CAR-encoding circRNA in lysing luciferase-expressing Raji cells in co-culture experiments.

Constructs including anabaena intron/exon regions, and a CAR expression sequence were circularized. THP-1 MO cells were either mock electroporated or electroporated with 250 ng circRNA encoding a CAR. 10,000 cells were seeded for coculture experiments. 1 day after electroporation, 10,000 Raji cells stably expressing firefly luciferase were cocultured with seeded THP-1 MO cells for 24 hours. Quantification of surviving Raji target cells determined by detection of firefly luminescence. Luminescence was also measured in supernatant 24 or 48 hours after electroporation of THP-1 MO cells with circRNA encoding *Gaussia* luciferase and 0-90 ng of dsCircRNA. (FIG. 43).

Example 50

CAR Expression in Human Monocytes

Figure 44:
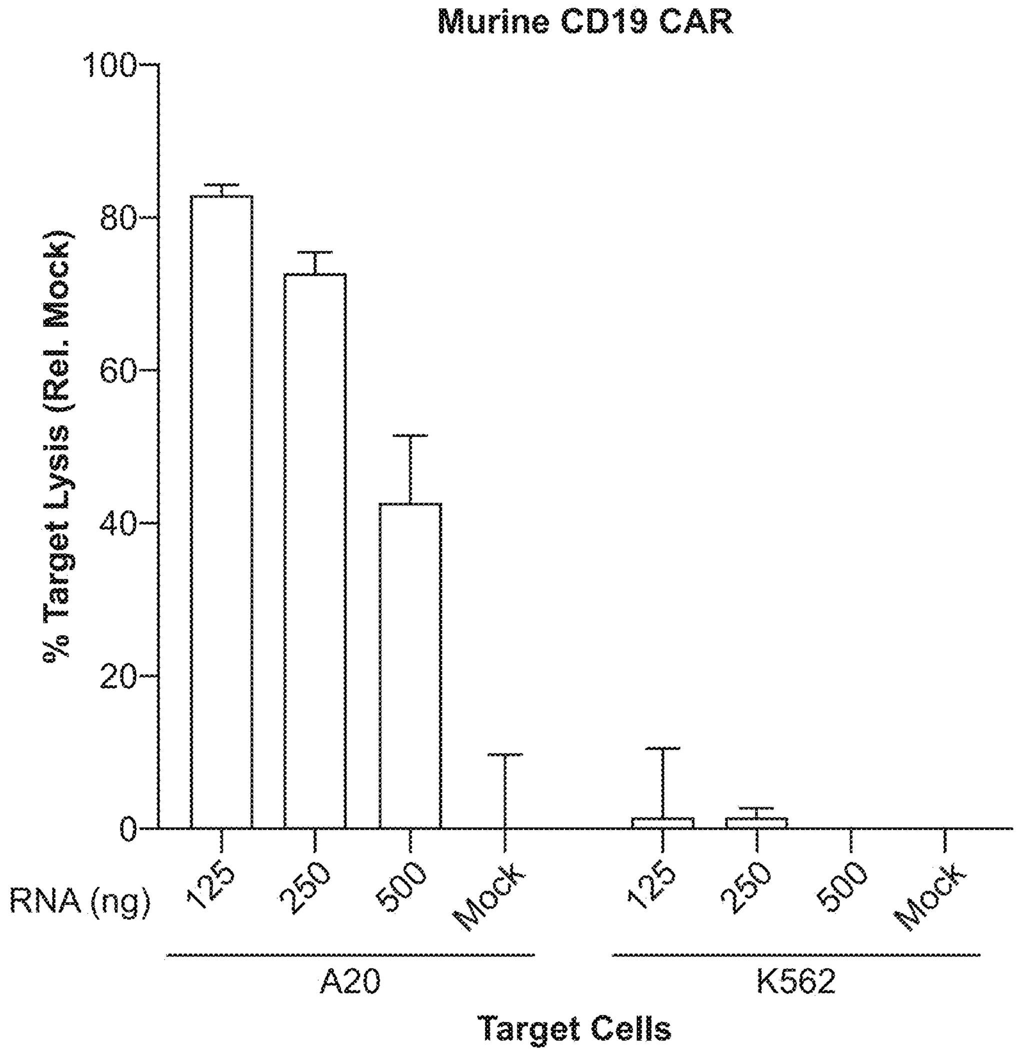
FIG. 44 shows the efficacy of T-cells electroporated with anti-murine CD19 CAR encoding circRNAs in lysing CD19+ A20 cells and CD19− K562 cells.

Constructs including anabaena intron/exon regions, and an anti-murine CD19 CAR expression sequence were circularized. CD3+ T cells were mock electroporated or electroporated with circular RNA and cocultured with A20 target cells or K462 non-target cells. Specific lysis was measured (FIG. 44).

What is claimed is:

1. A pharmaceutical composition comprising:

(a) a circular RNA polynucleotide comprising:

(i) a post-splicing 3' group I intron fragment;

(ii) an Internal Ribosome Entry Site (IRES);

(iii) an expression sequence encoding a chimeric antigen receptor (CAR) or T cell receptor (TCR) complex protein comprising an antigen-binding domain specific for an antigen selected from the group consisting of: CD19, CD123, CD22, CD30, CD171, CS-1, C-type lectin-like molecule-1, CD33, epidermal growth factor receptor variant III (EGFRvIII), disialoganglioside GD2, disialoganglioside GD3, TNF receptor family member, B cell maturation antigen (BCMA), Tn antigen ((TnAg) or (GalNAca-Ser/Thr)), prostate-specific membrane antigen (PSMA), receptor tyrosine kinase-like orphan receptor 1 (ROR1), FMS-like tyrosine kinase 3 (FLT3), tumor-associated glycoprotein 72 (TAG72), CD38, CD44v6, carcinoembryonic antigen (CEA), epithelial cell adhesion molecule (EPCAM), B7H3 (CD276), KIT (GDI17), interleukin-13 receptor subunit alpha-2 (IL-13Rα2), mesothelin, interleukin-11 receptor alpha (IL-11Rα), prostate stem cell antigen (PSCA), protease serine 21, vascular endothelial growth factor receptor 2 (VEGFR2), Lewis (Y) antigen, CD24, platelet-derived growth factor receptor beta (PDGFR-β), stage-specific embryonic antigen-4 (SSEA4), CD20, folate receptor alpha, HER2, HER3, Mucin 1 cell surface associated (MUC1), epidermal growth factor receptor (EGFR), neural cell adhesion molecule (NCAM), prostase, prostatic acid phosphatase (PAP), elongation factor 2 mutated (ELF2M), ephrin B2, fibroblast activation protein alpha (FAP), insulin-like growth factor 1 receptor (IGF-I receptor), carbonic anhydrase IX (CAIX), Proteasome Subunit Beta Type 9 (LMP2), glycoprotein 100 (gp100), oncogene fusion protein consisting of breakpoint cluster region (BCR) and Abelson murine leukemia viral oncogene homolog 1 (ABL) (BCR-ABL), tyrosinase, ephrin type-A receptor 2 (EPHA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, and CD179a; and (iv) a post-splicing 5' group I intron fragment; and (b) a transfer vehicle comprising at least one of:

(i) an ionizable lipid, wherein the ionizable lipid is cKK-E12;

(ii) a structural lipid; and;

(iii) a PEG-modified lipid;

wherein the transfer vehicle is capable of delivering the circular RNA polynucleotide to a human immune cell present in a human subject, such that the CAR or TCR complex protein is translated in the human immune cell and expressed on the surface of the human immune cell.

2. The pharmaceutical composition of claim 1, wherein the IRES is from Taura syndrome virus, Triatoma virus, Theiler's encephalomyelitis virus, Simian Virus 40, Solenopsis invicta virus 1, Rhopalosiphum padi virus, Reticuloendotheliosis virus, Human poliovirus 1, Plautia stali intestine virus, Kashmir bee virus, Human rhinovirus 2, Homalodisca coagulata virus-1, Human Immunodeficiency Virus type 1, Homalodisca coagulata virus-1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, Drosophila C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, Drosophila antennapedia, Human AQP4, Human AT1R, Human BAG-1, Human BCL2, Human BiP, Human c-IAPl, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24, or an aptamer to eIF4G.

3. The pharmaceutical composition of claim 1, wherein the IRES comprises a Enterovirus C, Enterovirus D, or Enterovirus J IRES.

4. The pharmaceutical composition of claim 1, wherein the circular RNA polynucleotide comprises a first internal spacer between the post-splicing 3' group I intron fragment and the IRES, and a second internal spacer between the expression sequence and the post-splicing 5' group I intron fragment.

5. The pharmaceutical composition of claim 4, wherein the first internal spacer and/or the second internal spacer comprises a polyAC sequence.

6. The pharmaceutical composition of claim 4, wherein the first internal spacer and/or the second internal spacer has a length of 10-100 nucleotides.

7. The pharmaceutical composition of claim 1, wherein the transfer vehicle comprises a lipid nanoparticle, a core-shell nanoparticle, a biodegradable nanoparticle, a biodegradable lipid nanoparticle, a polymer nanoparticle, or a biodegradable polymer nanoparticle.

8. The pharmaceutical composition of claim 7, further comprising a targeting moiety.

9. The pharmaceutical composition of claim 1, wherein the circular RNA polynucleotide has a size of at least 500 nucleotides.

10. The pharmaceutical composition of claim 9, the circular RNA polynucleotide has a size of at least 1,000 nucleotides.

11. The pharmaceutical composition of claim 1, wherein the post-splicing 3' Group I intron fragment and the post-splicing 5' Group I intron fragment are from a *Cyanobacterium Anabeana* sp. pre-tRNA-Leu gene or a T4 phage Td gene.

12. The pharmaceutical composition of claim 1, wherein elements (i)-(iv) of the circular RNA polynucleotide are arranged in the order (i)-(iv).

* * * * *